United States Patent
Kawai et al.

(10) Patent No.: US 11,981,686 B2
(45) Date of Patent: May 14, 2024

(54) UREA COMPOUND HAVING SUBSTITUENT

(71) Applicant: DAIICHI SANKYO COMPANY, LIMITED, Tokyo (JP)

(72) Inventors: Junya Kawai, Tokyo (JP); Osamu Iwamoto, Tokyo (JP); Yuma Umezaki, Tokyo (JP); Katsuyoshi Nakajima, Tokyo (JP); Hiroyuki Tsuruoka, Tokyo (JP); Keiji Saito, Tokyo (JP); Nobuya Kurikawa, Tokyo (JP); Natsumi Nishihama, Tokyo (JP); Shinji Tanaka, Tokyo (JP); Momoko Ogitani, Tokyo (JP); Tomohiro Honda, Tokyo (JP); Wataru Saitoh, Tokyo (JP); Tsuyoshi Soneda, Tokyo (JP); Nobuyuki Ohkawa, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 227 days.

(21) Appl. No.: 17/425,520

(22) PCT Filed: Jan. 23, 2020

(86) PCT No.: PCT/JP2020/002351
  § 371 (c)(1),
  (2) Date: Jul. 23, 2021

(87) PCT Pub. No.: WO2020/153433
  PCT Pub. Date: Jul. 30, 2020

(65) Prior Publication Data
  US 2023/0058950 A1    Feb. 23, 2023

(30) Foreign Application Priority Data
  Jan. 24, 2019 (JP) .................. 2019-010252

(51) Int. Cl.
  *C07D 513/18* (2006.01)
  *C07D 513/04* (2006.01)

(52) U.S. Cl.
  CPC ......... *C07D 513/18* (2013.01); *C07D 513/04* (2013.01)

(58) Field of Classification Search
  CPC .. C07D 513/18; C07D 513/04; C07D 513/08; A61P 1/02; A61P 1/04; A61P 1/16; A61P 1/18; A61P 3/10; A61P 9/04; A61P 9/10; A61P 11/00; A61P 11/02; A61P 11/04; A61P 11/06; A61P 11/08; A61P 17/00; A61P 17/02; A61P 17/04; A61P 17/06; A61P 17/08; A61P 17/14; A61P 19/02; A61P 25/00; A61P 25/02; A61P 27/02; A61P 27/16; A61P 29/00; A61P 37/02; A61P 37/08; A61P 43/00; A61P 1/00; A61K 31/437

USPC ....................................... 514/230.2
See application file for complete search history.

(56) References Cited

U.S. PATENT DOCUMENTS

| 4,289,524 A | 9/1981 | Belkind |
| 2011/0230472 A1* | 9/2011 | Mitsuoka ............... A61P 11/02 544/212 |
| 2012/0071475 A1 | 3/2012 | Taniyama et al. |

FOREIGN PATENT DOCUMENTS

| EP | 2 426 135 A1 | 7/2012 |
| JP | 2015-038046 A | 2/2015 |
| JP | 2015-097508 A | 5/2015 |
| WO | 2010/024258 A1 | 3/2010 |
| WO | 2010096389 A1 | 8/2010 |
| WO | 2010/125799 A1 | 11/2010 |
| WO | 2014/113191 A1 | 7/2014 |

OTHER PUBLICATIONS

International Search Report dated Apr. 14, 2020, issued in corresponding International Application No. PCT/JP2020/002351, filed Jan. 23, 2020, 7 pages.
Written Opinion dated Apr. 14, 2020, issued in corresponding International Application No. PCT/JP2020/002351, filed Jan. 23, 2020, 12 pages.
Imai, Shin-Ichiro et al., "Ten years of NAD-dependent SIR2 family deacetylases: implications for metabolic diseases," Trends Pharmacol Sci., 2010, pp. 212-220, 31(5), Elsevier Ltd.
Guarente, Leonard, "Calorie restriction and sirtuins revisited," Genes & Development, 2013 [retrieved on Oct. 18, 2021], pp. 2072-2085, 27(19), Cold Spring Harbor Laboratory Press.
Michishita, Eriko et al., "Evolutionarily Conserved and Nonconserved Cellular Localizations and Functions of Human SIRT Proteins," Molecular Biology of the Cell, Oct. 2005, pp. 4623-4635, 16(10), The American Society for Cell Biology.

(Continued)

*Primary Examiner* — Taylor V Oh
(74) *Attorney, Agent, or Firm* — CHRISTENSEN O'CONNOR JOHNSON KINDNESS PLLC

(57) ABSTRACT

An object of the present invention is to provide a compound that has a specific chemical structure having an activation effect on SIRT6 and is useful as an active component for preventing and treating inflammatory diseases, and the present invention relates to a compound represented by Formula (1) or a pharmaceutically acceptable salt thereof,

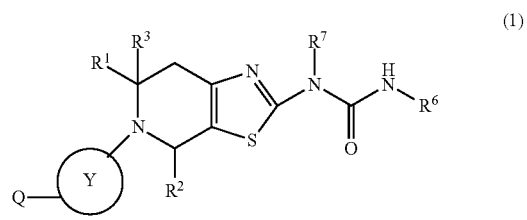

(1)

where each symbol in Formula (1) has the same definition as that described in the specification.

14 Claims, No Drawings

(56) References Cited

OTHER PUBLICATIONS

Michishita, Eriko et al., "SIRT6 is a histone H3 lysine 9 deacetylase that modulates telomeric chromatin," Nature, Mar. 27, 2009, pp. 492-496, 452(7186).
Michishita, Eriko et al., "Cell cycle-dependent deacetylation of telomeric histone H3 lysine K56 by human SIRT6," Cell Cycle, Aug. 15, 2009, pp. 2664-2666, 8(16), Landes Bioscience.
Mostoslavsky, Raul et al., "Genomic Instability and Aging-like Phenotype in the Absence of Mammalian SIRT6," Cell, Jan. 27, 2006, pp. 315-329, 124(2), Elsevier Inc.
Kawahara, Tiara L.A. et al., "SIRT6 Links Histone H3 Lysine 9 Deacetylation to NF-kappaB-dependent Gene Expression and Organismal Life Span," Cell, Jan. 9, 2009, pp. 62-74, 136(1), Elsevier Inc.
Kanfi, Yariv et al., "The sirtuin SIRT6 regulates lifespan in male mice," Nature, Mar. 8, 2012, pp. 218-221, 483 (7388), Macmillan Publishers Limited.
McCord, Ronald A. et al., "SIRT6 stabilizes DNA-dependent protein kinase at chromatin for DNA double-strand break repair," Aging, Jan. 2009, pp. 109-121, 1(1).
Kim, Hyun-Seok et al., "Hepatic-Specific Disruption of SIRT6 in Mice Results in Fatty Liver Formation Due to Enhanced Glycolysis and Triglyceride Synthesis," Cell Metabolism, Sep. 8, 2010, pp. 224-236, 12(3), Elsevier Inc.
Kanfi, Yariv et al., "SIRT6 protects against pathological damage caused by diet-induced obesity," Aging Cell, 2010, pp. 162-173, 9(2), Blackwell Publishing Ltd.
Stohr, R. et al., "ITCH modulates SIRT6 and SREBP2 to influence lipid metabolism and atherosclerosis in ApoE null mice," Scientific Reports, Mar. 17, 2015, pp. 1-8, vol. 5.
Minagawa, Shunsuke et al., "Accelerated epithelial cell senescence in IPF and the inhibitory role of SIRT6 in TGF-β-induced senescence of human bronchial epithelial cells," American Journal of Physiology—Lung Cellular and Molecular Physiology, 2011 [retrieved on Oct. 19, 2021], pp. L391-L401, 300(3), American Physiological Society.
Sundaresan, Nagalingam R., et al., "The sirtuin SIRT6 blocks IGF-Akt signaling and development of cardiac hypertrophy by targeting c-Jun," Nature Medicine, Nov. 2012, pp. 1643-1650, 18(11), Nature America, Inc.
Database Registry [online], Entered STN: May 15, 2015, [retrieval date : Mar. 16, 2020] Registry No. 1705447-81-9, 1705447-80-8, 1705369-78-3, 1705369-71-6, 1705367-06-1, 1705335-76-7, 1705317-92-5, 1705233-75-5, 1705003-44-6; and Database Registry [online], Entered STN: May 17, 2015, [retrieval date : Mar. 16, 2020] CAS Registry No. 1706365-47-0, 1706255-02-8, 1705947-31-4, 1705947-24-5, 1705703-75-8.
You, Weijie et al., "Structural Basis of Sirtuin 6 Activation by Synthetic Small Molecules," Angewandte Chemie International Edition, 2017, pp. 1007-1011, 56(4), Wiley-VCH Verlag Gmbh & Co. KGaA.
Extended European Search Report dated Aug. 29, 2022, issued in corresponding European Application No. 20744530.5, 7 pages.
Office Action dated Oct. 4, 2022, issued in corresponding Canadian Application No. 3,127,532, 5 pages.

\* cited by examiner

UREA COMPOUND HAVING SUBSTITUENT

CROSS-REFERENCES TO RELATED APPLICATIONS

This application is the US national phase of PCT/JP2020/002351, filed Jan. 23, 2020, which is based on Japanese Application No. 2019-010252, filed Jan. 24, 2019, each application expressly incorporated herein by reference in its entirety.

TECHNICAL FIELD

The present invention provides a compound that has a specific chemical structure having an activation effect on SIRT6 or a pharmaceutically acceptable salt thereof.

BACKGROUND ART

Sirtuins are nicotinamide-adenine dinucleotide (NAD)-dependent deacylating enzymes. Sirtuins are highly conserved from prokaryotes to eukaryotes and play an important role in various life phenomena such as DNA repair, energy metabolism control, and aging and lifespan (Non-Patent Document 1).

Calorie restriction has long been known to prolong lifespan and suppress various diseases which are referred to as aging-related diseases (such as metabolic diseases, cancer, cardiac/neurological diseases, and inflammatory diseases). For example, deficiency of sirtuins in model organisms such as yeasts or nematodes results in no extension of lifespan due to calorie restriction, and thus sirtuins are considered to play a central role in the mechanism of calorie restriction (Non-Patent Document 2).

Seven kinds of sirtuins, SIRT1-7, are present in mammals including humans. SIRT1, SIRT6, and SIRT7 are mainly localized in a nucleus, SIRT1 is mainly localized in a nucleoplasm, SIRT6 is mainly localized in a heterochromatin region, and SIRT7 is mainly localized in a nucleolus. SIRT2 is localized in a cytoplasm, and SIRT3-5 are localized in mitochondria (Non-Patent Document 3). SIRT6 has deacylation activity and mono-ADP ribosylation activity. The deacetylation activity of SIRT6 on histone H3K9 has higher substrate specificity than that of SIRT1 that is also localized in the nucleus and acetylation of H3K9 is enhanced in cells that SIRT6 is knocked out, and thus SIRT6 is considered to act as a main deacetylation enzyme (Non-Patent Documents 4 and 5).

SIRT6 knockout mice grow normally until approximately 2 to 3 weeks after birth, but then rapidly develop premature aging-like symptoms such as s decrease in subcutaneous fat, a decrease in bone density, spinal curvature, and a decrease in lymphocytes (Non-Patent Document 6). SIRT6 controls the transcription factor NF-κB, which is involved in inflammatory/immune response, through the deacetylase of H3K9, and in a SIRT6-deficient mouse, expression of inflammatory cytokines by NF-κB is constantly activated so that the mouse is in a chronic inflammatory state. The premature aging-like symptoms of the SIRT6 knockout mice are improved by suppression of NF-κB (Non-Patent Document 7). On the contrary, SIRT6 transgenic mice that highly express SIRT6 are resistant to high-fat diet load (HFD) similar to calorie restriction and thus have an extended lifespan (Non-Patent Document 8).

In recent years, research on sirtuins has progressed dramatically, and it is suggested that SIRT6 in particular has various functions such as an telomere stabilizing effect, a DNA repair effect, an anti-aging effect, an anti-fatty liver effect, an anti-obesity effect, an anti-diabetic effect, an anti-atherosclerosis effect, an anti-idiopathic pulmonary fibrosis (IPF) effect, a cardioprotective effect, and an anti-inflammatory/anti-rheumatic effect (Non-Patent Document 6-14). Based on the description above, a compound that increases the expression level of SIRT6 or enhances the activity of SIRT6 is expected to be a drug that exhibits medical effects on diseases including the above-described diseases.

Further, the following compounds are known as compounds having an inhibitory activity on phosphatidylinositol-3-kinase (Patent Documents 1 and 2).

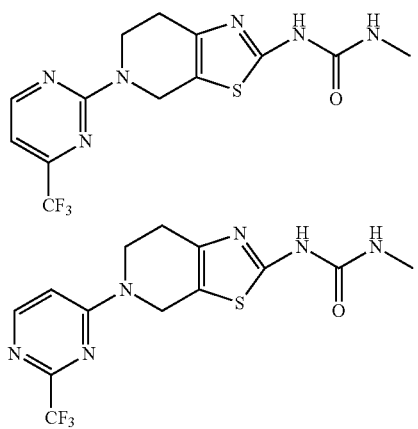

RELATED ART

Patent Document

[Patent Document 1] International Publication No. WO2010/024258

[Patent Document 2] International Publication No. WO2010/125799

Non-Patent Document

[Non-Patent Document 1] Imai S and Guarente L. Ten years of NAD-dependent SIR2 family deacetylases: implications for metabolic diseases. Trends Pharmacol Sci. 2010 31 (5): 212-220.

[Non-Patent Document 2] Guarente L. Calorie restriction and sirtuins revisited. Genes Dev. 2013 27 (19): 2072-2085.

[Non-Patent Document 3] Michishita E, Park J Y, Burneskis J M, et al. Evolutionarily conserved and nonconserved cellular localizations and functions of human SIRT proteins. Mol Biol Cell. 2005 16 (10): 4623-4635.

[Non-Patent Document 4] Michishita E, McCord R A, Berber E, et al. SIRT6 is a histone H3 lysine 9 deacetylase that modulates telomeric chromatin. Nature. 2008 452 (7186): 492-496.

[Non-Patent Document 5] Michishita E, McCord R A, Boxer L D, et al. Cell cycle-dependent deacetylation of telomeric histone H3 lysine K56 by human SIRT6. Cell Cycle. 2009 8 (16): 2664-2666.

[Non-Patent Document 6] Mostoslavsky R, Chua K F, Lombard D B, et al. Genomic instability and aging-like phenotype in the absence of mammalian SIRT6. Cell. 2006 124 (2): 315-329

[Non-Patent Document 7] Kawahara T L, Michishita E, Adler A S, et al. SIRT6 links histone H3 lysine 9 deacetylation to NF-kappaB-dependent gene expression and organismal lifespan. Cell. 2009 136 (1): 62-74.

[Non-Patent Document 8] Kanfi Y, Naiman S, Amir G, et al. The sirtuin SIRT6 regulates lifespan in male mice. Nature. 2012 483 (7388): 218-221

[Non-Patent Document 9] McCord R A, Michishita E, Hong T, et al. SIRT6 stabilizes DNA-dependent protein kinase at chromatin for DNA double-strand break repair. Aging 2009 1 (1): 109-121

[Non-Patent Document 10] Kim H S, Xiao C, Wang R H, et al. Hepatic-specific disruption of SIRT6 in mice results in fatty liver formation due to enhanced glycolysis and triglyceride synthesis. Cell Metab. 2010 12 (3): 224-236

[Non-Patent Document 11] Kanfi Y, Peshti V, Gil R, et al. SIRT6 protects against pathological damage caused by diet-induced obesity. Aging Cell. 2010 9 (2): 162-173.

[Non-Patent Document 12] Stohr R, Mavilio M, Marino A, et al. ITCH modulates SIRT6 and SREBP2 to influence lipid metabolism and atherosclerosis in ApoE null mice. Sci Rep. 2015 Mar. 17; 5: 9023.

[Non-Patent Document 13] Minagawa S, Araya J, Numata T, et al. Accelerated epithelial cell senescence in IPF and the inhibitory role of SIRT6 in TGF-β-induced senescence of human bronchial epithelial cells. Am J Physiol Lung Cell Mol Physiol. 2011 300 (3): L391-401

[Non-Patent Document 14] Sundaresan N R, Vasudevan P, Zhong L, et al. The sirtuin SIRT6 blocks IGF-Akt signaling and development of cardiac hypertrophy by targeting c-Jun. Nat Med. 2012 18 (11): 1643-1650

DISCLOSURE OF INVENTION

Problems to be Solved by the Invention

The present invention provides a compound which has a specific chemical structure having an activation effect on SIRT6 and is useful as an active component for preventing and treating inflammatory diseases, a pharmaceutically acceptable salt thereof, a new production method thereof, and an intermediate thereof. The compound of the present invention and the pharmaceutically acceptable salt thereof are considered to be useful as a new drug because the compound and the salt have characteristics different from those of anti-inflammatory agents of the related art in various aspects.

Means for Solving the Problems

As a result of intensive research on compounds useful as active components for preventing and treating inflammatory diseases and pharmaceutically acceptable salts thereof, the present inventors found the compound of the present invention and the pharmaceutically acceptable salt thereof. That is, the present invention is as described below.

[1]

A compound represented by Formula (1) or a pharmaceutically acceptable salt thereof.

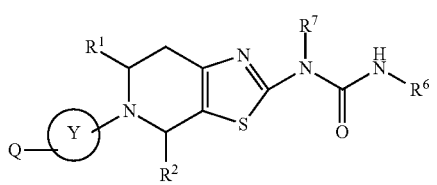

(1)

The symbols in Formula (1) have the following definitions.

$R^1$ and $R^2$ independently represent a hydrogen atom or a C1-C6 alkyl group and may be the same or different from each other, or $R^1$ and $R^2$ bond to each other to form a substituent and the substituent represents any group selected from the following groups.

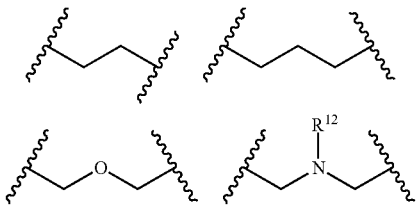

$R^{12}$ represents a C1-C6 alkyl group, a hydroxy C1-C6 alkyl group, a C1-C6 alkylcarbonyl group, or a C1-C6 alkoxycarbonyl group, $R^6$ represents a C1-C6 alkyl group that may be substituted with one or two groups selected from a group G, a C3-C6 cycloalkyl group that may be substituted with one or two groups selected from the group G, or a 4- to 7-membered saturated heterocyclic group that may be substituted with one or two groups selected from the group G, the group G includes a hydroxyl group, a halogen atom, an amino group, an amino C1-C6 alkyl group, a C1-C6 alkylsulfonyl group, a carbamoyl group that may be substituted with one or two groups selected from a group J, a C3-C6 cycloalkyl group that may be substituted with one or two groups selected from the group J, and a 4- to 7-membered saturated heterocyclic group that may be substituted with one or two groups selected from the group J, the group J includes an amino C1-C6 alkyl group, an amino group, and a C1-C6 alkyl group, and $R^7$ represents a hydrogen atom, or $R^6$ and $R^7$ bond to each other to form a substituent and the substituent represents a group shown below.

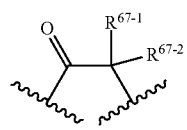

The above group is oriented in either a rightward or leftward direction.

$R^{67-1}$ and $R^{67-2}$ independently represent a hydrogen atom, a C1-C6 alkyl group, a hydroxy C1-C6 alkyl group, a C1-C4 alkylene group, or a C1-C6 alkoxy C1-C6 alkyl group and may be the same or different from each other, and Q represents a halogen atom, a C1-C6 alkyl group that is substituted with any of one to three groups selected from $R^{Q3}$, a C3-C6 cycloalkyl group that is substituted with any of one to three groups selected from $R^{Q3}$, a 4- to 7-membered saturated heterocyclic group that is substituted with any of one to three groups selected from $R^{Q3}$, an amino group that is substituted with any of one to three groups selected from $R^{Q3}$, or any group selected from the following groups.

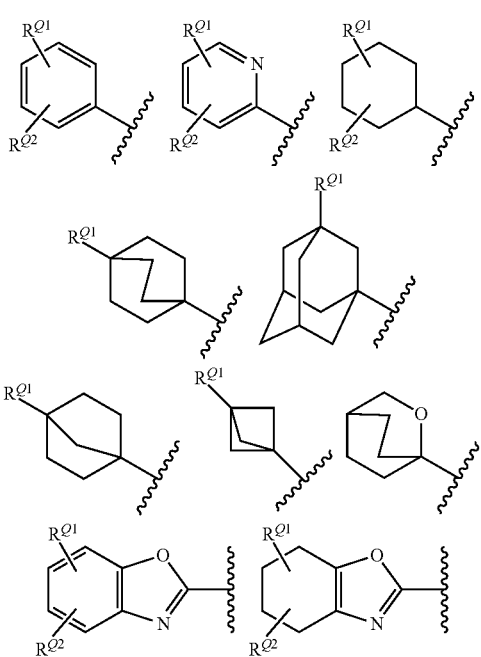

$R^{Q1}$ represents a halogen atom, a cyano group, a C1-C6 alkyl group, a C1-C6 alkoxy group, a halo-C1-C6 alkyl group, a halo-C1-C6 alkoxy group, a C3-C6 cycloalkylcarbonyl group, a C1-C6 alkylcarbamoyl group, a C1-C6 alkylsulfonyl group, or a mono(C1-C6 alkyl)aminosulfonyl group, and $R^{Q2}$ represents a hydrogen atom, a hydroxyl group, or a halogen atom, or $R^{Q1}$ and $R^{Q2}$ bond to each other to form a substituent and the substituent represents a group shown below.

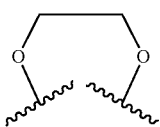

$R^{Q3}$ represents a halogen atom, a C1-C6 alkoxy group, a halo-C1-C6 alkyl group, a halo-C1-C6 alkoxy group, a C3-C6 cycloalkoxy group, a phenoxy group, a benzyloxy group, a C1-C6 alkylcarbamoyl group, or a C1-C4 alkylene group that may be substituted with a halogen group, and Y represents any group selected from the following groups or a single bond.

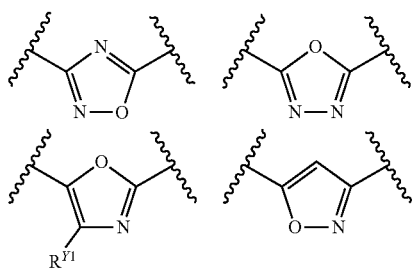

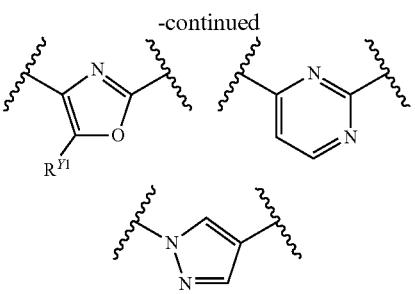

The above groups are oriented in either a rightward or leftward direction.

$R^{Y1}$ represents a hydrogen atom or a C1-C6 alkyl group.

The following compounds or pharmaceutically acceptable salts thereof are excluded.

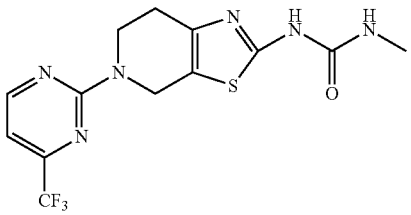

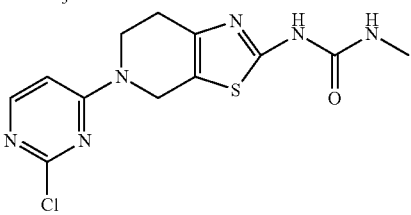

[2]

The compound or the pharmaceutically acceptable salt thereof according to [1], in which $R^1$ and $R^2$ represent a hydrogen atom, or $R^1$ and $R^2$ bond to each other to form a substituent and the substituent represents any group selected from the following groups.

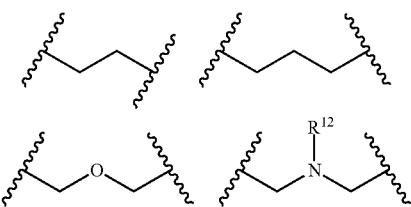

$R^{12}$ represents a methyl group, a hydroxyethyl group, an acetyl group, or a methoxycarbonyl group.

[3]

The compound or the pharmaceutically acceptable salt thereof according to [1] or [2], in which $R^6$ represents any group selected from the following groups:

a C1-C6 alkyl group;

a hydroxy C1-C6 alkyl group;

a hydroxy C3-C6 cycloalkyl group;

a tetrahydrofuranyl group; and a 2-oxopyrrolidin-3-yl group.

[4]
The compound or the pharmaceutically acceptable salt thereof according to [1] or [2], in which $R^6$ represents any group selected from the following groups:
 a methyl group;
 a hydroxypropyl group;
 a 2-hydroxy-2-methylpropyl group;
 a hydroxycyclobutyl group; and
 a tetrahydrofuranyl group.

[5]
The compound or the pharmaceutically acceptable salt thereof according to [1] or [2], in which $R^6$ and $R^7$ bond to each other to form a substituent and the substituent represents any group selected from the following groups.

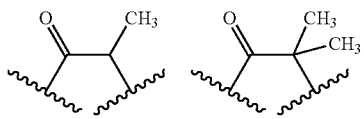

The above groups are oriented in either a rightward or leftward direction.

[6]
The compound or the pharmaceutically acceptable salt thereof according to any one of [1] to [5], in which Q represents any group selected from the following groups.

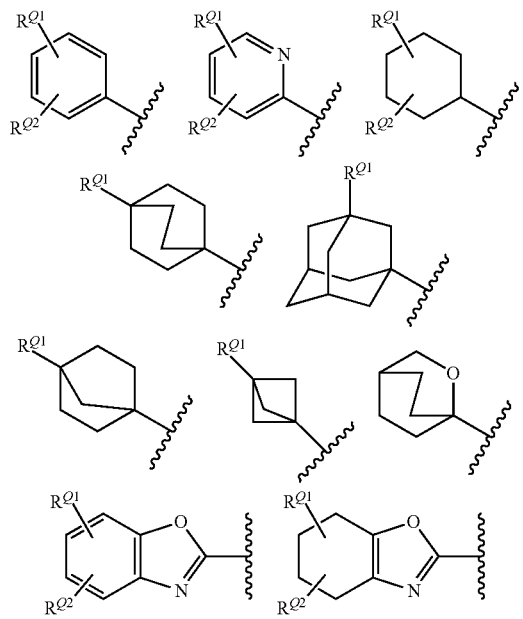

$R^{Q1}$ represents any group selected from the following groups:
 a halogen atom;
 a C1-C6 alkyl group;
 a C1-C6 alkoxy group;
 a halo-C1-C6 alkyl group; and
 a halo-C1-C6 alkoxy group,
 and $R^{Q2}$ represents any group selected from the following groups:
 a hydrogen atom;
 a hydroxyl group; and
 a fluorine atom.

[7]
The compound or the pharmaceutically acceptable salt thereof according to any one of [1] to [5], in which Q represents any group selected from the following groups.

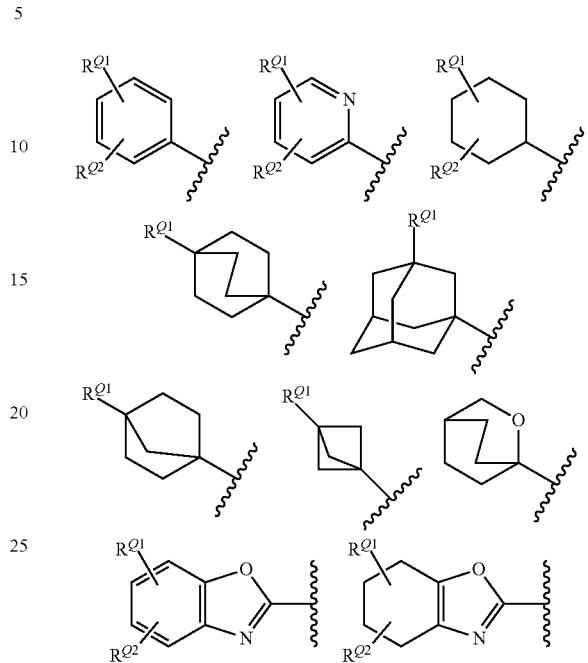

$R^{Q1}$ represents any group selected from the following groups:
 a fluorine atom;
 a chlorine atom;
 a methyl group;
 a methoxy group;
 a difluoromethyl group;
 a trifluoromethyl group;
 a difluoromethoxy group; and
 a trifluoromethoxy group,
 and $R^{Q2}$ represents any group selected from the following groups:
 a hydrogen atom;
 a hydroxyl group; and
 a fluorine atom.

[8]
The compound or the pharmaceutically acceptable salt thereof according to any one of [1] to [5], in which Q represents any group selected from the following groups:
 a C3-C6 cycloalkyl group that is substituted with any of one to three groups selected from $R^{Q3}$; and
 a 4- to 7-membered saturated heterocyclic group that is substituted with any of one to three groups selected from $R^{Q3}$, and
 $R^{Q3}$ represents any group selected from the following groups:
 a fluorine atom;
 a chlorine atom;
 a methoxy group;
 a difluoromethyl group;
 a trifluoromethyl group;
 a difluoromethoxy group;
 a trifluoromethoxy group; and
 an ethylene group.

[9]
The compound or the pharmaceutically acceptable salt thereof according to any one of [1] to [5], in which Q represents any group selected from the following groups:
a halogen atom;
a halo-C1-C6 alkyl group;
a halo-C1-C6 alkoxy C1-C6 alkyl group; and
a C1-C6 alkoxy C1-C6 alkyl group.

[10]
The compound or the pharmaceutically acceptable salt thereof according to any one of [1] to [5], in which Q represents any group selected from the following groups:
a fluorine atom;
a trifluoromethyl group;
a trifluoroethoxyethyl group; and
an ethoxyethyl group.

[11]
The compound or the pharmaceutically acceptable salt thereof according to any one of [1] to [10], in which Y represents any group selected from the following groups.

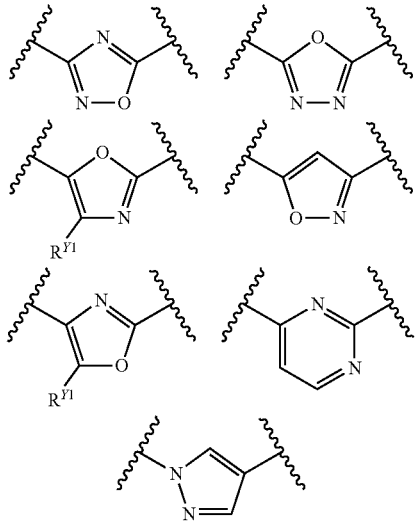

The above groups are oriented in either a rightward or leftward direction, and
$R^{Y1}$ represents a hydrogen atom or a methyl group.

The compound or the pharmaceutically acceptable salt thereof according to [1], in which the compound is selected from N-{5-[3-(4,4-difluorocyclohexyl)-1,2,4-oxadiazol-5-yl]-4,5,6,7-tetrahydro[1,3]thiazolo[5,4-c]pyridin-2-yl}-N'-methylurea, N-methyl-N'-{5-[5-(trifluoromethyl)-1,3,4-oxazol-2-yl]-4,5,6,7-tetrahydro[1,3]thiazolo[5,4-c]pyridin-2-yl}urea, N-(5-{5-[(1R)-1-ethoxyethyl]-1,3,4-oxadiazol-2-yl}-4,5,6,7-tetrahydro[1,3]thiazolo[5,4-c]pyridin-2-yl)-N'-methylurea, N-methyl-N'-(5-{3-[1-(2,2,2-trifluoroethoxy)ethyl]-1,2,4-oxadiazol-5-yl}-4,5,6,7-tetrahydro[1,3]thiazolo[5,4-c]pyridin-2-yl)urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(2R)-1-hydroxypropan-2-yl]urea, N-methyl-N'-(10-{3-[cis-4-(trifluoromethyl)cyclohexyl]-1,2,4-oxadiazol-5-yl}-4,7,8,9-tetrahydro-5H-4,8-epiminooxocino[5,4-d][1,3]thiazol-2-yl)urea, N-{(4S,8S)-10-[3-(4,4-difluorocyclohexyl)-1,2,4-oxadiazol-5-yl]-4,7,8,9-tetrahydro-5H-4,8-epiminooxocino[5,4-d][1,3]thiazol-2-yl}-N'-methylurea, N-methyl-N'-(5-{3-[3-(trifluoromethoxy)phenyl]-1,2,4-oxadiazol-5-yl}-4,5,6,7-tetrahydro[1,3]thiazolo[5,4-c]pyridin-2-yl)urea, N-{5-[5-(4-fluoro-3-methylphenyl)-1,3,4-oxazol-2-yl]-4,5,6,7-tetrahydro{[1,3]thiazolo[5,4-c]pyridin-2-yl}-N'-methylurea, N-{(5R*,8S*)-9-[3-(4-fluorophenyl)-1,2,4-oxadiazol-5-yl]-5,6,7,8-tetrahydro-4H-5,8-epiminocyclohepta[d][1,3]thiazol-2-yl}-N'-methylurea, N-{9-[5-(4-fluorophenyl)-1,2-oxazol-3-yl]-5,6,7,8-tetrahydro-4H-5,8-epiminocyclohepta[d][1,3]thiazol-2-yl}-N'-methylurea, N-{(5R*,9S*)-10-[3-(4-fluorophenyl)-1,2,4-oxadiazol-5-yl]-4,5,6,7,8,9-hexahydro-5,9-epiminocyclooocta[d][1,3]thiazol-2-yl}-N'-methylurea, N-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-methylurea, N-(10-{5-[3-(difluoromethyl)phenyl]-1,3-oxazol-2-yl}-4,7,8,9-tetrahydro-5H-4,8-epiminooxocino[5,4-d][1,3]thiazol-2-yl)-N'-methylurea, N-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}-N'-methylurea, N-{10-[5-(4-fluorophenyl)-1,2-oxazol-3-yl]-4,7,8,9-tetrahydro-5H-4,8-epiminooxocino[5,4-d][1,3]thiazol-2-yl}-N'-methylurea, N-{(4S,8S)-10-[4-(4-fluorophenyl)-1,3-oxazol-2-yl]-4,7,8,9-tetrahydro-5H-4,8-epiminooxocino[5,4-d][1,3]thiazol-2-yl}-N'-methylurea, N-{10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-[(2R)-1-hydroxypropan-2-yl]urea, N-{6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-methylurea, and (5R)-3-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}-5-methylimidazolidin-2,4-dione.

[13]
A SIRT6 activator comprising the compound or the pharmaceutically acceptable salt thereof according to any one of [1] to [12] as an active component.

[14]
A pharmaceutical composition comprising the compound or the pharmaceutically acceptable salt thereof according to any one of [1] to [12] as an active component.

[15]
The pharmaceutical composition according to [14], in which the pharmaceutical composition is an oral preparation.

[16]
The pharmaceutical composition according to [14] or [15] for treating and/or preventing a peripheral inflammatory disease.

[17]
The compound or the pharmaceutically acceptable salt thereof according to any one of [1] to [12] for use in treating and/or preventing a peripheral inflammatory disease.

The pharmaceutical composition according to [16], in which the peripheral inflammatory disease is any one selected from the group consisting of rheumatoid arthritis, systemic lupus erythematosus, scleroderma, bronchial asthma, asthmatic bronchitis, diffuse interstitial pneumonia, chronic obstructive pulmonary disease, ulcerative colitis, Crohn's disease, acute hepatitis, chronic hepatitis, fulminant hepatitis, autoimmune hepatitis, primary biliary cirrhosis, primary sclerosing cholangitis, alcoholic hepatitis, non-alcoholic steatohepatitis, hepatic cirrhosis, peripheral neuritis, ankylosing spondylitis, acute eczema, subacute eczema, chronic eczema, contact dermatitis, solar dermatitis due to sunlight and/or ultraviolet rays, radiation dermatitis, atopic dermatitis, seborrheic dermatitis, psoriasis vulgaris, psoriasis arthropica, psoriatic erythroderma, pustular psoriasis, lichen planus, erythema, rosacea, urticaria, alopetia areata, pemphigus, erythroderma, acne vulgaris, decubitus, wounds, burns, conjunctivitis, keratitis, scleritis, acute/chronic otitis media, perennial allergic rhinitis, pollinosis, sinusitis, laryngitis, esophagitis, refractory stomatitis, glossitis, acute/chronic sialadenitis, angular stomatitis, cheilitis, Behcet's disease, multiple sclerosis, type I diabetes, type II diabetes, atherosclerosis, pancreatitis, and chronic heart failure.

[19]

The pharmaceutical composition according to [16], in which the peripheral inflammatory disease is any one selected from the group consisting of rheumatoid arthritis, systemic lupus erythematosus, scleroderma, bronchial asthma, acute hepatitis, autoimmune hepatitis, primary biliary cirrhosis, primary sclerosing cholangitis, alcoholic hepatitis, non-alcoholic steatohepatitis, ankylosing spondylitis, contact dermatitis, solar dermatitis due to sunlight and/or ultraviolet rays, radiation dermatitis, atopic dermatitis, seborrheic dermatitis, psoriasis vulgaris, psoriasis arthropica, psoriatic erythroderma, pustular psoriasis, lichen planus, erythema, rosacea, urticaria, alopetia areata, pemphigus, erythroderma, acne vulgaris, decubitus, wounds, burns, sinusitis, laryngitis, esophagitis, refractory stomatitis, glossitis, acute/chronic sialadenitis, angular stomatitis, cheilitis, and Behcet's disease.

[20]

The pharmaceutical composition according to [16], in which the peripheral inflammatory disease is any one selected from the group consisting of rheumatoid arthritis, systemic lupus erythematosus, alcoholic hepatitis, non-alcoholic steatohepatitis, contact dermatitis, solar dermatitis due to sunlight and/or ultraviolet rays, radiation dermatitis, atopic dermatitis, seborrheic dermatitis, psoriasis vulgaris, psoriasis arthropica, psoriatic erythroderma, pustular psoriasis, lichen planus, erythema, rosacea, urticaria, alopetia areata, pemphigus, erythroderma, acne vulgaris, decubitus, wounds, burns, refractory stomatitis, glossitis, and Behcet's disease.

[21]

A method for treating and/or preventing a peripheral inflammatory disease, the method including: administering an effective dose of the pharmaceutical composition according to [14] or [15].

The present invention includes the following other aspects [1A] to [32A].

[1A] A compound represented by Formula (1) or a pharmaceutically acceptable salt thereof.

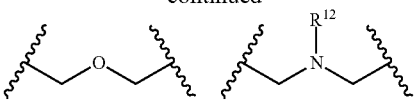

(1)

The symbols in Formula (1) have the following definitions.

$R^1$ and $R^2$ independently represent a hydrogen atom or a C1-C6 alkyl group and may be the same or different from each other, or $R^1$ and $R^2$ bond to each other to form a substituent and the substituent represents any group selected from the following groups.

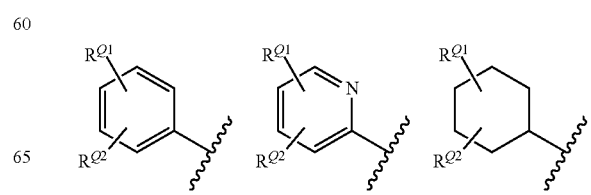

-continued

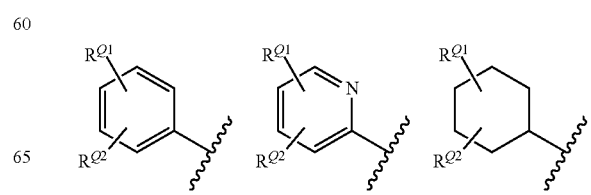

$R^{12}$ represents a C1-C6 alkyl group, a hydroxy C1-C6 alkyl group, a C1-C6 alkylcarbonyl group, a C1-C6 alkoxycarbonyl group, or a C1-C6 alkylsulfonyl group, $R^3$ represents a hydrogen atom or a C1-C6 alkyl group, $R^6$ represents a C1-C6 alkyl group that may be substituted with one to three groups selected from a group G, a C3-C6 cycloalkyl group that may be substituted with one or two groups selected from the group G, or a 4- to 7-membered heterocyclic group that may be substituted with one or two groups selected from the group G, the group G includes a hydroxyl group, a halogen atom, an amino group, a halo-C1-C6 alkyl group, a hydroxy C1-C6 alkyl group, an amino C1-C6 alkyl group, a C1-C6 alkoxy group, a C1-C6 alkylsulfonyl group, a hydroxy C1-C6 alkoxy group, a C1-C6 alkylcarbonyl group, a carbamoyl group that may be substituted with one or two groups selected from a group J, a C3-C6 cycloalkyl group that may be substituted with one or two groups selected from the group J, a 4- to 7-membered heterocyclic group that may be substituted with one or two groups selected from the group J, or a 5- to 6-membered heteroaryl group that may be substituted with one or two groups selected from the group J, the group J includes a hydroxyl group, an oxo group, an amino C1-C6 alkyl group, an amino group, a C1-C6 alkyl group, and a C1-C6 alkylcarbonyl group, $R^7$ represents a hydrogen atom, or $R^6$ and $R^7$ bond to each other to form a substituent and the substituent represents a group shown below.

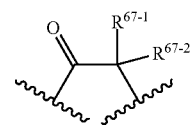

The group is oriented in either a rightward or leftward direction.

$R^{67-1}$ and $R^{67-2}$ independently represent a hydrogen atom, a C1-C6 alkyl group, a hydroxy C1-C6 alkyl group, a C1-C4 alkylene group, or a C1-C6 alkoxy C1-C6 alkyl group and may be the same or different from each other, Q represents a halogen atom, a C1-C6 alkyl group that is substituted with any of one to three groups selected from $R^{Q3}$, a C3-C6 cycloalkyl group that is substituted with any of one to three groups selected from $R^{Q3}$, a 4- to 7-membered saturated heterocyclic group that is substituted with any of one to three groups selected from $R^{Q3}$, an amino group that is substituted with any of one or two groups selected from $R^{Q3}$, or any group selected from the following groups.

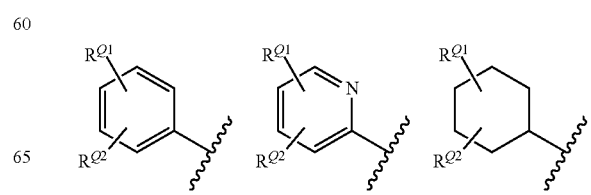

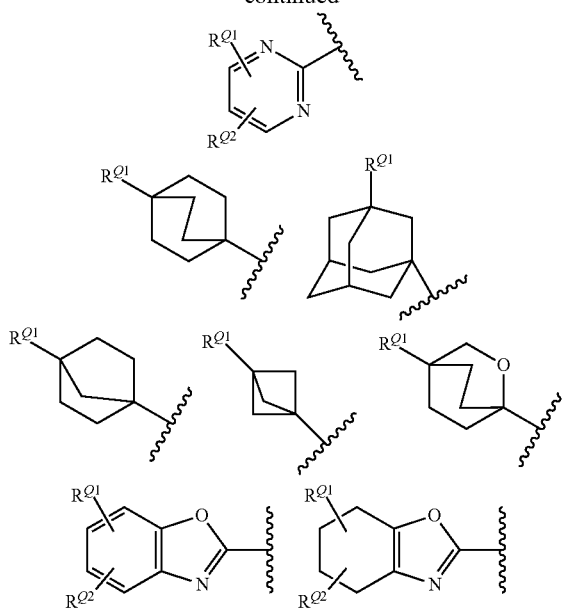
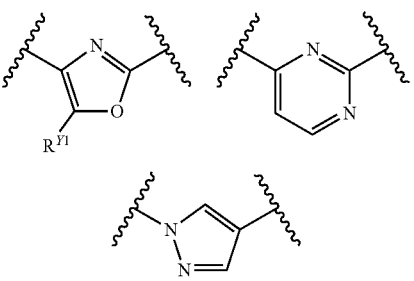

$R^{Q1}$ represents a halogen atom, a cyano group, a C1-C6 alkyl group, a C1-C6 alkoxy group, a halo-C1-C6 alkyl group, a halo-C1-C6 alkoxy group, a C3-C6 cycloalkylcarbonyl group, a C1-C6 alkylcarbamoyl group, a C1-C6 alkylsulfonyl group, a mono(C1-C6 alkyl)amino group, a di(C1-C6 alkyl)amino group, a mono(C1-C6 alkyl)aminosulfonyl group, or a tetrahydropyranyl group, $R^{Q2}$ represents a hydrogen atom, a hydroxyl group, a C1-C6 alkyl group, or a halogen atom, or $R^{Q1}$ and $R^{Q2}$ bond to each other to form a substituent and the substituent represents a group shown below.

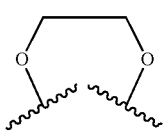

$R^{Q3}$ represents a halogen atom, a C1-C6 alkoxy group, a halo-C1-C6 alkyl group, a halo-C1-C6 alkoxy group, a C3-C6 cycloalkoxy group, a phenoxy group, a benzyloxy group, a C1-C6 alkylcarbamoyl group, or a C1-C4 alkylene group that may be substituted with a halogen group, and Y represents any group selected from the following groups or a single bond.

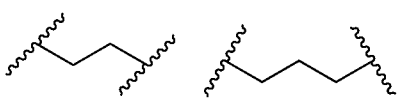

The groups are oriented in either a rightward or leftward direction.

$R^{Y1}$ represents a hydrogen atom or a C1-C6 alkyl group, where the following compounds or pharmaceutically acceptable salts thereof are excluded.

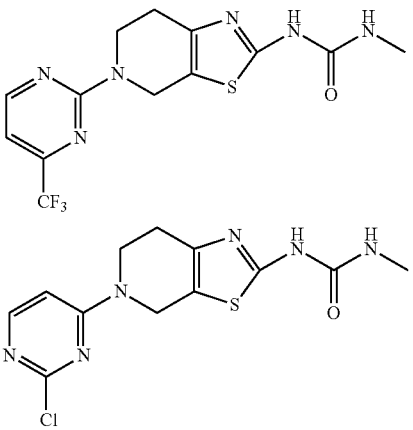

[2A] The compound or the pharmaceutically acceptable salt thereof according to [1A], in which both $R^1$ and $R^2$ represent a hydrogen atom, or $R^1$ and $R^2$ bond to each other to form a substituent and the substituent represents any group selected from the following groups.

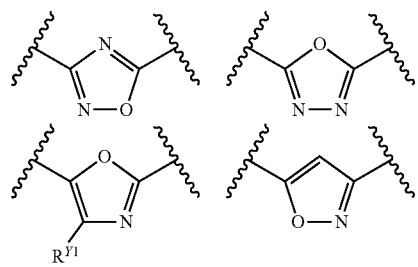

$R^{12}$ represents a methyl group, a hydroxyethyl group, an acetyl group, a methoxycarbonyl group, or a methanesulfonyl group, and $R^3$ represents a hydrogen atom or a methyl group.

[3A] The compound or the pharmaceutically acceptable salt thereof according to [1A], in which both $R^1$ and $R^2$ represent a hydrogen atom, or $R^1$ and $R^2$ bond to each other to form a substituent and the substituent represents any group selected from the following groups.

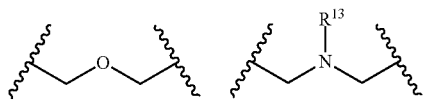

R[13] represents an acetyl group or a methoxycarbonyl group, and

R[3] represents a hydrogen atom.

[4A] The compound or the pharmaceutically acceptable salt thereof according to [1A], in which both R[1] and R[3] represent a methyl group, and R[2] represents a hydrogen atom.

[5A] The compound or the pharmaceutically acceptable salt thereof according to any one of [1A] to [4A], in which R[6] represents any group selected from a C1-C6 alkyl group, a hydroxy C1-C6 alkyl group, a hydroxy C3-C6 cycloalkyl group, a C1-C6 alkoxy C1-C6 alkyl group, a tetrahydrofuranyl group, a tetrahydropyranyl group, and a dioxanylmethyl group, and R[7] represents a hydrogen atom.

[6A] The compound or the pharmaceutically acceptable salt thereof according to any one of [1A] to [4A], in which R[6] represents any group selected from a methyl group, an isobutyl group, a 2-hydroxy-1-methylethyl group, a 2-hydroxy-2-methylpropyl group, a 3-hydroxybutyl group, a 2-hydroxycyclopentyl group, a 4-hydroxycyclohexyl group, a 2-methoxypropyl group, a 3-tetrahydrofuranyl group, a 4-tetrahydropyranyl group, and a 1,4-dioxan-2-ylmethyl group, and R[7] represents a hydrogen atom.

[7A] The compound or the pharmaceutically acceptable salt thereof according to any one of [1A] to [6A], in which Q represents any group selected from a C3-C6 cycloalkyl group that is substituted with any of one to three groups selected from R[Q4], a phenyl group that is substituted with any of one to three groups selected from R[Q4], a pyridyl group that is substituted with any of one to three groups selected from R[Q4], and a 1,3-benzoxazol-2-yl group that is substituted any of one to three groups selected from R[Q4], and R[Q4] represents a halogen atom, a cyano group, a C1-C6 alkyl group, a C1-C6 alkoxy group, a halo-C1-C6 alkyl group, a halo-C1-C6 alkoxy group, a C1-C6 alkylsulfonyl group, a di-C1-C6 alkylamino group, or a C3-C6 cycloalkylcarbonyl group.

[8A] The compound or the pharmaceutically acceptable salt thereof according to any one of [1A] to [6A], in which Q represents any group selected from a cyclohexyl group that is substituted with two fluorine atoms, a phenyl group that is substituted with a fluorine atom or a cyclopropylcarbonyl group, a pyridyl group that is substituted with one group selected from the group consisting of a methoxy group, an ethoxy group, and a difluoromethoxy group, and a 1,3-benzoxazol-2-yl group that is substituted with one or two groups independently selected from the group consisting of a fluorine atom, a methyl group, a methoxy group, an ethoxy group, a dimethylamino group, and a methanesulfonyl group.

[9A] The compound or the pharmaceutically acceptable salt thereof according to any one of [1A] to [8A], in which Y represents a single bond or any group selected from the following groups.

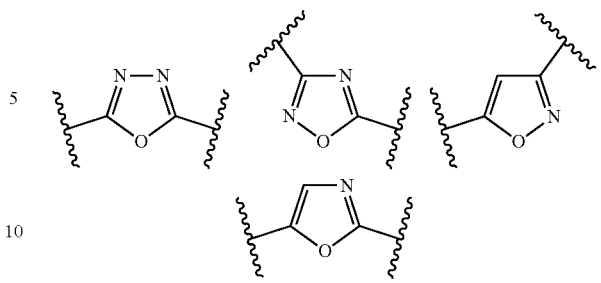

The groups are oriented in either a rightward or leftward direction.

[10A] The compound or the pharmaceutically acceptable salt thereof according to any one of [1A] to [6A], in which Q represents a 1,3-benzoxazol-2-yl group that is substituted with one or two groups independently selected from the group consisting of a fluorine atom, a methyl group, a methoxy group, an ethoxy group, a dimethylamino group, and a methanesulfonyl group, and Y represents a single bond.

[11A] The compound or the pharmaceutically acceptable salt thereof according to any one of [1A] to [6A], in which Q represents a cyclohexyl group that is substituted with two fluorine atoms, a phenyl group that is substituted with a fluorine atom or a cyclopropylcarbonyl group, or a pyridyl group that is substituted with one group selected from the group consisting of a methoxy group, an ethoxy group, and a difluoromethoxy group, and Y represents any group selected from the following groups.

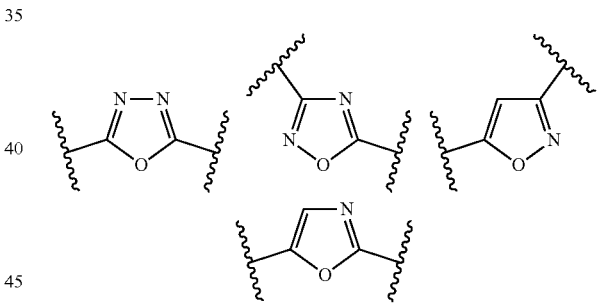

[12A] The compound or the pharmaceutically acceptable salt thereof according to [1A], in which the compound is selected from N-[(4S,8S)-10-{5-[3-(cyclopropanecarbonyl)phenyl]-1,3,4-oxadiazol-2-yl}-4,7,8,9-tetrahydro-5H-4,8-epiminooxocino[5,4-d][1,3]thiazol-2-yl]-N'-methylurea, (−)-N-{(4R*,8R*)-6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-methylurea, (−)-methyl(4R*,8R*)-10-[3-(4-fluorophenyl)-1,2,4-oxadiazol-5-yl]-2-[(methylcarbamoyl)amino]-4,7,8,9-tetrahydro-4,8-epimino[1,3]thiazolo[5,4-d]azocin-6(5H)-carboxylate, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1R,2R)-2-hydroxycyclopentyl]urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1r,4r)-4-hydroxycyclohexyl]urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-(3-methoxypropyl)urea, N-{[(2S)-1,4-dioxan-2-yl]methyl}-N'-{(4S,8S)-10-[3-(4-fluorophenyl)-1,2,4-oxadiazol-5-yl]-4,7,8,9- tetrahydro-5H-4,8-epiminooxocino[5,4-d][1,3]thiazol-2-yl}urea, N-[(2R)-1-hydroxypropan-2-yl]-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea, N-[(4S,8S)-10-(5-fluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea, N-[(4S,8S)-10-(5-ethoxy-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea, N-{(4S,8S)-10-[5-(dimethylamino)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea, N-[(4S,8S)-10-(5,6-difluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea, N-{(4S,8S)-10-[5-(methanesulfonyl)-1,3-benzoxazol-2-yl]-4,7,8,9-tetrahydro-5H-4,8-epiminooxocino[5,4-d][1,3]thiazol-2-yl}-N'-(2-methylpropyl)urea, N-(2-hydroxy-2-methylpropyl)-N'-[(4S,8S)-10-(5-methoxy-6-methyl-1,3-benzoxazol-2-yl)-4,7,8,9-tetrahydro-5H-4,8-epiminooxocino[5,4-d][1,3]thiazol-2-yl]urea, N-[(4S,8S)-10-(5-methoxy-6-methyl-1,3-benzoxazol-2-yl)-4,7,8,9-tetrahydro-5H-4,8-epiminooxocino[5,4-d][1,3]thiazol-2-yl]-N'-[(3R)-oxolan-3-yl]urea, N-(2-hydroxy-2-methylpropyl)-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea, N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-[(3R)-oxolan-3-yl]urea, N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-methylurea, N-methyl-N'-[(4S,8S)-10-(5-methyl-1,3-benzoxazol-2-yl)-4,7,8,9-tetrahydro-5H-4,8-epiminooxocino[5,4-d][1,3]thiazol-2-yl]urea, N-(2-hydroxy-2-methylpropyl)-N'-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]urea, N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(1s,4s)-4-hydroxycyclohexyl]urea, N-{(4S,8S)-10-[5-(6-methoxypyridin-2-yl)-1,2-oxazol-3-yl]-4,7,8,9-tetrahydro-5H-4,8-epiminooxocino[5,4-d][1,3]thiazol-2-yl}-N'-oxan-4-ylurea, N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(2R)-1-hydroxypropan-2-yl]urea, N-[(2R)-1-hydroxypropan-2-yl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea, N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-[(2R)-1-hydroxypropan-2-yl]urea, N-[(2R)-1-hydroxypropan-2-yl]-N'-{5-[5-(methanesulfonyl)-1,3-benzoxazol-2-yl]-6,6-dimethyl-4,5,6,7-tetrahydro[1,3]thiazolo[5,4-c]pyridin-2-yl}urea, N-(2-hydroxy-2-methylpropyl)-N'-{5-[5-(methanesulfonyl)-1,3-benzoxazol-2-yl]-6,6-dimethyl-4,5,6,7-tetrahydro[1,3]thiazolo[5,4-c]pyridin-2-yl}urea, N-[(2R)-1-hydroxypropan-2-yl]-N'-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]urea, N-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]-N'-[(3R)-oxolan-3-yl]urea, N-[(1r,3S)-3-hydroxycyclobutyl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea, N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-(2-hydroxy-2-methylpropyl)urea, N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-[(1r,3S)-3-hydroxycyclobutyl]urea, and N-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}-N'-oxan-4-ylurea.

[12A-1] N-[(4S,8S)-10-{5-[3-(cyclopropanecarbonyl)phenyl]-1,3,4-oxadiazol-2-yl}-4,7,8,9-tetrahydro-5H-4,8-epiminooxocino[5,4-d][1,3]thiazol-2-yl]-N'-methylurea or a pharmaceutically acceptable salt thereof.

[12A-2] (−)-N-{(4R*,8R*)-6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-methylurea or a pharmaceutically acceptable salt thereof.

[12A-3] (−)-Methyl(4R*,8R*)-10-[3-(4-fluorophenyl)-1,2,4-oxadiazol-5-yl]-2-[(methylcarbamoyl)amino]-4,7,8,9-tetrahydro-4,8-epimino[1,3]thiazolo[5,4-d]azocin-6(5H)-carboxylate or a pharmaceutically acceptable salt thereof.

[12A-4] N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1R,2R)-2-hydroxycyclopentyl]urea or a pharmaceutically acceptable salt thereof.

[12A-5] N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1r,4r)-4-hydroxycyclohexyl]urea or a pharmaceutically acceptable salt thereof.

[12A-6] N-{5-[3-(4,4-difluorocyclohexyl)-1,2,4-oxadiazol-5-yl]-4,5,6,7-tetrahydro[1,3]thiazolo[5,4-c]pyridin-2-yl}-N'-(3-methoxypropyl)urea or a pharmaceutically acceptable salt thereof.

[12A-7] N-{[(2S)-1,4-dioxan-2-yl]methyl}-N'-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}urea or a pharmaceutically acceptable salt thereof.

[12A-8] N-[(2R)-1-hydroxypropan-2-yl]-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea or a pharmaceutically acceptable salt thereof.

[12A-9] N-[(4S,8S)-10-(5-fluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea or a pharmaceutically acceptable salt thereof.

[12A-10] N-[(4S,8S)-10-(5-ethoxy-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea or a pharmaceutically acceptable salt thereof.

[12A-11] N-{(4S,8S)-10-[5-(dimethylamino)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea or a pharmaceutically acceptable salt thereof.

[12A-12] N-[(4S,8S)-10-(5,6-difluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea or a pharmaceutically acceptable salt thereof.

[12A-13] N-{(4S,8S)-10-[5-(methanesulfonyl)-1,3-benzoxazol-2-yl]-4,7,8,9-tetrahydro-5H-4,8-epiminooxocino[5,4-d][1,3]thiazol-2-yl}-N'-(2-methylpropyl)urea or a pharmaceutically acceptable salt thereof.

[12A-14] N-(2-hydroxy-2-methylpropyl)-N'-[(4S,8S)-10-(5-methoxy-6-methyl-1,3-benzoxazol-2-yl)-4,7,8,9-tetrahydro-5H-4,8-epiminooxocino[5,4-d][1,3]thiazol-2-yl]urea or a pharmaceutically acceptable salt thereof.

[12A-15] N-[(4S,8S)-10-(5-methoxy-6-methyl-1,3-benzoxazol-2-yl)-4,7,8,9-tetrahydro-5H-4,8-epiminooxocino[5, 4-d][1,3]thiazol-2-yl]-N'-[(3R)-oxolan-3-yl]urea or a pharmaceutically acceptable salt thereof.

[12A-16] N-(2-hydroxy-2-methylpropyl)-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea or a pharmaceutically acceptable salt thereof.

[12A-17] N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-[(3R)-oxolan-3-yl]urea or a pharmaceutically acceptable salt thereof.

[12A-18] N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-methylurea or a pharmaceutically acceptable salt thereof.

[12A-19] N-methyl-N'-[(4S,8S)-10-(5-methyl-1,3-benzoxazol-2-yl)-4,7,8,9-tetrahydro-5H-4,8-epiminooxocino[5,4-d][1,3]thiazol-2-yl]urea or a pharmaceutically acceptable salt thereof.

[12A-20] N-(2-hydroxy-2-methylpropyl)-N'-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]urea or a pharmaceutically acceptable salt thereof.

[12A-21] N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(1s,4s)-4-hydroxycyclohexyl]urea or a pharmaceutically acceptable salt thereof.

[12A-22] N-{(4S,8S)-10-[5-(6-methoxypyridin-2-yl)-1,2-oxazol-3-yl]-4,7,8,9-tetrahydro-5H-4,8-epiminooxocino[5,4-d][1,3]thiazol-2-yl}-N'-oxan-4-ylurea or a pharmaceutically acceptable salt thereof.

[12A-23] N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(2R)-1-hydroxypropan-2-yl]urea or a pharmaceutically acceptable salt thereof.

[12A-24] N-[(2R)-1-hydroxypropan-2-yl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea or a pharmaceutically acceptable salt thereof.

[12A-25] N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-[(2R)-1-hydroxypropan-2-yl]urea or a pharmaceutically acceptable salt thereof.

[12A-26] N-[(2R)-1-hydroxypropan-2-yl]-N'-{5-[5-(methanesulfonyl)-1,3-benzoxazol-2-yl]-6,6-dimethyl-4,5,6,7-tetrahydro[1,3]thiazolo[5,4-c]pyridin-2-yl}urea or a pharmaceutically acceptable salt thereof.

[12A-27] N-(2-hydroxy-2-methylpropyl)-N'-{5-[5-(methanesulfonyl)-1,3-benzoxazol-2-yl]-6,6-dimethyl-4,5,6,7-tetrahydro[1,3]thiazolo[5,4-c]pyridin-2-yl}urea or a pharmaceutically acceptable salt thereof.

[12A-28] N-[(2R)-1-hydroxypropan-2-yl]-N'-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]urea or a pharmaceutically acceptable salt thereof.

[12A-29] N-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]-N'-[(3R)-oxolan-3-yl]urea or a pharmaceutically acceptable salt thereof.

[12A-30] N-[(1r,3S)-3-hydroxycyclobutyl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea or a pharmaceutically acceptable salt thereof.

[12A-31] N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-(2-hydroxy-2-methylpropyl)urea or a pharmaceutically acceptable salt thereof.

[12A-32] N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-[(1r,3S)-3-hydroxycyclobutyl]urea or a pharmaceutically acceptable salt thereof.

[12A-33] N-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}-N'-oxan-4-ylurea or a pharmaceutically acceptable salt thereof.

[13A] A SIRT6 activator containing: the compound or the pharmaceutically acceptable salt thereof according to any one of [1A] to [12A] as an active component.

[14A] A pharmaceutical composition containing: the compound or the pharmaceutically acceptable salt thereof according to any one of [1A] to [12A] as an active component.

[15A] The pharmaceutical composition according to [14A], in which the pharmaceutical composition is an oral preparation.

[16A] The pharmaceutical composition according to [14A], in which the pharmaceutical composition is an external preparation.

[17A] The pharmaceutical composition according to any one of [14A] to [16A] for treating and/or preventing a peripheral inflammatory disease.

[18A] The pharmaceutical composition according to [17A], in which the peripheral inflammatory disease is any one selected from the group consisting of rheumatoid arthritis, systemic lupus erythematosus, scleroderma, bronchial asthma, asthmatic bronchitis, diffuse interstitial pneumonia, chronic obstructive pulmonary disease, ulcerative colitis, Crohn's disease, acute hepatitis, chronic hepatitis, fulminant hepatitis, autoimmune hepatitis, primary biliary cirrhosis, primary sclerosing cholangitis, alcoholic hepatitis, non-alcoholic steatohepatitis, hepatic cirrhosis, peripheral neuritis, ankylosing spondylitis, acute eczema, subacute eczema, chronic eczema, contact dermatitis, solar dermatitis due to sunlight and/or ultraviolet rays, radiation dermatitis, atopic dermatitis, seborrheic dermatitis, psoriasis vulgaris, psoriasis arthropica, psoriatic erythroderma, pustular psoriasis, lichen planus, erythema, rosacea, urticaria, alopetia areata, pemphigus, erythroderma, acne vulgaris, decubitus, wounds, burns, conjunctivitis, keratitis, scleritis, acute/chronic otitis media, perennial allergic rhinitis, pollinosis, sinusitis, laryngitis, esophagitis, refractory stomatitis, glossitis, acute/chronic sialadenitis, angular stomatitis, cheilitis, Behcet's disease, multiple sclerosis, type I diabetes, type II diabetes, atherosclerosis, pancreatitis, chronic heart failure, vitiligo vulgaris, verruca vulgaris, diabetic ulcer, ulcus cruris, keloid, hypertrophic scar, seborrhoic keratosis, male pattern alopecia, female pattern alopecia, senile alopecia, acne scar, pigmentation disorder, solar keratosis, gray hair, chronic hand eczema, chronic pruritus, generalized cutaneous pruritus, glaucoma, cataract, age-related macular degeneration, idiopathic pulmonary fibrosis, acute glomerulonephritis, chronic glomerulonephritis, diabetic glomerulonephritis, hypertrophic cardiomyopathy, osteoporosis, neurogenic muscular dystrophy, myogenic muscular dystrophy, and high blood pressure.

[19A] The pharmaceutical composition according to [17A], in which the peripheral inflammatory disease is any one selected from the group consisting of rheumatoid arthritis, systemic lupus erythematosus, scleroderma, bronchial asthma, acute hepatitis, autoimmune hepatitis, primary biliary cirrhosis, primary sclerosing cholangitis, alcoholic hepatitis, non-alcoholic steatohepatitis, ankylosing spondylitis, contact dermatitis, solar dermatitis due to sunlight and/or ultraviolet rays, radiation dermatitis, atopic dermatitis, seborrheic dermatitis, psoriasis vulgaris, psoriasis arthropica, psoriatic erythroderma, pustular psoriasis, lichen planus, erythema, rosacea, urticaria, alopetia areata, pemphigus, erythroderma, acne vulgaris, decubitus, wounds, burns, sinusitis, laryngitis, esophagitis, refractory stomatitis, glossitis, acute/chronic sialadenitis, angular stomatitis, cheilitis, Behcet's disease, vitiligo vulgaris, verruca vulgaris, vitiligo vulgaris, verruca vulgaris, diabetic ulcer, ulcus cruris, keloid, hypertrophic scar, seborrhoic keratosis, male pattern alopecia, female pattern alopecia, senile alopecia, acne scar, pigmentation disorder, solar keratosis, gray hair, chronic hand eczema, chronic pruritus, generalized cutaneous pruritus, and idiopathic pulmonary fibrosis.

[20A] The pharmaceutical composition according to [17A], in which the peripheral inflammatory disease is any one selected from the group consisting of rheumatoid arthritis, systemic lupus erythematosus, alcoholic hepatitis, non-alcoholic steatohepatitis, contact dermatitis, solar dermatitis due to sunlight and/or ultraviolet rays, radiation dermatitis, atopic dermatitis, seborrheic dermatitis, psoriasis vulgaris, psoriasis arthropica, psoriatic erythroderma, pustular psoriasis, lichen planus, erythema, rosacea, urticaria, alopetia areata, pemphigus, erythroderma, acne vulgaris, decubitus, wounds, burns, refractory stomatitis, glossitis, Behcet's disease, vitiligo vulgaris, verruca vulgaris, diabetic ulcer, ulcus cruris, keloid, hypertrophic scar, seborrhoic keratosis, male pattern alopecia, female pattern alopecia, senile alopecia, acne scar, pigmentation disorder, solar keratosis, gray hair, chronic hand eczema, chronic pruritus, generalized cutaneous pruritus, and idiopathic pulmonary fibrosis.

[21A] A method for treating and/or preventing a peripheral inflammatory disease, the method including: administering an effective dose of the pharmaceutical composition according to any one of [14A] to [16A].

[22A] The method according to [21A], in which the peripheral inflammatory disease is any one selected from the group consisting of rheumatoid arthritis, systemic lupus erythematosus, scleroderma, bronchial asthma, asthmatic bronchitis, diffuse interstitial pneumonia, chronic obstructive pulmonary disease, ulcerative colitis, Crohn's disease, acute hepatitis, chronic hepatitis, fulminant hepatitis, autoimmune hepatitis, primary biliary cirrhosis, primary sclerosing cholangitis, alcoholic hepatitis, non-alcoholic steatohepatitis, hepatic cirrhosis, peripheral neuritis, ankylosing spondylitis, acute eczema, subacute eczema, chronic eczema, contact dermatitis, solar dermatitis due to sunlight and/or ultraviolet rays, radiation dermatitis, atopic dermatitis, seborrheic dermatitis, psoriasis vulgaris, psoriasis arthropica, psoriatic erythroderma, pustular psoriasis, lichen planus, erythema, rosacea, urticaria, alopetia areata, pemphigus, erythroderma, acne vulgaris, decubitus, wounds, burns, conjunctivitis, keratitis, scleritis, acute/chronic otitis media, perennial allergic rhinitis, pollinosis, sinusitis, laryngitis, esophagitis, refractory stomatitis, glossitis, acute/chronic sialadenitis, angular stomatitis, cheilitis, Behcet's disease, multiple sclerosis, type I diabetes, type II diabetes, atherosclerosis, pancreatitis, chronic heart failure, vitiligo vulgaris, verruca vulgaris, diabetic ulcer, ulcus cruris, keloid, hypertrophic scar, seborrhoic keratosis, male pattern alopecia, female pattern alopecia, senile alopecia, acne scar, pigmentation disorder, solar keratosis, gray hair, chronic hand eczema, chronic pruritus, generalized cutaneous pruritus, glaucoma, cataract, age-related macular degeneration, idiopathic pulmonary fibrosis, acute glomerulonephritis, chronic glomerulonephritis, diabetic glomerulonephritis, hypertrophic cardiomyopathy, osteoporosis, neurogenic muscular dystrophy, myogenic muscular dystrophy, and high blood pressure.

[23A] The method according to [21A], in which the peripheral inflammatory disease is any one selected from the group consisting of rheumatoid arthritis, systemic lupus erythematosus, scleroderma, bronchial asthma, acute hepatitis, autoimmune hepatitis, primary biliary cirrhosis, primary sclerosing cholangitis, alcoholic hepatitis, non-alcoholic steatohepatitis, ankylosing spondylitis, contact dermatitis, solar dermatitis due to sunlight and/or ultraviolet rays, radiation dermatitis, atopic dermatitis, seborrheic dermatitis, psoriasis vulgaris, psoriasis arthropica, psoriatic erythroderma, pustular psoriasis, lichen planus, erythema, rosacea, urticaria, alopetia areata, pemphigus, erythroderma, acne vulgaris, decubitus, wounds, burns, sinusitis, laryngitis, esophagitis, refractory stomatitis, glossitis, acute/chronic sialadenitis, angular stomatitis, cheilitis, Behcet's disease, vitiligo vulgaris, verruca vulgaris, diabetic ulcer, ulcus cruris, keloid, hypertrophic scar, seborrhoic keratosis, male pattern alopecia, female pattern alopecia, senile alopecia, acne scar, pigmentation disorder, solar keratosis, gray hair, chronic hand eczema, chronic pruritus, generalized cutaneous pruritus, and idiopathic pulmonary fibrosis.

[24A] The method according to [21A], in which the peripheral inflammatory disease is any one selected from the group consisting of rheumatoid arthritis, systemic lupus erythematosus, alcoholic hepatitis, non-alcoholic steatohepatitis, contact dermatitis, solar dermatitis due to sunlight and/or ultraviolet rays, radiation dermatitis, atopic dermatitis, seborrheic dermatitis, psoriasis vulgaris, psoriasis arthropica, psoriatic erythroderma, pustular psoriasis, lichen planus, erythema, rosacea, urticaria, alopetia areata, pemphigus, erythroderma, acne vulgaris, decubitus, wounds, burns, refractory stomatitis, glossitis, Behcet's disease, vitiligo vulgaris, verruca vulgaris, diabetic ulcer, ulcus cruris, keloid, hypertrophic scar, seborrhoic keratosis, male pattern alopecia, female pattern alopecia, senile alopecia, acne scar, pigmentation disorder, solar keratosis, gray hair, chronic hand eczema, chronic pruritus, generalized cutaneous pruritus, and idiopathic pulmonary fibrosis.

[25A] The compound or the pharmaceutically acceptable salt thereof according to any one of [1A] to [12A] for use in treating and/or preventing a peripheral inflammatory disease.

[26A] The compound or the pharmaceutically acceptable salt thereof according to [25A], in which the peripheral inflammatory disease is any one selected from the group consisting of rheumatoid arthritis, systemic lupus erythematosus, scleroderma, bronchial asthma, asthmatic bronchitis, diffuse interstitial pneumonia, chronic obstructive pulmonary disease, ulcerative colitis, Crohn's disease, acute hepatitis, chronic hepatitis, fulminant hepatitis, autoimmune hepatitis, primary biliary cirrhosis, primary sclerosing cholangitis, alcoholic hepatitis, non-alcoholic steatohepatitis, hepatic cirrhosis, peripheral neuritis, ankylosing spondylitis, acute eczema, subacute eczema, chronic eczema, contact dermatitis, solar dermatitis due to sunlight and/or ultraviolet rays, radiation dermatitis, atopic dermatitis, seborrheic dermatitis, psoriasis vulgaris, psoriasis arthropica, psoriatic erythroderma, pustular psoriasis, lichen planus, erythema, rosacea, urticaria, alopetia areata, pemphigus, erythroderma, acne vulgaris, decubitus, wounds, burns, conjunctivitis, keratitis, scleritis, acute/chronic otitis media, perennial allergic rhinitis, pollinosis, sinusitis, laryngitis, esophagitis, refractory stomatitis, glossitis, acute/chronic sialadenitis, angular stomatitis, cheilitis, Behcet's disease, multiple sclerosis, type I diabetes, type II diabetes, atherosclerosis, pancreatitis, chronic heart failure, vitiligo vulgaris, verruca vulgaris, diabetic ulcer, ulcus cruris, keloid, hypertrophic scar, seborrhoic keratosis, male pattern alopecia, female pattern alopecia, senile alopecia, acne scar, pigmentation disorder, solar keratosis, gray hair, chronic hand eczema, chronic pruritus, generalized cutaneous pruritus, glaucoma, cataract, age-related macular degeneration, idiopathic pulmonary fibrosis, acute glomerulonephritis, chronic glomerulonephritis, diabetic glomerulonephritis, hypertrophic cardiomyopathy, osteoporosis, neurogenic muscular dystrophy, myogenic muscular dystrophy, and high blood pressure.

[27A] The compound or the pharmaceutically acceptable salt thereof according to [25A], in which the peripheral inflammatory disease is any one selected from the group consisting of rheumatoid arthritis, systemic lupus erythematosus, scleroderma, bronchial asthma, acute hepatitis, autoimmune hepatitis, primary biliary cirrhosis, primary sclerosing cholangitis, alcoholic hepatitis, non-alcoholic steatohepatitis, ankylosing spondylitis, contact dermatitis, solar dermatitis due to sunlight and/or ultraviolet rays, radiation dermatitis, atopic dermatitis, seborrheic dermatitis, psoriasis vulgaris, psoriasis arthropica, psoriatic erythroderma, pustular psoriasis, lichen planus, erythema, rosacea, urticaria, alopetia areata, pemphigus, erythroderma, acne vulgaris, decubitus, wounds, burns, sinusitis, laryngitis, esophagitis, refractory stomatitis, glossitis, acute/chronic sialadenitis, angular stomatitis, cheilitis, Behcet's disease, vitiligo vulgaris, verruca vulgaris, diabetic ulcer, ulcus cruris, keloid, hypertrophic scar, seborrhoic keratosis, male pattern alopecia, female pattern alopecia, senile alopecia, acne scar, pigmentation disorder, solar keratosis, gray hair, chronic hand eczema, chronic pruritus, generalized cutaneous pruritus, and idiopathic pulmonary fibrosis.

[28A] The compound or the pharmaceutically acceptable salt thereof according to [25A], in which the peripheral inflammatory disease is any one selected from the group consisting of rheumatoid arthritis, systemic lupus erythematosus, alcoholic hepatitis, non-alcoholic steatohepatitis, contact dermatitis, solar dermatitis due to sunlight and/or ultraviolet rays, radiation dermatitis, atopic dermatitis, seborrheic dermatitis, psoriasis vulgaris, psoriasis arthropica, psoriatic erythroderma, pustular psoriasis, lichen planus, erythema, rosacea, urticaria, alopetia areata, pemphigus, erythroderma, acne vulgaris, decubitus, wounds, burns, refractory stomatitis, glossitis, Behcet's disease, vitiligo vulgaris, verruca vulgaris, diabetic ulcer, ulcus cruris, keloid, hypertrophic scar, seborrhoic keratosis, male pattern alopecia, female pattern alopecia, senile alopecia, acne scar, pigmentation disorder, solar keratosis, gray hair, chronic hand eczema, chronic pruritus, generalized cutaneous pruritus, and idiopathic pulmonary fibrosis.

[29A] Use of the compound or the pharmaceutically acceptable salt thereof according to any one of [1A] to [12A], for the manufacture of a pharmaceutical composition used for treating and/or preventing a peripheral inflammatory disease.

[30A] The use according to [29A], in which the peripheral inflammatory disease is any one selected from the group consisting of rheumatoid arthritis, systemic lupus erythematosus, scleroderma, bronchial asthma, asthmatic bronchitis, diffuse interstitial pneumonia, chronic obstructive pulmonary disease, ulcerative colitis, Crohn's disease, acute hepatitis, chronic hepatitis, fulminant hepatitis, autoimmune hepatitis, primary biliary cirrhosis, primary sclerosing cholangitis, alcoholic hepatitis, non-alcoholic steatohepatitis, hepatic cirrhosis, peripheral neuritis, ankylosing spondylitis, acute eczema, subacute eczema, chronic eczema, contact dermatitis, solar dermatitis due to sunlight and/or ultraviolet rays, radiation dermatitis, atopic dermatitis, seborrheic dermatitis, psoriasis vulgaris, psoriasis arthropica, psoriatic erythroderma, pustular psoriasis, lichen planus, erythema, rosacea, urticaria, alopetia areata, pemphigus, erythroderma, acne vulgaris, decubitus, wounds, burns, conjunctivitis, keratitis, scleritis, acute/chronic otitis media, perennial allergic rhinitis, pollinosis, sinusitis, laryngitis, esophagitis, refractory stomatitis, glossitis, acute/chronic sialadenitis, angular stomatitis, cheilitis, Behcet's disease, multiple sclerosis, type I diabetes, type II diabetes, atherosclerosis, pancreatitis, chronic heart failure, vitiligo vulgaris, verruca vulgaris, diabetic ulcer, ulcus cruris, keloid, hypertrophic scar, seborrhoic keratosis, male pattern alopecia, female pattern alopecia, senile alopecia, acne scar, pigmentation disorder, solar keratosis, gray hair, chronic hand eczema, chronic pruritus, generalized cutaneous pruritus, glaucoma, cataract, age-related macular degeneration, idiopathic pulmonary fibrosis, acute glomerulonephritis, chronic glomerulonephritis, diabetic glomerulonephritis, hypertrophic cardiomyopathy, osteoporosis, neurogenic muscular dystrophy, myogenic muscular dystrophy, and high blood pressure.

[31A] The use according to [29A], in which the peripheral inflammatory disease is any one selected from the group consisting of rheumatoid arthritis, systemic lupus erythematosus, scleroderma, bronchial asthma, acute hepatitis, autoimmune hepatitis, primary biliary cirrhosis, primary sclerosing cholangitis, alcoholic hepatitis, non-alcoholic steatohepatitis, ankylosing spondylitis, contact dermatitis, solar dermatitis due to sunlight and/or ultraviolet rays, radiation dermatitis, atopic dermatitis, seborrheic dermatitis, psoriasis vulgaris, psoriasis arthropica, psoriatic erythroderma, pustular psoriasis, lichen planus, erythema, rosacea, urticaria, alopetia areata, pemphigus, erythroderma, acne vulgaris, decubitus, wounds, burns, sinusitis, laryngitis, esophagitis, refractory stomatitis, glossitis, acute/chronic sialadenitis, angular stomatitis, cheilitis, Behcet's disease, vitiligo vulgaris, verruca vulgaris, diabetic ulcer, ulcus cruris, keloid, hypertrophic scar, seborrhoic keratosis, male pattern alopecia, female pattern alopecia, senile alopecia, acne scar, pigmentation disorder, solar keratosis, gray hair, chronic hand eczema, chronic pruritus, generalized cutaneous pruritus, and idiopathic pulmonary fibrosis.

[32A] The use according to [29A], in which the peripheral inflammatory disease is any one selected from the group consisting of rheumatoid arthritis, systemic lupus erythematosus, alcoholic hepatitis, non-alcoholic steatohepatitis, contact dermatitis, solar dermatitis due to sunlight and/or ultraviolet rays, radiation dermatitis, atopic dermatitis, seborrheic dermatitis, psoriasis vulgaris, psoriasis arthropica, psoriatic erythroderma, pustular psoriasis, lichen planus, erythema, rosacea, urticaria, alopetia areata, pemphigus, erythroderma, acne vulgaris, decubitus, wounds, burns, refractory stomatitis, glossitis, Behcet's disease, vitiligo vulgaris, verruca vulgaris, diabetic ulcer, ulcus cruris, keloid, hypertrophic scar, seborrhoic keratosis, male pattern alopecia, female pattern alopecia, senile alopecia, acne scar, pigmentation disorder, solar keratosis, gray hair, chronic hand eczema, chronic pruritus, generalized cutaneous pruritus, and idiopathic pulmonary fibrosis.

Effects of the Invention

The compound of the present invention that has a specific chemical structure and has an anti-inflammatory effect or the pharmaceutically acceptable salt thereof is considered to be useful as a new drug because the compound and the salt have characteristics different from those of anti-inflammatory agents of the related art in various aspects.

Further, the compound of the present invention and the pharmaceutically acceptable salt thereof have excellent properties in terms of anti-inflammatory activity, bioavailability, solubility, cell membrane permeability, oral absorptivity, blood concentration, metabolic stability, tissue migration properties, in vitro activity, in vivo activity, ex vivo activity, quick expression of drug effects, sustainability of drug effects, physical stability, a drug interaction, and safety (for example, cardiotoxicity or hepatotoxicity), and thus are considered to be useful as a drug.

EMBODIMENTS FOR CARRYING OUT THE INVENTION

Hereinafter, the present invention will be described in detail.

Substituents, Explanation of Terms, and the Like

An embodiment of the present invention is a compound represented by Formula (1) or a pharmaceutically acceptable salt thereof.

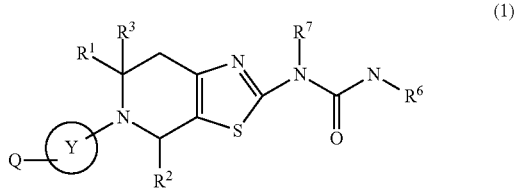
(1)

(The symbols representing each substituents in Formula (1) have the same definition as described above.)

Preferred embodiments of the compound represented by Formula (1) of the present invention are as follows.

For $R^1$ and $R^2$, preferably, both $R^1$ and $R^2$ represent a hydrogen atom, or bond to each other to form a substituent and the substituent represents a group selected from the following groups.

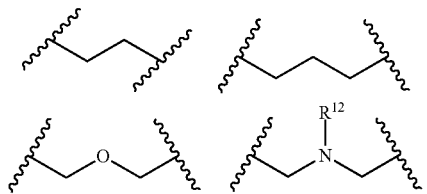

$R^{12}$ represents a methyl group, a hydroxyethyl group, an acetyl group, a methoxycarbonyl group, or a methanesulfonyl group.

$R^3$ preferably represents a hydrogen atom or a C1-C6 alkyl group.

For a preferred combination of $R^1$, $R^2$, and $R^3$, all $R^1$, $R^2$, and $R^3$ represent a hydrogen atom.

For another preferred combination of $R^1$, $R^2$, and $R^3$, both $R^1$ and $R^3$ represent a methyl group and $R^2$ represents a hydrogen atom.

For a still another preferred combination of R, $R^2$, and $R^3$, $R^1$ and $R^2$ bond to each other to form a substituent and the substituent represents any group selected from the following groups, and

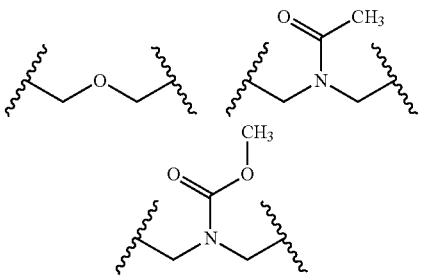

$R^3$ represents a hydrogen atom.

$R^6$ preferably represents a group described in any of the following items (1) and (2).

(1) Any group selected from the following groups:
a C1-C6 alkyl group;
a hydroxy C1-C6 alkyl group;
a hydroxy C3-C6 cycloalkyl group;
a tetrahydrofuranyl group; and
a tetrahydropyranyl group.

(2) Any group selected from the following groups:
a methyl group;
a hydroxypropyl group;
a 2-hydroxy-2-methylpropyl group;
a hydroxycyclobutyl group;
a tetrahydrofuranyl group; and
a tetrahydropyranyl group.

$R^7$ preferably represents a hydrogen atom.

For another embodiment of $R^6$ and $R^7$, it is preferable that $R^6$ and $R^7$ bond to each other to form any substituent selected from the following groups.

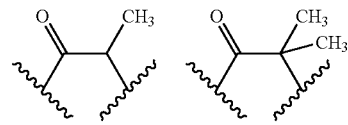

The groups are oriented in either a rightward or leftward direction.

For another preferred combination of $R^6$ and $R^7$, $R^6$ represents a methyl group and $R^7$ represents a hydrogen atom.

For a still another preferred combination of $R^6$ and $R^7$, $R^6$ represents a 2-hydroxy-2-methylpropyl group and $R^7$ represents a hydrogen atom.

For a still another preferred combination of $R^6$ and $R^7$, $R^6$ represents a 2-hydroxy-1-methylethyl group and $R^7$ represents a hydrogen atom.

For a still another preferred combination of $R^6$ and $R^7$, $R^6$ represents a 4-tetrahydropyranyl group and $R^7$ represents a hydrogen atom.

Q preferably represents a group described in any of the following items (1) to (4).

(1) Any group selected from the following groups:

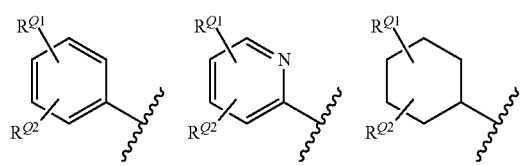

-continued

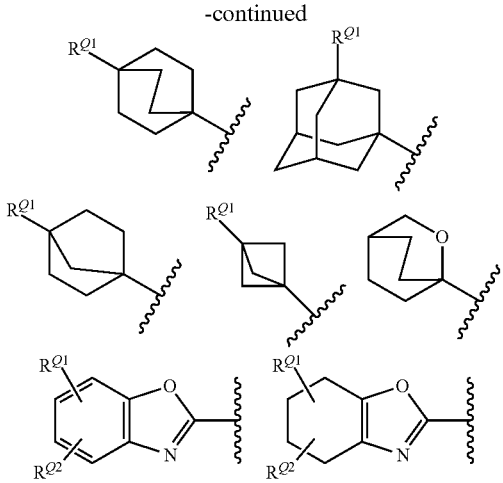

$R^{Q1}$ represents any group selected from the following groups:
  a halogen atom; a C1-C6 alkyl group; a C1-C6 alkoxy group; a halo-C1-C6 alkyl group; and a halo-C1-C6 alkoxy group, and
$R^{Q2}$ represents any group selected from the following groups:
  a hydrogen atom; a hydroxyl group; and a fluorine atom.

(2) Any group selected from the following groups:

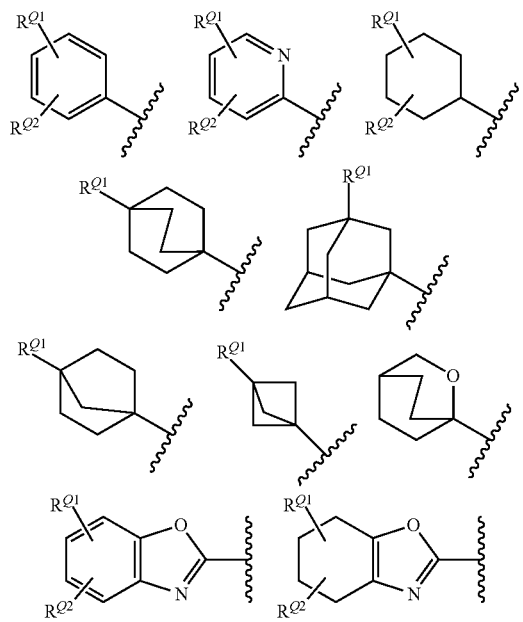

$R^{Q1}$ represents any group selected from the following groups:
  a fluorine atom; a chlorine atom; a methyl group; a methoxy group; a difluoromethyl group; a trifluoromethyl group; a difluoromethoxy group; and a trifluoromethoxy group, and
$R^{Q2}$ represents any group selected from the following groups:
  a hydrogen atom; a hydroxyl group; and a fluorine atom.

(3) Any group selected from the following groups:
  a C3-C6 cycloalkyl group that is substituted with any of one to three groups selected from $R^{Q3}$;
  a 4- to 7-membered saturated heterocyclic group that is substituted with any of one to three groups selected from $R^{Q3}$, in which $R^{Q3}$ represents any group selected from the following groups:
  a fluorine atom; a chlorine atom; a methoxy group; a difluoromethyl group; a trifluoromethyl group; a difluoromethoxy group; a trifluoromethoxy group; and an ethylene group.

(4) Any group selected from the following groups:
  a halogen atom; a halo-C1-C6 alkyl group; a halo-C1-C6 alkoxy C1-C6 alkyl group; and a C1-C6 alkoxy C1-C6 alkyl group For another preferred embodiment of Q, Q represents any group selected from the following groups:

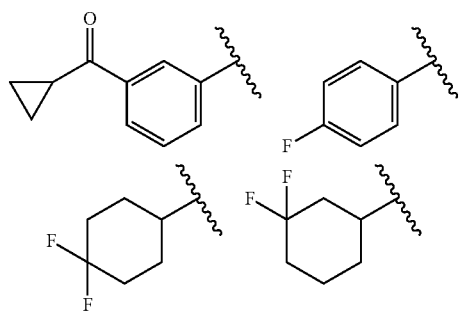

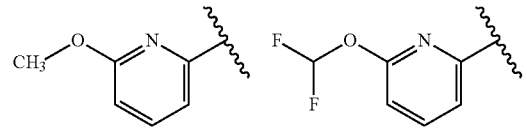

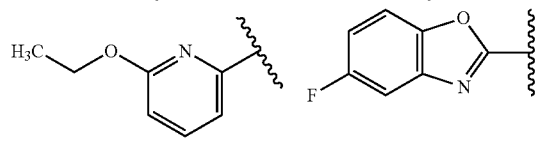

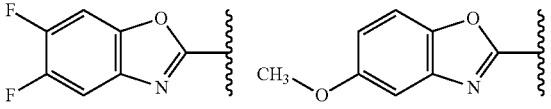

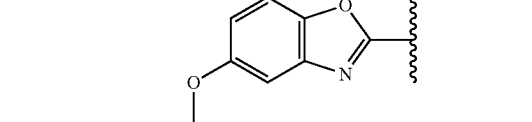

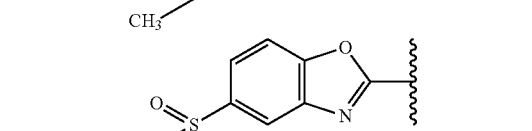

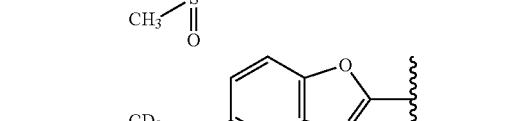

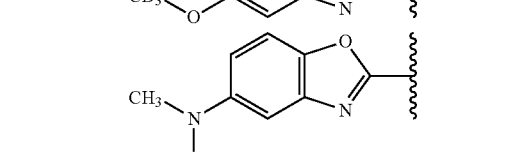

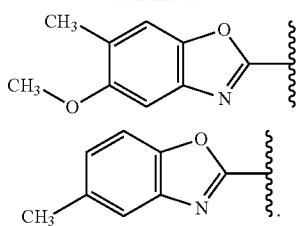

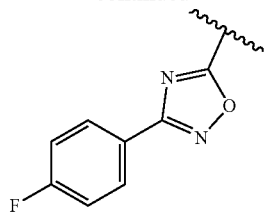

Y preferably represents any group selected from the following groups:

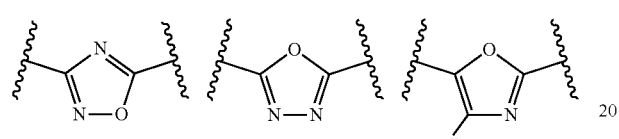

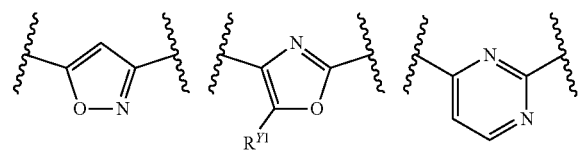

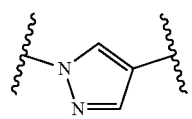

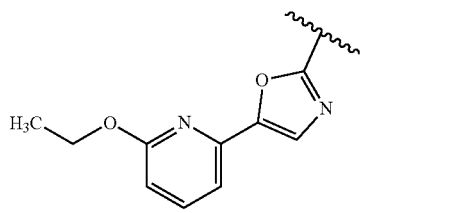

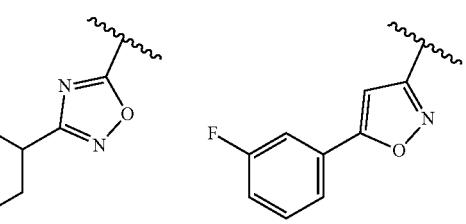

The groups are oriented in either a rightward or leftward direction.

$R^{Y1}$ represents a hydrogen atom or a methyl group.

For another preferred embodiment of Y, Y represents any group selected from the following groups:

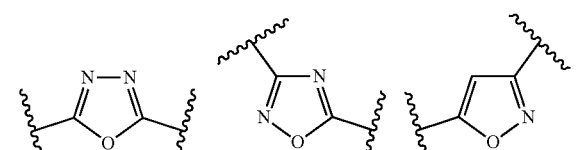

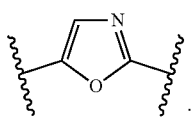

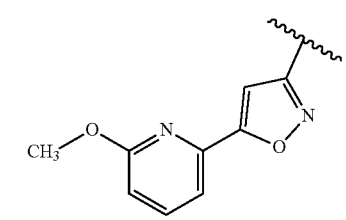

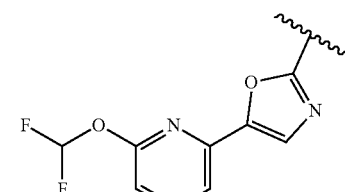

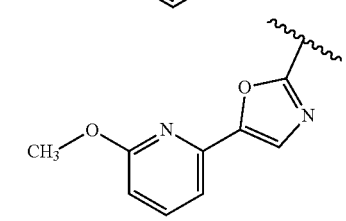

For a preferred combination of Q and Y, Q and Y represent any group selected from the following groups.

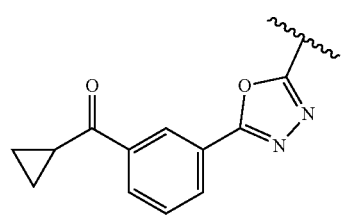

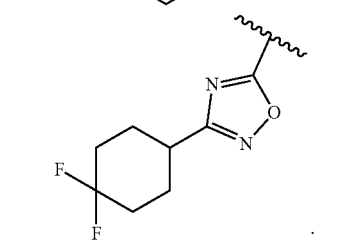

For another preferred combination of Q and Y, Y represents a single bond and Q represents a group selected from the following groups.

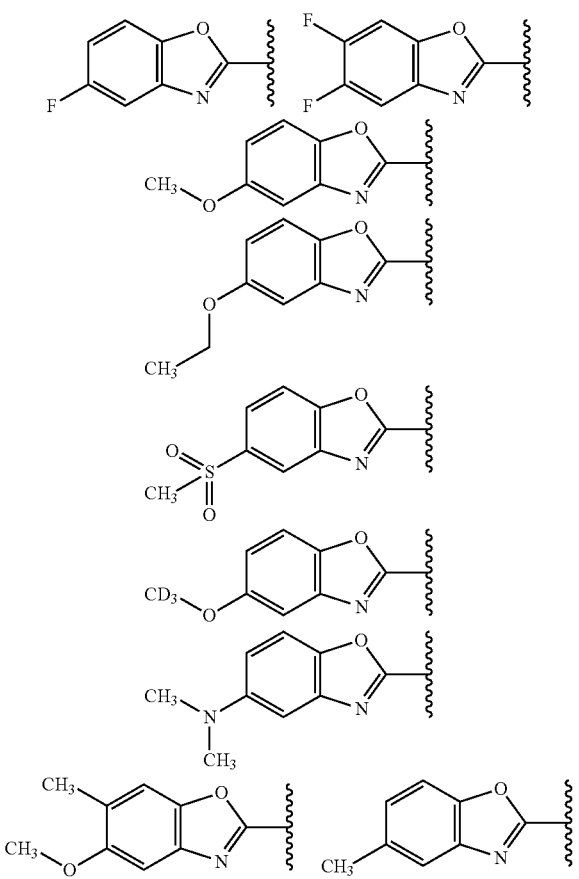

Another embodiment of the present invention is a compound selected from the following compounds or a pharmaceutically acceptable salt thereof:

N-{5-[3-(4,4-difluorocyclohexyl)-1,2,4-oxadiazol-5-yl]-4,5,6,7-tetrahydro[1,3]thiazolo[5,4-c]pyridin-2-yl}-N'-methylurea, N-methyl-N'-{5-[5-(trifluoromethyl)-1,3,4-oxadiazol-2-yl]-4,5,6,7-tetrahydro[1,3]thiazolo[5,4-c]pyridin-2-yl}urea, N-(5-{5-[(1R)-1-ethoxyethyl]-1,3,4-oxadiazol-2-yl}-4,5,6,7-tetrahydro[1,3]thiazolo[5,4-c]pyridin-2-yl)-N'-methylurea, N-methyl-N'-(5-{3-[1-(2,2,2-trifluoroethoxy)ethyl]-1,2,4-oxadiazol-5-yl}-4,5,6,7-tetrahydro[1,3]thiazolo[5,4-c]pyridin-2-yl)urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(2R)-1-hydroxypropan-2-yl]urea, N-methyl-N'-(10-{3-[(1s,4s)-4-(trifluoromethyl)cyclohexyl]-1,2,4-oxadiazol-5-yl}-4,7,8,9-tetrahydro-5H-4,8-epiminooxocino[5,4-d][1,3]thiazol-2-yl)urea, N-{(4S,8S)-10-[3-(4,4-difluorocyclohexyl)-1,2,4-oxadiazol-5-yl]-4,7,8,9-tetrahydro-5H-4,8-epiminooxocino[5,4-d][1,3]thiazol-2-yl}-N'-methylurea, N-methyl-N'-(5-{3-[3-(trifluoromethoxy)phenyl]-1,2,4-oxadiazol-5-yl}-4,5,6,7-tetrahydro[1,3]thiazolo[5,4-c]pyridin-2-yl)urea, N-{5-[5-(4-fluoro-3-methylphenyl)-1,3,4-oxadiazol-2-yl]-4,5,6,7-tetrahydro[[1,3]thiazolo[5,4-c]pyridin-2-yl}-N'-methylurea, N-{(5R*,8S*)-9-[3-(4-fluorophenyl)-1,2,4-oxadiazol-5-yl]-5,6,7,8-tetrahydro-4H-5,8-epiminocyclohepta[d][1,3]thiazol-2-yl}-N'-methylurea, N-{9-[5-(4-fluorophenyl)-1,2-oxazol-3-yl]-5,6,7,8-tetrahydro-4H-5,8-epiminocyclohepta[d][1,3]thiazol-2-yl}-N'-methylurea, N-{(5R*,9S*)-10-[3-(4-fluorophenyl)-1,2,4-oxadiazol-5-yl]-4,5,6,7,8,9-hexahydro-5,9-epiminocycloocta[d][1,3]thiazol-2-yl}-N'-methylurea, N-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-methylurea, N-(10-{5-[3-(difluoromethyl)phenyl]-1,3-oxazol-2-yl}-4,7,8,9-tetrahydro-5H-4,8-epiminooxocino[5,4-d][1,3]thiazol-2-yl)-N'-methylurea, N-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}-N'-methylurea, N-{10-[5-(4-fluorophenyl)-1,2-oxazol-3-yl]-4,7,8,9-tetrahydro-5H-4,8-epiminooxocino[5,4-d][1,3]thiazol-2-yl}-N'-methylurea, N-{(4S,8S)-10-[4-(4-fluorophenyl)-1,3-oxazol-2-yl]-4,7,8,9-tetrahydro-5H-4,8-epiminooxocino[5,4-d][1,3]thiazol-2-yl}-N'-methylurea, N-{10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-[(2R)-1-hydroxypropan-2-yl]urea, N-{6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-methylurea, (5R)-3-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}-5-methylimidazolidin-2,4-dione, N-[(4S,8S)-10-{5-[3-(cyclopropanecarbonyl)phenyl]-1,3,4-oxadiazol-2-yl}-4,7,8,9-tetrahydro-5H-4,8-epiminooxocino[5,4-d][1,3]thiazol-2-yl]-N'-methylurea, N-[(4S,8S)-10-{5-[3-(difluoromethoxy)phenyl]-1,3,4-oxadiazol-2-yl}-4,7,8,9-tetrahydro-5H-4,8-epiminooxocino[5,4-d][1,3]thiazol-2-yl]-N'-methylurea, (−)-N-{(4R*,8R*)-6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-methylurea, (−)-methyl (4R*,8R*)-10-[3-(4-fluorophenyl)-1,2,4-oxadiazol-5-yl]-2-[(methylcarbamoyl)amino]-4,7,8,9-tetrahydro-4,8-epimino[1,3]thiazolo[5,4-d]azocin-6(5H)-carboxylate, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1R,2R)-2-hydroxycyclopentyl]urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1r,4r)-4-hydroxycyclohexyl]urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-(3-methoxypropyl)urea, N-{5-[3-(3,3-difluorocyclohexyl)-1,2,4-oxadiazol-5-yl]-4,5,6,7-tetrahydro[1,3]thiazolo[5,4-c]pyridin-2-yl}-N'-(2-hydroxy-2-methylpropyl)urea, N-{[(2S)-1,4-dioxan-2-yl]methyl}-N'-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}urea, N-{10-[3-(4-fluorophenyl)-1,2,4-oxadiazol-5-yl]-6-(methanesulfonyl)-4,5,6,7,8,9-hexahydro-4,8-epimino[1,3]thiazolo[5,4-d]azocin-2-yl}-N'-oxan-4-ylurea, N-{10-[3-(4-fluorophenyl)-1,2,4-oxadiazol-5-yl]-6-(methanesulfonyl)-4,5,6,7,8,9-hexahydro-4,8-epimino[1,3]thiazolo[5,4-d]azocin-2-yl}-N'-methylurea, propan-2-yl-10-[3-(4-fluorophenyl)-1,2,4-oxadiazol-5-yl]-2-[(methylcarbamoyl)amino]-4,7,8,9-tetrahydro-4,8-epimino[1,3]thiazolo[5,4-d]azocin-6(5H)-carboxylate, methyl (4R*,8R*)-2-{[(2-hydroxy-2-methylpropyl)carbamoyl]amino}-10-{3-[1-(trifluoromethyl)cyclopropyl]-1,2,4-oxadiazol-5-yl}-4,7,8,9-tetrahydro-4,8-epimino[1,3]thiazolo[5,4-d]azocin-6(5H)-carboxylate, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[2-(2-hydroxyethoxy)ethyl]urea, N-{5-[3-(3,3-difluorocyclopentyl)-1,2,4-oxadiazol-5-yl]-4,5,6,7-tetrahydro[1,3]thiazolo[5,4-c]pyridin-2-yl}-N'-[(1r,3r)-3-hydroxycyclobutyl]urea, N-{5-[3-(3,3-difluorocyclohexyl)-1,2,4-oxadiazol-5-yl]-4,5,6,7-tetrahydro[1,3]thiazolo[5,4-c]pyridin-2-yl}-N'-methylurea, N-[(3R)-oxolan-3-yl]-N'-[(4S,8S)-10-{3-[1-(trifluoromethyl)cyclopropyl]-1,2,4-oxadiazole-5-yl}-4,7,8,9-tetrahydro-5H-4,8-epiminooxocino[5,4-d][1,3]thiazol-2-yl]urea, N-[(2R)-1-hydroxypropan-2-yl]-N'-[(4S,8S)-10-(5-methoxy-1,3- benzoxazol-2-yl)-4,7,8,9-tetrahydro-5H-4,8-epiminooxocino[5,4-d][1,3]thiazol-2-yl]urea, N-[(4S,8S)-10-(5-fluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea, N-[(4S,8S)-10-(5-ethoxy-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea, N-{(4S,8S)-10-[5-(dimethylamino)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea, N-[(4S,8S)-10-(5,6-difluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea, N-{(4S,8S)-10-[5-(methanesulfonyl)-1,3-benzoxazol-2-yl]-4,7,8,9-tetrahydro-5H-4,8-epiminooxocino[5,4-d][1,3]thiazol-2-yl}-N'-(2-methylpropyl)urea, N-(2-hydroxy-2-methylpropyl)-N'-[(4S,8S)-10-(5-methoxy-6-methyl-1,3-benzoxazol-2-yl)-4,7,8,9-tetrahydro-5H-4,8-epiminooxocino[5,4-d][1,3]thiazol-2-yl]urea, N-[(4S,8S)-10-(5-methoxy-6-methyl-1,3-benzoxazol-2-yl)-4,7,8,9-tetrahydro-5H-4,8-epiminooxocino[5,4-d][1,3]thiazol-2-yl]-N'-[(3R)-oxolan-3-yl]urea, N-(2-hydroxy-2-methylpropyl)-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea, N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-[(3R)-oxolan-3-yl]urea, N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-methylurea, N-methyl-N'-[(4S,8S)-10-(5-methyl-1,3-benzoxazol-2-yl)-4,7,8,9-tetrahydro-5H-4,8-epiminooxocino[5,4-d][1,3]thiazol-2-yl]urea, N-{(4S,8S)-10-[5-(methanesulfonyl)-1,3-benzoxazol-2-yl]-4,7,8,9-tetrahydro-5H-4,8-epiminooxocino[5,4-d][1,3]thiazol-2-yl}-N'-propan-2-ylurea, N-[(4S,8S)-10-(6-cyano-5-methyl-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea, N-[(4S,8S)-10-(5-ethoxy-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea, N-{(4S,8S)-10-[5-(difluoromethyl)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea, N-[(1r,3S)-3-hydroxycyclobutyl]-N'-[(4S,8S)-10-(5-trifluoromethoxy-1,3-benzoxazol-2-yl)-4,7,8,9-tetrahydro-5H-4,8-epiminooxocino[5,4-d][1,3]thiazol-2-yl]urea, N-{(4S,8S)-10-(5-cyano-6-fluoro-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea, N-{(4S,8S)-10-[5-(difluoromethyl)-1,3-benzoxazol-2-yl]-4,7,8,9-tetrahydro-5H-4,8-epiminooxocino[5,4-d][1,3]thiazol-2-yl}-N'-[(2R)-1-hydroxypropan-2-yl]urea, N-{(4S,8S)-10-[5-(fluoromethyl)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea, N-(1-hydroxy-2-methylpropan-2-yl)-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea, N-[(4S,8S)-10-(5-chloro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea, N-(2-hydroxy-2-methylpropyl)-N'-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]urea, N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(1s,4s)-4-hydroxycyclohexyl]urea, N-{(4S,8S)-10-[5-(6-methoxypyridin-2-yl)-1,2-oxazol-3-yl]-4,7,8,9-tetrahydro-5H-4,8-epiminooxocino[5,4-d][1,3]thiazol-2-yl}-N'-oxan-4-ylurea, N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-(2-hydroxy-2-methylpropyl)urea, methyl 10-[5-(4-fluorophenyl)-1,2-oxazol-3-yl]-2-[(methylcarbamoyl)amino]-4,7,8,9-tetrahydro-4,8-epimino[1,3]thiazolo[5,4-d]azocin-6(5H)-carboxylate, N-{(4S,8S)-10-[5-(4-fluorophenyl)-1,2-oxazol-3-yl]-4,7,8,9-tetrahydro-5H-4,8-epiminooxocino[5,4-d][1,3]thiazolo-2-yl}-N'-[(2R)-2-hydroxypropyl]urea, N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(2R)-1-hydroxypropan-2-yl]urea, N-[(2R)-1-hydroxypropan-2-yl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea, N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-[(2R)-1-hydroxypropan-2-yl]urea, N-[(4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-yl]-N'-(1-hydroxy-2-methylpropan-2-yl)urea, N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-[(2R)-1-hydroxypropan-2-yl]urea, N-[(4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-yl]-N'-[(2R)-1-hydroxypropan-2-yl]urea, N-[(4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-yl]-N'-[(2R)-2-hydroxypropyl]urea, N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-[(3R)-oxolan-3-yl]urea, N-[(2R)-1-hydroxypropan-2-yl]-N'-{5-[5-(methanesulfonyl)-1,3-benzoxazol-2-yl]-6,6-dimethyl-4,5,6,7-tetrahydro[1,3]thiazolo[5,4-c]pyridin-2-yl}urea, N-(2-hydroxy-2-methylpropyl)-N'-{5-[5-(methanesulfonyl)-1,3-benzoxazol-2-yl]-6,6-dimethyl-4,5,6,7-tetrahydro[1,3]thiazolo[5,4-c]pyridin-2-yl}urea, N-[(2R)-1-hydroxypropan-2-yl]-N'-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]urea, N-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]-N'-[(3R)-oxolan-3-yl]urea, N-[(1r,3S)-3-hydroxycyclobutyl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea, N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl]-N'-(2-hydroxy-2-methylpropyl)urea, N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-[(1r,3S)-3-hydroxycyclobutyl]urea, N-{10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-[(2S)-2-hydroxypropyl]urea, N-{10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-[(2R)-2-hydroxypropyl]urea, N-{10-[3-(4-fluoro-3-methoxyphenyl)-1,2,4-oxadiazol-5-yl]-4,7,8,9-tetrahydro-5H-4,8-epiminooxocino[5,4-d][1,3]thiazol-2-yl}-N'-[(2R)-1-hydroxypropan-2-yl]urea, N-{10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-[(1r,3r)-3-(hydroxymethyl)cyclobutyl]urea, N-{10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-[(1s,3s)-3-hydroxycyclobutyl]urea, N-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-[(1r,3S)-3-hydroxycyclobutyl]urea, N-{5-[3-(3,3-difluorocyclohexyl)-1,2,4-oxadiazol-5-yl]-4,5,6,7-tetrahydro[1,3]thiazolo[5,4-c]pyridin-2-yl}-N'-[(2R)-1-hydroxypropan-2-yl]urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-(2-hydroxy-2-methylpropyl)urea, N-[(2R)-1-hydroxypropan-2-yl]-N'-(5-{3-[1-(2,2,2-trifluoroethoxy)ethyl]-1,2,4-oxadiazol-5-yl}-4,5,6,7-tetrahydro[1,3]thiazolo[5,4-c]pyridin-2-yl)urea, N-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-(1-hydroxy-2-methylpropan-2-yl)urea, N-[(2R)-1-hydroxypropan-2-yl]-N'-(5-{3-[2-(2,2,2-trifluoroethoxy) propan-2-yl]-1,2,4-oxadiazol-5-yl}-4,5,6,7-tetrahydro[1,3]thiazolo[5,4-c]pyridin-2-yl)urea, N-(2-hydroxy-2-methylpropyl)-N'-(5-{3-[1-(trifluoromethyl)cyclopropyl]-1,2,4-oxadiazol-5-yl}-4,5,6,7-tetrahydro[1,3]thiazolo[5,4-c]pyridin-2-yl)urea, N-{5-[3-(4-fluorobicyclo[2.2.1]heptan-1-yl)-1,2,4-oxadiazol-5-yl]-4,5,6,7-tetrahydro[1,3]thiazolo[5,4-c]pyridin-2-yl}-N'-methylurea, N-{5-[3-(3,3-difluorocyclopentyl)-1,2,4-oxadiazol-5-yl]-4,5,6,7-tetrahydro[1,3]thiazolo[5,4-c]pyridin-2-yl}-N'-(2-hydroxy-2-methylpropyl)urea, N-{5-[3-(4,4-difluorooxan-2-yl)-1,2,4-oxadiazol-5-yl]-4,5,6,7-tetrahydro[1,3]thiazolo[5,4-c]pyridin-2-yl}-N'-[(3R)-oxolan-3-yl]urea, N-(5-{3-[3-(difluoromethoxy)bicyclo[1.1.1]pentan-1-yl]-1,2,4-oxadiazol-5-yl}-4,5,6,7-tetrahydro[1,3]thiazolo[5,4-c]pyridin-2-yl)-N'-(2-hydroxy-2-methylpropyl)urea, N-[(1r,3r)-3-hydroxycyclobutyl]-N'-(5-{3-[1-(trifluoromethyl)cyclopropyl]-1,2,4-oxadiazol-5-yl}-4,5,6,7-tetrahydro[1,3]thiazolo[5,4-c]pyridin-2-yl)urea, N-{5-[3-(4,4-difluorooxan-2-yl)-1,2,4-oxadiazol-5-yl]-4,5,6,7-tetrahydro[1,3]thiazolo[5,4-c]pyridin-2-yl}-N'-(2-methoxyethyl)urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(pyrimidin-5-yl)methyl]urea, N-{5-[3-(4-fluoro-3-methoxyphenyl)-1,2,4-oxadiazol-5-yl]-4,5,6,7-tetrahydro[1,3]thiazolo[5,4-c]pyridin-2-yl}-N'-[(1-methyl-1H-imidazole-2-yl)methyl]urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(2-oxo-1,2-dihydropyridin-4-yl)methyl]urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(4H-1,2,4-triazol-3-yl)methyl]urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(2-oxo-1,2-dihydropyridin-3-yl)methyl]urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1-hydroxycyclopropyl)methyl]urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[1-(hydroxymethyl)cyclopropyl]urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1-methyl-1H-1,2,4-triazol-3-yl)methyl]urea, N-{5-[3-(4-methoxyphenyl)-1,2,4-oxadiazol-5-yl]-4,5,6,7-tetrahydro[1,3]thiazolo[5,4-c]pyridin-2-yl}-N'-oxan-4-ylurea, N-{5-[3-(3-methoxyphenyl)-1,2,4-oxadiazol-5-yl]-4,5,6,7-tetrahydro[1,3]thiazolo[5,4-c]pyridin-2-yl}-N'-oxan-4-ylurea, N-(10-{5-[3-(difluoromethyl)phenyl]-1,3,4-oxadiazol-2-yl}-4,7,8,9-tetrahydro-5H-4,8-epiminooxocino[5,4-d][1,3]thiazol-2-yl)-N'-methylurea, N-methyl-N'-(10-{5-[3-(trifluoromethyl)phenyl]-1,3,4-oxadiazol-2-yl}-4,7,8,9-tetrahydro-5H-4,8-epiminooxocino[5,4-d][1,3]thiazol-2-yl)urea, N-{10-[5-(3-tert-butoxyphenyl)-1,3,4-oxadiazol-2-yl]-4,7,8,9-tetrahydro-5H-4,8-epiminooxocino[5,4-d][1,3]thiazol-2-yl}-N'-methylurea, N-(10-{3-[3-(cyclopropanecarbonyl)phenyl]-1,2,4-oxadiazol-5-yl}-4,7,8,9-tetrahydro-5H-4,8-epiminooxocino[5,4-d][1,3]thiazol-2-yl)-N'-methylurea, N-(10-{5-[3-(cyclobutanecarbonyl)phenyl]-1,3,4-oxadiazol-2-yl}-4,7,8,9-tetrahydro-5H-4,8-epiminooxocino[5,4-d][1,3]thiazol-2-yl)-N'-methylurea, N-(10-{5-[3-((cyclopropanecarbonyl)phenyl]-1,3,4-oxadiazol-2-yl}-4,7,8,9-tetrahydro-5H-4,8-epiminooxocino[5,4-d][1,3]thiazol-2-yl)-N'-(2,2,2-trifluoroethyl)urea, N-(10-{5-[3-(difluoromethoxy)phenyl]-1,3,4-oxadiazol-2-yl}-4,7,8,9-tetrahydro-5H-4,8-epiminooxocino[5,4-d][1,3]thiazol-2-yl)-N'-[(3S)-oxolan-3-yl]urea, N-(10-{5-[3-(cyclopropanecarbonyl)-2-fluorophenyl]-1,3-oxazol-2-yl}-4,7,8,9-tetrahydro-5H-4,8-epiminooxocino[5,4-d][1,3]thiazol-2-yl)-N'-methylurea, N-[(4S,8S)-10-{5-[3-(cyclopropanecarbonyl)phenyl]-1,3,4-oxadiazol-2-yl}-4,7,8,9-tetrahydro-5H-4,8-epiminooxocino[5,4-d][1,3]thiazol-2-yl]-N'-propan-2-ylurea, N-{(4S,8S)-10-[5-(3-ethylphenyl)-1,3,4-oxadiazol-2-yl]-4,7,8,9-tetrahydro-5H-4,8-epiminooxocino[5,4-d][1,3]thiazol-2-yl}-N'-methylurea, N-methyl-N'-[(4S,8S)-10-{5-[3-(propan-2-yl)phenyl]-1,3,4-oxadiazol-2-yl}-4,7,8,9-tetrahydro-5H-4,8-epiminooxocino[5,4-d][1,3]thiazol-2-yl]urea, N-{(4S,8S)-10-[5-(3-methoxyphenyl)-1,3,4-oxadiazol-2-yl]-4,7,8,9-tetrahydro-5H-4,8-epiminooxocino[5,4-d][1,3]thiazol-2-yl}-N'-methylurea, N-{(4S,8S)-10-[5-(3-ethoxyphenyl)-1,3,4-oxadiazol-2-yl]-4,7,8,9-tetrahydro-5H-4,8-epiminooxocino[5,4-d][1,3]thiazol-2-yl}-N'-methylurea, N-methyl-N'-[(4S,8S)-10-(5-{3-[(propan-2-yl)oxy]phenyl}-1,3,4-oxadiazol-2-yl)-4,7,8,9-tetrahydro-5H-4,8-epiminooxocino[5,4-d][1,3]thiazol-2-yl]urea, methyl 10-{5-[3-(cyclopropanecarbonyl)phenyl]-1,3,4-oxadiazol-2-yl}-2-[(methylcarbamoyl)amino]-4,7,8,9-tetrahydro-4,8-epimino[1,3]thiazolo[5,4-d]azocin-6(5H)-carboxylate, N-(10-{3-[3-(difluoromethyl)phenyl]-1,2,4-oxadiazol-5-yl}-4,7,8,9-tetrahydro-5H-4,8-epiminooxocino[5,4-d][1,3]thiazol-2-yl)-N'-[(2R)-1-hydroxypropan-2-yl]urea, N-[(4R,8R)-10-[3-(4-fluorophenyl)-1,2,4-oxadiazol-5-yl]-6-(2-methylpropanoyl)-4,5,6,7,8,9-hexahydro-4,8-epimino[1,3]thiazolo[5,4-d]azocin-2-yl]-N'-methylurea, N-{6-acetyl-10-[5-(6-methoxypyridin-2-yl)-1,3-oxazol-2-yl]-4,5,6,7,8,9-hexahydro-4,8-epimino[1,3]thiazolo[5,4-d]azocin-2-yl}-N'-methylurea, N-[(4R,8R)-10-[3-(4-fluorophenyl)-1,2,4-oxadiazol-5-yl]-6-(2-hydroxyethyl)-4,5,6,7,8,9-hexahydro-4,8-epimino[1,3]thiazolo[5,4-d]azocin-2-yl]-N'-methylurea, N-(6-acetyl-10-{5-[6-(difluoromethoxy)pyridin-2-yl]-1,3-oxazol-2-yl}-4,5,6,7,8,9-hexahydro-4,8-epimino[1,3]thiazolo[5,4-d]azocin-2-yl)-N'-methylurea, N-{6-acetyl-10-[5-(6-methoxypyridin-2-yl)-1,3-oxazol-2-yl]-4,5,6,7,8,9-hexahydro-4,8-epimino[1,3]thiazolo[5,4-d]azocin-2-yl}-N'-methylurea, N-[6-acetyl-10-(5-fluoro-1,3-benzoxazol-2-yl)-4,5,6,7,8,9-hexahydro-4,8-epimino[1,3]thiazolo[5,4-d]azocin-2-yl]-N'-methylurea, methyl 10-[3-(3,3-difluorocyclopentyl)-1,2,4-oxadiazol-5-yl]-2-[(methylcarbamoyl)amino]-4,7,8,9-tetrahydro-4,8-epimino[1,3]thiazolo[5,4-d]azocin-6(5H)-carboxylate, methyl 10-[3-(4,4-difluorocyclohexyl)-1,2,4-oxadiazol-5-yl]-2-[(methylcarbamoyl)amino]-4,7,8,9-tetrahydro-4,8-epimino[1,3]thiazolo[5,4-d]azocin-6(5H)-carboxylate, methyl 10-[3-(4-fluorobicyclo[2.2.1]heptan-1-yl)-1,2,4-oxadiazol-5-yl]-2-[(methylcarbamoyl)amino]-4,7,8,9-tetrahydro-4,8-epimino[1,3]thiazolo[5,4-d]azocin-6(5H)-carboxylate, ethyl 2-[(methylcarbamoyl)amino]-10-{3-[1-(trifluoromethyl)cyclopropyl]-1,2,4-oxadiazol-5-yl}-4,7,8,9-tetrahydro-4,8-epimino[1,3]thiazolo[5,4-d]azocin-6(5H)-carboxylate, methyl 10-{3-[3-(difluoromethyl)bicyclo[1.1.1]pentan-1-yl]-1,2,4-oxadiazol-5-yl}-2-[(methylcarbamoyl)amino]-4,7,8,9-tetrahydro-4,8-epimino[1,3]thiazolo[5,4-d]azocin-6(5H)-carboxylate, N-{6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-ethylurea, N-{6-acetyl-10-[3-(4-fluorophenyl)-1,2,4- oxadiazol-5-yl]-4,5,6,7,8,9-hexahydro-4,8-epimino[1,3]thiazolo[5,4-d]azocin-2-yl}-N'-propan-2-ylurea, N-{6-acetyl-10-[3-(3-fluorophenyl)-1,2,4-oxadiazol-5-yl]-4,5,6,7,8,9-hexahydro-4,8-epimino[1,3]thiazolo[5,4-d]azocin-2-yl}-N'-methylurea, N-{6-acetyl-10-[5-(3-chlorophenyl)-1,3-oxazol-2-yl]-4,5,6,7,8,9-hexahydro-4,8-epimino[1,3]thiazolo[5,4-d]azocin-2-yl}-N'-methylurea, N-{6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-[(3R)-oxolan-3-yl]urea, methyl 10-(5-methoxy-1,3-benzoxazol-2-yl)-2-[(methylcarbamoyl)amino]-4,7,8,9-tetrahydro-4,8-epimino[1,3]thiazolo[5,4-d]azocin-6(5H)-carboxylate, methyl 10-[3-(5-fluoropyridin-2-yl)-1,2,4-oxadiazol-5-yl]-2-[(methylcarbamoyl)amino]-4,7,8,9-tetrahydro-4,8-epimino[1,3]thiazolo[5,4-d]azocin-6(5H)-carboxylate, propan-2-yl-10-[3-(4-fluorophenyl)-1,2,4-oxadiazol-5-yl]-2-{[(oxan-4-yl)carbamoyl]amino}-4,7,8,9-tetrahydro-4,8-epimino[1,3]thiazolo[5,4-d]azocin-6(5H)-carboxylate, N-(2-hydroxy-2-methylpropyl)-N'-{(4S,8S)-10-[5-(trifluoromethyl)-1,3-benzoxazol-2-yl]-4,7,8,9-tetrahydro-5H-4,8-epiminooxocino[5,4-d][1,3]thiazol-2-yl}urea, N-(2-hydroxy-2-methylpropyl)-N'-[(4S,8S)-10-(5-methyl-1,3-benzoxazol-2-yl)-4,7,8,9-tetrahydro-5H-4,8-epiminooxocino[5,4-d][1,3]thiazol-2-yl]urea, N-[(4S,8S)-10-(5,6-difluoro-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea, N-[(4S,8S)-10-(5,7-difluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea, N-[(4S,8S)-10-(5,6-dimethyl-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea, N-[(4S,8S)-10-(5-chloro-1,3-benzoxazol-2-yl)-4,7,8,9-tetrahydro-5H-4,8-epiminooxocino[5,4-d][1,3]thiazol-2-yl]-N'-[(1r,4r)-4-hydroxycyclohexyl]urea, N-[(4S,8S)-10-(5-chloro-1,3-benzoxazol-2-yl)-4,7,8,9-tetrahydro-5H-4,8-epiminooxocino[5,4-d][1,3]thiazol-2-yl]-N'-[(4-hydroxyoxan-4-yl)methyl]urea, N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-[(3S)-oxolan-3-yl]urea, N-[(2R)-1-hydroxypropan-2-yl]-N'-{9-[5-(methanesulfonyl)-1,3-benzoxazol-2-yl]-5,6,7,8-tetrahydro-4H-5,8-epiminocyclohepta[d][1,3]thiazol-2-yl}urea, N-{5-[5-(4,4-difluorocyclohexyl)-1,2-oxazol-3-yl]-4,5,6,7-tetrahydro[1,3]thiazolo[5,4-c]pyridin-2-yl}-N'-[(2R)-2-hydroxypropyl]urea, N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(2R)-1-hydroxypropan-2-yl]urea, N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(2R)-1-hydroxypropan-2-yl]urea, N-[(4S,8S)-10-{5-[3-(difluoromethyl)phenyl]-1,2-oxazol-3-yl}-4,7,8,9-tetrahydro-5H-4,8-epiminooxocino[5,4-d][1,3]thiazol-2-yl]-N'-[(2R)-1-hydroxypropan-2-yl]urea, N-{(4S,8S)-10-[5-(4,4-difluorocyclohexyl)-1,2-oxazol-3-yl]-4,7,8,9-tetrahydro-5H-4,8-epiminooxocino[5,4-d][1,3]thiazol-2-yl}-N'-[(3R)-oxolan-3-yl]urea, N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(1s,3R)-3-hydroxycyclobutyl]urea, N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(1r,4r)-4-hydroxycyclohexyl]urea, N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-(1-hydroxy-2-methylpropan-2-yl)urea, N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-oxan-4-ylurea, N-{(4S,8S)-10-[5-(6-methoxypyridin-2-yl)-1,2-oxazol-3-yl]-4,7,8,9-tetrahydro-5H-4,8-epiminooxocino[5,4-d][1,3]thiazol-2-yl}-N'-[(3S)-oxolan-3-yl]urea, N-{(4S,8S)-10-[5-(6-methoxypyridin-2-yl)-1,2-oxazol-3-yl]-4,7,8,9-tetrahydro-5H-4,8-epiminooxocino[5,4-d][1,3]thiazol-2-yl}-N'-[(3R)-oxolan-3-yl]urea, N-{(4S,8S)-10-[5-(3-methoxyphenyl)-1,2-oxazol-3-yl]-4,7,8,9-tetrahydro-5H-4,8-epiminooxocino[5,4-d][1,3]thiazol-2-yl}-N'-[(3R)-oxolan-3-yl]urea, N-(1,1-dioxo-1$\lambda^6$-thian-4-yl)-N'-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}urea, N-(10-{5-[3-(difluoromethyl)phenyl]-1,3-oxazol-2-yl}-4,7,8,9-tetrahydro-5H-4,8-epiminooxocino[5,4-d][1,3]thiazol-2-yl)-N'-[(1r,3r)-3-hydroxycyclobutyl]urea, N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-[(1r,3S)-3-hydroxycyclobutyl]urea, N-[(4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-yl]-N'-[(2S)-1-hydroxypropan-2-yl]urea, N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(2S)-1-hydroxypropan-2-yl]urea, N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-(1-hydroxy-2-methylpropan-2-yl)urea, N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-[(2R)-2-hydroxypropyl]urea, N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-(2-hydroxy-2-methylpropyl)urea, N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-[(2S)-1-hydroxypropan-2-yl]urea, N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(2S)-2-hydroxypropyl]urea, N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(3R,4S)-4-hydroxyoxolan-3-yl]urea, N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(1r,4r)-4-hydroxycyclohexyl]urea, N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(2-hydroxypyridin-4-yl)methyl]urea, N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(1-methyl-2-oxo-1,2-dihydropyridin-4-yl)methyl]urea, N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(1-hydroxycyclopropyl)methyl]urea, N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-(1,1-dioxo-1$\lambda^6$-thian-4-yl)urea, N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[1-(hydroxymethyl)cyclopropyl]urea, N-[(3R)-1-acetylpyrrolidin-3-yl]-N'-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]urea, N-(1-acetylazetidin-3-yl)-N'-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]urea, N-(2-hydroxy-2-methylpropyl)-N'-{(4S,8S)-10-[5-(6-methoxypyridin-2-yl)-

1,3-oxazol-2-yl]-4,7,8,9-tetrahydro-5H-4,8-epiminooxocino[5,4-d][1,3]thiazol-2-yl}urea, N-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}-N'-[(3R)-oxolan-3-yl]urea, N-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}-N'-oxan-4-ylurea, N-[(1s,4s)-4-hydroxycyclohexyl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea, N-[(1r,4r)-4-hydroxycyclohexyl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea, N-[(2R)-1-hydroxypropan-2-yl]-N'-[5-(5-methoxy-1,3-benzoxazol-2-yl)-4,5,6,7-tetrahydro[1,3]thiazolo[5,4-c]pyridin-2-yl]urea, N-(2-hydroxy-2-methylpropyl)-N'-[5-(5-methoxy-1,3-benzoxazol-2-yl)-6,6-dimethyl-4,5,6,7-tetrahydro[1,3]thiazolo[5,4-c]pyridin-2-yl]urea, N-[(2R)-1-hydroxypropan-2-yl]-N'-{5-[4-(oxan-3-yl)pyrimidin-2-yl]-4,5,6,7-tetrahydro[1,3]thiazolo[5,4-c]pyridin-2-yl}urea, N-[(1r,3r)-3-hydroxycyclobutyl]-N'-{5-[4-(oxan-3-yl)pyrimidin-2-yl]-4,5,6,7-tetrahydro[1,3]thiazolo[5,4-c]pyridin-2-yl}urea, and N-[(2R)-1-hydroxypropan-2-yl]-N'-{(4S,8S)-10-[5-(6-methoxy-5-methylpyridin-2-yl)-1,3-oxazol-2-yl]-4,7,8,9-tetrahydro-5H-4,8-epiminooxocino[5,4-d][1,3]thiazol-2-yl}urea.

A preferred embodiment of the present invention is a compound selected from the following compounds or a pharmaceutically acceptable salt thereof.

The compound is selected from N-{5-[3-(4,4-difluorocyclohexyl)-1,2,4-oxadiazol-5-yl]-4,5,6,7-tetrahydro[1,3]thiazolo[5,4-c]pyridin-2-yl}-N'-methylurea, N-methyl-N'-{5-[5-(trifluoromethyl)-1,3,4-oxadiazol-2-yl]-4,5,6,7-tetrahydro[1,3]thiazolo[5,4-c]pyridin-2-yl}urea, N-(5-{5-[(1R)-1-ethoxyethyl]-1,3,4-oxadiazol-2-yl}-4,5,6,7-tetrahydro[1,3]thiazolo[5,4-c]pyridin-2-yl)-N'-methylurea, N-methyl-N'-(5-{3-[1-(2,2,2-trifluoroethoxy)ethyl]-1,2,4-oxadiazol-5-yl}-4,5,6,7-tetrahydro[1,3]thiazolo[5,4-c]pyridin-2-yl)urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(2R)-1-hydroxypropan-2-yl]urea, N-methyl-N'-(10-{3-[(1s,4s)-4-(trifluoromethyl)cyclohexyl]-1,2,4-oxadiazol-5-yl}-4,7,8,9-tetrahydro-5H-4,8-epiminooxocino[5,4-d][1,3]thiazol-2-yl)urea, N-{(4S,8S)-10-[3-(4,4-difluorocyclohexyl)-1,2,4-oxadiazol-5-yl]-4,7,8,9-tetrahydro-5H-4,8-epiminooxocino[5,4-d][1,3]thiazol-2-yl}-N'-methylurea, N-methyl-N'-(5-{3-[3-(trifluoromethoxy)phenyl]-1,2,4-oxadiazol-5-yl}-4,5,6,7-tetrahydro[1,3]thiazolo[5,4-c]pyridin-2-yl)urea, N-{5-[5-(4-fluoro-3-methylphenyl)-1,3,4-oxadiazol-2-yl]-4,5,6,7-tetrahydro[[1,3]thiazolo[5,4-c]pyridin-2-yl}-N'-methylurea, N-{(5R*,8S*)-9-[3-(4-fluorophenyl)-1,2,4-oxadiazol-5-yl]-5,6,7,8-tetrahydro-4H-5,8-epiminocyclohepta[d][1,3]thiazol-2-yl}-N'-methylurea, N-{9-[5-(4-fluorophenyl)-1,2-oxazol-3-yl]-5,6,7,8-tetrahydro-4H-5,8-epiminocyclohepta[d][1,3]thiazol-2-yl}-N'-methylurea, N-{(5R*,9S*)-10-[3-(4-fluorophenyl)-1,2,4-oxadiazol-5-yl]-4,5,6,7,8,9-hexahydro-5,9-epiminocycloocta[d][1,3]thiazol-2-yl}-N'-methylurea, N-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-methylurea, N-(10-{5-[3-(difluoromethyl)phenyl]-1,3-oxazol-2-yl}-4,7,8,9-tetrahydro-5H-4,8-epiminooxocino[5,4-d][1,3]thiazol-2-yl)-N'-methylurea, N-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}-N'-methylurea, N-{10-[5-(4-fluorophenyl)-1,2-oxazol-3-yl]-4,7,8,9-tetrahydro-5H-4,8-epiminooxocino[5,4-d][1,3]thiazol-2-yl}-N'-methylurea, N-{(4S,8S)-10-[4-(4-fluorophenyl)-1,3-oxazol-2-yl]-4,7,8,9-tetrahydro-5H-4,8-epiminooxocino[5,4-d][1,3]thiazol-2-yl}-N'-methylurea, N-{10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-[(2R)-1-hydroxypropan-2-yl]urea, N-{6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-methylurea, (5R)-3-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}-5-methylimidazolidin-2,4-dione, N-[(4S,8S)-10-{5-[3-(cyclopropanecarbonyl)phenyl]-1,3,4-oxadiazol-2-yl}-4,7,8,9-tetrahydro-5H-4,8-epiminooxocino[5,4-d][1,3]thiazol-2-yl]-N'-methylurea, N-[(4S,8S)-10-{5-[3-(difluoromethoxy)phenyl]-1,3,4-oxadiazol-2-yl}-4,7,8,9-tetrahydro-5H-4,8-epiminooxocino[5,4-d][1,3]thiazol-2-yl]-N'-methylurea, (−)-N-{(4R*,8R*)-6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-methylurea, (−)-methyl(4R*,8R*)-10-[3-(4-fluorophenyl)-1,2,4-oxadiazol-5-yl]-2-[(methylcarbamoyl)amino]-4,7,8,9-tetrahydro-4,8-epimino[1,3]thiazolo[5,4-d]azocin-6(5H)-carboxylate, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1R,2R)-2-hydroxycyclopentyl]urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1r,4r)-4-hydroxycyclohexyl]urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-(3-methoxypropyl)urea, N-{5-[3-(3,3-difluorocyclohexyl)-1,2,4-oxadiazol-5-yl]-4,5,6,7-tetrahydro[1,3]thiazolo[5,4-c]pyridin-2-yl}-N'-(2-hydroxy-2-methylpropyl)urea, N-{[(2S)-1,4-dioxan-2-yl]methyl}-N'-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}urea, N-{10-[3-(4-fluorophenyl)-1,2,4-oxadiazol-5-yl]-6-(methanesulfonyl)-4,5,6,7,8,9-hexahydro-4,8-epimino[1,3]thiazolo[5,4-d]azocin-2-yl}-N'-oxan-4-ylurea, N-{10-[3-(4-fluorophenyl)-1,2,4-oxadiazol-5-yl]-6-(methanesulfonyl)-4,5,6,7,8,9-hexahydro-4,8-epimino[1,3]thiazolo[5,4-d]azocin-2-yl}-N'-methylurea, propan-2-yl-10-[3-(4-fluorophenyl)-1,2,4-oxadiazol-5-yl]-2-[(methylcarbamoyl)amino]-4,7,8,9-tetrahydro-4,8-epimino[1,3]thiazolo[5,4-d]azocin-6(5H)-carboxylate, methyl(4R*,8R*)-2-{[(2-hydroxy-2-methylpropyl)carbamoyl]amino}-10-{3-[1-(trifluoromethyl)cyclopropyl]-1,2,4-oxadiazol-5-yl}-4,7,8,9-tetrahydro-4,8-epimino[1,3]thiazolo[5,4-d]azocin-6(5H)-carboxylate, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[2-(2-hydroxyethoxy)ethyl]urea, N-{5-[3-(3,3-difluorocyclopentyl)-1,2,4-oxadiazol-5-yl]-4,5,6,7-tetrahydro[1,3]thiazolo[5,4-c]pyridin-2-yl}-N'-[(1r,3r)-3-hydroxycyclobutyl]urea, N-{5-[3-(3,3-difluorocyclohexyl)-1,2,4-oxadiazol-5-yl]-4,5,6,7-tetrahydro[1,3]thiazolo[5,4-c]pyridin-2-yl}-N'-methylurea, N-[(3R)-oxolan-3-yl]-N'-[(4S,8S)-10-{3-[1-(trifluoromethyl)cyclopropyl]-1,2,4-oxadiazole-5-yl]-4,7,8,9-tetrahydro-5H-4,8-epiminooxocino[5,4-d][1,3]thiazol-2-yl]urea, N-[(2R)-1-hydroxypropan-2-yl]-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea, N-[(4S,8S)-10-(5-fluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea, N-[(4S,8S)-10-(5-ethoxy-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea, N-{(4S,8S)-10-[5-(dimethylamino)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea, N-[(4S,8S)-10-(5,6-difluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea, N-{(4S,8S)-10-[5-(methanesulfonyl)-1,3-benzoxazol-2-yl]-4,7,8,9-tetrahydro-5H-4,8-epiminooxocino[5,4-d][1,3]thiazol-2-yl}-N'-(2-methylpropyl)urea, N-(2-hydroxy-2-methylpropyl)-N'-[(4S,8S)-10-(5-methoxy-6-methyl-1,3-benzoxazol-2-yl)-4,7,8,9-tetrahydro-5H-4,8-epiminooxocino[5,4-d][1,3]thiazol-2-yl]urea, N-[(4S,8S)-10-(5-methoxy-6-methyl-1,3-benzoxazol-2-yl)-4,7,8,9-tetrahydro-5H-4,8-epiminooxocino[5,4-d][1,3]thiazol-2-yl]-N'-[(3R)-oxolan-3-yl]urea, N-(2-hydroxy-2-methylpropyl)-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea, N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-[(3R)-oxolan-3-yl]urea, N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-methylurea, N-methyl-N'-[(4S,8S)-10-(5-methyl-1,3-benzoxazol-2-yl)-4,7,8,9-tetrahydro-5H-4,8-epiminooxocino[5,4-d][1,3]thiazol-2-yl]urea, N-{(4S,8S)-10-[5-(methanesulfonyl)-1,3-benzoxazol-2-yl]-4,7,8,9-tetrahydro-5H-4,8-epiminooxocino[5,4-d][1,3]thiazol-2-yl}-N'-propan-2-ylurea, N-[(4S,8S)-10-(6-cyano-5-methyl-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea, N-[(4S,8S)-10-(5-ethoxy-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea, N-{(4S,8S)-10-[5-(difluoromethyl)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea, N-[(1r,3S)-3-hydroxycyclobutyl]-N'-[(4S,8S)-10-(5-trifluoromethoxy-1,3-benzoxazol-2-yl)-4,7,8,9-tetrahydro-5H-4,8-epiminooxocino[5,4-d][1,3]thiazol-2-yl]urea, N-{(4S,8S)-10-(5-cyano-6-fluoro-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea, N-{(4S,8S)-10-[5-(difluoromethyl)-1,3-benzoxazol-2-yl]-4,7,8,9-tetrahydro-5H-4,8-epiminooxocino[5,4-d][1,3]thiazol-2-yl}-N'-[(2R)-1-hydroxypropan-2-yl)urea, N-{(4S,8S)-10-[5-(fluoromethoxy)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea, N-(1-hydroxy-2-methylpropan-2-yl)-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea, N-[(4S,8S)-10-(5-chloro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea, N-(2-hydroxy-2-methylpropyl)-N'-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]urea, N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(1s,4s)-4-hydroxycyclohexyl]urea, N-{(4S,8S)-10-[5-(6-methoxypyridin-2-yl)-1,2-oxazol-3-yl]-4,7,8,9-tetrahydro-5H-4,8-epiminooxocino[5,4-d][1,3]thiazol-2-yl}-N'-oxan-4-ylurea, N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-(2-hydroxy-2-methylpropyl)urea, methyl 10-[5-(4-fluorophenyl)-1,2-oxazol-3-yl]-2-[(methylcarbamoyl)amino]-4,7,8,9-tetrahydro-4,8-epimino[1,3]thiazolo[5,4-d]azocin-6(5H)-carboxylate, N-{(4S,8S)-10-[5-(4-fluorophenyl)-1,2-oxazol-3-yl]-4,7,8,9-tetrahydro-5H-4,8-epiminooxocino[5,4-d][1,3]thiazolo-2-yl}-N'-[(2R)-2-hydroxypropyl]urea, N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(2R)-1-hydroxypropan-2-yl]urea, N-[(2R)-1-hydroxypropan-2-yl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea, N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-[(2R)-1-hydroxypropan-2-yl]urea, N-[(4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-yl]-N'-(1-hydroxy-2-methylpropan-2-yl)urea, N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-[(2R)-1-hydroxypropan-2-yl]urea, N-[(4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-yl]-N'-[(2R)-1-hydroxypropan-2-yl]urea, N-[(4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-yl]-N'-[(2R)-2-hydroxypropyl]urea, N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-[(3R)-oxolan-3-yl]urea, N-[(2R)-1-hydroxypropan-2-yl]-N'-{5-[5-(methanesulfonyl)-1,3-benzoxazol-2-yl]-6,6-dimethyl-4,5,6,7-tetrahydro[1,3]thiazolo[5,4-c]pyridin-2-yl}urea, N-(2-hydroxy-2-methylpropyl)-N'-{5-[5-(methanesulfonyl)-1,3-benzoxazol-2-yl]-6,6-dimethyl-4,5,6,7-tetrahydro[1,3]thiazolo[5,4-c]pyridin-2-yl}urea, N-[(2R)-1-hydroxypropan-2-yl]-N'-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]urea, N-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]-N'-[(3R)-oxolan-3-yl]urea, N-[(1r,3S)-3-hydroxycyclobutyl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea, N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-(2-hydroxy-2-methylpropyl)urea, and N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-[(1r,3S)-3-hydroxycyclobutyl]urea.

A more preferred embodiment of the present invention is a compound selected from the following compounds or a pharmaceutically acceptable salt thereof.

The compound is selected from N-[(4S,8S)-10-{5-[3-(cyclopropanecarbonyl)phenyl]-1,3,4-oxadiazol-2-yl}-4,7,8,9-tetrahydro-5H-4,8-epiminooxocino[5,4-d][1,3]thiazol-2-yl]-N'-methylurea, (–)-N-{(4R*,8R*)-6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-methylurea, (–)-methyl(4R*,8R*)-10-[3-(4-fluorophenyl)-1,2,4-oxadiazol-5-yl]-2-[(methylcarbamoyl)amino]-4,7,8,9-tetrahydro-4,8-epimino[1,3]thiazolo[5,4-d]azocin-6(5H)-carboxylate, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1R,2R)-2-hydroxycyclopentyl]urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1r,4r)-4-hydroxycyclohexyl]urea, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-(3-methoxypropyl)urea, N-{[(2S)-1,4-dioxan-2-yl]methyl}-N'-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}urea, N-[(2R)-1-hydroxypropan-2-yl]-N'-[(4S,8S)-10-(5-methoxy-1,3-benzoxazol-2-yl)-4,7,8,9-tetrahydro-5H-4,8-epiminooxocino[5,4-d][1,3]

thiazol-2-yl]urea, N-[(4S,8S)-10-(5-fluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea, N-[(4S,8S)-10-(5-ethoxy-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea, N-{(4S,8S)-10-[5-(dimethylamino)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea, N-[(4S,8S)-10-(5,6-difluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea, N-{(4S,8S)-10-[5-(methanesulfonyl)-1,3-benzoxazol-2-yl]-4,7,8,9-tetrahydro-5H-4,8-epiminooxocino[5,4-d][1,3]thiazol-2-yl}-N'-(2-methylpropyl)urea, N-(2-hydroxy-2-methylpropyl)-N'-[(4S,8S)-10-(5-methoxy-6-methyl-1,3-benzoxazol-2-yl)-4,7,8,9-tetrahydro-5H-4,8-epiminooxocino[5,4-d][1,3]thiazol-2-yl]urea, N-[(4S,8S)-10-(5-methoxy-6-methyl-1,3-benzoxazol-2-yl)-4,7,8,9-tetrahydro-5H-4,8-epiminooxocino[5,4-d][1,3]thiazol-2-yl]-N'-[(3R)-oxolan-3-yl]urea, N-(2-hydroxy-2-methylpropyl)-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea, N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-[(3R)-oxolan-3-yl]urea, N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-methylurea, N-methyl-N'-[(4S,8S)-10-(5-methyl-1,3-benzoxazol-2-yl)-4,7,8,9-tetrahydro-5H-4,8-epiminooxocino[5,4-d][1,3]thiazol-2-yl]urea, N-(2-hydroxy-2-methylpropyl)-N'-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]urea, N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(1s,4s)-4-hydroxycyclohexyl]urea, N-{(4S,8S)-10-[5-(6-methoxypyridin-2-yl)-1,2-oxazol-3-yl]-4,7,8,9-tetrahydro-5H-4,8-epiminooxocino[5,4-d][1,3]thiazol-2-yl}-N'-oxan-4-ylurea, N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(2R)-1-hydroxypropan-2-yl]urea, N-[(2R)-1-hydroxypropan-2-yl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea, N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-[(2R)-1-hydroxypropan-2-yl]urea, N-[(2R)-1-hydroxypropan-2-yl]-N'-{5-[5-(methanesulfonyl)-1,3-benzoxazol-2-yl]-6,6-dimethyl-4,5,6,7-tetrahydro[1,3]thiazolo[5,4-c]pyridin-2-yl}urea, N-(2-hydroxy-2-methylpropyl)-N'-{5-[5-(methanesulfonyl)-1,3-benzoxazol-2-yl]-6,6-dimethyl-4,5,6,7-tetrahydro[1,3]thiazolo[5,4-c]pyridin-2-yl}urea, N-[(2R)-1-hydroxypropan-2-yl]-N'-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]urea, N-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]-N'-[(3R)-oxolan-3-yl]urea, N-[(1r,3S)-3-hydroxycyclobutyl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea, N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-(2-hydroxy-2-methylpropyl)urea, and N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-[(1r,3S)-3-hydroxycyclobutyl]urea.

Hereinafter, the substituents and the terms used to represent the compound represented by Formula (1) or the pharmaceutically acceptable salt thereof will be described.

The "C1-C6 alkyl group" in the present specification is a linear or branched alkyl group having 1 to 6 carbon atoms, and examples thereof include a methyl group, an ethyl group, a 1-propyl group, an isopropyl group, a 1-butyl group, a 2-butyl group, a 2-methyl-1-propyl group, a 2-methyl-2-propyl group, a 1-pentyl group, a 2-pentyl group, a 3-pentyl group, a 2-methyl-2-butyl group, a 3-methyl-2-butyl group, a 1-hexyl group, a 2-hexyl group, a 3-hexyl group, a 2-methyl-1-pentyl group, a 3-methyl-1-pentyl group, a 2-ethyl-1-butyl group, a 2,2-dimethyl-1-butyl group, and a 2,3-dimethyl-1-butyl group.

The "C1-C6 alkoxy group" in the present specification is a group in which a C1-C6 alkyl group bonds to an oxy group, and examples thereof include a methoxy group, an ethoxy group, a 1-propoxy group, a 2-propoxy group, a 1-butoxy group, a 2-butoxy group, a 2-methyl-1-propoxy group, a 2-methyl-2-propoxy group, a 1-pentyloxy group, a 2-pentyloxy group, a 3-pentyloxy group, a 2-methyl-2-butoxy group, a 3-methyl-2-butoxy group, a 1-hexyloxy group, a 2-hexyloxy group, a 3-hexyloxy group, a 2-methyl-1-pentyloxy group, and a 3-methyl-1-pentyloxy group.

The "hydroxy C1-C6 alkyl group" in the present specification is a group in which a predetermined number of hydroxyl groups bond to a C1-C6 alkyl group. The "hydroxy C1-C6 alkyl group" is preferably a group in which one to three hydroxyl groups bond to a C1-C6 alkyl group and more preferably a group in which one hydroxyl group bonds to a C1-C6 alkyl group. Specific examples thereof include a hydroxymethyl group, a hydroxyethyl group, a hydroxypropyl group, a hydroxyisopropyl group, and a hydroxyisobutyl group.

The "C1-C6 alkylcarbonyl group" in the present specification is a group in which a C1-C6 alkyl group bonds to a carbonyl group, and examples thereof include an acetyl group, an ethylcarbonyl group, and a propylcarbonyl group.

The "C1-C6 alkylcarbamoyl group" in the present specification is a group in which a C1-C6 alkyl group bonds to a carbamoyl group, and examples thereof include a methylcarbamoyl group, an ethylcarbamoyl group, and a propylcarbamoyl group.

The "C1-C6 alkylsulfonyl group" in the present specification is a group in which a C1-C6 alkyl group bonds to a sulfonyl group, and examples thereof include a methanesulfonyl group, an ethanesulfonyl group, and a butanesulfonyl group.

The "C1-C6 alkoxycarbonyl group" in the present specification is a group in which a C1-C6 alkoxy group bonds to a carbonyl group, and examples thereof include a methoxycarbonyl group, an ethoxycarbonyl group, and a t-butoxycarbonyl group.

The "hydroxy C1-C6 alkoxy group" in the present specification is a group in which a predetermined number of hydroxyl groups bond to a C1-C6 alkoxy group. The "hydroxy C1-C6 alkoxy group" is preferably a group in which one to three hydroxyl groups bond to a C1-C6 alkoxy group and more preferably a group in which one hydroxyl group bonds to a C1-C6 alkoxy group. Specific examples thereof include a hydroxymethoxy group, a hydroxyethoxy group, a hydroxypropoxy group, a hydroxyisopropoxy group, and a hydroxyisobutoxy group.

The "C3-C6 cycloalkyl group" in the present specification is a cyclic alkyl group having 3 to 6 carbon atoms, and examples thereof include a cyclopropyl group, a cyclobutyl group, a cyclopentyl group, and a cyclohexyl group.

The "C3-C6 cycloalkoxy group" in the present specification is a group in which a C3-C6 cycloalkyl group bonds to an oxy group, and examples thereof include a cyclopropoxy group, a cyclobutoxy group, a cyclopentyloxy group, and a cyclohexyloxy group.

The "C3-C6 cycloalkylcarbonyl group" in the present specification is a group in which a cyclic alkyl group having 3 to 6 carbon atoms bonds to a carbonyl group, and examples thereof include a cyclopropylcarbonyl group, a cyclobutylcarbonyl group, a cyclopentylcarbonyl group, and a cyclohexylcarbonyl group.

The "hydroxy C3-C6 cycloalkyl group" in the present specification is a group in which a predetermined number of hydroxyl groups bond to a C3-C6 cycloalkyl group. The "hydroxy C3-C6 cycloalkyl group" is preferably a group in which one to three hydroxyl groups bond to a C3-C6 cycloalkyl group and more preferably a group in which one hydroxyl group bonds to a C3-C6 cycloalkyl group. Specific examples thereof include a hydroxycyclopropyl group, a hydroxycyclobutyl group, a hydroxycyclopentyl group, and a hydroxycyclohexyl group.

The "4- to 7-membered heterocyclic group" in the present specification is a monocyclic 4- to 7-membered heterocyclic group having 1 to 3 atoms selected from the group consisting of a nitrogen atom, an oxygen atom, and a sulfur atom, and may have one or two unsaturated bonds in the ring. Examples thereof include an azetidyl group, a pyrrolidyl group, an imidazolyl group, a pyrazolyl group, an oxazolyl group, a thiazolyl group, a piperidinyl group, an azepanyl group, a piperazinyl group, a hexahydropyrimidinyl group, a morphoryl group, thiomorphoryl group, an oxetanyl group, a tetrahydrofuranyl group, a tetrahydropyranyl group, a dioxanyl group, a thioxanyl group, an oxepanyl group, and a dihydropyridyl group. Preferred examples thereof include the following rings.

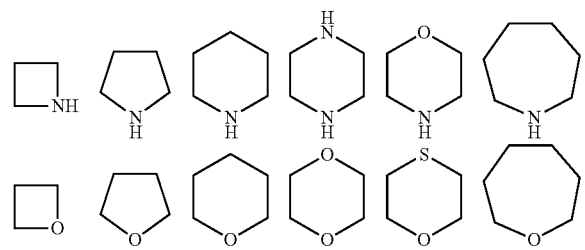

The "5- to 6-membered heterocyclic group" in the present specification is a monocyclic 5- to 6-membered aromatic heterocyclic group having one to three atoms selected from the group consisting of a nitrogen atom, an oxygen atom, and a sulfur atom, and examples thereof include an imidazolyl group, a triazolyl group, a pyridyl group, and a pyrimidyl group.

Examples of the "halogen atom" in the present specification include a fluorine atom, a chlorine atom, a bromine atom, and an iodine atom.

The "halo-C1-C6 alkyl group" in the present specification is a C1-C6 alkyl group substituting a predetermined number of halogen atoms. The "halo-C1-C6 alkyl group" is preferably a group in which one to three halogen atoms bond to a C1-C6 alkyl group. Specific examples thereof include a difluoromethyl group, a trifluoromethyl group, and a difluoroethyl group.

The "halo-C1-C6 alkoxy group" in the present specification is a C1-C6 alkoxy group substituting a predetermined number of halogen atoms. The "halo-C1-C6 alkoxy group" is preferably a group in which one to three halogen atoms bond to a C1-C6 alkoxy group. Specific examples thereof include a difluoromethoxy group, a trifluoromethoxy group, and a difluoroethoxy group.

The "C1-C6 alkoxy C1-C6 alkyl group" in the present specification is a group in which one C1-C6 alkoxy group bonds to a C1-C6 alkyl group, and examples thereof include a methoxymethyl group, an ethoxymethyl group, and an ethoxyethyl group.

The "halo-C1-C6 alkoxy C1-C6 alkyl group" in the present specification is a group in which one halo-C1-C6 alkoxy group bonds to a C1-C6 alkyl group, and examples thereof include a difluoromethoxymethyl group, a trifluoromethoxymethyl group, and a difluoroethoxyethyl group.

The "mono(C1-C6 alkyl)amino group" in the present specification is a group in which one C1-C6 alkyl group bonds to an amino group, and examples thereof include a methylamino group, an ethylamino group, and a propylamino group.

The "di(C1-C6 alkyl)amino group" in the present specification is a group in which two C1-C6 alkyl groups that are the same or different from each other bond to an amino group, and examples thereof include a dimethylamino group, a diethylamino group, and a dipropylamino group.

The "amino C1-C6 alkyl group" in the present specification is a group in which one amino group bonds to a C1-C6 alkyl group, and examples thereof include an aminomethyl group, an aminoethyl group, and an aminopropyl group.

The "mono (C1-C6 alkyl)aminosulfonyl group" in the present specification is a group in which a mono(C1-C6 alkyl)amino group bonds to a sulfonyl group, and examples thereof include a methylaminosulfonyl group and an ethylaminosulfonyl group.

The "C1-C4 alkylene group" in the present specification is a saturated chain-like alkylene group having 1 to 4 carbon atoms with two bonding sites, and examples thereof include a methylene group, an ethylene group, a propylene group, and a butylene group.

The "pharmaceutically acceptable salt thereof" refers to a salt that can be used as a drug. When a compound contains an acidic group or a basic group, the compound can form a basic salt or an acidic salt by allowing the acidic group or the basic group to react to the base or the acid, and thus the pharmaceutically acceptable salt thereof refers to such a salt.

Preferred examples of the pharmacologically acceptable "basic salt" of a compound include an alkali metal salt such as a sodium salt, a potassium salt, or a lithium salt; an alkaline earth metal salt such as a magnesium salt or a calcium salt; organic base salts such as a N-methylmorpholine salt, a triethylamine salt, a tributylamine salt, a diisopropylethylamine salt, a dicyclohexylamine salt, a N-methylpiperidine salt, a pyridine salt, a 4-pyrrolidinopyridine salt, and a picoline salt; and an amino acid salt such as a glycine salt, a lysine salt, an arginine salt, an ornithine salt, a glutamate, and an aspartate. Among these, an alkali metal salt is preferable.

Preferred examples of the pharmacologically acceptable "acidic salt" of a compound include an inorganic acid salt, for example, a hydrohalogenic acid salt such as a hydrofluoride, a hydrochloride, a hydrobromate, or a hydroiodide, a nitrate, a perchlorate, a sulfate, or a phosphate; an organic acid salt, for example, a lower alkane sulfonate such as a methane sulfonate, a trifluoromethane sulfonate, or an ethane sulfonate, an aryl sulfonate such as a benzene sulfonate or a p-toluene sulfonate, an acetate, a malate, a fumarate, a succinate, a citrate, an ascorbate, a tartrate, an oxalate, or a maleate; and an amino acid salt such as a glycine salt, a lysine salt, an arginine salt, an ornithine salt, a glutamate, or an aspartate. Among these, a hydrohalogenic acid salt (particularly a hydrochloride) is most preferable.

When the compound or the pharmaceutically acceptable salt thereof is allowed to stand in the air or recrystallized, the compound of the present invention or the pharmaceutically acceptable salt thereof may absorb moisture to have adsorbed water attached thereto or to form a hydrate, and the present invention also includes such various hydrates, solvates, and polymorphic compounds.

The compound of the present invention, the pharmaceutically acceptable salt thereof, or the solvate thereof can be in various forms of isomers such as geometric isomers such as cis isomers or trans isomers, and optical isomers (including enantiomers and diastereomers) such as tautomers, rotational isomers, d-isomers, and l-isomers, depending on the kind and the combination of substituents. Unless otherwise specified, the compound of the present invention includes all isomers, steric isomers, and mixtures of these isomers and steric isomers in any ratio. The mixtures of these isomers can be separated by known dividing means.

The compound of the present invention also include a labeled compound, that is, a compound in which one or more atoms of the compound are substituted with an isotope (such as 2H, 3H, 13C, 14C, or 35S).

The compound of the present invention is typically named according to the nomenclature of the International Union of Pure and Applied Chemistry (IUPAC).

In the compound name of the present invention, when a compound has an atom of an asymmetric center in the structure, the absolute configuration of the atom may be shown using R and S (noted together with the position number).

The relative configuration may be shown by adding a symbol "*" (R* and S*) to the position notation when the position of the asymmetric center described first is defined as R or S or may be shown by putting a prefix (symbol) rel- (meaning relative) in front of the name.

Particularly, the absolute configuration of a racemic mixture is typically shown without using R and S, but the absolute configuration may be shown by using symbols RS and SR in place of R* and S* or may be shown by putting a prefix (symbol) rac- (meaning racemic) in front of the name.

Further, the present invention also includes so-called prodrugs. A prodrug is a compound containing a group that can be converted to an amino group, a hydroxyl group, a carboxyl group, or the like of the compound through hydrolysis or under physiological conditions, and the group forming such a prodrug is a group described in Prog. Med., Vol. 5, 1985, pp. 2157-2161, and the like. More specific examples of the prodrug include (1) when an amino group is present in the compound, a compound in which the amino group is acylated, alkylated, or phosphorylated (such as a compound in which the amino group is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated); (2) when a hydroxyl group is present in the compound, a compound in which the hydroxyl group is acylated, alkylated, phosphorylated, or boronized (such as a compound in which the hydroxyl group is acetylated, palmitoylated, propanoylated, pivaloylated, succinylated, fumarylated, alanylated, or dimethylaminomethylcarbonylated); and (3) when a carboxy group is present in the compound, a compound in which the carboxy group is esterified and amidated (such as a compound in which the carboxy group is ethyl-esterified, phenyl-esterified, carboxymethyl-esterified, dimethylaminomethyl-esterified, pivaloyloxymethyl-esterified, ethoxycarbonyloxyethyl-esterified, amidated, or methylamidated).

(Production Method)

Hereinafter, the production method will be described. However, the method for producing the compound or the salt thereof is not limited to the following methods.

[Method A]

Method A is a method for producing a compound (A-V).

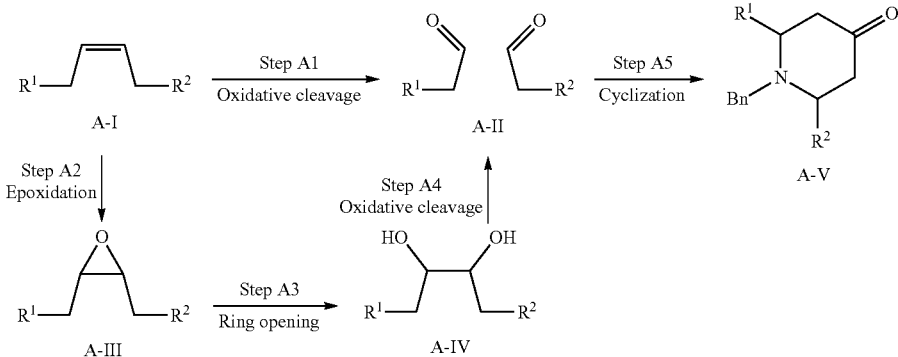

[In the formulae, Bn represents a benzyl group, and $R^1$ and $R^2$ bond to each other to form a substituent and the substituent represents any group selected from the following groups.

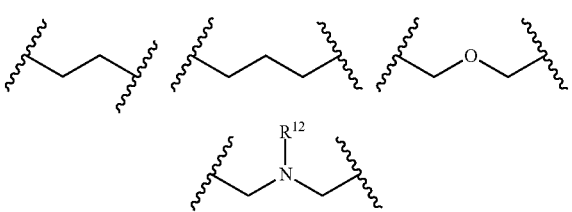

$R^{12}$ represents a C1-C6 alkyl group, a hydroxy C1-C6 alkyl group, a C1-C6 alkylcarbonyl group, or a C1-C6 alkoxycarbonyl group.]

(Step A1) Step of Performing Oxidative Cleavage (In the Case of Using Ozone)

This step is a step of obtaining a compound (A-II) from a compound (A-I) by carrying out a reaction using ozone and a reducing agent.

Examples of the reducing agent include triphenylphosphine and dimethyl sulfide.

Examples of the solvent include methanol, dichloromethane, and a mixture thereof.

The reaction temperature is typically in a range of −78° C. to room temperature, and the reaction time is typically in a range of 0.25 to 24 hours.

(In the Case of Using Oxidizing Agent)

This step is a step of obtaining a compound (A-II) from a compound (A-I) by carrying out a reaction using an oxidizing agent.

Examples of the oxidizing agent include potassium permanganate, osmium tetraoxide, sodium periodate, and a mixture thereof.

Examples of the solvent include tetrahydrofuran, acetonitrile, water, dichloromethane, and a mixture thereof.

The reaction temperature is typically in a range of 0° C. to room temperature, and the reaction time is typically in a range of 0.5 to 24 hours.

(Step A2) Step of Performing Epoxidation

This step is a step of obtaining a compound (A-III) from the compound (A-I) by carrying out a reaction using an oxidizing agent in the presence or absence of a base.

Examples of the base include sodium hydrogen carbonate and pyridine.

Examples of the oxidizing agent include 3-chloroperbenzoic acid (mCPBA) and hydrogen peroxide.

Examples of the solvent include dichloromethane, acetonitrile, methanol, water, and a mixture thereof.

The reaction temperature is typically in a range of 0° C. to 60° C., and the reaction time is typically in a range of 0.25 to 24 hours.

(Step A3) Step of Performing Ring-Opening of Epoxy Ring

This step is a step of obtaining a compound (A-IV) from the compound (A-III) by carrying out a reaction using an aqueous solvent in the presence or absence of an acid or a base.

Examples of the acid include sulfuric acid.

Examples of the base include sodium hydroxide.

Examples of the solvent include tetrahydrofuran, methanol, water, and a mixture thereof.

The reaction temperature is typically in a range of room temperature to 100° C., and the reaction time is typically in a range of 0.25 to 24 hours.

(Step A4) Step of Performing Oxidative Cleavage

This step is a step of obtaining a compound (A-II) from the compound (A-IV) by carrying out a reaction using an oxidizing agent.

Examples of the oxidizing agent include sodium periodate.

Examples of the solvent include tetrahydrofuran, acetonitrile, methanol, water, and a mixture thereof.

The reaction temperature is typically in a range of 0° C. to room temperature, and the reaction time is typically in a range of 0.5 to 24 hours.

(Step A5) Step of Performing Ring Formation

This step is a step of obtaining a compound (A-V) from the compound (A-II) by carrying out a reaction using benzylamine and 1,3-acetonedicarboxylic acid in the presence of an acid.

Examples of the acid include hydrochloric acid.

Examples of the solvent include tetrahydrofuran, acetonitrile, methanol, water, and a mixture thereof.

The reaction temperature is typically in a range of 0° C. to 60° C., and the reaction time is typically in a range of 0.5 to 24 hours.

[Method B]

Method B is a method for producing a compound (B-III).

[In the formulae, Bn represents a benzyl group, and $R^1$ and $R^2$ bond to each other to form a substituent and the substituent represents any group selected from the following groups.

$R^{12}$ represents a C1-C6 alkyl group, a hydroxy C1-C6 alkyl group, a C1-C6 alkylcarbonyl group, or a C1-C6 alkoxycarbonyl group, and $P^{a1}$ represents a protecting group of an amino group that is typically used.]

(Step B1) Step of Performing Deprotection

This step is a step of obtaining a compound (B-II) from a compound (B-I) by carrying out a reaction using a transition metal catalyst in the presence or absence of an acid in a hydrogen atmosphere.

Examples of the acid include hydrochloric acid, hydrogen chloride-1,4-dioxane, and hydrogen chloride-ethyl acetate.

Examples of the transition metal catalyst include palladium-carbon, palladium hydroxide-carbon, and Raney nickel.

Examples of the solvent include methanol, ethanol, ethyl acetate, chloroform, and a mixture thereof.

The reaction temperature is typically in a range of 0° C. to 100° C., and the reaction time is typically in a range of 0.5 to 24 hours.

(Step B2) Step of Performing Protection
(In the Case of Carbamate Group)

This step is a step of obtaining a compound (B-III) from the compound (B-II) by carrying out a reaction using a carbamating reagent in the presence of a base.

In this step, the carbamate group refers to a carbamate group typically used as a protecting group of an amino group in synthesis, such as a t-butoxycarbonyl (Boc) group, a 2-(trimethylsilyl)ethoxycarbonyl (Teoc) group, an allyloxycarbonyl (Alloc) group, a benzyloxycarbonyl (Cbz) group, or the like.

Examples of the base include triethylamine, diisopropylethylamine, sodium hydrogen carbonate, and 4-dimethylaminopyridine.

Examples of the carbamating reagent include chloroformate, dicarbonic acid diester, and succinimidyl carbonate.

Examples of the solvent include tetrahydrofuran, dichloromethane, N,N-dimethylformamide, water, and a mixture thereof.

The reaction temperature is typically in a range of 0° C. to 80° C., and the reaction time is typically in a range of 0.5 to 24 hours.

[Method C]
Method C is a method for producing a compound (C-II).

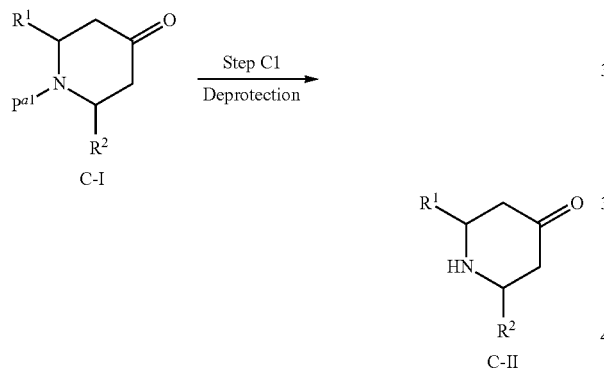

[In the formulae, $R^1$ and $R^2$ have the same definition as that in the case of the compound represented by Formula (1), and $P^{a1}$ has the same definition as described above.]

(Step C1) Step of Performing Deprotection
(In the Case of t-Butoxycarbonyl (Boc) Group)

This step is a step of obtaining a compound (C-II) from a compound (C-I) containing an amino group protected by a t-butoxycarbonyl group by carrying out a reaction using an acid.

Examples of the acid include hydrochloric acid, hydrogen chloride-1,4-dioxane, hydrogen chloride-ethyl acetate, trifluoroacetic acid, and p-toluenesulfonic acid.

Examples of the solvent include methanol, ethanol, tetrahydrofuran, dichloromethane, water, and a mixture thereof.

The reaction temperature is typically in a range of 0° C. to 100° C., and the reaction time is typically in a range of 0.5 to 24 hours.

(In the Case of Benzyl (Bn) Group)

This step is a step of obtaining a compound (C-II) from the compound (C-I) containing an amino group protected by a benzyl group by carrying out a reaction using a transition metal catalyst in the presence or absence of an acid in a hydrogen atmosphere.

This step can be performed according to the same method as in the (step B1).

[Method D]
Method D is a method for producing a compound (D-III).

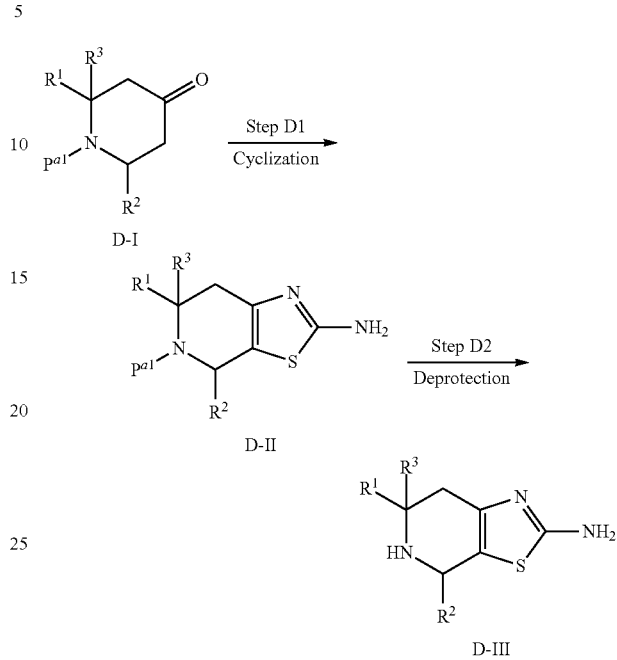

[In the formulae, $R^1$, $R^2$, and $R^3$ have the same definition as that in the case of the compound represented by Formula (1), and $P^{a1}$ has the same definition as described above.]

(Step D1) Step of Performing Formation of Thiazole Ring
(In the Case of Using Sulfur)

This step is a step of obtaining a compound (D-II) from a compound (D-I) by carrying out a reaction using a base, sulfur, cyanamide, and an acid.

Examples of the base include pyrrolidine, piperidine, diethylamine, and pyridine.

Examples of the acid include hydrogen chloride-1,4-dioxane and p-toluenesulfonic acid.

Examples of the solvent include methanol, ethanol, isopropanol, and toluene.

The reaction temperature is typically in a range of 0° C. to 130° C., and the reaction time is typically in a range of 0.5 to 24 hours.

(In the Case of Using Thiourea)

This step is a step of obtaining a compound (D-II) from the compound (D-I) by carrying out a reaction using a halogenating reagent and thiourea in the presence or absence of a base.

Examples of the halogenating reagent include N-bromosuccinimide, bromine, a bromine-1,4-dioxane complex, pyridinium bromide perbromide, iodine, and N-iodosuccinimide.

Examples of the base include sodium hydrogen carbonate.

Examples of the solvent include chloroform, ethanol, and a mixture thereof.

The reaction temperature is typically in a range of 0° C. to 100° C., and the reaction time is typically in a range of 0.5 to 24 hours.

(Step D2) Step of Performing Deprotection
(In the Case of t-Butoxycarbonyl (Boc) Group)

This step is a step of obtaining a compound (D-III) from the compound (D-II) containing an amino group protected by a t-butoxycarbonyl group by carrying out a reaction using an acid.

Examples of the acid include hydrochloric acid, hydrogen chloride-1,4-dioxane, hydrogen chloride-ethyl acetate, trifluoroacetic acid, and p-toluenesulfonic acid.

Examples of the solvent include methanol, ethanol, tetrahydrofuran, dichloromethane, water, and a mixture thereof.

The reaction temperature is typically in a range of 0° C. to 100° C., and the reaction time is typically in a range of 0.5 to 24 hours.

[Method E]

Method E is a method for producing a compound (E-IV).

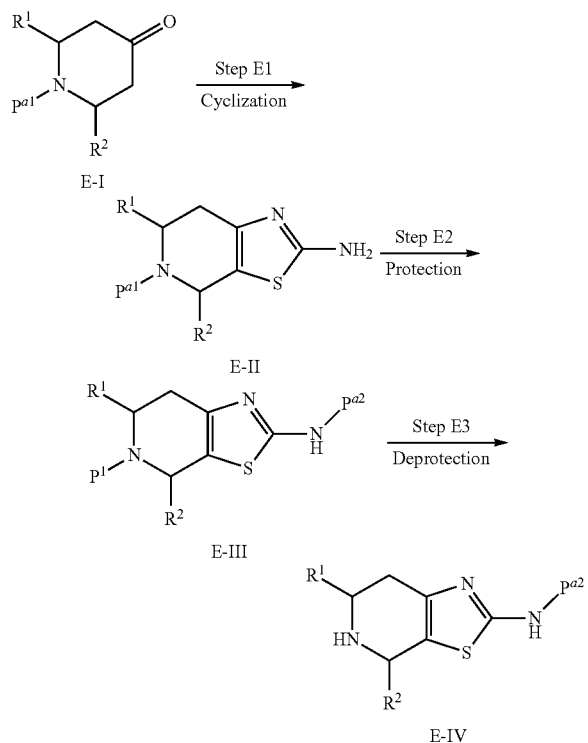

[In the formulae, $R^1$ and $R^2$ have the same definition as that in the case of the compound represented by Formula (1), $P^{a1}$ has the same definition as described above, and $P^{a2}$ represents a protecting group of an amino group that is typically used and is selected independently from $P^{a1}$.]

(Step E1) Step of Performing Formation of Thiazole Ring

This step is a step of obtaining a compound (E-II) from a compound (E-I).

This step can be performed according to the same method as in the (step D1).

(Step E2) Step of Performing Protection (In the Case of Carbamate Group)

This step is a step of obtaining a compound (E-III) from the compound (E-II) by carrying out a reaction using a base and a carbamating reagent.

This step can be performed according to the same method as in the (step B2).

In this step, the carbamate group refers to a carbamate group typically used as a protecting group of an amino group in synthesis, such as a t-butoxycarbonyl (Boc) group, a 2-(trimethylsilyl)ethoxycarbonyl (Teoc) group, an allyloxycarbonyl (Alloc) group, and a benzyloxycarbonyl (Cbz) group.

(In the Case of Acyl Group)

This step is a step of obtaining a compound (E-III) from the compound (E-II) by carrying out a reaction using a base and an acylating reagent.

In this step, the acyl group refers to an acyl group typically used as a protecting group of an amino group in synthesis, such as an acetyl group, a trifluoroacetyl group, and a benzoyl group.

Examples of the base include triethylamine, diisopropylethylamine, pyridine, and 4-dimethylaminopyridine.

Examples of the acylating reagent include acyl chloride and an acid anhydride.

Examples of the solvent include tetrahydrofuran, dichloromethane, and N,N-dimethylformamide.

The reaction temperature is typically in a range of 0° C. to 80° C., and the reaction time is typically in a range of 0.5 to 24 hours.

(Step E3) Step of Performing Deprotection (In the Case of t-Butoxycarbonyl (Boc) Group)

This step is a step of obtaining a compound (E-IV) from the compound (E-III) containing an amino group protected by a t-butoxycarbonyl group by carrying out a reaction using an acid.

This step can be performed according to the same method as in the (step C1).

(In the Case of 2-(Trimethylsilyl)Ethoxycarbonyl (Teoc) Group)

This step is a step of obtaining a compound (E-IV) from the compound (E-III) containing an amino group protected by a 2-(trimethylsilyl)ethoxycarbonyl group by carrying out a reaction using a desilylation reagent or an acid.

Examples of the desilylation reagent include tetrabutylammonium fluoride (TBAF), hydrogen fluoride, and hydrogen fluoride pyridine.

Examples of the acid include hydrochloric acid, sulfuric acid, hydrochloric acid-methanol, hydrochloric acid-1,4-dioxane, hydrochloric acid-ethyl acetate, acetic acid, p-toluenesulfonic acid, and trifluoroacetic acid. In this case, the reaction can be carried out in a catalytic amount.

Examples of the solvent include methanol, ethanol, tetrahydrofuran, 1,2-dimethoxyethane, 1,4-dioxane, acetonitrile, water, and a mixture thereof.

The reaction temperature is typically in a range of 0° C. to 60° C., and the reaction time is typically in a range of 0.5 to 24 hours.

[Method F]

Method F is a method for producing a compound (F-IV).

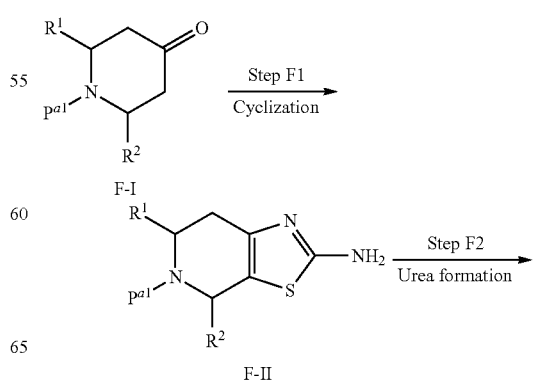

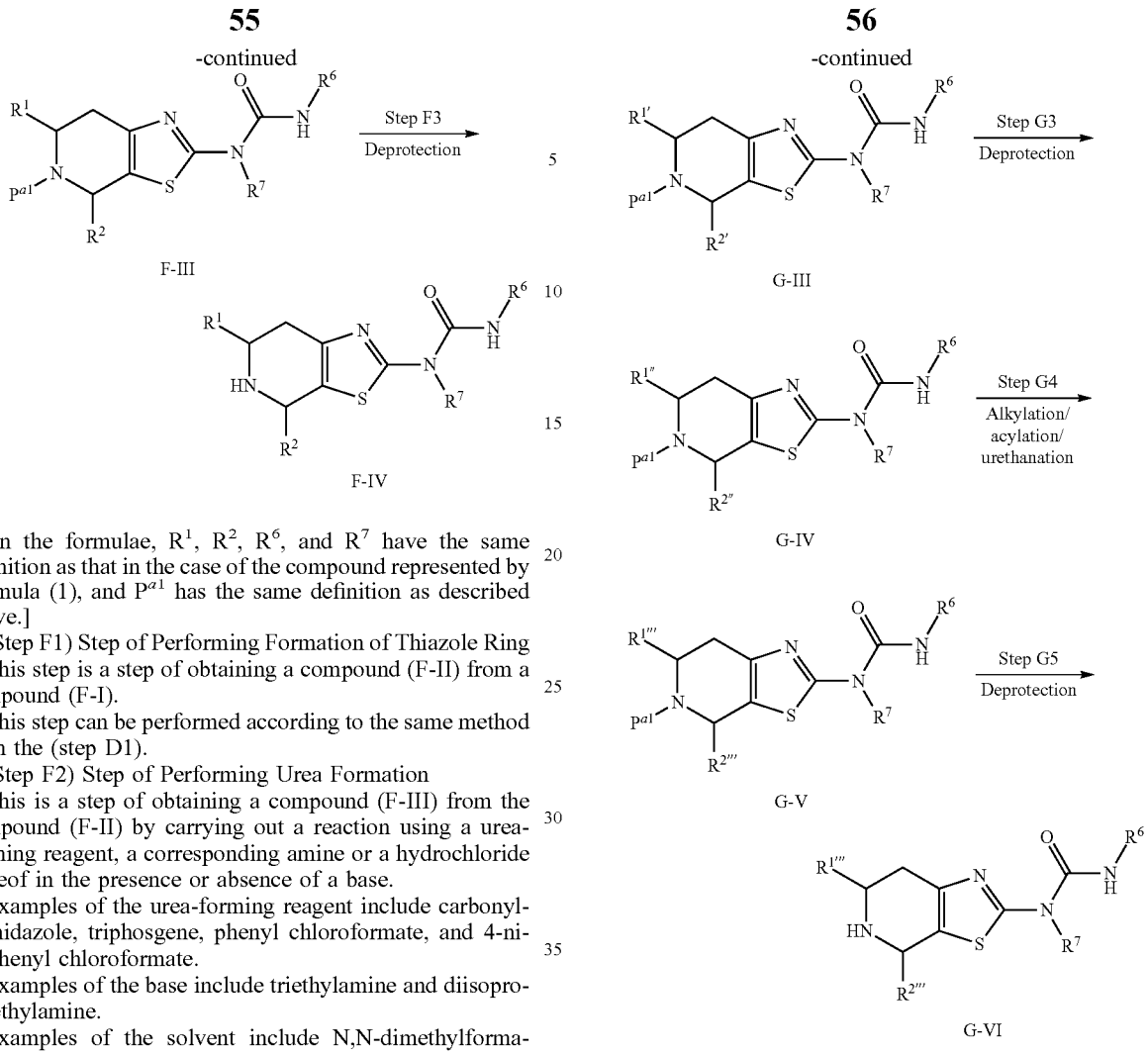

[In the formulae, $R^1$, $R^2$, $R^6$, and $R^7$ have the same definition as that in the case of the compound represented by Formula (1), and $P^{a1}$ has the same definition as described above.]

(Step F1) Step of Performing Formation of Thiazole Ring

This step is a step of obtaining a compound (F-II) from a compound (F-I).

This step can be performed according to the same method as in the (step D1).

(Step F2) Step of Performing Urea Formation

This is a step of obtaining a compound (F-III) from the compound (F-II) by carrying out a reaction using a urea-forming reagent, a corresponding amine or a hydrochloride thereof in the presence or absence of a base.

Examples of the urea-forming reagent include carbonyldiimidazole, triphosgene, phenyl chloroformate, and 4-nitrophenyl chloroformate.

Examples of the base include triethylamine and diisopropylethylamine.

Examples of the solvent include N,N-dimethylformamide, dichloromethane, and tetrahydrofuran.

The reaction temperature is typically in a range of 0° C. to 60° C., and the reaction time is typically in a range of 1 to 48 hours.

(Step F3) Step of Performing Deprotection

This step is a step of obtaining a compound (F-IV) from the compound (F-III).

This step can be performed according to the same method as in the (step E3).

[Method G]

Method G is a method for producing a compound (G-VI).

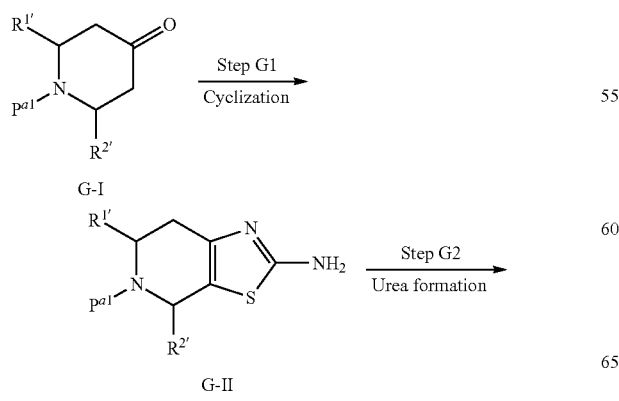

[In the formulae, $R^6$ and $R^7$ have the same definition as that in the case of the compound represented by Formula (1), and $P^{a1}$ has the same definition as described above.

$R^{1\prime}$ and $R^{2\prime}$ bond to each other to form a substituent and the substituent represents a group shown below.

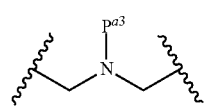

$P^{a3}$ represents a protecting group of an amino group that is typically used and selected independently from $P^{a1}$ and $P^{a2}$.

$R^{1\prime\prime}$ and $R^{2\prime\prime}$ bond to each other to form a substituent and the substituent represents a group shown below.

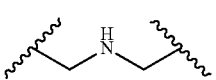 [SMILES: *CNC*]

$R^{1\prime\prime\prime}$ and $R^{2\prime\prime\prime}$ bond to each other to form a substituent and the substituent represents a group shown below.

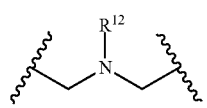

R$^{12}$ represents a C1-C6 alkyl group, a hydroxy C1-C6 alkyl group, a C1-C6 alkylcarbonyl group, or a C1-C6 alkoxycarbonyl group.]

(Step G1) Step of Performing Formation of Thiazole Ring

This step is a step of obtaining a compound (G-II) from a compound (G-I).

This step can be performed according to the same method as in the (step D1).

(Step G2) Step of Performing Urea Formation

This step is a step of obtaining a compound (G-III) from the compound (G-II).

This step can be performed according to the same method as in the (step F2).

(Step G3) Step of Performing Deprotection

This step is a step of obtaining a compound (G-IV) from the compound (G-III).

This step can be performed according to the same method as in the (step E3).

(Step G4) Step of Performing Modification of Amino Group (In the Case of Carbamation)

This step is a step of obtaining a compound (G-V) from the compound (G-IV) by carrying out a reaction using a base and a carbamating reagent.

Examples of the base include triethylamine, diisopropylethylamine, sodium hydrogen carbonate, and 4-dimethylaminopyridine.

Examples of the carbamating reagent include chloroformate and dicarbonic acid diester.

Examples of the solvent include tetrahydrofuran, dichloromethane, and N,N-dimethylformamide.

The reaction temperature is typically in a range of 0° C. to 80° C., and the reaction time is typically in a range of 0.5 to 24 hours.

(In the Case of Acylation)

This step is a step of obtaining a compound (G-V) from the compound (G-IV) by carrying out a reaction using a base and an acylating reagent.

Examples of the base include triethylamine, diisopropylethylamine, pyridine, and 4-dimethylaminopyridine.

Examples of the acylating reagent include acyl chloride and an acid anhydride.

Examples of the solvent include tetrahydrofuran, dichloromethane, and N,N-dimethylformamide.

The reaction temperature is typically in a range of 0° C. to 80° C., and the reaction time is typically in a range of 0.5 to 24 hours.

(In the Case of Alkylation)

(In the Case of Using Alkyl Halide)

This step is a step of obtaining a compound (G-V) from the compound (G-IV) by carrying out a reaction using a corresponding alkylating reagent in the presence of a base.

Examples of the alkylating reagent include alkyl halide such as alkyl iodide or alkyl bromide, and sulfonic acid ester such as alkyl tosylate or alkyl mesylate.

Examples of the base include triethylamine, diisopropylethylamine, and potassium carbonate.

Examples of the solvent include tetrahydrofuran, 1,4-dioxane, and N,N-dimethylformamide. The reaction temperature is typically in a range of 0° C. to 100° C., and the reaction time is typically in a range of 0.5 to 24 hours.

(In the Case of Using Reductive Amination Reaction)

This step is a step of obtaining a compound (G-V) from the compound (G-IV) by carrying out a reaction using a reducing agent and corresponding aldehyde in the presence or absence of an acid.

Examples of the reducing agent include sodium triacetoxyborohydride and sodium cyanoborohydride.

Examples of the acid include acetic acid, tetraisopropyl orthotitanate, and zinc chloride.

Examples of the solvent include methanol, acetonitrile, tetrahydrofuran, dichloromethane, and a mixture thereof.

The reaction temperature is typically in a range of 0° C. to 80° C., and the reaction time is typically in a range of 0.5 to 24 hours.

(Step G5) Step of Performing Deprotection

This step is a step of obtaining a compound (G-VI) from the compound (G-V).

This step can be performed according to the same method as in the (step E3).

In the following method H, method I, method J, method K, method L, method M, method N, method X, method Y, and method Z, for convenience, the production methods are described using the following compounds as starting materials.

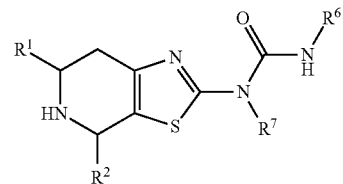

[In the formula, R$^1$, R$^2$, R$^6$, and R$^7$ have the same definition as that in the case of the compound represented by Formula (1).]

However, in each of the method H, the method I, the method J, the method K, the method L, the method M, the method N, the method X, the method Y, and the method Z, a desired compound of the present invention can be obtained by performing production using necessary compounds such as the following compounds as starting materials as appropriate.

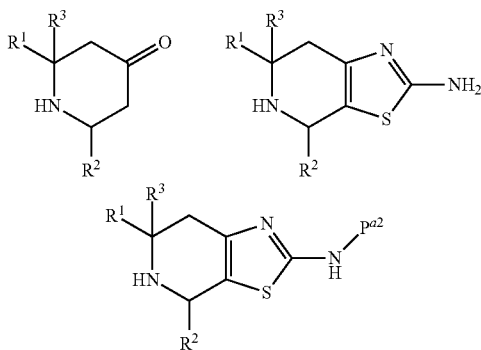

[In the formula, R$^1$, R$^2$, and R$^3$ have the same definition as that in the case of the compound represented by Formula (1), and P$^{a2}$ has the same definition as described above.]

[Method H]

Method H is a method for producing a compound (H-II) of the present invention.

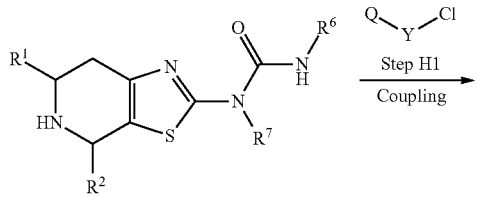

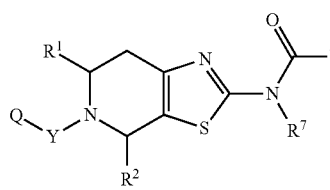

[In the formulae, $R^1$, $R^2$, $R^6$, $R^7$, Q, and Y have the same definition as that in the case of the compound represented by Formula (1).]

(Step H1) Step of Performing Coupling with Heterocycle

This step is a step of obtaining a compound (H-II) from a compound (H-I) by carrying out a reaction using Q-Y-Cl in the presence of a base.

Examples of the base include triethylamine, diisopropylethylamine, sodium hydrogen carbonate, and potassium carbonate.

Examples of the solvent include N,N-dimethylformamide and dimethyl sulfoxide.

The reaction temperature is typically in a range of 0° C. to 140° C., and the reaction time is typically in a range of 0.5 to 48 hours.

[Method I]

Method I is a method for producing a compound (I-II) of the present invention.

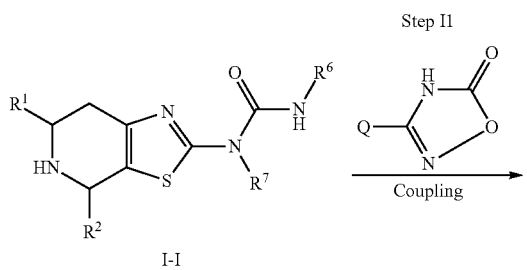

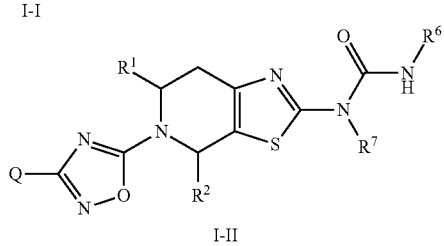

[In the formulae, $R^1$, $R^2$, $R^6$, $R^7$, and Q have the same definition as that in the case of the compound represented by Formula (1).]

(Step I1) Step of performing coupling with heterocycle

This step is a step of obtaining a compound (I-II) from a compound (I-I) by carrying out a reaction using a condensing agent in the presence of a base.

Examples of the base include triethylamine and diisopropylethylamine.

Examples of the condensing agent include phosphorus nitride chloride (trimer).

Examples of the solvent include N,N-dimethylformamide and dimethyl sulfoxide.

The reaction temperature is typically in a range of 0° C. to 140° C., and the reaction time is typically in a range of 0.5 to 48 hours.

[Method J]

Method J is a method for producing a compound (J-III) of the present invention.

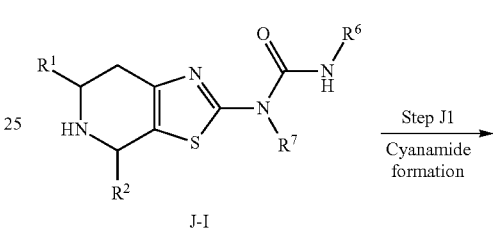

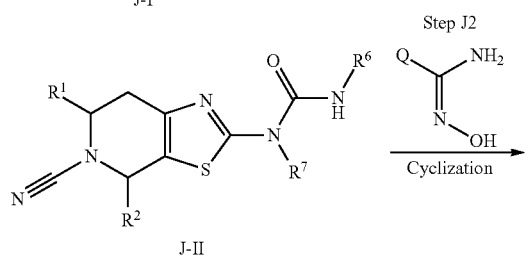

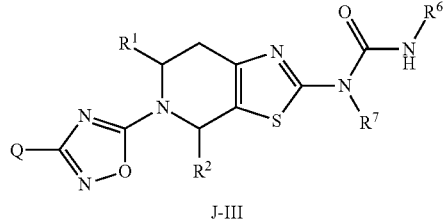

[In the formulae, $R^1$, $R^2$, $R^6$, $R^7$, and Q have the same definition as that in the case of the compound represented by Formula (1).]

(Step J1) Step of Performing Cyanamide Formation

This is a step of obtaining a compound (J-II) from a compound (J-I) by carrying out a reaction using cyanogen halide in the presence or absence of a base.

Examples of the base include triethylamine, diisopropylethylamine, sodium hydrogen carbonate, and potassium carbonate.

Examples of the solvent include acetonitrile, acetone, dichloromethane, and tetrahydrofuran.

The reaction temperature is typically in a range of 0° C. to room temperature, and the reaction time is typically in a range of 0.5 to 48 hours.

(Step J2) Step of Performing Ring Formation

This step is a step of obtaining a compound (J-III) from a compound (J-II) by carrying out a reaction using metal halide, an acid, and corresponding amide oxime.

Examples of the metal halide include zinc chloride and zinc bromide.

Examples of the acid include p-toluenesulfonic acid, sulfuric acid, and hydrochloric acid.

Examples of the solvent include diethyl ether, tetrahydrofuran, ethyl acetate, ethanol, water, and a mixture thereof.

The reaction temperature is typically in a range of 0° C. to 100° C., and the reaction time is typically in a range of 0.5 to 48 hours.

[Method K]

Method K is a method for producing a compound (K-V) of the present invention.

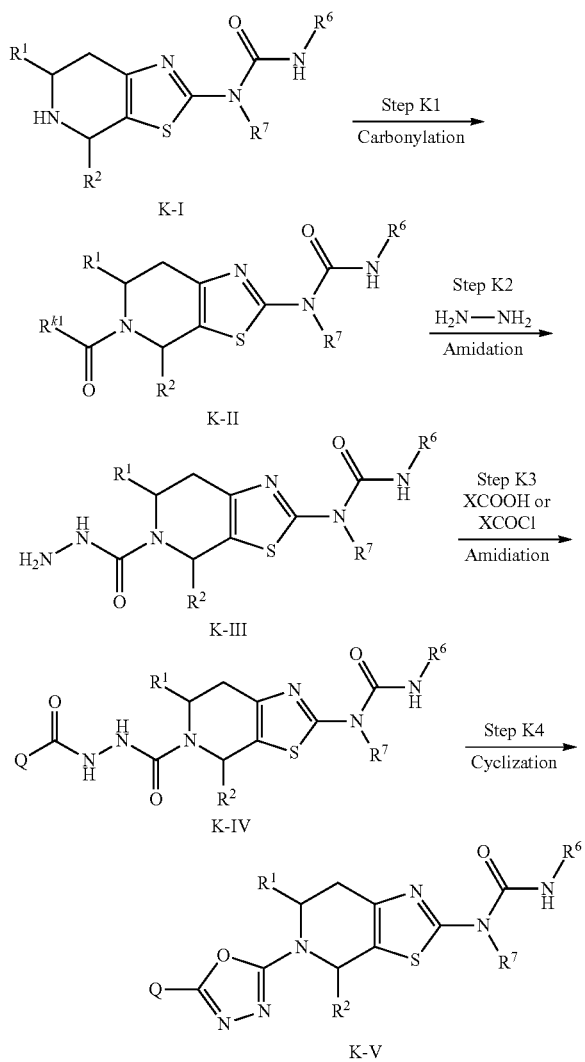

[In the formulae, $R^1$, $R^2$, $R^6$, $R^7$, and Q have the same definition as that in the case of the compound represented by Formula (1), and $R^{k1}$ represents a phenoxy group that may have a substituent or an imidazolyl group.]

(Step K1) Step of Performing Carbonylation

This step is a step of obtaining a compound (K-II) from a compound (K-I) by carrying out a reaction using a carbonylating agent in the presence of a base.

Examples of the base include triethylamine, diisopropylethylamine, and sodium hydrogen carbonate.

Examples of the carbonylating agent include carbonyldiimidazole, phenyl chloroformate, and 4-nitrophenyl chloroformate.

Examples of the solvent include tetrahydrofuran, dichloromethane, water, and a mixture thereof.

The reaction temperature is typically in a range of 0° C. to room temperature, and the reaction time is typically in a range of 0.5 to 24 hours.

(Step K2) Step of Performing Amidation Using Hydrazine

This step is a step of obtaining a compound (K-III) from a compound (K-II) by carrying out a reaction using a hydrazine hydrate in the presence or absence of a base.

Examples of the base include triethylamine, diisopropylethylamine, and dimethylaminopyridine.

Examples of the solvent include ethanol, tetrahydrofuran, acetonitrile, and a mixture thereof.

The reaction temperature is typically in a range of room temperature to 100° C., and the reaction time is typically in a range of 1 to 24 hours.

(Step K3) Step of Amidating Acyl Hydrazine (In the case of using corresponding carboxylic acid and condensing agent)

This step is a step of obtaining a compound (K-IV) from a compound (K-III) by carrying out a reaction using a condensing agent and a corresponding carboxylic acid in the presence or absence of a base.

Examples of the condensing agent include O-(7-azabenzotriazol-1-yl)-N,N,N',N'-tetramethylonium hexafluorophosphate (HATU), 4-(4,6-dimethoxy-1,3,5-triazin-2-yl)-4-methylmorpholine (DMT-MM), 1-(3-dimethylaminopropyl)-3-ethylcarbodiimide (WSC or EDCI), and 1H-benzotriazol-1-yloxytris(dimethylamino)phosphonium hexafluorophosphate (BOP reagent).

Examples of the base include triethylamine, diisopropylethylamine, and dimethylaminopyridine.

As an additive, N-hydroxysuccinimide (HOSu), 1-hydroxybenzotriazole (HOBt), or 1-hydroxy-7-azabenzotriazole (HOAt) can be added. The reaction may proceed smoothly by the additive.

Examples of the solvent include tetrahydrofuran, N,N-dimethylformamide, dichloromethane, and a mixed solvent thereof.

The reaction temperature is typically in a range of 0° C. to room temperature, and the reaction time is typically in a range of 0.5 to 24 hours.

(In the Case of Carrying Out Reaction Through Acid Chloride from Corresponding Carboxylic Acid)

This step is a step of obtaining a compound (K-IV) from a compound (K-III) by carrying out a reaction using a carboxylic acid chloride prepared using a dehydration chlorinating agent from a corresponding carboxylic acid in the presence of a base.

Examples of the dehydration chlorinating agent include oxalyl chloride, thionyl chloride, sulfuryl chloride, and phosphorus pentachloride.

Examples of the base include triethylamine, diisopropylethylamine, pyridine, and dimethylaminopyridine.

Examples of the solvent include tetrahydrofuran, dichloromethane, N,N-dimethylformamide, and a mixed solvent thereof.

The reaction temperature is typically in a range of 0° C. to 100° C., and the reaction time is typically in a range of 0.5 to 24 hours.

(In the Case of Using Corresponding Acid Chloride)

This step is a step of obtaining a compound (K-IV) from a compound (K-III) by carrying out a reaction using a corresponding carboxylic acid chloride in the presence of a base.

Examples of the base include triethylamine, diisopropylethylamine, pyridine, and dimethylaminopyridine.

Examples of the solvent include tetrahydrofuran, dichloromethane, N,N-dimethylformamide, and a mixed solvent thereof.

The reaction temperature is typically in a range of 0° C. to 100° C., and the reaction time is typically in a range of 0.5 to 24 hours.

(Step K4) Step of Performing Ring Formation

This step is a step of obtaining a compound (K-V) from a compound (K-IV) by carrying out a reaction using a dehydrating agent.

Examples of the dehydrating agent include a (methoxycarbonylsulfamoyl)triethylammonium hydroxide intramolecular salt and tosyl chloride.

Examples of the solvent include toluene, acetonitrile, and dichloromethane.

The reaction temperature is typically in a range of 0° C. to 100° C., and the reaction time is typically in a range of 0.5 to 24 hours.

[Method L]

The method L is a method for producing a compound (L-V) of the present invention.

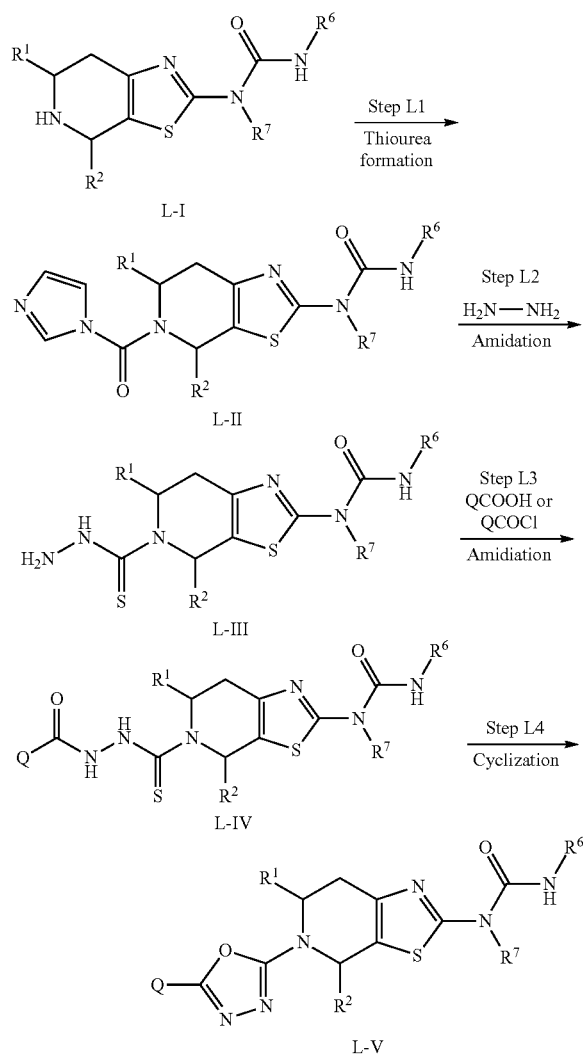

[In the formulae, $R^1$, $R^2$, $R^6$, $R^7$, and Q have the same definition as that in the case of the compound represented by Formula (1).]

(Step L1) Step of Performing Thiourea Formation

This step is a step of obtaining a compound (L-II) from a compound (L-I) by carrying out a reaction using 1,1'-thiocarbonyldiimidazole in the presence or absence of a base.

Examples of the base include triethylamine, 1,8-diazabicyclo[5.4.0]-7-undecene, and sodium carbonate.

Examples of the solvent include tetrahydrofuran, dichloromethane, N,N-dimethylformamide, acetonitrile, water, and a mixture thereof.

The reaction temperature is typically in a range of 0° C. to 80° C., and the reaction time is typically in a range of 0.5 to 24 hours.

(Step L2) Step of Performing Amidation Using Hydrazine

This step is a step of obtaining a compound (L-III) from the compound (L-II) by carrying out a reaction using a hydrazine hydrate in the presence or absence of a base.

Examples of the base include triethylamine, diisopropylethylamine, and dimethylaminopyridine.

Examples of the solvent include ethanol, tetrahydrofuran, acetonitrile, and a mixture thereof.

The reaction temperature is typically in a range of room temperature to 100° C., and the reaction time is typically in a range of 1 to 24 hours.

(Step L3) Step of Amidating Carbothiohydrazide

This step is a step of obtaining a compound (L-IV) from the compound (L-III).

This step can be performed according to the same method as that in the (step K3).

(Step L4) Step of Performing Ring Formation (In the Case of Using Condensing Agent)

This step is a step of obtaining a compound (L-V) from a compound (L-IV) by carrying out a reaction using a condensing agent in the presence or absence of a base.

Examples of the condensing agents include 1-(3-dimethylaminopropyl)-3-ethylcarbodiimide (WSC or EDCI), and 1H-benzotriazol-1-yloxytris(dimethylamino)phosphonium hexafluorophosphate (BOP reagent).

Examples of the base include triethylamine, diisopropylethylamine, and dimethylaminopyridine.

Examples of the solvent include dimethyl sulfoxide, tetrahydrofuran, N,N-dimethylformamide, and a mixed solvent thereof.

The reaction temperature is typically in a range of room temperature to 100° C., and the reaction time is typically in a range of 0.5 to 24 hours.

(In the Case of Using Dehydrating Agent)

This step is a step of obtaining a compound (L-V) from the compound (L-IV) by carrying out a reaction using a dehydrating agent.

Examples of the dehydrating agent include a (methoxycarbonylsulfamoyl)triethylammonium hydroxide intramolecular salt and tosyl chloride.

Examples of the solvent include toluene, acetonitrile, and dichloromethane.

The reaction temperature is typically in a range of 0° C. to 100° C., and the reaction time is typically in a range of 0.5 to 24 hours.

[Method M]

Method M is a method for producing a compound (M-II) of the present invention.

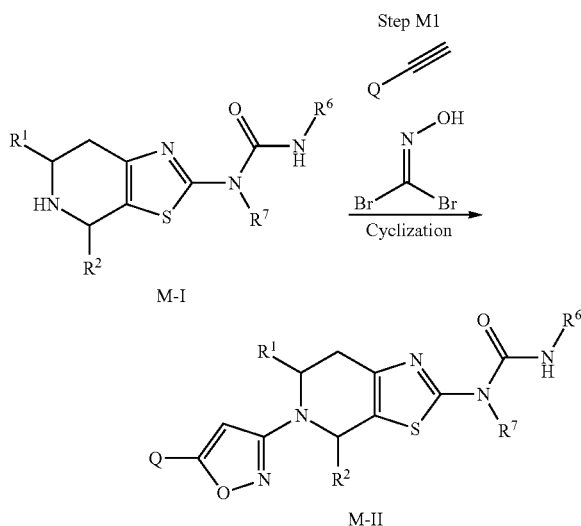

[In the formulae, $R^1$, $R^2$, $R^6$, $R^7$, and Q have the same definition as that in the case of the compound represented by Formula (1).]

(Step M1) Step of Performing Ring Formation

This is a step of obtaining a compound (M-II) from a compound (M-I) by carrying out a reaction using 1,1-dibromoformaldoxime and a corresponding alkyne in the presence of a base.

Examples of the base include triethylamine and diisopropylethylamine.

Examples of the solvent include tetrahydrofuran, N,N-dimethylformamide, and a mixture thereof.

The reaction temperature is typically in a range of 0° C. to room temperature, and the reaction time is typically in a range of 0.5 to 48 hours.

[Method X]

Method X is a method for producing a compound (X-VI) of the present invention.

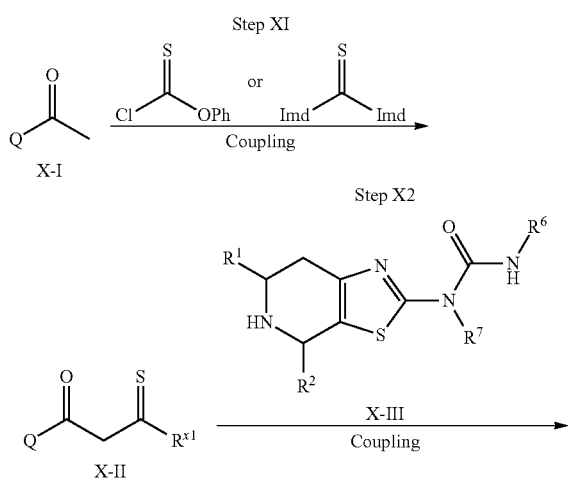

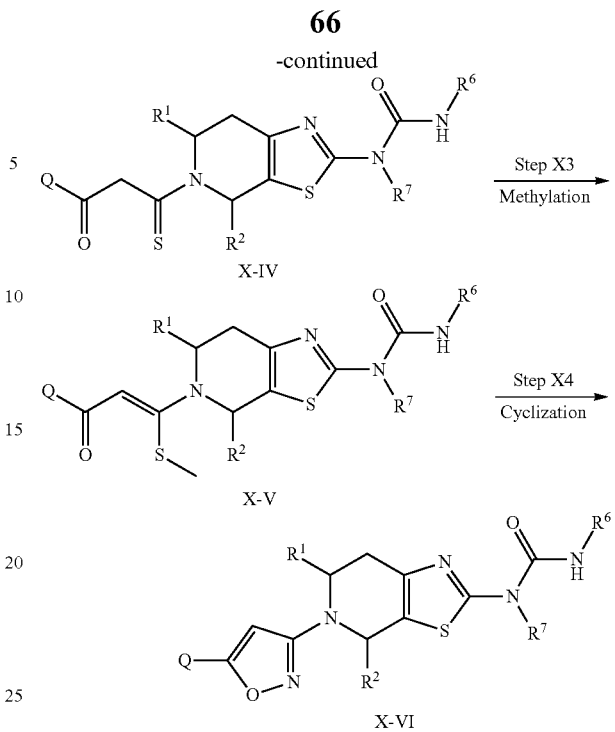

[In the formulae, $R^1$, $R^2$, $R^6$, $R^7$, and Q have the same definition as that in the case of the compound represented by Formula (1), Ph represents a phenyl group, Imd represents an imidazolyl group, and $R^{x1}$ represents OPh or Imd.]

(Step X1) Step of Performing Coupling

This step is a step of obtaining a compound (X-II) from a compound (X-I) by carrying out a reaction using 1,1'-thiocarbonyldiimidazole or phenyl chlorothionoformate in the presence of a base.

Examples of the base include sodium tert-butoxide and lithium bis(trimethylsilyl)amide.

Examples of the solvent include tetrahydrofuran, N,N-dimethylformamide, and a mixture thereof.

The reaction temperature is typically in a range of 0° C. to 60° C., and the reaction time is typically in a range of 0.5 to 24 hours.

(Step X2) Step of Performing Coupling

This step is a step of obtaining a compound (X-IV) from the compound (X-II) by performing a coupling reaction using a compound (X-III) in the presence or absence of a base.

Examples of the base include triethylamine, 1,8-diazabicyclo[5.4.0]-7-undecene, and sodium carbonate.

Examples of the solvent include tetrahydrofuran, N,N-dimethylformamide, ethanol, and a mixture thereof.

The reaction temperature is typically in a range of 0° C. to 100° C., and the reaction time is typically in a range of 0.5 to 24 hours.

(Step X3) Step of Performing Methylation

This step is a step of obtaining a compound (X-V) from a compound (X-IV) by carrying out a reaction using a methylating reagent in the presence of a base.

Examples of the methylating reagent include iodomethane and dimethylsulfuric acid.

Examples of the base include triethylamine, diisopropylethylamine, and potassium carbonate.

Examples of the solvent include tetrahydrofuran, acetonitrile, N,N-dimethylformamide, and a mixture thereof.

The reaction temperature is typically in a range of 0° C. to 100° C., and the reaction time is typically in a range of 0.5 to 24 hours.

(Step X4) Step of Performing Cyclization

This step is a step of obtaining a compound (X-VI) from the compound (X-V) by carrying out a reaction using hydroxylamine or a hydrochloride thereof in the presence or absence of a base.

Examples of the base include triethylamine, sodium acetate, and sodium hydrogen carbonate.

Examples of the solvent include methanol, ethanol, water, and a mixed solvent thereof.

The reaction temperature is typically in a range of room temperature to 100° C., and the reaction time is typically in a range of 0.5 to 24 hours.

[Method N]

Method N is a method for producing a compound (N-II) of the present invention.

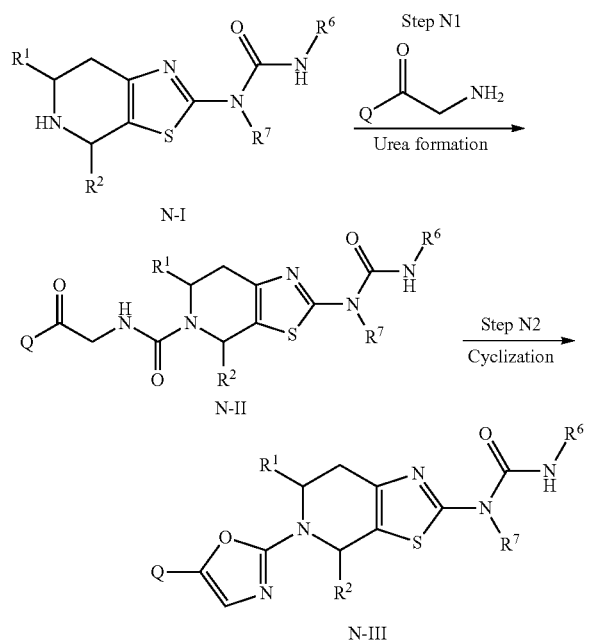

[In the formulae, $R^1$, $R^2$, $R^6$, $R^7$, and Q have the same definition as that in the case of the compound represented by Formula (1).]

(Step N1) Step of Performing Urea Formation

This step is a step of obtaining a compound (N-II) from a compound (N-I).

This step can be performed according to the same method as in the (step F2).

(Step N2) Step of Performing Ring Formation

This step is a step of obtaining a compound (N-III) from the compound (N-II) by carrying out a reaction using a dehydrating agent in the present or absence of a base.

Examples of the dehydrating agent include a trifluoroacetic anhydride and phosphorus oxychloride.

Examples of the base include triethylamine, diisopropylethylamine, and dimethylaminopyridine.

Examples of the solvent include dichloromethane and tetrahydrofuran. Alternatively, a solvent may not be used.

The reaction temperature is typically in a range of 0° C. to 100° C., and the reaction time is typically in a range of 0.5 to 24 hours.

[Method Y]

Method Y is a method for producing a compound (Y-II) of the present invention.

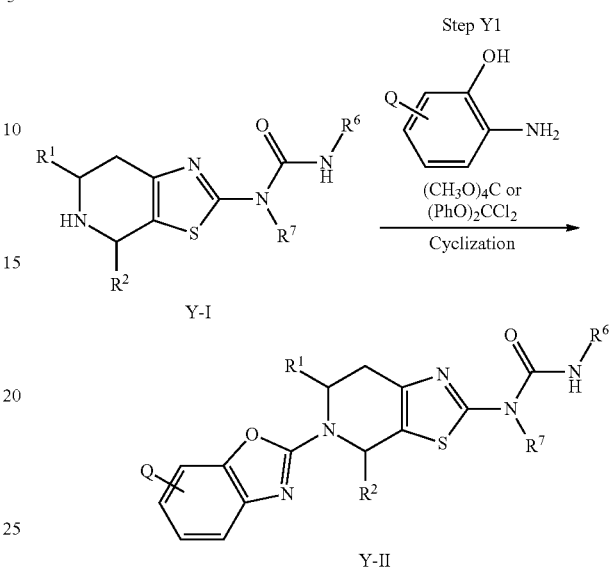

[In the formulae, $R^1$, $R^2$, $R^6$, $R^7$, and Q have the same definition as that in the case of the compound represented by Formula (1), and Ph represents a phenyl group.]

(Step Y1) Step of Performing Formation of Benzoxazole Ring

This step is a step of obtaining a compound (Y-II) from a compound (Y-I) by carrying out a reaction using tetramethoxymethane or dichlorodiphenoxymethane in the presence of an acid or a base.

Examples of the acid include acetic acid.

Examples of the base include triethylamine.

Examples of the solvent include chloroform and toluene.

The reaction temperature is typically in a range of 0° C. to 100° C., and the reaction time is typically in a range of 0.5 to 48 hours.

[Method Z]

Method Z is a method for producing a compound (Z-II) of the present invention.

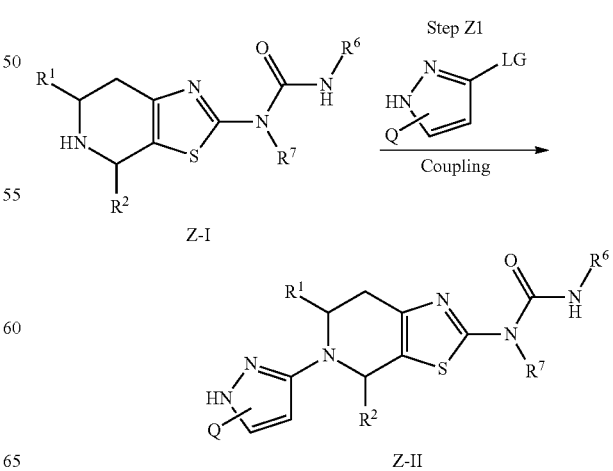

[In the formulae, $R^1$, $R^2$, $R^6$, $R^7$, and Q have the same definition as that in the case of the compound represented by Formula (1), and LG represents a leaving group.]

(Step Z1) Step of Performing Coupling Reaction Using Transition Metal Catalyst

This step is a step of obtaining a compound (Z-II) from a compound (Z-I) by carrying out a reaction using a copper catalyst or a palladium catalyst in the presence or absence of a base and a ligand.

Examples of the copper catalyst include copper iodide, copper chloride, copper acetate, and copper sulfate.

Examples of the palladium catalyst include tetrakis(triphenylphosphine) palladium, tris(dibenzylideneacetone) dipalladium, palladium acetate, and bis(triphenylphosphine) palladium dichloride.

Examples of the base include triethylamine, diisopropylethylamine, potassium carbonate, and cesium carbonate.

Examples of the solvent include tetrahydrofuran, 1,4-dioxane, water, N,N-dimethylformamide, dimethyl sulfoxide, toluene, and a mixture thereof.

The reaction temperature is typically in a range of room temperature to 150° C., and the reaction time is typically in a range of 0.5 to 48 hours.

[Method O]

Method O is a method for producing a compound (O-III) of the present invention.

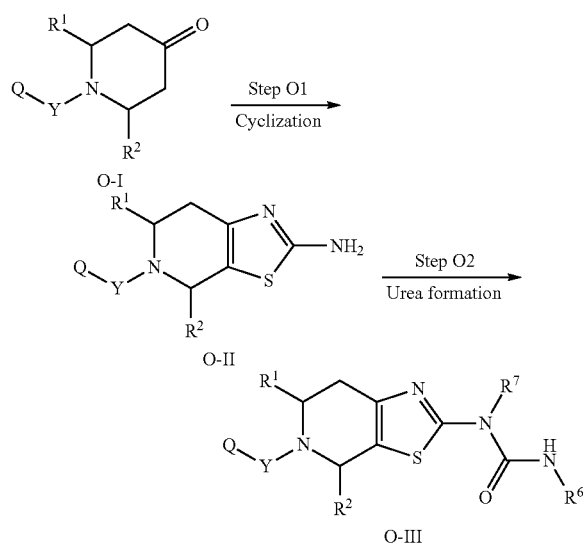

[In the formulae, $R^1$, $R^2$, $R^6$, $R^7$, Q, and Y have the same definition as that in the case of the compound represented by Formula (1).]

(Step O1) Step of Performing Formation of Thiazole Ring

This step is a step of obtaining a compound (O-II) from a compound (O-I).

This step can be performed according to the same method as in the (step D1).

(Step O2) Step of Performing Urea Formation

This step is a step of obtaining a compound (O-III) from a compound (O-II).

This step can be performed according to the same method as in the (step F2).

[Method Q]

Method Q is a method for producing a compound (Q-III) of the present invention.

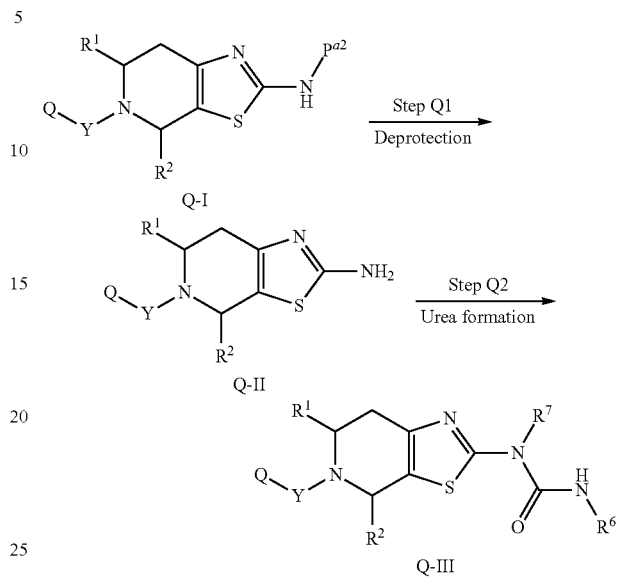

[In the formulae, $R^1$, $R^2$, $R^6$, $R^7$, Q, and Y have the same definition as that in the case of the compound represented by Formula (1), and $P^{a2}$ has the same definition as described above.]

(Step Q1) Step of Performing Deprotection (In the Case of t-Butoxycarbonyl (Boc) Group)

This step is a step of obtaining a compound (Q-II) from a compound (Q-I) containing an amino group protected by a t-butoxycarbonyl group by carrying out a reaction using an acid.

This step can be performed according to the same method as in the (step C1).

(In the Case of 2-(Trimethylsilyl)Ethoxycarbonyl (Teoc) Group)

This step is a step of obtaining a compound (Q-II) from the compound (Q-I) containing an amino group protected by a 2-(trimethylsilyl)ethoxycarbonyl group by carrying out a reaction using a desilylation reagent or an acid.

This step can be performed according to the same method as in the (step E3).

(In the Case of Allyloxycarbonyl (Alloc) Group)

A step of obtaining a compound (Q-II) from the compound (Q-I) containing an amino group protected by an allyloxycarbonyl (Alloc) group by carrying out a reaction using an amine in the presence of a palladium catalyst and a phosphine ligand.

Examples of the palladium catalysts include tetrakis(triphenylphosphine) palladium, [1,1'-bis(diphenylphosphino) ferrocene] dichloropalladium, tris(dibenzylideneacetone) dipalladium, palladium acetate, acetylacetone palladium, and bis(triphenylphosphine) palladium dichloride.

Examples of the phosphine ligand used simultaneously with the palladium catalyst include 4,5-bis(diphenylphosphino)-9,9-dimethylxanthene (xantphos), 1,1'-bis(diphenylphosphino) ferrocene (dppf), 2,2'-bis(diphenylphosphino)-1,1-binaphthyl (BINAP), bis(diphenylphosphino) methane (DPPM), triphenylphosphine, and 1,2-bis(diphenylphosphino) ethane (DPPE).

Examples of the base include diethylamine and morpholine.

Examples of the solvent include acetonitrile, tetrahydrofuran, dichloromethane, water, and a mixture thereof.

The reaction temperature is typically in a range of room temperature to 60° C., and the reaction time is typically in a range of 0.5 to 48 hours.

(In the Case of Benzyloxycarbonyl (Cbz) Group)

This step is a step of obtaining a compound (Q-II) from the compound (Q-I) containing an amino group protected by a benzyloxycarbonyl (Cbz) group by carrying out a reaction using a transition metal catalyst in a hydrogen atmosphere in the presence or absence of an acid.

Examples of the acid include hydrochloric acid, hydrogen chloride-1,4-dioxane, and hydrogen chloride-ethyl acetate.

Examples of the transition metal catalyst include palladium-carbon, palladium hydroxide-carbon, and Raney nickel.

Examples of the solvent include methanol, ethanol, ethyl acetate, chloroform, and a mixture thereof.

The reaction temperature is typically in a range of 0° C. to 100° C., and the reaction time is typically in a range of 0.5 to 24 hours.

(Step Q2) Step of Performing Urea Formation

This step is a step of obtaining a compound (Q-III) from the compound (Q-II).

This step can be performed according to the same method as in the (step F2).

[Method R]

Method R is a method for producing a compound (R-II) of the present invention.

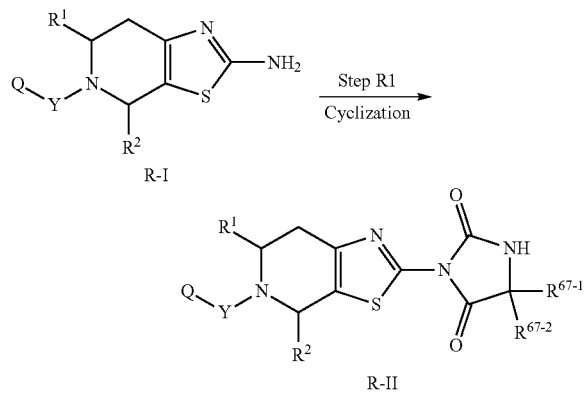

[In the formulae, $R^1$, $R^2$, $R^{67-1}$, $R^{67-2}$, Q, and Y have the same definition as that in the case of the compound represented by Formula (1).]

(Step R1) Step of Performing Formation of Hydantoin Ring

This step is a step of obtaining a compound (R-II) from a compound (R-I) by carrying out a reaction using a urea-forming reagent and a corresponding amine or a hydrochloride thereof in the presence or absence of a base.

Examples of the urea-forming reagent include carbonyldiimidazole, triphosgene, phenyl chloroformate, and 4-nitrophenyl chloroformate.

Examples of the base include triethylamine and diisopropylethylamine.

Examples of the solvent include N,N-dimethylformamide, dichloromethane, and tetrahydrofuran.

The reaction temperature is typically in a range of 0° C. to 100° C., and the reaction time is typically in a range of 1 to 48 hours.

[Method S]

Method S is a method for producing a compound (S-III) of the present invention.

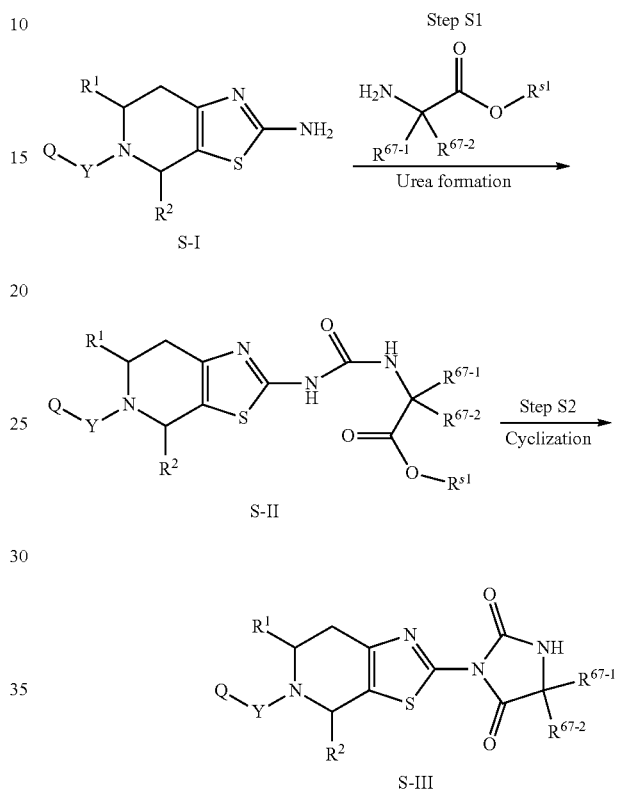

[In the formulae, $R^1$, $R^2$, $R^{67-1}$, $R^{67-2}$, Q, and Y have the same definition as that in the case of the compound represented by Formula (1), and $R^{s1}$ represents a C1-C6 alkyl group.]

(Step S1) Step of Performing Urea Formation

This step is a step of obtaining a compound (S-II) from a compound (S-I).

This step can be performed according to the same method as in the (step F2).

(Step S2) Step of Performing Ring Formation

This step is a step of obtaining a compound (S-III) from a compound (S-II) using a condensing agent in the presence or absence of a base.

Examples of the condensing agents include 1-(3-dimethylaminopropyl)-3-ethylcarbodiimide (WSC or EDCI), and 1H-benzotriazol-1-yloxytris(dimethylamino)phosphonium hexafluorophosphate (BOP reagent).

Examples of the base include triethylamine, diisopropylethylamine, and dimethylaminopyridine.

Examples of the solvent include N,N-dimethylformamide, tetrahydrofuran, and a mixed solvent thereof.

The reaction temperature is typically in a range of room temperature to 100° C., and the reaction time is typically in a range of 0.5 to 24 hours.

[Method T]

Method T is a method for producing a compound (T-IV) of the present invention.

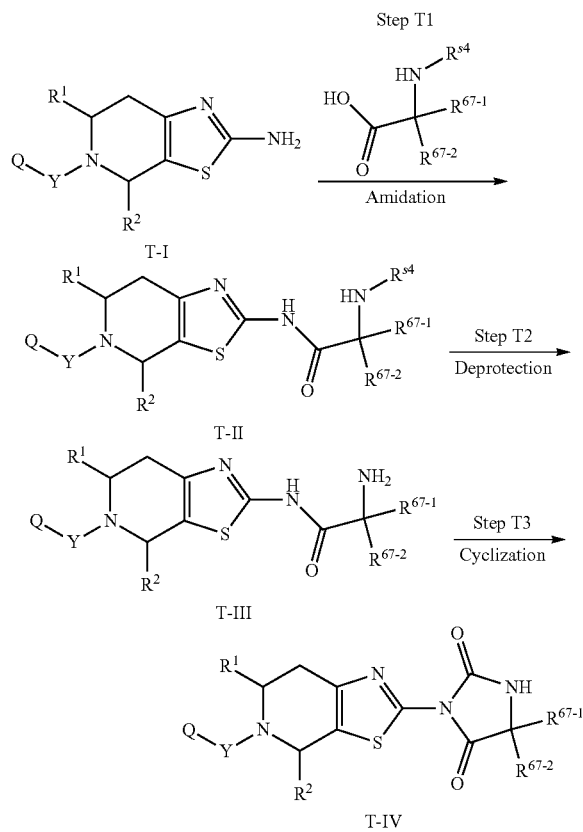

[In the formulae, $R^1$, $R^2$, $R^{67-1}$, $R^{67-2}$, Q, and Y have the same definition as that in the case of the compound represented by Formula (1), and $P^{a4}$ represents a protecting group of an amino group that is typically used.]

(Step T1) Step of Performing Amidation

This step is a step of obtaining a compound (T-II) from a compound (T-I) by carrying out a reaction using a condensing agent and a corresponding amino acid in the presence of a base.

Examples of the condensing agent include O-(7-azabenzotriazol-1-yl)-N,N,N',N'-tetramethylonium hexafluorophosphate (HATU), 4-(4,6-dimethoxy-1,3,5-triazin-2-yl)-4-methylmorpholine (DMT-MM), 1-(3-dimethylaminopropyl)-3-ethylcarbodiimide (WSC or EDCI), and 1H-benzotriazol-1-yloxytris(dimethylamino)phosphonium hexafluorophosphate (BOP reagent).

Examples of the base include triethylamine, diisopropylethylamine, and dimethylaminopyridine.

As an additive, N-hydroxysuccinimide (HOSu), 1-hydroxybenzotriazole (HOBt), or 1-hydroxy-7-azabenzotriazole (HOAt) can be added. The reaction may proceed smoothly by the additive.

Examples of the solvent include tetrahydrofuran, N,N-dimethylformamide, dichloromethane, and a mixed solvent thereof.

The reaction temperature is typically in a range of 0° C. to room temperature, and the reaction time is typically in a range of 0.5 to 24 hours.

(Step T2) Step of Performing Deprotection (In the Case of t-Butoxycarbonyl (Boc) Group)

This step is a step of obtaining a compound (T-III) from the compound (T-II) containing an amino group protected by a t-butoxycarbonyl group by carrying out a reaction using an acid.

This step can be performed according to the same method as in the (step C1).

(Step T3) Step of Performing Ring Formation

This step is a step of obtaining a compound (T-IV) from the compound (T-III) by carrying out a reaction using a urea-forming reagent in the presence or absence of a base.

Examples of the urea-forming reagent include carbonyldiimidazole and triphosgene.

Examples of the base include triethylamine and diisopropylethylamine.

Examples of the solvent include N,N-dimethylformamide, dichloromethane, and tetrahydrofuran.

The reaction temperature is typically in a range of 0° C. to 100° C., and the reaction time is typically in a range of 1 to 48 hours.

The compound produced by the above-described method can be isolated and purified by a known method such as extraction, precipitation, distillation, chromatography, fractional recrystallization, and recrystallization.

Further, when the compound or the intermediate of production has asymmetric carbon, an optical isomer is present. Each optical isomer can be isolated and purified by a conventional method such as fractional recrystallization (salt resolution) of carrying out recrystallization with an appropriate salt or column chromatography. Examples of reference documents to the method for resolution of optical isomers from racemates include "Enantiomers, Racemates and Resolution, John Wiley And Sons, Inc." written by J. Jacques et al.

(Administration Form)

The administration may be any of oral administration in the form of tablets, pills, capsules, granules, powders, or liquids; and parenteral administration in the form of injections for intra-articular use, intravenous use, intramuscular use, and the like, suppositories, eye drops, eye ointments, transdermal liquids, ointments, transdermal patches, transmucosal liquids, transmucosal patches, or inhalants.

For a solid composition for oral administration, tablets, powders, granules, and the like are used. Such a solid composition contains one or more active components and at least one inactive excipient such as lactose, mannitol, glucose, hydroxypropyl cellulose, microcrystalline cellulose, starch, polyvinylpyrrolidone, and/or magnesium meta-aluminosilicate. The solid composition may contain inactive additives, for example, a lubricant such as magnesium stearate, a disintegrant such as sodium carboxymethyl starch, a stabilizer, and a solubilizing agent, according to a conventional method. Tablets or pills may be coated with a sugar coating or a film formed of a gastrosoluble substance or enteric substance, as necessary.

For a liquid composition for oral administration, pharmaceutically acceptable emulsions, solutions, suspensions, syrups, elixirs, or the like are used. An inactive diluent that is typically used, such as purified water or ethanol, can be added to such a liquid composition. The liquid composition may contain an auxiliary agent such as a solubilizer or a wetting agent, a sweetening agent, a flavoring agent, a fragrance agent, and a preservative in addition to the inactive diluent.

For an injection for parenteral administration, sterile aqueous or non-aqueous solutions, suspensions, or emulsions, or the like are used. Examples of the aqueous solvents include distilled water for injection and physiological saline. Examples of the non-aqueous solvents include propylene glycol, polyethylene glycol, vegetable oils such as olive oil, alcohols such as ethanol, and polysorbate 80. Such an injection compositions may further contain an isotonizing agent, a preservative, a wetting agent, an emulsifier, a dispersant, a stabilizer, or a solubilizing agent. The injection compositions can be sterilized, for example, by filtration through a bacterial retention filter, combination with a germicide, or irradiation. In addition, the injection composition can also be used by producing a sterile solid composition and dissolving or suspending the sterile solid composition in sterile water or a sterile solvent for injection before use.

For an external preparation, ointments, plasters, creams, jellies, poultices, sprays, lotions, eye drops, eye ointments, or the like are used. The external preparation contains a typically-used ointment base, a typically-used lotion base, a typically-used aqueous or non-aqueous liquid, a typically-used suspension, a typically-used emulsion, and the like. For example, for the ointment base or lotion base, polyethylene glycol, propylene glycol, white petrolatum, white beeswax, polyoxyethylene hydrogenated castor oil, glyceryl monostearate, stearyl alcohol, cetyl alcohol, lauromacrogol, sorbitan sesquioleate, or the like is used.

For the transmucosal agent such as an inhalant or a nasal agent, a transmucosal agent in the form of a solid, liquid, or semi-solid one is used and can be produced according to a known conventional method. For example, a known excipient, a pH adjuster, a preservative, a surfactant, a lubricant, a stabilizer, a thickener, or the like may be appropriately added to the transmucosal agent. A suitable device for inhalation or blowing can be used for the method of administering such transmucosal agent. For example, the compound can be administered alone or in the form of powder of a prescribed mixture or in the form of a solution or suspension in combination with a pharmaceutically acceptable carrier using a sprayer or a known device such as a metered dose inhalation device. A dry powder inhaler or the like may be for single or multiple doses, and dry powder or powder-containing capsules can be used. Alternatively, a suitable ejection agent can also be used. For example, the device may be in the form of a pressurized aerosol spray using a suitable gas such as chlorofluoroalkane, hydrofluoroalkane, or carbon dioxide.

(Dose)

For typical oral administration, the appropriate daily dose is approximately 0.001 to 100 mg/kg per body weight, preferably in a range of 0.1 to 30 mg/kg, and more preferably in a range of 0.1 to 10 mg/kg, and the administration is performed once a day or in two or more divided doses. For intravenous administration, the appropriate daily dose is approximately 0.0001 to 10 mg/kg per body weight, and the administration is performed once a day or in multiple divided doses. Further, for a transmucosal agent, the daily dose is approximately 0.001 to 100 mg/kg per body weight, and the transmucosal agent is administered once a day or in multiple divided doses. The dose is appropriately determined according to an individual case in consideration of the symptoms, the age, the sex, and the like.

(Combined Use)

In the present invention, the administration can be made in combination with various therapeutic agents or preventive agents for diseases that are considered to show effectiveness. The combined use may be made by administration performed simultaneously, separately and consecutively, or at desired time intervals. A formulation for the simultaneous administration may be a combination preparation or may be a separately formulated one.

(Formulation Example 1) Powder

A powder is obtained by mixing 5 g of the compound of the present invention or the salt thereof, 895 g of lactose, and 100 g of corn starch using a blender.

(Formulation Example 2) Granule 5 g of the compound of the present invention or the salt thereof, 865 g of lactose, and 100 g of low-substituted hydroxypropyl cellulose are mixed, and 300 g of a 10% hydroxypropyl cellulose aqueous solution is added thereto and kneaded. A granule is obtained by granulating and drying the mixture using an extrusion granulator.

(Formulation Example 3) Tablet

A tablet is obtained by mixing 5 g of the compound of the present invention or the salt thereof, 90 g of lactose, 34 g of corn starch, 20 g of crystalline cellulose, and 1 g of magnesium stearate using a blender and tableting the mixture using a tablet machine.

(Formulation Example 4) Ointment 5 g of the compound of the present invention or the salt thereof was dissolved in a mixture of 50 g of propylene glycol, 50 g of polyethylene glycol, and 50 g of glyceryl monooleate (Capmul GMO-50 EP, NF) by heating at 60° C. to 80° C. A 1.0% ointment can be obtained by adding 350 g of white petrolatum to the mixture, stirring the mixture at 60° C. to 80° C. for 15 minutes, and slowly cooling the mixture with the mixture stirred.

EXAMPLES

The pharmacological activity of a compound of the present invention produced in examples described below or a pharmaceutically acceptable salt thereof was confirmed by the following test.

(Test Example) Measurement of Deacetylation Activity

The reaction was performed in duplicate using a white 384-well plate (3824, Corning or 6008350, PerkinElmer) at a final reaction liquid volume of 20.1 μL. As a control for calculating the enzyme activity, the enzyme-added (DMSO (+)) and enzyme-free (DMSO (−)) wells were set at n=8. Test substances (examples of final concentrations: 0.046, 0.14, 0.41, 1.2, 3.7, 11, 33, and 100 μM) at a concentration of 100 times or 0.1 μL of DMSO was dispensed into the plate and 5 μL of SIRT6 enzyme (prepared by Daiichi Sankyo RD Novare Co., Ltd., final concentration: 25 ng/mL) diluted with an assay buffer (10 mM Tris-HCl pH of 8.0, 0.1% BSA, 0.01% Tween 20, 1 mM DTT, 12.5% Glycerol) was added thereto. The enzymatic reaction was started by adding 5 μL of a mixed solution [Lys(Ac)9]-Histone H3 (1-21)-NH2, H3K9 (Ac), biotin-labeled, amide (AnaSpec, AS-64190, final concentration: 2 nM) and β-nicotinamide adenine dinucleotide (Sigma-Aldrich, N8285-15VL, final concentration: 10 μM), and the reaction was performed at room temperature for 30 minutes. 10 μL of a mixed solution of nicotinamide (Sigma-Aldrich, 72340-100G, final concentration: 100 mM) prepared with AlphaLISA Epigenetics Buffer (PerkinElmer, AL008C), AlphaLISA Anti-unmodified Histone H3 Lysine 9/Lysine 27 (H3K9/K27) Acceptor Beads (PerkinElmer, AL138, final concentration: 10 μg/mL), and AlphaScreen Streptavidin Donor beads (PerkinElmer, 6760002, final concentration: 5 μg/mL) was added thereto, the reaction was performed at room temperature for 60 minutes and then stopped, and acetylation was detected. The emission intensity was measured by EnVision (PerkinElmer).

The relative enzyme activity (%) of the test substance was calculated by the following equation.

Relative enzyme activity (%)=[(emission intensity of test substance-added well−emission intensity of DMSO (−) well)/(emission intensity of DMSO (+) well−emission intensity of DMSO (−) well)]×100

The $EC_{150}$ (the concentration of the compound showing a relative enzyme activity of 150%) of the test substance was calculated based on Sigmoidal dose-response (variable slope) of GraphPad Prism (GraphPad Software) using the value of the relative enzyme activity (%) at each concentration, and the results are listed in Tables 1-1 to 1-5.

TABLE 1-1

| Example number | $EC_{150}$ (μm) |
| --- | --- |
| 1 | 1.7 |
| 2 | 1.6 |
| 3 | 3.4 |
| 4 | 1.2 |
| 5 | 1.5 |
| 6 | 4.5 |
| 7 | 5.7 |
| 8 | 3.6 |
| 9 | 1.2 |
| 10 | 1.0 |
| 11 | 4.3 |
| 12 | 1.4 |
| 13 | 1.3 |
| 14 | 0.94 |
| 15 | 1.1 |
| 16 | 4.2 |
| 17 | 1.8 |
| 18 | 0.95 |
| 19 | 0.60 |
| 20 | 2.6 |
| 21 | 1.5 |
| 22 | 1.3 |
| 23 | 0.19 |
| 24 | 0.19 |
| 25 | 0.81 |
| 26 | 0.81 |
| 27 | 2.1 |
| 28 | 2.1 |
| 29 | 0.69 |
| 30 | 0.18 |
| 31 | 2.5 |
| 32 | 0.27 |
| 33 | 1.6 |
| 34 | 1.9 |
| 35 | 1 |
| 36 | 1.9 |
| 37 | 4.6 |
| 38 | 2 |
| 39 | 2.5 |
| 40 | 3.1 |

TABLE 1-2

| 41 | 2.5 |
| --- | --- |
| 42 | 1.3 |
| 43 | 1.5 |
| 44 | 2.3 |
| 45 | 0.79 |
| 46 | 2.1 |
| 47 | 0.83 |
| 48 | 1.2 |
| 49 | 1.5 |
| 50 | 1.5 |
| 51 | 0.47 |
| 52 | 1.9 |
| 53 | 0.29 |
| 54 | 0.48 |
| 55 | 2.3 |
| 56 | 0.19 |
| 57 | 0.93 |
| 58 | 2.4 |
| 59 | 0.44 |
| 60 | 1.7 |
| 61 | 1.9 |
| 62 | 2.6 |
| 63 | 2.3 |
| 64 | 0.49 |
| 65 | 2.1 |
| 66 | 0.39 |
| 67 | 0.75 |
| 68 | 1 |
| 69 | 0.59 |
| 70 | 0.45 |
| 71 | 0.34 |
| 72 | 0.36 |
| 73 | 0.4 |
| 74 | 0.68 |
| 75 | 0.94 |
| 76 | 1.3 |
| 77 | 0.79 |
| 78 | 0.41 |
| 79 | 1.2 |
| 80 | 0.48 |

TABLE 1-3

| 81 | 1.4 |
| --- | --- |
| 82 | 1.7 |
| 83 | 0.68 |
| 84 | 0.62 |
| 85 | 0.51 |
| 86 | 0.25 |
| 87 | 2.1 |
| 88 | 1.1 |
| 89 | 2.9 |
| 90 | 2.5 |
| 91 | 0.81 |
| 92 | 3.5 |
| 93 | 0.7 |
| 94 | 1.6 |
| 95 | 2.2 |
| 96 | 1.6 |
| 97 | 1.3 |
| 98 | 2.6 |
| 99 | 1.1 |
| 100 | 2.6 |
| 101 | 1.1 |
| 102 | 0.33 |
| 103 | 1.8 |
| 104 | 1.6 |
| 105 | 2 |
| 106 | 2.4 |
| 107 | 2.3 |
| 108 | 2.4 |
| 109 | 1.4 |
| 110 | 3.7 |
| 111 | 2.2 |
| 112 | 1.4 |
| 113 | 2.6 |
| 114 | 2.4 |

TABLE 1-3-continued

| | |
|---|---|
| 115 | 2 |
| 116 | 3.1 |
| 117 | 1 |
| 118 | 1.8 |
| 119 | 2.2 |
| 120 | 2.4 |

TABLE 1-4

| | |
|---|---|
| 121 | 2.1 |
| 122 | 1.5 |
| 123 | 0.66 |
| 124 | 0.39 |
| 125 | 2.4 |
| 126 | 1 |
| 127 | 2.1 |
| 128 | 0.43 |
| 129 | 0.38 |
| 130 | 3.7 |
| 131 | 1.4 |
| 132 | 0.39 |
| 133 | 1.4 |
| 134 | 3.5 |
| 135 | 2.1 |
| 136 | 0.34 |
| 137 | 0.36 |
| 138 | 0.46 |
| 139 | 0.36 |
| 140 | 0.16 |
| 141 | 0.58 |
| 142 | 3.3 |
| 143 | 0.62 |
| 144 | 0.61 |
| 145 | 2.2 |
| 146 | 1.9 |
| 147 | 3.3 |
| 148 | 0.95 |
| 149 | 0.45 |
| 150 | 0.43 |
| 151 | 0.78 |
| 152 | 2.7 |
| 153 | 2.1 |
| 154 | 0.82 |
| 155 | 0.51 |
| 156 | 1 |
| 157 | 4.6 |
| 158 | 1.1 |
| 159 | 1.3 |
| 160 | 3.2 |

TABLE 1-5

| | |
|---|---|
| 161 | 0.97 |
| 162 | 3.3 |
| 163 | 1.6 |
| 164 | 2.6 |
| 165 | 0.41 |
| 166 | 0.21 |
| 167 | 0.43 |
| 168 | 0.35 |
| 169 | 0.66 |
| 170 | 1.2 |
| 171 | 0.55 |
| 172 | 0.83 |
| 173 | 0.62 |
| 174 | 0.74 |
| 175 | 0.27 |
| 176 | 0.33 |
| 177 | 0.28 |
| 178 | 0.1 |
| 179 | 0.72 |
| 180 | 0.14 |
| 181 | 0.53 |
| 182 | 0.16 |
| 183 | 0.24 |

TABLE 1-5-continued

| | |
|---|---|
| 184 | 0.91 |
| 185 | 0.4 |
| 186 | 0.48 |
| 187 | 0.64 |
| 188 | 0.4 |
| 189 | 0.38 |
| 190 | 1.7 |
| 191 | 1.2 |
| 192 | 0.44 |
| 193 | 1.8 |

Hereinafter, the present invention will be described in more detail with reference to examples and test examples, but the scope of the present invention is not limited thereto.

In the following examples, for the nuclear magnetic resonance (hereinafter, $^1$H NMR) spectrum, the chemical shift value is described at a δ value (ppm) using tetramethylsilane as a standard substance or using the chemical shift value of the deuteration solvent used as a reference value. The split pattern is shown such that the single line is described as s, the double line is described as d, the triple line is described as t, the quadruple line is described as q, the multiple line is described as m, and broad is described as br.

Example 1

N-{5-[3-(4,4-difluorocyclohexyl)-1,2,4-oxadiazol-5-yl]-4,5,6,7-tetrahydro[1,3]thiazolo[5,4-c]pyridin-2-yl}-N'-methylurea (1a)

4,4-Difluorocyclohexane-1-carbonitrile 4,4-Difluorocyclohexane-1-carbonitrile

4-Oxocyclohexane-1-carbonitrile (CAS Registry number: 34916-10-4) (1.0 g) was dissolved in dichloromethane (10 mL) and a dichloromethane solution (10 mL) of (diethylamino)sulfur trifluoride (1.6 g) was added thereto at 0° C., and the solution was stirred at 0° C. for 2 hours.

The reaction mixture was poured into a sodium hydrogen carbonate aqueous solution, and the reaction mixture was extracted three times with dichloromethane. The combined organic layers were washed with a saturated saline solution and dried over anhydrous sodium sulfate. After filtration, the residues obtained by distilling off the solvent under reduced pressure were purified by silica gel column chromatography [eluting solvent:petroleum ether/ethyl acetate=20/1 (V/V)], thereby obtaining 0.70 g (yield: 50%) of the title compound as a yellow solid.

(1b)

4,4-Difluoro-N'-hydroxycyclohexane-1-carboximidamide 4,4-Difluoro-N'-hydroxycyclohexane-1-carboximidamide 4,4-Difluorocyclohexane-1-carbonitrile (0.70 g) of Example 1 (1a) was dissolved in tetrahydrofuran (10 mL), hydroxylamine hydrochloride (0.37 g) and triethylamine (1.24 g) were added thereto, and the mixture was stirred at 65° C. for 12 hours.

Water was added to the residues obtained by distilling off the solvent from the reaction mixture under reduced pressure, and the reaction mixture was extracted three times with ethyl acetate. The combined organic layers were washed with a saturated saline solution, dried over anhydrous sodium sulfate, and filtered, and the solvent was distilled off under reduced pressure, thereby obtaining 0.50 g (yield: 69%) of the title compound as a white solid.

(1c)

N-(5-cyano-4,5,6,7-tetrahydro[1,3]thiazolo[5,4-c]pyridin-2-yl)-N'-methylurea

N-(5-cyano-4,5,6,7-tetrahydro[1,3]thiazolo[5,4-c]pyridin-2-yl)-N'-methylurea

N-methyl-N'-(4,5,6,7-tetrahydro[1,3]thiazolo[5,4-c]pyridin-2-yl)urea (International Publication No. WO2010/024258) (17 g) and sodium hydrogen carbonate (13 g) were dissolved in dichloromethane (500 mL) and water (100 mL), and a dichloromethane solution (100 mL) of bromocyan (10 g) was added dropwise thereto at 0° C. The mixture was stirred at 0° C. for 2 hours and further stirred at room temperature for 13 hours.

The reaction mixture was poured into water and the reaction mixture was extracted three times with dichloromethane. The combined organic layers were washed with water and a saturated saline solution and dried over anhydrous sodium sulfate. After filtration, the solvent was distilled off under reduced pressure, thereby obtaining 13.0 g (yield: 68%) of the title compound as a yellow solid.

(1d)

N-{5-[3-(4,4-difluorocyclohexyl)-1,2,4-oxadiazol-5-yl]-4,5,6,7-tetrahydro[1,3]thiazolo[5,4-c]pyridin-2-yl}-N'-methylurea N-{5-[3-(4,4-difluorocyclohexyl)-1,2,4-oxadiazol-5-yl]-4,5,6,7-tetrahydro[1,3]thiazolo[5,4-c]pyridin-2-yl}-N'-methylurea 4,4-Difluoro-N'-hydroxycyclohexane-1-carboximidamide (150 mg) of Example 1 (1b) was dissolved in N,N-dimethylformamide (5 mL), and N-(5-cyano-4,5,6,7-tetrahydro[1,3]thiazolo[5,4-c]pyridin-2-yl)-N'-methylurea (222 mg) of Example 1 (1c), zinc chloride (34.4 mg), and tosylic acid monohydrate (48.0 mg) were sequentially added thereto at room temperature, and the mixture was stirred at 80° C. for 12 hours.

The reaction mixture was poured into water, the reaction mixture was extracted three times with ethyl acetate, and the combined organic layers were washed with a saturated saline solution and dried over anhydrous sodium sulfate. After filtration, the residues obtained by distilling off the solvent under reduced pressure were purified by high performance liquid chromatography [column: Phenomenex luna C18; mobile phase:acetonitrile/0.225% formic acid aqueous solution=30/70 to 60/40 (V/V)], thereby obtaining 111 mg (yield: 32%) of the title compound as a white solid.

Example 2

N-methyl-N'-{5-[5-(trifluoromethyl)-1,3,4-oxadiazol-2-yl]-4,5,6,7-tetrahydro[1,3]thiazolo[5,4-c]pyridin-2-yl}urea (2a)

N-[5-(1H-imidazole-1-carbothioyl)-4,5,6,7-tetrahydro[1,3]thiazolo[5,4-c]pyridin-2-yl]-N'-methylurea N-[5-(1H-imidazole-1-carbothioyl)-4,5,6,7-tetrahydro[1,3]thiazolo[5,4-c]pyridin-2-yl]-N'-methylurea N-methyl-N'-(4,5,6,7-tetrahydro[1,3]thiazolo[5,4-c]pyridin-2-yl)urea (International Publication No. WO2010/024258A) (5.0 g) was suspended in tetrahydrofuran (50 mL), 1,1'-thiocarbonyldiimidazole (4.6 g) was added thereto, and the solution was allowed to stand at room temperature for 2 days.

The precipitated solid was collected by filtration and washed with tetrahydrofuran, thereby obtaining 7.5 g (yield: 99%) of the title compound as a white solid.

(2b)

N-[5-(hydrazinecarbothioyl)-4,5,6,7-tetrahydro[1,3]thiazolo[5,4-c]pyridin-2-yl]-N'-methylurea N-[5-(hydrazinecarbothioyl)-4,5,6,7-tetrahydro[1,3]thiazolo[5,4-c]pyridin-2-yl]-N'-methylurea N-[5-(1H-imidazole-1-carbothioyl)-4,5,6,7-tetrahydro[1,3]thiazolo[5,4-c]pyridin-2-yl]-N'-methylurea (7.5 g) of Example 2 (2a) was suspended in ethanol (100 mL), a hydrazine monohydrate (3.4 mL) was added thereto, and the solution was allowed to stand at room temperature overnight.

The precipitated solid was collected by filtration and washed with ethanol, thereby obtaining 5.7 g (yield: 86%) of the title compound as a white solid.

(2c)

N-methyl-N'-{5-[2-(trifluoroacetyl)hydrazinecarbothioyl]-4,5,6,7-tetrahydro[1,3]thiazolo[5,4-c]pyridin-2-yl}urea N-methyl-N'-{5-[2-(trifluoroacetyl)hydrazinecarbothioyl]-4,5,6,7-tetrahydro[1,3]thiazolo[5,4-c]pyridin-2-yl}urea N-[5-(hydrazinecarbothioyl)-4,5,6,7-tetrahydro[1,3]thiazolo[5,4-c]pyridin-2-yl]-N'-methylurea (6.54 g) of Example 2 (2b) was suspended in dichloromethane (30 mL), a trifluoroacetic anhydride (4.80 mL) and trifluoroacetic acid (5.24 mL) were added thereto, and the solution was stirred at room temperature for 3 hours.

The reaction solution was concentrated and subjected to azeotropy twice with toluene, and the obtained solid was triturated with ethyl acetate/n-hexane and collected by filtration, thereby obtaining 8.8 g (yield: quantitative) of the title compound as a pale yellow solid.

(2d)

N-methyl-N'-{5-[5-(trifluoromethyl)-1,3,4-oxadiazol-2-yl]-4,5,6,7-tetrahydro[1,3]thiazolo[5,4-c]pyridin-2-yl}urea N-methyl-N'-{5-[5-(trifluoromethyl)-1,3,4-oxadiazol-2-yl]-4,5,6,7-tetrahydro[1,3]thiazolo[5,4-c]pyridin-2-yl}urea N-methyl-N'-{5-[2-(trifluoroacetyl)hydrazinecarbothioyl]-4,5,6,7-tetrahydro[1,3]thiazolo[5,4-c]pyridin-2-yl}urea (8.8 g) of Example 2 (2c) was dissolved in dimethyl sulfoxide (100 mL), 1-ethyl-3-(3-dimethylaminopropyl)carbodiimide hydrochloride (5.3 g) was added thereto, and the mixture was stirred at 70° C. for 2 hours.

Water was added to the reaction mixture, and the precipitated solid was collected by filtration and washed with water and ethyl acetate. The obtained solid was suspended in ethyl acetate/ethanol and stirred for a period of time while being heated. The precipitated solid was recovered by hot filtration, thereby obtaining 4.1 g (yield: 51%) of the title compound as a pale yellow solid.

Example 3

N-(5-{5-[(1R)-1-ethoxyethyl]-1,3,4-oxadiazol-2-yl}-4,5,6,7-tetrahydro[1,3]thiazolo[5,4-c]pyridin-2-yl)-N'-methylurea (3a)

Methyl (2R)-2-ethoxypropanoate

Methyl (2R)-2-ethoxypropanoate

D-(+)-methyl lactate (CAS Registry number: 17392-83-5) (2.0 g) and iodoethane (5.99 g) were dissolved in diethyl ether (20 mL), silver oxide (8.90 g) was added thereto at room temperature, and the mixture was stirred at room temperature for 12 hours. Further, iodoethane (3.00 g) and silver oxide (4.45 g) were added thereto, and the mixture was stirred at room temperature for 24 hours.

The reaction mixture was filtered, and the solvent was distilled off from the filtrate under reduced pressure, thereby obtaining 1.00 g (yield: 32%) of the title compound as a pale yellow oily material.

(3b)

(2R)-2-ethoxypropanoic acid (2R)-2-ethoxypropanoic acid

Methyl (2R)-2-ethoxypropanoate (1.0 g) of Example 3 (3a) was dissolved in tetrahydrofuran (6 mL), methanol (6 mL), and water (3 mL), a lithium hydroxide monohydrate (0.79 g) was added thereto, and the mixture was stirred at room temperature for 2 hours.

The solvent was distilled off from the reaction mixture under reduced pressure, water was added to the obtained residues, and the reaction mixture was washed with ethyl acetate. The pH of the water layer was adjusted to 2 with 1 M hydrochloric acid and the water layer was extracted 5 times with ethyl acetate. The combined organic layers were washed with a saturated saline solution, dried over anhydrous sodium sulfate, and filtered, and the solvent was distilled off under reduced pressure, thereby obtaining 0.60 g (yield: 67%) of the title compound as a pale yellow oily material.

(3c)

N-(5-{2-[(2R)-2-ethoxypropanoyl]hydrazinecarbothioyl}-4,5,6,7-tetrahydro[1,3]thiazolo[5,4-c]pyridin-2-yl)-N'-methylurea N-(5-{2-[(2R)-2-ethoxypropanoyl]hydrazinecarbothioyl}-4,5,6,7-tetrahydro[1,3]thiazolo[5,4-c]pyridin-2-yl)-N'-methylurea (2R)-2-ethoxypropanoic acid (112 mg) of Example 3 (3b) was dissolved in N,N-dimethylformamide (5 mL), 4-methylmorpholine (0.208 mL), 1H-benzotriazol-1-yloxytripyrrolidinophosphonium hexafluorophosphate (981 mg), and N-[5-(hydrazinecarbothioyl)-4,5,6,7-tetrahydro[1,3]thiazolo[5,4-c]pyridin-2-yl]-N'-methylurea (150 mg) of Example 2 (2b) were added thereto at room temperature, and the mixture was stirred at 40° C. for 12 hours.

The residues obtained by distilling off the solvent from the reaction mixture under reduced pressure was purified by silica gel column chromatography [eluting solvent:ethyl acetate/methanol=1/0 to 30/1 (V/V)], thereby obtaining 110 mg (yield: 60%) of the title compound as a yellow solid.

(3d)

N-(5-{5-[(1R)-1-ethoxyethyl]-1,3,4-oxadiazol-2-yl}-4,5,6,7-tetrahydro[1,3]thiazolo[5,4-c]pyridin-2-yl)-N'-methylurea N-(5-{5-[(1R)-1-ethoxyethyl]-1,3,4-oxadiazol-2-yl}-4,5,6,7-tetrahydro[1,3]thiazolo[5,4-c]pyridin-2-yl)-N'-methylurea N-(5-{2-[(2R)-2-ethoxypropanoyl]hydrazinecarbothioyl}-4,5,6,7-tetrahydro[1,3]thiazolo[5,4-c]pyridin-2-yl)-N'-methylurea (90 mg) of Example 3 (3c) was dissolved in dimethyl sulfoxide (3 mL), 1-ethyl-3-(3-dimethylaminopropyl)carbodiimide hydrochloride (112 mg) was added thereto, and the mixture was stirred at 60° C. for 15 minutes.

The filtrate obtained by filtering the reaction mixture was purified by high performance liquid chromatography [column: Phenomenex Gemini C18; mobile phase:acetonitrile/0.05% ammonia water=18/82 to 42/58 (V/V)], thereby obtaining 26 mg (yield: 32%) of the title compound as a pale yellow solid.

Example 4

N-methyl-N'-(5-{3-[1-(2,2,2-trifluoroethoxy)ethyl]-1,2,4-oxadiazol-5-yl}-4,5,6,7-tetrahydro[1,3]thiazolo[5,4-c]pyridin-2-yl)urea (4a)

2-(2,2,2-Trifluoroethoxy)propanoic acid 2-(2,2,2-Trifluoroethoxy)propanoic acid 2,2,2-Trifluoroethanol (6.54 g) was dissolved in tetrahydrofuran (30 mL) and sodium (601 mg) was added thereto at 0° C. After the sodium was dissolved, 2-bromopropanoic acid (CAS Registry number: 598-72-1) (2.00 g) was added thereto, and the mixture was stirred at 50° C. for 12 hours.

Water was added to the reaction mixture, the pH thereof was adjusted to 9 with a 2 M sodium hydroxide aqueous solution, and the solution was washed with ethyl acetate. The pH of the water layer was adjusted to 2 with 2 M hydrochloric acid and the water layer was extracted 3 times with ethyl acetate. The combined organic layers were washed with a saturated saline solution, dried over anhydrous sodium sulfate, and filtered, and the solvent was distilled off under reduced pressure, thereby obtaining 2.20 g (yield: 98%) of the title compound as a colorless oily material.

(4b)

2-(2,2,2-trifluoroethoxy)propanamide 2-(2,2,2-trifluoroethoxy)propanamide

Thionyl chloride (10 mL) was added to 2-(2,2,2-trifluoroethoxy)propanoic acid (2.2 g) of Example 4 (4a), and the mixture was stirred at room temperature for 12 hours. The residues obtained by distilling off the solvent from the reaction mixture under reduced pressure was dissolved in tetrahydrofuran (5 mL), ammonia (4 mol/L tetrahydrofuran solution, 14.7 mL) was added thereto at 0° C., and the solution was stirred at room temperature for 12 hours.

The residues obtained by concentrating the reaction solution were triturated with ethyl acetate/petroleum ether and collected by filtration, thereby obtaining 0.78 g (yield: 36%) of the title compound as a yellow solid.

(4c)

2-(2,2,2-trifluoroethoxy)propanenitrile 2-(2,2,2-trifluoroethoxy)propanenitrile

Thionyl chloride (1.0 mL) was added to 2-(2,2,2-trifluoroethoxy)propanamide (0.58 g) of Example 4 (4b), and the mixture was stirred at 90° C. for 12 hours.

The solvent was distilled off from the reaction mixture under reduced pressure, thereby obtaining 0.52 g (yield: quantitative) of the title compound as a yellow oily material.

(4d)

N-methyl-N'-(5-{3-[1-(2,2,2-trifluoroethoxy)ethyl]-1,2,4-oxadiazol-5-yl}-4,5,6,7-tetrahydro[1,3]thiazolo[5,4-c]pyridin-2-yl)urea N-methyl-N'-(5-{3-[1-(2,2,2-trifluoroethoxy)ethyl]-1,2,4-oxadiazol-5-yl}-4,5,6,7-tetrahydro[1,3]thiazolo[5,4-c]pyridin-2-yl)urea 52 mg (yield: 32%) of the title compound was obtained as a white solid according to the same method as in Example 1 (1d) using N'-hydroxy-2-(2,2,2-trifluoroethoxy)propane imidamide (77 mg) synthesized from 2-(2,2,2-trifluoroethoxy)propanenitrile of Example 4 (4c) in the same manner as in Example 1 (1b) and N-(5-cyano-4,5,6,7-tetrahydro[1,3]thiazolo[5,4-c]pyridin-2-yl)-N'-methylurea (100 mg) of Example 1 (1c).

Example 5

N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(2R)-1-hydroxypropan-2-yl]urea (5a)

tert-Butyl 2-({[(prop-2-en-1-yl)oxy]carbonyl}amino)-6,7-dihydro[1,3]thiazolo[5,4-c]pyridin-5(4H)-carboxylate tert-Butyl 2-({[(prop-2-en-1-yl)oxy]carbonyl}amino)-6,7-dihydro[1,3]thiazolo[5,4-c]pyridin-5(4H)-carboxylate tert-Butyl 2-amino-6,7-dihydro[1,3]thiazolo[5,4-c]pyridine-5(4H)-carboxylate (CAS Registry number: 365996-05-0) (10.0 g) and N,N-diisopropylethylamine (19.5 mL) were dissolved in tetrahydrofuran (100 mL), allyl chloroformate (5.90 mL) was added thereto, and the mixture was stirred at room temperature for 12 hours.

Methanol was added to the reaction mixture, the residues obtained by distilling off the solvent under reduced pressure were purified by silica gel column chromatography [eluting solvent:petroleum ether/ethyl acetate=3/1 (V/V)], thereby obtaining 8.40 g (yield: 67%) of the title compound as a pale yellow solid.

(5b)

Prop-2-en-1-yl{5-[3-(4,4-difluorocyclohexyl)-1,2,4-oxadiazol-5-yl]-4,5,6,7-tetrahydro[1,3]thiazolo[5,4-c]pyridin-2-yl}carbamate Prop-2-en-1-yl{5-[3-(4,4-difluorocyclohexyl)-1,2,4-oxadiazol-5-yl]-4,5,6,7-tetrahydro[1,3]thiazolo[5,4-c]pyridin-2-yl}carbamate 160 mg (yield: 35%) of the title compound was obtained as a pale yellow solid according to the same method as in Example 1 (1d) using prop-2-en-1-yl(5-cyano-4,5,6,7-tetrahydro[1,3]thiazolo[5,4-c]pyridin-2-yl)carbamate (282 mg) synthesized from tert-butyl 2-({[(prop-2-en-1-yl)oxy]carbonyl}amino)-6,7-dihydro[1,3]thiazolo[5,4-c]pyridine-5(4H)-carboxylate of Example 5 (5a) in the same manner as in Examples 6 (6h) and 1 (1c) and 4,4-difluoro-N'-hydroxycyclohexane-1-carboximidamide (190 mg) of Example 1 (1b).

(5c)

5-[3-(4,4-difluorocyclohexyl)-1,2,4-oxadiazol-5-yl]-4,5,6,7-tetrahydro[1,3]thiazolo[5,4-c]pyridin-2-amine 5-[3-(4,4-difluorocyclohexyl)-1,2,4-oxadiazol-5-yl]-4,5,6,7-tetrahydro[1,3]thiazolo[5,4-c]pyridin-2-amine Prop-2-en-1-yl {5-[3-(4,4-difluorocyclohexyl)-1,2,4-oxadiazol-5-yl]-4,5,6,7-tetrahydro[1,3]thiazolo[5,4-c]pyridin-2-yl} carbamate (150 mg) of Example 5 (5b) and dimedone (240 mg) were dissolved in dichloromethane (5 mL) in a nitrogen atmosphere, and tetrakistriphenylphosphine palladium (45 mg) was added thereto, and the mixture was stirred at room temperature for 12 hours.

The residues obtained by distilling off the solvent from the reaction mixture under reduced pressure were purified by silica gel column chromatography [eluting solvent:petroleum ether/ethyl acetate/methanol=1/1/0 to 0/100/1 (V/V/V)], thereby obtaining 100 mg (yield: 66%) of the title compound as a yellow solid.

(5d)

N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(2R)-1-hydroxypropan-2-yl]urea N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(2R)-1-hydroxypropan-2-yl]urea

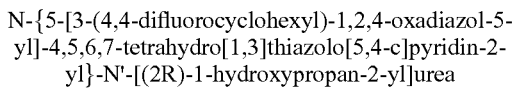
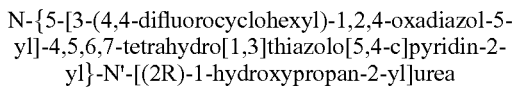

5-[3-(4,4-Difluorocyclohexyl)-1,2,4-oxadiazol-5-yl]-4,5,6,7-tetrahydro[1,3]thiazolo[5,4-c]pyridin-2-amine (100 mg) of Example 5 (5c) was dissolved in N,N-dimethylformamide (5 mL), 1,1'-carbonyldiimidazole (95 mg) was added thereto, and the mixture was stirred at room temperature for 5.5 hours. (R)-(−)-2-amino-1-propanol (0.069 mL) was added to the reaction mixture, and the mixture was stirred at room temperature for 12 hours.

The reaction mixture was poured into water and the reaction mixture was extracted 3 times with ethyl acetate. The combined organic layers were washed with a saturated saline solution and dried over anhydrous sodium sulfate. After filtration, the residues obtained by distilling off the solvent under reduced pressure were purified by high performance liquid chromatography [column: Phenomenex Synergi C18; mobile phase:acetonitrile/0.225% formic acid aqueous solution=28/72 to 58/42 (V/V)], thereby obtaining 23 mg (yield: 17%) of the title compound as a yellow solid.

Example 6

N-methyl-N'-(10-{3-[(1s,4s)-4-(trifluoromethyl)cyclohexyl]-1,2,4-oxadiazol-5-yl}-4,7,8,9-tetrahydro-5H-4,8-epiminooxocino[5,4-d][1,3]thiazol-2-yl)urea (6a)

(1s,4s)-4-(trifluoromethyl)cyclohexane-1-carboxamide (1s,4s)-4-(trifluoromethyl)cyclohexane-1-carboxamide

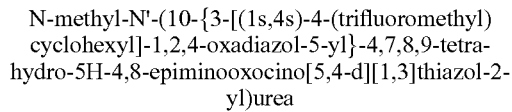

(1s,4s)-4-(Trifluoromethyl)cyclohexane-1-carboxylic acid (CAS Registry number: 1202578-27-5) (1.00 g) and triethylamine (1.04 mL) were dissolved in dichloromethane (25 mL), isobutyl chloroformate (0.87 mL) was added dropwise thereto at 0° C., and the mixture was stirred at 0° C. for 1 hour. The reaction mixture was added dropwise to a 28% ammonia aqueous solution (19 mL) at 0° C., and the mixture was stirred at room temperature for 2 hours.

The reaction mixture was poured into water and extracted 3 times with dichloromethane. The combined organic layers were washed with a saturated saline solution and dried over anhydrous sodium sulfate. After filtration, the solvent was distilled off under reduced pressure, thereby obtaining 1.04 g (yield: quantitative) of the title compound as a white solid.

(6b)

(1s,4s)-4-(trifluoromethyl)cyclohexane-1-carbonitrile (1s,4s)-4-(trifluoromethyl)cyclohexane-1-carbonitrile

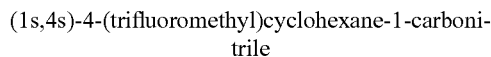
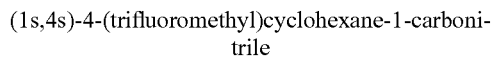

(1s,4s)-4-(Trifluoromethyl)cyclohexane-1-carboxamide (1.04 g) of Example 6 (6a) was suspended in dichloromethane (20 mL), triethylamine (1.41 mL) was added thereto at 0° C., a trifluoroacetic anhydride (0.785 mL) was added dropwise thereto for 5 minutes, and the solution was stirred at 0° C. for 2 hours.

The reaction solution was diluted with water and extracted twice with dichloromethane. The combined organic layers were sequentially washed with water and a saturated saline solution and dried over anhydrous sodium sulfate. After filtration, the residues obtained by distilling off the solvent under reduced pressure were purified by silica gel column chromatography [eluting solvent:ethyl acetate/n-hexane=1/4 to 2/1 (V/V)], thereby obtaining 804 mg (yield: 89%) of the title compound as a white solid.

(6c)

(1s,4s)-N'-hydroxy-4-(trifluoromethyl)cyclohexane-1-carboximidamide (1s,4s)-N'-hydroxy-4-(trifluoromethyl)cyclohexane-1-carboximidamide

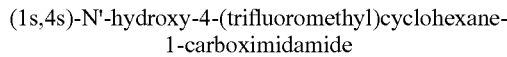
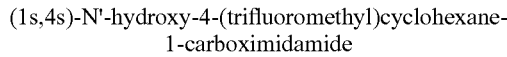

(1s,4s)-4-(Trifluoromethyl)cyclohexane-1-carbonitrile (278 mg) of Example 6 (6b) was dissolved in ethanol (8 mL), a 50% hydroxylamine aqueous solution (0.15 mL) was added thereto, and the mixture was stirred at 50° C. for 3.5 hours.

The solvent was distilled off from the reaction mixture under reduced pressure and the mixture was subjected to azeotropy with ethanol, chloroform and water were added to the residues, the mixture was stirred, the organic layer was separated by a phase separator (Biotage Japan Ltd.), and the solvent was distilled off under reduced pressure. The obtained residues were dissolved in ethanol (4 mL), a 50% hydroxylamine aqueous solution (2.0 mL) was added thereto, and the solution was stirred at 60° C. for 4 hours.

The reaction mixture was cooled to room temperature, the solvent was distilled off under reduced pressure, and the mixture was subjected to azeotropy with ethanol and vacuum-dried at 50° C., thereby obtaining 187 mg (yield: 57%) of the title compound as a white solid.

(6d)

9-Benzyl-3-oxa-9-azabicyclo[3.3.1]nonan-7-one

9-Benzyl-3-oxa-9-azabicyclo[3.3.1]nonan-7-one

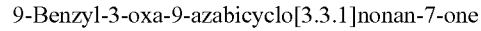
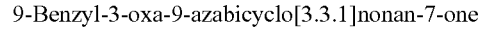

3,6-Dioxabicyclo[3.1.0]hexane (CAS registry number: 285-69-8) (2.40 kg) was dissolved in water (12 L), concentrated sulfuric acid (25.2 g) was added thereto at 15° C., and the mixture was stirred at 95° C. for 16 hours. The reaction mixture was cooled to 15° C., and a 3 M sodium hydroxide aqueous solution (97 mL) was added thereto so that the pH thereof was adjusted to 7 to 8.

Subsequently, sodium periodate (5.33 kg) was added thereto at 5° C. to 10° C. for 3 hours, and the mixture was stirred at 10° C. to 15° C. for 16 hours. Acetonitrile (12 L) was added to the reaction mixture, and the mixture was stirred at room temperature for 30 minutes, the precipitated solid was filtered off, the filtrate was concentrated under reduced pressure, and most of the acetonitrile was distilled off.

Subsequently, 1,3-acetonedicarboxylic acid (4.47 kg), acetonitrile (8 L), and 12 M hydrochloric acid (719 mL) were added thereto, the solution was cooled to 10° C., and benzylamine (2.98 kg) was added dropwise thereto at 10° C. to 30° C. The mixture was stirred at 10° C. to 20° C. for 1 hour and further stirred at 50° C. for 16 hours.

The precipitated solid was collected by filtration and washed with ethanol (300 mL), thereby obtaining 2.70 kg (yield: 33%) of the title compound as a pale yellow solid.
(6e)

tert-Butyl 7-oxo-3-oxa-9-azabicyclo[3.3.1]nonane-9-carboxylate tert-Butyl 7-oxo-3-oxa-9-azabicyclo[3.3.1]nonane-9-carboxylate Example 6E-1

9-Benzyl-3-oxa-9-azabicyclo[3.3.1]nonan-7-one (150 g) of Example 6 (6d) was dissolved in 1 M hydrochloric acid (1.0 L) and ethanol (700 mL), 10% palladium carbon (20 g) was added thereto, and the mixture was stirred at 50° C. for 20 hours in a hydrogen (50 psi) atmosphere. By filtering off the insoluble material and concentrating the filtrate under reduced pressure, most of the ethanol was distilled off, thereby obtaining a mixture containing 3-oxa-9-azabicyclo [3.3.1]nonan-7-one hydrochloride.

Example 6E-2

Tetrahydrofuran (1.2 L) and sodium hydrogen carbonate (327 g) were added to the mixture obtained in Example 6e-1, the mixture was stirred at room temperature for 1 hour, di-tert-butyl dicarbonate (339 g) was added thereto, and the mixture was stirred at 30° C. to 40° C. for 16 hours.

The reaction mixture was filtered, and the filtrate was extracted 3 times with ethyl acetate. The combined organic layers were dried over anhydrous sodium sulfate, and the residues obtained by distilling off the solvent under reduced pressure were triturated with ethyl acetate/petroleum ether and collected by filtration, thereby obtaining 190 g (yield: 61%) of the title compound as a yellow solid.
(6f)

tert-Butyl 2-amino-4,7,8,9-tetrahydro-5H-4,8-epiminooxocino[5,4-d][1,3]thiazole-10-carboxylate tert-Butyl 2-amino-4,7,8,9-tetrahydro-5H-4,8-epiminooxocino[5,4-d][1,3]thiazole-10-carboxylate tert-Butyl 7-oxo-3-oxa-9-azabicyclo[3.3.1]nonane-9-carboxylate (300 g) of Example 6 (6e) was dissolved in toluene (1.4 L), pyrrolidine (146 mL) and a tosylic acid monohydrate (30.0 g) were added thereto at room temperature, and the mixture was stirred at 135° C. for 4 hours using a Dean-Stark apparatus.

The residues obtained by distilling off the solvent from the reaction mixture under reduced pressure were dissolved in methanol (1.5 L), sulfur (43.0 g) and cyanamide (68.0 g) were added thereto, and the mixture was stirred at room temperature for 18 hours.

The reaction mixture was concentrated under reduced pressure, most of the methanol was distilled off, and dichloromethane was added thereto. The organic layer was washed with a saturated sodium hydrogen carbonate aqueous solution and dried over anhydrous sodium sulfate. The residues obtained by distilling off the solvent under reduced pressure were triturated with ethyl acetate/petroleum ether and collected by filtration, thereby obtaining 190 g (yield: 61%) of the title compound as a yellow solid.
(6g)

tert-Butyl 2-[(methylcarbamoyl)amino]-4,7,8,9-tetrahydro-5H-4,8-epiminooxocino[5,4-d][1,3]thiazole-10-carboxylate tert-Butyl 2-[(methylcarbamoyl)amino]-4,7,8,9-tetrahydro-5H-4,8-epiminooxocino[5,4-d][1,3]thiazole-10-carboxylate tert-Butyl 2-amino-4,7,8,9-tetrahydro-5H-4,8-epiminooxocino[5,4-d][1,3]thiazole-10-carboxylate (95 g) of Example 6 (6f) and N,N-diisopropylethylamine (133 mL) were dissolved in tetrahydrofuran (1 L), N-methylcarbamoyl chloride (57 g) was added dropwise thereto at 0° C., and the mixture was stirred at 60° C. for 12 hours.

The residues obtained by distilling off the solvent from the reaction mixture under reduced pressure were triturated with petroleum ether/ethyl acetate, and the precipitated solid was collected by filtration. The obtained solid was dissolved in dichloromethane, washed with water and a saturated saline solution, and dried over anhydrous sodium sulfate. The solvent was distilled off under reduced pressure, thereby obtaining 100 g (yield: 84%) of the title compound as a yellow solid.
(6h)

N-methyl-N'-(4,7,8,9-tetrahydro-5H-4,8-epiminooxocino[5,4-d][1,3]thiazol-2-yl)urea monohydrochloride N-methyl-N'-(4,7,8,9-tetrahydro-5H-4,8-epiminooxocino[5,4-d][1,3]thiazol-2-yl)urea-hydrogen chloride (1/1)

tert-Butyl 2-[(methylcarbamoyl)amino]-4,7,8,9-tetrahydro-5H-4,8-epiminooxocino[5,4-d][1,3]thiazole-10-carboxylate (100 g) of Example 6 (6 g) was dissolved in dichloromethane (1 L), a 4 M hydrogen chloride-ethyl acetate solution (300 mL) was added thereto, and the mixture was stirred at room temperature for 12 hours.

The solvent was distilled off under reduced pressure, thereby obtaining 83 g (yield: 95%) of the title compound as a pale yellow solid.
(6i)

N-[10-cyano-4,7,8,9-tetrahydro-5H-4,8-epiminooxocino[5,4-d][1,3]thiazol-2-yl]-N'-methylurea N-[10-cyano-4,7,8,9-tetrahydro-5H-4,8-epiminooxocino[5,4-d][1,3]thiazol-2-yl]-N'-methylurea 1.58 g (yield: 75%) of the title compound was obtained as a white solid according to the same method as in Example 1 (1c) using N-methyl-N'-(4,7,8,9-tetrahydro-5H-4,8-epiminooxocino[5,4-d][1,3]thiazol-2-yl)urea monohydrochloride (2.19 g) of Example 6 (6h).

(6j)

N-methyl-N'-(10-{3-[(1s,4s)-4-(trifluoromethyl)cyclohexyl]-1,2,4-oxadiazol-5-yl}-4,7,8,9-tetrahydro-5H-4,8-epiminooxocino[5,4-d][1,3]thiazol-2-yl)urea N-methyl-N'-(10-{3-[(1s,4s)-4-(trifluoromethyl)cyclohexyl]-1,2,4-oxadiazol-5-yl}-4,7,8,9-tetrahydro-5H-4,8-epiminooxocino[5,4-d][1,3]thiazol-2-yl)urea N-[10-cyano-4,7,8,9-tetrahydro-5H-4,8-epiminooxocino[5,4-d][1,3]thiazol-2-yl]-N'-methylurea (120 mg) of Example 6 (6i), (1s,4s)-N'-hydroxy-4-(trifluoromethyl)cyclohexane-1-carboximidamide (101 mg) of Example 6 (6c), and zinc chloride (77 mg) were suspended in N,N-dimethylformamide (5 mL), and the mixture was stirred at 60° C. for 2 hours in a nitrogen atmosphere. Concentrated sulfuric acid (0.1 mL) was added to the reaction mixture, and the mixture was further stirred at 80° C. for 3 hours.

The reaction mixture was cooled to room temperature, poured into water, and extracted twice with ethyl acetate. The combined organic layers were washed twice with water and once with a saturated saline solution and dried over anhydrous sodium sulfate. After filtration, the residues obtained by distilling off the solvent under reduced pressure were purified by silica gel column chromatography [eluting solvent:ethyl acetate/methanol=1/0 to 9/1 (V/V)], thereby obtaining 105 mg (yield: 52%) of the title compound as a white solid.

Example 7

N-{(4S,8S)-10-[3-(4,4-difluorocyclohexyl)-1,2,4-oxadiazol-5-yl]-4,7,8,9-tetrahydro-5H-4,8-epiminooxocino[5,4-d][1,3]thiazol-2-yl}-N'-methylurea (7a)

tert-Butyl (4S,8S)-2-amino-4,7,8,9-tetrahydro-5H-4,8-epiminooxocino[5,4-d][1,3]thiazole-10-carboxylate tert-Butyl (4S,8S)-2-amino-4,7,8,9-tetrahydro-5H-4,8-epiminooxocino[5,4-d][1,3]thiazole-10-carboxylate (Optical Resolution Using Chiral Column)

tert-Butyl 2-amino-4,7,8,9-tetrahydro-5H-4,8-epiminooxocino[5,4-d][1,3]thiazole-10-carboxylate (160 g) of Example 6 (6f) was applied to chiral SFC (column: CHIRALPAK AD (250 mm*30 mm, 10 m)) [mobile phase: 0.1% ammonia water/isopropanol/carbon dioxide] to obtain 67 g (yield: 42%) of tert-butyl(4S,8S)-2-amino-4,7,8,9-tetrahydro-5H-4,8-epiminooxocino[5,4-d][1,3]thiazole-10-carboxylate (Peak 1, retention time: 2.370 min) as a yellow solid and 69 g (yield: 43%) of tert-butyl (4R,8R)-2-[(methylcarbamoyl)amino]-4,7,8,9-tetrahydro-5H-4,8-epiminooxocino[5,4-d][1,3]thiazole-10-carboxylate (peak 2, retention time: 2.573 min) as a yellow solid.

In addition, the absolute configuration of tert-butyl (4S,8S)-2-amino-4,7,8,9-tetrahydro-5H-4,8-epiminooxocino[5,4-d][1,3]thiazole-10-carboxylate was determined by X-ray crystallography of an intermediate (Example 20 (20a)) synthesized using the present compound.

(Optical Resolution Using Diastereomer Salt Method)

Ethyl acetate (15 L) was added to tert-butyl 2-amino-4,7,8,9-tetrahydro-5H-4,8-epiminooxocino[5,4-d][1,3]thiazole-10-carboxylate (1.0 kg) of Example 6 (6f) and (+)-di-p-toluoyl-D-tartaric acid (CAS Registry number: 32634-68-7) (580 g), and the mixture was stirred at 70° C. for 3 hours. The mixture was slowly cooled to room temperature, and the precipitated solid was collected by filtration and washed with ethyl acetate (1 L).

The obtained solid was added to a 1 M sodium hydroxide aqueous solution and extracted 3 times with ethyl acetate. The combined organic layers were dried over anhydrous sodium sulfate, and the solvent was distilled off under reduced pressure. The obtained residues were dissolved in ethyl acetate (1 L) at 60° C., and petroleum ether (1 L) was added thereto. The mixture was stirred at 60° C. for 0.5 hours and slowly cooled to room temperature, and the precipitated solid was collected by filtration and wash with ethyl acetate/petroleum ether (100 mL/100 mL), thereby obtaining 285 g (yield: 29%) of the title compound as a white solid.

(7b)

N-methyl-N'-[(4S,8S)-4,7,8,9-tetrahydro-5H-4,8-epiminooxocino[5,4-d][1,3]thiazol-2-yl]urea monohydrochloride N-methyl-N'-[(4S,8S)-4,7,8,9-tetrahydro-5H-4,8-epiminooxocino[5,4-d][1,3]thiazol-2-yl]urea-hydrogen chloride (1/1)

6.0 g (yield: quantitative) of the title compound was obtained as a white solid according to the same method as in Example 6 (6h) using tert-butyl (4S,8S)-2-[(methylcarbamoyl)amino]-4,7,8,9-tetrahydro-5H-4,8-epiminooxocino[5,4-d][1,3]thiazole-10-carboxylate (6.0 g) synthesized from tert-butyl (4S,8S)-2-amino-4,7,8,9-tetrahydro-5H-4,8-epiminooxocino[5,4-d][1,3]thiazole-10-carboxylate of Example 7 (7a) in the same manner as in Example 6 (6h).

(7c)

N-{(4S,8S)-10-[3-(4,4-difluorocyclohexyl)-1,2,4-oxadiazol-5-yl]-4,7,8,9-tetrahydro-5H-4,8-epiminooxocino[5,4-d][1,3]thiazol-2-yl}-N'-methylurea N-{(4S,8S)-10-[3-(4,4-difluorocyclohexyl)-1,2,4-oxadiazol-5-yl]-4,7,8,9-tetrahydro-5H-4,8-epiminooxocino[5,4-d][1,3]thiazol-2-yl}-N'-methylurea 39 mg (yield: 32%) of the title compound was obtained as a white solid according to the same method as in Example 1 (1d) using N-[(4S,8S)-10-cyano-4,7,8,9-tetrahydro-5H-4,8-epiminooxocino[5,4-d][1,3]thiazol-2-yl]-N'-methylurea (80 mg) synthesized from N-methyl-N'-[(4S,8S)-4,7,8,9-tetrahydro-5H-4,8-epiminooxocino[5,4-d][1,3]thiazol-2-yl]urea monohydrochloride of Example 7 (7b) in the same manner as in Example 1 (1c) and 4,4-difluoro-N'-hydroxycyclohexane-1-carboximidamide (50 mg) of Example 1 (1b).

93

Example 8

N-methyl-N'-(5-{3-[3-(trifluoromethoxy)phenyl]-1,2,4-oxadiazol-5-yl}-4,5,6,7-tetrahydro[1,3]thiazolo[5,4-c]pyridin-2-yl)urea (8a)

N'-hydroxy-3-(trifluoromethoxy)benzene-1-carboximidamide

N'-hydroxy-3-(trifluoromethoxy)benzene-1-carboximidamide 300 mg (yield: 46%) of the title compound was obtained as a white solid according to the same method as in Example 1 (1b) using 3-(trifluoromethoxy)benzonitrile (CAS Registry number: 52771-22-9) (500 mg).

(8b)

N-methyl-N'-(5-{3-[3-(trifluoromethoxy)phenyl]-1,2,4-oxadiazol-5-yl}-4,5,6,7-tetrahydro[1,3]thiazolo[5,4-c]pyridin-2-yl)urea N-methyl-N'-(5-{3-[3-(trifluoromethoxy)phenyl]-1,2,4-oxadiazol-5-yl}-4,5,6,7-tetrahydro[1,3]thiazolo[5,4-c]pyridin-2-yl)urea N-(5-cyano-4,5,6,7-tetrahydro[1,3]thiazolo[5,4-c]pyridin-2-yl)-N'-methylurea (120 mg)) of Example 1 (1c) and N'-hydroxy-3-(trifluoromethoxy)benzene-1-carboximidamide (167 mg) of Example 8 (8a) were dissolved in ethyl acetate (3 mL), a tetrahydrofuran solution (3 mL) of zinc chloride (124 mg) was added thereto, and the mixture was stirred at 60° C. for 15 hours. The residues obtained by distilling off the solvent from the reaction mixture under reduced pressure were dissolved in ethanol (3 mL), concentrated hydrochloric acid (3 mL) was added thereto, and the mixture was stirred at 80° C. for 1 hour.

Methanol was added to the residues obtained by distilling off the solvent from the reaction mixture under reduced pressure, and the precipitated solid was collected by filtration and washed with methanol to give 46 mg (yield: 22%) of the title compound as a white solid.

Example 9

N-{5-[5-(4-fluoro-3-methylphenyl)-1,3,4-oxadiazol-2-yl]-4,5,6,7-tetrahydro[[1,3]thiazolo[5,4-c]pyridin-2-yl}-N'-methylurea N-{5-[5-(4-fluoro-3-methylphenyl)-1,3,4-oxadiazol-2-yl]-4,5,6,7-tetrahydro[1,3]thiazolo[5,4-c]pyridin-2-yl}-N'-methylurea N-[5-(hydrazinecarbothioyl)-4,5,6,7-tetrahydro[1,3]thiazolo[5,4-c]pyridin-2-yl]-N'-methylurea (0.40 g) of Example 2 (2b) was dissolved in dimethyl sulfoxide (6 mL), 4-fluoro-3-methylbenzoic acid (0.24 g) and 1-ethyl-3-(3-dimethylaminopropyl)carbodiimide hydrochloride (0.80 g) were added thereto, and the mixture was stirred at 60° C. for 7 hours.

Water was added to the reaction mixture, and the precipitated solid was collected by filtration and sequentially washed with ethanol and ethyl acetate, thereby obtaining 162 mg (yield: 30%) of the title compound as a brown solid.

94

Example 10

N-{(5R*,8S*)-9-[3-(4-fluorophenyl)-1,2,4-oxadiazol-5-yl]-5,6,7,8-tetrahydro-4H-5,8-epiminocyclohepta[d][1,3]thiazol-2-yl}-N'-methylurea (10a)

tert-Butyl 2-amino-5,6,7,8-tetrahydro-4H-5,8-epiminocyclohepta[d][1,3]thiazole-9-carboxylate tert-Butyl 2-amino-5,6,7,8-tetrahydro-4H-5,8-epiminocyclohepta[d][1,3]thiazole-9-carboxylate tert-Butyl 3-oxo-8-azabicyclo[3.2.1]octane-8-carboxylate (CAS registry number: 185099-67-6) (110 g) was dissolved in toluene (500 mL), pyrrolidine (49 mL)) and a tosylic acid monohydrate (8.4 g) were added thereto at room temperature, and the mixture was stirred at 130° C. for 18 hours using a Dean-Stark apparatus. The residues obtained by distilling off the solvent from the reaction mixture under reduced pressure were dissolved in methanol (500 mL) and cooled to 0° C. A methanol solution (100 mL) of sulfur (15.7 g) and cyanamide (22.6 g) was added thereto at 0° C., and the mixture was stirred at room temperature for 16 hours.

The residue obtained by distilling off the solvent from the reaction mixture under reduced pressure were purified by silica gel column chromatography [eluting solvent:petroleum ether/ethyl acetate/dichloromethane=20/5/1 to 5/5/1 (V/V/V)], thereby obtaining 91.8 g (yield: 67%) of the title compound as a yellow solid.

(10b)

tert-Butyl (5R*,8S*)-2-amino-5,6,7,8-tetrahydro-4H-5,8-epiminocyclohepta[d][1,3]thiazole-9-carboxylate tert-Butyl (5R*,8S*)-2-amino-5,6,7,8-tetrahydro-4H-5,8-epiminocyclohepta[d][1,3]thiazole-9-carboxylate tert-Butyl 2-amino-5,6,7,8-tetrahydro-4H-5,8-epiminocyclohepta[d][1,3]thiazole-9-carboxylate (150 g) of Example 10 (10a) was applied to chiral SFC (column: CHIRALPAK AD (150 mm*4.6 mm, 3 μm)) [mobile phase: 0.05% diethylamine/ethanol/carbon dioxide] to obtain 80 g of a peak 1 (retention time: 1.962 min) of an enantiomer and 78 g of a peak 2 (retention time: 2.183 min) of an enantiomer. Petroleum ether/ethyl acetate/dichloromethane (100 mL/10 mL/5 mL) was added to the peak 2 of the enantiomer, and the mixture was stirred at 50° C. for 20 minutes. The solid which had been cooled to room temperature and precipitated was collected by filtration, thereby obtaining 35 g (yield: 24%) of the title compound as a pale yellow solid.

(10c)

tert-Butyl (5R*,8S*)-2-[(methylcarbamoyl)amino]-5,6,7,8-tetrahydro-4H-5,8-epiminocyclohepta[d][1,3]thiazole-9-carboxylate tert-Butyl (5R*,8S*)-2-[(methylcarbamoyl)amino]-5,6,7,8-tetrahydro-4H-5,8-epiminocyclohepta[d][1,3]thiazole-9-carboxylate 5.4 g (yield: 95%) of the title compound was obtained as a yellow solid according to the same method as in Example 6 (6g) using tert-butyl (5R*,8S*)-2-amino-5,6,7,8-tetrahydro-4H-5,8-epiminocyclohepta[d][1,3]thiazole-9-carboxylate (5.0 g) of Example 10 (10b).

(10d)

N-methyl-N'-[(5R*,8S*)-5,6,7,8-tetrahydro-4H-5,8-epiminocyclohepta[d][1,3]thiazol-2-yl]urea monohydrochloride N-methyl-N'-[(5R*,8S*)-5,6,7,8-tetrahydro-4H-5,8-epiminocyclohepta[d][1,3]thiazol-2-yl]urea-hydrogen chloride (1/1)

4.2 g (yield: 96%) of the title compound was obtained as a yellow solid according to the same method as in Example 6 (6h) using tert-butyl (5R*,8S*)-2-[(methylcarbamoyl)amino]-5,6,7,8-tetrahydro-4H-5,8-epiminocyclohepta[d][1,3]thiazole-9-carboxylate (5.4 g) of Example 10 (10c).

(10e)

3-(4-Fluorophenyl)-1,2,4-oxadiazol-5(4H)-one 3-(4-Fluorophenyl)-1,2,4-oxadiazol-5(4H)-one 4-Fluoro-N'-hydroxybenzene-1-carboximidamide (CAS registry number: 22179-78-8) (24.0 g) was dissolved in tetrahydrofuran (300 mL), N,N-diisopropylethylamine (54.2 mL) was added thereto, and a solution of triphosgene (18.5 g) in tetrahydrofuran (50 mL) was added dropwise thereto. The mixture was stirred at room temperature for 1 hour and further stirred at 60° C. for 1 hour.

The reaction mixture was cooled to room temperature, and the solvent was distilled off under reduced pressure. The obtained residues were dissolved in dichloromethane and extracted 3 times with a 1 M sodium hydroxide aqueous solution. The combined water layers were acidified with 1 M hydrochloric acid, and the precipitated solid was collected by filtration, washed with water, and dried at 50° C. under reduced pressure, thereby obtaining 13.9 g (yield: 50%) of the title compound as a pale yellow solid.

(10f)

5-Chloro-3-(4-fluorophenyl)-1,2,4-oxadiazole

5-Chloro-3-(4-fluorophenyl)-1,2,4-oxadiazole

Phosphorus oxychloride (148 g) and pyridine (7.5 mL) were added to 3-(4-fluorophenyl)-1,2,4-oxadiazol-5(4H)-one (13.9 g) of Example 10 (10e) at room temperature, and the mixture was stirred at 130° C. for 3 hours.

The reaction mixture was cooled to room temperature, the solvent was distilled off under reduced pressure, and the obtained residues were dissolved in dichloromethane and washed with water and a saturated sodium hydrogen carbonate aqueous solution. The organic layer was dried over anhydrous sodium sulfate and filtered, and the residues obtained by distilling of the solvent under reduced pressure were purified by silica gel column chromatography [eluting solvent:n-hexane/ethyl acetate=99/1 to 80/20 (V/V)], thereby obtaining 11.2 g (yield: 73%) of the title compound as a pale yellow solid.

(10g)

N-{(5R*,8S*)-9-[3-(4-fluorophenyl)-1,2,4-oxadiazol-5-yl]-5,6,7,8-tetrahydro-4H-5,8-epiminocyclohepta[d][1,3]thiazol-2-yl}-N'-methylurea N-{(5R*,8S*)-9-[3-(4-fluorophenyl)-1,2,4-oxadiazol-5-yl]-5,6,7,8-tetrahydro-4H-5,8-epiminocyclohepta[d][1,3]thiazol-2-yl}-N'-methylurea N-methyl-N'-[(5R*,8S*)-5,6,7,8-tetrahydro-4H-5,8-epiminocyclohepta[d][1,3]thiazol-2-yl]urea monohydrochloride (800 mg) of Example 10 (10d) was dissolved in N,N-dimethylformamide (10 mL), 5-chloro-3-(4-fluorophenyl)-1,2,4-oxadiazole (609 mg) of Example 10 (10f) and potassium carbonate (2.01 g) were added thereto, and the mixture was stirred at room temperature for 12 hours.

The reaction mixture was poured into water and the reaction mixture was extracted 3 times with ethyl acetate. The combined organic layers were washed with a saturated saline solution and dried over anhydrous sodium sulfate. After filtration, the residues obtained by distilling off the solvent under reduced pressure were purified by silica gel column chromatography [eluting solvent:methanol/ethyl acetate=1/99 to 20/80 (V/V)], thereby obtaining 560 mg (yield: 48%) of the title compound as a yellow solid.

Example 11

N-{9-[5-(4-fluorophenyl)-1,2-oxazol-3-yl]-5,6,7,8-tetrahydro-4H-5,8-epiminocyclohepta[d][1,3]thiazol-2-yl}-N'-methylurea (11a)

8-Azabicyclo[3.2.1]octan-3-one monohydrochloride

8-Azabicyclo[3.2.1]octan-3-one-hydrogen chloride (1/1)

tert-Butyl 3-oxo-8-azabicyclo[3.2.1]octane-8-carboxylate (CAS registry number: 185099-67-6) (103 g) was dissolved in methanol (300 mL), a 4 M hydrogen chloride-1,4-dioxane solution (320 mL) was added thereto, and the mixture was stirred at room temperature for 20 hours.

The solvent was distilled off from the reaction mixture under reduced pressure, thereby obtaining 81 g (yield: quantitative) of the title compound as a pale yellow solid.

(11b)

8-[5-(4-fluorophenyl)-1,2-oxazol-3-yl]-8-azabicyclo[3.2.1]octan-3-one

8-[5-(4-fluorophenyl)-1,2-oxazol-3-yl]-8-azabicyclo[3.2.1]octan-3-one

8-Azabicyclo[3.2.1]octan-3-one monohydrochloride (2.0 g) of Example 11 (11a) and N,N-diisopropylethylamine (5.4 mL) were dissolved in tetrahydrofuran (15 mL), the mixture was added dropwise to a tetrahydrofuran solution (15 mL) of 1,1-dibromoformaldoxime (3.7 g) cooled to −20° C. in a nitrogen atmosphere, and the mixture was stirred at 0° C. for 30 minutes. Subsequently, a toluene solution (30 mL) of triethylamine (5.2 mL) and 1-ethynyl-4-fluorobenzene (CAS registry number: 766-98-3) (1.8 g) was added thereto, and the mixture was stirred at 80° C. for 9.5 hours.

The reaction mixture was poured into water and the reaction mixture was extracted 3 times with ethyl acetate. The combined organic layers were dried over anhydrous sodium sulfate and filtered, and the residues obtained by distilling off the solvent under reduced pressure was purified by silica gel column chromatography [eluting solvent:petroleum ether/ethyl acetate=1/0 to 3/1 (V/V)], thereby obtaining 350 mg (yield: 8.4%) of the title compound as a yellow solid.

(11c)

9-[5-(4-fluorophenyl)-1,2-oxazol-3-yl]-5,6,7,8-tetrahydro-4H-5,8-epiminocyclohepta[d][1,3]thiazol-2-amine 9-[5-(4-fluorophenyl)-1,2-oxazol-3-yl]-5,6,7,8-tetrahydro-4H-5,8-epiminocyclohepta[d][1,3]thiazol-2-amine 8-[5-(4-Fluorophenyl)-1,2-oxazol-3-yl]-8-azabicyclo[3.2.1]octan-3-one (0.15 g) of Example 11 (11b) was dissolved in pyridine (15 mL), sulfur (29 mg) and cyanamide (340 mg) were added thereto, and the mixture was stirred at 130° C. for 1.5 hours.

The residues obtained by distilling off the solvent from the reaction mixture under reduced pressure were purified by thin layer silica gel chromatography [developing solvent: petroleum ether/ethyl acetate=1/1 (V/V)], thereby obtaining 20 mg (yield: 12%) of the title compound as a yellow solid.

(11d)

N-{9-[5-(4-fluorophenyl)-1,2-oxazol-3-yl]-5,6,7,8-tetrahydro-4H-5,8-epiminocyclohepta[d][1,3]thiazol-2-yl}-N'-methylurea N-{9-[5-(4-fluorophenyl)-1,2-oxazol-3-yl]-5,6,7,8-tetrahydro-4H-5,8-epiminocyclohepta[d][1,3]thiazol-2-yl}-N'-methylurea 4.5 mg (yield: 7.9%) of the title compound was obtained as a pale yellow solid according to the same method as in Example 6 (6 g) using 9-[5-(4-fluorophenyl)-1,2-oxazol-3-yl]-5,6,7,8-tetrahydro-4H-5,8-epiminocyclohepta[d][1,3]thiazol-2-amine (50 mg) of Example 11 (11c).

Example 12

N-{(5R*,9S*)-10-[3-(4-fluorophenyl)-1,2,4-oxadiazol-5-yl]-4,5,6,7,8,9-hexahydro-5,9-epiminocycloocta[d][1,3]thiazol-2-yl}-N'-methylurea (12a)

N-{10-[3-(4-fluorophenyl)-1,2,4-oxadiazol-5-yl]-4,5,6,7,8,9-hexahydro-5,9-epiminocycloocta[d][1,3]thiazol-2-yl}-N'-methylurea N-{10-[3-(4-fluorophenyl)-1,2,4-oxadiazol-5-yl]-4,5,6,7,8,9-hexahydro-5,9-epiminocycloocta[d][1,3]thiazol-2-yl}-N'-methylurea 2.8 g (yield: 95%) of the title compound was obtained as a yellow solid according to the same method as in Example 10 (10g) using N-(4,5,6,7,8,9-hexahydro-5,9-epiminocycloocta[d][1,3]thiazol-2-yl)-N'-methylurea monohydrochloride (2.5 g) synthesized from tert-butyl 3-oxo-9-azabicyclo[3.3.1]nonane-9-carboxylate (CAS Registry number: 512822-27-4) in the same manner as in Examples 6 (6f), 6 (6g), and 6 (6h) and 5-chloro-3-(4-fluorophenyl)-1,2,4-oxadiazole (1.5 g) of Example 10 (10f).

(12b)

N-{(5R*,9S*)-10-[3-(4-fluorophenyl)-1,2,4-oxadiazol-5-yl]-4,5,6,7,8,9-hexahydro-5,9-epiminocycloocta[d][1,3]thiazol-2-yl}-N'-methylurea N-{(5R*,9S*)-10-[3-(4-fluorophenyl)-1,2,4-oxadiazol-5-yl]-4,5,6,7,8,9-hexahydro-5,9-epiminocycloocta[d][1,3]thiazol-2-yl}-N'-methylurea N-{10-[3-(4-fluorophenyl)-1,2,4-oxadiazol-5-yl]-4,5,6,7,8,9-hexahydro-5,9-epiminocycloocta[d][1,3]thiazol-2-yl}-N'-methylurea (3.8 g) of Example 12 (12a) was applied to chiral SFC (column: CHIRALPAK AD (100 mm*4.6 mm, 3 µm)) [mobile phase: 0.05% diethylamine/isopropanol/carbon dioxide], and an enantiomer of a peak 1 (retention time: 1.827 min) and an enantiomer of a peak 2 (retention time: 4.412 min) were separated. 1.5 g of the title compound (yield: 41%, pale yellow solid) was obtained as the enantiomer of the peak 1.

Example 13

N-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-methylurea (13a)

N-{10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-methylurea N-{10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-methylurea 25 g (yield: 51%) of the title compound was obtained as a white solid according to the same method as in Example 10 (10g) using N-methyl-N'-(4,7,8,9-tetrahydro-5H-4,8-epiminooxocino[5,4-d][1,3]thiazol-2-yl)urea monohydrochloride (40 g) of Example 6 (6h) and 5-chloro-3-(4-fluorophenyl)-1,2,4-oxadiazole (32 g) of Example 10 (10f).

(13b)

N-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-methylurea N-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-methylurea N-{10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-methylurea (50 g) of Example 13 (13a) was applied to chiral SFC (column: CHIRALCEL OD (100 mm*4.6 mm, 3 µm)) [mobile phase: 0.05% diethylamine/methanol/carbon dioxide] to obtain 22 g (yield: 45%) of N-{(4R,8R)-10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-methylurea (peak 1, retention time: 1.054 min) as a white solid and 20 g (yield: 43%) of N-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-methylurea (peak 2, retention time: 1.599 min) as a white solid.

It was confirmed that the enantiomer of the peak 2 had the absolute configuration of the title compound, since the title compound was also separately produced from the compound of Example 7 (7a), which was an intermediate whose absolute configuration had been determined.

Example 14

N-(10-{5-[3-(difluoromethyl)phenyl]-1,3-oxazol-2-yl}-4,7,8,9-tetrahydro-5H-4,8-epiminooxocino[5,4-d][1,3]thiazol-2-yl)-N'-methylurea (14a)

3-(Difluoromethyl)benzaldehyde 3-(Difluoromethyl)benzaldehyde

1-Bromo-3-(difluoromethyl)benzene (CAS Registry number: 29848-59-7) (2.0 g) was dissolved in tetrahydrofuran (40 mL) in a nitrogen atmosphere, and n-butyllithium (2.5 M n-hexane solution, 4.1 mL) was slowly added thereto at −78° C. The mixture was stirred at −78° C. for 30 minutes, N,N-dimethylformamide (2 mL) was added thereto, and the mixture was stirred at room temperature for 12 hours.

The reaction mixture was poured into a saturated ammonium chloride aqueous solution and extracted 3 times with ethyl acetate. The combined organic layers were washed with a saturated saline solution and dried over anhydrous sodium sulfate. After filtration, the residues obtained by distilling off the solvent under reduced pressure were purified by silica gel column chromatography [eluting solvent: petroleum ether/ethyl acetate=I/O to 10/1 (V/V)], thereby obtaining 0.30 g (yield: 20%) of the title compound as a yellow oily material.

(14b)

5-[3-(Difluoromethyl)phenyl]-1,3-oxazole

5-[3-(Difluoromethyl)phenyl]-1,3-oxazole 3-(Difluoromethyl)benzaldehyde (0.30 g) of Example 14 (14a) was dissolved in methanol (10 mL), p-toluenesulfonylmethylisocyanide (0.38 g) and potassium carbonate (0.38 g) were added thereto, and the mixture was stirred at 70° C. for 1 hour.

Water was added to the residues obtained by distilling off the solvent from the reaction mixture under reduced pressure, and the reaction mixture was extracted three times with ethyl acetate. The combined organic layers were washed with a saturated saline solution, dried over anhydrous sodium sulfate, and filtered, and the solvent was distilled off under reduced pressure, thereby obtaining 0.29 g (yield: 77%) of the title compound as a yellow oily material.

(14c)

2-Chloro-5-[3-(difluoromethyl)phenyl]-1,3-oxazole

2-Chloro-5-[3-(difluoromethyl)phenyl]-1,3-oxazole

5-[3-(Difluoromethyl)phenyl]-1,3-oxazole (0.29 g) of Example 14 (14b) was dissolved in tetrahydrofuran (10 mL) in a nitrogen atmosphere, and lithium bis(trimethylsilyl)amide (1 M tetrahydrofuran solution, 1.8 mL) was slowly added thereto at −78° C. The mixture was stirred at −78° C. for 30 minutes, hexachloroethane (0.42 g) was added thereto, and the mixture was stirred at −78° C. for 30 minutes and further stirred at room temperature for 12 hours.

The reaction mixture was poured into a saturated ammonium chloride aqueous solution and extracted 3 times with ethyl acetate, and the combined organic layers were dried over anhydrous sodium sulfate. After filtration, the residues obtained by distilling off the solvent under reduced pressure were purified by thin layer chromatography [developing solvent:petroleum ether/ethyl acetate=10/1 (V/V)], thereby obtaining 0.16 g (yield: 47%) of the title compound as a white solid.

(14d)

N-(10-{5-[3-(difluoromethyl)phenyl]-1,3-oxazol-2-yl}-4,7,8,9-tetrahydro-5H-4,8-epiminooxocino[5,4-d][1,3]thiazol-2-yl)-N'-methylurea N-(10-{5-[3-(difluoromethyl)phenyl]-1,3-oxazol-2-yl}-4,7,8,9-tetrahydro-5H-4,8-epiminooxocino[5,4-d][1,3]thiazol-2-yl)-N'-methylurea N-methyl-N'-(4,7,8,9-tetrahydro-5H-4,8-epiminooxocino[5,4-d][1,3]thiazol-2-yl)urea monohydrochloride (0.24 g) of Example 6 (6h) was dissolved in dimethyl sulfoxide (2 mL), 2-chloro-5-[3-(difluoromethyl)phenyl]-1,3-oxazole (0.16 g) of Example 14 (14c) and N,N-diisopropylethylamine (0.61 mL) were added thereto, and the mixture was stirred at 100° C. for 24 hours.

The reaction mixture was poured into water and extracted 3 times with ethyl acetate, and the combined organic layers were dried over anhydrous sodium sulfate. After filtration, the residues obtained by distilling off the solvent under reduced pressure were purified by high performance liquid chromatography [column: Waters Xbridge; mobile phase: acetonitrile /0.05% ammonia water=25/75 to 55/45 (V/V)], thereby obtaining 97 mg (yield: 31%) of the title compound as a white solid.

Example 15

N-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}-N'-methylurea N-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}-N'-methylurea 67 mg (yield: 35%) of the title compound was obtained as a pink solid according to the same method as in Example 14 (14d) using 2-(2-chloro-1,3-oxazol-5-yl)-6-methoxypyridine (0.10 g) synthesized from 6-methoxypyridine-2-carbaldehyde (CAS Registry number: 54221-96-4) in the same manner as in Examples 14 (14b) and 14 (14c) and N-methyl-N'-[(4S,8S)-4,7,8,9-tetrahydro-5H-4,8-epiminooxocino[5,4-d][1,3]thiazol-2-yl]urea monohydrochloride (0.13 g) of Example 7(7b).

Example 16

N-{10-[5-(4-fluorophenyl)-1,2-oxazol-3-yl]-4,7,8,9-tetrahydro-5H-4,8-epiminooxocino[5,4-d][1,3]thiazol-2-yl}-N'-methylurea N-{10-[5-(4-fluorophenyl)-1,2-oxazol-3-yl]-4,7,8,9-tetrahydro-5H-4,8-epiminooxocino[5,4-d][1,3]thiazol-2-yl}-N'-methylurea 8 mg (yield: 6.3%) of the title compound was obtained as a yellow oily material which was synthesized in the same manner as in Example 11 (11b) using N-methyl-N'-(4,7,8, 9-tetrahydro-5H-4,8-epiminooxocino[5,4-d][1,3]thiazol-2-yl)urea monohydrochloride (0.65 g) of Example 6 (6h).

Example 17

N-{(4S,8S)-10-[4-(4-fluorophenyl)-1,3-oxazol-2-yl]-4,7,8,9-tetrahydro-5H-4,8-epiminooxocino[5,4-d][1,3]thiazol-2-yl}-N'-methylurea (17a)

4-(4-Fluorophenyl)-1,3-oxazole 4-(4-Fluorophenyl)-1,3-oxazole

2-Bromo-1-(4-fluorophenyl)ethan-1-one (CAS Registry number: 403-29-2) (5.0 g) was dissolved in formic acid (10 mL), ammonium formate (14.5 g) was added thereto, and the mixture was stirred at 130° C. for 8 hours.

Water was added to the reaction mixture, and the reaction mixture was extracted 3 times with ethyl acetate. The combined organic layers were washed with water and a saturated saline solution and dried over anhydrous sodium sulfate. After filtration, the residues obtained by distilling off the solvent under reduced pressure were purified by silica gel column chromatography [eluting solvent:n-hexane/ethyl acetate=10/0 to 7/3 (V/V)], thereby obtaining 1.2 g (yield: 32%) of the title compound as a yellow solid.

(17b)

2-Chloro-4-(4-fluorophenyl)-1,3-oxazole

2-Chloro-4-(4-fluorophenyl)-1,3-oxazole 1.4 g (yield: 96%) of the title compound was obtained as a pale yellow solid which was synthesized in the same manner as in Example 14 (14c) using 4-(4-fluorophenyl)-1,3-oxazole (1.2 g) of Example 17 (17a).

(17c)

(4S,8S)-4,7,8,9-tetrahydro-5H-4,8-epiminooxocino[5,4-d][1,3]thiazol-2-amine dihydrochloride (4S,8S)-4,7,8,9-tetrahydro-5H-4,8-epiminooxocino[5,4-d][1,3]thiazol-2-amine-hydrogen chloride (1/2)

tert-Butyl (4S,8S)-2-amino-4,7,8,9-tetrahydro-5H-4,8-epiminooxocino[5,4-d][1,3]thiazole-10-carboxylate (15 g) of Example 7 (7a) was dissolved in ethanol (100 mL), a 4 M hydrogen chloride-1,4-dioxane solution (100 mL) was added thereto, and the mixture was stirred at room temperature for 5 hours.

The solvent was distilled off from the reaction mixture under reduced pressure, the mixture was subjected to azeotropy twice with toluene, and the precipitated solid was washed with ethyl acetate/n-hexane, thereby obtaining 13.4 g (yield: 98%) of the title compound as a pale yellow solid.

(17d)

(4S,8S)-10-[4-(4-fluorophenyl)-1,3-oxazol-2-yl]-4,7,8,9-tetrahydro-5H-4,8-epiminooxocino[5,4-d][1,3]thiazol-2-amine (4S,8S)-10-[4-(4-fluorophenyl)-1,3-oxazol-2-yl]-4,7,8,9-tetrahydro-5H-4,8-epiminooxocino[5,4-d][1,3]thiazol-2-amine (4S,8S)-4,7,8,9-tetrahydro-5H-4,8-epiminooxocino[5,4-d][1,3]thiazol-2-amine dihydrochloride (2.0 g) of Example 17 (17c) was dissolved in dimethyl sulfoxide (20 mL), 2-chloro-4-(4-fluorophenyl)-1,3-oxazole (1.4 g) of Example 17 (17b) and N,N-diisopropylethylamine (6.4 mL) were added thereto, and the mixture was stirred at 100° C. for 12 hours and was allowed to stand at room temperature overnight. Thereafter, the mixture was stirred at 100° C. for 11 hours and allowed to stand at room temperature overnight. Further, the reaction mixture was stirred at 100° C. for 12 hours, poured into water, and extracted 3 times with ethyl acetate. The combined organic layers were washed with water and a saturated saline solution and dried over anhydrous sodium sulfate. After filtration, the residues obtained by distilling off the solvent under reduced pressure were purified by NH silica gel column chromatography [eluting solvent:methanol/ethyl acetate=0/10 to 1/9 (V/V)], thereby obtaining 0.64 g (yield: 24%) of the title compound as a yellow solid.

(17e)

N-{(4S,8S)-10-[4-(4-fluorophenyl)-1,3-oxazol-2-yl]-4,7,8,9-tetrahydro-5H-4,8-epiminooxocino[5,4-d][1,3]thiazol-2-yl}-N'-methylurea N-{(4S,8S)-10-[4-(4-fluorophenyl)-1,3-oxazol-2-yl]-4,7,8,9-tetrahydro-5H-4,8-epiminooxocino[5,4-d][1,3]thiazol-2-yl}-N'-methylurea (4S,8S)-10-[4-(4-fluorophenyl)-1,3-oxazol-2-yl]-4,7,8,9-tetrahydro-5H-4,8-epiminooxocino[5,4-d][1,3]thiazol-2-amine (0.20 g) of Example 17 (17d) was dissolved in tetrahydrofuran (4 mL), 1,1'-carbonyldiimidazole (0.14 g) was added thereto, and the mixture was allowed to stand at room temperature overnight. Methylamine (2 mol/L tetrahydrofuran solution, 0.84 mL) was added thereto, and the mixture was stirred at room temperature for 8 hours.

The solvent was distilled off from the reaction mixture under reduced pressure, ethyl acetate was added to the obtained residues, and the organic layer was washed with water and a saturated saline solution and dried over anhydrous sodium sulfate. After filtration, the residues obtained by distilling off the solvent under reduced pressure were purified by silica gel column chromatography [eluting solvent:methanol/ethyl acetate=0/10 to 1/19 (V/V)], thereby obtaining 0.13 g (yield: 57%) of the title compound as a pale yellow solid.

Example 18

N-{10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-[(2R)-1-hydroxypropan-2-yl]urea (18a)

2-(Trimethylsilyl)ethyl 7-oxo-3-oxa-9-azabicyclo[3.3.1]nonane-9-carboxylate 2-(Trimethylsilyl)ethyl 7-oxo-3-oxa-9-azabicyclo[3.3.1]nonane-9-carboxylate 2-(Trimethylsilyl) ethanol (199 g) and triethylamine (240 mL) were dissolved in tetrahydrofuran (800 mL), and a tetrahydrofuran solution (400 mL) of triphosgene (173 g) was added dropwise thereto at −10° C. to −5° C. for 40 minutes. The mixture was stirred at the same temperature for 20 minutes and further stirred at room temperature for 2.5 hours. The precipitated white solid was removed by filtration, and the solvent was distilled off from the filtrate under reduced pressure to obtain residues.

Tetrahydrofuran (600 mL) and sodium hydrogen carbonate (234 g) were added to an aqueous solution (700 mL) of 3-oxa-9-azabicyclo[3.3.1]nonan-7-one hydrochloride (99 g) of Example 6 (6e-1), a tetrahydrofuran solution (450 mL) of the obtained residues was added thereto for 30 minutes, and the mixture was stirred at room temperature for 16 hours. The reaction mixture was extracted 3 times with ethyl acetate, and the combined organic layers were dried over anhydrous sodium sulfate. The residues obtained by distilling off the solvent under reduced pressure were triturated with ethyl acetate/petroleum ether and collected by filtration, thereby obtaining 93 g (yield: 58%) of the title compound as a pale yellow solid.

(18b)

2-(Trimethylsilyl)ethyl 2-amino-4,7,8,9-tetrahydro-5H-4,8-epiminooxocino[5,4-d][1,3]thiazole-10-carboxylate 2-(Trimethylsilyl)ethyl 2-amino-4,7,8,9-tetrahydro-5H-4,8-epiminooxocino[5,4-d][1,3]thiazole-10-carboxylate 90 g (yield: 61%) of the title compound was obtained as a pale yellow solid which was synthesized in the same manner as in Example 6 (6f) using 2-(trimethylsilyl)ethyl 7-oxo-3-oxa-9-azabicyclo[3.3.1]nonane-9-carboxylate (90 g) of Example 18 (18a).

(18c)

2-(Trimethylsilyl)ethyl 2-[(tert-butoxycarbonyl)amino]-4,7,8,9-tetrahydro-5H-4,8-epiminooxocino[5,4-d][1,3]thiazole-10-carboxylate 2-(Trimethylsilyl)ethyl 2-[(tert-butoxycarbonyl)amino]-4,7,8,9-tetrahydro-5H-4,8-epiminooxocino[5,4-d][1,3]thiazole-10-carboxylate 2-(Trimethylsilyl)ethyl 2-amino-4,7,8,9-tetrahydro-5H-4,8-epiminooxocino[5,4-d][1,3]thiazole-10-carboxylate (180 g) of Example 18 (18b) was dissolved in tetrahydrofuran (1 L), and triethylamine (102 g) and dimethylaminopyridine (1.5 g) were added thereto. Subsequently, di-tert-butyl dicarbonate (152 g) was slowly added thereto at 35° C. to 40° C. for 5 hours, and the mixture was stirred at 40° C. for 16 hours.

A saturated saline solution was added to the reaction mixture, and the reaction mixture was stirred at room temperature for 30 minutes and extracted 3 times with ethyl acetate. The combined organic layers were dried over anhydrous sodium sulfate and filtered, and the residues obtained by distilling off the solvent under reduced pressure were purified by silica gel column chromatography [eluting solvent:petroleum ether/ethyl acetate=5/1 to 2/1 (V/V)], thereby obtaining 180 g (yield: 77%) of the title compound as a white solid.

(18d)

tert-Butyl 4,7,8,9-tetrahydro-5H-4,8-epiminooxocino[5,4-d][1,3]thiazol-2-ylcarbamate tert-Butyl 4,7,8,9-tetrahydro-5H-4,8-epiminooxocino[5,4-d][1,3]thiazol-2-ylcarbamate 2-(Trimethylsilyl)ethyl 2-[(tert-butoxycarbonyl)amino]-4,7,8,9-tetrahydro-5H-4,8-epiminooxocino[5,4-d][1,3]thiazole-10-carboxylate (183 g) of Example 18 (18c) was dissolved in tetrahydrofuran (600 mL), tetrabutylammonium fluoride (1 mol/L tetrahydrofuran solution, 580 mL) was added thereto, and the mixture was stirred at 40° C. to 45° C. for 16 hours.

Water was added to the residues obtained by distilling off the solvent from the reaction mixture under reduced pressure, and the reaction mixture was extracted three times with ethyl acetate. The combined organic layers were dried over anhydrous sodium sulfate and filtered, and most of the solvent was distilled off under reduced pressure. The precipitated solid was collected by filtration and washed with ethyl acetate (30 mL), thereby obtaining 98 g (yield: 78%) of the title compound as a white solid.

(18e)

10-[3-(4-Fluorophenyl)-1,2,4-oxadiazol-5-yl]-4,7,8,9-tetrahydro-5H-4,8-epiminooxocino[5,4-d][1,3]thiazol-2-amine monohydrochloride 10-[3-(4-Fluorophenyl)-1,2,4-oxadiazol-5-yl]-4,7,8,9-tetrahydro-5H-4,8-epiminooxocino[5,4-d][1,3]thiazol-2-amine-hydrogen chloride (1/1)

1.5 g (yield: quantitative) of the title compound was obtained as a white solid according to the same method as in Example 6 (6h) using tert-butyl {10-[3-(4-fluorophenyl)-1,2,4-oxadiazol-5-yl]-4,7,8,9-tetrahydro-5H-4,8-epiminooxocino[5,4-d][1,3]thiazol-2-yl}carbamate (1.6 g) synthesized from tert-butyl 4,7,8,9-tetrahydro-5H-4,8-epiminooxocino[5,4-d][1,3]thiazol-2-ylcarbamate of Example 18 (18d) in the same manner as in Example 10 (10g).

(18f)

Phenyl {10-[3-(4-fluorophenyl)-1,2,4-oxadiazol-5-yl]-4,7,8,9-tetrahydro-5H-4,8-epiminooxocino[5,4-d][1,3]thiazol-2-yl} carbamate Phenyl {10-[3-(4-fluorophenyl)-1,2,4-oxadiazol-5-yl]-4,7,8,9-tetrahydro-5H-4,8-epiminooxocino[5,4-d][1,3]thiazol-2-yl} carbamate 10-[3-(4-Fluorophenyl)-1,2,4-oxadiazol-5-yl]-4,7,8,9-tetrahydro-5H-4,8-epiminooxocino[5,4-d][1,3]thiazol-2-amine monohydrochloride (1.4 g) of Example 18 (18e) was suspended in dichloromethane (50 mL), triethylamine (2.0 mL) and phenyl chloroformate (1.1 g) were added thereto, and the mixture was stirred at 40° C. for 3 hours. Phenyl chloroformate (1.1 g) was further added thereto, and the mixture was stirred at 40° C. for 12 hours.

Water was added to the residues obtained by distilling off the solvent from the reaction mixture under reduced pressure, and the reaction mixture was extracted three times with ethyl acetate. The combined organic layers were washed with a saturated saline solution and dried over anhydrous sodium sulfate. After filtration, the solvent was distilled off under reduced pressure, thereby obtaining 3.0 g (yield: quantitative) of the title compound as a brown oily material.

(18g)

N-{10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-[(2R)-1-hydroxypropan-2-yl]urea N-{10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-[(2R)-1-hydroxypropan-2-yl]urea Phenyl {10-[3-(4-fluorophenyl)-1,2,4-oxadiazol-5-yl]-4,7,8,9-tetrahydro-5H-4,8-epiminooxocino[5,4-d][1,3]thiazol-2-yl}carbamate (192 mg) of Example 18 (18f) was dissolved in 1,4-dioxane (2 mL), pyridine (0.128 mL) and (2R)-2-aminopropan-1-ol (90 mg) were added thereto, and the mixture was stirred at 80° C. for 2 hours.

The residues obtained by distilling off the solvent from the reaction mixture under reduced pressure were purified by silica gel column chromatography [eluting solvent:petroleum ether/ethyl acetate=5/1 to 1/1 (V/V)], and the residues obtained by distilling off the solvent under reduced pressure were purified by high performance liquid chromatography [column: Phenomenex luna C18; mobile phase:acetonitrile/ 0.225% formic acid aqueous solution=36/64 to 56/44 (V/V)], thereby obtaining 84 mg (yield: 45%) of the title compound as a white solid.

Example 19

N-{6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-methylurea (19a)

2,5-Dihydro-1H-pyrrole monohydrochloride 2,5-Dihydro-1H-pyrrole-hydrogen chloride (1/1)

6.8 g (yield: 98%) of the title compound was obtained as a gray solid by being synthesized in the same manner as in Example 6 (6h) using tert-butyl 2,5-dihydro-1H-pyrrole-1-carboxylate (CAS Registry number: 73286-70-1) (10 g).

(19b)

1-(2,5-Dihydro-1H-pyrrol-1-yl)ethan-1-one 1-(2,5-Dihydro-1H-pyrrol-1-yl)ethan-1-one 2,5-Dihydro-1H-pyrrole monohydrochloride (8.9 g) of Example 19 (19a) and triethylamine (23.5 mL) were dissolved in dichloromethane (150 mL), acetyl chloride (7.3 mL) was added dropwise thereto at 0° C., and the mixture was stirred at 15° C. for 2 hours.

The reaction mixture was diluted with dichloromethane, and the organic layer was washed with water and a saturated saline solution and dried over anhydrous sodium sulfate. After filtration, the residues obtained by distilling off the solvent under reduced pressure were triturated with petroleum ether/ethyl acetate and collected by filtration, thereby obtaining 8.3 g (yield: 80%) of the title compound as a yellow solid.

(19c)

3-Acetyl-9-benzyl-3,9-diazabicyclo[3.3.1]nonan-7-one

3-Acetyl-9-benzyl-3,9-diazabicyclo[3.3.1]nonan-7-one 1-(2,5-Dihydro-1H-pyrrol-1-yl)ethan-1-one (7.0 g) of Example 19 (19b) was dissolved in dichloromethane/methanol (100 mL/10 mL), and sodium hydrogen carbonate (4.8 g) was added thereto. While the reaction mixture was stirred at −78° C., ozone gas was blown thereinto for 15 minutes. Next, nitrogen gas was blown thereinto at −78° C. for 15 minutes. Subsequently, triphenylphosphine (7.4 g) was added thereto, and the mixture was slowly heated and stirred at room temperature for 12 hours. The reaction mixture was filtered, 1,3-acetonedicarboxylic acid (5.6 g), 12 M hydrochloric acid (1.6 mL), and benzylamine (4.2 mL) were added to the residues obtained by distilling off approximately half of the solvent from the filtrate under reduced pressure, and the mixture was stirred at 15° C. for 1 hour and further stirred at 50° C. for 12 hours. The residues obtained by distilling off the solvent from the reaction mixture under reduced pressure were purified by silica gel column chromatography [eluting solvent:petroleum ether/ethyl acetate=3/1 to 0/1 (V/V)], thereby obtaining 2.0 g (yield: 12%) of the title compound as a yellow solid.

(19d)

tert-Butyl 3-acetyl-7-oxo-3,9-diazabicyclo[3.3.1]nonane-9-carboxylate tert-Butyl 3-acetyl-7-oxo-3,9-diazabicyclo[3.3.1]nonane-9-carboxylate 3-Acetyl-9-benzyl-3,9-diazabicyclo[3.3.1]nonan-7-one (1.4 g) of Example 19 (19c) was dissolved in ethanol (8 mL), 1 M hydrochloric acid (7.1 mL) and 10% palladium carbon (200 mg) were added thereto, and the mixture was stirred at 20° C. for 16 hours in a hydrogen (30 psi) atmosphere.

The reaction mixture was filtered, sodium hydrogen carbonate (333 mg) and di-tert-butyl dicarbonate (317 mg) were added to the obtained filtrate, and the mixture was stirred at 15° C. for 16 hours.

Water was added to the residues obtained by distilling off the solvent from the reaction mixture under reduced pressure, and the reaction mixture was extracted 3 times with ethyl acetate. The combined organic layers were washed with a saturated saline solution, dried over anhydrous sodium sulfate, and filtered, and the residues obtained by distilling off the solvent under reduced pressure were purified by silica gel column chromatography [eluting solvent: petroleum ether/ethyl acetate=3/1 to 2/1 (V/V)], thereby obtaining 270 mg (yield: 72%) of the title compound as a colorless oily material.

(19e)

N-{6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-methylurea N-{6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-methylurea 21 mg (yield: 30%) of the title compound was obtained as a white solid according to the same method as in Example 10 (10 g) using N-(6-acetyl-4,5,6,7,8,9-hexahydro-4,8-epimino[1,3]thiazolo[5,4-d]azocin-2-yl)-N'-methylurea monohydrochloride (50 mg) synthesized from tert-butyl 3-acetyl-7-oxo-3,9-diazabicyclo[3.3.1]nonane-9-carboxylate of Example 19 (19d) in the same manner as in Examples 6 (6f), 6 (6g), and 6 (6h) and 5-chloro-3-(4-fluorophenyl)-1,2,4-oxadiazole (30 mg) of Example 10 (10f).

Example 20

(5R)-3-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}-5-methylimidazolidine-2,4-dione (20a)

(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-amine (4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-amine (4S,8S)-4,7,8,9-tetrahydro-5H-4,8-epiminooxocino[5,4-d][1,3]thiazol-2-amine dihydrochloride (4.59 g) of Example 17 (17c) was dissolved in N,N-dimethylformamide (100 mL), 5-chloro-3-(4-fluorophenyl)-1,2,4-oxadiazole (4.04 g) of Example 10 (10f) and potassium carbonate (7.04 g) were added thereto, and the mixture was stirred at room temperature for 24 hours.

The reaction mixture was poured into water and the reaction mixture was extracted 3 times with ethyl acetate. The combined organic layers were washed with a saturated saline solution and dried over anhydrous sodium sulfate. After filtration, the residues obtained by distilling off the solvent under reduced pressure were triturated with ethyl acetate, and the precipitated solid was collected by filtration, thereby obtaining 4.08 g (yield: 67%) of the title compound as a pale yellow solid.

(20b)

N-({(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}carbamoyl)-D-alanine N-({(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}carbamoyl)-D-alanine (4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-amine (0.30 g) of Example 20 (20a) was dissolved in N,N-dimethylformamide (6 mL), 1,1'-carbonyldiimidazole (0.20 g) was added thereto, and the mixture was allowed to stand at room temperature overnight. D-alanine (0.22 g) and triethylamine (0.58 mL) were added to the reaction mixture, and the mixture was stirred at 50° C. for 3 hours. Ethyl acetate was added to the reaction solution, and the organic layer was washed with a saturated saline solution and dried over anhydrous sodium sulfate. After filtration, the solvent was distilled off under reduced pressure, thereby obtaining 0.46 g (yield: quantitative) of the title compound as a yellow solid.

(20c)

(5R)-3-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}-5-methylimidazolidin-2,4-dione (5R)-3-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}-5-methylimidazolidin-2,4-dione N-({(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}carbamoyl)-D-alanine (0.46 g) of Example 20 (20b) was dissolved in N,N-dimethylformamide (8 mL), 1-ethyl-3-(3-dimethylaminopropyl)carbodiimide hydrochloride (0.28 g) and 4-dimethylaminopyridine (0.024 g) were added thereto, and the mixture was allowed to stand at room temperature overnight.

Water was added to the reaction mixture, and the reaction mixture was extracted 3 times with ethyl acetate. The combined organic layers were washed with water and a saturated saline solution and dried over anhydrous sodium sulfate. After filtration, the residues obtained by distilling off the solvent under reduced pressure were purified by silica gel column chromatography [eluting solvent:methanol/ethyl acetate=0/10 to 1/9 (V/V)], and the obtained solid was washed with ethyl acetate/n-hexane, thereby obtaining 0.21 g (yield: 48%) of the title compound as a pale yellow solid.

Example 21

N-[(4S,8S)-10-{5-[3-(cyclopropanecarbonyl)phenyl]-1,3,4-oxadiazol-2-yl}-4,7,8,9-tetrahydro-5H-4,8-epiminooxocino[5,4-d][1,3]thiazol-2-yl]-N'-methylurea (21a)

4-Nitrophenyl (4S,8S)-2-[(methylcarbamoyl)amino]-4,7,8,9-tetrahydro-5H-4,8-epiminooxocino[5,4-d][1,3]thiazole-10-carboxylate 4-Nitrophenyl (4S,8S)-2-[(methylcarbamoyl)amino]-4,7,8,9-tetrahydro-5H-4,8-epiminooxocino[5,4-d][1,3]thiazole-10-carboxylate N-methyl-N'-[(4S,8S)-4,7,8,9-tetrahydro-5H-4,8-epiminooxocino[5,4-d][1,3]thiazol-2-yl]-N'-methylurea monohydrochloride (70 g) of Example 7 (7b) was suspended in tetrahydrofuran (600 mL), and triethylamine (107 mL) was added thereto. The reaction mixture was stirred for 10 minutes, 4-nitrophenyl chloroformate (46 g) was added thereto, and the mixture was stirred at room temperature for 12 hours.

The reaction mixture was filtered and washed with tetrahydrofuran (200 mL), and the residues obtained by concentrating the filtrate under reduced pressure were purified by silica gel column chromatography [eluting solvent:petroleum ether/ethyl acetate=1/1 to 0/1 (V/V)], thereby obtaining 60 g (yield: 60%) of the title compound as a yellow solid.

(21b)

N-[(4S,8S)-10-(hydrazinecarbonyl)-4,7,8,9-tetrahydro-5H-4,8-epiminooxocino[5,4-d][1,3]thiazol-2-yl]-N'-methylurea N-[(4S,8S)-10-(hydrazinecarbonyl)-4,7,8,9-tetrahydro-5H-4,8-epiminooxocino[5,4-d][1,3]thiazol-2-yl]-N'-methylurea 4-Nitrophenyl (4S,8S)-2-[(methylcarbamoyl)amino]-4,7,8,9-tetrahydro-5H-4,8-epiminooxocino[5,4-d][1,3]thiazole-10-carboxylate (60 g) of Example 21 (21a) was dissolved in tetrahydrofuran (600 mL), a hydrazine monohydrate (55.6 mL) was added thereto, and the mixture was stirred at 70° C. for 16 hours. The reaction mixture was cooled to room temperature, and the precipitated solid was collected by filtration and washed with tetrahydrofuran (150 mL). The obtained solid was triturated with ethyl acetate (150 mL)/ methanol (45 mL) and collected by filtration, thereby obtaining 36 g (yield: 81%) of the title compound as a yellow solid.

(21c)

N-[(4S,8S)-10-{2-[3-(cyclopropanecarbonyl)benzoyl]hydrazinecarbonyl}-4,7,8,9-tetrahydro-5H-4,8-epiminooxocino[5,4-d][1,3]thiazol-2-yl]-N'-methylurea N-[(4S,8S)-10-{2-[3-(cyclopropanecarbonyl)benzoyl]hydrazinecarbonyl}-4,7,8,9-tetrahydro-5H-4,8-epiminooxocino[5,4-d][1,3]thiazol-2-yl]-N'-methylurea N-[(4S,8S)-10-(hydrazinecarbonyl)-4,7,8,9-tetrahydro-5H-4,8-epiminooxocino[5,4-d][1,3]thiazol-2-yl]-N'-methylurea (7.4 g) of Example 21 (21b) was dissolved in N,N-dimethylformamide (150 mL), 3-(cyclopropanecarbonyl) benzoic acid (CAS Registry number: 34916-10-4) (5 g), 1H-benzotriazol-1-yloxytris(dimethylamino)phosphonium hexafluorophosphate (11.5 g), and triethylamine (10 mL) were added thereto, and the mixture was allowed to stand at room temperature overnight. The reaction mixture was poured into water, acidified with 1N hydrochloric acid, and neutralized with a saturated sodium bicarbonate aqueous solution, and the reaction mixture was extracted twice with dichloromethane. The organic layer was washed with a saturated saline solution and dried over anhydrous sodium sulfate. The residues obtained by distilling off the solvent under reduced pressure were purified by silica gel column chromatography [eluting solvent:methanol /ethyl acetate=0/10 to 1/9 (V/V)], thereby obtaining 12.4 g (yield: quantitative) of the title compound as a yellow solid.

(21d)

N-[(4S,8S)-10-{5-[3-(cyclopropanecarbonyl)phenyl]-1,3,4-oxadiazol-2-yl}-4,7,8,9-tetrahydro-5H-4,8-epiminooxocino[5,4-d][1,3]thiazol-2-yl]-N'-methylurea N-[(4S,8S)-10-{5-[3-(cyclopropanecarbonyl)phenyl]-1,3,4-oxadiazol-2-yl}-4,7,8,9-tetrahydro-5H-4,8-epiminooxocino[5,4-d][1,3]thiazol-2-yl]-N'-methylurea N-[(4S,8S)-10-{2-[3-(cyclopropanecarbonyl)benzoyl]hydrazinecarbonyl}-4,7,8,9-tetrahydro-5H-4,8-epiminooxocino[5,4-d][1,3]thiazol-2-yl]-N'-methylurea (12.4 g) of Example 21 (21c) was suspended in dichloromethane (130 mL), tosyl chloride (7.3 g) and triethylamine (10.7 mL) were added thereto, and the mixture was allowed to stand at room temperature overnight. Water was added to the reaction mixture, and the reaction mixture was extracted with dichloromethane. The organic layer was washed with a saturated saline solution and dried over anhydrous sodium sulfate. After filtration, the residues obtained by distilling off the solvent under reduced pressure were purified by silica gel column chromatography [eluting solvent:methanol/ethyl acetate=0/10 to 1/9 (V/V)], thereby obtaining 7.5 g (yield: 63%) of the title compound as a pale yellow solid.

Example 22

N-[(4S,8S)-10-{5-[3-(difluoromethoxy)phenyl]-1,3,4-oxadiazol-2-yl}-4,7,8,9-tetrahydro-5H-4,8-epiminooxocino[5,4-d][1,3]thiazol-2-yl]-N'-methylurea N-[(4S,8S)-10-{5-[3-(difluoromethoxy)phenyl]-1,3,4-oxadiazol-2-yl}-4,7,8,9-tetrahydro-5H-4,8-epiminooxocino[5,4-d][1,3]thiazol-2-yl]-N'-methylurea 970 mg (yield: 27%) of the title compound was obtained as a white solid according to the same method as in Example 2 (2d) using N-[(4S,8S)-10-{2-[3-(difluoromethoxy)benzoyl]hydrazinecarbothioyl}-4,7,8,9-tetrahydro-5H-4,8-epiminooxocino[5,4-d][1,3]thiazol-2-yl]-N'-methylurea (3.8 g) synthesized from N-methyl-N'-[(4S,8S)-4,7,8,9-tetrahydro-5H-4,8-epiminooxocino[5,4-d][1,3]thiazol-2-yl]urea monohydrochloride of Example 7 (7b) in the same manner as in Examples 2 (2a), 2 (2b), and 3 (3c).

Example 23

(−)-N-{(4R*,8R*)-6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-methylurea (23a)

2-(Trimethylsilyl)ethyl 2,5-dihydro-1H-pyrrole-1-carboxylate 2-(Trimethylsilyl)ethyl 2,5-dihydro-1H-pyrrole-1-carboxylate 2-(Trimethylsilyl)ethanol (269 g) and triethylamine (330 mL) were dissolved in tetrahydrofuran (1.5 L), and a tetrahydrofuran solution (400 mL) of triphosgene (225 g) was added dropwise thereto at −10° C. to −5° C. for 60 minutes. The mixture was stirred at the same temperature for 30 minutes and further stirred at room temperature for 1.5 hours. The precipitated white solid was removed by filtration, and the solvent was distilled off from the filtrate under reduced pressure to obtain residues.

2,5-Dihydro-1H-pyrrole monohydrochloride of Example 19 (19a) was dissolved in tetrahydrofuran/water (500 mL/700 mL), sodium hydrogen carbonate (250 g) was added thereto, the tetrahydrofuran solution (400 mL) of the previously obtained residues was added thereto for 60 minutes, and the mixture was stirred at room temperature for 16 hours. The organic layer was separated from the water layer, and the residues obtained by distilling off the solvent under reduced pressure were purified by silica gel column chromatography [eluting solvent:petroleum ether], thereby obtaining 730 g of the title compound (yield: quantitative) as a yellow oily material.

(23b)

2-(Trimethylsilyl)ethyl 9-benzyl-7-oxo-3,9-diazabicyclo[3.3.1]nonane-3-carboxylate 2-(Trimethylsilyl)ethyl 9-benzyl-7-oxo-3,9-diazabicyclo[3.3.1]nonane-3-carboxylate Example 23B-1

2-(Trimethylsilyl)ethyl 2,5-dihydro-1H-pyrrole-1-carboxylate (180 g) of Example 23 (23a) was dissolved in dichloromethane/methanol (1.5 L/300 mL), and sodium hydrogen carbonate (56.7 g) was added thereto. While the reaction mixture was stirred at −70° C., ozone gas was blown thereinto for 8 hours. Next, nitrogen gas was blown thereinto for nitrogen substitution, triphenylphosphine (155 g) was added thereto at −60° C. to −20° C. for 10 minutes, and the mixture was slowly heated and stirred at room temperature for 16 hours. The mixture was filtered to obtain a filtrate (0.84 mol, 1.8 L).

Example 23B-2

The reaction of Example 23b-1 was carried out in two batches, and the filtrate was combined with the mixture and used for the following reaction.

1,3-Acetonedicarboxylic acid (244 g) and 12 M hydrochloric acid (40 mL) were added to the filtrate, and the mixture was cooled to 0° C. Benzylamine (200 mL) was added to the reaction mixture, and the mixture was stirred at 10° C. to 20° C. for 1 hour and further stirred at 50° C. for 16 hours.

The solvent was distilled off from the reaction mixture under reduced pressure, petroleum ether/ethyl acetate (3 L/600 mL) was added to the residues, the precipitate was filtered, and the residues obtained by distilling off the solvent from the filtrate under reduced pressure were purified by silica gel column chromatography [eluting solvent: petroleum ether/ethyl acetate=50/1 to 5/1 (V/V)], thereby obtaining 340 g (yield: 54%) of the title compound as a white solid.

(23c)

3-Acetyl-9-benzyl-3,9-diazabicyclo[3.3.1]nonan-7-one

3-Acetyl-9-benzyl-3,9-diazabicyclo[3.3.1]nonan-7-one 2-(Trimethylsilyl)ethyl 9-benzyl-7-oxo-3,9-diazabicyclo[3.3.1]nonane-3-carboxylate (296 g) of Example 23 (23b) was dissolved in tetrahydrofuran (100 mL), tetrabutylammonium fluoride (1 mol/L tetrahydrofuran solution, 1.39 L) was added thereto, and the mixture was stirred at 50° C. to 55° C. for 16 hours in a nitrogen atmosphere. N,N-diisopropylethylamine (280 mL) was added to the reaction mixture, the mixture was cooled to 5° C., acetyl chloride (100 mL) was slowly added thereto at 5° C. to 10° C. for 30 minutes, and the mixture was stirred at 15° C. for 16 hours. Ethyl acetate and water were added to the residues obtained by distilling off the solvent from the reaction mixture under reduced pressure, and the mixture was extracted 3 times with ethyl acetate. The residues obtained by distilling off the solvent from the combined organic layer under reduced pressure were purified by silica gel column chromatography [eluting solvent:petroleum ether/ethyl acetate/=5/1 to 0/1 (V/V); dichloromethane/ethyl acetate=1/20 (V/V)], thereby obtaining 298 g (yield: quantitative) of the title compound as a yellow oily material.

(23d)

tert-Butyl 3-acetyl-7-oxo-3,9-diazabicyclo[3.3.1]nonane-9-carboxylate tert-Butyl 3-acetyl-7-oxo-3,9-diazabicyclo[3.3.1]nonane-9-carboxylate 3-Acetyl-9-benzyl-3,9-diazabicyclo[3.3.1]nonan-7-one (217 g) of Example 23 (23c) was dissolved in ethanol (700 mL), 1 M hydrochloric acid (700 mL) and 10% palladium carbon (20 g) were added thereto, and the mixture was stirred at 40° C. for 16 hours in a hydrogen (50 psi) atmosphere.

The reaction mixture was filtered, sodium hydrogen carbonate (134 g) was added to the obtained filtrate and stirred for 30 minutes, di-tert-butyl dicarbonate (240 g) was added thereto, and the mixture was stirred at 25° C. for 16 hours. Ethanol was distilled off from the reaction mixture under reduced pressure, and the residues were extracted 5 times with ethyl acetate. The combined organic layers were washed with water and a saturated saline solution and dried over anhydrous sodium sulfate. After filtration, the residues obtained by distilling off the solvent under reduced pressure were purified by silica gel column chromatography [eluting solvent:petroleum ether/ethyl acetate=3/1 to 1/1 (V/V); petroleum ether/ethyl acetate/dichloromethane=1/1/1 (V/V/V)], thereby obtaining 180 g (yield: 80%) of the title compound as a white solid.

(23e)

tert-Butyl 6-acetyl-2-amino-4,5,6,7,8,9-hexahydro-4,8-epimino[1,3]thiazolo[5,4-d]azocine-10-carboxylate tert-Butyl 6-acetyl-2-amino-4,5,6,7,8,9-hexahydro-4,8-epimino[1,3]thiazolo[5,4-d]azocine-10-carboxylate 115 g (yield: 51%) of the title compound was obtained as a pale yellow solid according to the same method as in Example 6 (6f) using tert-butyl 3-acetyl-7-oxo-3,9-diazabicyclo[3.3.1]nonane-9-carboxylate (180 g) of Example 23 (23d).

(23f)

tert-Butyl (4R*,8R*)-6-acetyl-2-amino-4,5,6,7,8,9-hexahydro-4,8-epimino[1,3]thiazolo[5,4-d]azocine-10-carboxylate tert-Butyl (4R*,8R*)-6-acetyl-2-amino-4,5,6,7,8,9-hexahydro-4,8-epimino[1,3]thiazolo[5,4-d]azocine-10-carboxylate (Optical Resolution Using Chiral Column)

tert-Butyl 6-acetyl-2-amino-4,5,6,7,8,9-hexahydro-4,8-epimino[1,3]thiazolo[5,4-d]azocine-10-carboxylate (115 g) of Example 23 (23e) was applied to chiral SFC (column: CHIRALPAK OD (250 mm*50 mm, 10 m)) [mobile phase: 0.1% ammonia water/isopropanol/carbon dioxide], and an enantiomer of a peak 1 (retention time: 1.414 min) and an enantiomer of a peak 2 (retention time: 1.676 min) were separated. 55 g of the title compound (yield: 49%, pale yellow solid) was obtained as the enantiomer of the peak 2.

(Optical Resolution Using Diastereomer Salt Method)

tert-Butyl 6-acetyl-2-amino-4,5,6,7,8,9-hexahydro-4,8-epimino[1,3]thiazolo[5,4-d]azocine-10-carboxylate (80 g) of Example 23 (23e) was dissolved in acetonitrile (800 mL), ethyl acetate (15 L) was added to (+)-di-p-anisoyl-L-tartaric acid (CAS Registry number: 50583-51-2) (94 g), and the mixture was stirred at 30° C. for 1 hour and further stirred at 70° C. for 2 hours. The mixture was stirred for 16 hours while being slowly cooled to room temperature. The precipitated solid was collected by filtration and washed with acetonitrile (50 mL). The obtained solid (87 g) was dissolved in acetonitrile (500 mL), and the mixture was stirred at 70° C. for 2 hours and further stirred for 10 hours while being slowly cooled to room temperature. The precipitated solid was collected by filtration and washed with acetonitrile (50 mL). Water (250 mL) was added to the obtained solid (80 g), and a 2 M lithium hydroxide aqueous solution was added thereto to adjust the pH thereof to 7. The water layer was extracted 10 times with ethyl acetate (400 mL). The combined organic layers were washed with a 1 M lithium hydroxide aqueous solution (500 mL) and dried over anhydrous sodium sulfate, and the solvent was distilled off under reduced pressure, thereby obtaining 31.5 g (yield: 41%) of the title compound as a white solid.

(23g)

tert-Butyl (4R*,8R*)-6-acetyl-2-[(methylcarbamoyl)amino]-4,5,6,7,8,9-hexahydro-4,8-epimino[1,3]thiazolo[5,4-d]azocine-10-carboxylate tert-Butyl (4R*,8R*)-6-acetyl-2-[(methylcarbamoyl)amino]-4,5,6,7,8,9-hexahydro-4,8-epimino[1,3]thiazolo[5,4-d]azocine-10-carboxylate 30 g (yield: quantitative) of the title compound was obtained as a yellow solid according to the same method as in Example 6 (6 g) using tert-butyl (4R*,8R*)-6-acetyl-2-amino-4,5,6,7,8,9-hexahydro-4,8-epimino[1,3]thiazolo[5,4-d]azocine-10-carboxylate (20.0 g) of Example 23 (23f).

(23h)

N-[(4R*,8R*)-6-acetyl-4,5,6,7,8,9-hexahydro-4,8-epimino[1,3]thiazolo[5,4-d]azocin-2-yl]-N'-methylurea monohydrochloride N-[(4R*,8R*)-6-acetyl-4,5,6,7,8,9-hexahydro-4,8-epimino[1,3]thiazolo[5,4-d]azocin-2-yl]-N'-methylurea-hydrogen chloride (1/1)

31 g (yield: quantitative) of the title compound was obtained as a yellow solid according to the same method as in Example 6 (6h) using tert-butyl (4R*,8R*)-6-acetyl-2-[(methylcarbamoyl)amino]-4,5,6,7,8,9-hexahydro-4,8-epimino[1,3]thiazolo[5,4-d]azocine-10-carboxylate (30.0 g) of Example 23 (23 g).

(23i)

(−)-N-{(4R*,8R*)-6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-methylurea (−)-N-{(4R*,8R*)-6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-methylurea 19 g (yield: 47%) of the title compound was obtained as a yellow solid according to the same method as in Example 10 (10g) using N-[(4R*,8R*)-6-acetyl-4,5,6,7,8,9-hexahydro-4,8-epimino[1,3]thiazolo[5,4-d]azocin-2-yl]-N'-methylurea monohydrochloride (31 g) of Example 23 (23h).

Example 24

(−)-Methyl (4R*,8R*)-10-[3-(4-fluorophenyl)-1,2,4-oxadiazol-5-yl]-2-[(methylcarbamoyl)amino]-4,7,8,9-tetrahydro-4,8-epimino[1,3]thiazolo[5,4-d]azocine-6(5H)-carboxylate (24a)

9-tert-Butyl 3-[2-(trimethylsilyl)ethyl]7-oxo-3,9-diazabicyclo[3.3.1]nonane-3,9-dicarboxylate 9-tert-Butyl 3-[2-(trimethylsilyl)ethyl]7-oxo-3,9-diazabicyclo[3.3.1]nonane-3,9-dicarboxylate 2-(Trimethylsilyl)ethyl 9-benzyl-7-oxo-3,9-diazabicyclo[3.3.1]nonane-3-carboxylate (190 g) of Example 23 (23b) was dissolved in ethanol (700 mL), 1 M hydrochloric acid (665 mL) and 10% palladium carbon (10 g) were added thereto, and the mixture was stirred at 40° C. for 16 hours in a hydrogen (50 psi) atmosphere.

The reaction mixture was filtered, sodium hydrogen carbonate (70 g) was added to the obtained filtrate and stirred for 30 minutes, di-tert-butyl dicarbonate (152 g) was added thereto, and the mixture was stirred at 15° C. for 16 hours. Ethanol was distilled off from the reaction mixture under reduced pressure, and the precipitated solid was collected by filtration, thereby obtaining 190 g (yield: 98%) of the title compound as a white solid.

(24b)

10-tert-Butyl 6-[2-(trimethylsilyl)ethyl]2-amino-4,7,8,9-tetrahydro-4,8-epimino[1,3]thiazolo[5,4-d]azocine-6,10(5H)-dicarboxylate 10-tert-Butyl 6-[2-(trimethylsilyl)ethyl]2-amino-4,7,8,9-tetrahydro-4,8-epimino[1,3]thiazolo[5,4-d]azocine-6,10 (5H)-dicarboxylate 150 g (yield: 69%) of the title compound was obtained as a white solid according to the same method as in Example 6 (6f) using 9-tert-butyl 3-[2-(trimethylsilyl)ethyl]7-oxo-3,9-diazabicyclo[3.3.1]nonane-3,9-dicarboxylate (190 g) of Example 24 (24a).

(24c)

Methyl 2-amino-4,7,8,9-tetrahydro-4,8-epimino[1,3]thiazolo[5,4-d]azocine-6(5H)-10-carboxylate dihydrochloride Methyl 2-amino-4,7,8,9-tetrahydro-4,8-epimino[1,3]thiazolo[5,4-d]azocine-6(5H)-carboxylate-hydrogen chloride (1/2)

10-tert-Butyl 6-[2-(trimethylsilyl)ethyl]2-amino-4,7,8,9-tetrahydro-4,8-epimino[1,3]thiazolo[5,4-d]azocine-6,10 (5H)-dicarboxylate (50 g) of Example 24 (24b) was dissolved in tetrahydrofuran (50 mL), tetrabutylammonium fluoride (1 mol/L tetrahydrofuran solution) (200 mL) was added thereto, and the mixture was stirred at 50° C. to 55° C. for 16 hours in a nitrogen atmosphere. N,N-diisopropylethylamine (30 mL) was added to the reaction mixture, the mixture was cooled to 5° C., methyl chloroformate (9.4 mL) was slowly added thereto at 5° C. to 10° C. for 30 minutes, and the mixture was stirred at 15° C. for 16 hours. Ethyl acetate was added to the residues obtained by distilling off the solvent from the reaction mixture under reduced pressure, the mixture was washed with water three times, a 4 M hydrogen chloride-ethyl acetate solution (120 mL) was added thereto, and the mixture was stirred 15° C. for 16 hours. The precipitated solid was collected by filtration and washed with ethyl acetate, thereby obtaining 38 g (yield: quantitative) of the title compound as a white solid.

(24d)

Methyl 2-amino-10-cyano-4,7,8,9-tetrahydro-4,8-epimino[1,3]thiazolo[5,4-d]azocine-6(5H)-10-carboxylate Methyl 2-amino-10-cyano-4,7,8,9-tetrahydro-4,8-epimino[1,3]thiazolo[5,4-d]azocine-6(5H)-carboxylate Methyl 2-amino-4,7,8,9-tetrahydro-4,8-epimino[1,3]thiazolo[5,4-d]azocine-6(5H)-10-carboxylate of Example 24 (24c), dihydrochloride (36 g), and sodium hydrogen carbonate (37 g) were dissolved in dichloromethane (300 mL) and water (50 mL), bromocyan (18 g) was added thereto, and the mixture was stirred at 15° C. for 16 hours. The reaction mixture was filtered and washed with dichloromethane/methanol (100 mL/10 mL). The water layer was extracted 4 times with dichloromethane, and the combined organic layers were dried over anhydrous sodium sulfate. After filtration, the residues obtained by distilling off the solvent under reduced pressure were purified by silica gel column chromatography [eluting solvent:dichloromethane /methanol=1/0 to 20/1 (V/V)], thereby obtaining 17 g (yield: 60%) of the title compound as a white solid.

(24e)

Methyl (4R*,8R*)-2-amino-10-cyano-4,7,8,9-tetrahydro-4,8-epimino[1,3]thiazolo[5,4-d]azocine-6(5H)-carboxylate Methyl (4R*,8R*)-2-amino-10-cyano-4,7,8,9-tetrahydro-4,8-epimino[1,3]thiazolo[5,4-d]azocine-6(5H)-carboxylate Methyl 2-amino-10-cyano-4,7,8,9-tetrahydro-4,8-epimino[1,3]thiazolo[5,4-d]azocine-6(5H)-10-carboxylate (32 g) of Example 24 (24d) was applied to chiral SFC (column: CHIRALPAK IC (250 mm*30 mm, 10 µm)) [mobile phase: 0.1% ammonia water/ethanol/carbon dioxide], and an enantiomer of a peak 1 (retention time: 0.591 min) and an enantiomer of a peak 2 (retention time: 0.964 min) were separated. 13.3 g (yield: 43%, pale yellow solid) of the title compound was obtained as the enantiomer of the peak 2.

(24f)

Methyl (4R*,8R*)-10-cyano-2-[(methylcarbamoyl)amino]-4,7,8,9-tetrahydro-4,8-epimino[1,3]thiazolo[5,4-d]azocine-6(5H)-carboxylate Methyl (4R*,8R*)-10-cyano-2-[(methylcarbamoyl)amino]-4,7,8,9-tetrahydro-4,8-epimino[1,3]thiazolo[5,4-d]azocine-6(5H)-carboxylate Methyl (4R*,8R*)-2-amino-10-cyano-4,7,8,9-tetrahydro-4,8-epimino[1,3]thiazolo[5,4-d]azocine-6(5H)-carboxylate (500 mg) of Example 24 (24e) and N,N-diisopropylethylamine (0.312 mL) were dissolved in tetrahydrofuran (5 mL), N-methylcarbamoyl chloride (251 mg) was added thereto, and the mixture was stirred at 60° C. for 12 hours. Ethyl acetate and water were added to the reaction mixture, and the mixture was extracted twice with ethyl acetate. The combined organic layers were washed with water and a saturated saline solution and dried over anhydrous sodium sulfate. After filtration, the residues obtained by distilling off the solvent under reduced pressure were purified by high performance liquid chromatography [column: Phenomenex lina C18; mobile phase:acetonitrile/0.225% ammonium hydroxide aqueous solution=3/97 to 33/67 (V/V)], thereby obtaining 321 mg (yield: 53%) of the title compound as a white solid.

(24g)

(−)-Methyl (4R*,8R*)-10-[3-(4-fluorophenyl)-1,2,4-oxadiazol-5-yl]-2-[(methylcarbamoyl)amino]-4,7,8,9-tetrahydro-4,8-epimino[1,3]thiazolo[5,4-d]azocine-6(5H)-carboxylate (−)-Methyl (4R*,8R*)-10-[3-(4-fluorophenyl)-1,2,4-oxadiazol-5-yl]-2-[(methylcarbamoyl)amino]-4,7,8,9-tetrahydro-4,8-epimino[1,3]thiazolo[5,4-d]azocine-6(5H)-carboxylate Methyl (4R*,8R*)-10-cyano-2-[(methylcarbamoyl)amino]-4,7,8,9-tetrahydro-4,8-epimino[1,3]thiazolo[5,4-d]azocine-6(5H)-carboxylate (150 mg) of Example 24 (24f) was dissolved in N,N-dimethylformamide (2 mL), 4-fluoro-N'-hydroxybenzen-1-carboximidamide (CAS Registry Number: 22179-78-8) (89.4 mg), zinc chloride (12.2 mg), and a tosylic acid monohydrate (15.4 mg) were sequentially added thereto at room temperature, and the mixture was stirred at 80° C. for 12 hours. The reaction mixture was filtered, and the filtrate was purified by high performance liquid chromatography [column: Waters Xbridge; mobile phase:acetonitrile/10 mM ammonium hydrogen carbonate aqueous solution=21/79 to 51/49 (V/V)], thereby obtaining 31.4 mg (yield: 15%) of the title compound as a white solid.

Example 25

N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1R,2R)-2-hydroxycyclopentyl]urea N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1R,2R)-2-hydroxycyclopentyl]urea 66.6 mg (yield: 32%) of the title compound was obtained as a pale yellow solid according to the same method as in Example 5 (5d) using 5-[3-(4,4-difluorocyclohexyl)-1,2,4-oxadiazol-5-yl]-4,5,6,7-tetrahydro[1,3]thiazolo[5,4-c]pyridin-2-amine (150 mg) of Example 5 (5c) and (1R,2R)-2-aminocyclopentan-1-ol hydrochloride (CAS Registry number: 68327-11-7) (242 mg).

Example 26

N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1r,4r)-4-hydroxycyclohexyl]urea N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1r,4r)-4-hydroxycyclohexyl]urea 119 mg (yield: 56%) of the title compound was obtained as an orange solid according to the same method as in Example 5 (5d) using 5-[3-(4,4-difluorocyclohexyl)-1,2,4-oxadiazol-5-yl]-4,5,6,7-tetrahydro[1,3]thiazolo[5,4-c]pyridin-2-amine (150 mg) of Example 5 (5c) and trans-4-aminocyclohexan-1-ol (CAS Registry number: 27489-62-9) (202 mg).

Example 27

N-{5-[3-(4,4-difluorocyclohexyl)-1,2,4-oxadiazol-5-yl]-4,5,6,7-tetrahydro[1,3]thiazolo[5,4-c]pyridin-2-yl}-N'-(3-methoxypropyl)urea N-{5-[3-(4,4-difluorocyclohexyl)-1,2,4-oxadiazol-5-yl]-4,5,6,7-tetrahydro[1,3]thiazolo[5,4-c]pyridin-2-yl}-N'-(3-methoxypropyl)urea 99.5 mg (yield: 50%) of the title compound was obtained as a pale yellow solid according to the same method as in Example 5 (5d) using 5-[3-(4,4-difluorocyclohexyl)-1,2,4-oxadiazol-5-yl]-4,5,6,7-tetrahydro[1,3]thiazolo[5,4-c]pyridin-2-amine (150 mg) of Example 5 (5c) and 3-methoxypropan-1-amine (CAS Registry number: 5332-73-0) (0.179 mL).

Example 28

N-{5-[3-(3,3-difluorocyclohexyl)-1,2,4-oxadiazol-5-yl]-4,5,6,7-tetrahydro[1,3]thiazolo[5,4-c]pyridin-2-yl}-N'-(2-hydroxy-2-methylpropyl)urea N-{5-[3-(3,3-difluorocyclohexyl)-1,2,4-oxadiazol-5-yl]-4,5,6,7-tetrahydro[1,3]thiazolo[5,4-c]pyridin-2-yl}-N'-(2-hydroxy-2-methylpropyl)urea 84.6 mg (yield: 48%) of the title compound was obtained as a white solid according to the same method as in Example 5 (5d) using 5-[3-(3,3-difluorocyclohexyl)-1,2,4-oxadiazol-5-yl]-4,5,6,7-tetrahydro[1,3]thiazolo[5,4-c]pyridin-2-amine (132 mg) synthesized from tert-butyl 4,5,6,7-tetrahydro[1,3]thiazolo[5,4-c]pyridin-2-ylcarbamate (International Publication No. WO2013/134226) and 3-oxocyclohexanecarbonitrile (CAS Registry number: 17983-30-1) in the same manner as in Examples 1 (1a), 1 (1b), 1 (1c), 1 (1d), and 29 (29b) and 1-amino-2-methylpropan-2-ol (0.146 mL).

Example 29

N-{[(2S)-1,4-dioxan-2-yl]methyl}-N'-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}urea (29a)

tert-Butyl(4S,8S)-2-[({[(2S)-1,4-dioxan-2-yl]methyl}carbamoyl)amino]-4,7,8,9-tetrahydro-5H-4,8-epiminooxocino[5,4-d][1,3]thiazole-10-carboxylate tert-Butyl(4S,8S)-2-[({[(2S)-1,4-dioxan-2-yl]methyl}carbamoyl)amino]-4,7,8,9-tetrahydro-5H-4,8-epiminooxocino[5,4-d][1,3]thiazole-10-carboxylate tert-Butyl (4S,8S)-2-amino-4,7,8,9-tetrahydro-5H-4,8-epiminooxocino[5,4-d][1,3]thiazole-10-carboxylate (2 g) of Example 7 (7a) was dissolved in N,N-dimethylformamide (40 mL), 1,1'-carbonyldiimidazole (1.64 g) was added thereto, and the mixture was allowed to stand at room temperature overnight. (S)-(1,4-dioxan-2-yl)methanamine hydrochloride (2.07 g) and triethylamine (4.69 mL) were added thereto, and the mixture was stirred at room temperature for 2 hours. Ethyl acetate was added to the reaction solution, and the organic layer was washed with water and a saturated saline solution and dried over anhydrous sodium sulfate. The residues obtained by distilling off the solvent under reduced pressure were purified by silica gel column chromatography [eluting solvent:n-hexane/ethyl acetate=1/1 to 0/1 (V/V)], thereby obtaining 2.9 g (yield: 98%) of the title compound as a pale yellow solid.

(29b)

N-{[(2S)-1,4-dioxan-2-yl]methyl}-N'-[(4S,8S)-4,7,8,9-tetrahydro-5H-4,8-epiminooxocino[5,4-d][1,3]thiazol-2-yl]urea N-{[(2S)-1,4-dioxan-2-yl]methyl}-N'-[(4S,8S)-4,7,8,9-tetrahydro-5H-4,8-epiminooxocino[5,4-d][1,3]thiazol-2-yl]urea tert-Butyl (4S,8S)-2-[({[(2S)-1,4-dioxan-2-yl]methyl}carbamoyl)amino]-4,7,8,9-tetrahydro-5H-4,8-epiminooxocino[5,4-d][1,3]thiazole-10-carboxylate (2.9 g) of Example 29 (29a) was dissolved in dichloromethane (24 mL), trifluoroacetic acid (6 mL) was added thereto, and the mixture was stirred at room temperature for 5 hours. The reaction solution was concentrated and subjected to azeotropy twice with toluene, and the obtained residues were purified by NH silica gel column chromatography [eluting solvent:methanol/ethyl acetate=0/10 to 25/75 (V/V)], thereby obtaining 1.75 g (yield: 78%) of the title compound as a yellow solid.

(29c)

N-{[(2S)-1,4-dioxan-2-yl]methyl}-N'-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}urea N-{[(2S)-1,4-dioxan-2-yl]methyl}-N'-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}urea N-{[(2S)-1,4-dioxan-2-yl]methyl}-N'-[(4S,8S)-4,7,8,9-tetrahydro-5H-4,8-epiminooxocino[5,4-d][1,3]thiazol-2-yl]urea (300 mg) of Example 29 (29b) was dissolved in N,N-dimethylformamide (5 mL), 5-chloro-3-(4-fluorophenyl)-1,2,4-oxadiazole (210 mg) of Example 10 (10f) and potassium carbonate (365 mg) were added thereto, and the mixture was stirred at room temperature for 6 hours. Water was added to the reaction mixture, and the reaction mixture was extracted with ethyl acetate. The organic layer was washed with water and a saturated saline solution and dried over anhydrous sodium sulfate. The residues obtained by distilling off the solvent under reduced pressure were purified by silica gel column chromatography [eluting solvent: methanol/ethyl acetate=0/10 to 15/85 (V/V)], thereby obtaining 386 mg (yield: 87%) of the title compound as a pale yellow solid.

Example 30

N-{10-[3-(4-fluorophenyl)-1,2,4-oxadiazol-5-yl]-6-(methanesulfonyl)-4,5,6,7,8,9-hexahydro-4,8-epimino[1,3]thiazolo[5,4-d]azocin-2-yl}-N'-oxan-4-ylurea N-{10-[3-(4-fluorophenyl)-1,2,4-oxadiazol-5-yl]-6-(methanesulfonyl)-4,5,6,7,8,9-hexahydro-4,8-epimino[1,3]thiazolo[5,4-d]azocin-2-yl}-N'-oxan-4-ylurea 12.9 mg (yield: 13%) of the title compound was obtained as a white solid according to the same method as in Example 31 (31d) using N-{10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-oxan-4-ylurea (85 mg) synthesized from 2-(trimethylsilyl)ethyl 2-amino-10-cyano-4,7,8,9-tetrahydro-4,8-epimino[1,3]thiazolo[5,4-d]azocine-6(5H)-carboxylate of Example 31 (31b) and tetrahydro-2H-pyran-4-amine in the same manner as in Examples 5 (5d), 1 (1d), and 18 (18d).

Example 31

N-{10-[3-(4-fluorophenyl)-1,2,4-oxadiazol-5-yl]-6-(methanesulfonyl)-4,5,6,7,8,9-hexahydro-4,8-epimino[1,3]thiazolo[5,4-d]azocin-2-yl}-N'-methylurea (31a)

2-(Trimethylsilyl)ethyl 2-amino-4,7,8,9-tetrahydro-4,8-epimino[1,3]thiazolo[5,4-d]azocine-6(5H)-carboxylate 2-(Trimethylsilyl)ethyl 2-amino-4,7,8,9-tetrahydro-4,8-epimino[1,3]thiazolo[5,4-d]azocine-6(5H)-carboxylate 10-tert-Butyl 6-[2-(trimethylsilyl)ethyl]2-amino-4,7,8,9-tetrahydro-4,8-epimino[1,3]thiazolo[5,4-d]azocine-6,10(5H)-dicarboxylate (2.5 g) of Example 24 (24b) was dissolved in ethanol (11 mL), a tosylic acid monohydrate (2.37 g) was added thereto, and the mixture was stirred at 65° C. for 7 hours. Water was added to the reaction mixture, and the reaction mixture was extracted 3 times with chloroform. The combined organic layers were washed with a saturated sodium hydrogen carbonate aqueous solution and a saturated saline solution and dried over anhydrous sodium sulfate. After filtration, the solvent was distilled off under reduced pressure, thereby obtaining 1.45 g (yield: 74%) of the title compound as a pale yellow solid.

(31b)

2-(Trimethylsilyl)ethyl 2-amino-10-cyano-4,7,8,9-tetrahydro-4,8-epimino[1,3]thiazolo[5,4-d]azocine-6(5H)-carboxylate 2-(Trimethylsilyl)ethyl 2-amino-10-cyano-4,7,8,9-tetrahydro-4,8-epimino[1,3]thiazolo[5,4-d]azocine-6(5H)-carboxylate 1.55 g (yield: quantitative) of the title compound was obtained as a pale orange solid according to the same method as in Example 1 (1c) using 2-(trimethylsilyl)ethyl 2-amino-4,7,8,9-tetrahydro-4,8-epimino[1,3]thiazolo[5,4-d]azocine-6 (5H)-carboxylate (1.45 g) of Example 31 (31a).

(31c)

2-(Trimethylsilyl)ethyl 10-[3-(4-fluorophenyl)-1,2,4-oxadiazol-5-yl]-2-[(methylcarbamoyl)amino]-4,7,8,9-tetrahydro-4,8-epimino[1,3]thiazolo[5,4-d]azocine-6(5H)-carboxylate 2-(Trimethylsilyl)ethyl 10-[3-(4-fluorophenyl)-1,2,4-oxadiazol-5-yl]-2-[(methylcarbamoyl)amino]-4,7,8,9-tetrahydro-4,8-epimino[1,3]thiazolo[5,4-d]azocine-6(5H)-carboxylate 7 mg (yield: 26%) of the title compound was obtained as a pale yellow solid according to the same method as in Example 1 (1d) using 2-(trimethylsilyl)ethyl 10-cyano-2-[(methylcarbamoyl)amino]-4,7,8,9-tetrahydro-4,8-epimino[1,3]thiazolo[5,4-d]azocine-6(5H)-carboxylate (600 mg) synthesized from 2-(trimethylsilyl)ethyl 2-amino-10-cyano-4,7,8,9-tetrahydro-4,8-epimino[1,3]thiazolo[5,4-d]azocine-6(5H)-carboxylate of Example 31 (31b) and a methylamine monohydrochloride in the same manner as in Example 5 (5d) and 4-fluoro-N'-hydroxybenzene-1-carboximidamide (CAS Registry Number: 22179-78-8) (219 mg).

(31d)

N-{10-[3-(4-fluorophenyl)-1,2,4-oxadiazol-5-yl]-6-(methanesulfonyl)-4,5,6,7,8,9-hexahydro-4,8-epimino[1,3]thiazolo[5,4-d]azocin-2-yl}-N'-methylurea N-{10-[3-(4-fluorophenyl)-1,2,4-oxadiazol-5-yl]-6-(methanesulfonyl)-4,5,6,7,8,9-hexahydro-4,8-epimino[1,3]thiazolo[5,4-d]azocin-2-yl}-N'-methylurea N-{10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-methylurea (51.1 mg) synthesized from 2-(trimethylsilyl)ethyl 10-[3-(4-fluorophenyl)-1,2,4-oxadiazol-5-yl]-2-[(methylcarbamoyl)amino]-4,7,8,9-tetrahydro-4,8-epimino[1,3]thiazolo[5,4-d]azocine-6(5H)-carboxylate of Example 31 (31c) according to the same method as in Example 18 (18d) was dissolved in dichloromethane (1 mL), triethylamine (0.051 mL) and methanesulfonyl chloride (0.014 mL) were added thereto at 0° C., and the mixture was stirred at 0° C. for 1.5 hours. Triethylamine (0.111 mL) and methanesulfonyl chloride (0.048 mL) were added to the reaction mixture, the mixture was stirred at 0° C. for 3.5 hours, triethylamine (0.111 mL) and methanesulfonyl chloride (0.048 mL) were added thereto, and the mixture was stirred at 0° C. for 2 hours.

Water was added to the reaction mixture, the mixture was extracted 3 times with chloroform using a phase separator (Biotage Japan Ltd.), and the combined organic layers were dried over anhydrous sodium sulfate. After filtration, the residues obtained by distilling off the solvent under reduced pressure were purified by silica gel chromatography [eluting solvent:hexane/ethyl acetate=88/12 to 0/100 (V/V); ethyl acetate/methanol=100/0 to 80/20 (V/V)], thereby obtaining 7.1 mg (yield: 12%) of the title compound as a white solid.

Example 32

Propan-2-yl 10-[3-(4-fluorophenyl)-1,2,4-oxadiazol-5-yl]-2-[(methylcarbamoyl)amino]-4,7,8,9-tetrahydro-4,8-epimino[1,3]thiazolo[5,4-d]azocine-6(5H)-carboxylate Propan-2-yl 10-[3-(4-fluorophenyl)-1,2,4-oxadiazol-5-yl]-2-[(methylcarbamoyl)amino]-4,7,8,9-tetrahydro-4,8-epimino[1,3]thiazolo[5,4-d]azocine-6(5H)-carboxylate N-{10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-methylurea (51.1 mg) synthesized from 2-(trimethylsilyl)ethyl 10-[3-(4-fluorophenyl)-1,2,4-oxadiazol-5-yl]-2-[(methylcarbamoyl)amino]-4,7,8,9-tetrahydro-4,8-epimino[1,3]thiazolo[5,4-d]azocine-6(5H)-carboxylate of Example 31 (31c) according to the same method as in Example 18 (18d) was dissolved in dichloromethane (1 mL), triethylamine (0.051 mL) and isopropyl chloroformate (0.021 mL) were added thereto at 0° C., and the mixture was stirred at 0° C. for 16 hours. Triethylamine (0.111 mL) and isopropyl chloroformate (0.070 mL) were added to the reaction mixture, the mixture was stirred at 0° C. for 2.5 hours.

Water was added to the reaction mixture, the mixture was extracted 3 times with chloroform using a phase separator (Biotage Japan Ltd.), and the combined organic layers were dried over anhydrous sodium sulfate. After filtration, the residues obtained by distilling off the solvent under reduced pressure were purified by silica gel chromatography [eluting solvent:hexane/ethyl acetate=88/12 to 0/100 (V/V)], thereby obtaining 26.9 mg (yield: 44%) of the title compound as a white solid.

Example 33

Methyl (4R*,8R*)-2-{[(2-hydroxy-2-methylpropyl)carbamoyl]amino}-10-{3-[1-(trifluoromethyl)cyclopropyl]-1,2,4-oxadiazol-5-yl}-4,7,8,9-tetrahydro-4,8-epimino[1,3]thiazolo[5,4-d]azocine-6(5H)-carboxylate (33a)

Methyl (4R*,8R*)-2-[(tert-butoxycarbonyl)amino]-10-{3-[1-(trifluoromethyl)cyclopropyl]-1,2,4-oxadiazol-5-yl}-4,7,8,9-tetrahydro-4,8-epimino[1,3]thiazolo[5,4-d]azocine-6(5H)-carboxylate Methyl (4R*,8R*)-2-[(tert-butoxycarbonyl)amino]-10-{3-[1-(trifluoromethyl)cyclopropyl]-1,2,4-oxadiazol-5-yl}-4,7,8,9-tetrahydro-4,8-epimino[1,3]thiazolo[5,4-d]azocine-6(5H)-carboxylate 300 mg (yield: 63%) of the title compound was obtained as a yellow solid according to the same method as in Example 1 (1d) using methyl (4R*,8R*)-2-[(tert-butoxycarbonyl)amino]-10-cyano-4,7,8,9-tetrahydro-4,8-epimino[1,3]thiazolo[5,4-d]azocine-6(5H)-carboxylate (400 mg) synthesized from methyl (4R*,8R*)-2-amino-10-cyano-4,7,8,9-tetrahydro-4,8-epimino[1,3]thiazolo[5,4-d]azocine-6(5H)-carboxylate of Example 24 (24e) in the same manner as in Example 18 (18c) and N'-hydroxy-1-(trifluoromethyl)cyclopropane-1-carboximidamide (160 mg) of Example 37 (37a).

(33b)

Methyl (4R*,8R*)-2-{[(2-hydroxy-2-methylpropyl)carbamoyl]amino}-10-{3-[1-(trifluoromethyl)cyclopropyl]-1,2,4-oxadiazol-5-yl}-4,7,8,9-tetrahydro-4,8-epimino[1,3]thiazolo[5,4-d]azocine-6(5H)-carboxylate Methyl (4R*,8R*)-2-{[(2-hydroxy-2-methylpropyl)carbamoyl]amino}-10-{3-[1-(trifluoromethyl)cyclopropyl]-1,2,4-oxadiazol-5-yl}-4,7,8,9-tetrahydro-4,8-epimino[1,3]thiazolo[5,4-d]azocine-6(5H)-carboxylate 40 mg (yield: 24%) of the title compound was obtained as a white solid according to the same method as in Example 5 (5d) using methyl (4R*,8R*)-2-amino-10-{3-[1-(trifluoromethyl)cyclopropyl]-1,2,4-oxadiazol-5-yl}-4,7,8,9-tetrahydro-4,8-epimino[1,3]thiazolo[5,4-d]azocine-6(5H)-carboxylate (130 mg) synthesized from methyl (4R*,8R*)-2-[(tert-butoxycarbonyl)amino]-10-{3-[1-(trifluoromethyl)cyclopropyl]-1,2,4-oxadiazol-5-yl}-4,7,8,9-tetrahydro-4,8-epimino[1,3]thiazolo[5,4-d]azocine-6(5H)-carboxylate of Example 33 (33a) in the same manner as in Example 6 (6h) and 1-amino-2-methylpropan-2-ol (100 mg).

Example 34

N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[2-(2-hydroxyethoxy)ethyl]urea N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[2-(2-hydroxyethoxy)ethyl]urea 71.3 mg (yield: 34%) of the title compound was obtained as a white solid according to the same method as in Example 5 (5d) using 5-[3-(4,4-difluorocyclohexyl)-1,2,4-oxadiazol-5-yl]-4,5,6,7-tetrahydro[1,3]thiazolo[5,4-c]pyridin-2-amine (150 mg) of Example 5 (5c) and 2-(2-aminoethoxy)ethan-1-ol (0.126 mL).

Example 35

N-{5-[3-(3,3-difluorocyclopentyl)-1,2,4-oxadiazol-5-yl]-4,5,6,7-tetrahydro[1,3]thiazolo[5,4-c]pyridin-2-yl}-N'-[(1r,3r)-3-hydroxycyclobutyl]urea N-{5-[3-(3,3-difluorocyclopentyl)-1,2,4-oxadiazol-5-yl]-4,5,6,7-tetrahydro[1,3]thiazolo[5,4-c]pyridin-2-yl}-N'-[(1r,3r)-3-hydroxycyclobutyl]urea 81 mg (yield: 22%) of the title compound was obtained as a white solid according to the same method as in Example 5 (5d) using 5-[3-(3,3-difluorocyclopentyl)-1,2,4-oxazol-5-yl]-4,5,6,7-tetrahydro[1,3]thiazolo[5,4-c]pyridin-2-amine (60 mg) synthesized from 3-oxocyclopentanecarbonitrile (CAS Registry number: 41171-91-9) in the same manner as in Examples 1 (1a), 1 (1b), 5 (5b), and 5 (5c) and (1r,3r)-3-aminocyclobutan-1-ol (CAS Registry number: 1036260-45-3) (50 mg).

Example 36

N-{5-[3-(3,3-difluorocyclohexyl)-1,2,4-oxadiazol-5-yl]-4,5,6,7-tetrahydro[1,3]thiazolo[5,4-c]pyridin-2-yl}-N'-methylurea N-{5-[3-(3,3-difluorocyclohexyl)-1,2,4-oxadiazol-5-yl]-4,5,6,7-tetrahydro[1,3]thiazolo[5,4-c]pyridin-2-yl}-N'-methylurea 44 mg (yield: 43%) of the title compound was obtained as a white solid according to the same method as in Example 1 (1d) using 3,3-difluoro-N'-hydroxycyclohexane-1-carboximidamide (50 mg) synthesized from 3-oxocyclohexanecarbonitrile (CAS Registry number: 17983-30-1) in the same manner as in Examples 1 (1a) and 1 (1b).

Example 37

N-[(3R)-oxolan-3-yl]-N'-[(4S,8S)-10-{3-[1-(trifluoromethyl)cyclopropyl]-1,2,4-oxadiazol-5-yl}-4,7,8,9-tetrahydro-5H-4,8-epiminooxocino[5,4-d][1,3]thiazol-2-yl]urea (37a)

N'-Hydroxy-1-(trifluoromethyl)cyclopropane-1-carboximidamide

N'-Hydroxy-1-(trifluoromethyl)cyclopropane-1-carboximidamide 1-(Trifluoromethyl)cyclopropane-1-carboxamide (CAS Registry number: 1628184-67-7) (38.3 g) was dissolved in N,N-dimethylformamide (400 mL), 2,4,6-trichloro-1,3,5-triazine (69 g) was added thereto, and the mixture was stirred at room temperature for 12 hours. The reaction mixture was poured into ice water (2 L) and extracted 3 times with tert-butyl methyl ether (150 mL), and the combined organic layers were washed with a saturated saline solution. Ethanol (500 mL) and a 50% hydroxylamine aqueous solution (53 g) were added to the obtained organic layer, and the mixture was stirred at 60° C. for 12 hours. The reaction mixture was concentrated under reduced pressure, water (500 mL) was added thereto, and the mixture was extracted 3 times with ethyl acetate. The combined organic layers were washed with a saturated saline solution and dried over anhydrous sodium sulfate. After filtration, the solvent was distilled off under reduced pressure, thereby obtaining 35.5 g (yield: 84%) of the title compound as a white solid.

(37b)

N-[(3R)-oxolan-3-yl]-N'-[(4S,8S)-10-{3-[1-(trifluoromethyl)cyclopropyl]-1,2,4-oxadiazol-5-yl}-4,7,8,9-tetrahydro-5H-4,8-epiminooxocino[5,4-d][1,3]thiazol-2-yl]urea N-[(3R)-oxolan-3-yl]-N'-[(4S,8S)-10-{3-[1-(trifluoromethyl)cyclopropyl]-1,2,4-oxadiazol-5-yl}-4,7,8,9-tetrahydro-5H-4,8-epiminooxocino[5,4-d][1,3]thiazol-2-yl]urea 1.73 g (yield: 46%) of the title compound was obtained as a white solid according to the same method as in Example 1 (1d) using N-[(4S,8S)-10-cyano-4,7,8,9-tetrahydro-5H-4,8-epiminooxocino[5,4-d][1,3]thiazol-2-yl]-N'-[(3R)-oxolan-3-yl]urea (2.60 g) synthesized from tert-butyl (4S,8S)-2-amino-4,7,8,9-tetrahydro-5H-4,8-epiminooxocino[5,4-d][1,3]thiazole-10-carboxylate of Example 7 (7a) and (R)-3-aminotetrahydrofuran in the same manner as in Examples 5 (5d), 6 (6h), and 1 (1c) and N'-hydroxy-1-(trifluoromethyl)cyclopropane-1-carboximidamide (1.31 g) of Example 37 (37a).

Example 38

N-[(2R)-1-hydroxypropan-2-yl]-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea (38a)

2-Chloro-5-methoxy-1,3-benzoxazole

2-Chloro-5-methoxy-1,3-benzoxazole

5-Methoxybenzoxazole (CAS Registry number: 132227-03-3) (2.4 g) was suspended in tetrahydrofuran (50 mL), and lithium bis(trimethylsilyl)amide (1 M tetrahydrofuran solution, 16 mL) was slowly added dropwise thereto at −78° C. The mixture was stirred at −78° C. for 20 minutes, hexachloroethane (5.7 g) was added thereto, and the mixture was stirred at −78° C. for 10 minutes and further stirred at room temperature for 1 hour. Water was added to the reaction mixture, and the reaction mixture was extracted with ethyl acetate. The organic layer was washed with a saturated saline solution and dried over anhydrous sodium sulfate. The residues obtained by distilling off the solvent under reduced pressure were purified by silica gel column chromatography [eluting solvent:n-hexane/ethyl acetate=1/0 to 7/3 (V/V)], thereby obtaining 2.6 g (yield: 88%) of the title compound as a white solid.

(38b)

(4S,8S)-10-(5-methoxy-1,3-benzoxazol-2-yl)-4,7,8,9-tetrahydro-5H-4,8-epiminooxocino[5,4-d][1,3]thiazol-2-amine (4S,8S)-10-(5-methoxy-1,3-benzoxazol-2-yl)-4,7,8,9-tetrahydro-5H-4,8-epiminooxocino[5,4-d][1,3]thiazol-2-amine (4S,8S)-4,7,8,9-tetrahydro-5H-4,8-epiminooxocino[5,4-d][1,3]thiazol-2-amine dihydrochloride (9 g) of Example 17 (17c) was dissolved in dimethylsulfoxide (50 mL), N,N-diisopropylethylamine (25 mL) and 2-chloro-5-methoxy-1,3-benzoxazole (6.2 g) of Example 38 (38a) were added thereto, and the mixture was stirred at 20° C. for 12 hours. The reaction mixture was poured into ice water, the reaction mixture was extracted 3 times with ethyl acetate, and the combined organic layers were washed with a saturated saline solution and dried over anhydrous sodium sulfate. After filtration, the residues obtained by distilling off the solvent under reduced pressure were purified by silica gel column chromatography [eluting solvent:petroleum ether/ethyl acetate=1/1 (V/V); dichloromethane/methanol=15/1 (V/V)], thereby obtaining 7.3 g (yield: 56%) of the title compound as a brown solid.

(38c)

N-[(2R)-1-hydroxypropan-2-yl]-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea N-[(2R)-1-hydroxypropan-2-yl]-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea 1.95 g (yield: 52%) of the title compound was obtained as a pale gray solid according to the same method as in Example 5 (5d) using (4S,8S)-10-(5-methoxy-1,3-benzoxazol-2-yl)-4,7,8,9-tetrahydro-5H-4,8-epiminooxocino[5,4-d][1,3]thiazol-2-amine (3 g) of Example 38 (38b) and (R)-2-aminopropan-1-ol (1.25 g).

Example 39

N-[(4S,8S)-10-(5-fluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea (39a)

(4S,8S)-10-(5-Fluoro-1,3-benzoxazol-2-yl)-4,7,8,9-tetrahydro-5H-4,8-epiminooxocino[5,4-d][1,3]thiazol-2-amine (4S,8S)-10-(5-fluoro-1,3-benzoxazol-2-yl)-4,7,8,9-tetrahydro-5H-4,8-epiminooxocino[5,4-d][1,3]thiazol-2-amine 4.1 g (yield: 56%) of the title compound was obtained as a brown solid according to the same method as in Example 38 (38b) using (4S,8S)-4,7,8,9-tetrahydro-5H-4,8-epiminooxocino[5,4-d][1,3]thiazol-2-amine dihydrochloride (6.8 g) of Example 17 (17c) and 2-chloro-5-fluorobenzoxazole (International Publication No. WO2016/025669) (3.8 g).

(39b)

N-[(4S,8S)-10-(5-fluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea N-[(4S,8S)-10-(5-fluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea 1.5 g (yield: 56%) of the title compound was obtained as a white solid according to the same method as in Example 5 (5d) using (4S,8S)-10-(5-fluoro-1,3-benzoxazol-2-yl)-4,7,8,9-tetrahydro-5H-4,8-epiminooxocino[5,4-d][1,3]thiazol-2-amine (2 g) of Example 39 (39a) and (R)-2-aminopropan-1-ol (1 g).

Example 40

N-[(4S,8S)-10-(5-ethoxy-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea (40a)

2-Amino-4-ethoxyphenol

2-Amino-4-ethoxyphenol

4-Ethoxy-2-nitrophenol (Synthetic Communications (2009), 39 (11), 2053 to 2057) (0.3 g) was dissolved in ethanol (5 mL), 10% palladium carbon (50 mg) was added thereto, and the mixture was stirred at 25° C. for 3 hours in a hydrogen (15 psi) atmosphere. The reaction mixture was filtered, and the filtrate was concentrated under reduced pressure, thereby obtaining 0.23 g (yield: 92%) of the title compound as a gray solid.

(40b)

5-Ethoxy-1,3-benzoxazole-2-thiol

5-Ethoxy-1,3-benzoxazole-2-thiol

A mixture of 2-amino-4-ethoxyphenol (1.5 g) of Example 40 (40a), potassium O-ethyl carbonodithioate (CAS registry number: 140-89-6) (3.27 g), and ethanol (10 mL) was stirred at 80° C. for 16 hours. The solvent was distilled off under reduced pressure, the reaction mixture was diluted with water (20 mL), and 2 M hydrochloric acid was further added thereto so that the mixture was acidified. The mixture was extracted 3 times with ethyl acetate, and the combined organic layers were washed twice with a saturated sodium hydrogen carbonate aqueous solution and dried over anhydrous sodium sulfate. After filtration, the residues obtained by distilling off the solvent under reduced pressure were triturated with ethyl acetate/petroleum ether and collected by filtration, thereby obtaining 1.6 g (yield: 84%) of the title compound as a gray solid.

(40c)

2-Chloro-5-ethoxy-1,3-benzoxazole

2-Chloro-5-ethoxy-1,3-benzoxazole

A mixture of 5-ethoxy-1,3-benzoxazol-2-thiol (50 mg) of Example 40 (40b) and thionyl chloride (2 mL) was stirred at 80° C. for 2 hours. The reaction mixture was concentrated under reduced pressure, thereby obtaining 50 mg (yield: quantitative) of the title compound as a gray solid.

(40d)

(4S,8S)-10-(5-ethoxy-1,3-benzoxazol-2-yl)-4,7,8,9-tetrahydro-5H-4,8-epiminooxocino[5,4-d][1,3]thiazol-2-amine (4S,8S)-10-(5-ethoxy-1,3-benzoxazol-2-yl)-4,7,8,9-tetrahydro-5H-4,8-epiminooxocino[5,4-d][1,3]thiazol-2-amine 40 mg (yield: 44%) of the title compound was obtained as a gray solid according to the same method as in Example 38 (38b) using (4S,8S)-4,7,8,9-tetrahydro-5H-4,8-epiminooxocino[5,4-d][1,3]thiazol-2-amine dihydrochloride (68 mg) of Example 17 (17c) and 2-chloro-5-ethoxy-1,3-benzoxazole (50 mg) of Example 40 (40c).

(40e)

N-[(4S,8S)-10-(5-ethoxy-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea N-[(4S,8S)-10-(5-ethoxy-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea 1 mg (yield: 38%) of the title compound was obtained as a pale gray solid according to the same method as in Example 5 (5d) using (4S,8S)-10-(5-ethoxy-1,3-benzoxazol-2-yl)-4,7,8,9-tetrahydro-5H-4,8-epiminooxocino[5,4-d] [1,3]thiazol-2-amine (0.20 g) of Example 40 (40d) and 1-amino-2-methylpropan-2-ol (0.20 g).

Example 41

N-{(4S,8S)-10-[5-(dimethylamino)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea (41a)

(4S,8S)-10-(5-nitro-1,3-benzoxazol-2-yl)-4,7,8,9-tetrahydro-5H-4,8-epiminooxocino[5,4-d][1,3]thiazol-2-amine (4S,8S)-10-(5-nitro-1,3-benzoxazol-2-yl)-4,7,8,9-tetrahydro-5H-4,8-epiminooxocino[5,4-d][1,3]thiazol-2-amine 1.8 g (yield: 77%) of the title compound was obtained as a yellow solid according to the same method as in Example 38 (38b) using (4S,8S)-4,7,8,9-tetrahydro-5H-4,8-epiminooxocino[5,4-d][1,3]thiazol-2-amine dihydrochloride (1.5 g) of Example 17 (17c) and 2-chloro-5-nitro-1,3-benzoxazole (International Publication No. WO2016/207785) (1.3 g).

(41b)

tert-Butyl [(4S,8S)-10-(5-nitro-1,3-benzoxazol-2-yl)-4,7,8,9-tetrahydro-5H-4,8-epiminooxocino[5,4-d][1,3]thiazol-2-yl]carbamate tert-Butyl [(4S,8S)-10-(5-nitro-1,3-benzoxazol-2-yl)-4,7,8,9-tetrahydro-5H-4,8-epiminooxocino[5,4-d][1,3]thiazol-2-yl]carbamate (4S,8S)-10-(5-nitro-1,3-benzoxazol-2-yl)-4,7,8,9-tetrahydro-5H-4,8-epiminooxocino[5,4-d][1,3]thiazol-2-amine (1.7 g) of Example 41 (41a) was dissolved in dichloromethane (30 mL), 4-dimethylaminopyridine (200 mg) and di-tert-butyl dicarbonate (1.2 g) were added thereto, and the mixture was stirred at room temperature for 2 hours. The residues obtained by distilling off the solvent from the reaction mixture under reduced pressure were purified by silica gel column chromatography [eluting solvent:petroleum ether/ethyl acetate=1/0 to 7/3 (V/V)], thereby obtaining 1.5 g (yield: 69%) of the title compound as a yellow solid.

(41c)

tert-Butyl [(4S,8S)-10-(5-amino-1,3-benzoxazol-2-yl)-4,7,8,9-tetrahydro-5H-4,8-epiminooxocino[5,4-d][1,3]thiazol-2-yl]carbamate tert-Butyl [(4S,8S)-10-(5-amino-1,3-benzoxazol-2-yl)-4,7,8,9-tetrahydro-5H-4,8-epiminooxocino[5,4-d][1,3]thiazol-2-yl]carbamate tert-Butyl [(4S,8S)-10-(5-nitro-1,3-benzoxazol-2-yl)-4,7,8,9-tetrahydro-5H-4,8-epiminooxocino[5,4-d][1,3]thiazol-2-yl]carbamate (1.5 g) of Example 41 (41b) was dissolved in methanol (20 mL), 10% palladium carbon (0.2 g) was added thereto, and the mixture was stirred at room temperature for 10 hours in a hydrogen (15 psi) atmosphere. The reaction mixture was filtered, and the filtrate was concentrated under reduced pressure, thereby obtaining 1 g (yield: 71%) of the title compound as a brown solid.

(41d)

tert-Butyl {(4S,8S)-10-[5-(dimethylamino)-1,3-benzoxazol-2-yl]-4,7,8,9-tetrahydro-5H-4,8-epiminooxocino[5,4-d][1,3]thiazol-2-yl}carbamate tert-Butyl {(4S,8S)-10-[5-(dimethylamino)-1,3-benzoxazol-2-yl]-4,7,8,9-tetrahydro-5H-4,8-epiminooxocino[5,4-d][1,3]thiazol-2-yl}carbamate tert-Butyl [(4S,8S)-10-(5-amino-1,3-benzoxazol-2-yl)-4,7,8,9-tetrahydro-5H-4,8-epiminooxocino[5,4-d][1,3]thiazol-2-yl]carbamate (500 mg) of Example 41 (41c) was dissolved in methanol (30 mL), formaldehyde (164 mg) and tetraisopropyl orthotitanium (385 mg) were added thereto, and the mixture was stirred at room temperature for 10 hours. Sodium cyanoborohydride (150 mg) was added thereto, and the mixture was stirred at room temperature for 1 hour. Water was added to the residues obtained by distilling off the solvent from the reaction mixture under reduced pressure, and the mixture was extracted twice with ethyl acetate. The combined organic layers were washed with a saturated saline solution and dried over anhydrous sodium sulfate. After filtration, the solvent was distilled off under reduced pressure, thereby obtaining 500 mg (yield: 94%) of the title compound as a gray solid.

(41e)

(4S,8S)-10-[5-(dimethylamino)-1,3-benzoxazol-2-yl]-4,7,8,9-tetrahydro-5H-4,8-epiminooxocino[5,4-d][1,3]thiazol-2-amine (4S,8S)-10-[5-(dimethylamino)-1,3-benzoxazol-2-yl]-4,7,8,9-tetrahydro-5H-4,8-epiminooxocino[5,4-d][1,3]thiazol-2-amine tert-Butyl {(4S,8S)-10-[5-(dimethylamino)-1,3-benzoxazol-2-yl]-4,7,8,9-tetrahydro-5H-4,8-epiminooxocino[5,4-d][1,3]thiazol-2-yl}carbamate (600 mg) of Example 41 (41d) was dissolved in dichloromethane (40 mL), a 4 M hydrogen chloride-ethyl acetate solution (18 mL) was added thereto, and the mixture was stirred at room temperature for 1 hour. Dichloromethane (30 mL) and a 3 M sodium hydrogen carbonate aqueous solution (20 mL) were added to the residues obtained by distilling off the solvent from the reaction mixture under reduced pressure, and the mixture was stirred at 20° C. for 30 minutes. The reaction mixture was poured into water and extracted 3 times with dichloromethane, and the combined organic layers were washed with a saturated saline solution and dried over anhydrous sodium sulfate. After filtration, the solvent was distilled off under reduced pressure, thereby obtaining 400 mg (yield: 84%) of the title compound as a pale gray solid.

(41f)

N-{(4S,8S)-10-[5-(dimethylamino)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea N-{(4S,8S)-10-[5-(dimethylamino)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea 87 mg (yield: 43%) of the title compound was obtained as a pale gray solid according to the same method as in Example 5 (5d) using (4S,8S)-10-[5-(dimethylamino)-1,3-benzoxazol-2-yl]-4,7,8,9-tetrahydro-5H-4,8-epiminooxocino[5,4-d][1,3]thiazol-2-amine (150 mg) of Example 41 (41e) and 1-amino-2-methylpropan-2-ol (75 mg).

Example 42

N-[(4S,8S)-10-(5,6-difluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea (42a)

(4S,8S)-10-(5,6-difluoro-1,3-benzoxazol-2-yl)-4,7,8,9-tetrahydro-5H-4,8-epiminooxocino[5,4-d][1,3]thiazol-2-amine (4S,8S)-10-(5,6-difluoro-1,3-benzoxazol-2-yl)-4,7,8,9-tetrahydro-5H-4,8-epiminooxocino[5,4-d][1,3]thiazol-2-amine 150 mg (yield: 74%) of the title compound was obtained as a yellow solid according to the same method as in Example 38 (38b) using (4S,8S)-4,7,8,9-tetrahydro-5H-4,8-epiminooxocino[5,4-d][1,3]thiazol-2-amine dihydrochloride (180 mg) of Example 17 (17c) and 2-chloro-5,6-difluoro-1,3-benzoxazole (International Publication No. WO2018/037223) (110 mg).

(42b)

N-[(4S,8S)-10-(5,6-difluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea N-[(4S,8S)-10-(5,6-difluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea 96 mg (yield: 49%) of the title compound was obtained as a white solid according to the same method as in Example 5 (5d) using (4S,8S)-10-(5,6-difluoro-1,3-benzoxazol-2-yl)-4,7,8,9-tetrahydro-5H-4,8-epiminooxocino[5,4-d][1,3]thiazol-2-amine (150 mg) of Example 42 (42a) and (R)-2-aminopropan-1-ol (35 mg).

Example 43

N-{(4S,8S)-10-[5-(methanesulfonyl)-1,3-benzoxazol-2-yl]-4,7,8,9-tetrahydro-5H-4,8-epiminooxocino[5,4-d][1,3]thiazol-2-yl}-N'-(2-methylpropyl)urea (43a)

(4S,8S)-4,7,8,9-tetrahydro-5H-4,8-epiminooxocino[5,4-d][1,3]thiazol-2-amine (4S,8S)-4,7,8,9-tetrahydro-5H-4,8-epiminooxocino[5,4-d][1,3]thiazol-2-amine tert-Butyl (4S,8S)-2-amino-4,7,8,9-tetrahydro-5H-4,8-epiminooxocino[5,4-d][1,3]thiazole-10-carboxylate (30 g) of Example 7 (7a) was dissolved in dichloromethane (240 mL), trifluoroacetic acid (60 mL) was added thereto, and the mixture was stirred at room temperature for 2 hours. The reaction solution was concentrated and subjected to azeotropy twice with toluene, and the obtained residues were purified by NH silica gel column chromatography [eluting solvent:methanol/ethyl acetate=0/10 to 3/7 (V/V)], and the obtained solid was washed with ethyl acetate-hexane, thereby obtaining 18.1 g (yield: 91%) of the title compound as a pale yellow solid.

(43b)

(4S,8S)-10-[5-(methanesulfonyl)-1,3-benzoxazol-2-yl]-4,7,8,9-tetrahydro-5H-4,8-epiminooxocino[5,4-d][1,3]thiazol-2-amine (4S,8S)-10-[5-(methanesulfonyl)-1,3-benzoxazol-2-yl]-4,7,8,9-tetrahydro-5H-4,8-epiminooxocino[5,4-d][1,3]thiazol-2-amine (4S,8S)-4,7,8,9-tetrahydro-5H-4,8-epiminooxocino[5,4-d][1,3]thiazol-2-amine (2 g) of Example 43 (43a) was dissolved in chloroform (40 mL), acetic acid (3.48 mL), 3-amino-4-hydroxyphenyl methyl sulfone (CAS Registry number: 98-30-6) (2.85 g), and tetramethoxymethane (4.06 mL) were added thereto, and the mixture was stirred at 60° C. for 29 hours. Water was added to the reaction mixture, and the reaction mixture was extracted with ethyl acetate. The organic layer was washed with a saturated saline solution and dried over anhydrous sodium sulfate. The residues obtained by distilling off the solvent under reduced pressure were purified by silica gel column chromatography [eluting solvent:methanol /ethyl acetate=0/10 to 1/9 (V/V)], thereby obtaining 0.98 g (yield: 25%) of the title compound as a yellow solid.

(43c)

N-{(4S,8S)-10-[5-(methanesulfonyl)-1,3-benzoxazol-2-yl]-4,7,8,9-tetrahydro-5H-4,8-epiminooxocino[5,4-d][1,3]thiazol-2-yl}-N'-(2-methylpropyl)urea N-{(4S,8S)-10-[5-(methanesulfonyl)-1,3-benzoxazol-2-yl]-4,7,8,9-tetrahydro-5H-4,8-epiminooxocino[5,4-d][1,3]thiazol-2-yl}-N'-(2-methylpropyl)urea (4S,8S)-10-[5-(methanesulfonyl)-1,3-benzoxazol-2-yl]-4,7,8,9-tetrahydro-5H-4,8-epiminooxocino[5,4-d][1,3]thiazol-2-amine (150 mg) of Example 43 (43b) was dissolved in N,N-dimethylformamide (3 mL), 1,1'-carbonyldiimidazole (124 mg) was added thereto, and the mixture was allowed to stand at room temperature overnight. Isobutylamine (0.09 mL) was added thereto, and the mixture was stirred at room temperature for 5 hours. Ethyl acetate was added to the reaction solution, and the organic layer was washed with water and a saturated saline solution and dried over anhydrous sodium sulfate. The residues obtained by distilling off the solvent under reduced pressure were purified by silica gel column chromatography [eluting solvent:methanol/ethyl acetate=0/10 to 1/9 (V/V)], thereby obtaining 132 mg (yield: 70%) of the title compound as a pale yellow solid.

Example 44

N-(2-hydroxy-2-methylpropyl)-N'-[(4S,8S)-10-(5-methoxy-6-methyl-1,3-benzoxazol-2-yl)-4,7,8,9-tetrahydro-5H-4,8-epiminooxocino[5,4-d][1,3]thiazol-2-yl]urea (44a)

5-Methoxy-6-methyl-1,3-benzoxazole

5-Methoxy-6-methyl-1,3-benzoxazole

2-Amino-4-methoxy-5-methyl-phenol (Chemistry—A European Journal (2017), 23 (50), 12363 to 12371) (2.4 g) was dissolved in N,N-dimethylformamide (40 mL), trimethyl orthoformate (13 mL) and a tosylic acid monohydrate (0.30 g) were added thereto, and the mixture was stirred at 60° C. for 3 hours. Water was added to the reaction mixture, and the reaction mixture was extracted with ethyl acetate. The organic layer was washed with water and a saturated saline solution and dried over anhydrous sodium sulfate. The residues obtained by distilling off the solvent under reduced pressure were purified by silica gel column chromatography [eluting solvent:n-hexane/ethyl acetate=9/1 to 7/3 (V/V)], thereby obtaining 2.2 g (yield: 86%) of the title compound as a red solid.

(44b)

2-Chloro-5-methoxy-6-methyl-1,3-benzoxazole

2-Chloro-5-methoxy-6-methyl-1,3-benzoxazole

5-Methoxy-6-methyl-1,3-benzoxazole (2.70 g) of Example 44 (44a) was dissolved in tetrahydrofuran (50 mL), and lithium bis(trimethylsilyl)amide (1M tetrahydrofuran solution, 16.5 mL) was slowly added dropwise thereto at −78° C. The mixture was stirred at −78° C. for 20 minutes, hexachloroethane (5.88 g) was added thereto, and the mixture was stirred at −78° C. for 20 minutes and further stirred at room temperature for 3 hours. Water was added to the reaction mixture, and the reaction mixture was extracted with ethyl acetate. The organic layer was washed with a saturated saline solution and dried over anhydrous sodium sulfate. The residues obtained by distilling off the solvent under reduced pressure were purified by silica gel column chromatography [eluting solvent:n-hexane/ethyl acetate=10/0 to 7/3 (V/V)], thereby obtaining 3.05 g (yield: 93%) of the title compound as a yellow solid.

(44c)

(4S,8S)-10-(5-methoxy-6-methyl-1,3-benzoxazol-2-yl)-4,7,8,9-tetrahydro-5H-4,8-epiminooxocino[5,4-d][1,3]thiazol-2-amine (4S,8S)-10-(5-methoxy-6-methyl-1,3-benzoxazol-2-yl)-4,7,8,9-tetrahydro-5H-4,8-epiminooxocino[5,4-d][1,3]thiazol-2-amine (4S,8S)-4,7,8,9-tetrahydro-5H-4,8-epiminooxocino[5,4-d][1,3]thiazol-2-amine dihydrochloride (2 g) of Example 17 (17c) was dissolved in dimethyl sulfoxide (30 mL), 2-chloro-5-methoxy-6-methyl-1,3-benzoxazole (1.46 g) of Example 44 (44b) and N,N-diisopropylethylamine (6.45 mL) were added thereto, and the mixture was stirred at 60° C. for 10 hours and allowed to stand at room temperature overnight. Water was added to the reaction mixture, the precipitated solid was collected by filtration, and the obtained solid was washed with ethyl acetate-hexane, thereby obtaining 2.2 g (yield: 83%) of the title compound as a pale yellow solid.

(44d)

N-(2-hydroxy-2-methylpropyl)-N'-[(4S,8S)-10-(5-methoxy-6-methyl-1,3-benzoxazol-2-yl)-4,7,8,9-tetrahydro-5H-4,8-epiminooxocino[5,4-d][1,3]thiazol-2-yl]urea N-(2-hydroxy-2-methylpropyl)-N'-[(4S,8S)-10-(5-methoxy-6-methyl-1,3-benzoxazol-2-yl)-4,7,8,9-tetrahydro-5H-4,8-epiminooxocino[5,4-d][1,3]thiazol-2-yl]urea (4S,8S)-10-(5-methoxy-6-methyl-1,3-benzoxazol-2-yl)-4,7,8,9-tetrahydro-5H-4,8-epiminooxocino[5,4-d][1,3]thiazol-2-amine (200 mg) of Example 44 (44c) was dissolved in N,N-dimethylformamide (4 mL), 1,1'-carbonyldiimidazole (181 mg) was added thereto, and the mixture was allowed to stand at room temperature overnight. 1-Amino-2-methyl-2-propanol (0.159 mL) was added thereto, and the mixture was stirred at room temperature for 3 hours. Ethyl acetate was added to the reaction solution, and the organic layer was washed with water and a saturated saline solution and dried over anhydrous sodium sulfate. The residues obtained by distilling off the solvent under reduced pressure were purified by NH silica gel column chromatography [eluting solvent:methanol/ethyl acetate=0/10 to 1/9 (V/V)], thereby obtaining 208 mg (yield: 79%) of the title compound as a pale yellow solid.

Example 45

N-[(4S,8S)-10-(5-methoxy-6-methyl-1,3-benzoxazol-2-yl)-4,7,8,9-tetrahydro-5H-4,8-epiminooxocino[5,4-d][1,3]thiazol-2-yl]-N'-[(3R)-oxolan-3-yl]urea N-[(4S,8S)-10-(5-methoxy-6-methyl-1,3-benzoxazol-2-yl)-4,7,8,9-tetrahydro-5H-4,8-epiminooxocino[5,4-d][1,3]thiazol-2-yl]-N'-[(3R)-oxolan-3-yl]urea (4S,8S)-10-(5-methoxy-6-methyl-1,3-benzoxazol-2-yl)-4,7,8,9-tetrahydro-5H-4,8-epiminooxocino[5,4-d][1,3]thiazol-2-amine (200 mg) of Example 44 (44c) was dissolved in N,N-dimethylformamide (4 mL), 1,1'-carbonyldiimidazole (181 mg) was added thereto, and the mixture was allowed to stand at room temperature overnight. (R)-3-aminotetrahydrofuran (146 mg) was added thereto, and the mixture was stirred at room temperature for 5 hours. Ethyl acetate was added to the reaction solution, and the organic layer was washed with water and a saturated saline solution and dried over anhydrous sodium sulfate. The residues obtained by distilling off the solvent under reduced pressure were purified by NH silica gel column chromatography [eluting solvent:methanol/ethyl acetate=0/10 to 1/9 (V/V)], thereby obtaining 181 mg (yield: 69%) of the title compound as a pale yellow solid.

Example 46

N-(2-hydroxy-2-methylpropyl)-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea N-(2-hydroxy-2-methylpropyl)-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea (4S,8S)-10-(5-methoxy-1,3-benzoxazol-2-yl)-4,7,8,9-tetrahydro-5H-4,8-epiminooxocino[5,4-d][1,3]thiazol-2-amine (200 mg) of Example 38 (38b) was dissolved in N,N-dimethylformamide (4 mL), 1,1'-carbonyldiimidazole (190 mg) was added thereto, and the mixture was allowed to stand at room temperature overnight. 1-Amino-2-methyl-2-propanol (0.17 mL) was added thereto, and the mixture was stirred at room temperature for 5 hours. Ethyl acetate was added to the reaction solution, and the organic layer was washed with water and a saturated saline solution and dried over anhydrous sodium sulfate. The residues obtained by distilling off the solvent under reduced pressure were purified by NH silica gel column chromatography [eluting solvent:methanol/ethyl acetate=0/10 to 1/9 (V/V)], thereby obtaining 194 mg (yield: 73%) of the title compound as a pale yellow solid.

Example 47

N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-[(3R)-oxolan-3-yl]urea N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-[(3R)-oxolan-3-yl]urea (4S,8S)-10-(5-methoxy-1,3-benzoxazol-2-yl)-4,7,8,9-tetrahydro-5H-4,8-epiminooxocino[5,4-d][1,3]thiazol-2-amine (200 mg) of Example 38 (38b) was dissolved in N,N-dimethylformamide (4 mL), 1,1'-carbonyldiimidazole (188 mg) was added thereto, and the mixture was allowed to stand at room temperature overnight. (R)-3-aminotetrahydrofuran (152 mg) was added thereto, and the mixture was stirred at room temperature for 5 hours. Ethyl acetate was added to the reaction solution, and the organic layer was washed with water and a saturated saline solution and dried over anhydrous sodium sulfate. The residues obtained by distilling off the solvent under reduced pressure were purified by NH silica gel column chromatography [eluting solvent:methanol/ethyl acetate=0/10 to 1/9 (V/V)], thereby obtaining 181 mg (yield: 68%) of the title compound as a pale yellow solid.

Example 48

N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-methylurea N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-methylurea N-methyl-N'-[(4S,8S)-4,7,8,9-tetrahydro-5H-4,8-epiminooxocino[5,4-d][1,3]thiazol-2-yl]urea monohydrochloride (200 mg) of Example 7 (7b) was dissolved in dimethyl sulfoxide (4 mL), 2-chloro-5-methoxy-1,3-benzoxazole (110 mg) of Example 38 (38a) and N,N-diisopropylethylamine (0.53 mL) were added thereto, and the mixture was allowed to stand at room temperature overnight. Water was added to the reaction mixture, and the reaction mixture was extracted with ethyl acetate. The organic layer was washed with water and a saturated saline solution and dried over anhydrous sodium sulfate. The residues obtained by distilling off the solvent under reduced pressure were purified by silica gel column chromatography [eluting solvent:methanol/ethyl acetate=0/10 to 1/9 (V/V)], thereby obtaining 142 mg (yield: 58%) of the title compound as a white solid.

Example 49

N-methyl-N'-[(4S,8S)-10-(5-methyl-1,3-benzoxazol-2-yl)-4,7,8,9-tetrahydro-5H-4,8-epiminooxocino[5,4-d][1,3]thiazol-2-yl]urea N-methyl-N'-[(4S,8S)-10-(5-methyl-1,3-benzoxazol-2-yl)-4,7,8,9-tetrahydro-5H-4,8-epiminooxocino[5,4-d][1,3]thiazol-2-yl]urea N-methyl-N'-[(4S,8S)-4,7,8,9-tetrahydro-5H-4,8-epiminooxocino[5,4-d][1,3]thiazol-2-yl]urea monohydrochloride (200 mg) of Example 7 (7b) was dissolved in dimethyl sulfoxide (4 mL), 2-chloro-5-methyl-1,3-benzoxazole (CAS Registry number: 3770-60-3) (102 mg) and N,N-diisopropylethylamine (0.53 mL) were added thereto, and the mixture was allowed to stand at room temperature overnight. Water was added to the reaction mixture, and the reaction mixture was extracted with ethyl acetate. The organic layer was washed with water and a saturated saline solution and dried over anhydrous sodium sulfate. The residues obtained by distilling off the solvent under reduced pressure were purified by silica gel column chromatography [eluting solvent:methanol/ethyl acetate=0/10 to 1/9 (V/V)], and the obtained solid was washed with ethyl acetate-hexane, thereby obtaining 111 mg (yield: 47%) of the title compound as a white solid.

Example 50

N-{(4S,8S)-10-[5-(methanesulfonyl)-1,3-benzoxazol-2-yl]-4,7,8,9-tetrahydro-5H-4,8-epiminooxocino[5,4-d][1,3]thiazol-2-yl}-N'-propan-2-ylurea N-{(4S,8S)-10-[5-(methanesulfonyl)-1,3-benzoxazol-2-yl]-4,7,8,9-tetrahydro-5H-4,8-epiminooxocino[5,4-d][1,3]thiazol-2-yl}-N'-propan-2-ylurea 112 mg (yield: 61%) of the title compound was obtained as a pale yellow solid according to the same method as in Example 5 (5d) using (4S,8S)-10-[5-(methanesulfonyl)-1,3-benzoxazol-2-yl]-4,7,8,9-tetrahydro-5H-4,8-epiminooxocino[5,4-d][1,3]thiazol-2-amine (150 mg) of Example 43 (43b) and isobutylamine (0.1 mL).

Example 51

N-[(4S,8S)-10-(6-cyano-5-methyl-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea N-[(4S,8S)-10-(6-cyano-5-methyl-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea 83 mg (yield: 63%) of the title compound was obtained as a pale yellow solid according to the same method as in Example 5 (5d) using 2-[(4S,8S)-2-amino-4,7,8,9-tetrahydro-5H-4,8-epiminooxocino[5,4-d][1,3]thiazol-10-yl]-5-methyl-1,3-benzoxazole-6-carbonitrile (100 mg) synthesized from 5-hydroxy-2-methylbenzonitrile (CAS Registry number: 101349-82-0) (4.1 g) according to the same method as in International Publication No. WO2009/037296 and Examples 40 (40b), 40 (40c), and 38 (38b) and 1-amino-2-methyl-2-propanol (0.11 mL).

Example 52

N-[(4S,8S)-10-(5-ethoxy-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea N-[(4S,8S)-10-(5-ethoxy-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea 78 mg (yield: 30%) of the title compound was obtained as a pale gray solid according to the same method as in Example 5 (5d) using (4S,8S)-10-(5-ethoxy-1,3-benzoxazol-2-yl)-4,7,8,9-tetrahydro-5H-4,8-epiminooxocino[5,4-d][1,3]thiazol-2-amine (200 mg) of Example 40 (40d) and (2R)-2-aminopropan-1-ol (166 mg).

Example 53

N-{(4S,8S)-10-[5-(difluoromethyl)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea (53a)

1-(Benzyloxy)-4-(difluoromethyl)-2-nitrobenzene 1-(Benzyloxy)-4-(difluoromethyl)-2-nitrobenzene 4-Benzyloxy-3-nitro-benzaldehyde (CAS Registry number: 22955-07-3) (4.6 g) was dissolved in dichloromethane (90 mL), bis(2-methoxyethyl)amino sulfur trifluoride (8.8 mL) was slowly added thereto at 0° C., and the mixture was stirred at 0° C. for 1 hour and further stirred at room temperature for 4 hours. Water was added to the reaction mixture, the mixture was extracted with dichloromethane, and the combined organic layers were washed with a saturated saline solution and dried over anhydrous sodium sulfate. The residues obtained by distilling off the solvent under reduced pressure were purified by silica gel column chromatography [eluting solvent:n-hexane/ethyl acetate=10/0 to 7/3 (V/V)], thereby obtaining 4.7 g (yield: 94%) of the title compound as a pale yellow liquid.
(53b)

2-Amino-4-(difluoromethyl)phenol

2-Amino-4-(difluoromethyl)phenol 1-(Benzyloxy)-4-(difluoromethyl)-2-nitrobenzene (4.7 g) of Example 53 (53a) was dissolved in ethanol (50 mL), 20% palladium hydroxide carbon (wet, 0.5 g) was added thereto, and the mixture was vigorously stirred at room temperature for 2 hours in a hydrogen atmosphere. The insoluble material was removed by filtration, and the solid obtained by distilling off the solvent from the filtrate under reduced pressure was washed with ethyl acetate-hexane, thereby obtaining 2.6 g (yield 97%) of the title compound as a brown solid.
(53c)

N-{(4S,8S)-10-[5-(difluoromethyl)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea N-{(4S,8S)-10-[5-(difluoromethyl)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea 215 mg (yield: 82%) of the title compound was obtained as a pale yellow solid according to the same method as in Example 5 (5d) using (4S,8S)-10-[5-(difluoromethyl)-1,3-benzoxazol-2-yl]-4,7,8,9-tetrahydro-5H-4,8-epiminooxocino[5,4-d][1,3]thiazol-2-amine (200 mg) synthesized from 2-amino-4-(difluoromethyl)phenol (2.6 g) of Example 53 (53b) in the same manner as in Examples 44 (44a), 44 (44b), and 38 (38b) and 1-amino-2-methyl-2-propanol (0.16 mL).

Example 54

N-[(1r,3S)-3-hydroxycyclobutyl]-N'-[(4S,8S)-10-(5-trifluoromethoxy-1,3-benzoxazol-2-yl)-4,7,8,9-tetrahydro-5H-4,8-epiminooxocino[5,4-d][1,3]thiazol-2-yl]urea N-[(1r,3S)-3-hydroxycyclobutyl]-N'-{(4S,8S)-10-[5-(trifluoromethoxy)-1,3-benzoxazol-2-yl]-4,7,8,9-tetrahydro-5H-4,8-epiminooxocino[5,4-d][1,3]thiazol-2-yl}urea (4S,8S)-10-[5-(trifluoromethoxy)-1,3-Benzoxazol-2-yl]-4,7,8,9-tetrahydro-5H-4,8-epiminooxocino[5,4-d][1,3]thiazol-2-amine (200 mg) synthesized from 2-amino-4-(trifluoromethoxy)phenol (CAS Registry number: 461699-34-3) in the same manner as in Example 43 (43b) was dissolved in N,N-dimethylformamide (4 mL), 1,1'-carbonyldiimidazole (163 mg) was added thereto, and the mixture was allowed to stand at room temperature overnight. Triethylamine (0.35 mL) and trans-3-aminocyclobutan-1-ol hydrochloride (186 mg) were added thereto, and the mixture was stirred at room temperature for 4 hours. Ethyl acetate was added to the reaction solution, and the organic layer was washed with water and a saturated saline solution and dried over anhydrous sodium sulfate. The residues obtained by distilling off the solvent under reduced pressure were purified by NH silica gel column chromatography [eluting solvent:methanol/ethyl acetate=0/10 to 1/9 (V/V)], thereby obtaining 186 mg (yield: 72%) of the title compound as a pale yellow solid.

Example 55

N-{(4S,8S)-10-(5-cyano-6-fluoro-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea N-[(4S,8S)-10-(5-cyano-6-fluoro-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea 68 mg (yield: 51%) of the title compound was obtained as a pale yellow solid according to the same method as in Example 5 (5d) using 2-[(4S,8S)-2-amino-4,7,8,9-tetrahydro-5H-4,8-epiminooxocino[5,4-d][1,3]thiazol-10-yl]-6-fluoro-1,3-benzoxazol-5-carbonitrile (100 mg) synthesized from 5-amino-2-fluoro-4-hydroxybenzonitrile (CAS Registry number: 388091-38-1) in the same manner as in Example 43 (43b) and 1-amino-2-methyl-2-propanol (0.08 mL).

Example 56

N-{(4S,8S)-10-[5-(difluoromethyl)-1,3-benzoxazol-2-yl]-4,7,8,9-tetrahydro-5H-4,8-epiminooxocino[5,4-d][1,3]thiazol-2-yl}-N'-[(2R)-1-hydroxypropan-2-yl)urea N-{(4S,8S)-10-[5-(difluoromethyl)-1,3-benzoxazol-2-yl]-4,7,8,9-tetrahydro-5H-4,8-epiminooxocino[5,4-d][1,3]thiazol-2-yl}-N'-[(2R)-1-hydroxypropan-2-yl]urea 200 mg (yield: 78%) of the title compound was obtained as a pale yellow solid according to the same method as in Example 5 (5d) using (4S,8S)-10-[5-(difluoromethyl)-1,3-benzoxazol-2-yl]-4,7,8,9-tetrahydro-5H-4,8-epiminooxocino[5,4-d][1,3]thiazol-2-amine (200 mg) synthesized from 2-amino-4-(difluoromethyl)phenol (2.6 g) of Example 53 (53b) in the same manner as in Examples 44 (44a), 44 (44b), and 38 (38b) and (R)-(−)-2-amino-1-propanol (0.13 mL).

Example 57

N-{(4S,8S)-10-[5-(fluoromethoxy)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea (57a)

5-(Fluoromethoxy)-1,3-benzoxazole 5-(Fluoromethoxy)-1,3-benzoxazole

Fluoroiodomethane (3.23 g) was added to a mixture of 5-hydroxybenzoxazole (CAS Registry number: 180716-28-3) (1.7 g), potassium carbonate (3.48 g), and N,N-dimethylformamide (30 mL) at room temperature, and the mixture was stirred for 30 minutes. Water was added to the reaction mixture, and the mixture was extracted 3 times with ethyl acetate. The combined organic layers were washed with a saturated saline solution and dried over anhydrous sodium sulfate. After filtration, the residues obtained by distilling off the solvent under reduced pressure were purified by silica gel column chromatography [eluting solvent:petroleum ether/ethyl acetate=30/1 to 10/1 (V/V)], thereby obtaining 1.2 g (yield: 57%) of the title compound as a yellow solid.
(57b)

N-{(4S,8S)-10-[5-(fluoromethoxy)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea N-{(4S,8S)-10-[5-(fluoromethoxy)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea 75.3 mg (yield: 38%) of the title compound was obtained as a white solid according to the same method as in Example 5 (5d) using (4S,8S)-10-[5-(fluoromethoxy)-1,3-benzoxazol-2-yl]-4,7,8,9-tetrahydro-5H-4,8-epiminooxocino[5,4-d][1,3]thiazol-2-amine (300 mg) synthesized from 5-(fluoromethoxy)-1,3-benzoxazole of Example 57 (57a) in the same manner as in Examples 14 (14c) and 69 (69a) and 1-amino-2-methylpropan-2-ol (160 mg).

Example 58

N-(1-hydroxy-2-methylpropan-2-yl)-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea N-(1-hydroxy-2-methylpropan-2-yl)-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea 70.5 mg (yield: 35%) of the title compound was obtained as a white solid according to the same method as in Example 5 (5d) using (4S,8S)-10-(5-methoxy-1,3-benzoxazol-2-yl)-4,7,8,9-tetrahydro-5H-4,8-epiminooxocino[5,4-d][1,3]thiazol-2-amine (150 mg) of Example 38 (38b) and 2-amino-2-methylpropan-1-ol (120 mg).

Example 59

N-[(4S,8S)-10-(5-chloro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea N-[(4S,8S)-10-(5-chloro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea 969 mg (yield: 41%) of the title compound was obtained as a white solid according to the same method as in Example 5 (5d) using (4S,8S)-10-(5-chloro-1,3-benzoxazol-2-yl)-4,7,8,9-tetrahydro-5H-4,8-epiminooxocino[5,4-d][1,3]thiazol-2-amine (1.8 g) synthesized from 2,5-dichlorobenzoxazole (CAS Registry number: 3621-81-6) in the same manner as in Example 38 (38b) and (R)-2-aminopropan-1-ol (800 mg).

Example 60

N-(2-hydroxy-2-methylpropyl)-N'-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]urea (60a)

5-[($^2$H$_3$)methyloxy]-1,3-benzoxazole

5-[($^2$H$_3$)methyloxy]-1,3-benzoxazole 2.57 g (yield: 76%) of the title compound was obtained as a white solid according to the same method as in Example 57 (57a) using 5-hydroxybenzoxazole (CAS Registry number: 180716-28-3) (3 g) and iodo($^2$H$_3$)methane (2.4 mL).
(60b)

2-Chloro-5-[($^2$H$_3$)methyloxy]-1,3-benzoxazole

2-Chloro-5-[($^2$H$_3$)methyloxy]-1,3-benzoxazole 1.31 g (yield: 71%) of the title compound was obtained as a pink solid according to the same method as in Example 14 (14c) using 5-[($^2$H$_3$)methyloxy]-1,3-benzoxazole (1.5 g) of Example 60 (60a).

(60c)

(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-amine (4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-amine 0.4 g (yield: 72%) of the title compound was obtained as a yellow solid according to the same method as in Example 38 (38b) using (4S,8S)-4,7,8,9-tetrahydro-5H-4,8-epiminooxocino[5,4-d][1,3]thiazol-2-amine dihydrochloride (641 mg) of Example 17 (17c) and 2-chloro-5-[($^2$H$_3$)methyloxy]-1,3-benzoxazole (0.3 g) of Example 60 (60b).

(60d)

N-(2-hydroxy-2-methylpropyl)-N'-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]urea N-(2-hydroxy-2-methylpropyl)-N'-[(4S,8S)-10-{5-[($^2$H$_3$)methyloxy]-1,3-benzoxazol-2-yl}-4,7,8,9-tetrahydro-5H-4,8-epiminooxocino[5,4-d] [1,3]thiazol-2-yl]urea 112 mg (yield: 62%) of the title compound was obtained as a grayish white solid according to the same method as in Example 5 (5d) using (4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-amine (133 mg) of Example 60 (60c) and 2-amino-2-methylpropan-1-ol (136 mg).

Example 61

N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(1s,4s)-4-hydroxycyclohexyl]urea (61a)

2-(Trimethylsilyl)ethyl (4S,8S)-2-amino-4,7,8,9-tetrahydro-5H-4,8-epiminooxocino[5,4-d][1,3]thiazole-10-carboxylate 2-(trimethylsilyl)ethyl (4S,8S)-2-amino-4,7,8,9-tetrahydro-5H-4,8-epiminooxocino[5,4-d][1,3]thiazole-10-carboxylate 1 g (yield: 67%) of the title compound was obtained as a yellow solid according to the same method as in Example 18 (18a) using (4S,8S)-4,7,8,9-tetrahydro-5H-4,8-epiminooxocino[5,4-d][1,3]thiazol-2-amine dihydrochloride (120 g) of Example 17 (17c).

(61b)

2-(Trimethylsilyl)ethyl (4S,8S)-2-[(tert-butoxycarbonyl)amino]-4,7,8,9-tetrahydro-5H-4,8-epiminooxocino[5,4-d][1,3]thiazole-10-carboxylate 2-(Trimethylsilyl)ethyl (4S,8S)-2-[(tert-butoxycarbonyl)amino]-4,7,8,9-tetrahydro-5H-4,8-epiminooxocino[5,4-d][1,3]thiazole-10-carboxylate 90 g (yield: 57%) of the title compound was obtained as a yellow oily material according to the same method as in Example 18 (18c) using 2-(trimethylsilyl)ethyl(4S,8S)-2-amino-4,7,8,9-tetrahydro-5H-4,8-epiminooxocino[5,4-d][1,3]thiazole-10-carboxylate (110 g) of Example 61 (61a).

(61c)

tert-Butyl (4S,8S)-4,7,8,9-tetrahydro-5H-4,8-epiminooxocino[5,4-d][1,3]thiazol-2-ylcarbamate tert-Butyl (4S,8S)-4,7,8,9-tetrahydro-5H-4,8-epiminooxocino[5,4-d][1,3]thiazol-2-ylcarbamate 8.6 g (yield: 57%) of the title compound was obtained as a yellow solid according to the same method as in Example 18 (18d) using 2-(trimethylsilyl)ethyl(4S,8S)-2-[(tert-butoxycarbonyl)amino]-4,7,8,9-tetrahydro-5H-4,8-epiminooxocino[5,4-d][1,3]thiazole-10-carboxylate (18 g) of Example 61 (61b).

(61d)

tert-Butyl {(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}carbamate tert-Butyl {(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}carbamate 900 mg (yield: 12%) of the title compound was obtained as a yellow solid according to the same method as in Example 11 (11b) using tert-butyl(4S,8S)-4,7,8,9-tetrahydro-5H-4,8-epiminooxocino[5,4-d][1,3]thiazol-2-ylcarbamate (4.84 g) of Example 61 (61c).

(61e)

(4S,8S)-10-[5-(4-fluorophenyl)-1,2-oxazol-3-yl]-4,7,8,9-tetrahydro-5H-4,8-epiminooxocino[5,4-d][1,3]thiazol-2-amine (4S,8S)-10-[5-(4-fluorophenyl)-1,2-oxazol-3-yl]-4,7,8,9-tetrahydro-5H-4,8-epiminooxocino[5,4-d][1,3]thiazol-2-amine tert-Butyl{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}carbamate (1.2 g) of Example 61 (61d) was dissolved in ethyl acetate (5 mL), a 4 M hydrogen chloride-ethyl acetate solution (20 mL) was added thereto, and the mixture was stirred at 20° C. for 12 hours. A saturated sodium hydrogen carbonate aqueous solution was added to the residues obtained by distilling off the solvent from the reaction mixture under reduced pressure, and the mixture was extracted twice with ethyl acetate. The combined organic layers were washed with a saturated saline solution and dried over anhydrous sodium sulfate. After filtration, the solvent was distilled off under reduced pressure, thereby obtaining 850 mg (yield: 91%) of the title compound as a yellow solid.

(61f)

N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(1s,4s)-4-hydroxycyclohexyl]urea N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(1s,4s)-4-hydroxycyclohexyl]urea 38.8 mg (yield: 46%) of the title compound was obtained as a white solid according to the same method as in Example 5 (5d) using (4S,8S)-10-[5-(4-fluorophenyl)-1,2-oxazol-3-yl]-4,7,8,9-tetrahydro-5H-4,8-epiminooxocino[5,4-d][1,3]thiazol-2-amine (60 mg) of Example 61 (61e) and cis-4-aminocyclohexanol (58 mg).

Example 62

N-{(4S,8S)-10-[5-(6-methoxypyridin-2-yl)-1,2-oxazol-3-yl]-4,7,8,9-tetrahydro-5H-4,8-epiminooxocino[5,4-d][1,3]thiazol-2-yl}-N'-oxan-4-ylurea (62a)

tert-Butyl (4S,8S)-2-{[(oxan-4-yl)carbamoyl]amino}-tetrahydro-5H-4,8-epiminooxocino[5,4-d][1,3]thiazole-10-carboxylate tert-Butyl (4S,8S)-2-{[(oxan-4-yl)carbamoyl]amino}-4,7,8,9-tetrahydro-5H-4,8-epiminooxocino[5,4-d][1,3]thiazole-10-carboxylate tert-Butyl (4S,8S)-2-amino-4,7,8,9-tetrahydro-5H-4,8-epiminooxocino[5,4-d][1,3]thiazole-10-carboxylate (1.34 g) of Example 7 (7a) was dissolved in N,N-dimethylformamide (12 mL), carbonyldiimidazole (1.51 g) was added thereto, and the mixture was stirred for 3 hours. Tetrahydro-2H-pyran-4-amine (CAS Registry number: 38041-19-9) (1.39 mL) was added to the reaction mixture, and the mixture was stirred for 65 hours. The reaction solution was diluted with a 5% saline solution, extracted twice with a mixed solution of ethyl acetate/hexane (=1/1), and extracted with ethyl acetate. The combined organic layers were washed with water and a saturated saline solution and dried over anhydrous sodium sulfate. After filtration, the residues obtained by distilling off the solvent under reduced pressure were purified by NH silica gel column chromatography [eluting solvent:ethyl acetate/hexane=24/76 to 100/0 (V/V)], thereby obtaining 2.01 g (yield: quantitative) of the title compound as a white solid.

(62b)

N-oxan-4-yl-N'-[(4S,8S)-4,7,8,9-tetrahydro-5H-4,8-epiminooxocino[5,4-d][1,3]thiazol-2-yl]urea monohydrochloride N-oxan-4-yl-N'-[(4S,8S)-4,7,8,9-tetrahydro-5H-4,8-epiminooxocino[5,4-d][1,3]thiazol-2-yl]urea-hydrogen chloride (1/1)

tert-Butyl (4S,8S)-2-{[(oxan-4-yl)carbamoyl]amino}-tetrahydro-5H-4,8-epiminooxocino[5,4-d][1,3]thiazole-10-carboxylate (1.91 g) of Example 62 (62a) was dissolved in ethyl acetate (15 mL), a 4 M hydrogen chloride-ethyl acetate solution (15 mL) was added thereto at room temperature, and the mixture was stirred for 18 hours. The reaction mixture was filtered, thereby obtaining 1.68 g (yield: quantitative) of the title compound as a pale yellow solid.

(62c)

N-{(4S,8S)-10-[5-(6-methoxypyridin-2-yl)-1,2-oxazol-3-yl]-4,7,8,9-tetrahydro-5H-4,8-epiminooxocino[5,4-d][1,3]thiazol-2-yl}-N'-oxan-4-ylurea N-{(4S,8S)-10-[5-(6-methoxypyridin-2-yl)-1,2-oxazol-3-yl]-4,7,8,9-tetrahydro-5H-4,8-epiminooxocino[5,4-d][1,3]thiazol-2-yl}-N'-oxan-4-ylurea 6-Methoxy-2-acetylpyridine (CAS Registry number: 21190-93-2) (728 mg) was dissolved in tetrahydrofuran (15 mL) and N,N-dimethylformamide (3 mL), sodium tert-butoxide (926 mg) was added thereto at room temperature, the mixture was stirred for 1 hour, 1,1'-thiocarbonyldiimidazole (858 mg) was added thereto, and the mixture was stirred for 6 hours. N-oxan-4-yl-N'-[(4S,8S)-4,7,8,9-tetrahydro-5H-4,8-epiminooxocino[5,4-d][1,3]thiazol-2-yl]urea monohydrochloride (1.74 g) of Example 62 (62b) was added to the reaction mixture, and the mixture was stirred for 19 hours. The reaction mixture was diluted with ethyl acetate and a 5% saline solution, and the organic layer and the water layer were separated. The organic layer was washed with 1M hydrochloric acid and water. The combined water layers were extracted twice with ethyl acetate, and the combined organic layers were washed with water and a saturated saline solution. The mixture was dried over anhydrous sodium sulfate and filtered, and the solvent was distilled off under reduced pressure to obtain residues.

The residues (1.85 g) were dissolved in acetonitrile (20 mL) and N,N-dimethylformamide (4 mL), sodium carbonate (947 mg) and methyl iodide (0.358 mL) were added thereto, the mixture was stirred at room temperature for 5 hours, sodium carbonate (475 mg) and methyl iodide (0.180 mL) were added thereto, and the mixture was further stirred for 19 hours. The reaction mixture was diluted with ethyl acetate and water, and the organic layer and the water layer were separated. The water layer was extracted twice with ethyl acetate, and the combined organic layers were washed with water and a saturated saline solution. The organic layer was dried over anhydrous sodium sulfate and filtered, and the solvent was distilled off under reduced pressure to obtain residues.

The residues (1.90 g) were dissolved in ethanol (20 mL) and water (4 mL), sodium acetate (1.78 g) and hydroxylamine hydrochloride (1.53 g) were added thereto at room temperature, and the mixture was heated to 80° C. and stirred for 19 hours. The reaction mixture was allowed to be naturally cooled to room temperature, and the solvent was distilled off. Water and ethyl acetate were added to the residues, and the water layer and the organic layer were separated. The water layer was extracted twice with ethyl acetate, and the combined organic layers were washed with water and a saturated saline solution. The organic layer was dried over anhydrous sodium sulfate and filtered, the residues obtained by distilling off the solvent under reduced pressure were purified by NH silica gel column chromatography [eluting solvent:ethyl acetate/hexane/methanol=24/76/0 to 90/0/10 (V/V)], and the fraction containing the title compound was further purified by high performance liquid chromatography [column: YMC-Actus Triart C18 mobile phase: 0.1% formic acid aqueous solution/0.1% formic acid methanol solution=0/50 to 30/70 (V/V)], thereby obtaining 237 mg (yield: 13%) of the title compound as a white solid.

Example 63

N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-(2-hydroxy-2-methylpropyl)urea N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-(2-hydroxy-2-methylpropyl)urea 105 mg (yield: 79%) of the title compound was obtained as a white solid according to the same method as in Example 5 (5d) using (4S,8S)-10-[5-(4-fluorophenyl)-1,2-oxazol-3-yl]-4,7,8,9-tetrahydro-5H-4,8-epiminooxocino[5,4-d][1,3]

thiazol-2-amine (100 mg) of Example 61 (61e) and 1-amino-2-methylpropan-2-ol (100 mg).

Example 64

Methyl 10-[5-(4-fluorophenyl)-1,2-oxazol-3-yl]-2-[(methylcarbamoyl)amino]-4,7,8,9-tetrahydro-4,8-epimino[1,3]thiazolo[5,4-d]azocine-6(5H)-carboxylate (64a)

10-tert-Butyl 6-[2-(trimethylsilyl)ethyl]2-{[(benzyloxy)carbonyl]amino}-4,7,8,9-tetrahydro-4,8-epimino[1,3]thiazolo[5,4-d]azocine-6,10(5H)-dicarboxylate 10-tert-Butyl 6-[2-(trimethylsilyl)ethyl]2-{[(benzyloxy)carbonyl]amino}-4,7,8,9-tetrahydro-4,8-epimino[1,3]thiazolo[5,4-d]azocine-6,10(5H)-dicarboxylate Benzyl chloroformate (2 mL) was added to a mixture of 10-tert-Butyl 6-[2-(trimethylsilyl)ethyl]2-amino-4,7,8,9-tetrahydro-4,8-epimino[1,3]thiazolo[5,4-d]azocine-6,10 (5H)-dicarboxylate (3 g) of Example 24 (24b), triethylamine (3 mL), and dichloromethane (50 mL) at 9° C. to 16° C., and the mixture was stirred at 40° C. for 12 hours. The reaction solution was washed 3 times with water and dried over anhydrous sodium sulfate. After filtration, the residues obtained by distilling off the solvent under reduced pressure were purified by silica gel column chromatography [eluting solvent:petroleum ether/ethyl acetate=5/1 to 3/1 (V/V)], thereby obtaining 3 g (yield: 77%) of the title compound as a yellow solid.

(64b)

Methyl 2-amino-10-[5-(4-fluorophenyl)-1,2-oxazol-3-yl]-4,7,8,9-tetrahydro-4,8-epimino[1,3]thiazolo[5,4-d]azocine-6(5H)-carboxylate Methyl 2-amino-10-[5-(4-fluorophenyl)-1,2-oxazol-3-yl]-4,7,8,9-tetrahydro-4,8-epimino[1,3]thiazolo[5,4-d]azocine-6(5H)-carboxylate A mixture of methyl 2-{[(benzyloxy)carbonyl]amino}-10-[5-(4-fluorophenyl)-1,2-oxazol-3-yl]-4,7,8,9-tetrahydro-4,8-epimino[1,3]thiazolo[5,4-d]azocine-6(5H)-carboxylate (1.5 g) synthesized from 10-tert-butyl 6-[2-(trimethylsilyl)ethyl] 2-{[(benzyloxy)carbonyl]amino}-4,7,8,9-tetrahydro-4,8-epimino[1,3]thiazolo[5,4-d]azocine-6,10(5H)-dicarboxylate of Example 64 (64a) in the same manner as in Examples 24 (24c) and 11 (11b) and trifluoroacetic acid (15 mL) was stirred at 80° C. for 2 hours. The reaction mixture was poured into water, neutralized with sodium carbonate, and extracted 4 times with ethyl acetate. The combined organic layers were washed with a saturated saline solution and dried over anhydrous sodium sulfate. After filtration, the residues obtained by distilling off the solvent under reduced pressure were purified by silica gel column chromatography [eluting solvent:petroleum ether/ethyl acetate/ethanol=12/3/1 to 4/3/1 (V/V)], thereby obtaining 1 g (yield: 88%) of the title compound as a yellow solid.

(64c)

Methyl 10-[5-(4-fluorophenyl)-1,2-oxazol-3-yl]-2-[(methylcarbamoyl)amino]-4,7,8,9-tetrahydro-4,8-epimino[1,3]thiazolo[5,4-d]azocine-6(5H)-carboxylate Methyl 10-[5-(4-fluorophenyl)-1,2-oxazol-3-yl]-2-[(methylcarbamoyl)amino]-4,7,8,9-tetrahydro-4,8-epimino[1,3]thiazolo[5,4-d]azocine-6(5H)-carboxylate 82.7 mg (yield: 73%) of the title compound was obtained as a white solid according to the same method as in Example 6 (6g) using methyl 2-amino-10-[5-(4-fluorophenyl)-1,2-oxazol-3-yl]-4,7,8,9-tetrahydro-4,8-epimino[1,3]thiazolo[5,4-d]azocine-6(5H)-carboxylate (100 mg) of Example 64 (64b).

Example 65

N-{(4S,8S)-10-[5-(4-fluorophenyl)-1,2-oxazol-3-yl]-4,7,8,9-tetrahydro-5H-4,8-epiminooxocino[5,4-d][1,3]thiazolo-2-yl}-N'-[(2R)-2-hydroxypropyl]urea N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(2R)-2-hydroxypropyl]urea 38.3 mg (yield: 50%) of the title compound was obtained as a white solid according to the same method as in Example 5 (5d) using (4S,8S)-10-[5-(4-fluorophenyl)-1,2-oxazol-3-yl]-4,7,8,9-tetrahydro-5H-4,8-epiminooxocino[5,4-d][1,3]thiazol-2-amine (60 mg) of Example 61 (61e) and (R)-1-aminopropan-2-ol (37.7 mg).

Example 66

N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(2R)-1-hydroxypropan-2-yl]urea (66a)

2-(Difluoromethoxy)-6-(1,3-oxazol-5-yl)pyridine 2-(Difluoromethoxy)-6-(1,3-oxazol-5-yl)pyridine 3.6 g (yield: 82%) of the title compound was obtained as a yellow solid according to the same method as in Example 14 (14b) using 6-(difluoromethoxy)pyridine-2-carbaldehyde (International Publication No. WO2013/150416) (3.6 g).

(66b)

2-(2-Chloro-1,3-oxazol-5-yl)-6-(difluoromethoxy)pyridine 2-(2-Chloro-1,3-oxazol-5-yl)-6-(difluoromethoxy)pyridine 3 g (yield: 72%) of the title compound was obtained as a white solid according to the same method as in Example 14 (14c) using 2-(difluoromethoxy)-6-(1,3-oxazol-5-yl)pyridine (3.6 g) of Example 66 (66a).

(66c)

(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-amine (4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-amine 300 mg (yield: 60%) of the title compound was obtained as a brown solid according to the same method as in Example 14 (14d) using (4S,8S)-4,7,8,9-tetrahydro-5H-4,8-epiminooxocino[5,4-d][1,3]thiazol-2-amine dihydrochloride (366 mg) of Example 17 (17c) and 2-(2-chloro-1,3-oxazol-5-yl)-6-(difluoromethoxy)pyridine (300 mg) of Example 66 (66b).

(66d)

N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(2R)-1-hydroxypropan-2-yl]urea N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(2R)-1-hydroxypropan-2-yl]urea 120 mg (yield: 64%) of the title compound was obtained as a white solid according to the same method as in Example 5 (5d) using (4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-amine (150 mg) of Example 66 (66c) and (R)-2-aminopropan-1-ol (60 mg).

Example 67

N-[(2R)-1-hydroxypropan-2-yl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea (67a)

6-Methoxypyridine-2-carbaldehyde

6-Methoxypyridine-2-carbaldehyde

A mixture of (6-methoxypyridin-2-yl)methanol (International Publication No. WO2011/106114) (36 g), manganese dioxide (300 g), and dichloromethane (800 mL) was stirred at room temperature for 48 hours in an oxygen (15 psi) atmosphere. The reaction mixture was filtered, and the filtrate was concentrated under reduced pressure, thereby obtaining 23 g (yield: 65%) of the title compound as a yellow oily material.

(67b)

2-Methoxy-6-(1,3-oxazol-5-yl)pyridine

2-Methoxy-6-(1,3-oxazol-5-yl)pyridine 50 g (yield: 85%) of the title compound was obtained as a white solid according to the same method as in Example 14 (14b) using 6-methoxypyridine-2-carbaldehyde (46 g) of Example 67 (67a).

(67c)

2-(2-Chloro-1,3-oxazol-5-yl)-6-methoxypyridine 2-(2-Chloro-1,3-oxazol-5-yl)-6-methoxypyridine 24.5 g (yield: 82%) of the title compound was obtained as a yellow solid according to the same method as in Example 14 (14c) using 2-methoxy-6-(1,3-oxazol-5-yl)pyridine (25 g) of Example 67 (67b).

(67d)

(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-amine (4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-amine 1.6 g (yield: 91%) of the title compound was obtained as a yellow solid according to the same method in Example 14 (14d) using (4S,8S)-4,7,8,9-tetrahydro-5H-4,8-epiminooxocino[5,4-d][1,3]thiazol-2-amine dihydrochloride (1.5 g) of Example 17 (17c) and 2-(2-chloro-1,3-oxazol-5-yl)-6-methoxypyridine (1 g) of Example 67 (67c).

(67e)

N-[(2R)-1-hydroxypropan-2-yl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea N-[(2R)-1-hydroxypropan-2-yl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea 460 mg (yield: 57%) of the title compound was obtained as a yellow solid according to the same method as in Example 5 (5d) using (4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-amine (600 mg) of Example 67 (67d) and (R)-2-aminopropan-1-ol (150 mg).

Example 68

N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-[(2R)-1-hydroxypropan-2-yl]urea (68a)

6-Ethoxypyridine-2-carbaldehyde

6-Ethoxypyridine-2-carbaldehyde 360 mg (yield: 57%) of the title compound was obtained as a white solid according to the same method as in Example 67 (67a) using (6-ethoxypyridin-2-yl)methanol (International Publication No. WO2012/082689) (640 mg).

(68b)

2-Ethoxy-6-(1,3-oxazol-5-yl)pyridine

2-Ethoxy-6-(1,3-oxazol-5-yl)pyridine 420 mg (yield: 93%) of the title compound was obtained as a yellow oily material according to the same method as in Example 14 (14b) using 6-ethoxypyridine-2-carbaldehyde (360 mg) of Example 68 (68a).

(68c)

2-(2-Chloro-1,3-oxazol-5-yl)-6-ethoxypyridine 2-(2-Chloro-1,3-oxazol-5-yl)-6-ethoxypyridine 240 mg (yield: 48%) of the title compound was obtained as a white solid according to the same method as in Example 14 (14c) using 2-ethoxy-6-(1,3-oxazol-5-yl)pyridine (420 mg) of Example 68 (68b).

(68d)

(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-amine (4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-amine 110 mg (yield: 27%) of the title compound was obtained as a yellow solid according to the same method as in Example 14 (14d) using (4S,8S)-4,7,8,9-tetrahydro-5H-4,8-epiminooxocino[5,4-d][1,3]thiazol-2-amine dihydrochloride (430 mg) of Example 17 (17c) and 2-(2-chloro-1,3-oxazol-5-yl)-6-ethoxypyridine (240 mg) of Example 68 (68c).

(68e)

N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-[(2R)-1-hydroxypropan-2-yl]urea N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-[(2R)-1-hydroxypropan-2-yl]urea 31.8 mg (yield: 23%) of the title compound was obtained as a pale gray solid according to the same method as in Example 5 (5d) using (4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-amine (110 mg) of Example 68 (68d) and (R)-2-aminopropan-1-ol (42.6 mg).

Example 69

N-[(4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-yl]-N'-(1-hydroxy-2-methylpropan-2-yl)urea (69a)

(4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-amine (4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-amine 850 mg (yield: 45%) of the title compound was obtained as a brown solid according to the same method as in Example 14 (14d) using (4S,8S)-4,7,8,9-tetrahydro-5H-4,8-epiminooxocino[5,4-d][1,3]thiazol-2-amine (990 mg) of Example 43 (43a) and 2-chloro-5-[3-(difluoromethyl)phenyl]-1,3-oxazole (1.10 g) of Example 14 (14c).

(69b)

N-[(4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-yl]-N'-(1-hydroxy-2-methylpropan-2-yl)urea N-[(4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-yl]-N'-(1-hydroxy-2-methylpropan-2-yl)urea 38 mg (yield: 21%) of the title compound was obtained as a pale yellow solid according to the same method as in Example 5 (5d) using (4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-amine (142 mg) of Example 69 (69a) and 2-amino-2-methylpropan-1-ol (0.1 mL).

Example 70

N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-[(2R)-1-hydroxypropan-2-yl]urea N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-[(2R)-1-hydroxypropan-2-yl]urea 80 mg (yield: 64%) of the title compound was obtained as a yellow solid according to the same method as in Example 5 (5d) using (4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-amine (100 mg) synthesized from 3-(difluoromethoxy) benzaldehyde (CAS Registry number: 85684-61-3) in the same manner as in Examples 14 (14b), 14 (14c), and 69 (69a) and (R)-2-aminopropan-1-ol (60 mg).

Example 71

N-[(4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-yl]-N'-[(2R)-1-hydroxypropan-2-yl]urea N-[(4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-yl]-N'-[(2R)-1-hydroxypropan-2-yl]urea 322 mg (yield: 60 mg) of the title compound was obtained as a pale yellow solid according to the same method as in Example 5 (5d) using (4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-amine (425 mg) of Example 69 (69a) and (R)-(−)-2-aminopropan-1-ol (0.32 mL).

Example 72

N-[(4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-yl]-N'-[(2R)-2-hydroxypropyl]urea N-[(4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-yl]-N'-[(2R)-2-hydroxypropyl]urea 94 mg (yield: 53%) of the title compound was obtained as a pale yellow solid according to the same method as in Example 5 (5d) using (4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-amine (142 mg) of Example 69 (69a) and (R)-(−)-1-aminopropan-2-ol (0.1 mL).

Example 73

N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-[(3R)-oxolan-3-yl]urea N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-[(3R)-oxolan-3-yl]urea 52 mg (yield: 41%) of the title compound was obtained as a yellow solid according to the same method as in Example 5 (5d) using (4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-amine (100 mg) synthesized from 3-(difluoromethoxy)benzaldehyde (CAS Registry number: 85684-61-3) in the same manner as in Examples 14 (14b), 14 (14c), and 69 (69a) and (R)-tetrahydrofuran-3-amine (60 mg).

Example 74

N-[(2R)-1-hydroxypropan-2-yl]-N'-{5-[5-(methanesulfonyl)-1,3-benzoxazol-2-yl]-6,6-dimethyl-4,5,6,7-tetrahydro[1,3]thiazolo[5,4-c]pyridin-2-yl}urea (74a)

tert-Butyl 2-amino-6,6-dimethyl-6,7-dihydro[1,3]thiazolo[5,4-c]pyridine-5(4H)-carboxylate tert-Butyl 2-amino-6,6-dimethyl-6,7-dihydro[1,3]thiazolo[5,4-c]pyridine-5(4H)-carboxylate tert-Butyl 2,2-dimethyl-4-oxopiperidine-1-carboxylate (3.50 g) was dissolved in toluene (70 mL), pyrrolidine (1.91 mL) and a tosylic acid monohydrate (0.146 g) were added thereto, and the mixture was stirred at 120° C. for 2 hours. The reaction solution was concentrated, the obtained residues were dissolved in methanol (70 mL), sulfur (0.494 g) and cyanamide (0.647 g) were added thereto, and the mixture was allowed to stand at room temperature overnight. The residues obtained by distilling off the solvent under reduced pressure were purified by silica gel column chromatography [eluting solvent:n-hexane/ethyl acetate=7/3 to 2/8 (V/V)], thereby obtaining 3.5 g (yield: 80%) of the title compound as a yellow solid.

(74b)

6,6-Dimethyl-4,5,6,7-tetrahydro[1,3]thiazolo[5,4-c]pyridin-2-amine dihydrochloride 6,6-Dimethyl-4,5,6,7-tetrahydro[1,3]thiazolo[5,4-c]pyridin-2-amine-hydrogen chloride (1/2)

tert-Butyl 2-amino-6,6-dimethyl-6,7-dihydro[1,3]thiazolo[5,4-c]pyridine-5 (4H)-carboxylate (3.5 g) of Example 74 (74a) was dissolved in ethanol (35 mL), a 4 M hydrogen chloride-1,4-dioxane solution (35 mL) was added thereto, the mixture was stirred at room temperature for 2 hours, and toluene was added thereto for concentration. The obtained residues were subjected to azeotropy with toluene, and the obtained residues were collected by filtration and washed with ethyl acetate, thereby obtaining 3.1 g (yield: 98%) of the title compound as a yellow solid.

(74c)

5-(Methanesulfonyl)-1,3-benzoxazole-2-thiol 5-(Methanesulfonyl)-1,3-benzoxazole-2-thiol 2-Amino-4-(methanesulfonyl)phenol (CAS registry number: 98-30-6) (1.99 g) and potassium O-ethyl carbonodithioate (CAS registry number: 140-89-6) (3.43 g) were suspended in ethanol (25 mL), and heated and refluxed for 9 hours. The mixture was allowed to be naturally cooled, water (50 mL) was added to the reaction solution, acetic acid was added dropwise thereto until the pH thereof reached approximately 4, dichloromethane was added thereto, the mixture was stirred, and the organic layer was separated by a phase separator (Biotage Japan Ltd.), concentrated under reduced pressure, and dried, thereby obtaining 2.16 g (yield: 88%) of the title compound as a gray solid.

(74d)

2-Chloro-5-(methanesulfonyl)-1,3-benzoxazole

2-Chloro-5-(methanesulfonyl)-1,3-benzoxazole

N,N-dimethylformamide (0.575 mL) was added to a suspension of 5-(methanesulfonyl)-1,3-benzoxazole-2-thiol (1.14 g) in thionyl chloride (25 mL) of Example 74 (74c), and the mixture was stirred at 80° C. for 5 hours. The reaction solution was cooled to room temperature, concentrated under reduced pressure, and subjected to azeotropy twice with toluene, thereby obtaining 1.33 g (yield: quantitative) of the title compound as a brown solid.

(74e)

5-[5-(Methanesulfonyl)-1,3-benzoxazol-2-yl]-6,6-dimethyl-4,5,6,7-tetrahydro[1,3]thiazolo[5,4-c]pyridin-2-amine 5-[5-(Methanesulfonyl)-1,3-benzoxazol-2-yl]-6,6-dimethyl-4,5,6,7-tetrahydro[1,3]thiazolo[5,4-c]pyridin-2-amine 160 mg (yield: 14%) of the title compound was obtained as a light yellow solid according to the same method as in Example 44 (44c) using 6,6-dimethyl-4,5,6,7-tetrahydro[1,3]thiazolo[5,4-c]pyridin-2-amine dihydrochloride (798 mg) of Example 74 (74b) and 2-chloro-5-(methanesulfonyl)-1,3-benzoxazole (784 mg) of Example 74 (74d).

(74f)

N-[(2R)-1-hydroxypropan-2-yl]-N'-{5-[5-(methanesulfonyl)-1,3-benzoxazol-2-yl]-6,6-dimethyl-4,5,6,7-tetrahydro[1,3]thiazolo[5,4-c]pyridin-2-yl}urea N-[(2R)-1-hydroxypropan-2-yl]-N'-{5-[5-(methanesulfonyl)-1,3-benzoxazol-2-yl]-6,6-dimethyl-4,5,6,7-tetrahydro[1,3]thiazolo[5,4-c]pyridin-2-yl}urea 46 mg (yield: 45%) of the title compound was obtained as a light yellow solid according to the same method as in Example 5 (5d) using 5-[5-(methanesulfonyl)-1,3-benzoxazol-2-yl]-6,6-dimethyl-4,5,6,7-tetrahydro[1,3]thiazolo[5,4-c]pyridin-2-amine (80 mg) of Example 74 (74e) and (R)-2-aminopropan-1-ol (0.070 mL).

Example 75

N-(2-hydroxy-2-methylpropyl)-N'-{5-[5-(methanesulfonyl)-1,3-benzoxazol-2-yl]-6,6-dimethyl-4,5,6,7-tetrahydro[1,3]thiazolo[5,4-c]pyridin-2-yl}urea N-(2-hydroxy-2-methylpropyl)-N'-{5-[5-(methanesulfonyl)-1,3-benzoxazol-2-yl]-6,6-dimethyl-4,5,6,7-tetrahydro[1,3]thiazolo[5,4-c]pyridin-2-yl}urea 62 mg (yield: 59%) of the title compound was obtained as a light yellow solid according to the same method as in Example 5 (5d) using 5-[5-(methanesulfonyl)-1,3-benzoxazol-2-yl]-6,6-dimethyl-4,5,6,7-tetrahydro[1,3]thiazolo[5,4-c]pyridin-2-amine (80 mg) of Example 74 (74e) and 1-amino-2-methylpropan-2-ol (0.090 mL).

Example 76

N-[(2R)-1-hydroxypropan-2-yl]-N'-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]urea N-[(2R)-1-hydroxypropan-2-yl]-N'-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]urea 61.8 mg (yield: 36%) of the title compound was obtained as a grayish white solid according to the same method as in Example 5 (5d) using (4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-amine (133 mg) of Example 60 (60c) and (R)-2-aminopropan-1-ol (87 mg).

Example 77

N-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]-N'-[(3R)-oxolan-3-yl]urea N-[(4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-yl]-N'-[(3R)-oxolan-3-yl]urea 117 mg (yield: 66%) of the title compound was obtained as a grayish white solid according to the same method as in Example 5 (5d) using (4S,8S)-10-{5-[($^2$H$_3$)methyloxy]-1,3-benzoxazol-2-yl}-4,7,8,9-tetrahydro-5H-4,8-epiminooxocino[5,4-d][1,3]thiazol-2-amine (133 mg) of Example 60 (60c) and (R)-3-aminotetrahydrofuran (133 mg).

Example 78

N-[(1r,3S)-3-hydroxycyclobutyl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea N-[(1r,3S)-3-hydroxycyclobutyl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea 177 mg (yield: 83%) of the title compound was obtained as a grayish white solid according to the same method as in Example 5 (5d) using (4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-amine (160 mg) of Example 67 (67d) and trans-3-aminocyclobutan-1-ol hydrochloride (220 mg).

Example 79

N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-(2-hydroxy-2-methylpropyl)urea N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-(2-hydroxy-2-methylpropyl)urea 7 mg (yield: 50%) of the title compound was obtained as a pale gray solid according to the same method as in Example 5 (5d) using (4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-amine (161 mg) of Example 68 (68d) and 1-amino-2-methylpropan-2-ol (150 mg).

Example 80

N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-[(1r,3S)-3-hydroxycyclobutyl]urea N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-[(1r,3S)-3-hydroxycyclobutyl]urea 113 mg (yield: 54%) of the title compound was obtained as a pale gray solid according to the same method as in Example 5 (5d) using (4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-amine (160 mg) of Example 68 (68d) and trans-3-aminocyclobutan-1-ol hydrochloride (210 mg).

The chemical structures and the device data of the compounds of Examples 1-80 are listed in Tables 2-1 to 2-32.

Example 81-193

The compounds of Examples 81 to 193 were synthesized according to the typical production methods described above and Examples 1 to 80. The names of the synthesized compounds are described below. Further, the structures of the synthesized compounds are listed in Tables 3-1 to 3-24.

Example 81

N-{10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-[(2S)-2-hydroxypropyl]urea

Example 82

N-{10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-[(2R)-2-hydroxypropyl]urea

Example 83

N-{10-[3-(4-fluoro-3-methoxyphenyl)-1,2,4-oxadiazol-5-yl]-4,7,8,9-tetrahydro-5H-4,8-epiminooxocino[5,4-d][1,3]thiazol-2-yl}-N'-[(2R)-1-hydroxypropan-2-yl]urea

Example 84

N-{10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-[(1r,3r)-3-(hydroxymethyl)cyclobutyl]urea

Example 85

N-{10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-[(1s,3s)-3-hydroxycyclobutyl]urea

Example 86

N-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-[(1r,3S)-3-hydroxycyclobutyl]urea

Example 87

N-{5-[3-(3,3-difluorocyclohexyl)-1,2,4-oxadiazol-5-yl]-4,5,6,7-tetrahydro[1,3]thiazolo[5,4-c]pyridin-2-yl}-N'-[(2R)-1-hydroxypropan-2-yl]urea

Example 88

N-{5-[3-(4,4-difluorocyclohexyl)-1,2,4-oxadiazol-5-yl]-4,5,6,7-tetrahydro[1,3]thiazolo[5,4-c]pyridin-2-yl}-N'-(2-hydroxy-2-methylpropyl)urea

Example 89

N-[(2R)-1-hydroxypropan-2-yl]-N'-(5-{3-[1-(2,2,2-trifluoroethoxy)ethyl]-1,2,4-oxadiazol-5-yl}-4,5,6,7-tetrahydro[1,3]thiazolo[5,4-c]pyridin-2-yl)urea

Example 90

N-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}-N'-(1-hydroxy-2-methylpropan-2-yl)urea

Example 91

N-[(2R)-1-hydroxypropan-2-yl]-N'-(5-{3-[2-(2,2,2-trifluoroethoxy)propan-2-yl]-1,2,4-oxadiazol-5-yl}-4,5,6,7-tetrahydro[1,3]thiazolo[5,4-c]pyridin-2-yl)urea

Example 92

N-(2-hydroxy-2-methylpropyl)-N'-(5-{3-[1-(trifluoromethyl)cyclopropyl]-1,2,4-oxadiazol-5-yl}-4,5,6,7-tetrahydro[1,3]thiazolo[5,4-c]pyridin-2-yl)urea

Example 93

N-{5-[3-(4-fluorobicyclo[2.2.1]heptan-1-yl)-1,2,4-oxadiazol-5-yl]-4,5,6,7-tetrahydro[1,3]thiazolo[5,4-c]pyridin-2-yl}-N'-methylurea

Example 94

N-{5-[3-(3,3-difluorocyclopentyl)-1,2,4-oxadiazol-5-yl]-4,5,6,7-tetrahydro[1,3]thiazolo[5,4-c]pyridin-2-yl}-N'-(2-hydroxy-2-methylpropyl)urea

Example 95

N-{5-[3-(4,4-difluorooxan-2-yl)-1,2,4-oxadiazol-5-yl]-4,5,6,7-tetrahydro[1,3]thiazolo[5,4-c]pyridin-2-yl}-N'-[(3R)-oxolan-3-yl]urea

Example 96

N-(5-{3-[3-(difluoromethyl)bicyclo[1.1.1]pentan-1-yl]-1,2,4-oxadiazol-5-yl}-4,5,6,7-tetrahydro[1,3]thiazolo[5,4-c]pyridin-2-yl)-N'-(2-hydroxy-2-methylpropyl)urea

Example 97

N-[(1r,3r)-3-hydroxycyclobutyl]-N'-(5-{3-[1-(trifluoromethyl)cyclopropyl]-1,2,4-oxadiazol-5-yl}-4,5,6,7-tetrahydro[1,3]thiazolo[5,4-c]pyridin-2-yl)urea

Example 98

N-{5-[3-(4,4-difluorooxan-2-yl)-1,2,4-oxadiazol-5-yl]-4,5,6,7-tetrahydro[1,3]thiazolo[5,4-c]pyridin-2-yl}-N'-(2-methoxyethyl)urea

Example 99

N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(pyrimidin-5-yl)methyl]urea

Example 100

N-{5-[3-(4-fluoro-3-methoxyphenyl)-1,2,4-oxadiazol-5-yl]-4,5,6,7-tetrahydro[1,3]thiazolo[5,4-c]pyridin-2-yl}-N'-[(1-methyl-1H-imidazol-2-yl)methyl]urea

Example 101

N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(2-oxo-1,2-dihydropyridin-4-yl)methyl]urea

Example 102

N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(4H-1,2,4-triazol-3-yl)methyl]urea

Example 103

N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(2-oxo-1,2-dihydropyridin-3-yl)methyl]urea

Example 104

N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1-hydroxycyclopropyl)methyl]urea

Example 105

N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[1-(hydroxymethyl)cyclopropyl]urea

Example 106

N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1-methyl-1H-1,2,4-triazol-3-yl)methyl]urea

Example 107

N-{5-[3-(4-methoxyphenyl)-1,2,4-oxadiazol-5-yl]-4,5,6,7-tetrahydro[1,3]thiazolo[5,4-c]pyridin-2-yl}-N'-oxan-4-ylurea

Example 108

N-{5-[3-(3-methoxyphenyl)-1,2,4-oxadiazol-5-yl]-4,5,6,7-tetrahydro[1,3]thiazolo[5,4-c]pyridin-2-yl}-N'-oxan-4-ylurea

Example 109

N-(10-{5-[3-(difluoromethyl)phenyl]-1,3,4-oxadiazol-2-yl}-4,7,8,9-tetrahydro-5H-4,8-epiminooxocino[5,4-d][1,3]thiazol-2-yl)-N'-methylurea

Example 110

N-methyl-N'-(10-{5-[3-(trifluoromethyl)phenyl]-1,3,4-oxadiazol-2-yl}-4,7,8,9-tetrahydro-5H-4,8-epiminooxocino[5,4-d][1,3]thiazol-2-yl)urea

Example 111

N-{10-[5-(3-tert-butoxyphenyl)-1,3,4-oxadiazol-2-yl]-4,7,8,9-tetrahydro-5H-4,8-epiminooxocino[5,4-d][1,3]thiazol-2-yl}-N'-methylurea

Example 112

N-(10-{3-[3-(cyclopropanecarbonyl)phenyl]-1,2,4-oxadiazol-5-yl}-4,7,8,9-tetrahydro-5H-4,8-epiminooxocino[5,4-d][1,3]thiazol-2-yl)-N'-methylurea

Example 113

N-(10-{5-[3-(cyclobutanecarbonyl)phenyl]-1,3,4-oxadiazol-2-yl}-4,7,8,9-tetrahydro-5H-4,8-epiminooxocino[5,4-d][1,3]thiazol-2-yl)-N'-methylurea

Example 114

N-(10-{5-[3-((cyclopropanecarbonyl)phenyl]-1,3,4-oxadiazol-2-yl}-4,7,8,9-tetrahydro-5H-4,8-epiminooxocino[5,4-d][1,3]thiazol-2-yl)-N'-(2,2,2-trifluoroethyl)urea

Example 115

N-(10-{5-[3-(difluoromethoxy)phenyl]-1,3,4-oxadiazol-2-yl}-4,7,8,9-tetrahydro-5H-4,8-epiminooxocino[5,4-d][1,3]thiazol-2-yl)-N'-[(3S)-oxolan-3-yl]urea

Example 116

N-(10-{5-[3-(cyclopropanecarbonyl)-2-fluorophenyl]-1,3-oxazol-2-yl}-4,7,8,9-tetrahydro-5H-4,8-epiminooxocino[5,4-d][1,3]thiazol-2-yl)-N'-methylurea

Example 117

N-[(4S,8S)-10-{5-[3-(cyclopropanecarbonyl)phenyl]-1,3,4-oxadiazol-2-yl}-4,7,8,9-tetrahydro-5H-4,8-epiminooxocino[5,4-d][1,3]thiazol-2-yl]-N'-propan-2-ylurea

Example 118

N-{(4S,8S)-10-[5-(3-ethylphenyl)-1,3,4-oxadiazol-2-yl]-4,7,8,9-tetrahydro-5H-4,8-epiminooxocino[5,4-d][1,3]thiazol-2-yl}-N'-methylurea

Example 119

N-methyl-N'-[(4S,8S)-10-{5-[3-(propan-2-yl)phenyl]-1,3,4-oxadiazol-2-yl}-4,7,8,9-tetrahydro-5H-4,8-epiminooxocino[5,4-d][1,3]thiazol-2-yl]urea

Example 120

N-{(4S,8S)-10-[5-(3-methoxyphenyl)-1,3,4-oxadiazol-2-yl]-4,7,8,9-tetrahydro-5H-4,8-epiminooxocino[5,4-d][1,3]thiazol-2-yl}-N'-methylurea

Example 121

N-{(4S,8S)-10-[5-(3-ethoxyphenyl)-1,3,4-oxadiazol-2-yl]-4,7,8,9-tetrahydro-5H-4,8-epiminooxocino[5,4-d][1,3]thiazol-2-yl}-N'-methylurea

Example 122

N-methyl-N'-[(4S,8S)-10-(5-{3-[(propan-2-yl)oxy]phenyl}-1,3,4-oxadiazol-2-yl)-4,7,8,9-tetrahydro-5H-4,8-epiminooxocino[5,4-d][1,3]thiazol-2-yl]urea

Example 123

Methyl 10-{5-[3-(cyclopropanecarbonyl)phenyl]-1,3,4-oxadiazol-2-yl}-2-[(methylcarbamoyl)amino]-4,7,8,9-tetrahydro-4,8-epimino[1,3]thiazolo[5,4-d]azocine-6(5H)-carboxylate

Example 124

N-(10-{3-[3-(difluoromethyl)phenyl]-1,2,4-oxadiazol-5-yl}-4,7,8,9-tetrahydro-5H-4,8-epiminooxocino[5,4-d][1,3]thiazol-2-yl)-N'-[(2R)-1-hydroxypropan-2-yl]urea

Example 125

N-[(4R,8R)-10-[3-(4-fluorophenyl)-1,2,4-oxadiazol-5-yl]-6-(2-methylpropanoyl)-4,5,6,7,8,9-hexahydro-4,8-epimino[1,3]thiazolo[5,4-d]azocin-2-yl]-N'-methylurea

Example 126

N-{6-acetyl-10-[5-(6-methoxypyridin-2-yl)-1,3-oxazol-2-yl]-4,5,6,7,8,9-hexahydro-4,8-epimino[1,3]thiazolo[5,4-d]azocin-2-yl}-N'-methylurea

Example 127

N-[(4R,8R)-10-[3-(4-fluorophenyl)-1,2,4-oxadiazol-5-yl]-6-(2-hydroxyethyl)-4,5,6,7,8,9-hexahydro-4,8-epimino[1,3]thiazolo[5,4-d]azocin-2-yl]-N'-methylurea

Example 128

N-(6-acetyl-10-{5-[6-(difluoromethoxy)pyridin-2-yl]-1,3-oxazol-2-yl}-4,5,6,7,8,9-hexahydro-4,8-epimino[1,3]thiazolo[5,4-d]azocin-2-yl)-N'-methylurea

Example 129

N-{6-acetyl-10-[5-(6-methoxypyridin-2-yl)-1,3-oxazol-2-yl]-4,5,6,7,8,9-hexahydro-4,8-epimino[1,3]thiazolo[5,4-d]azocin-2-yl}-N'-methylurea

Example 130

N-[6-acetyl-10-(5-fluoro-1,3-benzoxazol-2-yl)-4,5,6,7,8,9-hexahydro-4,8-epimino[1,3]thiazolo[5,4-d]azocin-2-yl]-N'-methylurea

Example 131

Methyl 10-[3-(3,3-difluorocyclopentyl)-1,2,4-oxadiazol-5-yl]-2-[(methylcarbamoyl)amino]-4,7,8,9-tetrahydro-4,8-epimino[1,3]thiazolo[5,4-d]azocin-6(5H)-carboxylate

Example 132

Methyl 10-[3-(4,4-difluorocyclohexyl)-1,2,4-oxadiazol-5-yl]-2-[(methylcarbamoyl)amino]-4,7,8,9-tetrahydro-4,8-epimino[1,3]thiazolo[5,4-d]azocine-6(5H)-carboxylate

Example 133

Methyl 10-[3-(4-fluorobicyclo[2.2.1]heptan-1-yl)-1,2,4-oxadiazol-5-yl]-2-[(methylcarbamoyl)amino]-4,7,8,9-tetrahydro-4,8-epimino[1,3]thiazolo[5,4-d]azocin-6(5H)-carboxylate

Example 134

Ethyl 2-[(methylcarbamoyl)amino]-10-{3-[1-(trifluoromethyl)cyclopropyl]-1,2,4-oxadiazol-5-yl}-4,7,8,9-tetrahydro-4,8-epimino[1,3]thiazolo[5,4-d]azocine-6(5H)-carboxylate

Example 135

Methyl 10-{3-[3-(difluoromethyl)bicyclo[1.1.1]pentan-1-yl]-1,2,4-oxadiazol-5-yl}-2-[(methylcarbamoyl)amino]-4,7,8,9-tetrahydro-4,8-epimino[1,3]thiazolo[5,4-d]azocine-6(5H)-carboxylate

Example 136

N-{6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-ethylurea

Example 137

N-{6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-propan-2-ylurea

Example 138

N-{6-acetyl-10-[3-(3-fluorophenyl)-1,2,4-oxadiazol-5-yl]-4,5,6,7,8,9-hexahydro-4,8-epimino[1,3]thiazolo[5,4-d]azocin-2-yl}-N'-methylurea

Example 139

N-{6-acetyl-10-[5-(3-chlorophenyl)-1,3-oxazol-2-yl]-4,5,6,7,8,9-hexahydro-4,8-epimino[1,3]thiazolo[5,4-d]azocin-2-yl}-N'-methylurea

Example 140

N-{6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-[(3R)-oxolan-3-yl]urea

Example 141

Methyl 10-(5-methoxy-1,3-benzoxazol-2-yl)-2-[(methylcarbamoyl)amino]-4,7,8,9-tetrahydro-4,8-epimino[1,3]thiazolo[5,4-d]azocine-6(5H)-carboxylate (Example 142)

Methyl 10-[3-(5-fluoropyridin-2-yl)-1,2,4-oxadiazol-5-yl]-2-[(methylcarbamoyl)amino]-4,7,8,9-tetrahydro-4,8-epimino[1,3]thiazolo[5,4-d]azocine-6(5H)-carboxylate

Example 143

Propan-2-yl-10-[3-(4-fluorophenyl)-1,2,4-oxadiazol-5-yl]-2-{[(oxan-4-yl)carbamoyl]amino}-4,7,8,9-tetrahydro-4,8-epimino[1,3]thiazolo[5,4-d]azocine-6(5H)-carboxylate

Example 144

N-(2-hydroxy-2-methylpropyl)-N'-{(4S,8S)-10-[5-(trifluoromethyl)-1,3-benzoxazol-2-yl]-4,7,8,9-tetrahydro-5H-4,8-epiminooxocino[5,4-d][1,3]thiazol-2-yl}urea

Example 145

N-(2-hydroxy-2-methylpropyl)-N'-[(4S,8S)-10-(5-methyl-1,3-benzoxazol-2-yl)-4,7,8,9-tetrahydro-5H-4,8-epiminooxocino[5,4-d][1,3]thiazol-2-yl]urea

Example 146

N-[(4S,8S)-10-(5,6-difluoro-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea

Example 147

N-[(4S,8S)-10-(5,7-difluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea

Example 148

N-[(4S,8S)-10-(5,6-dimethyl-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea

Example 149

N-[(4S,8S)-10-(5-chloro-1,3-benzoxazol-2-yl)-4,7,8,9-tetrahydro-5H-4,8-epiminooxocino[5,4-d][1,3]thiazol-2-yl]-N'-[(1r,4r)-4-hydroxycyclohexyl]urea

Example 150

N-[(4S,8S)-10-(5-chloro-1,3-benzoxazol-2-yl)-4,7,8,9-tetrahydro-5H-4,8-epiminooxocino[5,4-d][1,3]thiazol-2-yl]-N'-[(4-hydroxyoxan-4-yl)methyl]urea

Example 151

N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-[(3S)-oxolan-3-yl]urea

Example 152

N-[(2R)-1-hydroxypropan-2-yl]-N'-{9-[5-(methanesulfonyl)-1,3-benzoxazol-2-yl]-5,6,7,8-tetrahydro-4H-5,8-epiminocyclohepta[d][1,3]thiazol-2-yl}urea

Example 153

N-{5-[5-(4,4-difluorocyclohexyl)-1,2-oxazol-3-yl]-4,5,6,7-tetrahydro[1,3]thiazolo[5,4-c]pyridin-2-yl}-N'-[(2R)-2-hydroxypropyl]urea

Example 154

N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(2R)-1-hydroxypropan-2-yl]urea

Example 155

N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(2R)-1-hydroxypropan-2-yl]urea

Example 156

N-[(4S,8S)-10-{5-[3-(difluoromethyl)phenyl]-1,2-oxazol-3-yl}-4,7,8,9-tetrahydro-5H-4,8-epiminooxocino[5,4-d][1,3]thiazol-2-yl]-N'-[(2R)-1-hydroxypropan-2-yl]urea

Example 157

N-{(4S,8S)-10-[5-(4,4-difluorocyclohexyl)-1,2-oxazol-3-yl]-4,7,8,9-tetrahydro-5H-4,8-epiminooxocino[5,4-d][1,3]thiazol-2-yl}-N'-[(3R)-oxolan-3-yl]urea

Example 158

N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(1s,3R)-3-hydroxycyclobutyl]urea

Example 159

N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(1r,4r)-4-hydroxycyclohexyl]urea

Example 160

N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-(1-hydroxy-2-methylpropan-2-yl)urea

Example 161

N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-oxan-4-ylurea

Example 162

N-{(4S,8S)-10-[5-(6-methoxypyridin-2-yl)-1,2-oxazol-3-yl]-4,7,8,9-tetrahydro-5H-4,8-epiminooxocino[5,4-d][1,3]thiazol-2-yl}-N'-[(3S)-oxolan-3-yl]urea

Example 163

N-{(4S,8S)-10-[5-(6-methoxypyridin-2-yl)-1,2-oxazol-3-yl]-4,7,8,9-tetrahydro-5H-4,8-epiminooxocino[5,4-d][1,3]thiazol-2-yl}-N'-[(3R)-oxolan-3-yl]urea

Example 164

N-{(4S,8S)-10-[5-(3-methoxyphenyl)-1,2-oxazol-3-yl]-4,7,8,9-tetrahydro-5H-4,8-epiminooxocino[5,4-d][1,3]thiazol-2-yl}-N'-[(3R)-oxolan-3-yl]urea

Example 165

N-(1,1-dioxo-1$\lambda^6$-thian-4-yl)-N'-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}urea

Example 166

N-(10-{5-[3-(difluoromethyl)phenyl]-1,3-oxazol-2-yl}-4,7,8,9-tetrahydro-5H-4,8-epiminooxocino[5,4-d][1,3]thiazol-2-yl)-N'-[(1r,3r)-3-hydroxycyclobutyl]urea

Example 167

N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-[(1r,3S)-3-hydroxycyclobutyl]urea

Example 168

N-[(4S,8S)-10-{5-[3-(difluoromethyl)phenyl]-1,3-oxazol-2-yl}-4,7,8,9-tetrahydro-5H-4,8-epiminooxocino[5,4-d][1,3]thiazol-2-yl]-N'-[(2S)-1-hydroxypropan-2-yl]urea

Example 169

N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(2S)-1-hydroxypropan-2-yl]urea

Example 170

N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-(1-hydroxy-2-methylpropan-2-yl)urea

Example 171

N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-[(2R)-2-hydroxypropyl]urea

Example 172

N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-(2-hydroxy-2-methylpropyl)urea

Example 173

N-[(4S,8S)-10-{5-[3-(difluoromethoxy)phenyl]-1,3-oxazol-2-yl}-4,7,8,9-tetrahydro-5H-4,8-epiminooxocino[5,4-d][1,3]thiazol-2-yl]-N'-[(2S)-1-hydroxypropan-2-yl]urea

Example 174

N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(2S)-2-hydroxypropyl]urea

Example 175

N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(3R,4S)-4-hydroxyoxolan-3-yl]urea

Example 176

N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(1r,4r)-4-hydroxycyclohexyl]urea

Example 177

N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(2-hydroxypyridin-4-yl)methyl]urea

Example 178

N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(1-methyl-2-oxo-1,2-dihydropyridin-4-yl)methyl]urea

Example 179

N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(1-hydroxycyclopropyl)methyl]urea

Example 180

N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-(1,1-dioxo-1$\lambda^6$ thian-4-yl)urea

Example 181

N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[1-(hydroxymethyl)cyclopropyl]urea

Example 182

N-[(3R)-1-acetylpyrrolidin-3-yl]-N'-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]urea

Example 183

N-(1-acetylazetidin-3-yl)-N'-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]urea

Example 184

N-(2-hydroxy-2-methylpropyl)-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea

Example 185

N-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}-N'-[(3R)-oxolan-3-yl]urea

Example 186

N-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}-N'-oxan-4-ylurea

Example 187

N-[(1s,4s)-4-hydroxycyclohexyl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea

Example 188

N-[(1r,4r)-4-hydroxycyclohexyl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea

Example 189

N-[(2R)-1-hydroxypropan-2-yl]-N'-[5-(5-methoxy-1,3-benzoxazol-2-yl)-4,5,6,7-tetrahydro[1,3]thiazolo[5,4-c]pyridin-2-yl]urea

Example 190

N-(2-hydroxy-2-methylpropyl)-N'-[5-(5-methoxy-1,3-benzoxazol-2-yl)-6,6-dimethyl-4,5,6,7-tetrahydro[1,3]thiazolo[5,4-c]pyridin-2-yl]urea

Example 191

N-[(2R)-1-hydroxypropan-2-yl]-N'-{5-[4-(oxan-3-yl)pyrimidin-2-yl]-4,5,6,7-tetrahydro[1,3]thiazolo[5,4-c]pyridin-2-yl}urea

Example 192

N-[(1r,3r)-3-hydroxycyclobutyl]-N'-{5-[4-(oxan-3-yl)pyrimidin-2-yl]-4,5,6,7-tetrahydro[1,3]thiazolo[5,4-c]pyridin-2-yl}urea

Example 193

N-[(2R)-1-hydroxypropan-2-yl]-N'-{(4S,8S)-10-[5-(6-methoxy-5-methylpyridin-2-yl)-1,3-oxazol-2-yl]-4,7,8,9-tetrahydro-5H-4,8-epiminooxocino[5,4-d][1,3]thiazol-2-yl}urea Hereinafter, the structural formulae of the compounds described in the examples and the physicochemical data thereof are collectively described.

TABLE 2-1

| No. | Structure | Data |
|---|---|---|
| 1 (1a) | 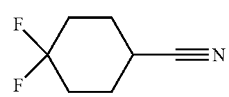 | $^1$H NMR (400 MHz, CDCl$_3$): δ (ppm) = 2.86-2.74 (1H, m), 2.50-1.92 (8H, m). |
| 1 (1c) | 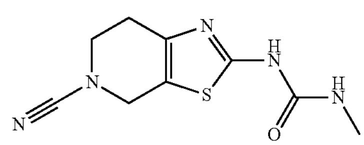 [SMILES: CNC(=O)Nc1nc2c(s1)CN(C#N)CC2] | $^1$H NMR (400 MHz, DMSO-d$_6$): δ (ppm) = 10.43 (1H, br s), 6.43 (1H, br s), 4.37 (2H, s), 3.50 (2H, t, J = 6.0 Hz), 2.71-2.67 (5H, m). |
| 1 (1d) | 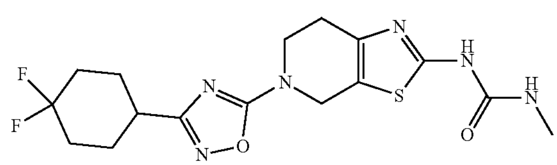 [SMILES: CNC(=O)Nc1nc2c(s1)CN(c1nc(C3CCC(F)(F)CC3)no1)CC2] | $^1$H NMR (500 MHz, DMSO-d$_6$): δ (ppm) = 10.62-10.34 (1H, br s), 6.56-6.35 (1H, m), 4.65 (2H, s), 3.84 (2H, t, J = 5.6 Hz), 2.86-2.75 (1H, m), 2.73-2.63 (5H, m), 2.32-1.86 (6H, m), 1.84-1.61 (2H, m). MS (ESI) m/z: 399 (M + H)$^+$ |
| 2 (2a) | 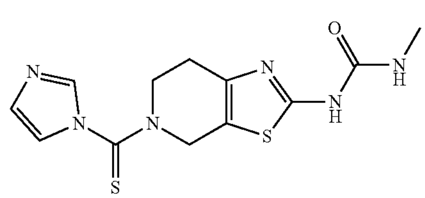 [SMILES: CNC(=O)Nc1nc2c(s1)CN(C(=S)n1ccnc1)CC2] | $^1$H NMR (500 MHz, DMSO-d$_6$): δ (ppm) = 10.53 (1H, br s), 8.10 (1H, br s), 7.57 (1H, s), 7.06 (1H, br s), 6.59 (1H, br s), 4.97 (2H, br s), 4.27 (1H, br s), 3.86 (1H, br s), 2.89-2.84 (2H, m), 2.67 (3H, d, J = 4.9 Hz). MS (APCI) m/z: 323 (M + H)$^+$ |
| 2 (2b) | 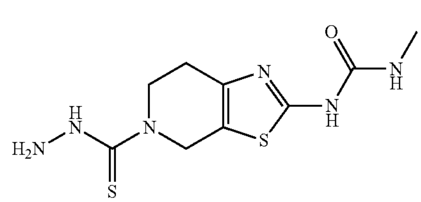 [SMILES: CNC(=O)Nc1nc2c(s1)CN(C(=S)NN)CC2] | $^1$H NMR (500 MHz, DMSO-d$_6$): δ (ppm) = 9.25 (1H, br s), 7.07 (1H, br s), 6.45 (1H, br s), 4.81 (2H, br s), 4.03 (2H, t, J = 5.6 Hz), 2.67 (3H, d, J = 4.9 Hz), 2.64-2.59 (2H, m). MS (APCI) m/z: 287 (M + H)$^+$ |

TABLE 2-1-continued

| No. | Structure | Data |
|---|---|---|
| 2 (2c) | 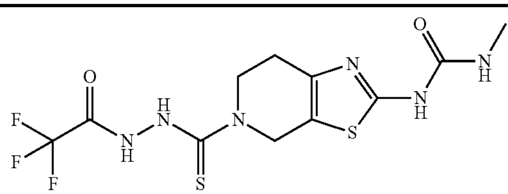 | ¹H NMR (500 MHz, DMSO-d₆): δ (ppm) = 11.56 (1H, s), 10.40 (1H, s), 10.02 (1H, s), 6.42 (1H, s), 4.94 (2H, s), 4.13 (2H, t, J = 5.4 Hz), 2.71-2.65 (5H, m). MS (APCI) m/z: 383 (M + H)⁺ |
| 2 (2d) | 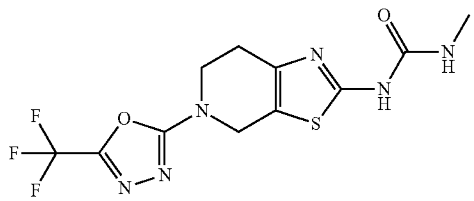 [SMILES: CNC(=O)Nc1nc2c(s1)CN(c1nnc(C(F)(F)F)o1)CC2] | ¹H NMR (500 MHz, DMSO-d₆): δ (ppm) = 10.42 (1H, s), 6.41 (1H, s), 4.66 (2H, s), 3.85 (2H, t, J = 5.7 Hz), 2.75 (2H, t, J = 5.7 Hz), 2.68 (3H, d, J = 4.4 Hz). MS (APCI) m/z: 349 (M + H)⁺ |

TABLE 2-2

| No. | Structure | Data |
|---|---|---|
| 3 (3a) | 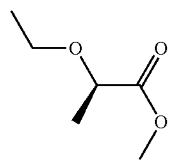 | ¹H NMR (400 MHz, CDCl₃): δ (ppm) = 3.94-3.88 (1H, m), 3.68 (3H, s), 3.56-3.52 (1H, m), 3.40-3.36 (1H, m), 1.33 (3H, d, J = 7.6 Hz), 1.16 (3H, t, J = 7.2 Hz). |
| 3 (3b) | 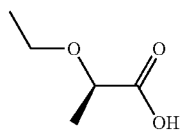 | ¹H NMR (400 MHz, CDCl₃): δ (ppm) = 10.13 (1H, br s), 4.04-3.99 (1H, m), 3.69-3.62 (1H, m), 3.57-3.49 (1H, m), 1.46 (3H, d, J = 7.2 Hz), 1.25 (3H, t, J = 7.2 Hz). |
| 3 (3c) | 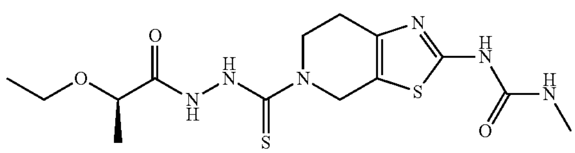 [SMILES: CCO[C@H](C)C(=O)NNC(=S)N1CCc2nc(NC(=O)NC)sc2C1] | MS (ESI) m/z: 387 (M + H)⁺ |
| 3 (3d) | 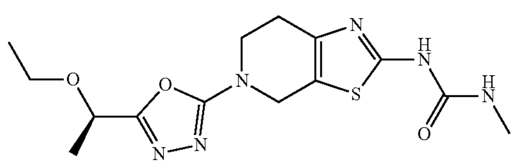 [SMILES: CCO[C@H](C)c1nnc(N2CCc3nc(NC(=O)NC)sc3C2)o1] | ¹H NMR (400 MHz, DMSO-d₆): δ (ppm) = 6.87 (1H, br s), 4.61-4.55 (3H, m), 3.76 (2H, t, J = 6.0 Hz), 3.47-3.42 (2H, m), 2.71-2.66 (5H, m), 1.44 (3H, d, J = 6.8 Hz), 1.09 (3H, t, J = 7.2 Hz). MS (ESI) m/z: 353 (M + H)⁺. |
| 4 (4a) | 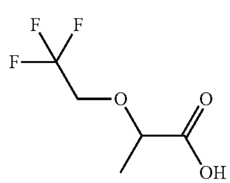 | ¹H NMR (400 MHz, DMSO-d₆): δ (ppm) = 12.85 (1H, br s), 4.22-4.04 (3H, m), 1.33 (3H, d, J = 6.8 Hz). |
| 4 (4b) | 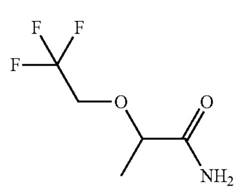 | ¹H NMR (400 MHz, DMSO-d₆): δ (ppm) = 7.25 (2H, d, J = 16.8 Hz), 4.14-3.93 (3H, m), 1.28 (3H, d, J = 6.8 Hz). |

TABLE 2-2-continued

| 4 (4c) | 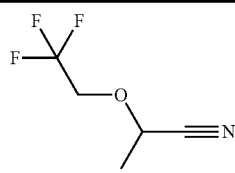 | $^1$H NMR (400 MHz, CDCl$_3$): δ (ppm) = 4.82-4.77 (1H, m), 4.32-4.21 (2H, m), 1.52 (3H, d, J = 6.8 Hz). |
| --- | --- | --- |
| 4 (4d) | 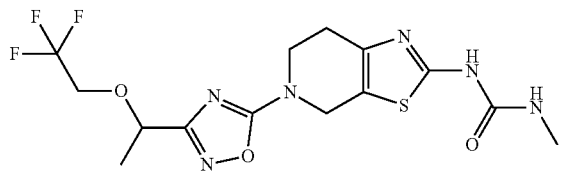 [SMILES: CNC(=O)Nc1nc2c(s1)CN(c1nc(C(C)OCC(F)(F)F)no1)CC2] | $^1$H NMR (400 MHz, DMSO-d$_6$): δ (ppm) = 10.45 (1H, br s), 6.48-6.40 (1H, m), 4.72-4.63 (3H, m), 4.15-4.02 (2H, m), 3.88 (2H, t, J = 5.6 Hz), 2.73 (2H, t, J = 5.6 Hz), 2.68 (3H, d, J = 4.4 Hz), 1.46 (3H, d, J = 6.8 Hz). MS (ESI) m/z: 407 (M + H)$^+$ |

TABLE 2-3

| 5 (5a) | 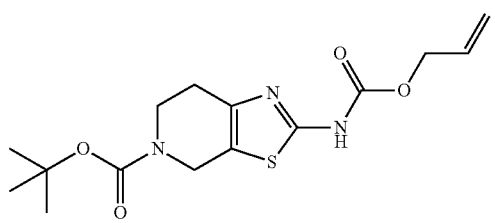 [SMILES: C=CCOC(=O)Nc1nc2c(s1)CN(C(=O)OC(C)(C)C)CC2] | $^1$H NMR (400 MHz, DMSO-d$_6$): δ (ppm) = 11.70 (1H, br s), 6.02-5.90 (1H, m), 5.41-5.32 (1H, m), 5.28-5.23 (1H, m), 4.67 (2H, d, J = 5.6 Hz), 4.46 (2H, s), 3.62 (2H, t, J = 5.6 Hz), 2.59 (2H, t, J = 5.6 Hz), 1.42 (9H, s). |
| --- | --- | --- |
| 5 (5b) | 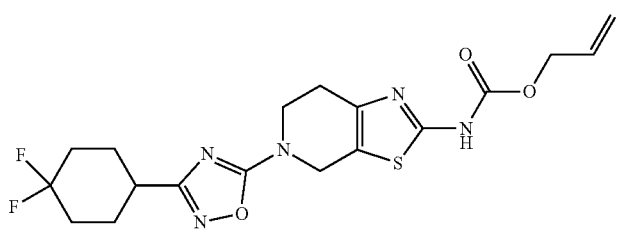 [SMILES: C=CCOC(=O)Nc1nc2c(s1)CN(c1nc(C3CCC(F)(F)CC3)no1)CC2] | $^1$H NMR (400 MHz, DMSO-d$_6$): δ (ppm) = 11.76 (1H, br s), 6.03-5.90 (1H, m), 5.37 (1H, dd, J = 17.2, 1.6 Hz), 5.31-5.19 (1H, m), 4.74-4.63 (4H, m), 3.86 (2H, t, J = 5.6 Hz), 2.87-2.69 (3H, m), 2.10-1.87 (6H, m), 1.77-1.61 (2H, m). MS (ESI) m/z: 426 (M + H)$^+$ |
| 5 (5c) | 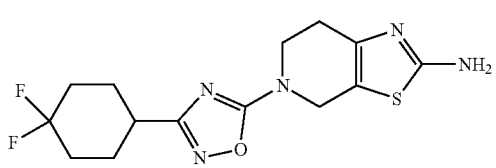 [SMILES: Nc1nc2c(s1)CN(c1nc(C3CCC(F)(F)CC3)no1)CC2] | $^1$H NMR (400 MHz, DMSO-d$_6$): δ (ppm) = 6.90 (2H, s), 4.53 (2H, s), 3.81 (2H, t, J = 5.6 Hz), 2.87-2.74 (1H, m), 2.62-2.55 (2H, m), 2.31-1.85 (6H, m), 1.81-1.62 (2H, m). MS (APCI) m/z: 342 (M + H)$^+$ |
| 5 (5d) | 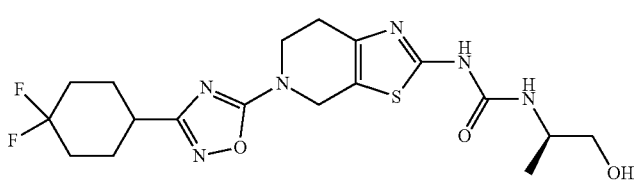 [SMILES: C[C@H](CO)NC(=O)Nc1nc2c(s1)CN(c1nc(C3CCC(F)(F)CC3)no1)CC2] | $^1$H NMR (400 MHz, DMSO-d$_6$): δ (ppm) = 10.21 (1H, br s), 6.57 (1H, d, J = 8.0 Hz), 4.88-4.84 (1H, m), 4.65 (2H, s), 3.84 (2H, t, J = 6.0 Hz), 3.75-3.63 (1H, m), 3.36 (2H, t, J = 4.4 Hz), 2.85-2.77 (1H, m), 2.73-2.68 (2H, m), 2.11-1.85 (6H, m), 1.77-1.64 (2H, m), 1.08 (3H, d, J = 6.6 Hz). MS (APCI) m/z: 443 (M + H)$^+$ |
| 6 (6a) | 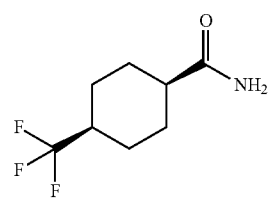 [SMILES: NC(=O)[C@H]1CC[C@@H](C(F)(F)F)CC1] | MS (APCI/ESI) m/z: 196 (M + H)$^+$ |

TABLE 2-3-continued

| 6 (6b) | 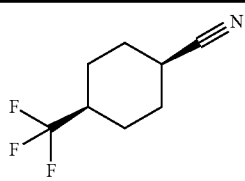 | ¹H NMR (500 MHz, CDCl₃): δ (ppm) = 2.98-2.94 (1H, m), 2.12-2.06 (2H, m), 2.06-1.96 (1H, m), 1.96-1.90 (2H, m), 1.74-1.65 (2H, m), 1.60-1.52 (2H, m). |
|---|---|---|
| 6 (6c) | 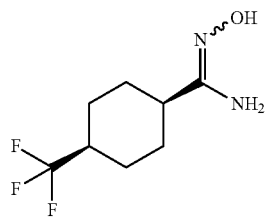 [SMILES: NC(=NO)[C@H]1CC[C@@H](C(F)(F)F)CC1] | ¹H NMR (500 MHz, CDCl₃): δ (ppm) = 6.43 (1H, br s), 4.46 (2H, br s), 2.41-2.37 (1H, m), 2.15-2.05 (1H, m), 1.97-1.90 (2H, m), 1.84-1.76 (2H, m), 1.70-1.63 (2H, m), 1.63-1.56 (2H, m). |

TABLE 2-4

| 6 (6d) | 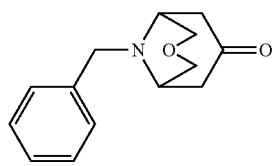 [SMILES: O=C1CC2COCC(C1)N2Cc1ccccc1] | ¹H NMR (400 MHz, CDCl₃): δ (ppm) = 7.50-7.30 (5H, m), 4.00-3.79 (4H, m), 3.78-3.64 (2H, m), 3.19 (2H, d, J = 4.8 Hz), 2.77 (2H, dd, J = 15.2, 4.8 Hz), 2.42-2.26 (2H, m). MS (ESI) m/z: 232 (M + H)⁺ |
|---|---|---|
| 6 (6e) | 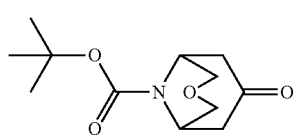 [SMILES: CC(C)(C)OC(=O)N1C2COCC1CC(=O)C2] | ¹H NMR (400 MHz, CDCl₃): δ (ppm) = 4.54-4.35 (2H, m), 3.89-3.61 (4H, m), 2.75-2.39 (4H, m), 1.57-1.46 (9H, m). |
| 6 (6f) | 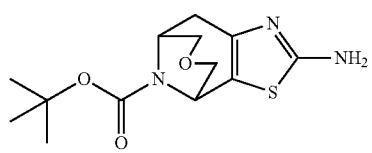 [SMILES: CC(C)(C)OC(=O)N1C2COCC1c1sc(N)nc1C2] | ¹H NMR (400 MHz, CDCl₃): δ (ppm) = 5.11-4.86 (3H, m), 4.42-4.20 (1H, m), 3.95-3.77 (2H, m), 3.76-3.57 (2H, m), 3.22-3.02 (1H, m), 2.64 (1H, dd, J = 17.2, 5.6 Hz), 1.46 (9H, d, J = 6.0 Hz). MS (ESI) m/z: 298 (M + H)⁺ |
| 6 (6g) | 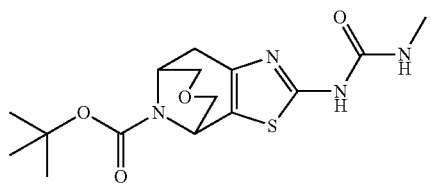 [SMILES: CNC(=O)Nc1nc2c(s1)C1COCC(C2)N1C(=O)OC(C)(C)C] | ¹H NMR (400 MHz, CDCl₃): δ (ppm) = 10.47 (1H, br s), 5.20-4.95 (1H, m), 4.47-4.25 (1H, m), 3.97-3.70 (3H, m), 3.68-3.57 (1H, m), 3.33-3.07 (1H, m), 2.92 (3H, d, J = 4.8 Hz), 2.79-2.67 (1H, m), 1.52-1.37 (9H, m). MS (ESI) m/z: 355 (M + H)⁺ |
| 6 (6h) | 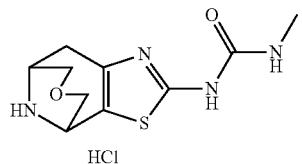 | ¹H NMR (400 MHz, DMSO-d₆): δ (ppm) = 10.63 (1H, d, J = 10.0 Hz), 9.57 (1H, d, J = 10.0 Hz), 6.95 (1H, br s), 6.48 (1H, br s), 4.80 (1H, s), 4.09-3.88 (3H, m), 3.82 (1H, d, J = 6.4 Hz), 3.59 (1H, d, J = 12.0 Hz), 3.22-3.09 (1H, m), 2.86 (1H, d, J = 17.6 Hz), 2.68 (3H, s). MS (ESI) m/z: 255 (M + H)⁺ |
| 6 (6i) | 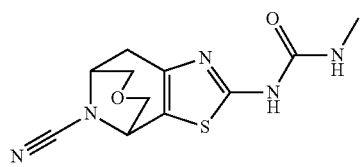 [SMILES: CNC(=O)Nc1nc2c(s1)C1COCC(C2)N1C#N] | ¹H NMR (500 MHz, DMSO-d₆): δ (ppm) = 10.43 (1H, s), 6.39 (1H, br s), 4.73 (1H, s), 3.84-3.81 (2H, m), 3.79-3.76 (1H, m), 3.75-3.72 (1H, m), 3.49-3.45 (1H, m), 3.10 (1H, dd, J = 17.6, 7.3 Hz), 2.69 (1H, d, J = 17.6 Hz), 2.65 (3H, d, J = 4.4 Hz). MS (APCI/ESI) m/z: 280 (M + H)⁺ |

TABLE 2-4-continued

| 6 (6j) | 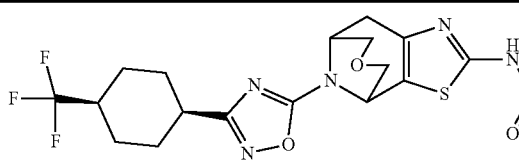 | ¹H NMR (500 MHz, DMSO-d₆): δ (ppm) = 10.36 (1H, s), 6.36 (1H, br s), 5.18 (1H, s), 4.30 (1H, d, J = 6.3 Hz), 3.90 (1H, d, J = 11.7 Hz), 3.82-3.78 (1H, m), 3.76-3.73 (1H, m), 3.57-3.54 (1H, m), 3.04 (1H, dd, J = 17.3, 7.1 Hz), 2.96-2.91 (1H, m), 2.70 (1H, d, J = 17.3 Hz), 2.64 (3H, d, J = 4.4 Hz), 2.36-2.26 (1H, m), 2.05-1.97 (2H, m), 1.71-1.63 (4H, m), 1.50-1.38 (2H, m). MS (APCI/ESI) m/z: 473 (M + H)⁺ |

TABLE 2-5

| 7 (7a) | 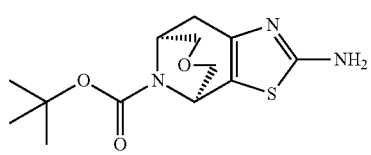 [SMILES: CC(C)(C)OC(=O)N1[C@@H]2COC[C@H]1c1sc(N)nc1C2] | ¹H NMR (400 MHz, CDCl₃): δ (ppm) = 5.08-4.88 (1H, m), 4.83-4.77 (2H, m), 4.40-4.21 (1H, m), 3.95-3.77 (2H, m), 3.76-3.56 (2H, m), 3.22-3.03 (1H, m), 2.65 (1H, dd, J = 17.2, 5.6 Hz), 1.45 (9H, d, J = 6.0 Hz). MS (ESI) m/z: 298 (M + H)⁺ |
| 7 (7b) | 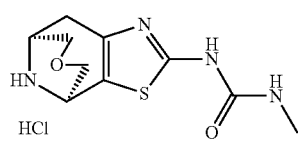 [SMILES: Cl ; CNC(=O)Nc1nc2c(s1)[C@@H]1COC[C@H](C2)N1] | ¹H NMR (400 MHz, DMSO-d₆): δ (ppm) = 10.54 (1H, d, J = 10.0 Hz), 9.52 (1H, d, J = 9.6 Hz), 6.86 (1H, s), 5.36-5.23 (2H, m), 4.80 (1H, s), 4.00-3.88 (2H, m), 3.82 (1H, d, J = 6.0 Hz), 3.65-3.55 (1H, m), 3.23-3.10 (1H, m), 2.90-2.82 (1H, m), 2.68 (3H, s). MS (ESI) m/z: 255 (M + H)⁺ |
| 7 (7c) | 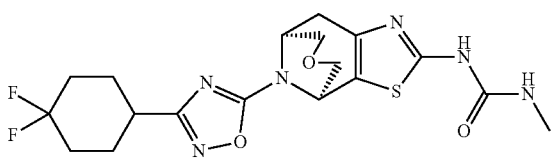 [SMILES: CNC(=O)Nc1nc2c(s1)[C@@H]1COC[C@H](C2)N1c1nc(C2CCC(F)(F)CC2)no1] | ¹H NMR (400 MHz, CD₃OD): δ (ppm) = 5.23 (1H, s), 4.43 (1H, d, J = 6.8 Hz), 4.04-3.84 (3H, m), 3.72 (1H, d, J = 11.2 Hz), 3.22 (1H, dd, J = 17.2, 7.2 Hz), 2.86-2.71 (5H, m), 2.39-2.20 (1H, m), 2.17-1.75 (7H, m). MS (ESI) m/z: 441 (M + H)⁺ |
| 8 (8a) | 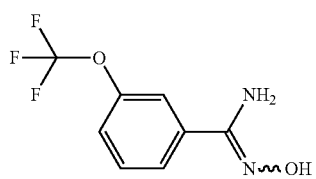 [SMILES: NC(=NO)c1cccc(OC(F)(F)F)c1] | ¹H NMR (400 MHz, CDCl₃): δ (ppm) = 8.41 (1H, br s), 7.50-7.48 (1H, m), 7.44 (1H, s), 7.37 (1H, t, J = 8.4 Hz), 7.25-7.21 (1H, m), 4.83 (2H, s). |
| 8 (8b) | 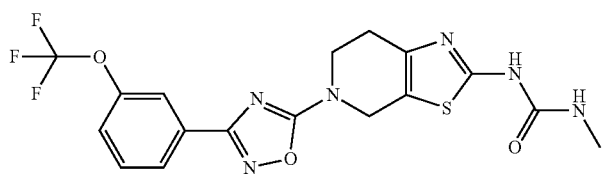 [SMILES: CNC(=O)Nc1nc2c(s1)CN(c1nc(-c3cccc(OC(F)(F)F)c3)no1)CC2] | ¹H NMR (400 MHz, CD₃OD): δ (ppm) = 8.04-7.97 (1H, m), 7.87 (1H, s), 7.62 (1H, t, J = 8.0 Hz), 7.47-7.46 (1H, m), 4.87 (2H, s), 4.11 (2H, t, J = 5.8 Hz), 2.95 (2H, t, J = 5.8 Hz), 2.88 (3H, s). MS (ESI) m/z: 441 (M + H)⁺ |
| 9 | 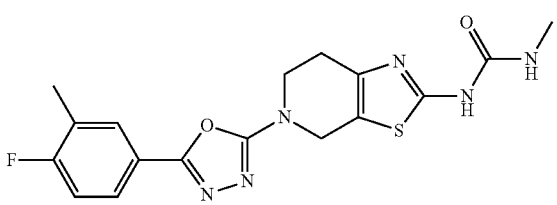 [SMILES: CNC(=O)Nc1nc2c(s1)CN(c1nnc(-c3ccc(F)c(C)c3)o1)CC2] | ¹H NMR (500 MHz, DMSO-d₆): δ (ppm) = 10.41 (1H, s), 7.87 (1H, dd, J = 7.3, 1.5 Hz), 7.80-7.76 (1H, m), 7.32 (1H, t, J = 9.3 Hz), 6.41 (1H, s), 4.67 (2H, s), 3.86 (2H, t, J = 5.9 Hz), 2.75 (2H, t, J = 5.9 Hz), 2.68 (3H, d, J = 4.4 Hz), 2.31 (3H, d, J = 1.0 Hz). MS (APCI) m/z: 389 (M + H)⁺ |
| 10 (10a) | 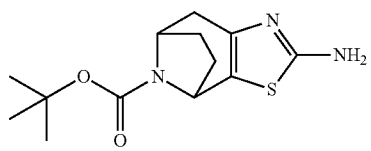 [SMILES: CC(C)(C)OC(=O)N1C2CCC1c1sc(N)nc1C2] | ¹H NMR (400 MHz, CDCl₃): δ (ppm) = 5.12-4.96 (2H, m), 4.94-4.69 (1H, m), 4.61-4.32 (1H, m), 3.34-3.04 (1H, m), 2.44-2.19 (2H, m), 2.16-2.02 (1H, m), 2.01-1.90 (1H, m), 1.70-1.60 (1H, m), 1.43 (9H, s). MS (ESI) m/z: 282 (M + H)⁺ |

TABLE 2-5-continued

| | | |
|---|---|---|
| 10 (10b) | 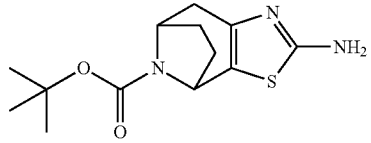 [SMILES: CC(C)(C)OC(=O)N1C2CCC1c1sc(N)nc1C2]<br>optically active isomer | $^1$H NMR (400 MHz, CDCl$_3$): δ (ppm) = 4.96-4.83 (3H, m), 4.59-4.36 (1H, m), 3.34-3.07 (1H, m), 2.44-2.19 (2H, m), 2.16-2.04 (1H, m), 1.98 (1H, t, J = 9.6 Hz), 1.70-1.61 (1H, m), 1.43 (9H, s). MS (ESI) m/z: 282 (M + H)$^+$ |

TABLE 2-6

| | | |
|---|---|---|
| 10 (10c) | 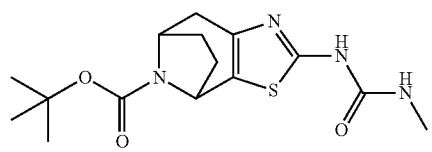 [SMILES: CNC(=O)Nc1nc2c(s1)C1CCC(C2)N1C(=O)OC(C)(C)C]<br>optically active isomer | $^1$H NMR (400 MHz, CDCl$_3$): δ (ppm) = 5.13-4.86 (1H, m), 4.67-4.44 (1H, m), 3.43-3.07 (1H, m), 2.92 (3H, d, J = 4.8 Hz), 2.45 (1H, d, J = 16.4 Hz), 2.36-2.09 (2H, m), 2.00 (1H, t, J = 9.6 Hz), 1.68-1.62 (1H, m), 1.41 (9H, s). MS (ESI) m/z: 339 (M + H)$^+$ |
| 10 (10e) | 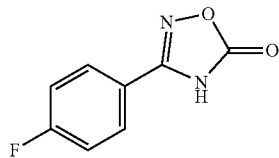 [SMILES: O=c1[nH]c(-c2ccc(F)cc2)no1] | $^1$H NMR (500 MHz, DMSO-d$_6$): δ (ppm) = 12.99 (1H, s), 7.90-7.85 (2H, m), 7.48-7.43 (2H, m). MS (APCI) m/z: 179 (M − H)$^-$ |
| 10 (10f) | 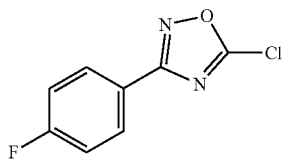 [SMILES: Fc1ccc(-c2noc(Cl)n2)cc1] | $^1$H NMR (500 MHz, CDCl$_3$): δ (ppm) = 8.06-8.04 (2H, m), 7.19 (2H, t, J = 8.5 Hz). |
| 10 (10g) | 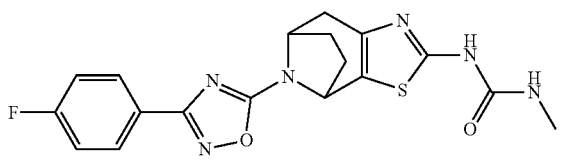 [SMILES: CNC(=O)Nc1nc2c(s1)C1CCC(C2)N1c1nc(-c2ccc(F)cc2)no1]<br>optically active isomer | $^1$H NMR (400 MHz, CDCl$_3$): δ (ppm) = 10.24 (1H, br s), 8.03-7.91 (2H, m), 7.16-7.06 (2H, m), 5.24 (1H, d, J = 5.6 Hz), 4.83 (1H, dd, J = 7.6, 4.4 Hz), 3.54-3.42 (1H, m), 2.89 (3H, d, J = 4.8 Hz), 2.60 (1H, d, J = 16.4 Hz), 2.55-2.43 (1H, m), 2.42-2.30 (1H, m), 2.25-2.14 (1H, m), 1.92-1.83 (1H, m). MS (ESI) m/z: 401 (M + H)$^+$ |
| 11 (11a) | 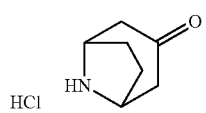 | $^1$H NMR (400 MHz, CD$_3$OD): δ (ppm) = 4.37 (2H, br s), 3.11-2.94 (2H, m), 2.66-2.49 (2H, m), 2.33-2.25 (2H, m), 2.04-1.97 (2H, m). |
| 11 (11b) | 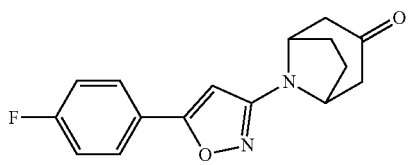 [SMILES: O=C1CC2CCC(C1)N2c1cc(-c2ccc(F)cc2)on1] | $^1$H NMR (400 MHz, CDCl$_3$): δ (ppm) = 7.78-7.75 (2H, m), 7.20-7.16 (2H, m), 6.22 (1H, s), 4.45-4.42 (2H, m), 2.92-2.88 (2H, m), 2.43-2.40 (2H, m), 2.25-2.18 (2H, m), 1.79-1.78 (2H, m). |
| 11 (11c) | 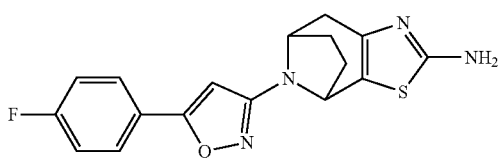 [SMILES: Nc1nc2c(s1)C1CCC(C2)N1c1cc(-c2ccc(F)cc2)on1] | $^1$H NMR (400 MHz, CDCl$_3$): δ (ppm) = 7.64-7.60 (2H, m), 7.07-7.02 (2H, m), 6.06 (1H, s), 4.93-4.90 (2H, m), 4.70-4.69 (1H, m), 4.38-4.35 (1H, m), 3.24-3.20 (1H, m), 2.08-2.03 (1H, m), 1.80-1.73 (2H, m), 1.28-1.19 (2H, m). |

TABLE 2-6-continued

| | | |
|---|---|---|
| 11 (11d) | 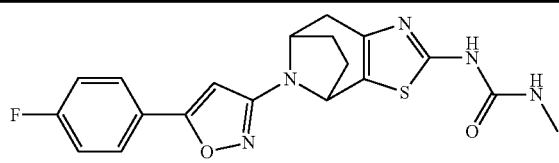 | ¹H NMR (400 MHz, CDCl₃): δ (ppm) = 7.72-7.69 (2H, m), 7.13 (2H, t, J = 8.6 Hz), 6.14 (1H, s), 4.84 (1H, d, J = 5.6 Hz), 4.55-4.52 (1H, m), 3.48-3.43 (1H, m), 2.90 (3H, d, J = 4.8 Hz), 2.48-2.44 (2H, m), 2.38-2.33 (1H, m), 2.17-2.12 (1H, m), 1.88-1.80 (1H, m). MS (ESI) m/z: 400 (M + H)⁺ |
| 12 (12b) | 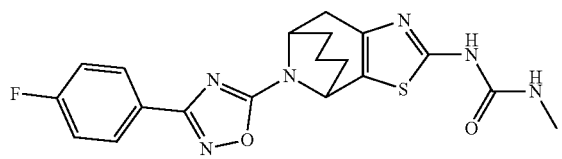 [SMILES: CNC(=O)Nc1nc2c(s1)C1CCCC(C2)N1c1nc(-c2ccc(F)cc2)no1] | ¹H NMR (400 MHz, DMSO-d₆): δ (ppm) = 10.38 (1H, s), 8.03-7.86 (2H, m), 7.40-7.30 (2H, m), 6.40 (1H, d, J = 4.4 Hz), 5.45 (1H, s), 4.69-4.63 (1H, m), 3.13 (1H, dd, J = 17.2, 7.6 Hz), 2.67 (3H, d, J = 4.8 Hz), 2.61 (1H, d, J = 17.6 Hz), 1.99-1.82 (2H, m), 1.82-1.73 (1H, m), 1.71-1.63 (1H, m), 1.57-1.46 (1H, m), 1.48-1.31 (1H, m). MS (ESI) m/z: 415 (M + H)⁺ | optically active isomer

TABLE 2-7

| | | |
|---|---|---|
| 13(13a) | 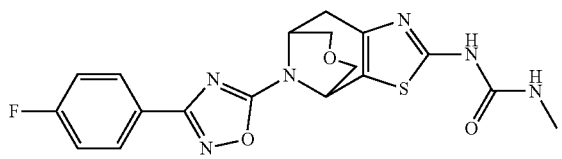 | MS (ESI) m/z: 417 (M + H)⁺ |
| 13(13b) | 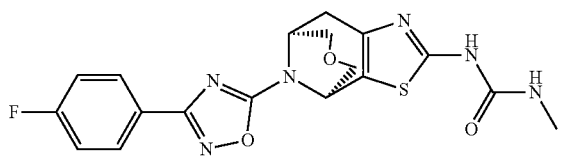 [SMILES: CNC(=O)Nc1nc2c(s1)[C@@H]1COC[C@H](C2)N1c1nc(-c2ccc(F)cc2)no1] | ¹H NMR (400 MHz, DMSO-d₆): δ (ppm) = 10.41 (1H, s), 8.00-7.83 (2H, m), 7.35 (2H, t, J = 8.8 Hz), 6.39 (1H, s), 5.33 (1H, s), 4.45 (1H, d, J = 6.4 Hz), 4.00-3.90 (1H, m), 3.94-3.78 (2H, m), 3.63 (1H, d, J = 11.2 Hz), 3.15 (1H, dd, J = 17.2, 7.2 Hz), 2.77 (1H, d, J = 17.2 Hz), 2.67 (3H, d, J = 4.4 Hz). MS (ESI) m/z: 417 (M + H)⁺ |
| 14(14a) | 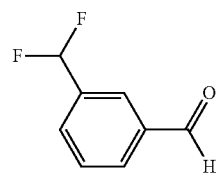 [SMILES: O=Cc1cccc(C(F)F)c1] | ¹H NMR (400 MHz, DMSO-d₆): δ (ppm) = 10.08 (1H, s), 8.14-8.04 (2H, m), 7.91 (1H, d, J = 7.6 Hz), 7.81-7.74 (1H, m), 7.17 (1H, t, J = 55.6 Hz). |
| 14(14b) | 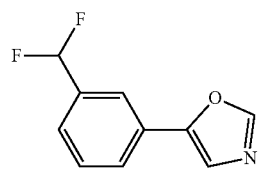 [SMILES: FC(F)c1cccc(-c2cnco2)c1] | ¹H NMR (400 MHz, CDCl₃): δ (ppm) = 7.96 (1H, s), 7.84-7.75 (2H, m), 7.57-7.47 (2H, m), 7.44 (1H, s), 6.70 (1H, t, J = 56.4 Hz). |
| 14(14c) | 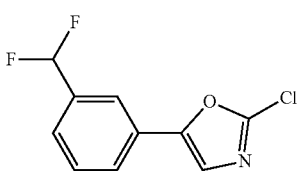 [SMILES: FC(F)c1cccc(-c2cnc(Cl)o2)c1] | ¹H NMR (400 MHz, CDCl₃): δ (ppm) = 7.77-7.69 (2H, m), 7.58-7.48 (2H, m), 7.37 (1H, s), 6.70 (1H, t, J = 56.4 Hz). |
| 14(14d) | 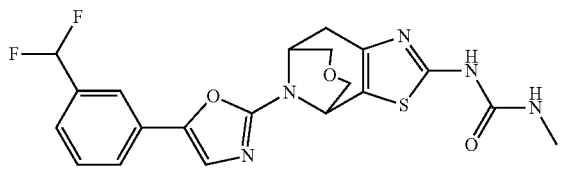 [SMILES: CNC(=O)Nc1nc2c(s1)C1COCC(C2)N1c1ncc(-c2cccc(C(F)F)c2)o1] | ¹H NMR (400 MHz, DMSO-d₆): δ (ppm) = 10.45 (1H, br s), 7.76-7.70 (2H, m), 7.54 (1H, t, J = 8.0 Hz), 7.47 (1H, s), 7.43 (1H, d, J = 8.0 Hz), 7.04 (1H, t, J = 56 Hz), 6.57 (1H, br s), 5.26 (1H, s), 4.36 (1H, d, J = 6.4 Hz), 4.00-3.93 (1H, m), 3.90-3.78 (2H, m), 3.63 (1H, d, J = 10.8 Hz), 3.13 (1H, dd, J = 17.2, 7.2 Hz), 2.73-2.64 (4H, m). MS (ESI) m/z: 448 (M + H)⁺ |

TABLE 2-7-continued

| 15 | [structure: 6-methoxypyridin-2-yl oxazole linked to bridged oxa-thiazole with methylurea] | ¹H NMR (400 MHz, CDCl₃): δ (ppm) = 10.36 (1H, br s), 7.74-7.68 (1H, m), 7.39 (1H, s), 7.13 (1H, d, J = 7.6 Hz), 6.66-6.62 (1H, m), 6.41 (1H, d, J = 4.8 Hz), 5.25 (1H, s), 4.36 (1H, d, J = 6.8 Hz), 3.99-3.93 (1H, m), 3.89-3.78 (5H, m), 3.62-3.59 (1H, m), 3.12 (1H, dd, J = 17.2, 7.2 Hz), 2.73-2.63 (4H, m). |
| --- | --- | --- |
| 16 | [structure: 4-fluorophenyl isoxazole linked to bridged oxa-thiazole with methylurea] | ¹H NMR (400 MHz, DMSO-d₆): δ (ppm) = 10.28 (1H, br s), 7.86-7.71 (2H, m), 7.37 (2H, t, J = 8.8 Hz), 6.95 (1H, s), 6.53-6.35 (1H, m), 4.88 (1H, s), 4.09-4.02 (1H, m), 3.99-3.78 (4H, m), 3.66-3.57 (1H, m), 3.15-3.03 (1H, m), 2.66 (3H, d, J = 4.8 Hz). MS (ESI) m/z: 416 (M + H)⁺ |

TABLE 2-8

| 17 (17a) | [structure: 4-(4-fluorophenyl)oxazole] | ¹H NMR (500 MHz, CDCl₃): δ (ppm) = 7.93 (1H, s), 7.91 (1H, s), 7.75-7.70 (2H, m), 7.14-7.08 (2H, m). MS (APCI) m/z: 164 (M + H)⁺ |
| --- | --- | --- |
| 17 (17b) | [structure: 2-chloro-4-(4-fluorophenyl)oxazole] | ¹H NMR (500 MHz, CDCl₃): δ (ppm) = 7.85 (1H, s), 7.70-7.64 (2H, m), 7.14-7.08 (2H, m). MS (APCI) m/z: 198 (M + H)⁺ |
| 17 (17c) | [structure: bridged oxa-thiazole amine, 2HCl] | ¹H NMR (500 MHz, DMSO-d₆): δ (ppm) = 11.37-11.25 (1H, m), 5.19-5.10 (1H, m), 4.30-3.99 (4H, m), 3.92-3.81 (1H, m), 3.69-3.49 (3H, m), 2.99-2.91 (1H, m), 2.70-2.60 (1H, m). MS (APCI) m/z: 198 (M + H)⁺ |
| 17 (17d) | [structure: 4-(4-fluorophenyl)oxazole linked to bridged oxa-thiazole amine] | ¹H NMR (500 MHz, DMSO-d₆): δ (ppm) = 8.12 (1H, s), 7.72-7.67 (2H, m), 7.25-7.20 (2H, m), 6.81 (2H, s), 4.99 (1H, s), 4.24 (1H, d, J = 6.8 Hz), 3.92 (1H, d, J = 11.2 Hz), 3.82 (1H, d, J = 9.8 Hz), 3.75 (1H, d, J = 9.8 Hz), 3.57 (1H, d, J = 11.2 Hz), 3.03 (1H, dd, J = 17.1, 6.8 Hz), 2.53 (1H, d, J = 17.1 Hz). MS (APCI) m/z: 359 (M + H)⁺ |
| 17 (17e) | [structure: 4-(4-fluorophenyl)oxazole linked to bridged oxa-thiazole with methylurea] | ¹H NMR (500 MHz, DMSO-d₆): δ (ppm) = 10.35 (1H, s), 8.12 (1H, s), 7.72-7.66 (2H, m), 7.26-7.19 (2H, m), 6.38 (1H, s), 5.16 (1H, s), 4.30 (1H, d, J = 7.1 Hz), 3.95 (1H, d, J = 11.2 Hz), 3.85 (1H, d, J = 11.2 Hz), 3.80 (1H, d, J = 11.2 Hz), 3.61 (1H, d, J = 11.2 Hz), 3.13 (1H, dd, J = 17.3, 7.1 Hz), 2.70-2.65 (4H, m). MS (APCI) m/z: 416 (M + H)⁺ |
| 18 (18a) | [structure: Teoc-protected bridged oxa-ketone] | ¹H NMR (400 MHz, CDCl₃): δ (ppm) = 4.58-4.33 (2H, m), 4.25-4.12 (2H, m), 3.87-3.54 (4H, m), 2.68-2.33 (4H, m), 1.03-0.92 (2H, m), 0.00 (9H, s). |
| 18 (18b) | [structure: Teoc-protected bridged oxa-thiazole amine] | ¹H NMR (400 MHz, CDCl₃): δ (ppm) = 5.36 (2H, br s), 5.12-4.85 (1H, m), 4.45-3.97 (3H, m), 3.93-3.46 (4H, m), 3.15-2.96 (1H, m), 2.60 (1H, dd, J = 17.2, 4.8 Hz), 0.96 (2H, t, J = 8.4 Hz), 0.00 (9 H, s). |

TABLE 2-8-continued

| | | |
|---|---|---|
| 18 (18c) | 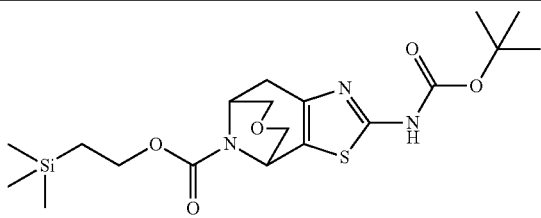 | $^1$H NMR (400 MHz, CDCl$_3$): δ (ppm) = 10.4 (1H, br s), 5.32-5.08 (1H, m), 4.50-4.31 (1H, m), 4.29-4.15 (2H, m), 3.96-3.74 (3H, m), 3.72-3.60 (1H, m), 3.36-3.10 (1H, m), 2.83 (1H, dd, J = 16.8, 2.8 Hz), 1.56 (9H, s), 1.05-0.94 (2H, m), 0.04 (9H, s). |

TABLE 2-9

| | | |
|---|---|---|
| 18 (18d) | 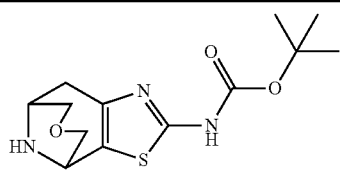 | $^1$H NMR (400 MHz, CDCl$_3$): δ (ppm) = 11.74-9.55 (1H, m), 4.09 (1 H, s), 4.01 (1H, dd, J = 11.2, 2.4 Hz), 3.95 (1H, dd, J = 10.8, 2.0 Hz), 3.85 (1 H, d, J = 11.2 Hz), 3.62 (1H, d, J = 9.6 Hz), 3.51-3.30 (1H, m), 3.20-3.04 (1H, m), 2.88 (1H, d, J = 17.2 Hz), 1.56 (9H, s). |
| 18 (18e) | 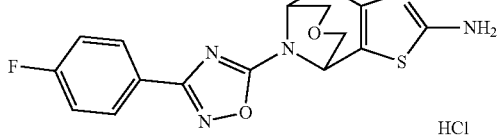 | MS (ESI) m/z: 360 (M + H)$^+$ |
| 18 (18f) | 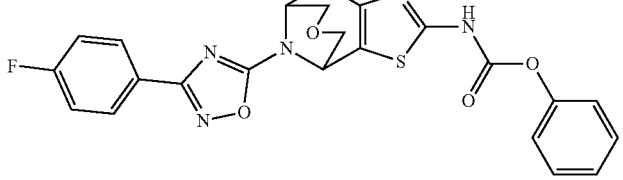 | MS (ESI) m/z: 480 (M + H)$^+$ |
| 18 (18g) | 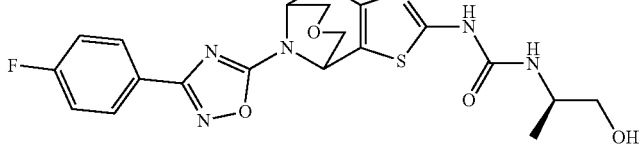 | $^1$H NMR (400 MHz, CD$_3$OD): δ (ppm) = 7.98 (2H, dd, J = 5.6, 8.4 Hz), 7.20 (2H, t, J = 8.4 Hz), 5.32 (1H, s), 4.52 (1H, d, J = 6.8 Hz), 4.06-3.91 (3H, m), 3.90-3.81 (1H, m), 3.74 (1H, d, J = 11.2 Hz), 3.58-3.46 (2H, m), 3.26 (1H, d, J = 7.2 Hz), 2.84 (1H, d, J = 17.6 Hz), 1.22-1.12 (3H, m). MS (ESI) m/z: 461 (M + H)$^+$ |
| 19 (19a) | 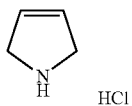 | $^1$H NMR (400 MHz, DMSO-d$_6$): δ (ppm) = 9.94 (2H, br s), 5.88 (2H, s), 3.89 (4H, br s). |
| 19 (19b) | 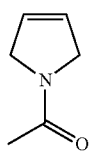 | $^1$H NMR (400 MHz, CDCl$_3$): δ (ppm) = 5.90-5.86 (1H, m), 5.83-5.72 (1H, m), 4.24 (4H, d, J = 7.6 Hz), 2.07 (3H, s). |
| 19 (19c) | 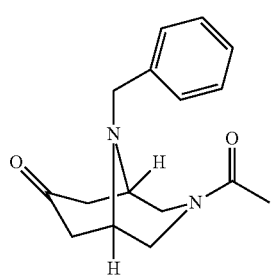 [SMILES: CC(=O)N1CC2CC(=O)CC(C1)N2Cc1ccccc1] | $^1$H NMR (400 MHz, CDCl$_3$): δ (ppm) = 7.44-7.27 (5H, m), 4.45 (1H, d, J = 13.2 Hz), 3.93 (2H, s), 3.64-3.55 (1H, m), 3.52-3.43 (1H, m), 3.34 (2H, s), 2.92 (1H, d, J = 12.8 Hz), 2.83-2.60 (2H, m), 2.24 (2H, t, J = 16.8 Hz), 1.99 (3H, s). |

TABLE 2-9-continued

| | | |
|---|---|---|
| 19 (194) | 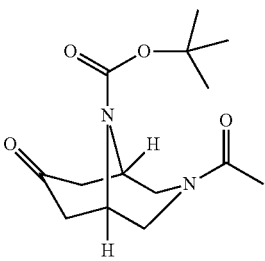 [SMILES: CC(=O)N1CC2CC(=O)CC(C1)N2C(=O)OC(C)(C)C] | $^1$H NMR (400 MHz, CDCl$_3$): δ (ppm) = 4.80-4.48 (3H, m), 3.73-3.69 (1H, m), 3.42-3.30 (1H, m), 2.77 (1H, d, J = 13.2 Hz), 2.71-2.43 (2H, m), 2.35 (2H, dd, J = 16.0, 5.6 Hz), 2.01 (3H, s), 1.52 (9H, s). |
| 19 (19e) | 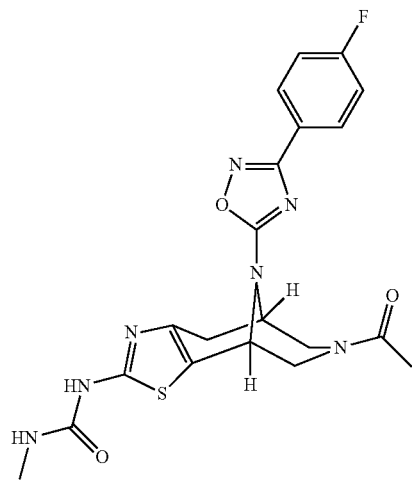 [SMILES: CNC(=O)Nc1nc2c(s1)C1CN(C(C)=O)CC(C2)N1c1nc(-c2ccc(F)cc2)no1] | $^1$H NMR (400 MHz, CDCl$_3$): δ (ppm) = 8.01-7.95 (2H, m), 7.17-7.09 (2H, m), 5.52 (1H, s), 4.91 (1H, d, J = 13.2 Hz), 4.77-4.63 (1H, m), 4.02-3.88 (1H, m), 3.84-3.70 (2H, m), 3.27 (1H, dd, J = 17.2, 6.8 Hz), 3.11 (1H, d, J = 13.2 Hz), 2.96-2.83 (4H, m), 2.13-2.08 (1H, m), 1.80 (3H, s). MS (APCI) m/z: 458 (M + H)$^+$ |

TABLE 2-10

| | | |
|---|---|---|
| 20 (20a) | 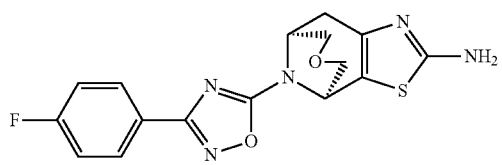 [SMILES: Nc1nc2c(s1)[C@@H]1COC[C@H](C2)N1c1nc(-c2ccc(F)cc2)no1] | $^1$H NMR (500 MHz, CDCl$_3$): δ (ppm) = 8.00-7.93 (2H, m), 7.12 (2H, t, J = 8.8 Hz), 5.13 (1H, s), 4.90 (2H, s), 4.48 (1H, d, J = 6.8 Hz), 4.05-3.98 (2H, m), 3.93 (1H, dd, J = 11.0, 1.7 Hz), 3.75 (1H, d, J = 11.2 Hz), 3.33 (1H, dd, J = 17.3, 7.1 Hz), 2.80 (1H, d, J = 17.6 Hz). MS (APCI) m/z: 360 (M + H)$^+$ |
| 20 (20b) | 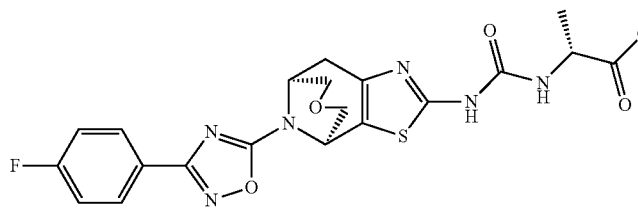 | $^1$H NMR (500 MHz, DMSO-d$_6$): δ (ppm) = 12.83 (1H, s), 10.34 (1H, s), 7.97-7.91 (2H, m), 7.39-7.33 (2H, m), 6.91-6.86 (1H, m), 5.35 (1H, s), 4.45 (1H, d, J = 6.8 Hz), 4.24-4.16 (1H, m), 3.98 (1H, d, J = 11.7 Hz), 3.91-3.80 (2H, m), 3.63 (1H, d, J = 10.3 Hz), 3.15 (1H, dd, J = 17.6, 6.8 Hz), 2.79 (1H, d, J = 17.6 Hz), 1.32 (3H, d, J = 6.8 Hz). MS (APCI) m/z: 475 (M + H)$^+$ |
| 20 (20c) | 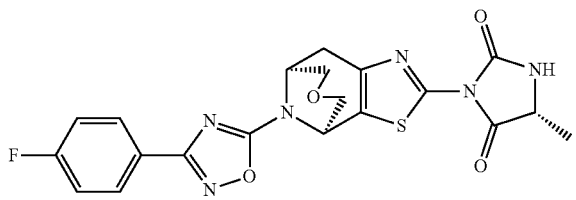 [SMILES: C[C@H]1NC(=O)N(c2nc3c(s2)[C@@H]2COC[C@H](C3)N2c2nc(-c3ccc(F)cc3)no2)C1=O] | $^1$H NMR (500 MHz, DMSO-d$_6$): δ (ppm) = 8.77 (1H, s), 7.97-7.92 (2H, m), 7.39-7.33 (2H, m), 5.58 (1H, s), 4.54 (1H, d, J = 6.8 Hz), 4.04 (1H, d, J = 11.2 Hz), 3.96-3.88 (2H, m), 3.71 (1H, d, J = 11.2 Hz), 3.34-3.27 (2H, m), 2.99 (1H, d, J = 17.6 Hz), 1.34 (3H, d, J = 6.8 Hz). MS (APCI) m/z: 457 (M + H)$^+$ |

TABLE 2-10-continued

| 21 (21a) | 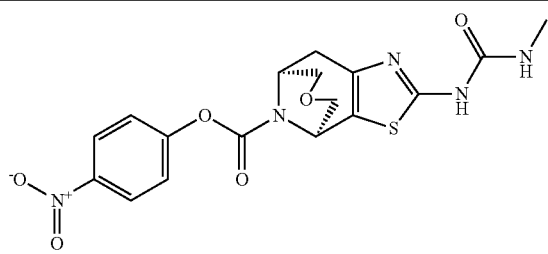 | ¹H NMR (400 MHz,CDCl₃): δ (ppm) = 8.25 (2H, dd, J = 9.1, 3.6 Hz), 7.21-7.39 (2H, m), 5.24-5.37 (1H, m), 4.49-4.66 (1H, m), 3.83-4.06 (3H, m), 3.74 (1H, d, J = 11.0 Hz), 3.34 (1H, dt, J = 17.0, 8.3 Hz), 2.81-2.99 (4H, m). MS (ESI) m/z: 420 (M + H)⁺ |
|---|---|---|
| 21 (21b) | 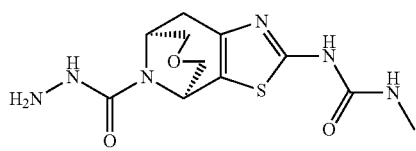 [SMILES: CNC(=O)Nc1nc2c(s1)[C@@H]1COC[C@H](C2)N1C(=O)NN] | ¹H NMR (400 MHz, DMSO-d₆): δ (ppm) = 9.72-10.22 (1H, m), 7.93 (1H, br s), 6.41 (1H, br d, J = 4.5 Hz), 5.05 (1H, s), 4.18 (1H, br d, J = 6.6 Hz), 3.91 (2H, br s), 3.83 (1H, d, J = 11.1 Hz), 3.55-3.67 (2H, m), 3.47-3.54 (1H, m), 2.94 (1H, dd, J = 17.0, 7.0 Hz), 2.67 (3H, s), 2.54 (1H, s). MS (ESI) m/z: 313 (M + H)⁺ |
| 21 (21c) | 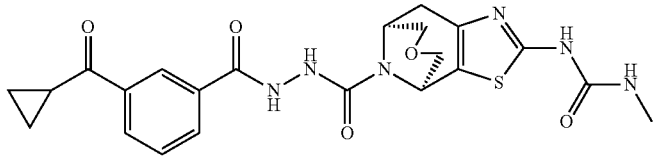 [SMILES: CNC(=O)Nc1nc2c(s1)[C@@H]1COC[C@H](C2)N1C(=O)NNC(=O)c1cccc(C(=O)C2CC2)c1] | ¹H NMR (400 MHz, DMSO-d₆): δ (ppm) = 10.36-10.34 (2H, m), 9.03 (1H, s), 8.52 (1H, s), 8.19 (1H, d, J = 7.6 Hz), 8.11 (1H, d, J = 7.6 Hz), 7.66 (1H, t, J = 7.6 Hz), 6.56-6.43 (1H, m), 5.17 (1H, s), 4.34 (1H, d, J = 6.4 Hz), 3.91 (1H, d, J = 11.2 Hz), 3.76-3.64 (2H, m), 3.57 (1H, d, J = 10.8 Hz), 3.11-3.05 (1H, m), 2.97-2.88 (1H, m), 2.68 (3H, d, J = 4.8 Hz), 2.61 (1H, d, J = 16.8 Hz), 1.11-1.02 (4H, m). MS (ESI) m/z: 485 (M + H)⁺ |

TABLE 2-11

| 21 (21d) | 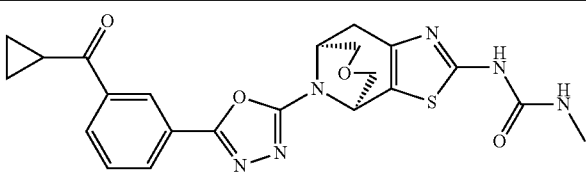 | ¹H NMR (400 MHz, CDCl₃): δ (ppm) = 10.06 (1H, br s), 8.49 (1H, s), 8.11 (2H, dd, J = 7.6, 1.6 Hz), 7.58 (1H, t, J = 7.6 Hz), 7.20 (1H, br s), 5.16 (1H, s), 4.48 (1H, d, J = 6.8 Hz), 4.11-4.04 (2H, m), 4.02 (1H, dd, J = 11.2, 1.6 Hz), 3.79 (1H, d, J = 10.0 Hz), 3.50 (1H, dd, J = 17.2, 7.2 Hz), 2.90 (3H, d, J = 4.8 Hz), 2.85 (1H, d, J = 17.2 Hz), 2.75-2.66 (1H, m), 1.32-1.27 (2H, m), 1.15-1.08 (2H, m). MS (ESI) m/z: 467 (M + H)⁺ |
|---|---|---|
| 22 | 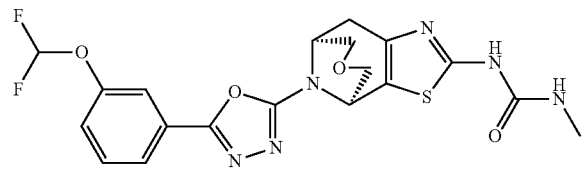 [SMILES: CNC(=O)Nc1nc2c(s1)[C@@H]1COC[C@H](C2)N1c1nnc(-c2cccc(OC(F)F)c2)o1] | ¹H NMR (500 MHz, DMSO-d₆): δ (ppm) = 10.38 (1H, s), 7.77 (1H, d, J = 8.1 Hz), 7.67-7.65 (1H, m), 7.61 (1H, t, J = 8.1 Hz), 7.36 (1H, dd, J = 8.1, 2.4 Hz), 7.35 (1H, t, J = 73.7 Hz), 6.42-6.36 (1H, m), 5.26 (1H, s), 4.35 (1H, d, J = 7.1 Hz), 3.97 (1H, d, J = 11.7 Hz), 3.90 (1H, dd, J = 11.7, 2.0 Hz), 3.85 (1H, dd, J = 11.0, 1.7 Hz), 3.63 (1H, d, J = 11.0 Hz), 3.18 (1H, dd, J = 17.3, 7.1 Hz), 2.73 (1H, d, J = 17.3 Hz), 2.66 (3H, d, J = 4.9 Hz). MS (APCI) m/z: 465 (M + H)⁺ |
| 23 (23a) | 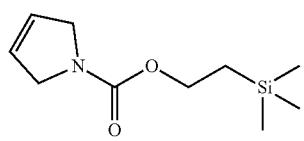 | ¹H NMR (400 MHz, CDCl₃): δ (ppm) = 5.87-5.65 (1H, m), 5.86-5.62 (1H, m), 4.19-4.11 (4H, m), 4.11-4.06 (2H, m), 1.00-0.94 (2H, m), 0.00 (9H, s). |
| 23 (23b) | 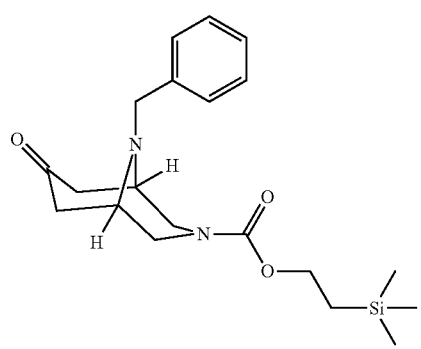 [SMILES: C[Si](C)(C)CCOC(=O)N1CC2CC(=O)CC(C1)N2Cc1ccccc1] | ¹H NMR (400 MHz, CDCl₃): δ (ppm) = 7.50-7.24 (5H, m), 4.27-4.14 (2H, m), 4.10-3.84 (4H, m), 3.39-3.07 (4H, m), 2.71 (2H, dd, J = 15.6, 6.0 Hz), 2.27 (2H, d, J = 15.6 Hz), 1.11-0.94 (2H, m), 0.08-0.03 (9H, m). MS (ESI) m/z: 375 (M + H)⁺ |

TABLE 2-11-continued
| 23 (23d) | 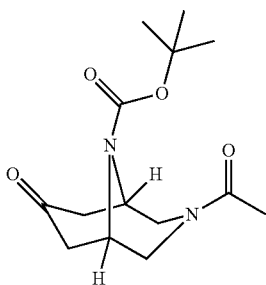 [SMILES: CC(=O)N1CC2CC(=O)CC(C1)N2C(=O)OC(C)(C)C] | $^1$H NMR (400 MHz, CDCl$_3$): δ (ppm) = 4.80-4.48 (3H, m), 3.73-3.69 (1H, m), 3.42-3.30 (1H, m), 2.77 (1H, d, J = 13.2 Hz), 2.71-2.43 (2H, m), 2.35 (2H, dd, J = 16.0, 5.6 Hz), 2.01 (3H, s), 1.52 (9H, s). MS (ESI) m/z: 283 (M + H)$^+$ |
TABLE 2-12
| 23 (23e) | 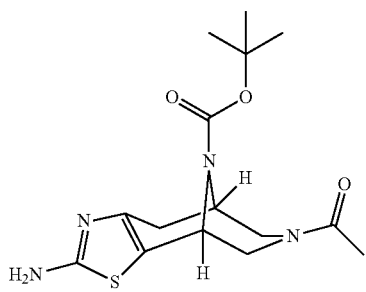 [SMILES: CC(=O)N1CC2Cc3nc(N)sc3C(C1)N2C(=O)OC(C)(C)C] | $^1$H NMR (400 MHz, CDCl$_3$): δ (ppm) = 5.36-5.05 (1H, m), 5.01-4.82 (2H, m), 4.71-4.37 (2H, m), 3.85-3.61 (1H, m), 3.51-3.39 (1H, m), 3.21-2.93 2.87 (1H, d, J = 12.8 Hz), 2.64-2.45 (1H, m), 2.04 (1H, s), 1.81 (2H, s), 1.47 (9H, s). MS (ESI) m/z: 339 (M + H)$^+$ |
| 23 (23g) | 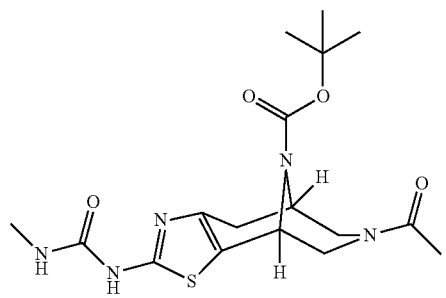 [SMILES: CNC(=O)Nc1nc2c(s1)C1CN(C(C)=O)CC(C2)N1C(=O)OC(C)(C)C]<br>optically active isomer | $^1$H NMR (400 MHz, CDCl$_3$): δ (ppm) = 5.42-5.12 (1H, m), 4.67 (1H, d, J = 8.8 Hz), 4.55-4.29 (1H, m), 3.56 (1H, d, J = 12.4 Hz), 3.50-3.34 (1H, m), 3.28 (1H, s), 2.88-2.77 (4H, m), 2.61 (1H, d, J = 17.6 Hz), 1.66 (3H, s), 1.39 (9H, s). MS (ESI) m/z: 396 (M + H)$^+$ |
| 23 (23h) | 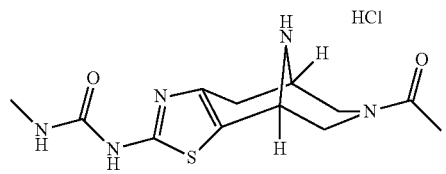 [SMILES: Cl ; CNC(=O)Nc1nc2c(s1)C1CN(C(C)=O)CC(C2)N1]<br>optically active isomer | MS (ESI) m/z: 296 (M + H)$^+$ |

TABLE 2-12-continued

| | | |
|---|---|---|
| 23 (23i) | 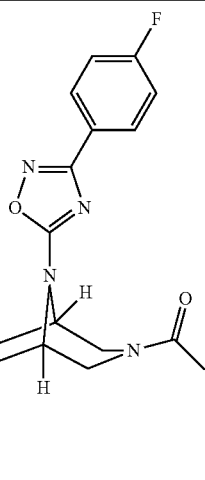<br>optically active isomer | $^1$H NMR (400 MHz, CDCl$_3$): δ (ppm) = 8.01-7.95 (2H, m), 7.17-7.09 (2H, m), 5.52 (1H, s), 4.91 (1H, d, J = 13.2 Hz), 4.77-4.63 (1H, m), 4.02-3.88 (1H, m), 3.84-3.70 (2H, m), 3.27 (1H, dd, J = 17.2, 6.8 Hz), 3.11 (1H, d, J = 13.2 Hz), 2.96-2.83 (4H, m), 2.13-2.08 (1H, m), 1.80 (3H, s). MS (APCI) m/z: 458 (M + H)$^+$, [□]$^{20}$$_D$ −207.8 (c 1.005, CHCl$_3$) |
| 24 (24a) | 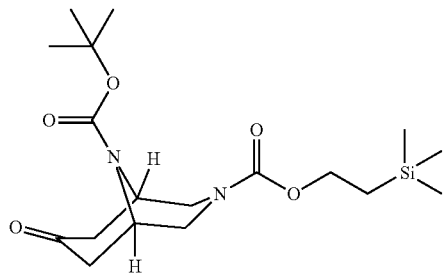 [SMILES: CC(C)(C)OC(=O)N1C2CC(=O)CC1CN(C(=O)OCC[Si](C)(C)C)C2] | $^1$H NMR (400 MHz, CDCl$_3$): δ (ppm) = 4.73-4.41 (2H, m), 4.24-3.83 (4H, m), 2.98 (2H, br s), 2.62-2.19 (4H, m), 1.46 (9H, s), 0.95 (2H, d, J = 6.8 Hz), 0.00 (9H, s). |

TABLE 2-13

| | | |
|---|---|---|
| 24(24b) | 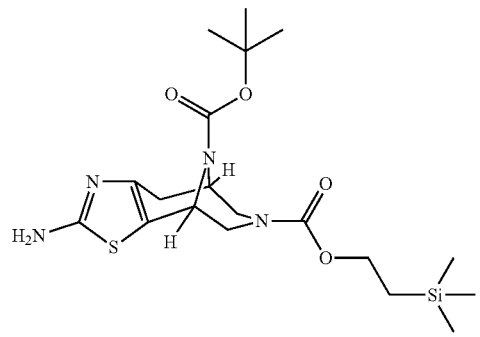 [SMILES: CC(C)(C)OC(=O)N1C2Cc3nc(N)sc3C1CN(C(=O)OCC[Si](C)(C)C)C2] | $^1$H NMR (400 MHz, CDCl$_3$): δ (ppm) = 5.29-4.98 (1H, m), 4.82 (2H, s), 4.58-3.81 (5H, m), 3.28-2.91 (3H, m), 2.70-2.49 (1H, m), 1.44 (9H, s), 1.02-0.75 (2H, m), 0.10-0.00 (9H, m). |
| 24(24f) | 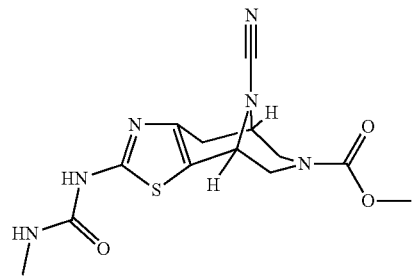<br>optically active isomer | $^1$H NMR (400 MHz, CDCl$_3$): δ (ppm) = 4.63 (1H, s), 4.35 (1H, d, J = 14.0 Hz), 3.97 (1H, d, J = 14.8 Hz), 3.85 (1H, s), 3.61 (1H, s), 3.51-3.46 (1H, m), 3.43 (3H, s), 3.40-3.30 (1H, m), 2.93 (3H, d, J = 4.8 Hz), 2.85 (1H, d, J = 17.2 Hz). MS (ESI) m/z: 337 (M + H)$^+$ |

TABLE 2-13-continued

| 24(24g) | 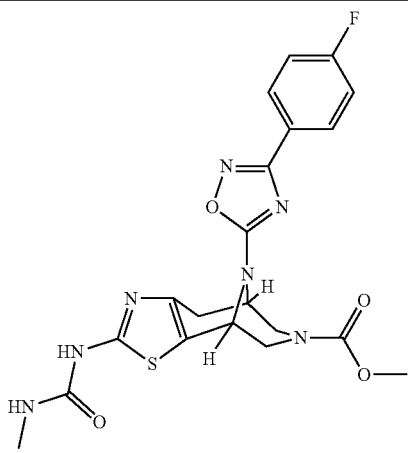 optically active isomer | $^1$H NMR (400 MHz, CDCl$_3$): δ (ppm) = 7.97 (2H, dd, J = 8.8, 5.4 Hz), 7.12 (2H, t, J = 8.8 Hz), 6.45 (1H, br m), 5.44 (1H, s), 5.85-5.16 (1H, m), 4.47-4.05 (3H, m), 3.65 (1H, s), 3.53-3.41 (3H, m), 3.39-3.23 (2H, m), 3.01-2.69 (4H, m). MS (ESI) m/z: 474 (M + H)$^+$, $[α]^{20}_D$ −133.0 (c 0.967, CHCl$_3$) |
|---|---|---|
| 25 | 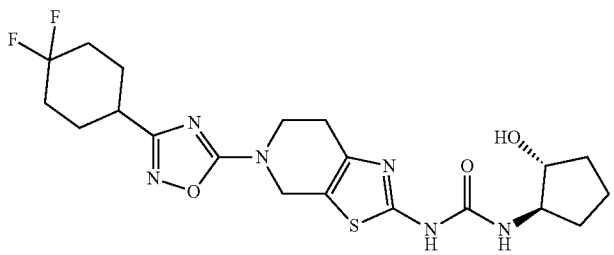 [SMILES: O=C(Nc1nc2c(s1)CN(c1nc(C3CCC(F)(F)CC3)no1)CC2)N[C@@H]1CCC[C@H]1O] | $^1$H NMR (400 MHz, DMSO-d$_6$): δ (ppm) = 10.03 (1H, s), 6.56 (1H, d, J = 6.4 Hz), 4.81 (1H, s), 4.61 (2H, s), 3.81-3.75 (3H, m), 3.66-3.64 (1H, m), 2.77 (1H, t, J = 11.4 Hz), 2.66 (2H, t, J = 5.7 Hz), 2.05-1.27 (14H, m). MS (ESI) m/z: 469 (M + H)$^+$ |
| 26 | 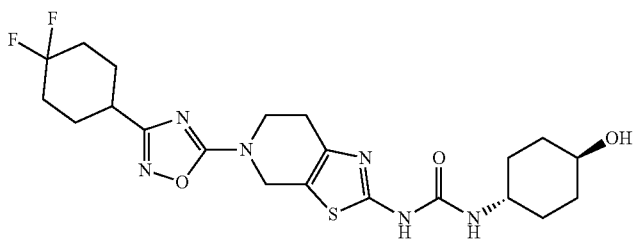 [SMILES: O=C(Nc1nc2c(s1)CN(c1nc(C3CCC(F)(F)CC3)no1)CC2)N[C@H]1CC[C@H](O)CC1] | $^1$H NMR (400 MHz, DMSO-d$_6$): δ (ppm) = 10.03 (1H, s), 6.40 (1H, d, J = 7.8 Hz), 4.61 (2H, s), 4.51-4.50 (1H, m), 3.80 (2H, t, J = 5.7 Hz), 3.37-3.36 (2H, m), 2.76 (1H, s), 2.67-2.64 (2H, m), 2.05-1.64 (12H, m), 1.20-1.10 (4H, m). MS (ESI) m/z: 483 (M + H)$^+$ |

TABLE 2-14

| 27 | 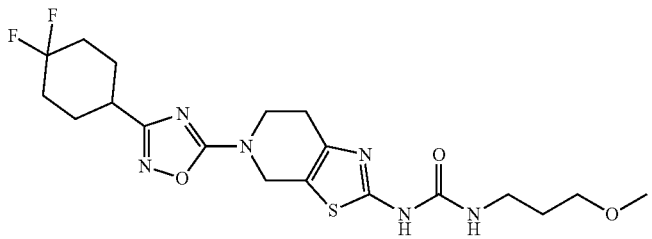 [SMILES: COCCCNC(=O)Nc1nc2c(s1)CN(c1nc(C3CCC(F)(F)CC3)no1)CC2] | $^1$H NMR (400 MHz, DMSO-d$_6$): δ (ppm) = 10.28 (1H, s), 6.53 (1H, t, J = 5.5 Hz), 4.61 (2H, s), 3.80 (2H, t, J = 5.9 Hz), 3.32-3.31 (2H, m), 3.19 (3H, s), 3.15-3.10 (2H, m), 2.79-2.73 (1H, m), 2.68-2.65 (2H, m), 2.04-1.83 (6H, m), 1.71-1.59 (4H, m). MS (ESI) m/z: 457.4 (M + H)$^+$ |
|---|---|---|
| 28 | 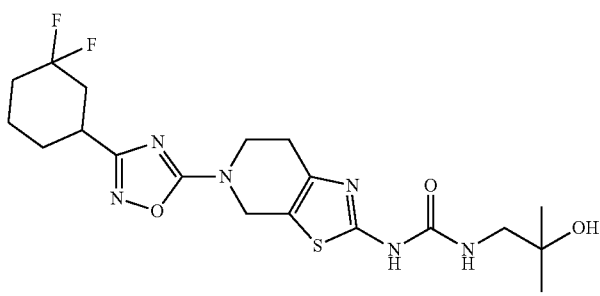 [SMILES: CC(C)(O)CNC(=O)Nc1nc2c(s1)CN(c1nc(C3CCCC(F)(F)C3)no1)CC2] | $^1$H NMR (400 MHz, DMSO-d$_6$): δ (ppm) = 10.22 (1H, s), 6.61 (1H, s), 4.61 (2H, s), 4.55 (1H, s), 3.80 (2H, t, J = 5.5 Hz), 3.02 (2H, d, J = 5.5 Hz), 2.81-2.75 (1H, m), 2.68-2.61 (2H, m), 2.29-1.38 (8H, m), 1.04 (6H, s). MS (ESI) m/z: 457 (M + H)$^+$ |

TABLE 2-14-continued

| | | |
|---|---|---|
| 29(29a) | 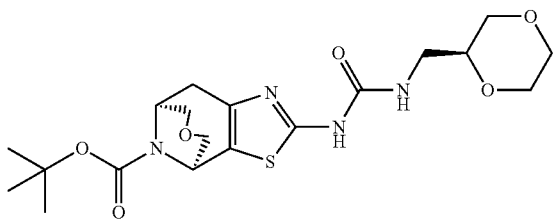 [SMILES: CC(C)(C)OC(=O)N1[C@@H]2COC[C@H]1c1sc(NC(=O)NC[C@H]3COCCO3)nc1C2] | ¹H NMR (500 MHz, DMSO-d₆): δ (ppm) = 10.20 (1H, s), 6.68 (1H, s), 5.08-5.01 (1H, m), 4.22-4.15 (1H, m), 3.88-3.80 (1H, m), 3.78-3.68 (2H, m), 3.67-3.42 (7H, m), 3.28-3.17 (2H, m), 3.15-3.05 (1H, m), 2.99-2.89 (1H, m), 2.64-2.57 (1H, m), 1.42-1.31 (9H, m). |
| 29(29b) | 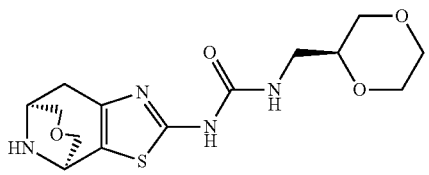 [SMILES: O=C(NC[C@H]1COCCO1)Nc1nc2c(s1)[C@@H]1COC[C@H](C2)N1] | ¹H NMR (500 MHz, DMSO-d₆): δ (ppm) = 10.12 (1H, s), 6.71 (1H, s), 3.92 (1H, s), 3.77-3.53 (9H, m), 3.48-3.41 (1H, m), 3.40-3.35 (1H, m), 3.25-3.19 (2H, m), 3.14-3.06 (2H, m), 2.88-2.82 (1H, m), 2.50-2.47 (1H, m). MS (APCI) m/z: 341 (M + H)⁺ |
| 29(29c) | 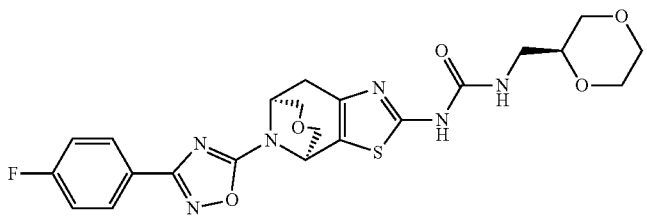 [SMILES: O=C(NC[C@H]1COCCO1)Nc1nc2c(s1)[C@@H]1COC[C@H](C2)N1c1nc(-c2ccc(F)cc2)no1] | ¹H NMR (500 MHz, DMSO-d₆): δ (ppm) = 10.27 (1H, s), 7.96-7.91 (2H, m), 7.38-7.33 (2H, m), 6.66 (1H, s), 5.34 (1H, s), 4.45 (1H, d, J = 6.3 Hz), 3.97 (1H, d, J = 11.7 Hz), 3.88 (1H, d, J = 11.7 Hz), 3.83 (1H, d, J = 11.0 Hz), 3.76-3.67 (2H, m), 3.65-3.51 (4H, m), 3.48-3.39 (1H, m), 3.26-3.06 (4H, m), 2.78 (1H, d, J = 17.1 Hz). MS (APCI) m/z: 503 (M + H)⁺ |
| 30 | 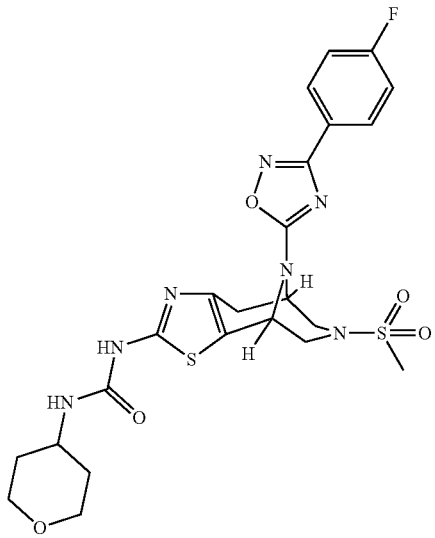 [SMILES: CS(=O)(=O)N1CC2Cc3nc(NC(=O)NC4CCOCC4)sc3C(C1)N2c1nc(-c2ccc(F)cc2)no1] | ¹H NMR (400 MHz, DMSO-d₆): δ (ppm) = 10.07 (1H, br s), 7.91 (2H, dd, J = 8.9, 5.5 Hz), 7.32 (2H, t, J = 8.9 Hz), 6.60-6.58 (1H, m), 5.58 (1H, s), 4.70-4.68 (1H, m), 3.78-3.61 (4H, m), 3.49 (1H, d, J = 11.4 Hz), 3.36-3.24 (4H, m), 3.14 (1H, dd, J = 17.4, 7.3 Hz), 2.74 (3H, s), 2.67 (1H, d, J = 17.4 Hz), 1.74 (2H, m), 1.40-1.31 (2H, m). MS (ESI) m/z: 564 (M + H)⁺ |

TABLE 2-15

| | | |
|---|---|---|
| 31(31a) | 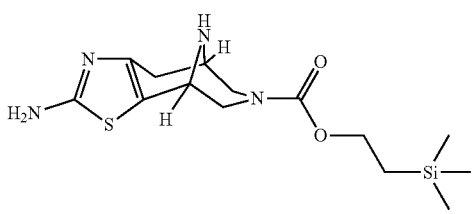 [SMILES: C[Si](C)(C)CCOC(=O)N1CC2Cc3nc(N)sc3C(C1)N2] | ¹H NMR (400 MHz, CDCl₃): δ (ppm) = 4.77 (2H, s), 4.24-3.83 (5H, m), 3.41-3.37 (1H, m), 3.30-3.17 (2H, m), 2.93-2.88 (1H, m), 2.68-2.57 (1H, m), 1.86 (1H, br s), 0.93-0.80 (2H, m), −0.01 (9H, s). MS (ESI) m/z: 341 (M + H)⁺ |

TABLE 2-15-continued
31(31b) 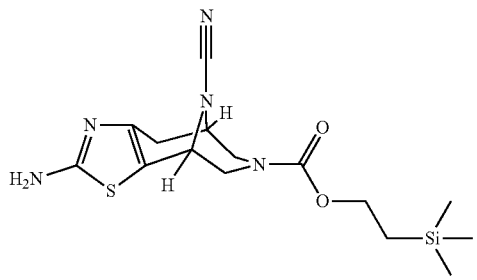 [SMILES: C[Si](C)(C)CCOC(=O)N1CC2Cc3nc(N)sc3C(C1)N2C#N]
¹H NMR (400 MHz, CDCl₃): δ (ppm) = 4.86-4.85 (2H, m), 4.49-4.43 (1H, m), 4.36-4.25 (1H, m), 4.10-3.91 (3H, m), 3.78-3.74 (1H, m), 3.39-3.36 (1H, m), 3.28-3.20 (2H, m), 2.77-2.65 (1H, m), 0.93-0.78 (2H, m), −0.01 (9H, s). MS (ESI) m/z: 366 (M + H)⁺
31(31c) 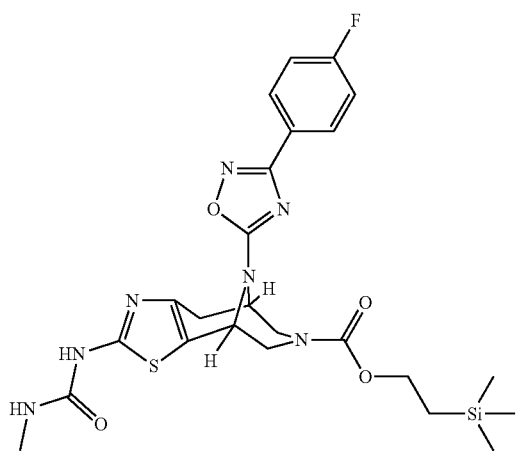
¹H NMR (400 MHz, CDCl₃): δ (ppm) = 10.41 (1H, br s), 7.95 (2H, dd, J = 8.7, 5.5 Hz), 7.10 (2H, t, J = 8.0 Hz), 5.99 (1H, br s), 5.40 (1H, br s), 4.61 (1H, br s), 4.47-3.81 (4H, m), 3.48-3.23 (3H, m), 2.90-2.87 (4H, m), 0.93-0.73 (2H, m), −0.01--0.06 (9H, m). MS (ESI) m/z: 558 (M − H)⁻
31(31d) 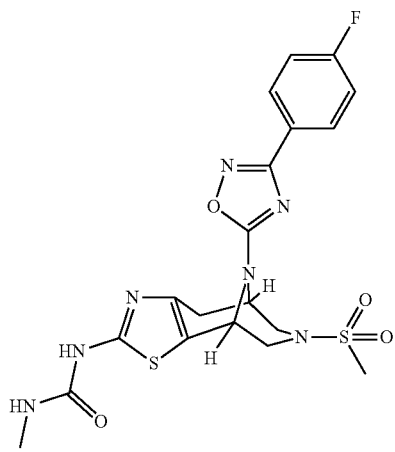 [SMILES: CNC(=O)Nc1nc2c(s1)C1CN(S(C)(=O)=O)CC(C2)N1c1nc(-c2ccc(F)cc2)no1]
¹H NMR (400 MHz, CD₃OD): δ (ppm) = 7.97 (2H, t, J = 5.9 Hz), 7.18 (2H, dd, J = 8.7, 6.4 Hz), 5.57 (1H, s), 4.77 (1H, d, J = 4.6 Hz), 3.89 (1H, d, J = 12.3 Hz), 3.70 (1H, d, J = 12.3 Hz), 3.36 (2H, d, J = 12.3 Hz), 3.28-3.24 (1H, m), 2.82-2.72 (7H, m). MS (ESI) m/z: 494 (M + H)⁺

TABLE 2-16
| 32 | 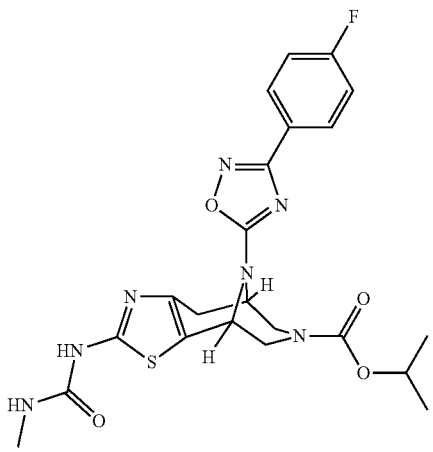 [SMILES: CNC(=O)Nc1nc2c(s1)C1CN(C(=O)OC(C)C)CC(C2)N1c1nc(-c2ccc(F)cc2)no1] | $^1$H NMR (400 MHz, DMSO-d$_6$): δ (ppm) = 10.36 (1H, br s), 7.92-7.88 (2H, m), 7.31 (2H, t, J = 8.7 Hz), 6.33 (1H, br s), 5.44 (1H, br s), 4.57-4.46 (2H, m), 4.25-4.11 (1H, m), 3.97-3.88 (1H, m), 3.27-3.22 (2H, m), 3.10-3.02 (1H, m), 2.63-2.59 (4H, m), 1.11-0.73 (6H, m). MS (ESI) m/z: 502 (M + H)$^+$ |
|---|---|---|
| 33(33a) | 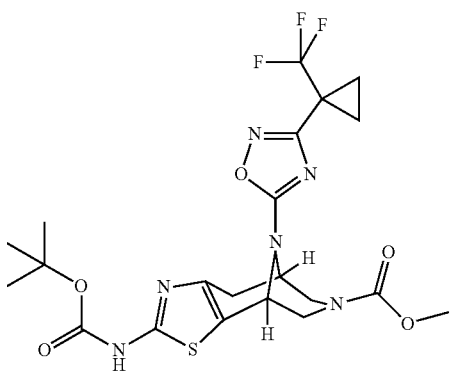<br>optically active isomer | MS (ESI) m/z: 531 (M + H)$^+$ |
| 33(33b) | 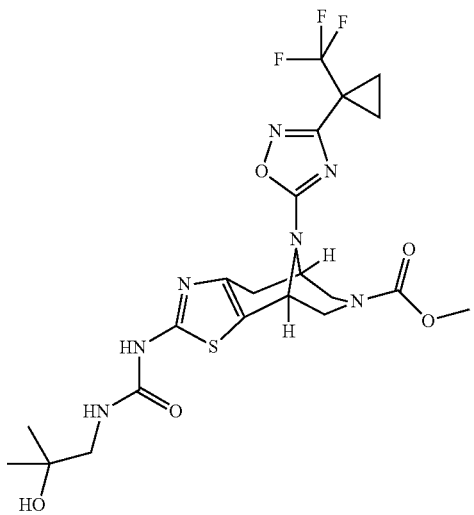<br>optically active isomer | $^1$H NMR (400 MHz, CDCl$_3$): δ (ppm) = 5.31 (1H, s), 4.52 (1H, br s), 4.41-3.95 (2H, m), 3.63 (1H, br s), 3.46 (2H, s), 3.44-3.18 (5H, m), 2.90 (1H, d, J = 17.2 Hz), 1.46-1.35 (4H, m), 1.26 (6H, d, J = 2.0 Hz). MS (ESI) m/z: 546 (M + H)$^+$ |
| 34 | 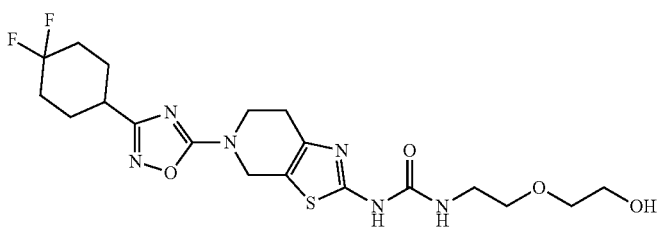 [SMILES: O=C(NCCOCCO)Nc1nc2c(s1)CN(c1nc(C3CCC(F)(F)CC3)no1)CC2] | $^1$H NMR (400 MHz, DMSO-d$_6$): δ (ppm) = 10.29 (1H, s), 6.62 (1H, s), 4.61 (2H, s), 4.57-4.55 (1H, m), 3.80 (2H, t, J = 5.7 Hz), 3.49-3.38 (6H, m), 3.27-3.22 (2H, m), 2.79-2.74 (1H, m), 2.68-2.65 (2H, m), 2.05-1.83 (6H, m), 1.71-1.62 (2H, m). MS (ESI) m/z: 473 (M + H)$^+$ |

TABLE 2-17

| | | |
|---|---|---|
| 35 | 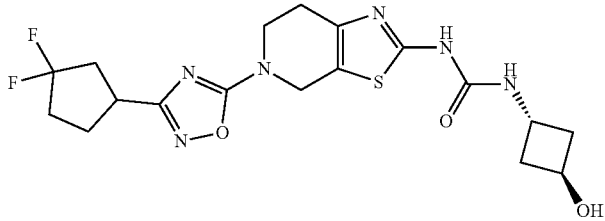 [SMILES: O=C(Nc1nc2c(s1)CN(c1nc(C3CCC(F)(F)C3)no1)CC2)N[C@H]1C[C@H](O)C1] | $^1$H NMR (400 MHz, CDCl$_3$): δ (ppm) = 4.73 (2H, s), 4.63-4.55 (1H, m), 4.52-4.42 (1H, m), 3.96 (2H, t, J = 5.6 Hz), 3.40-3.29 (1H, m), 2.94-2.84 (2H, m), 2.60-2.07 (10H, m). MS (ESI) m/z:441 (M + H)$^+$ |
| 36 | 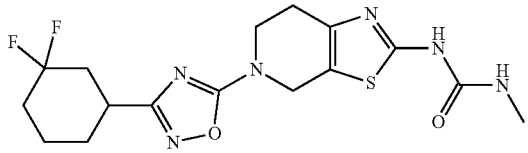 [SMILES: CNC(=O)Nc1nc2c(s1)CN(c1nc(C3CCCC(F)(F)C3)no1)CC2] | $^1$H NMR (400 MHz, DMSO-d$_6$): δ (ppm) = 10.65-10.30 (1H, br s), 6.56 (1H, s), 4.66 (2H, s), 3.85 (2H, t, J = 5.6 Hz), 2.82 (1H, t, J = 11.6 Hz), 2.74-2.69 (2H, m), 2.68 (3H, d, J = 4.8 Hz), 2.37-2.21 (1H, m), 2.17-1.99 (2H, m), 1.96-1.73 (3H, m), 1.67-1.40 (2H, m). MS (ESI) m/z: 399 (M + H)$^+$ |
| 37(37b) | 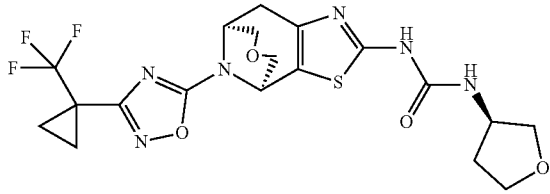 [SMILES: O=C(Nc1nc2c(s1)[C@@H]1COC[C@H](C2)N1c1nc(C2(C(F)(F)F)CC2)no1)N[C@@H]1CCOC1] | $^1$H NMR (500 MHz, DMSO-d$_6$): δ (ppm) = 10.08 (1H, s), 6.83 (1H, d, J = 6.8 Hz), 5.24 (1H, s), 4.33 (1H, d, J = 7.1 Hz), 4.27-4.18 (1H, m), 3.93 (1H, d, J = 11.2 Hz), 3.85-3.67 (5H, m), 3.58 (1H, d, J = 10.7 Hz), 3.50 (1H, dd, J = 9.0, 3.2 Hz), 3.08 (1H, dd, J = 17.3, 7.1 Hz), 2.74 (1H, d, J = 17.3 Hz), 2.19-2.09 (1H, m), 1.76-1.67 (1H, m), 1.49-1.43 (2H, m), 1.43-1.35 (2H, m). MS (APCI/ESI) m/z: 487 (M + H)$^+$ |
| 38(38a) | 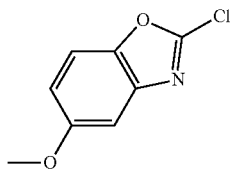 | $^1$H NMR (500 MHz, CDCl$_3$): δ (ppm) = 7.38 (1H, d, J = 9.3 Hz), 7.15 (1H, d, J = 2.4 Hz), 6.95 (1H, dd, J = 9.3, 2.4 Hz), 3.85 (3H, s). MS (APCI) m/z: 184 (M + H)$^+$ |
| 38(38b) | 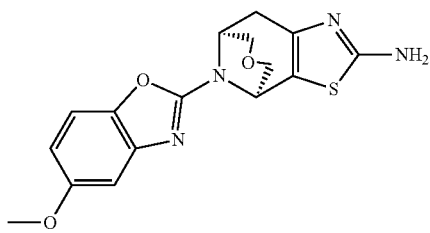 [SMILES: COc1ccc2oc(N3[C@@H]4COC[C@H]3c3sc(N)nc3C4)nc2c1] | $^1$H NMR (400 MHz, CDCl$_3$): δ (ppm) = 7.07 (1H, d, J = 8.8 Hz), 6.87 (1H, d, J = 2.4 Hz), 6.55 (1H, dd, J = 8.8, 2.4 Hz), 5.10 (1H, s), 4.89 (2H, s), 4.44 (1H, d, J = 6.8 Hz), 3.94 (2H, s), 3.85 (1H, dd, J = 11.2, 2.0 Hz), 3.73 (3H, s), 3.69-3.65 (1H, m), 3.26 (1H, dd, J = 17.2, 7.2 Hz), 2.69 (1H, d, J = 17.2 Hz). |
| 38(38c) | 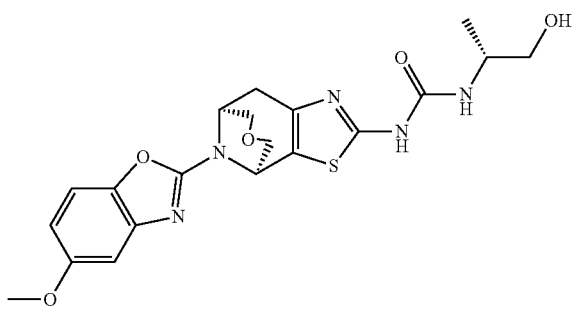 [SMILES: COc1ccc2oc(N3[C@@H]4COC[C@H]3c3sc(NC(=O)N[C@H](C)CO)nc3C4)nc2c1] | $^1$H NMR (400 MHz, CDCl$_3$): δ (ppm) = 7.16 (1H, d, J = 8.8 Hz), 6.94 (1H, d, J = 2.4 Hz), 6.64 (1H, dd, J = 8.8, 2.4 Hz), 5.27 (1H, s), 4.55 (1H, d, J = 7.2 Hz), 4.05-3.95 (4H, m), 3.81 (3H, s), 3.76 (1H, d, J = 10.0 Hz), 3.70 (1H, dd, J = 11.2, 4.0 Hz), 3.57 (1H, dd, J = 11.2, 5.6 Hz), 3.41 (1H, dd, J = 17.2, 7.2 Hz), 2.81 (1H, d, J = 17.2 Hz), 1.20 (3H, d, J = 6.8 Hz). MS (ESI) m/z: 446 (M + H)$^+$ |

TABLE 2-18

| | | |
|---|---|---|
| 39(39a) | 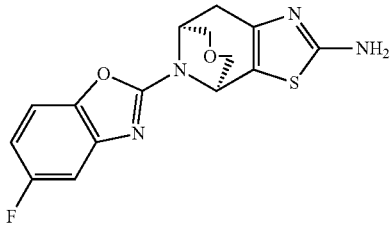 [SMILES: Nc1nc2c(s1)[C@@H]1COC[C@H](C2)N1c1nc2cc(F)ccc2o1] | $^1$H NMR (400 MHz, DMSO-$d_6$): δ (ppm) = 7.43 (1H, dd, J = 8.8, 4.4 Hz), 7.19 (1H, dd, J = 8.8, 2.8 Hz), 6.92-6.82 (3H, m), 5.17 (1H, s), 4.40 (1H, d, J = 6.4 Hz), 3.95 (1H, d, J = 11.6 Hz), 3.85 (1H, dd, J = 11.6, 2.4 Hz), 3.77 (1H, dd, J = 11.2, 1.6 Hz), 3.60 (1H, d, J = 11.2 Hz), 3.04 (1H, dd, J = 17.2, 6.4 Hz), 2.61 (1H, d, J = 17.2 Hz). MS (ESI) m/z: 333 (M + H)$^+$ |
| 39(39b) | 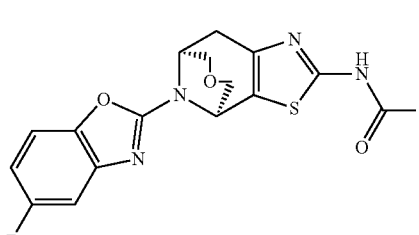 | $^1$H NMR (400 MHz, DMSO-$d_6$): δ (ppm) = 7.44 (1H, dd, J = 8.8, 4.4 Hz), 7.18 (1H, dd, J = 8.8, 2.4 Hz), 6.91-6.83 (1H, m), 6.47 (1H, d, J = 8.0 Hz), 5.34 (1H, s), 4.85-4.82 (1H, m), 4.45 (1H, d, J = 7.2 Hz), 3.97 (1H, d, J = 11.6 Hz), 3.89-3.78 (2H, m), 3.73-3.62 (2H, m), 3.37-3.31 (2H, m), 3.15 (1H, dd, J = 17.2, 6.8 Hz), 2.74 (1H, d, J = 17.6 Hz), 1.05 (3H, d, J = 6.8 Hz). MS (ESI) m/z: 434 (M + H)$^+$ |
| 40(40a) | 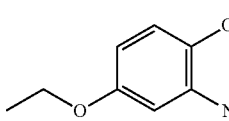 | $^1$H NMR (400 MHz, DMSO-$d_6$): δ (ppm) = 8.43 (1H, br s), 6.50 (1H, d, J = 8.4 Hz), 6.19 (1H, d, J = 2.8 Hz), 5.94 (1H, dd, J = 8.4, 2.8 Hz), 4.51 (2H, br s), 3.84 (2H, q, J = 7.2 Hz), 1.25 (3H, t, J = 7.2 Hz). |
| 40(40b) | 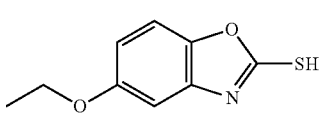 | $^1$H NMR (400 MHz, CDCl$_3$): δ (ppm) = 10.93 (1H, br s), 7.16 (1H, d, J = 8.8 Hz), 6.71 (1H, dd, J = 8.8 Hz, 2.4 Hz), 6.66 (1H, d, J = 2.4 Hz), 3.97 (2H, q, J = 7.2 Hz), 1.36 (3H, t, J = 7.2 Hz). MS (ESI) m/z: 196 (M + H)$^+$ |
| 40(40c) | 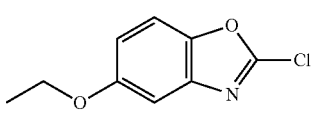 | MS (ESI) m/z: 198 (M + H)$^+$ |
| 40(40d) | 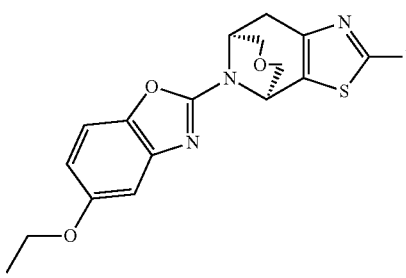 | $^1$H NMR (400 MHz, CD$_3$OD): δ (ppm) = 7.24 (1H, d, J = 8.8 Hz), 6.88 (1H, d, J = 2.4 Hz), 6.68 (1H, dd, J = 8.8 Hz, 2.4 Hz), 5.16 (1H, s), 4.48 (1H, d, J = 6.0 Hz), 4.06-3.96 (4H, m), 3.92-3.89 (1H, m), 3.74-3.72 (1H, m), 3.24-3.18 (1H, m), 2.71 (1H, d, J = 7.2 Hz), 1.39 (3H, t, J = 6.8 Hz). MS (ESI) m/z: 359 (M + H)$^+$ |
| 40(40e) | 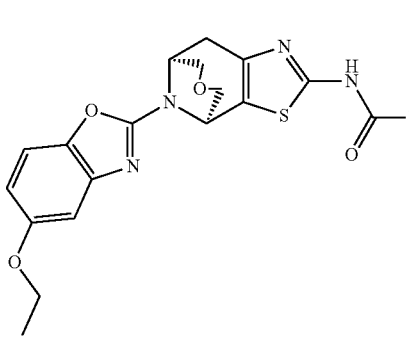 | $^1$H NMR (400 MHz, CD$_3$OD): δ (ppm) = 7.24 (1H, d, J = 8.8 Hz,), 6.88 (1H, d, J = 2.4 Hz), 6.67 (1H, dd, J = 2.4, 8.8 Hz), 5.32 (1H, s), 4.56-4.50 (1H, m), 4.09-3.94 (5H, m), 3.77 (1H, d, J = 10.0 Hz), 3.28 (1H, d, J = 7.2 Hz), 3.23 (2H, s), 2.84 (1H, d, J = 17.6 Hz), 1.39 (3H, t, J = 7.2 Hz), 1.21 (6H, d, J = 2.0 Hz). MS (ESI) m/z: 474 (M + H)$^+$ |

TABLE 2-19

| | | |
|---|---|---|
| 41(41a) | 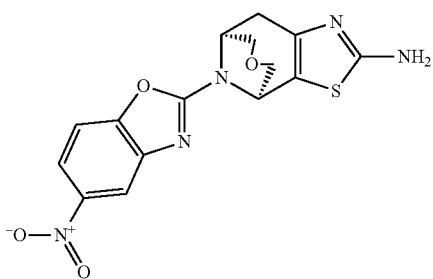 | ¹H NMR (400 MHz, DMSO-d₆): δ (ppm) = 8.13 (1H, d, J = 2.4 Hz), 8.04-8.00 (1H, m), 7.67 (1H, d, J = 8.8 Hz), 6.87 (2H, s), 5.26 (1H, s), 4.48 (1H, d, J = 6.4 Hz), 4.00-3.95 (1H, m), 3.89-3.84 (1H, m), 3.79 (1H, d, J = 10.8 Hz), 3.62 (1H, d, J = 10.8 Hz), 3.07 (1H, dd, J = 17.2,7.2 Hz), 2.66 (1H, d, J = 17.2 Hz). |
| 41(41b) | 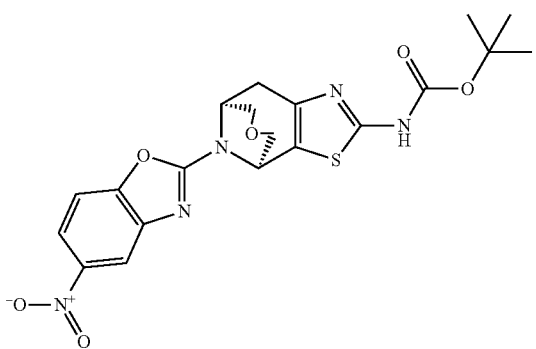 | ¹H NMR (400 MHz, CDCl₃): δ (ppm) = 9.63 (1H, s), 8.19 (1H, d, J = 2.4 Hz), 8.05 (1H, dd, J = 8.8, 2.4 Hz), 7.34 (1H, d, J = 8.8 Hz), 5.36 (1H, s), 4.61 (1H, d, J = 6.8 Hz), 4.05 (2H, s), 4.00 (1H, dd, J = 11.2, 1.6 Hz), 3.81 (1H, d, J = 10.8 Hz), 3.45 (1H, dd, J = 17.2, 7.2 Hz), 2.95 (1H, d, J = 17.2 Hz), 1.54 (9H, s). |
| 41(41c) | 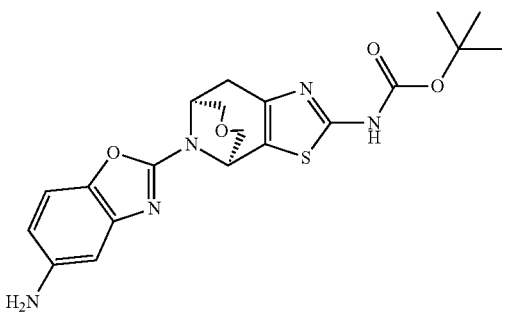 [SMILES: CC(C)(C)OC(=O)Nc1nc2c(s1)[C@@H]1COC[C@H](C2)N1c1nc2cc(N)ccc2o1] | ¹H NMR (400 MHz, CDCl₃): δ (ppm) = 10.11 (1H, d, J = 1.2 Hz), 7.02 (1H, d, J = 8.4 Hz), 6.69 (1H, d, J = 2.4 Hz), 6.39 (1H, dd, J = 8.4, 2.4 Hz), 5.29 (1H, s), 4.53 (1H, d, J = 6.8 Hz), 4.02-3.95 (3H, m), 3.77 (1H, dd, J = 10.8, 1.2 Hz), 3.60 (2H, s), 3.44 (1H, dd, J = 17.2, 7.2 Hz), 2.90 (1H, d, J = 17.2 Hz), 1.53 (9H, s). |
| 41(41d) | 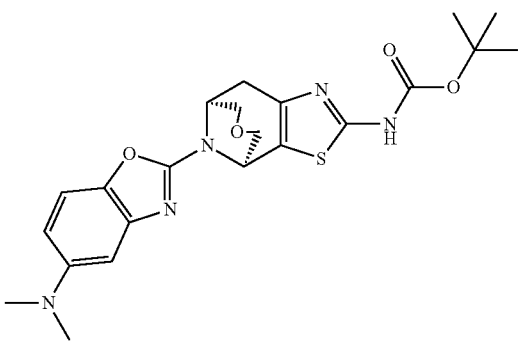 [SMILES: CN(C)c1ccc2oc(N3[C@@H]4COC[C@H]3c3sc(NC(=O)OC(C)(C)C)nc3C4)nc2c1] | MS (ESI) m/z: 458 (M + H)⁺ |
| 41(41e) | 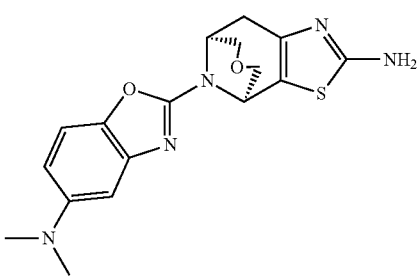 [SMILES: CN(C)c1ccc2oc(N3[C@@H]4COC[C@H]3c3sc(N)nc3C4)nc2c1] | ¹H NMR (400 MHz, CDCl₃): δ (ppm) = 7.05 (1H, d, J = 8.8 Hz), 6.75 (1H, d, J = 2.4 Hz), 6.43 (1H, dd, J = 8.8, 2.4 Hz), 5.10 (1H, s), 4.82 (2H, s), 4.44-4.41 (1H, m), 3.95-3.80 (3H, m), 3.70-3.60 (1H, m), 3.27 (1H, dd, J = 17.2, 7.2 Hz), 2.84 (6H, s), 2.68 (1H, d, J = 17.2 Hz). MS (ESI) m/z: 358 (M + H)⁺ |

TABLE 2-19-continued

| | | |
|---|---|---|
| 41(41f) | 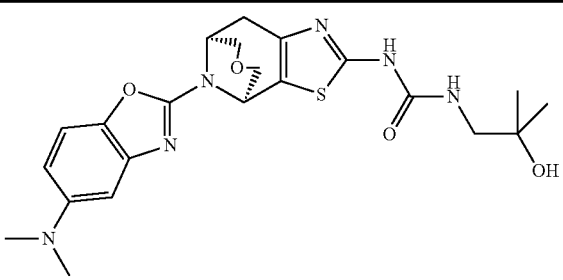 | ¹H NMR (400 MHz, CDCl₃): δ (ppm) = 7.14 (1H, d, J = 8.8 Hz), 6.83 (1H, d, J = 2.4 Hz), 6.53 (1H, dd, J = 8.8, 2.4 Hz), 5.27 (1H, s), 4.55 (1H, d, J = 6.8 Hz), 4.10-3.92 (3H, m), 3.76 (1H, dd, J = 11.2, 1.2 Hz), 3.41 (1H, dd, J = 17.2, 7.2 Hz), 3.31 (2H, d, J = 6.0 Hz), 2.93 (6H, s), 2.80 (1H, s), 1.24 (6H, d, J = 2.0 Hz). MS (ESI) m/z: 473 (M + H)⁺ |

TABLE 2-20

| | | |
|---|---|---|
| 42(42a) | 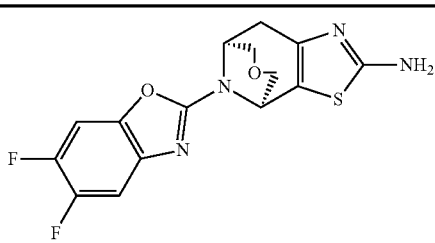 | MS (ESI) m/z: 351 (M + H)⁺ |
| 42(42b) | 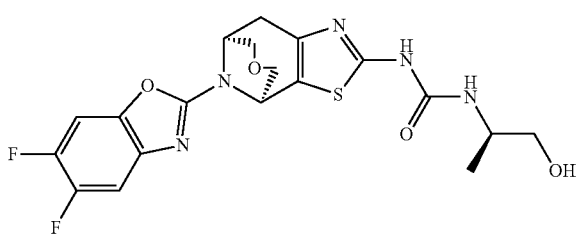 [SMILES: C[C@H](CO)NC(=O)Nc1nc2c(s1)[C@@H]1COC[C@H](C2)N1c1nc2cc(F)c(F)cc2o1] | ¹H NMR (400 MHz, CDCl₃): δ (ppm) = 7.21-7.11 (2H, m), 5.25 (1H, s), 4.53 (1H, d, J = 6.8 Hz), 4.10-3.91 (4H, m), 3.83-3.67 (2H, m), 3.59 (1H, dd, J = 10.8, 5.6 Hz), 3.40 (1H, dd, J = 17.2, 7.2 Hz), 2.84 (1H, d, J = 17.2 Hz), 1.23 (3H, d, J = 6.8 Hz) MS (ESI) m/z: 452 (M + H)⁺ |
| 43(43a) | 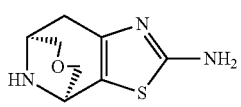 [SMILES: Nc1nc2c(s1)[C@@H]1COC[C@H](C2)N1] | ¹H NMR (500 MHz, DMSO-d₆): δ (ppm) = 6.63 (2H, s), 3.75 (1H, s), 3.71 (1H, dd, J = 10.8, 2.5 Hz), 3.66 (1H, d, J = 10.8 Hz), 3.61 (1H, dd, J = 10.3, 1.9 Hz), 3.33 (1H, d, J = 10.3 Hz), 3.07 (1H, d, J = 7.0 Hz), 2.75 (1H, dd, J = 16.7, 7.0 Hz), 2.67-2.59 (1H, m), 2.37 (1H, d, J = 16.7 Hz). MS (APCI) m/z: 198 (M + H)⁺ |
| 43(43b) | 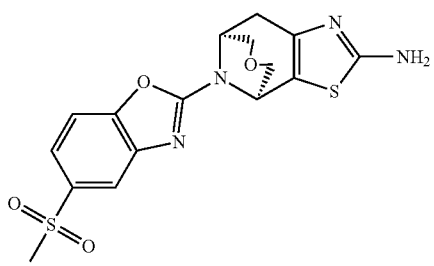 [SMILES: CS(=O)(=O)c1ccc2oc(N3[C@@H]4COC[C@H]3c3sc(N)nc3C4)nc2c1] | ¹H NMR (500 MHz, DMSO-d₆): δ (ppm) = 7.84 (1H, d, J = 1.5 Hz), 7.70 (1H, d, J = 8.3 Hz), 7.65 (1H, dd, J = 8.3, 1.5 Hz), 7.10 (2H, s), 5.26 (1H, s), 4.48 (1H, d, J = 6.8 Hz), 3.98 (1H, d, J = 11.2 Hz), 3.86 (1H, d, J = 11.2 Hz), 3.79 (1H, d, J = 11.2 Hz), 3.62 (1H, d, J = 11.2 Hz), 3.20 (3H, s), 3.07 (1H, dd, J = 17.1, 6.8 Hz), 2.65 (1H, d, J = 17.1 Hz). MS (APCI) m/z: 393 (M + H)⁺ |
| 43(43c) | 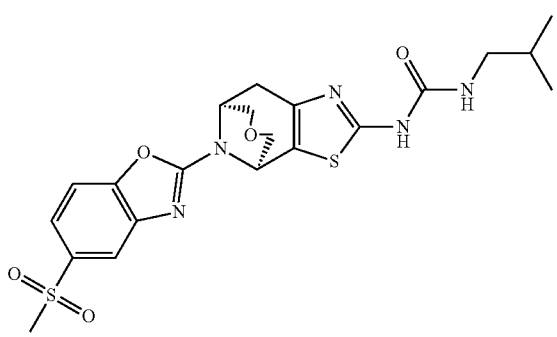 [SMILES: CC(C)CNC(=O)Nc1nc2c(s1)[C@@H]1COC[C@H](C2)N1c1nc2cc(S(C)(=O)=O)ccc2o1] | ¹H NMR (500 MHz, DMSO-d₆): δ (ppm) = 10.17 (1H, s), 7.83 (1H, s), 7.70 (1H, d, J = 8.3 Hz), 7.64 (1H, dd, J = 8.3, 1.5 Hz), 6.57 (1H, s), 5.41 (1H, s), 4.53 (1H, d, J = 6.8 Hz), 3.99 (1H, d, J = 11.7 Hz), 3.89 (1H, d, J = 11.7 Hz), 3.84 (1H, d, J = 10.7 Hz), 3.65 (1H, d, J = 10.7 Hz), 3.20 (3H, s), 3.17 (1H, dd, J = 17.1, 6.8 Hz), 2.95 (2H, t, J = 5.4 Hz), 2.77 (1H, d, J = 17.1 Hz), 1.72-1.66 (1H, m), 0.85 (6H, d, J = 6.8 Hz). MS (APCI) m/z: 492 (M + H)⁺ |

TABLE 2-20-continued

| 44(44a) | 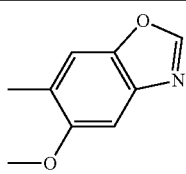 | ¹H NMR (500 MHz, CDCl₃): δ (ppm) = 8.00 (1H, s), 7.35 (1H, s), 7.18 (1H, s), 3.89 (3H, s), 2.34 (3H, s). MS (APCI) m/z: 164 (M + H)⁺ |

TABLE 2-21

| 44(44b) | 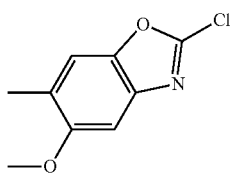 | ¹H NMR (500 MHz, CDCl₃): δ (ppm) = 7.26 (1H, s), 7.07 (1H, s), 3.90-3.86 (3H, m), 2.31 (3H, s). MS (APCI) m/z: 198 (M + H)⁺ |
| 44(44c) | 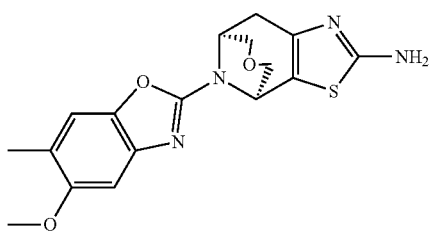 [SMILES: COc1cc2nc(N3[C@@H]4COC[C@H]3c3sc(N)nc3C4)oc2cc1C] | ¹H NMR (500 MHz, DMSO-d₆): δ (ppm) = 7.24 (1H, s), 6.97 ( H, s), 6.82 (2H, s), 5.11 (1H, s), 4.35 (1H, d, J = 6.7 Hz), 3.95 (1H, d, J = 11.2 Hz), 3.84 (1H, d, J = 11.2 Hz), 3.80-3.74 (4H, m), 3.59 (1H, d, J = 11.2 Hz), 3.03 (1H, dd, J = 17.3, 6.7 Hz), 2.58 (1H, d, J = 17.1 Hz), 2.17 (3H, s). MS (APCI) m/z: 359 (M + H)⁺ |
| 44(44d) | 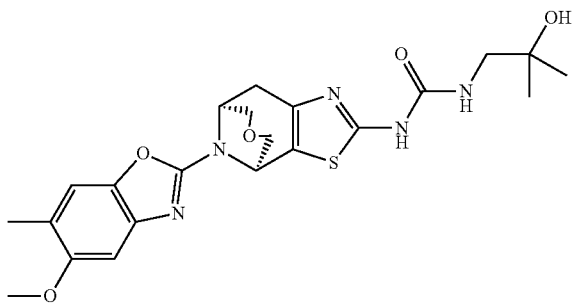 [SMILES: COc1cc2nc(N3[C@@H]4COC[C@H]3c3sc(NC(=O)NCC(C)(C)O)nc3C4)oc2cc1C] | ¹H NMR (500 MHz, DMSO-d₆): δ (ppm) = 10.21 (1H, s), 7.23 (1H, s), 6.96 (1H, s), 6.59 (1H, s), 5.27 (1H, s), 4.56 (1H, s), 4.40 (1H, d, J = 7.1 Hz), 3.97 (1H, d, J = 11.2 Hz), 3.86 (1H, d, J = 11.2 Hz), 3.81 (1H, d, J = 10.7 Hz), 3.76 (3H, s), 3.63 (1H, d, J = 10.7 Hz), 3.13 (1H, dd, J = 17.3, 7.1 Hz), 3.05 (2H, d, J = 5.4 Hz), 2.71 (1H, d, J = 17.3 Hz), 2.16 (3H, s), 1.06 (6H, d, J = 2.0 Hz). MS (APCI) m/z: 474 (M + H)⁺ |
| 45 | 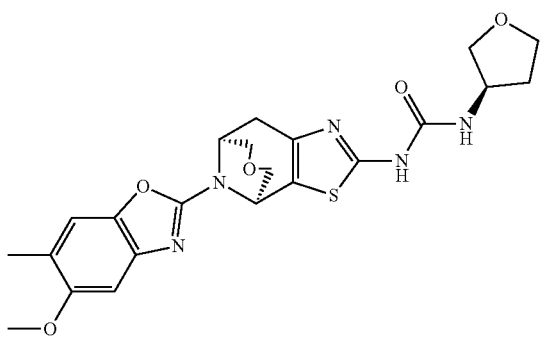 [SMILES: COc1cc2nc(N3[C@@H]4COC[C@H]3c3sc(NC(=O)N[C@@H]5CCOC5)nc3C4)oc2cc1C] | ¹H NMR (500 MHz, DMSO-d₆): δ (ppm) = 10.02 (1H, s), 7.23 (1H, s), 6.96 (1H, s), 6.81 (1H, d, J = 6.8 Hz), 5.28 (1H, s), 4.41 (1H, d, J = 7.1 Hz), 4.22 (1H, s), 3.97 (1H, d, J = 11.2 Hz), 3.89-3.61 (9H, m), 3.49 (1H, dd, J = 9.0, 3.2 Hz), 3.13 (1H, dd, J = 17.2, 7.1 Hz), 2.72 (1H, d, J = 17.2 Hz), 2.16 (3H, s), 2.15-2.08 (1H, m), 1.74-1.66 (1H, m). MS (APCI) m/z: 472 (M + H)⁺ |

TABLE 2-21-continued

| 46 | 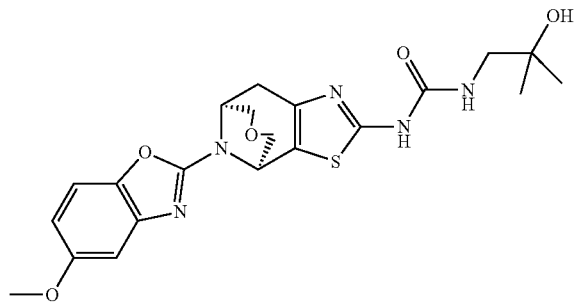 [SMILES: COc1ccc2oc(N3[C@@H]4COC[C@H]3c3sc(NC(=O)NCC(C)(C)O)nc3C4)nc2c1] | $^1$H NMR (500 MHz, DMSO-$d_6$): δ (ppm) = 10.22 (1H, s), 7.31 (1H, d, J = 8.8 Hz), 6.93 (1H, d, J = 2.4 Hz), 6.62 (1H, dd, J = 8.8, 2.4 Hz), 6.59 (1H, s), 5.31 (1H, s), 4.56 (1H, s), 4.44 (1H, d, J = 6.9 Hz), 3.97 (1H, d, J = 11.7 Hz), 3.86 (1H, d, J = 11.7 Hz), 3.81 (1H, d, J = 10.7 Hz), 3.73 (3H, s), 3.64 (1H, d, J = 10.7 Hz), 3.13 (1H, dd, J = 17.1, 6.9 Hz), 3.05 (2H, d, J = 5.4 Hz), 2.73 (1H, d, J = 17.1 Hz), 1.07 (6H, s). MS (APCI) m/z: 460 (M + H)$^+$ |

15

TABLE 2-22

| 47 | 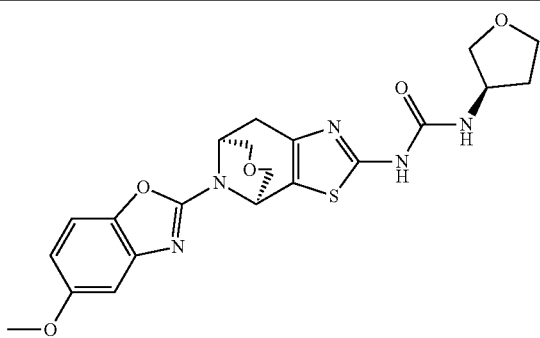 | $^1$H NMR (500 MHz, DMSO-$d_6$): δ (ppm) = 10.03 (1H, s), 7.32 (1H, d, J = 8.8 Hz), 6.94 (1H, d, J = 2.4 Hz), 6.81 (1H, d, J = 6.8 Hz), 6.62 (1H, dd, J = 8.8, 2.4 Hz), 5.32 (1H, s), 4.44 (1H, d, J = 7.1 Hz), 4.22 (1H, s), 3.98 (1H, d, J = 11.7 Hz), 3.91-3.61 (9H, m), 3.51-3.47 (1H, m), 3.14 (1H, dd, J = 17.3, 7.1 Hz), 2.74 (1H, d, J = 17.3 Hz), 2.18-2.08 (1H, m), 1.75-1.67 (1H, m). MS (APCI) m/z: 458 (M + H)$^+$ |
| 48 | 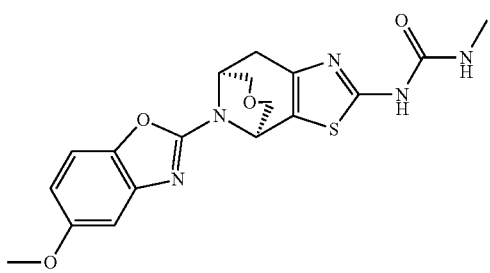 | $^1$H NMR (500 MHz, DMSO-$d_6$): δ (ppm) = δ: 10.37 (1H, s), 7.32 (1H, d, J = 8.8 Hz), 6.93 (1H, d, J = 2.4 Hz), 6.62 (1H, dd, J = 8.8, 2.4 Hz), 6.38 (1H, s), 5.31 (1H, s), 4.44 (1H, d, J = 7.3 Hz), 3.97 (1H, d, J = 11.2 Hz), 3.86 (1H, d, J = 11.2 Hz), 3.82 (1H, d, J = 10.7 Hz), 3.73 (3H, s), 3.64 (1H, d, J = 10.7 Hz), 3.14 (1H, dd, J = 17.1, 7.3 Hz), 2.73 (1H, d, J = 17.1 Hz), 2.66 (3H, d, J = 4.9 Hz). MS (APCI) m/z: 402 (M + H)$^+$ |
| 49 | 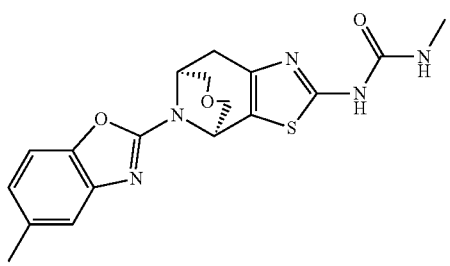 [SMILES: CNC(=O)Nc1nc2c(s1)[C@@H]1COC[C@H](C2)N1c1nc2cc(C)ccc2o1] | $^1$H NMR (500 MHz, DMSO-$d_6$): δ (ppm) = 10.37 (1H, s), 7.30 (1H, d, J = 7.8 Hz), 7.14 (1H, s), 6.87 (1H, d, J = 7.8 Hz), 6.38 (1H, s), 5.32 (1H, s), 4.45 (1H, d, J = 7.1 Hz), 3.97 (1H, d, J = 11.5 Hz), 3.87 (1H, d, J = 11.5 Hz), 3.82 (1H, d, J = 11.2 Hz), 3.64 (1H, d, J = 11.2 Hz), 3.14 (1H, dd, J = 17.3, 7.1 Hz), 2.73 (1H, d, J = 17.1 Hz), 2.66 (3H, d, J = 4.9 Hz), 2.33 (3H, s). MS (APCI) m/z: 386 (M + H)$^+$ |
| 50 | 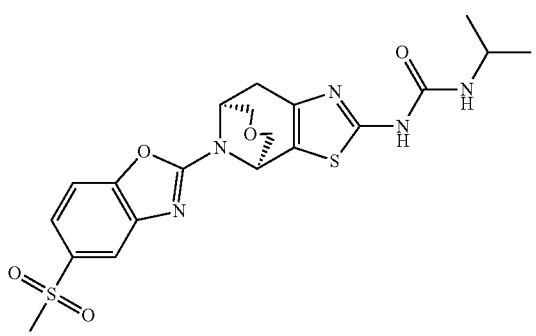 [SMILES: CC(C)NC(=O)Nc1nc2c(s1)[C@@H]1COC[C@H](C2)N1c1nc2cc(S(C)(=O)=O)ccc2o1] | $^1$H NMR (500 MHz, DMSO-$d_6$): δ (ppm) = 10.04 (1H, s), 7.83 (1H, d, J = 1.5 Hz), 7.70 (1H, d, J = 8.3 Hz), 7.64 (1H, dd, J = 8.5, 1.7 Hz), 6.38 (1H, d, J = 7.3 Hz), 5.41 (1H, s), 4.53 (1H, d, J = 7.3 Hz), 3.99 (1H, d, J = 11.2 Hz), 3.88 (1H, d, J = 11.2 Hz), 3.84 (1H, d, J = 11.2 Hz), 3.80-3.72 (1H, m), 3.65 (1H, d, J = 11.2 Hz), 3.21-3.13 (4H, m), 2.77 (1H, d, J = 17.6 Hz), 1.09 (6H, t, J = 5.9 Hz). MS (APCI) m/z: 478 (M + H)$^+$ |

TABLE 2-22-continued

| 51 | 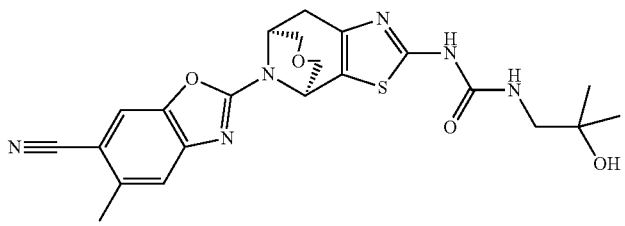 [SMILES: Cc1cc2nc(N3[C@@H]4COC[C@H]3c3sc(NC(=O)NCC(C)(C)O)nc3C4)oc2cc1C#N] | ¹H NMR (500 MHz, DMSO-d₆): δ (ppm) = 10.24 (1H, s), 7.90 (1H, s), 7.36 (1H, s), 6.60 (1H, s), 5.41 (1H, s), 4.55 (1H, s), 4.52 (1H, d, J = 7.1 Hz), 3.98 (1H, d, J = 11.6 Hz), 3.87 (1H, dd, J = 11.6, 2.6 Hz), 3.82 (1H, dd, J = 11.2, 1.8 Hz), 3.64 (1H, d, J = 11.2 Hz), 3.15 (1H, dd, J = 17.3, 7.1 Hz), 3.09-3.01 (2H, m), 2.77 (1H, d, J = 17.3 Hz), 2.48 (3H, s), 1.07 (6H, d, J = 1.4 Hz). MS (APCI) m/z: 469 (M + H)⁺ |

TABLE 2-23

| 52 | 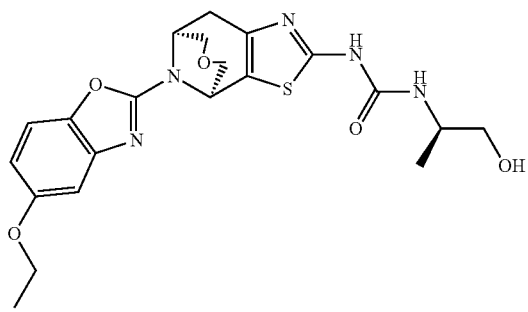 [SMILES: CCOc1ccc2oc(N3[C@@H]4COC[C@H]3c3sc(NC(=O)N[C@H](C)CO)nc3C4)nc2c1] | ¹H NMR (400 MHz, CD₃OD): δ (ppm) = 7.22 (1H, d, J = 8.8 Hz), 6.86 (1H, d, J = 2.4 Hz), 6.65 (1H, dd, J = 8.8, 2.4 Hz), 5.30 (1H, s), 4.51 (1H, br d, J = 7.2 Hz), 4.06-3.91 (5H, m), 3.90-3.81 (1H, m), 3.75 (1H, dd, J = 11.2, 1.2 Hz), 3.58-3.48 (2H, m), 3.30-3.23 (1H, m), 2.81 (1H, d, J = 17.2 Hz), 1.37 (3H, t, J = 7.2 Hz), 1.17 (3H, d, J = 6.8 Hz). MS (ESI) m/z: 460 (M + H)⁺ |
| 53(53a) | 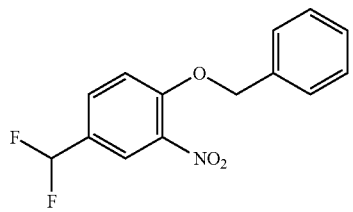 [SMILES: O=[N+]([O-])c1cc(C(F)F)ccc1OCc1ccccc1] | ¹H NMR (500 MHz, CDCl₃): δ (ppm) = 8.01 (1H, s), 7.64 (1H, d, J = 8.8 Hz), 7.47-7.32 (5H, m), 7.20 (1H, d, J = 8.8 Hz), 6.63 (1H, t, J = 56.1 Hz), 5.28 (2H, s). |
| 53(53b) | 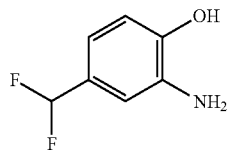 [SMILES: Nc1cc(C(F)F)ccc1O] | ¹H NMR (500 MHz, DMSO-d₆): δ (ppm) = 9.52 (1H, s), 6.76 (1H, s), 6.74 (1H, t, J = 56.6 Hz), 6.69 (1H, d, J = 7.8 Hz), 6.58 (1H, d, J = 7.8 Hz), 4.79 (2H, s). |
| 53(53c) | 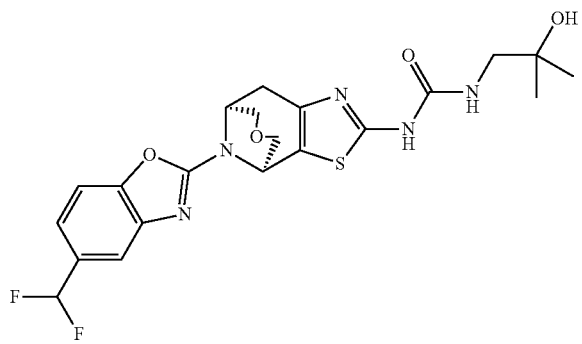 [SMILES: CC(C)(O)CNC(=O)Nc1nc2c(s1)[C@@H]1COC[C@H](C2)N1c1nc2cc(C(F)F)ccc2o1] | ¹H NMR (500 MHz, DMSO-d₆): δ (ppm) = 10.23 (1H, s), 7.57 (1H, d, J = 8.3 Hz), 7.52 (1H, s), 7.29 (1H, d, J = 8.3 Hz), 7.04 (1H, t, J = 56.1 Hz), 6.59 (1H, s), 5.38 (1H, s), 4.56 (1H, s), 4.50 (1H, d, J = 7.1 Hz), 3.99 (1H, d, J = 11.7 Hz), 3.88 (1H, d, J = 11.7 Hz), 3.83 (1H, d, J = 10.7 Hz), 3.65 (1H, d, J = 10.7 Hz), 3.16 (1H, dd, J = 17.3, 7.1 Hz), 3.10-3.01 (2H, m), 2.75 (1H, d, J = 17.3 Hz), 1.07-1.07 (6H, m). MS (APCI) m/z: 480 (M + H)⁺ |

TABLE 2-23-continued

| 54 | 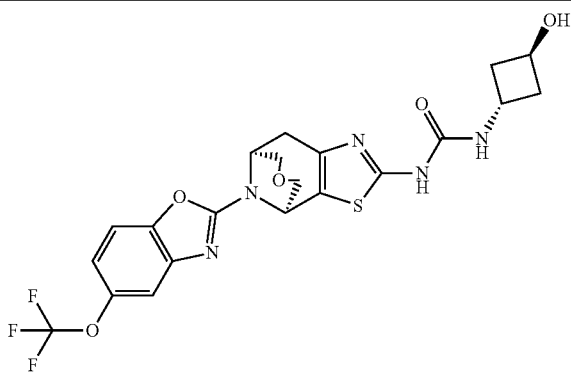 | ¹H NMR (500 MHz, DMSO-d₆): δ (ppm) = 10.08 (1H, s), 7.54 (1H, d, J = 8.8 Hz), 7.37 (1H, s), 7.06 (1H, d, J = 8.8 Hz), 6.80 (1H, d, J = 5.9 Hz), 5.37 (1H, s), 5.03 (1H, d, J = 5.4 Hz), 4.49 (1H, d, J = 7.1 Hz), 4.27-4.12 (2H, m), 3.98 (1H, d, J = 11.2 Hz), 3.87 (1H, d, J = 11.2 Hz), 3.82 (1H, d, J = 10.7 Hz), 3.64 (1H, d, J = 10.7 Hz), 3.16 (1H, dd, J = 17.3, 7.1 Hz), 2.76 (1H, d, J = 17.3 Hz), 2.16-2.05 (4H, m). MS (APCI) m/z: 512 (M + H)⁺ |
| --- | --- | --- |
| 55 | 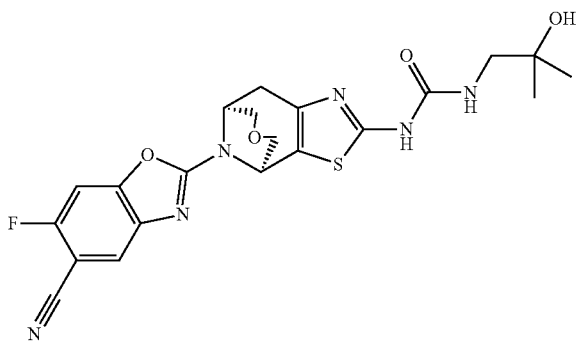 [SMILES: CC(C)(O)CNC(=O)Nc1nc2c(s1)[C@@H]1COC[C@H](C2)N1c1nc2cc(C#N)c(F)cc2o1] | ¹H NMR (500 MHz, DMSO-d₆): δ (ppm) = 10.24 (1H, s), 7.91-7.88 (1H, m), 7.86-7.82 (1H, m), 6.59 (1H, s), 5.36 (1H, s), 4.57 (1H, s), 4.48 (1H, d, J = 7.1 Hz), 3.98 (1H, d, J = 11.7 Hz), 3.87 (1H, d, J = 11.7 Hz), 3.82 (1H, d, J = 11.2 Hz), 3.64 (1H, d, J = 11.2 Hz), 3.15 (1H, dd, J = 17.3, 7.1 Hz), 3.08-3.03 (2H, m), 2.77 (1H, d, J = 17.3 Hz), 1.07 (6H, s). MS (APCI) m/z: 473 (M + H)⁺ |

TABLE 2-24

| 56 | 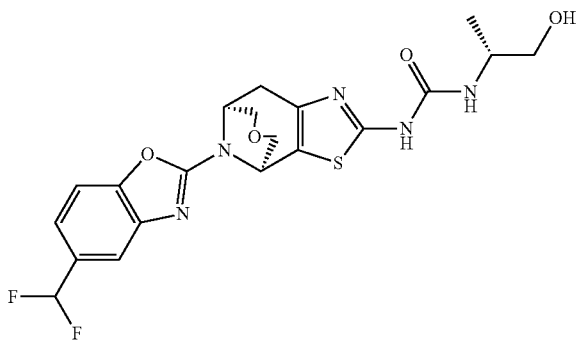 [SMILES: C[C@H](CO)NC(=O)Nc1nc2c(s1)[C@@H]1COC[C@H](C2)N1c1nc2cc(C(F)F)ccc2o1] | ¹H NMR (500 MHz, DMSO-d₆): δ (ppm) = 10.13 (1H, s), 7.57 (1H, d, J = 8.3 Hz), 7.53 (1H, s), 7.29 (1H, d, J = 8.3 Hz), 7.04 (1H, t, J = 55.9 Hz), 6.47 (1H, d, J = 8.3 Hz), 5.38 (1H, s), 4.50 (1H, d, J = 7.3 Hz), 3.98 (1H, d, J = 11.2 Hz), 3.88 (1H, d, J = 11.2 Hz), 3.83 (1H, d, J = 10.7 Hz), 3.73-3.66 (1H, m), 3.64 (1H, d, J = 10.7 Hz), 3.37-3.34 (2H, m), 3.16 (1H, dd, J = 17.1, 7.3 Hz), 2.75 (1H, d, J = 17.1 Hz), 1.22 (1H, br s), 1.05 (3H, d, J = 6.3 Hz). MS (APCI) m/z: 466 (M + H)⁺ |
| --- | --- | --- |
| 57(57a) | 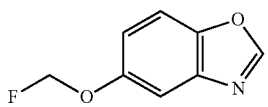 [SMILES: FCOc1ccc2ocnc2c1] | ¹H NMR (400 MHz, CDCl₃): δ (ppm) = 8.11 (1H, s), 7.57-7.49 (2H, m), 7.16 (1H, dd, J = 8.8, 2.4 Hz), 5.75 (2H, d, J = 54.4 Hz). |
| 57(57b) | 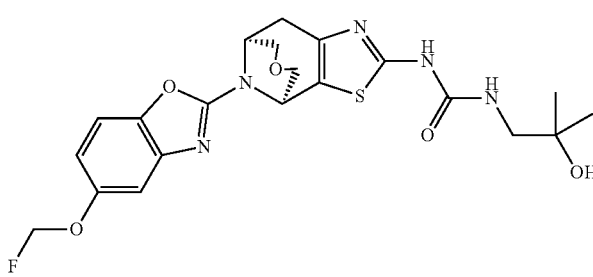 [SMILES: CC(C)(O)CNC(=O)Nc1nc2c(s1)[C@@H]1COC[C@H](C2)N1c1nc2cc(OCF)ccc2o1] | ¹H NMR (400 MHz, CDCl₃): δ (ppm) = 7.19 (1H, d, J = 8.8 Hz), 7.13 (1H, d, J = 2.4 Hz), 6.81 (1H, dd, J = 8.8, 2.4 Hz), 5.75 (1H, s), 5.61 (1H, s), 5.26 (1H, s), 4.55 (1H, d, J = 7.2 Hz), 4.02 (2H, s), 3.96 (1H, dd, J = 11.2, 2.0 Hz), 3.78-3.73 (1H, m), 3.40 (1H, d, J = 17.2, 7.2 Hz), 3.35-3.24 (2H, m), 2.83 (1H, d, J =17.2 Hz), 1.25-1.20 (6H, m). MS (ESI) m/z: 478 (M + H)⁺ |

TABLE 2-24-continued

| | | |
|---|---|---|
| 58 | 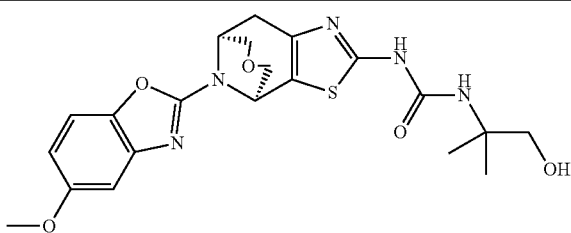 | $^1$H NMR (400 MHz, CDCl$_3$): δ (ppm) = 7.16 (1H, d, J = 8.8 Hz), 6.94 (1H, d, J = 2.4 Hz), 6.64 (1H, dd, J = 8.8, 2.4 Hz), 5.26 (1H, s), 4.55 (1H, d, J = 6.4 Hz), 4.03 (2H, d, J = 1.6 Hz), 3.97 (1H, dd, J = 11.2, 1.6 Hz), 3.81 (3H, s), 3.76 (1H, dd, J = 10.8, 1.2 Hz), 3.62 (2H, s), 3.44 (1H, dd, J = 17.2, 7.2 Hz), 2.84 (1H, d, J = 17.2 Hz), 1.35 (6H, s). MS (ESI) m/z: 460 (M + H)$^+$ |
| 59 | 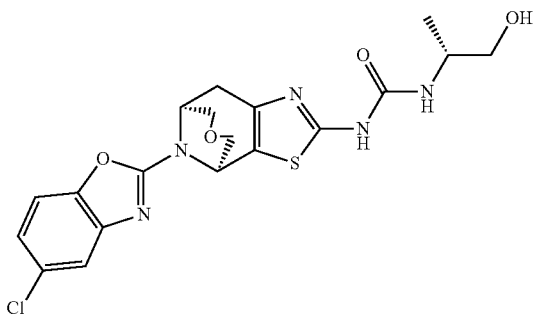 [SMILES: C[C@H](CO)NC(=O)Nc1nc2c(s1)[C@@H]1COC[C@H](C2)N1c1nc2cc(Cl)ccc2o1] | $^1$H NMR (400 MHz, CDCl$_3$): δ (ppm) = 7.32 (1H, d, J = 2.0 Hz), 7.17 (1H, d, J = 8.4 Hz), 7.03 (1H, dd, J = 8.4, 2.0 Hz), 5.26 (1H, s), 4.53 (1H, d, J = 7.2 Hz), 4.03-3.93 (4H, m), 3.76-3.66 (2H, m), 3.58-3.53 (1H, m), 3.41-3.34 (1H, dd, J = 17.2, 6.8 Hz), 2.80 (1H, d, J = 17.2 Hz), 1.19 (3H, d, J = 6.8 Hz). MS (ESI) m/z: 450 (M + H)$^+$ |

TABLE 2-25

| | | |
|---|---|---|
| 60(60a) | 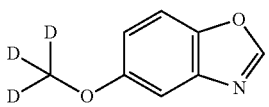 | $^1$H NMR (400 MHz, CDCl$_3$): δ (ppm) = 8.06 (1H, s), 7.47 (1H, d, J = 8.8 Hz), 7.27 (1H, m), 7.00 (1H, dd, J = 8.8, 2.4 Hz). MS (ESI) m/z: 153 (M + H)$^+$ |
| 60(60b) | 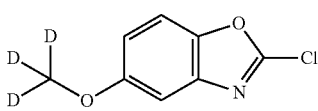 [SMILES: [2H]C([2H])([2H])Oc1ccc2oc(Cl)nc2c1] | $^1$H NMR (400 MHz, CDCl$_3$): δ (ppm) = 7.38 (1H, d, J = 8.8 Hz), 7.15 (1H, s), 6.94 (1H, d, J = 8.8 Hz). MS (ESI) m/z: 187 (M + H)$^+$ |
| 60(60c) | 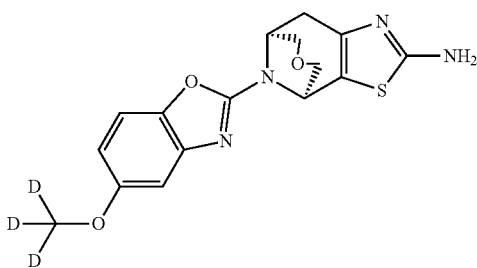 [SMILES: [2H]C([2H])([2H])Oc1ccc2oc(N3[C@@H]4COC[C@H]3c3sc(N)nc3C4)nc2c1] | $^1$H NMR (400 MHz, CDCl$_3$): δ (ppm) = 7.19 (1H, d, J = 7.2 Hz), 7.07 (1H, d, J = 2.4 Hz), 6.55 (1H, dd, J = 8.4, 2.4 Hz), 5.11 (1H, s), 4.77 (2H, s), 4.44 (1H, d, J = 6.8 Hz), 3.95-3.93 (2H, m), 3.87-3.84 (1H, m), 3.67 (1H, d, J = 10.8 Hz), 3.27 (1H, dd, J = 17.2, 7.2 Hz), 2.70 (1H, d, J = 17.2 Hz). MS (ESI) m/z: 348 (M + H)$^+$ |
| 60(60d) | 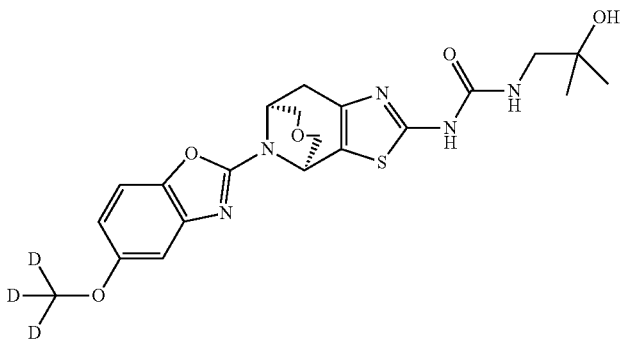 [SMILES: [2H]C([2H])([2H])Oc1ccc2oc(N3[C@@H]4COC[C@H]3c3sc(NC(=O)NCC(C)(C)O)nc3C4)nc2c1] | $^1$H NMR (400 MHz, CD$_3$OD): δ (ppm) = 7.23 (1H, d, J = 8.8 Hz), 6.88 (1H, d, J = 2.4 Hz), 6.66 (1H, dd, J = 8.8, 2.4 Hz), 5.31 (1H, s), 4.52 (1H, d, J = 6.8 Hz), 4.06-3.93 (3H, m), 3.76 (1H, d, J = 10.8 Hz), 3.26-3.32 (1H, m), 3.23 (2H, s), 2.83 (1H, d, J = 17.2 Hz), 1.21 (6H, s). MS (ESI) m/z: 463 (M + H)$^+$ |

TABLE 2-25-continued

| | | |
|---|---|---|
| 61(61b) | 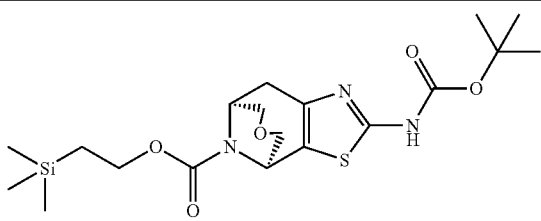 | $^1$H NMR (400 MHz, CDCl$_3$): δ (ppm) = 10.83 (1H, br s), 5.46-5.06 (1H, m), 4.50-4.31 (1H, m), 4.28-4.14 (2H, m), 3.94-3.59 (4H, m), 3.34-3.14 (1H, m), 2.83 (1H, d, J = 17.2 Hz), 1.51-1.36 (9H, m), 1.25 (2H, t, J = 7.2 Hz), 0.02 (9H, s). MS (ESI) m/z: 442 (M + H)$^+$ |
| 61(61c) | 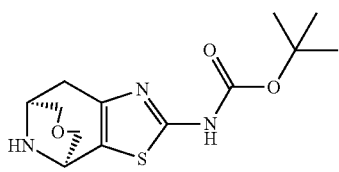 [SMILES: CC(C)(C)OC(=O)Nc1nc2c(s1)[C@@H]1COC[C@H](C2)N1] | $^1$H NMR (400 MHz, CDCl$_3$): δ (ppm) = 10.58-9.18 (1H, m), 5.32 (1H, s), 4.08 (1H, s), 4.02 (1H, dd, J = 11.2, 2.4 Hz), 3.95 (1H, dd, J = 10.4, 1.6 Hz), 3.86 (1H, d, J = 11.2 Hz), 3.63 (1H, d, J = 10.8 Hz), 3.41-3.33 (1H, m), 3.17-3.04 (1H, m), 2.87 (1H, d, J = 17.2 Hz), 1.56 (9H, s). MS (ESI) m/z: 298 (M + H)$^+$ |
| 61(61d) | 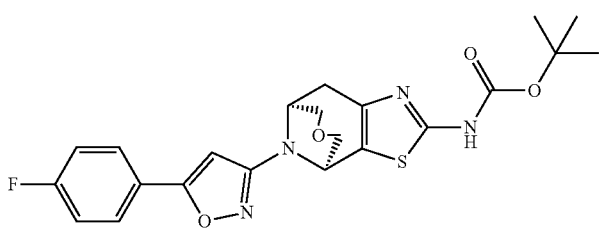 [SMILES: CC(C)(C)OC(=O)Nc1nc2c(s1)[C@@H]1COC[C@H](C2)N1c1cc(-c2ccc(F)cc2)on1] | $^1$H NMR (400 MHz, DMSO-d$_6$): δ (ppm) = 11.25 (1H, br s), 7.86-7.73 (2H, m), 7.42-7.26 (2H, m), 6.93 (1H, s), 4.91 (1H, s), 4.06 (1H, br s), 3.98-3.92 (1H, m), 3.90-3.82 (2H, m), 3.67-3.58 (1H, m), 3.10 (1H, dd, J = 17.2, 7.2 Hz), 2.65 (1H, d, J = 17.2 Hz), 1.46 (9H, s). MS (ESI) m/z: 459 (M + H)$^+$ |

TABLE 2-26

| | | |
|---|---|---|
| 61(61e) | 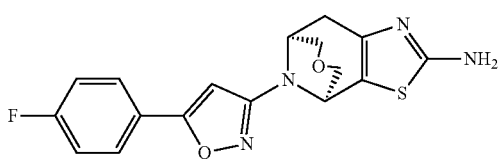 [SMILES: Nc1nc2c(s1)[C@@H]1COC[C@H](C2)N1c1cc(-c2ccc(F)cc2)on1] | $^1$H NMR (400 MHz, DMSO-d$_6$): δ (ppm) = 7.83-7.75 (2H, m), 7.42-7.29 (2H, m), 6.92 (1H, s), 6.76 (2H, s), 4.71 (1H, s), 3.98-3.71 (4H, m), 3.55 (1H, d, J = 10.4 Hz), 2.98 (1H, dd, J = 17.6, 7.2 Hz), 2.60-2.40 (1H, m). |
| 61(61f) | 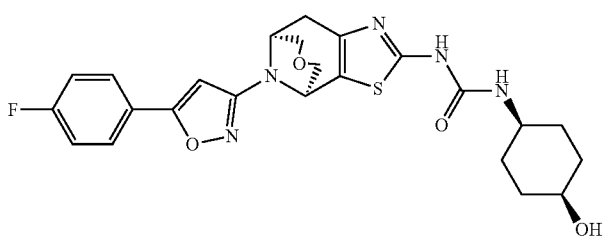 [SMILES: O=C(Nc1nc2c(s1)[C@@H]1COC[C@H](C2)N1c1cc(-c2ccc(F)cc2)on1)N[C@H]1CC[C@@H](O)CC1] | $^1$H NMR (400 MHz, DMSO-d$_6$): δ (ppm) = 9.97 (1H, br s), 7.83-7.73 (2H, m), 7.35 (2H, t, J = 8.8 Hz), 6.93 (1H, s), 6.82-6.71 (1H, m), 4.87 (1H, s), 4.46 (1H, br s), 4.04 (1H, d, J = 6.0 Hz), 3.99-3.77 (3H, m), 3.67-3.54 (3H, m), 3.07 (1H, dd, J = 17.2, 7.2 Hz), 2.69-2.58 (1H, m), 1.60-1.43 (8H, m). MS (ESI) m/z: 500 (M + H)$^+$ |
| 62(62a) | 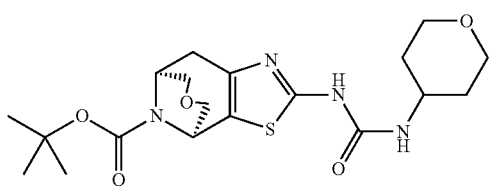 [SMILES: CC(C)(C)OC(=O)N1[C@@H]2COC[C@H]1c1sc(NC(=O)NC3CCOCC3)nc1C2] | $^1$H NMR (400 MHz, CDCl$_3$): δ (ppm) = 5.16-5.01 (1H, m), 4.42-4.29 (1H, m), 3.98-3.74 (6H, m), 3.66-3.50 (3H, m), 3.28-3.11 (1H, m), 2.76-2.70 (1H, m), 2.00-1.97 (2H, m), 1.62-1.56 (2H, m), 1.46-1.44 (9H, m) MS (ESI) m/z: 425 (M +H)$^+$ |
| 62(62b) | 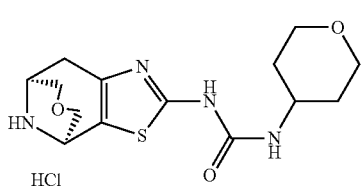 [SMILES: O=C(Nc1nc2c(s1)[C@@H]1COC[C@H](C2)N1)NC1CCOCC1 ; Cl] | $^1$H NMR (400 MHz, DMSO-d$_6$): δ (ppm) = 10.5 (1H, d, J = 10.4 Hz), 9.52 (1H, d, J = 10.0 Hz), 7.20 (1H, d, J = 7.2 Hz), 4.97 (1H, br s), 4.80 (1H, s), 4.02-3.91 (3H, m), 3.82-3.79 (3H, m), 3.73-3.66 (1H, m), 3.59 (1H, d, J = 12.0 Hz), 3.37 (1H, t, J = 10.0 Hz), 3.14 (1H, dd, J = 6.8, 17.0 Hz), 2.86 (1H, d, J = 18.0 Hz), 1.79-1.76 (2H, m), 1.44-1.34 (2H, m) MS (ESI) m/z: 325 (M +H)$^+$ |

TABLE 2-26-continued

| | | |
|---|---|---|
| 62(62c) | 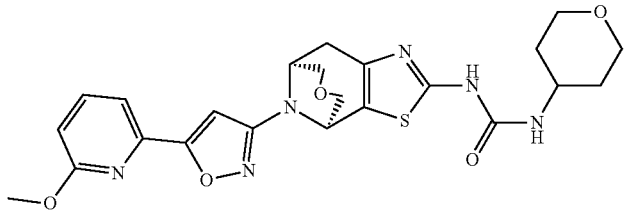 [SMILES: COc1cccc(-c2cc(N3[C@@H]4COC[C@H]3c3sc(NC(=O)NC5CCOCC5)nc3C4)no2)n1] | $^1$H NMR (400 MHz, CDCl$_3$): δ (ppm) = 9.16 (1H, br s), 7.64 (1H, t, J = 8.0 Hz), 7.39 (1H, d, J = 8.0 Hz), 6.77 (1H, d, J = 8.0 Hz), 6.54 (1H, s), 4.78 (1H, s), 4.15-4.07 (3H, m), 4.03-4.10 (4H, m), 3.97 (3H, s), 3.95-3.91 (1H, m), 3.74 (1H, d, J = 9.6 Hz), 3.54-3.47 (2H, m), 3.39 (1H, dd, J = 7.2, 16.8 Hz), 2.78 (1H, d, J = 16.8 Hz), 1.98-1.91 (2H, m), 1.57-1.47 (2H, m) MS (APCI/ESI) m/z: 499 (M +H)$^+$ |
| 63 | 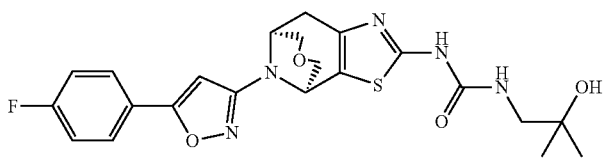 [SMILES: CC(C)(O)CNC(=O)Nc1nc2c(s1)[C@@H]1COC[C@H](C2)N1c1cc(-c2ccc(F)cc2)on1] | $^1$H NMR (400 MHz, CDCl$_3$): δ (ppm) = 7.68-7.64 (2H, m), 7.13-7.09 (2H, m), 6.13 (1H, s), 4.67 (1H, s), 4.14-3.95 (4H, m), 3.71 (1H, d, J = 10.8 Hz), 3.41-3.21 (3H, m), 2.72 (1H, d, J = 16.4 Hz), 1.20 (6H, d, J = 5.6 Hz). MS (ESI) m/z: 474 (M + H)$^+$ |

TABLE 2-27

| | | |
|---|---|---|
| 64(64a) | 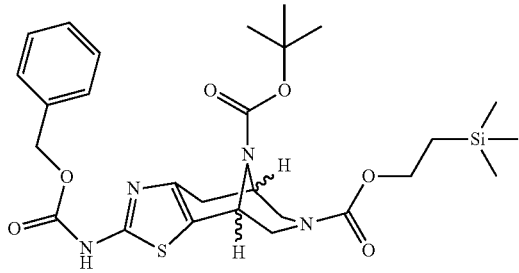 [SMILES: CC(C)(C)OC(=O)N1C2Cc3nc(NC(=O)OCc4ccccc4)sc3C1CN(C(=O)OCC[Si](C)(C)C)C2] | $^1$H NMR (400 MHz, CDCl$_3$): δ (ppm) = 7.44-7.36 (5H, m), 5.36-5.10 (3H, m), 4.25-3.75 (5H, m), 3.23-2.67 (3H, m), 2.56-2.32 (1H, m), 1.50-1.35 (9H, m), 0.93-0.67 (2H, m), 0.06 (9H, s). MS (ESI) m/z: 575 (M + H)$^+$ |
| 64(64b) | 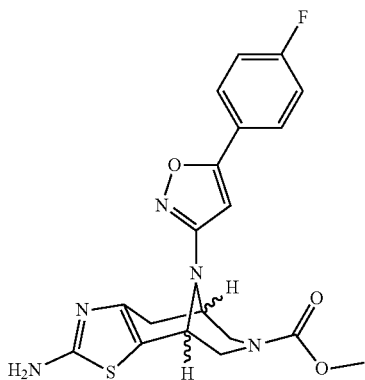 [SMILES: COC(=O)N1CC2Cc3nc(N)sc3C(C1)N2c1cc(-c2ccc(F)cc2)on1] | $^1$H NMR (400 MHz, CDCl$_3$): δ (ppm) = 7.78-7.64 (2H, m), 7.12-7.07 (2H, m), 6.15 (1H, s), 4.99 (2H, br s), 4.83 (1H, s), 4.42-3.90 (3H, m), 3.67-3.09 (6H, m), 2.72-2.55 (1H, m). MS (ESI) m/z: 416 (M + H)$^+$ |
| 64(64c) | 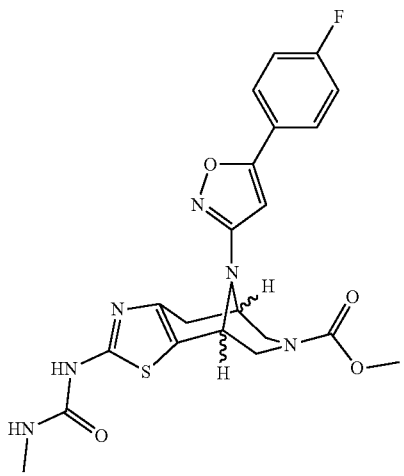 | $^1$H NMR (400 MHz, CDCl$_3$): δ (ppm) = 7.72-7.63 (2H, m), 7.16-7.08 (2H, m), 6.15 (1H, s), 4.89 (1H, s), 4.43-3.95 (3H, m), 3.67-3.22 (6H, m), 2.90 (3H, d, J = 4.4 Hz), 2.79-2.62 (1H, m). MS (ESI) m/z: 473 (M + H)$^+$ |

TABLE 2-27-continued

| 65 | 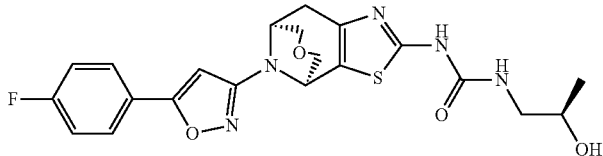 [SMILES: C[C@@H](O)CNC(=O)Nc1nc2c(s1)[C@@H]1COC[C@H](C2)N1c1cc(-c2ccc(F)cc2)on1] | ¹H NMR (400 MHz, DMSO-d$_6$): δ (ppm) = 10.20 (1H, br s), 7.83-7.73 (2H, m), 7.35 (2H, t, J = 8.8 Hz), 6.93 (1H, s), 6.74-6.62 (1H, m), 4.91-4.73 (2H, m), 4.04 (1H, d, J = 6.4 Hz), 3.98-3.80 (3H, m), 3.71-3.56 (2H, m), 3.18-3.05 (2H, m), 3.01-2.90 (1H, m), 2.70-2.59 (1H, m), 1.03 (3H, d, J = 6.4 Hz). MS (ESI) m/z: 460 (M + H)⁺ |

TABLE 2-28

| 66(66a) | 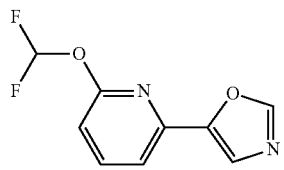 [SMILES: FC(F)Oc1cccc(-c2cnco2)n1] | ¹H NMR(400 MHz, CDCl$_3$): δ (ppm) = 7.97 (1H, s), 7.83-7.79 (1H, m), 7.65 (1H, s), 7.55 (1H, t, J = 72.8 Hz), 7.48-7.45 (1H, m), 6.86 (1H, d, J = 8.4 Hz). |
| 66(66b) | 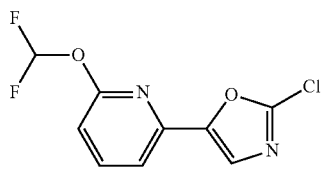 [SMILES: FC(F)Oc1cccc(-c2cnc(Cl)o2)n1] | ¹H NMR(400 MHz, CDCl$_3$): δ (ppm) = 7.84-7.79 (1H, m), 7.58 (1H, s), 7.52 (1H, t, J = 72.6 Hz), 7.42-7.39 (1H, m), 6.87 (1H, d, J = 8.4 Hz). |
| 66(66c) | 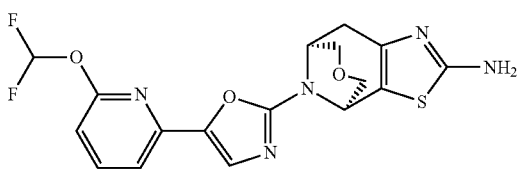 [SMILES: Nc1nc2c(s1)[C@@H]1COC[C@H](C2)N1c1ncc(-c2cccc(OC(F)F)n2)o1] | ¹H NMR(400 MHz, CDCl$_3$): δ (ppm) = 7.73-7.31 (3H, m), 7.18 (1H, d, J = 7.6 Hz), 6.71 (1H, d, J = 8.0 Hz), 5.08 (1H, s), 4.84 (2H, s), 4.42 (1H, d, J = 6.8 Hz), 4.04-4.01 (2H, m), 3.95 (1H, dd, J = 11.0, 2.0 Hz), 3.75 (1H, dd, J = 11.0, 1.6 Hz), 3.32 (1H, dd, J = 17.2, 7.2 Hz), 2.76 (1H, d, J = 17.2 Hz). MS(ESI) m/z: 408 (M + H)⁺ |
| 66(66d) | 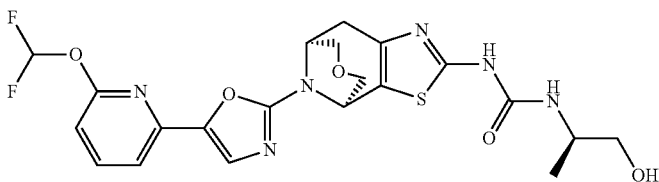 [SMILES: C[C@H](CO)NC(=O)Nc1nc2c(s1)[C@@H]1COC[C@H](C2)N1c1ncc(-c2cccc(OC(F)F)n2)o1] | ¹H NMR(400 MHz, CDCl$_3$): δ (ppm) = 7.74-7.29 (3H, m), 7.16 (1H, d, J = 7.6 Hz), 6.71 (1H, d, J = 8.0 Hz), 5.15 (1H, s), 4.42 (1H, d, J = 7.2 Hz), 4.08-3.91 (4H, m), 3.80-3.63 (2H, m), 3.54 (1H, dd, J = 11.2, 5.6 Hz), 3.37 (1H, dd, J = 17.2, 7.2 Hz), 2.77 (1H, d, J = 17.2 Hz), 1.19 (3H, d, J = 6.8 Hz). MS(ESI) m/z: 509 (M + H)⁺ |
| 67(67a) | 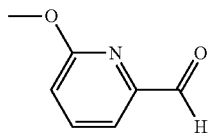 | ¹H NMR(400 MHz, CDCl$_3$): δ (ppm) = 9.89 (1H, s), 7.69-7.62 (1H, m), 7.52-7.47 (1H, m), 6.93-6.88 (1H, m), 3.95 (3H, s). |
| 67(67b) | 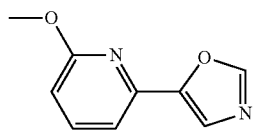 | ¹H NMR(400 MHz, CDCl$_3$): δ (ppm) = 7.95 (1H, s), 7.68-7.61 (2H, m), 7.27 (1H, d, J = 7.6 Hz), 6.75-6.69 (1H, m), 4.00 (s, 3H). |
| 67(67c) | 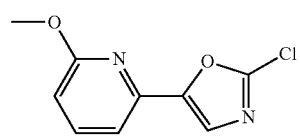 | ¹H NMR(400 MHz, CDCl$_3$): δ (ppm) = 7.68-7.62 (1H, m), 7.59 (1H, s), 7.21 (1H, d, J = 7.4 Hz), 6.74 (1H, d, J = 8.0 Hz), 3.99 (3H, s). |

TABLE 2-29

| 67(67d) | 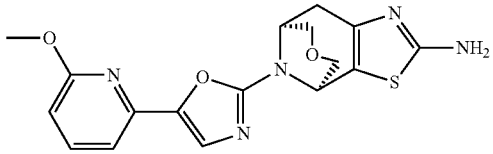 [SMILES: COc1cccc(-c2cnc(N3[C@@H]4COC[C@H]3c3sc(N)nc3C4)o2)n1] | $^1$H NMR(400 MHz, CDCl$_3$): δ (ppm) = 7.58-7.54 (1H, m), 7.37 (1H, s), 6.99 (1H, d, J = 7.2 Hz), 6.58 (1H, d, J = 8.0 Hz), 5.11-5.03 (3H, m), 4.42 (1H, d, J = 7.2 Hz), 4.03-4.01 (2H, m), 3.97-3.93 (4H, m), 3.7-3.71 (1H, m), 3.33 (1H, dd, J = 17.2, 7.2 Hz), 2.75 (1H, d, J = 17.2 Hz). MS(ESI) m/z: 372 (M + H)$^+$ |
|---|---|---|
| 67(67e) | 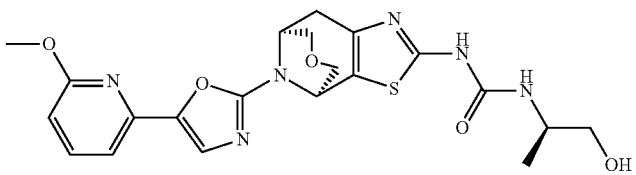 [SMILES: COc1cccc(-c2cnc(N3[C@@H]4COC[C@H]3c3sc(NC(=O)N[C@H](C)CO)nc3C4)o2)n1] | $^1$H NMR(400 MHz, DMSO-d$_6$): δ (ppm) = 10.13 (1 H, br s), 7.75-7.69 (1H, m), 7.41 (1H, s), 7.14 (1H, d, J = 7.2 Hz), 6.66 (1H, d, J = 8.0 Hz), 6.50 (1H, d, J = 7.6 Hz), 5.26 (1H, s), 4.84 (1H, br s), 4.37 (1H, d, J = 6.8 Hz), 4.00-3.94 (1H, m), 3.89-3.81 (5H, m), 3.74-3.61 (2H, m), 3.39-3.32 (2H, m), 3.13 (1H, dd, J = 17.2, 7.2 Hz), 2.70 (1H, d, J = 17.2 Hz), 1.06 (3H, d, J = 6.8 Hz). MS(ESI) m/z: 473 (M + H)$^+$ |
| 68(68a) | 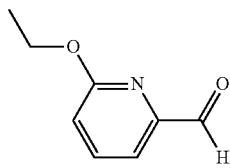 | $^1$H NMR(400 MHz, CDCl$_3$): δ (ppm) = 9.94 (1H, s), 7.77-7.70 (1H, m), 7.55 (1H, dd, J = 7.2, 0.8 Hz), 6.96 (1H, dd, J = 8.0, 0.8 Hz), 4.48 (2H, q, J = 7.2 Hz), 1.44 (3H, t, J = 7.2 Hz). |
| 68(68b) | 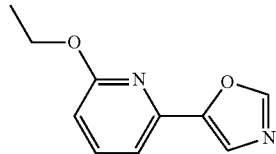 | $^1$H NMR(400 MHz, CDCl$_3$): δ (ppm) = 7.93 (1H, s), 7.66-7.59 (2H, m), 7.23 (1H, d, J = 7.6 Hz), 6.68 (1H, d, J = 8.4 Hz), 4.42 (2H, q, J = 7.2 Hz), 1.43 (3H, t, J = 7.2 Hz). |
| 68(68c) | 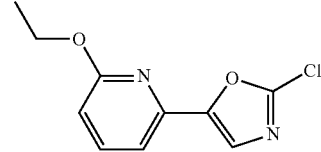 | $^1$H NMR(400 MHz, CDCl$_3$): δ (ppm) = 7.62 (1H, dd, J = 8.4, 7.2 Hz), 7.57-7.53 (1H, m), 7.17 (1H, d, J = 7.2 Hz), 6.69 (1H, d, J = 8.4 Hz), 4.40 (2H, q, J = 7.2 Hz), 1.45-1.39 (3H, m). |
| 68(68d) | 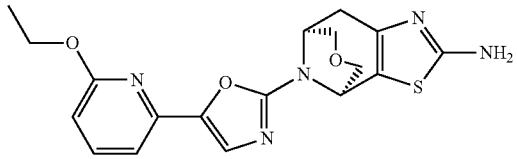 [SMILES: CCOc1cccc(-c2cnc(N3[C@@H]4COC[C@H]3c3sc(N)nc3C4)o2)n1] | $^1$H NMR(400 MHz, CDCl$_3$): δ (ppm) = 7.60-7.49 (1H, m), 7.34 (1H, s), 6.97 (1H, d, J = 7.2 Hz), 6.55 (1H, d, J = 8.4 Hz), 5.08 (1H, s), 4.89 (2H, br s), 4.46-4.30 (3H, m), 4.08-3.88 (3H, m), 3.74 (1H, dd, J = 10.8, 1.2 Hz), 3.33 (1H, dd, J = 17.2, 7.2 Hz), 2.75 (1H, d, J = 17.2 Hz), 1.40 (3H, t, J = 7.2 Hz). MS(ESI) m/z: 386 (M + H)$^+$ |
| 68(68e) | 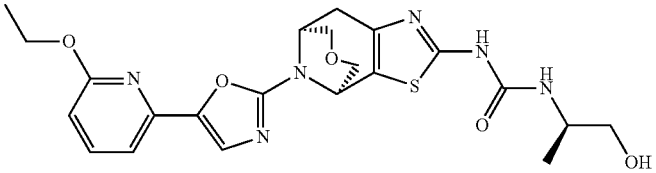 [SMILES: CCOc1cccc(-c2cnc(N3[C@@H]4COC[C@H]3c3sc(NC(=O)N[C@H](C)CO)nc3C4)o2)n1] | $^1$H NMR(400 MHz, CDCl$_3$): δ (ppm) = 7.57-7.52 (1H, m), 7.31 (1H, s), 6.96 (1H, d, J = 7.2 Hz), 6.55 (1H, d, J = 8.4 Hz), 5.16 (1H, s), 4.46-4.30 (3H, m), 4.07-3.92 (4H, m), 3.79-3.66 (2H, m), 3.56 (1H, dd, J = 11.2, 6.0 Hz), 3.41 (1H, dd, J = 17.2, 7.2 Hz), 2.79 (1H, d, J = 17.2 Hz), 1.40 (3H, t, J = 7.2 Hz), 1.20 (3H, d, J = 6.8 Hz). MS(ESI) m/z: 487 (M + H)$^+$ |

TABLE 2-30

| 69(69a) | 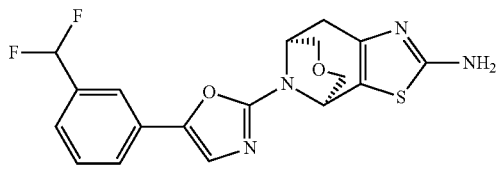 [SMILES: Nc1nc2c(s1)[C@@H]1COC[C@H](C2)N1c1ncc(-c2cccc(C(F)F)c2)o1] | $^1$H NMR(500 MHz, DMSO-d$_6$): δ (ppm) = 7.72-7.68 (2H, m), 7.56-7.52 (1H, m), 7.46 (1H, s), 7.40 (1H, d, J = 7.8 Hz), 7.01 (1H, t, J = 55.9 Hz), 6.78 (2H, s), 5.06 (1H, s), 4.27 (1H, d, J = 6.3 Hz), 3.91 (1H, d, J = 11.2 Hz), 3.85-3.81 (1H, m), 3.78-3.75 (1H, m), 3.56 (1H, d, J = 10.7 Hz), 3.05-3.00 (1H, m), 2.53 (1H, d, J = 17.1 Hz). MS(APCI/ESI) m/z: 391 (M + H)$^+$ |

TABLE 2-30-continued

| 69(69b) | 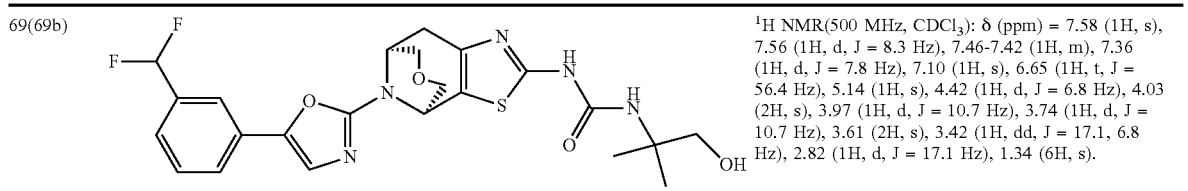 | ¹H NMR(500 MHz, CDCl₃): δ (ppm) = 7.58 (1H, s), 7.56 (1H, d, J = 8.3 Hz), 7.46-7.42 (1H, m), 7.36 (1H, d, J = 7.8 Hz), 7.10 (1H, s), 6.65 (1H, t, J = 56.4 Hz), 5.14 (1H, s), 4.42 (1H, d, J = 6.8 Hz), 4.03 (2H, s), 3.97 (1H, d, J = 10.7 Hz), 3.74 (1H, d, J = 10.7 Hz), 3.61 (2H, s), 3.42 (1H, dd, J = 17.1, 6.8 Hz), 2.82 (1H, d, J = 17.1 Hz), 1.34 (6H, s). |
| --- | --- | --- |
| 70 | 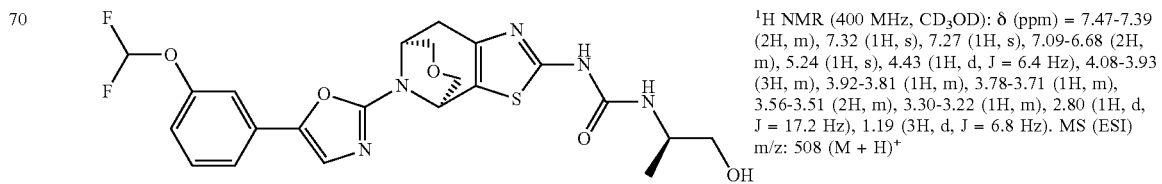 | ¹H NMR (400 MHz, CD₃OD): δ (ppm) = 7.47-7.39 (2H, m), 7.32 (1H, s), 7.27 (1H, s), 7.09-6.68 (2H, m), 5.24 (1H, s), 4.43 (1H, d, J = 6.4 Hz), 4.08-3.93 (3H, m), 3.92-3.81 (1H, m), 3.78-3.71 (1H, m), 3.56-3.51 (2H, m), 3.30-3.22 (1H, m), 2.80 (1H, d, J = 17.2 Hz), 1.19 (3H, d, J = 6.8 Hz). MS (ESI) m/z: 508 (M + H)⁺ |
| 71 | 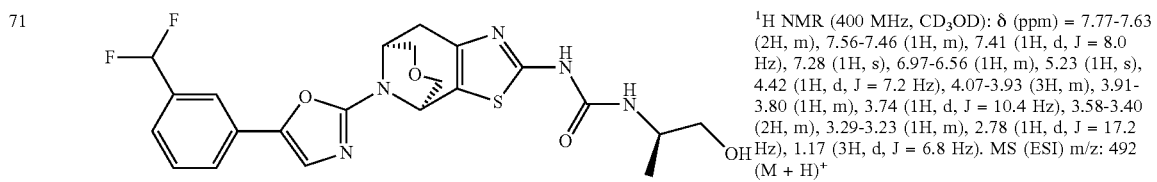 | ¹H NMR (400 MHz, CD₃OD): δ (ppm) = 7.77-7.63 (2H, m), 7.56-7.46 (1H, m), 7.41 (1H, d, J = 8.0 Hz), 7.28 (1H, s), 6.97-6.56 (1H, m), 5.23 (1H, s), 4.42 (1H, d, J = 7.2 Hz), 4.07-3.93 (3H, m), 3.91-3.80 (1H, m), 3.74 (1H, d, J = 10.4 Hz), 3.58-3.40 (2H, m), 3.29-3.23 (1H, m), 2.78 (1H, d, J = 17.2 Hz), 1.17 (3H, d, J = 6.8 Hz). MS (ESI) m/z: 492 (M + H)⁺ |
| 72 | 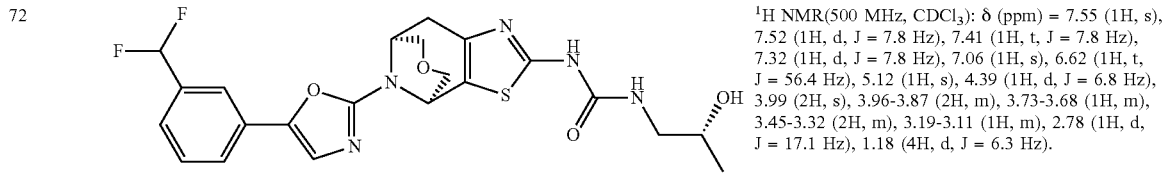 | ¹H NMR(500 MHz, CDCl₃): δ (ppm) = 7.55 (1H, s), 7.52 (1H, d, J = 7.8 Hz), 7.41 (1H, t, J = 7.8 Hz), 7.32 (1H, d, J = 7.8 Hz), 7.06 (1H, s), 6.62 (1H, t, J = 56.4 Hz), 5.12 (1H, s), 4.39 (1H, d, J = 6.8 Hz), 3.99 (2H, s), 3.96-3.87 (2H, m), 3.73-3.68 (1H, m), 3.45-3.32 (2H, m), 3.19-3.11 (1H, m), 2.78 (1H, d, J = 17.1 Hz), 1.18 (4H, d, J = 6.3 Hz). |
| 73 | 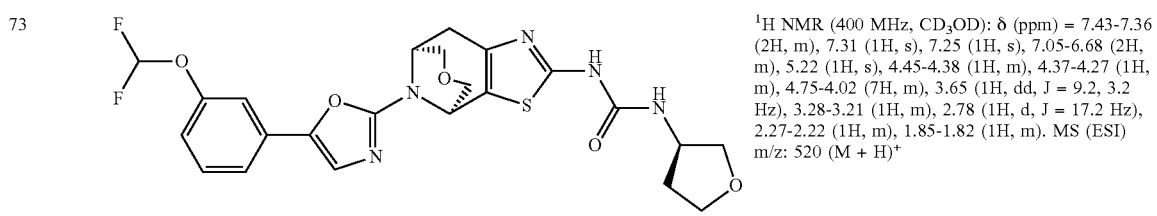 | ¹H NMR (400 MHz, CD₃OD): δ (ppm) = 7.43-7.36 (2H, m), 7.31 (1H, s), 7.25 (1H, s), 7.05-6.68 (2H, m), 5.22 (1H, s), 4.45-4.38 (1H, m), 4.37-4.27 (1H, m), 4.75-4.02 (7H, m), 3.65 (1H, dd, J = 9.2, 3.2 Hz), 3.28-3.21 (1H, m), 2.78 (1H, d, J = 17.2 Hz), 2.27-2.22 (1H, m), 1.85-1.82 (1H, m). MS (ESI) m/z: 520 (M + H)⁺ |

TABLE 2-31

| 74(74a) | 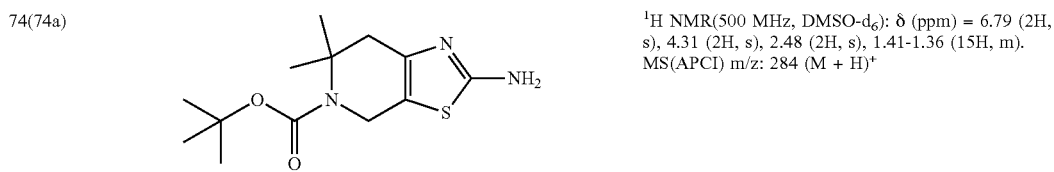 | ¹H NMR(500 MHz, DMSO-d₆): δ (ppm) = 6.79 (2H, s), 4.31 (2H, s), 2.48 (2H, s), 1.41-1.36 (15H, m). MS(APCI) m/z: 284 (M + H)⁺ |
| --- | --- | --- |
| 74(74b) | 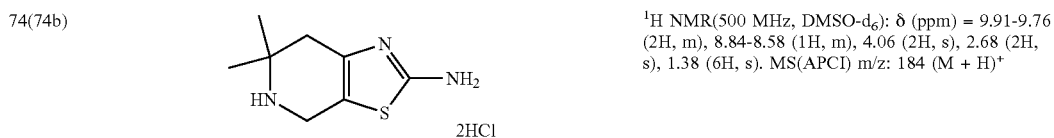 | ¹H NMR(500 MHz, DMSO-d₆): δ (ppm) = 9.91-9.76 (2H, m), 8.84-8.58 (1H, m), 4.06 (2H, s), 2.68 (2H, s), 1.38 (6H, s). MS(APCI) m/z: 184 (M + H)⁺ |
| 74(74c) | 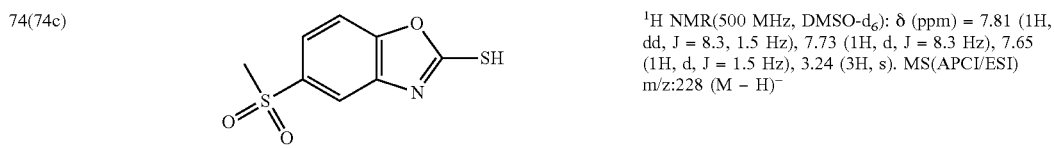 | ¹H NMR(500 MHz, DMSO-d₆): δ (ppm) = 7.81 (1H, dd, J = 8.3, 1.5 Hz), 7.73 (1H, d, J = 8.3 Hz), 7.65 (1H, d, J = 1.5 Hz), 3.24 (3H, s). MS(APCI/ESI) m/z:228 (M − H)⁻ |

TABLE 2-31-continued

| 74(74d) | 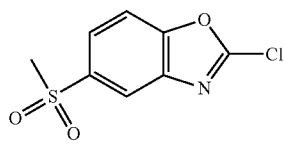 | ¹H NMR(500 MHz, DMSO-d₆): δ (ppm) = 8.30 (1H, d, J = 1.5 Hz), 8.04 (1H, d, J = 8.3 Hz), 8.01 (1H, dd, J = 8.3, 1.5 Hz), 3.28 (3H, s). |
|---|---|---|
| 74(74e) | 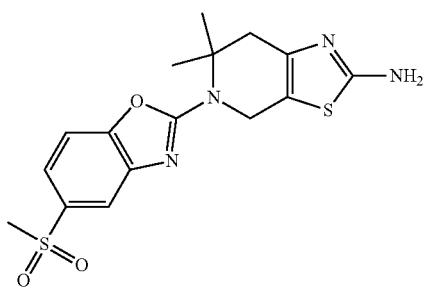 [SMILES: CC1(C)Cc2nc(N)sc2CN1c1nc2cc(S(C)(=O)=O)ccc2o1] | ¹H NMR(500 MHz, CDCl₃): δ (ppm) = 7.93-7.91 (1H, m), 7.69-7.66 (1H, m), 7.39 (1H, d, J = 8.3 Hz), 4.78 (2H, br s), 4.75 (2H, s), 3.03 (3H, s), 2.79 (2H, s), 1.66 (6H, s). MS(APCI/ESI) m/z: 379 (M + H)⁺ |
| 74(74f) | 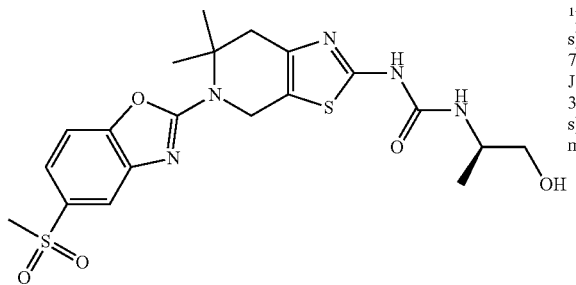 | ¹H NMR(500 MHz, DMSO-d₆): δ (ppm) = 10.14 (1H, s), 7.85-7.84 (1H, m), 7.67 (1H, d, J = 8.3 Hz), 7.64-7.61 (1H, m), 6.46 (1H, d, J = 7.8 Hz), 4.83 (1H, t, J = 5.1 Hz), 4.78 (2H, s), 3.72-3.64 (1H, m), 3.35-3.32 (2H, m), 3.18 (3H, s), 2.77 (2H, s), 1.59 (6H, s), 1.04 (3H, d, J = 6.8 Hz). MS(APCI/ESI) m/z: (M + H)⁺ |
| 75 | 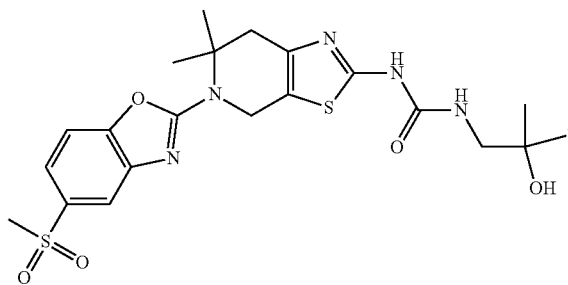 [SMILES: CC(C)(O)CNC(=O)Nc1nc2c(s1)CN(c1nc3cc(S(C)(=O)=O)ccc3o1)C(C)(C)C2] | ¹H NMR(500 MHz, DMSO-d₆): δ (ppm) = 10.24 (1H, s), 7.85-7.84 (1H, m), 7.67 (1H, d, J = 8.3 Hz), 7.64-7.61 (1H, m), 6.58 (1H, br s), 4.78 (2H, s), 4.55 (1H, br s), 3.18 (3H, s), 3.03 (2H, d, J = 5.4 Hz), 2.77 (2H, s), 1.59 (6H, s), 1.05 (6H, s). MS(APCI/ESI) m/z: 494 (M + H)⁺ |

TABLE 2-32

| 76 | 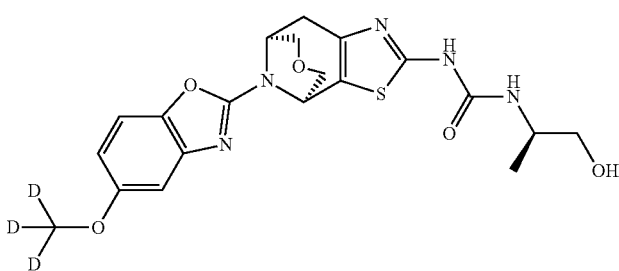 [SMILES: [2H]C([2H])([2H])Oc1ccc2oc(N3[C@@H]4COC[C@H]3c3sc(NC(=O)N[C@H](C)CO)nc3C4)nc2c1] | ¹H NMR (400 MHz, CD₃OD): δ (ppm) = 7.24 (1H, d, J = 8.8 Hz), 6.89 (1H, d, J = 2.4 Hz), 6.67 (1H, dd, J = 8.8, 2.4 Hz), 5.32 (1H, s), 4.52 (1H, d, J = 6.8 Hz), 4.07-3.94 (3H, m), 3.89-3.85 (1H, m), 3.76 (1H, d, J = 11.2 Hz), 3.56-3.52 (2H, m), 3.31-3.27 (1H, m), 2.83 (1H, d, J = 17.2 Hz), 1.19 (3H, d, J = 6.8 Hz). MS (ESI) m/z: 449 (M + H)⁺ |
|---|---|---|

TABLE 2-32-continued

| 77 | 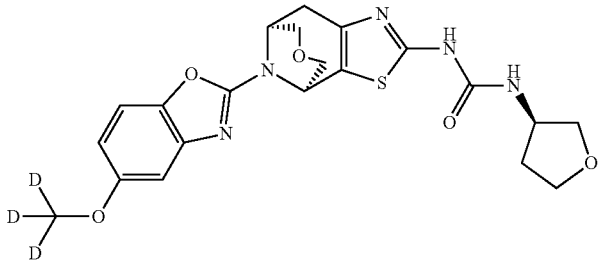 [SMILES: [2H]C([2H])([2H])Oc1ccc2oc(N3[C@@H]4COC[C@H]3c3sc(NC(=O)N[C@@H]5CCOC5)nc3C4)nc2c1] | ¹H NMR (400 MHz, CD₃OD): δ (ppm) = 7.24 (1H, d, J = 8.8 Hz), 6.89 (1H, d, J = 2.4 Hz), 6.67 (1H, dd, J = 8.8, 2.4 Hz), 5.32 (1H, s), 4.52 (1H, d, J = 6.8 Hz), 4.38-4.32 (1H, m), 4.04-3.75 (7H, m), 3.67 (1H, dd, J = 10.4, 2.4 Hz), 3.31-3.27 (1H, m), 2.84 (1H, d, J = 17.2 Hz), 2.31-2.22 (1H, m), 1.88-1.82 (1H, m). MS (ESI) m/z: 461 (M + H)⁺ |
| --- | --- | --- |
| 78 | 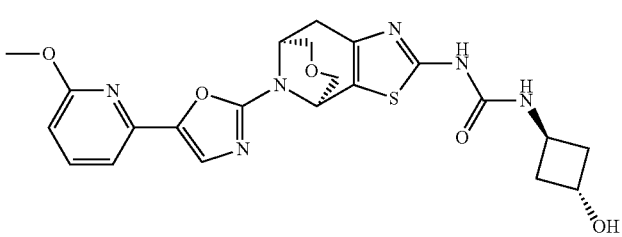 [SMILES: COc1cccc(-c2cnc(N3[C@@H]4COC[C@H]3c3sc(NC(=O)N[C@H]5C[C@H](O)C5)nc3C4)o2)n1] | ¹H NMR(400 MHz, CDCl₃): δ (ppm) = 7.55 (1H, t, J = 7.6 Hz), 7.34 (1H, s), 6.98 (1H, d, J = 7.2 Hz), 6.58 (1H, d, J = 8.4 Hz), 5.16 (1H, s), 4.55-4.43 (2H, m), 4.38 (1H, d, J = 6.2 Hz), 4.03 (2H, s), 3.98 (1H, dd, J = 11.2, 1.6 Hz), 3.93 (3H, s), 3.75 (1H, d, J = 9.9 Hz), 3.41 (1H, dd, J = 17.2, 7.2, Hz), 2.82 (1H, d, J = 17.2 Hz), 2.41-2.24 (4H, m). MS(ESI) m/z: 485 (M + H)⁺ |
| 79 | 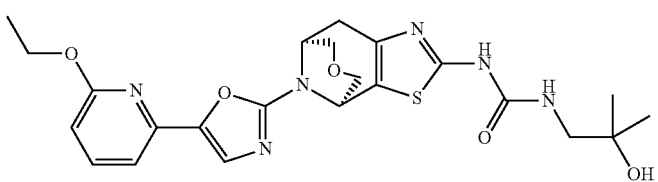 [SMILES: CCOc1cccc(-c2cnc(N3[C@@H]4COC[C@H]3c3sc(NC(=O)NCC(C)(C)O)nc3C4)o2)n1] | ¹H NMR(400 MHz, CDCl₃): δ (ppm) = 7.54 (1H, t, J = 7.6 Hz), 7.32 (1H, s), 6.96 (1H, d, J = 7.2 Hz), 6.55 (1H, d, J = 8.0 Hz), 5.15 (1H, s), 4.43 (1H, d, J = 7.2 Hz), 4.36 (2H, q, J = 7.2 Hz), 4.09-3.90 (3H, m), 3.74 (1H, d, J = 10.0 Hz), 3.39 (1H, dd, J = 17.2, 7.2 Hz), 3.30 (2H, d, J = 6.0 Hz), 2.79 (1H, d, J = 17.2 Hz), 1.39 (3H, t, J = 7.2 Hz), 1.30-1.18 (6H, m). MS(ESI) m/z: 501 (M + H)⁺ |
| 80 | 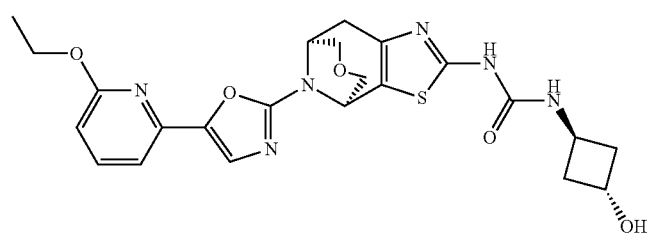 [SMILES: CCOc1cccc(-c2cnc(N3[C@@H]4COC[C@H]3c3sc(NC(=O)N[C@H]5C[C@H](O)C5)nc3C4)o2)n1] | ¹H NMR(400 MHz, CDCl₃): δ (ppm) = 7.55 (1H, t, J = 8.0 Hz), 7.32 (1H, s), 6.96 (1H, d, J = 7.6 Hz), 6.55 (1H, d, J = 8.4 Hz), 5.15 (1H, s), 4.51 (1H, q, J = 6.0 Hz), 4.45 (1H, d, J = 6.8 Hz), 4.45-4.30 (3H, m), 4.07-3.94 (3H, m), 3.75 (1H, d, J = 10.0 Hz), 3.39 (1H, dd, J = 17.2, 7.2 Hz), 2.81 (1H, d, J = 17.2 Hz), 2.38-2.26 (4H, m), 1.39 (3H, t, J = 7.2 Hz). MS(ESI) m/z: 499 (M + H)⁺ |

TABLE 3-1

| No. | Structure | Data |
| --- | --- | --- |
| 81 | 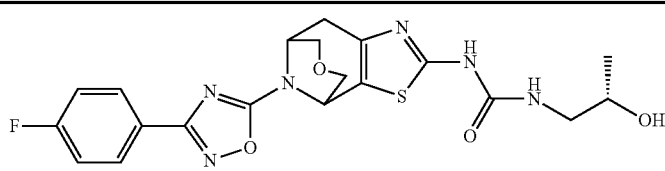 | ¹H NMR (400 MHz, CD₃OD): δ (ppm) = 7.98 (2H, dd, J = 5.6, 8.4 Hz), 7.20 (2H, t, J = 8.4 Hz), 5.32 (1H, s), 4.52 (1H, d, J = 7.2 Hz), 4.07-3.90 (3H, m), 3.89-3.80 (1H, m), 3.73 (1H, d, J = 11.2 Hz), 3.36-3.33 (1H, m), 3.26 (1H, d, J = 7.2 Hz), 3.10 (1H, dd, J = 7.2, 13.6 Hz), 2.84 (1H, d, J = 17.2 Hz), 1.16 (3H, d, J = 6.0 Hz). MS(ESI) m/z: 461 (M + H)⁺ |
| 82 | 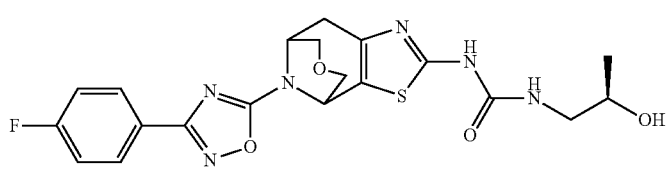 [SMILES: C[C@@H](O)CNC(=O)Nc1nc2c(s1)C1COCC(C2)N1c1nc(-c2ccc(F)cc2)no1] | ¹H NMR (400 MHz, CD₃OD): δ (ppm) = 7.98 (2H, dd, J = 5.6, 8.4 Hz), 7.20 (2H, t, J = 8.4 Hz), 5.32 (1H, s), 4.52 (1H, d, J = 6.8 Hz), 4.06-3.90 (3H, m), 3.80-3.89 (1H, m), 3.73 (1H, d, J = 11.2 Hz), 3.37-3.34 (1H, m), 3.26 (1H, d, J = 7.2 Hz), 3.10 (1H, dd, J = 7.2, 13.6 Hz), 2.84 (1H, d, J = 17.6 Hz), 1.16 (3H, d, J = 6.4 Hz). MS(ESI) m/z: 461 (M + H)⁺ |
| 83 | 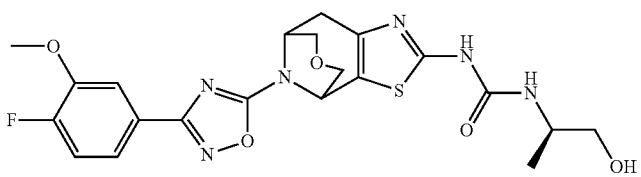 [SMILES: COc1cc(-c2noc(N3C4COCC3c3sc(NC(=O)N[C@H](C)CO)nc3C4)n2)ccc1F] | ¹H NMR(400 MHz, CDCl₃): δ (ppm) = 7.62-7.50 (2H, m), 7.13 (1H, dd, J = 10.4, 8.8 Hz), 5.25 (1H, br s), 4.57-4.44 (1H, m), 4.08-3.99 (3H, m), 3.98-3.91 (4H, m), 3.78-3.66 (2H, m), 3.62-3.52 (1H, m), 3.43-3.31 (1H, m), 2.85 (1H, d, J = 16.8 Hz), 1.23 (3H, d, J = 6.8 Hz). MS(ESI) m/z: 491 (M + H)⁺ |

TABLE 3-1-continued

| No. | Structure | Data |
|---|---|---|
| 84 | 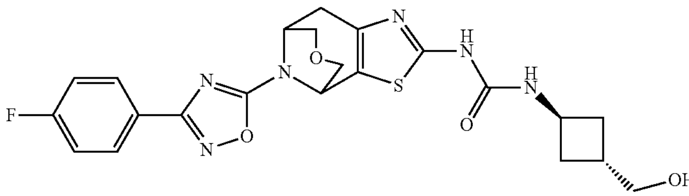 [SMILES: O=C(Nc1nc2c(s1)C1COCC(C2)N1c1nc(-c2ccc(F)cc2)no1)N[C@H]1C[C@H](CO)C1] | ¹H NMR(400 MHz, DMSO-d₆): δ (ppm) = 10.13 (1H, br s), 7.93 (2H, dd, J = 8.8, 5.2 Hz), 7.34 (2H, t, J = 8.8 Hz), 6.79 (1H, d, J = 5.6 Hz), 5.32 (1H, s), 4.55 (1H, t, J = 5.2 Hz), 4.44 (1H, d, J = 7.2 Hz), 4.22-4.07 (1H, m), 4.00-3.93 (1H, m), 3.90-3.76 (2H, m), 3.61 (1H, d, J = 11.2 Hz), 3.38-3.46 (2H, m), 3.14 (1H, dd, J = 17.2, 7.2 Hz), 2.77 (1H, d, J = 17.2 Hz), 2.26-2.12 (1H, m), 2.10-1.99 (2H, m), 1.98-1.84 (2H, m). MS(ESI) m/z: 487 (M + H)⁺ |
| 85 | 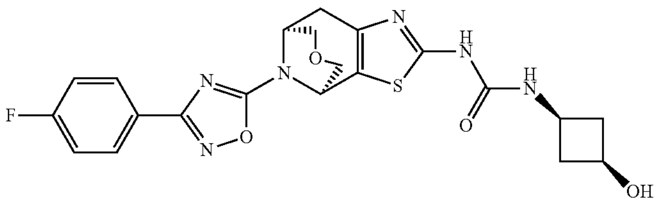 [SMILES: O=C(Nc1nc2c(s1)[C@@H]1COC[C@H](C2)N1c1nc(-c2ccc(F)cc2)no1)N[C@H]1C[C@@H](O)C1] | ¹H NMR (400 MHz, CD₃OD): δ (ppm) = 8.06-7.90 (2H, m), 7.21 (2H, t, J = 8.8 Hz), 5.32 (1H, s), 4.53 (1H, d, J = 6.8 Hz), 4.09-3.89 (4H, m), 3.82-3.68 (2H, m), 3.30-3.22 (1H, m), 2.84 (1H, d, J = 17.2 Hz), 2.78-2.65 (2H, m), 1.89-1.75 (2H, m). MS(ESI) m/z: 473 (M + H)⁺ |
| 86 | 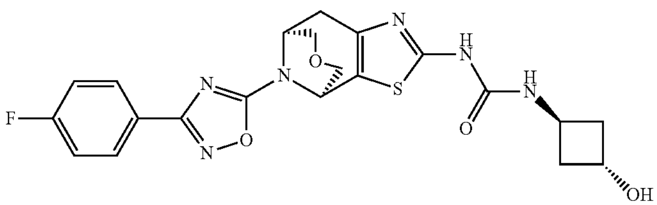 [SMILES: O=C(Nc1nc2c(s1)[C@@H]1COC[C@H](C2)N1c1nc(-c2ccc(F)cc2)no1)N[C@H]1C[C@H](O)C1] | ¹H NMR(400 MHz, CDCl₃): δ (ppm) = 7.93-7.84 (2H, m), 7.08-7.01 (2H, m), 5.17 (1H, s), 4.47-4.39 (2H, m), 4.38-4.27 (1H, m), 3.95 (2H, d, J = 0.8 Hz), 3.88 (1H, dd, J = 11.2, 2.0 Hz), 3.72-3.65 (1H, m), 3.35-3.28 (1H, m), 2.80 (1H, d, J = 17.2 Hz), 2.35-2.16 (4H, m). MS(ESI) m/z: 473 (M + H)⁺ |

TABLE 3-2

| No. | Structure | Data |
|---|---|---|
| 87 | 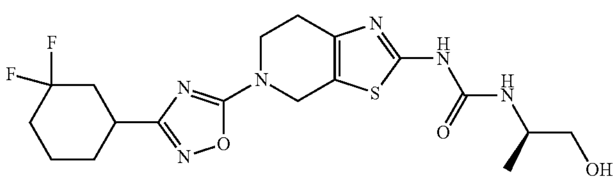 [SMILES: C[C@H](CO)NC(=O)Nc1nc2c(s1)CN(c1nc(C3CCCC(F)(F)C3)no1)CC2] | ¹H NMR(400 MHz, DMSO-d₆): δ (ppm) = 10.15 (1H, br s), 6.49 (1H, d, J = 8.0 Hz), 4.66 (2H, s), 3.85 (2H, t, J = 5.8 Hz), 3.75-3.66 (1H, m), 3.37 (2H, d, J = 4.8 Hz), 2.87-2.78 (2H, m), 2.74-2.69 (2H, m), 2.31-2.21 (1H, m), 2.11-1.70 (6H, m), 1.61-1.41 (2H, m), 1.08 (3H, d, J = 6.8 Hz). MS(ESI) m/z: 443 (M + H)⁺ |
| 88 | 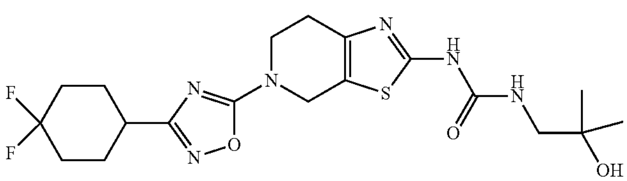 [SMILES: CC(C)(O)CNC(=O)Nc1nc2c(s1)CN(c1nc(C3CCC(F)(F)CC3)no1)CC2] | ¹H NMR (400 MHz, CD₃OD): δ (ppm) = 4.73 (2H, s), 3.96 (2H, t, J = 5.6 Hz), 3.24 (2H, s), 2.81 (3H, t, J = 5.6 Hz), 2.18-2.02 (4H, m), 2.01-1.80 (4H, m), 1.23 (6H, s). MS(ESI) m/z: 457 (M + H)⁺ |
| 89 | 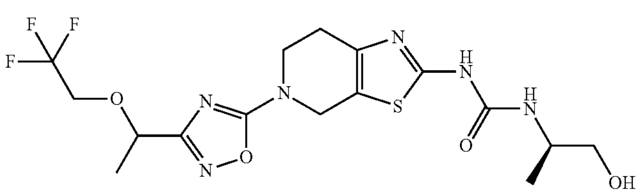 [SMILES: CC(OCC(F)(F)F)c1noc(N2CCc3nc(NC(=O)N[C@H](C)CO)sc3C2)n1] | ¹H NMR(400 MHz, CDCl₃): δ (ppm) = 4.74 (2H, s), 4.63 (1H, q, J = 6.8 Hz), 4.07 (1H, s), 4.01-3.91 (3H, m), 3.89-3.78 (1H, m), 3.76-3.69 (1H, m), 3.66-3.57 (1H, m), 2.86 (2H, s), 1.59 (3H, d, J = 6.4 Hz), 1.27 (3H, d, J = 6.4 Hz). MS(ESI) m/z: 451 (M + H)⁺ |
| 90 | 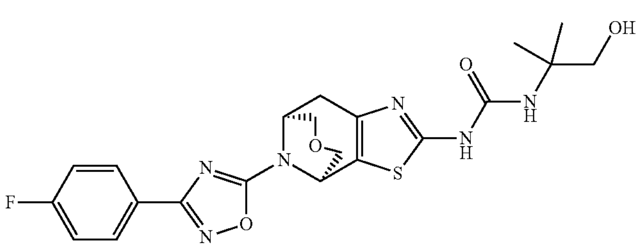 [SMILES: CC(C)(CO)NC(=O)Nc1nc2c(s1)[C@@H]1COC[C@H](C2)N1c1nc(-c2ccc(F)cc2)no1] | ¹H NMR(500 MHz, DMSO-d₆): δ (ppm) = 10.13 (1H, s), 7.97-7.91 (2H, m), 7.39-7.33 (2H, m), 6.39 (1H, s), 5.33 (1H, s), 4.97 (1H, t, J = 5.6 Hz), 4.44 (1H, d, J = 7.1 Hz), 3.97 (1H, d, J = 11.2 Hz), 3.87 (1H, d, J = 11.2 Hz), 3.83 (1H, d, J = 11.2 Hz), 3.62 (1H, d, J = 11.2 Hz), 3.36 (2H, d, J = 5.5 Hz), 3.14 (1H, dd, J = 17.3, 7.1 Hz), 2.77 (1H, d, J = 17.3 Hz), 1.22 (6H, s). MS(APCI) m/z: 475 (M + H)⁺ |

TABLE 3-2-continued

| | | |
|---|---|---|
| 91 | | $^1$H NMR(400 MHz, CDCl$_3$): δ (ppm) = 4.72 (2H, s), 4.06 (1H, d, J = 4.8 Hz), 3.99-3.91 (2H, m), 3.81 (2H, q, J = 8.4 Hz), 3.74 (1H, dd, J = 11.2, 4.0 Hz), 3.63-3.55 (1H, m), 2.85 (2H, s), 1.62 (6H, s), 1.25 (3H, d, J = 6.8 Hz). MS(ESI) m/z: 465 (M + H)$^+$ |
| 92 | | $^1$H NMR(400 MHz, CDCl$_3$): δ (ppm) = 4.69 (2H, s), 3.93 (2H, t, J = 6.0 Hz), 3.36 (2H, d, J = 6.0 Hz), 2.85 (2H, t, J = 5.6 Hz), 1.43 (4H, s), 1.28 (6H, s). MS(ESI) m/z: 447 (M + H)$^+$ |
| 93 | | $^1$H NMR(400 MHz, CDCl$_3$): δ (ppm) = 5.89 (1H, br s), 4.70 (2H, s), 3.97 (2H, t, J = 5.6 Hz), 3.02-2.89 (5H, m), 2.28-2.17 (2H, m), 2.11-1.96 (4H, m), 1.92-1.78 (4H, m). MS(ESI) m/z: 393 (M + H)$^+$ |

TABLE 3-3

| | | |
|---|---|---|
| 94 | | $^1$H NMR(400 MHz, DMSO-d$_6$): δ (ppm) = 10.29 (1H, br s), 6.62 (1H, br s), 4.67-4.55 (3H, m), 3.87-3.79 (2H, m), 3.06 (2H, d, J = 6.0 Hz), 2.72-2.67 (2H, m), 2.60-2.40 (1H, m), 2.37-1.88 (6H, m), 1.08 (6H, s). MS(ESI) m/z: 443 (M + H)$^+$ |
| 95 | | $^1$H NMR(400 MHz, CDCl$_3$): δ (ppm) = 4.75 (2H, s), 4.64 (1H, dd, J = 11.2, 2.0 Hz), 4.56-4.48 (1H, m), 4.27-4.18 (1H, m), 4.03-3.93 (3H, m), 3.93-3.84 (2H, m), 3.83-3.75 (2H, m), 2.87 (2H, t, J = 5.6 Hz), 2.41-2.08 (5H, m), 1.93 (1H, m). MS(ESI) m/z: 457 (M + H)$^+$ |
| 96 | | $^1$H NMR(400 MHz, DMSO-d$_6$): δ (ppm) = 6.68 (1H, br s) 6.11 (1H, t, J = 56.4 Hz), 4.66-4.56 (3H, m), 3.83 (2H, t, J = 6.0 Hz), 3.05 (2H, d, J = 5.6 Hz), 2.73-2.67 (2H, m), 2.14 (6H, s), 1.07 (6H, s). MS(ESI) m/z: 455 (M + H)$^+$ |
| 97 | | $^1$H NMR(400 MHz, CDCl$_3$): δ (ppm) = 4.72 (2H, s), 4.64-4.42 (2H, m), 3.96 (2H, t, J = 6.0 Hz), 2.90-2.87 (2H, m), 2.52-2.32 (4H, m), 1.45 (4H, s). MS(ESI) m/z: 445 (M + H)$^+$ |
| 98 | | $^1$H NMR(400 MHz, CDCl$_3$): δ (ppm) = 4.77 (2H, s), 4.68-4.64 (1H, m), 4.29-4.20 (1H, m), 3.99 (2H, t, J = 5.6 Hz), 3.88-3.75 (1H, m), 3.60-3.51 (4H, m), 3.42 (3H, s), 2.94-2.86 (2H, m), 2.46-2.08 (4H, m). MS(ESI) m/z: 445 (M + H)$^+$ |

TABLE 3-3-continued

| | | |
|---|---|---|
| 99 | 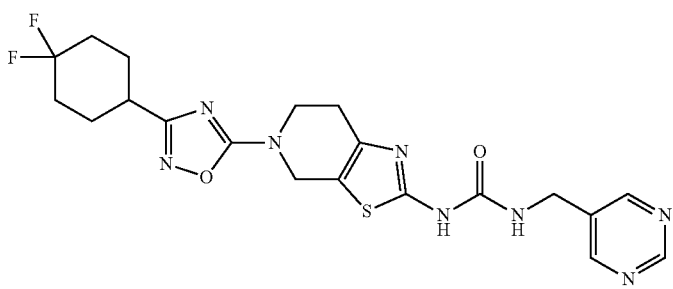 [SMILES: O=C(NCc1cncnc1)Nc1nc2c(s1)CN(c1nc(C3CCC(F)(F)CC3)no1)CC2] | ¹H NMR (400 MHz, DMSO-d$_6$): δ (ppm) = 10.63 (1H, s), 9.05-9.04 (1H, m), 8.71-8.70 (2H, m), 7.16-7.15 (1H, m), 4.61 (2H, s), 4.32 (2H, d, J = 5.5 Hz), 3.81-3.78 (2H, m), 2.76 (1H, s), 2.67 (2H, s), 2.07-1.86 (6H, m), 1.71-1.65 (2H, m). MS(ESI) m/z: 477 (M + H)⁺ |
| 100 | 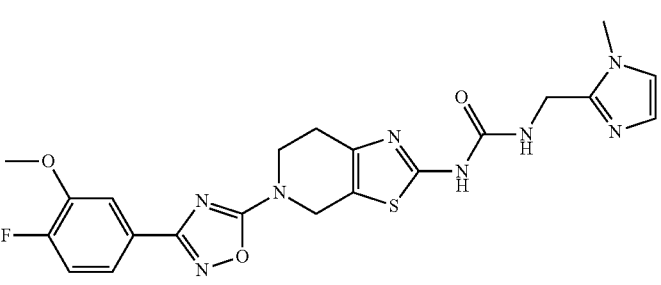 [SMILES: COc1cc(-c2noc(N3CCc4nc(NC(=O)NCc5nccn5C)sc4C3)n2)ccc1F] | ¹H NMR(400 MHz, DMSO-d$_6$): δ (ppm) = 8.15 (1H, s), 7.61-7.57 (1H, m), 7.55-7.49 (1H, m), 7.39-7.32 (1H, m), 7.11-7.06 (2H, m), 6.84 (1H, s), 4.76 (2H, s), 4.39 (2H, 5.6 Hz), 3.91 (3H, s), 3.62 (3H, s), 2.77 (2H, t, J = 5.2 Hz). MS(ESI) m/z: 485 (M + H)⁺ |

TABLE 3-4

| | | |
|---|---|---|
| 101 | 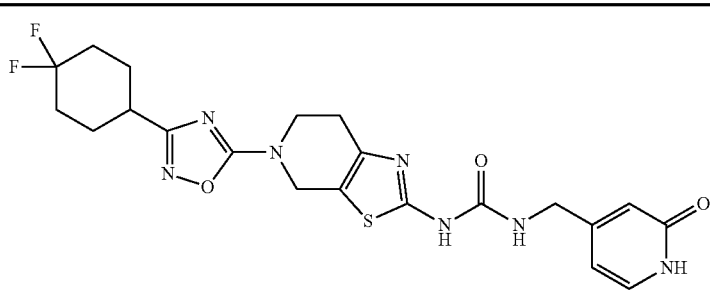 | ¹H NMR (400 MHz, DMSO-d$_6$): δ (ppm) = 11.36 (1H, s), 10.57 (1H, s), 7.26 (1H, d, J = 6.9 Hz), 7.03-7.01 (1H, m), 6.09-6.02 (2H, m), 4.61 (2H, s), 4.11 (2H, d, J = 5.9 Hz), 3.81 (2H, t, J = 5.9 Hz), 2.79-2.74 (1H, m), 2.67 (2H, d, J = 5.9 Hz), 2.05-1.62 (8H, m). MS(ESI) m/z: 492 (M + H)⁺ |
| 102 | 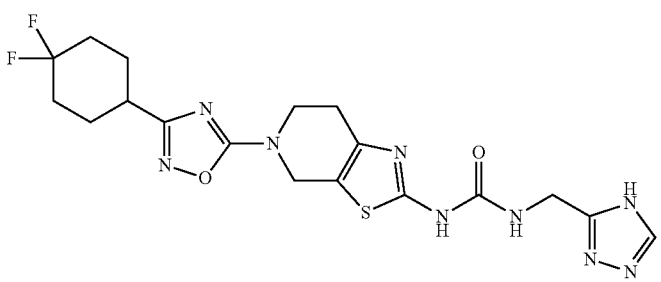 [SMILES: O=C(NCc1nnc[nH]1)Nc1nc2c(s1)CN(c1nc(C3CCC(F)(F)CC3)no1)CC2] | ¹H NMR (400 MHz, DMSO-d$_6$): δ (ppm) = 7.03 (1H, s), 4.62 (2H, s), 4.37 (2H, d, J = 5.7 Hz), 3.80 (2H, t, J = 5.7 Hz), 2.76-2.66 (3H, m), 2.02-1.86 (6H, m), 1.71-1.65 (2H, m). MS(ESI) m/z: 466 (M + H)⁺ |
| 103 | 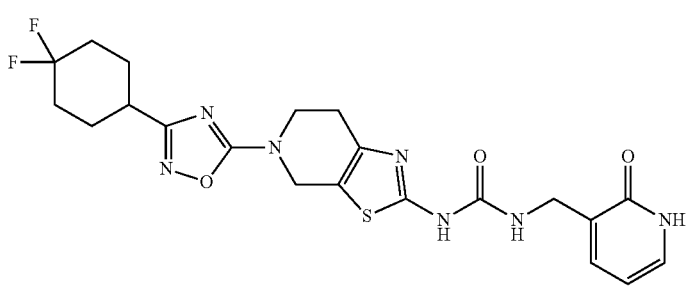 [SMILES: O=C(NCc1ccc[nH]c1=O)Nc1nc2c(s1)CN(c1nc(C3CCC(F)(F)CC3)no1)CC2] | ¹H NMR (400 MHz, DMSO-d$_6$): δ (ppm) = 11.66 (1H, s), 10.48 (1H, s), 7.29-7.28 (2H, m), 7.08 (1H, s), 6.15-6.12 (1H, m), 4.60 (2H, s), 4.03 (2H, d, J = 5.7 Hz), 3.80 (2H, t, J = 5.7 Hz), 2.79-2.66 (3H, m), 2.02-1.62 (8H, m). MS(ESI) m/z: 492 (M + H)⁺ |

TABLE 3-4-continued

| 104 | (structure) | ¹H NMR (400 MHz, DMSO-d₆): δ (ppm) = 10.19 (1H, s), 6.69-6.68 (1H, m), 5.40 (1H, s), 4.61 (2H, s), 3.80 (2H, t, J = 5.9 Hz), 3.18 (2H, d, J = 5.5 Hz), 2.80-2.65 (3H, m), 2.05-1.82 (6H, m), 1.71-1.62 (2H, m), 0.55-0.43 (4H, m). MS(ESI) m/z: 455 (M + H)⁺ |
|---|---|---|
| 105 | (structure) | ¹H NMR (400 MHz, DMSO-d₆): δ (ppm) = 10.16 (1H, s), 6.88 (1H, s), 4.77 (1H, s), 4.61 (2H, s), 3.80 (2H, t, J = 5.7 Hz), 3.43-3.32 (2H, m), 2.80-2.74 (1H, m), 2.66-2.61 (2H, m), 2.02-1.83 (6H, m), 1.71-1.62 (2H, m), 0.67-0.62 (4H, m). MS(ESI) m/z: 455 (M + H)⁺ |
| 106 | (structure) | ¹H NMR(400 MHz, DMSO-d₆): δ (ppm) = 10.43 (1H, s), 8.36 (1H, s), 7.03 (1H, s), 4.62 (2H, s), 4.30 (2H, d, J = 5.9 Hz), 3.82-3.76 (5H, m), 2.80-2.63 (3H, m), 2.05-1.86 (6H, m), 1.71-1.65 (2H, m). MS(ESI) m/z: 480 (M + H)⁺ |
| 107 | (structure) | ¹H NMR(400 MHz, DMSO-d₆): δ (ppm) = 10.14 (1H, br s), 7.85 (2H, d, J = 8.8 Hz), 7.06 (2H, d, J = 8.8 Hz), 6.64 (1H, J = 7.2 Hz, d), 4.74 (2H, s), 3.92 (2H, t, J = 5.6 Hz), 3.83-3.79 (5H, m), 3.73-3.65 (1H, m), 3.42-3.35 (2H, m), 2.76-2.71 (2H, m), 1.79 (2H, d, J = 10.4 Hz), 1.45-1.35 (2H, m). MS(ESI) m/z: 457 (M + H)⁺ |

TABLE 3-5

| 108 | (structure) | ¹H NMR(400 MHz, DMSO-d₆): δ (ppm) = 10.14 (1H, s), 7.52-7.49 (1H, m), 7.46-7.40 (2H, m), 7.14-7.10 (1H, m), 6.63 (1H, d, J = 6.8 Hz), 4.75 (2H, s), 3.94 (2H, t, J = 5.6 Hz), 3.85-3.78 (5H, m), 3.74-3.65 (1H, m), 3.41-3.36 (2H, m), 2.76 (2H, s), 1.79 (2H, d, J = 11.6 Hz), 1.45-1.35 (2H, m). MS(ESI) m/z: 457 (M + H)⁺ |
|---|---|---|

TABLE 3-5-continued

| 109 | | ¹H NMR(500 MHz, DMSO-d₆): δ (ppm) = 10.39 (1H, s), 8.08-8.04 (2H, m), 7.77-7.67 (2H, m), 7.14 (1H, t, J = 55.4 Hz), 6.38 (1H, s), 5.26 (1H, s), 4.36 (1H, d, J = 7.2 Hz), 3.98 (1H, d, J = 11.7 Hz), 3.90 (1H, dd, J = 11.7, 2.7 Hz), 3.86 (1H, dd, J = 11.2, 2.0 Hz), 3.63 (1H, d, J = 11.2 Hz), 3.19 (1H, dd, J = 17.3, 7.1 Hz), 2.73 (1H, d, J = 17.3 Hz), 2.66 (3H, d, J = 4.9 Hz). MS(APCI) m/z: 449 (M + H)⁺ |
| 110 | | ¹H NMR(500 MHz, DMSO-d₆): δ (ppm) = 10.39 (1H, s), 8.20 (1H, d, J = 7.8 Hz), 8.16 (1H, s), 7.92 (1H, d, J = 7.8 Hz), 7.79 (1H, t, J = 7.8 Hz), 6.38 (1H, s), 5.29 (1H, s), 4.39 (1H, d, J = 7.1 Hz), 3.98 (1H, d, J = 11.7 Hz), 3.90 (1H, dd, J = 11.7, 2.4 Hz), 3.86 (1H, dd, J = 11.2, 2.0 Hz), 3.63 (1H, d, J = 11.2 Hz), 3.20 (1H, dd, J = 17.6, 7.1 Hz), 2.74 (1H, d, J = 17.6 Hz), 2.66 (3H, d, J = 4.9 Hz). MS(APCI) m/z: 467 (M + H)⁺ |
| 111 | | ¹H NMR(500 MHz, DMSO-d₆): δ (ppm) = 10.37 (1H, s), 7.59 (1H, d, J = 8.1 Hz), 7.45 (1H, t, J = 8.1 Hz), 7.42 (1H, t, J = 2.0 Hz), 7.17 (1H, dd, J = 8.1, 2.0 Hz), 6.38 (1H, s), 5.23 (1H, s), 4.33 (1H, d, J = 6.6 Hz), 3.97 (1H, d, J = 11.2 Hz), 3.89 (1H, d, J = 11.2 Hz), 3.85 (1H, d, J = 11.0 Hz), 3.63 (1H, d, J = 11.0 Hz), 3.17 (1H, dd, J = 17.1, 6.6 Hz), 2.72 (1H, d, J = 17.1 Hz), 2.66 (3H, d, J = 4.4 Hz), 1.33 (9H, s). MS(APCI) m/z: 471 (M + H)⁺ |
| 112 | | ¹H NMR(400 MHz, DMSO-d₆): δ (ppm) = 10.75-10.40 (1H, br s), 8.45 (1H, s), 8.25 (1H, d, J = 7.2 Hz), 8.15 (1H, d, J = 7.6 Hz), 7.75-7.66 (1H, m), 6.69-6.65 (1H, br s), 5.38 (1H, s), 4.49 (1H, d, J = 6.4 Hz), 4.03-3.95 (1H, m), 3.93-3.80 (2H, m), 3.64 (1H, d, J = 11.2 Hz), 3.17 (1 H, dd, J = 17.2, 7.2 Hz), 2.97-2.88 (1H, m), 2.79 (1H, d, J = 17.2 Hz), 2.67 (3H, d, J = 4.4 Hz), 1.16-1.02 (4H, m). MS(ESI) m/z: 467 (M + H)⁺ |

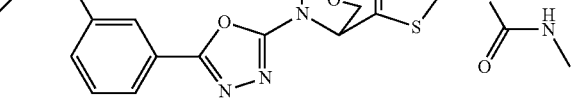

TABLE 3-6

| 113 | | ¹H NMR(500 MHz, DMSO-d₆): δ (ppm) = 10.39 (1H, s), 8.30 (1H, s), 8.11 (1H, d, J = 7.8 Hz), 8.03 (1H, d, J = 7.8 Hz), 7.69 (1H, t, J = 7.8 Hz), 6.38 (1H, s), 5.26 (1H, s), 4.36 (1H, d, J = 6.3 Hz), 4.24-4.17 (1H, m), 3.98 (1H, d, J = 11.7 Hz), 3.91 (1H, dd, J = 11.7, 2.4 Hz), 3.86 (1H, dd, J = 11.0, 1.7 Hz), 3.64 (1H, d, J = 11.0 Hz), 3.19 (1H, dd, J = 17.8, 7.1 Hz), 2.74 (1H, d, J = 17.8 Hz), 2.68-2.65 (4H, m), 2.31-2.22 (4H, m), 2.11-2.02 (1H, m). MS(APCI) m/z: 481 (M + H)⁺ |
| 114 | | ¹H NMR(500 MHz, DMSO-d₆): δ (ppm) = 10.59 (1H, s), 8.42 (1H, t, J = 1.5 Hz), 8.22 (1H, dt, J = 7.8, 1.5 Hz), 8.15 (1H, dt, J = 7.8, 1.5 Hz), 7.73 (1H, t, J = 7.8 Hz), 7.09 (1H, s), 5.30 (1H, s), 4.38 (1H, d, J = 7.3 Hz), 4.02-3.85 (5H, m), 3.65 (1H, d, J = 11.0 Hz), 3.22 (1H, dd, J = 17.1, 7.3 Hz), 3.00-2.93 (1H, m), 2.76 (1H, d, J = 17.1 Hz), 1.14-1.05 (4H, m). MS(APCI) m/z: 535 (M + H)⁺ |
| 115 | | ¹H NMR(400 MHz, CDCl₃): δ (ppm) = 7.77 (1 H, d, J = 8.0 Hz), 7.68 (1H, s), 7.47 (1H, t, J = 8.0 Hz), 7.25 (1H, d, J = 8.0 Hz), 6.85-6.42 (1H, m), 5.20 (1H, br s), 4.51 (2H, br s), 4.12-3.99 (3H, m), 3.98-3.70 (5H, m), 3.49 (1H, dd, J = 17.2, 5.2 Hz), 2.85 (1H, d, J = 17.2 Hz), 2.34-2.22 (1H, m), 1.97-1.84 (1H, m). MS(ESI) m/z: 521 (M + H)⁺ |

TABLE 3-6-continued

| 116 | 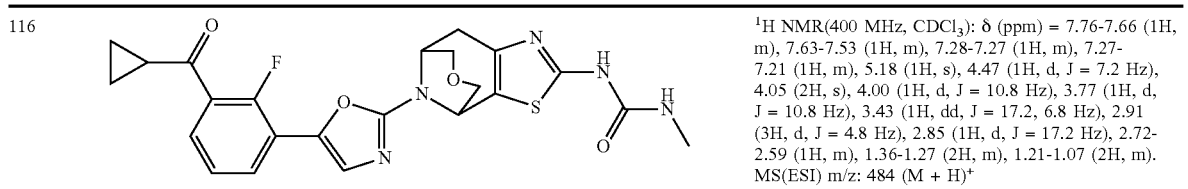 | ¹H NMR(400 MHz, CDCl₃): δ (ppm) = 7.76-7.66 (1H, m), 7.63-7.53 (1H, m), 7.28-7.27 (1H, m), 7.27-7.21 (1H, m), 5.18 (1H, s), 4.47 (1H, d, J = 7.2 Hz), 4.05 (2H, s), 4.00 (1H, d, J = 10.8 Hz), 3.77 (1H, d, J = 10.8 Hz), 3.43 (1H, dd, J = 17.2, 6.8 Hz), 2.91 (3H, d, J = 4.8 Hz), 2.85 (1H, d, J = 17.2 Hz), 2.72-2.59 (1H, m), 1.36-1.27 (2H, m), 1.21-1.07 (2H, m). MS(ESI) m/z: 484 (M + H)⁺ |
|---|---|---|
| 117 | 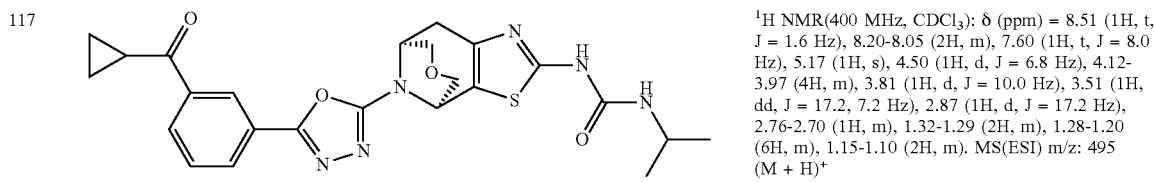 | ¹H NMR(400 MHz, CDCl₃): δ (ppm) = 8.51 (1H, t, J = 1.6 Hz), 8.20-8.05 (2H, m), 7.60 (1H, t, J = 8.0 Hz), 5.17 (1H, s), 4.50 (1H, d, J = 6.8 Hz), 4.12-3.97 (4H, m), 3.81 (1H, d, J = 10.0 Hz), 3.51 (1H, dd, J = 17.2, 7.2 Hz), 2.87 (1H, d, J = 17.2 Hz), 2.76-2.70 (1H, m), 1.32-1.29 (2H, m), 1.28-1.20 (6H, m), 1.15-1.10 (2H, m). MS(ESI) m/z: 495 (M + H)⁺ |

TABLE 3-7

| 118 | 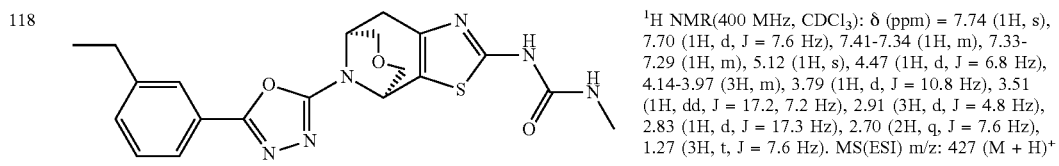 | ¹H NMR(400 MHz, CDCl₃): δ (ppm) = 7.74 (1H, s), 7.70 (1H, d, J = 7.6 Hz), 7.41-7.34 (1H, m), 7.33-7.29 (1H, m), 5.12 (1H, s), 4.47 (1H, d, J = 6.8 Hz), 4.14-3.97 (3H, m), 3.79 (1H, d, J = 10.8 Hz), 3.51 (1H, dd, J = 17.2, 7.2 Hz), 2.91 (3H, d, J = 4.8 Hz), 2.83 (1H, d, J = 17.3 Hz), 2.70 (2H, q, J = 7.6 Hz), 1.27 (3H, t, J = 7.6 Hz). MS(ESI) m/z: 427 (M + H)⁺ |
|---|---|---|
| 119 | 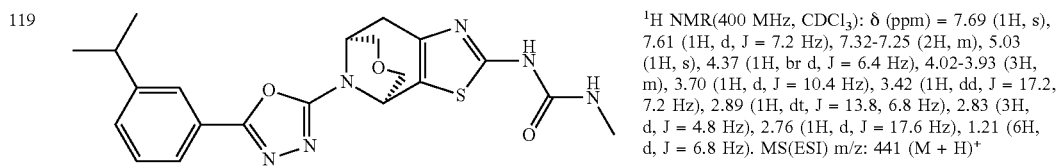 | ¹H NMR(400 MHz, CDCl₃): δ (ppm) = 7.69 (1H, s), 7.61 (1H, d, J = 7.2 Hz), 7.32-7.25 (2H, m), 5.03 (1H, s), 4.37 (1H, br d, J = 6.4 Hz), 4.02-3.93 (3H, m), 3.70 (1H, d, J = 10.4 Hz), 3.42 (1H, dd, J = 17.2, 7.2 Hz), 2.89 (1H, dt, J = 13.8, 6.8 Hz), 2.83 (3H, d, J = 4.8 Hz), 2.76 (1H, d, J = 17.6 Hz), 1.21 (6H, d, J = 6.8 Hz). MS(ESI) m/z: 441 (M + H)⁺ |
| 120 | 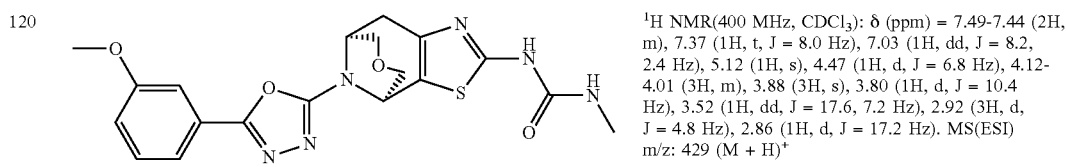 | ¹H NMR(400 MHz, CDCl₃): δ (ppm) = 7.49-7.44 (2H, m), 7.37 (1H, t, J = 8.0 Hz), 7.03 (1H, dd, J = 8.2, 2.4 Hz), 5.12 (1H, s), 4.47 (1H, d, J = 6.8 Hz), 4.12-4.01 (3H, m), 3.88 (3H, s), 3.80 (1H, d, J = 10.4 Hz), 3.52 (1H, dd, J = 17.6, 7.2 Hz), 2.92 (3H, d, J = 4.8 Hz), 2.86 (1H, d, J = 17.2 Hz). MS(ESI) m/z: 429 (M + H)⁺ |
| 121 | 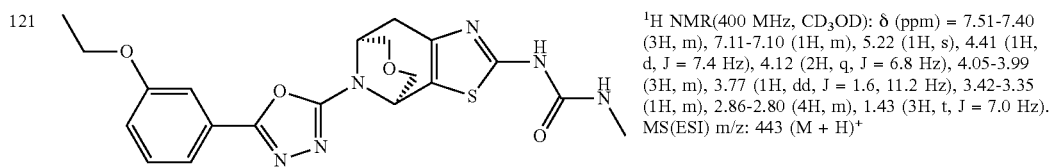 | ¹H NMR(400 MHz, CD₃OD): δ (ppm) = 7.51-7.40 (3H, m), 7.11-7.10 (1H, m), 5.22 (1H, s), 4.41 (1H, d, J = 7.4 Hz), 4.12 (2H, q, J = 6.8 Hz), 4.05-3.99 (3H, m), 3.77 (1H, dd, J = 1.6, 11.2 Hz), 3.42-3.35 (1H, m), 2.86-2.80 (4H, m), 1.43 (3H, t, J = 7.0 Hz). MS(ESI) m/z: 443 (M + H)⁺ |
| 122 | 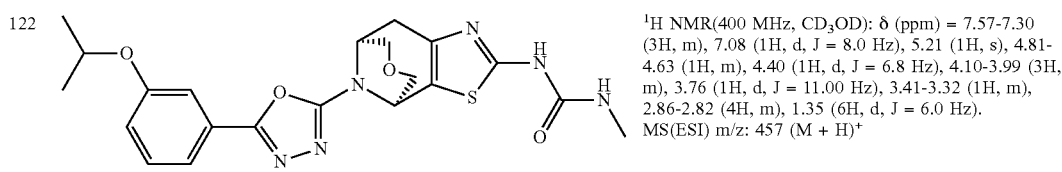 | ¹H NMR(400 MHz, CD₃OD): δ (ppm) = 7.57-7.30 (3H, m), 7.08 (1H, d, J = 8.0 Hz), 5.21 (1H, s), 4.81-4.63 (1H, m), 4.40 (1H, d, J = 6.8 Hz), 4.10-3.99 (3H, m), 3.76 (1H, d, J = 11.00 Hz), 3.41-3.32 (1H, m), 2.86-2.82 (4H, m), 1.35 (6H, d, J = 6.0 Hz). MS(ESI) m/z: 457 (M + H)⁺ |

TABLE 3-7-continued
| 123 | 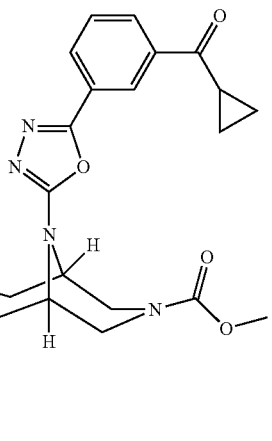 | ¹H NMR(400 MHz, CDCl₃): δ (ppm) = 8.51 (1H, s), 8.14 (2H, dd, J = 7.6, 1.6 Hz), 7.62 (1H, t, J = 8.0 Hz), 5.46-5.34 (1H, m), 4.63-4.58 (1H, m), 4.51-4.07 (2H, m), 3.72-3.33 (6H, m), 2.97-2.77 (4H, m), 2.74-2.66 (1H, m), 1.34-1.28 (2H, m), 1.17-1.12 (2H, m). MS(ESI) m/z: 524 (M + H)⁺ |
TABLE 3-8
| 124 | 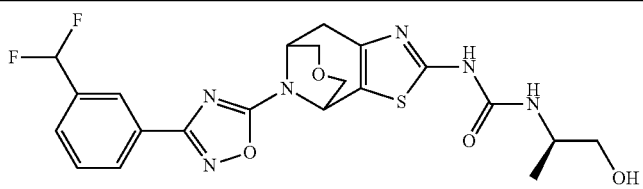 | ¹H NMR(400 MHz, CDCl₃): δ (ppm) = 8.16-8.05 (2H, m), 7.66-7.60 (1H, m), 7.58-7.51 (1H, m), 6.69 (1H, t, J = 56.4 Hz), 5.25 (1H, d, J = 4.4 Hz), 4.52 (1H, s), 4.07-3.90 (4H, m), 3.79-3.64 (2H, m), 3.62-3.52 (1H, m), 3.45-3.31 (1H, m), 2.86 (1H, dd, J = 17.2, 3.6 Hz), 1.22 (3H, d, J = 6.8 Hz). MS(ESI) m/z: 493 (M + H)⁺ |
| 125 | 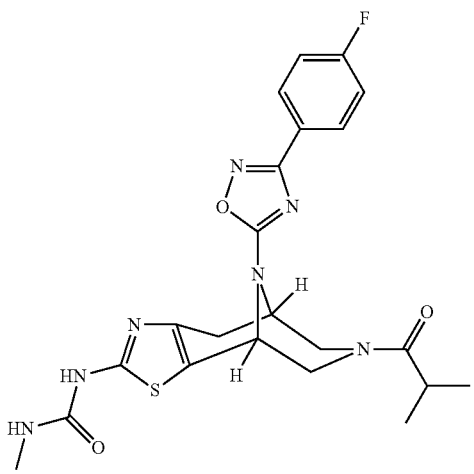 [SMILES: CNC(=O)Nc1nc2c(s1)C1CN(C(=O)C(C)C)CC(C2)N1c1nc(-c2ccc(F)cc2)no1]<br>optically active isomer | ¹H NMR(400 MHz, CDCl₃): δ (ppm) = 8.02-7.95 (2H, m), 7.13 (2H, t, J = 8.8 Hz), 5.50 (1H, s), 4.95 (1H, d, J = 13.6 Hz), 4.68 (1H, br s), 3.96-3.85 (1H, m), 3.75 (1H, d, J = 11.6 Hz), 3.25 (1H, dd, J = 17.2, 6.85 Hz), 3.17-3.07 (1H, m), 3.03-2.86 (4H, m), 2.52-2.39 (1H, m), 1.02 (3H, d, J = 6.8 Hz), 0.70 (3H, d, J = 6.8 Hz). MS(ESI) m/z: 486 (M + H)⁺ |

TABLE 3-8-continued
| 126 | 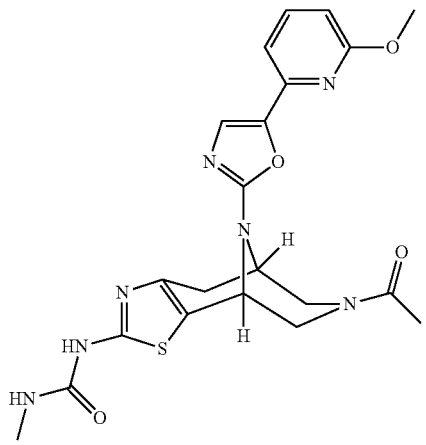 [SMILES: CNC(=O)Nc1nc2c(s1)C1CN(C(C)=O)CC(C2)N1c1ncc(-c2cccc(OC)n2)o1] | ¹H NMR(400 MHz, CDCl₃): δ (ppm) = 7.60-7.53 (1H, m), 7.37-7.33 (1H, m), 7.03-6.97 (1H, m), 6.62-6.55 (1H, m), 5.49-5.40 (1H, m), 4.88 (1H, d, J = 12.8 Hz), 4.73-4.56 (1H, m), 3.94 (3H, s), 3.77 (2H, s), 3.27 (1H, dd, J = 17.2, 7.2 Hz), 3.18-3.06 (1H, m), 2.97-2.87 (3H, m), 2.80 (1H, d, J = 17.2 Hz), 1.78 (3H, s). MS(ESI) m/z: 470 (M + H)⁺ |
TABLE 3-9
| 127 | 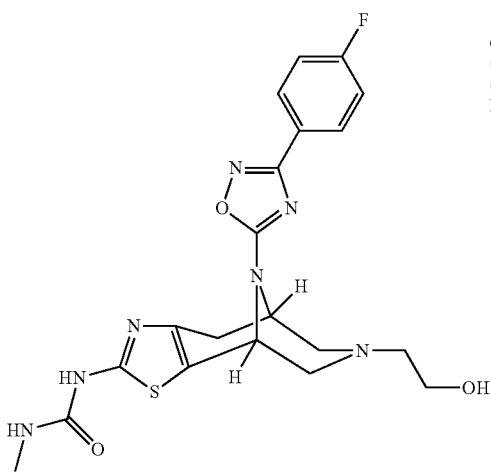 [SMILES: CNC(=O)Nc1nc2c(s1)C1CN(CCO)CC(C2)N1c1nc(-c2ccc(F)cc2)no1]<br>optically active isomer | ¹H NMR(400 MHz, CDCl₃): δ (ppm) = 8.01-7.95 (2H, dd, J = 8.8, 5.4 Hz), 7.15 (2H, t, J = 8.4 Hz), 5.40 (1H, s), 4.77 (1H, br s), 3.70-3.58 (2H, m), 3.41 (1H, dd, J = 17.2, 7.2 Hz), 3.16-2.69 (10H, m). MS(ESI) m/z: 460 (M + H)⁺ |
| 128 | 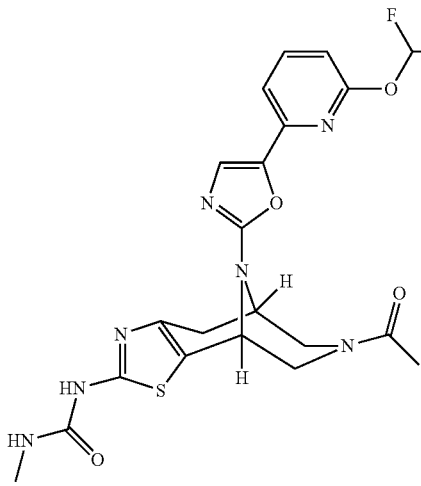 | ¹H NMR(400 MHz, CDCl₃): δ (ppm) = 7.76-7.30 (3H, m), 7.23-7.16 (1H, m), 6.75-6.68 (1H, m), 5.48-5.38 (1H, m), 4.93-4.67 (1H, m), 4.61 (1H, d, J = 5.6 Hz), 4.01-3.68 (2H, m), 3.47-3.21 (1H, m), 3.19-3.06 (1H, m), 2.97-2.87 (3H, m), 2.85-2.60 (1H, m), 2.11-1.78 (3H, m). MS(ESI) m/z: 506 (M + H)⁺ |

TABLE 3-9-continued
| 129 | 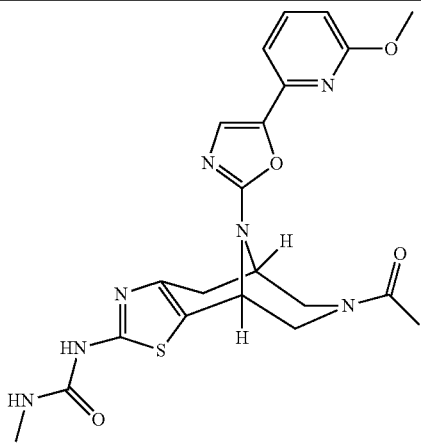 | ¹H NMR(400 MHz, CDCl₃): δ (ppm) = 7.61-7.53 (1H, m), 7.39-7.34 (1H, m), 7.05-6.97 (1H, m), 6.62-6.57 (1H, m), 5.50-5.39 (1H, m), 4.89 (1H, d, J = 13.2 Hz), 4.72-4.53 (1H, m), 3.95 (3H, s), 3.82-3.69 (2H, m), 3.46-3.22 (1H, m), 3.21-3.08 (1H, m), 2.97-2.89 (3H, m), 2.87-2.69 (1H, m), 1.79 (3H, s). MS(ESI) m/z: 470 (M + H)⁺ |
TABLE 3-10
| 130 | 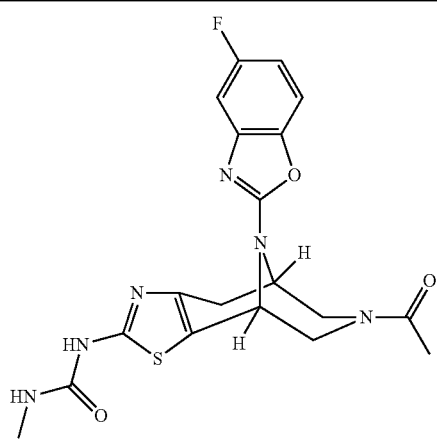 | ¹H NMR (400 MHz, CDCl₃): δ (ppm) = 7.20 (1H, dd, J = 8.8, 4.4 Hz), 7.07 (1H, dd, J = 8.8, 2.8 Hz), 6.84-6.74 (1H, m), 5.60-5.49 (1H, m), 4.90 (1H, d, J = 13.6 Hz), 4.76-4.66 (1H, m), 3.84-3.67 (2H, m), 3.28 (1H, dd, J = 17.2, 7.2 Hz), 3.10 (1H, dd, J = 13.2, 3.2 Hz), 2.92 (3H, d, J = 4.8 Hz), 2.90-2.82 (1H, m), 1.80 (3H, s). MS(ESI) m/z: 431 (M + H)⁺ |
| 131 | 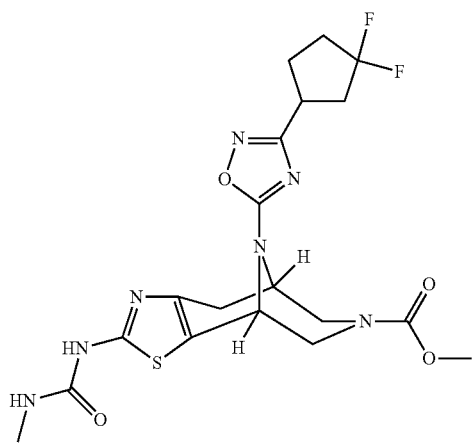 | ¹H NMR (400 MHz, DMSO-d₆): δ (ppm) = 5.40-5.31 (1H, m), 4.59-4.49 (1H, m), 4.44-4.02 (2H, m), 3.65-3.63 (1H, m), 3.49-3.39 (3H, m), 3.33-3.20 (3H, m), 2.94-2.89 (3H, m), 2.86-2.74 (1H, m), 2.52-2.30 (3H, m), 2.18-2.04 (3H, m). MS(ESI) m/z: 484 (M + H)⁺ |

TABLE 3-10-continued
| 132 | 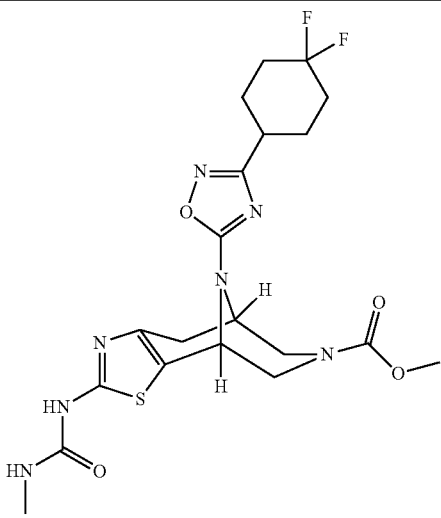 | ¹H NMR (400 MHz, CD₃OD): δ (ppm) = 5.39-5.21 (1H, m), 4.45 (1H, br s), 4.30-4.12 (1H, m), 4.05-3.91 (1H, m), 3.47 (1H, s), 3.39-3.22 (4H, m), 3.05 (1H, dd, J = 17.2, 6.4 Hz), 2.70 (3H, s), 2.68-2.58 (2H, m), 2.03-1.89 (4H, m), 1.82-1.68 (4H, m). MS(ESI) m/z: 498 (M + H)⁺ |
TABLE 3-11
| 133 | 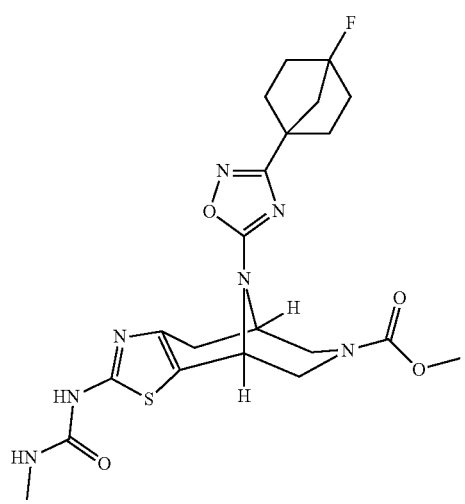 | ¹H NMR (400 MHz, CDCl₃): δ (ppm) = 5.38-5.29 (1H, m), 4.57-4.50 (1H, m), 4.44-3.98 (2H, m), 3.68-3.38 (4H, m), 3.35-3.17 (2H, m), 2.92 (3H, d, J = 4.8 Hz), 2.86-2.72 (1H, m), 2.24-2.13 (2H, m), 2.05-1.95 (4H, m), 1.90-1.77 (4H, m). MS (ESI) m/z: 492 (M + H)⁺ |
| 134 | 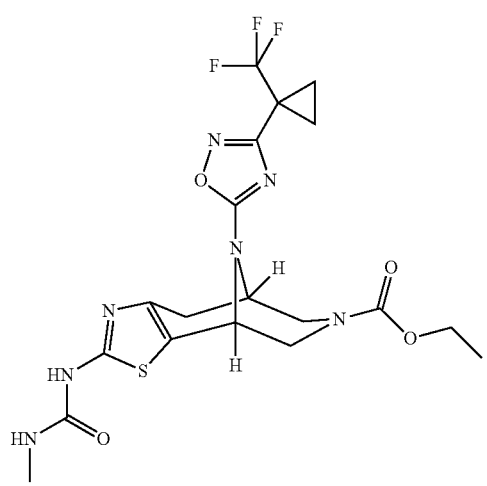 [SMILES: CCOC(=O)N1CC2Cc3nc(NC(=O)NC)sc3C(C1)N2c1nc(C2(C(F)(F)F)CC2)no1] | ¹H NMR (400 MHz, CDCl₃): δ (ppm) = 5.39-5.28 (1H, m), 4.55-4.53 (1H, m), 4.47-4.19 (1H, m), 4.16-3.84 (3H, m), 3.47-3.19 (3H, m), 2.93-2.75 (3H, m), 2.89-2.71 (1H, m), 1.52-1.36 (4H, m), 1.31-1.14 (1H, m), 1.05 (2H, t, J = 7.2 Hz). MS (ESI) m/z: 502 (M + H)⁺ |

TABLE 3-11-continued
| 135 | 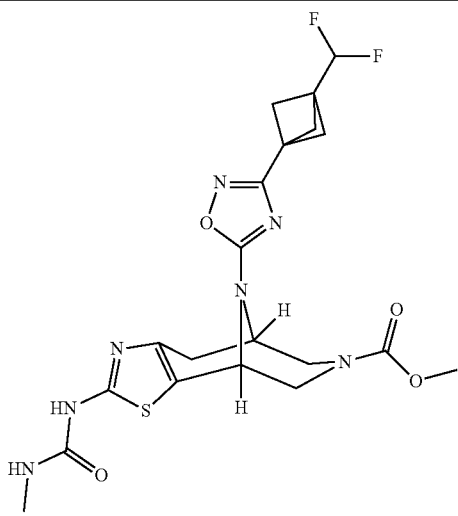 | $^1$H NMR (400 MHz, CDCl$_3$): δ (ppm) = 5.77 (1H, t, J = 56.4 Hz), 5.45-5.31 (1H, m), 4.56 (1H, br s), 4.45-3.58 (3H, m), 3.50-3.37 (3H, m), 3.35-3.18 (2H, m), 2.94 (3H, d, J = 4.4 Hz), 2.89-2.74 (1H, m), 2.25 (6H, s). MS (ESI) m/z: 496 (M + H)$^+$ |
| --- | --- | --- |
| 136 | 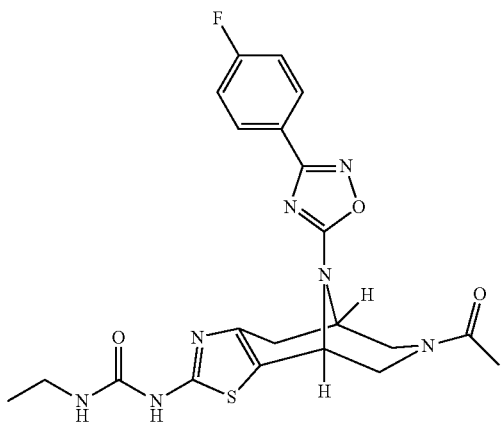 [SMILES: CCNC(=O)Nc1nc2c(s1)C1CN(C(C)=O)CC(C2)N1c1nc(-c2ccc(F)cc2)no1] | $^1$H NMR (500 MHz, DMSO-d$_6$): δ (ppm) = 10.32-10.17 (1H, m), 7.99-7.92 (2H, m), 7.41-7.33 (2H, m), 6.50 (1H, s), 5.53 (1H, s), 4.68-4.37 (2H, m), 4.09-3.80 (1H, m), 3.68-3.56 (1H, m), 3.18-2.99 (4H, m), 2.84-2.52 (1H, m), 1.97-1.59 (3H, m), 1.08-1.02 (3H, m). MS (APCI) m/z: 472 (M + H)$^+$ |
TABLE 3-12
| 137 | 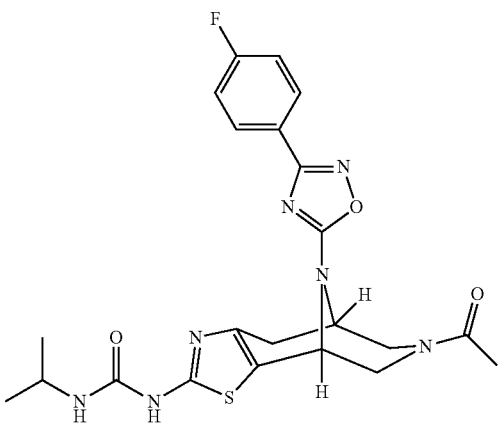 [SMILES: CC(=O)N1CC2Cc3nc(NC(=O)NC(C)C)sc3C(C1)N2c1nc(-c2ccc(F)cc2)no1] | $^1$H NMR (500 MHz, DMSO-d$_6$): δ (ppm) = 10.07-9.95 (1H, m), 7.99-7.91 (2H, m), 7.41-7.31 (2H, m), 6.45-6.34 (1H, m), 5.53 (1H, s), 4.67-4.35 (2H, m), 4.08-3.81 (1H, m), 3.81-3.71 (1H, m), 3.68-3.55 (1H, m), 3.16-3.01 (2H, m), 2.84-2.52 (1H, m), 1.99-1.56 (3H, m), 1.13-1.07 (6H, m). MS (APCI) m/z: 486 (M + H)$^+$ |
| --- | --- | --- |

TABLE 3-12-continued
| 138 | 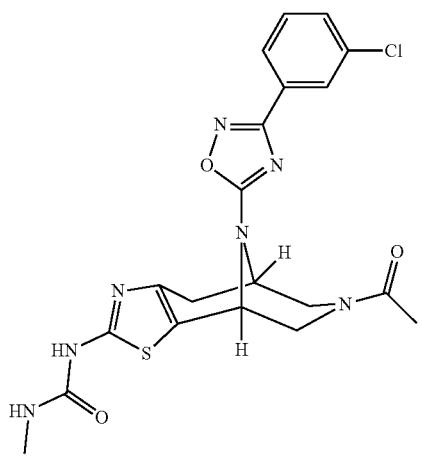 | ¹H NMR (400 MHz, CDCl₃): δ (ppm) = 7.77 (1H, d, J = 7.6 Hz), 7.68 (1H, dd, J = 9.6, 1.6 Hz), 7.42 (1H, td, J = 8.0, 5.6 Hz), 7.18 (1H, td, J = 8.4, 2.4 Hz), 5.53 (1H, s), 4.91 (1H, d, J = 13.6 Hz), 4.79-4.64 (1H, m), 4.04-3.69 (2H, m), 3.46-3.22 (1H, m), 3.19-3.07 (1H, m), 3.00-2.71 (4H, m), 2.11-1.79 (3H, m). MS (ESI) m/z: 458 (M + H)⁺ |
| --- | --- | --- |
| 139 | 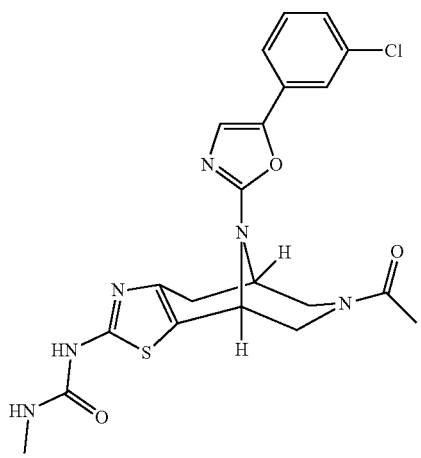 [SMILES: CNC(=O)Nc1nc2c(s1)C1CN(C(C)=O)CC(C2)N1c1ncc(-c2cccc(Cl)c2)o1] | ¹H NMR (400 MHz, CDCl₃): δ (ppm) = 7.47-7.43 (1H, m), 7.37-7.32 (1H, m), 7.32-7.28 (1H, m), 7.23-7.19 (1H, m), 7.09-7.06 (1H, m), 5.49-5.39 (1H, m), 4.95-4.67 (1H, m), 4.64-4.54 (1H, m), 4.01-3.67 (2H, m), 3.49-3.21 (1H, m), 3.19-3.07 (1H, m), 2.97-2.86 (3H, m), 2.85-2.62 (1H, m), 2.11-1.78 (3H, m). MS (ESI) m/z: 473 (M + H)⁺ |
| 140 | 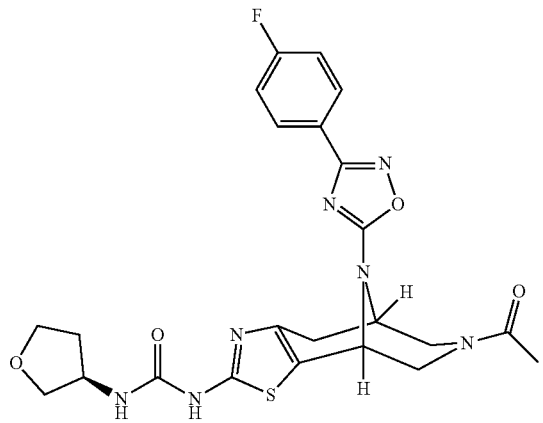 [SMILES: CC(=O)N1CC2Cc3nc(NC(=O)N[C@@H]4CCOC4)sc3C(C1)N2c1nc(-c2ccc(F)cc2)no1] | ¹H NMR (500 MHz, DMSO-d₆): δ (ppm) = 10.12-9.94 (1H, m), 7.97-7.92 (2H, m), 7.39-7.33 (2H, m), 6.87-6.80 (1H, m), 5.53 (1H, s), 4.67-4.37 (2H, m), 4.26-4.19 (1H, m), 4.08-3.46 (6H, m), 3.17-3.00 (2H, m), 2.84-2.53 (1H, m), 2.19-2.08 (1H, m), 1.96-1.59 (4H, m). MS (APCI) m/z: 514 (M + H)⁺ |

TABLE 3-13

| | | |
|---|---|---|
| 141 | 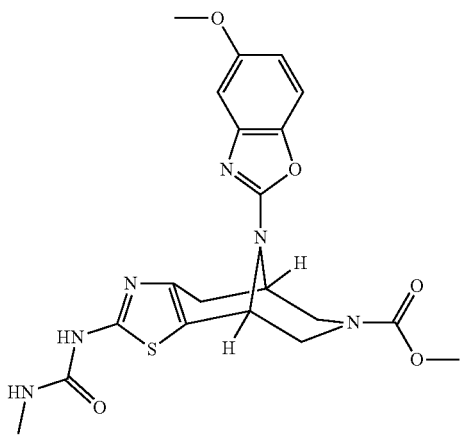 | $^1$H NMR (400 MHz, CDCl$_3$): δ (ppm) = 7.16 (1H, d, J = 8.8 Hz), 6.94 (1H, d, J = 2.4 Hz), 6.64 (1H, dd, J = 8.8, 2.4 Hz), 5.47 (1H, s), 4.70 (1H, s), 4.53-3.98 (2H, m), 3.81 (3H, s), 3.63 (1H, s), 3.54-3.43 (3H, m), 3.39-3.24 (2H, m), 2.91 (3H, d, J = 4.4 Hz), 2.83 (1H, d, J = 17.2 Hz). MS (ESI) m/z: 459 (M + H)$^+$ |
| 142 | 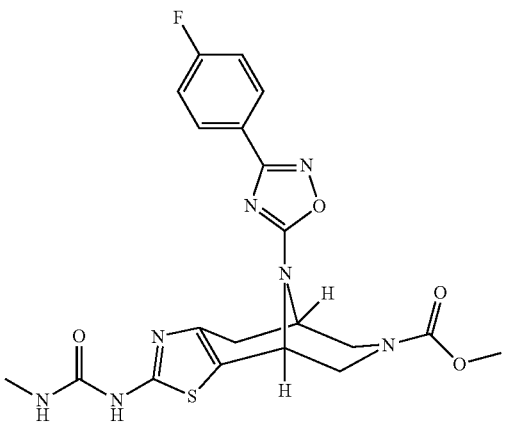 | $^1$H NMR (400 MHz, CDCl$_3$): δ (ppm) = 8.60 (1H, d, J = 2.7 Hz), 8.07-8.04 (1H, m), 7.53-7.48 (1H, m), 5.51 (1H, s), 4.72 (1H, s), 4.45-4.04 (2H, m), 3.61 (1H, s), 3.46-3.26 (5H, m), 2.91-2.84 (4H, m). MS (ESI) m/z: 475 (M + H)$^+$ |
| 143 | 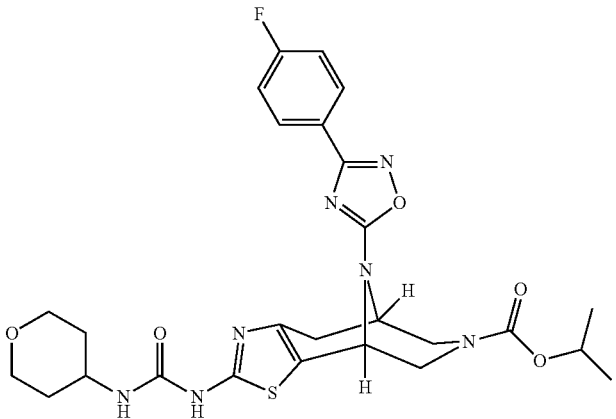 [SMILES: CC(C)OC(=O)N1CC2Cc3nc(NC(=O)NC4CCOCC4)sc3C(C1)N2c1nc(-c2ccc(F)cc2)no1] | $^1$H NMR (400 MHz, DMSO-d$_6$): δ (ppm) = 10.05 (1H, br s), 7.92-7.89 (2H, m), 7.31 (2H, t, J = 8.7 Hz), 6.54 (1H, br s), 5.45 (1H, s), 4.52-4.46 (2H, m), 4.25-4.12 (1H, m), 3.97-3.64 (4H, m), 3.36-3.21 (4H, m), 3.09-3.04 (1H, m), 2.61 (1H, m), 1.74-1.71 (2H, m), 1.38-1.31 (2H, m), 1.11-0.74 (6H, m). MS (ESI) m/z: 572 (M + H)$^+$ |
| 144 | 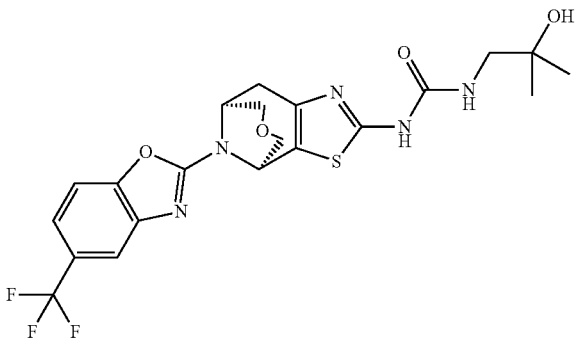 [SMILES: CC(C)(O)CNC(=O)Nc1nc2c(s1)[C@@H]1COC[C@H](C2)N1c1nc2cc(C(F)(F)F)ccc2o1] | $^1$H NMR (500 MHz, DMSO-d$_6$): δ (ppm) = 10.24 (1H, s), 7.69 (1H, s), 7.66 (1H, d, J = 8.5 Hz), 7.44 (1H, d, J = 8.5 Hz), 6.60 (1H, s), 5.40 (1H, s), 4.57 (1H, s), 4.52 (1H, d, J = 6.8 Hz), 4.00 (1H, d, J = 11.7 Hz), 3.89 (1H, d, J = 11.7 Hz), 3.84 (1H, d, J = 11.2 Hz), 3.66 (1H, d, J = 11.2 Hz), 3.17 (1H, dd, J = 17.1, 6.8 Hz), 3.10-3.02 (2H, m), 2.77 (1H, d, J = 17.1 Hz), 1.07 (6H, d, J = 1.5 Hz). MS (APCI) m/z: 498 (M + H)$^+$ |

TABLE 3-14

| 145 | 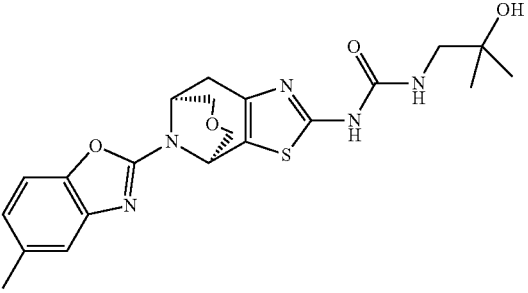 [SMILES: Cc1ccc2oc(N3[C@@H]4COC[C@H]3c3sc(NC(=O)NCC(C)(C)O)nc3C4)nc2c1] | $^1$H NMR (500 MHz, DMSO-$d_6$): δ (ppm) = 10.22 (1H, s), 7.30 (1H, d, J = 7.8 Hz), 7.15 (1H, s), 6.87 (1H, d, J = 7.8 Hz), 6.60 (1H, s), 5.32 (1H, s), 4.57 (1H, s), 4.45 (1H, d, J = 7.1 Hz), 3.98 (1H, d, J = 11.2 Hz), 3.87 (1H, d, J = 11.2 Hz), 3.82 (1H, d, J = 10.7 Hz), 3.64 (1H, d, J = 10.7 Hz), 3.14 (1H, dd, J = 17.1, 7.1 Hz), 3.09-3.01 (2H, m), 2.73 (1H, d, J = 17.1 Hz), 2.33 (3H, s), 1.07 (6H, d, J = 2.0 Hz). MS (APCI) m/z: 444 (M + H)$^+$ |
| --- | --- | --- |
| 146 | 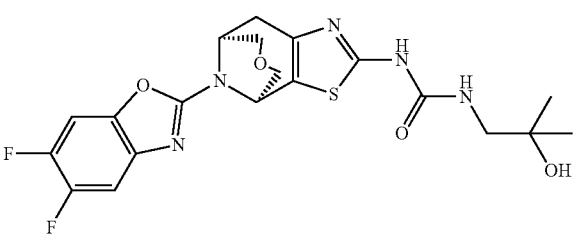 [SMILES: CC(C)(O)CNC(=O)Nc1nc2c(s1)[C@@H]1COC[C@H](C2)N1c1nc2cc(F)c(F)cc2o1] | $^1$H NMR (400 MHz, CD$_3$OD): δ (ppm) = 7.41 (1H, dd, J = 9.6, 6.8 Hz), 7.21 (1H, dd, J = 10.4, 7.2 Hz), 5.33 (1H, s), 4.54 (1H, d, J = 6.8 Hz), 4.10-3.92 (3H, m), 3.77 (1H, d, J = 10.4 Hz), 3.28 (1H, d, J = 7.2 Hz), 3.23 (2H, s), 2.84 (1H, d, J = 17.6 Hz), 1.21 (6H, d, J = 2.0 Hz). MS (ESI) m/z: 466 (M + H)$^+$ |
| 147 | 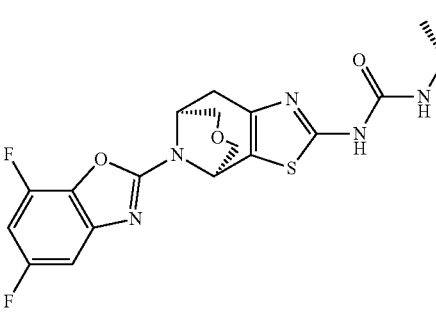 | $^1$H NMR (500 MHz, DMSO-$d_6$): δ (ppm) = 10.14 (1H, s), 7.13-7.10 (1H, m), 7.07-7.02 (1H, m), 6.47 (1H, d, J = 7.8 Hz), 5.40 (1H, s), 4.50 (1H, d, J = 7.1 Hz), 3.98 (1H, d, J = 11.2 Hz), 3.87 (1H, d, J = 11.2 Hz), 3.82 (1H, d, J = 10.7 Hz), 3.70 (1H, s), 3.63 (1H, d, J = 10.7 Hz), 3.50 (1H, s), 3.39-3.32 (2H, m), 3.16 (1H, dd, J = 17.3, 7.1 Hz), 2.76 (1H, d, J = 17.3 Hz), 1.06 (3H, d, J = 6.3 Hz). MS (APCI) m/z: 452 (M + H)$^+$ |
| 148 | 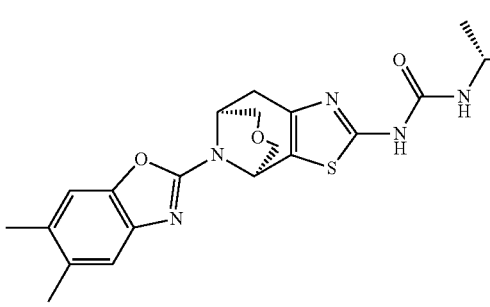 | $^1$H NMR (500 MHz, DMSO-$d_6$): δ (ppm) = 10.10 (1H, s), 7.22 (1H, s), 7.12 (1H, s), 6.46 (1H, d, J = 7.8 Hz), 5.29 (1H, s), 4.41 (1H, d, J = 7.1 Hz), 3.96 (1H, d, J = 11.7 Hz), 3.86 (1H, d, J = 11.7 Hz), 3.81 (1H, d, J = 10.7 Hz), 3.73-3.65 (1H, m), 3.62 (1H, d, J = 10.7 Hz), 3.53-3.40 (1H, m), 3.37-3.32 (2H, m), 3.13 (1H, dd, J = 17.3, 7.1 Hz), 2.71 (1H, d, J = 17.3 Hz), 2.23 (3H, s), 2.22 (3H, s), 1.05 (3H, d, J = 6.3 Hz). MS (APCI) m/z: 444 (M + H)$^+$ |
| 149 | 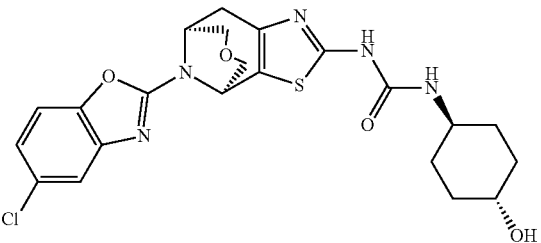 [SMILES: O=C(Nc1nc2c(s1)[C@@H]1COC[C@H](C2)N1c1nc2cc(Cl)ccc2o1)N[C@H]1CC[C@H](O)CC1] | $^1$H NMR (400 MHz, CDCl$_3$): δ (ppm) = 7.34 (1H, d, J = 2.0 Hz), 7.19 (1H, d, J = 8.4 Hz), 7.04 (1H, dd, J = 8.4, 2.0 Hz), 5.28 (1H, s), 4.57 (1H, d, J = 6.8 Hz), 4.05 (2H, s), 4.00-3.94 (1H, m), 3.78 (1H, d, J = 10.8 Hz), 3.73-3.60 (2H, m), 3.42 (1H, d, J = 17.2, 7.2 Hz), 2.86 (1H, d, J = 17.2 Hz), 2.11-1.96 (4H, m), 1.45-1.26 (4H, m). MS (ESI) m/z: 490 (M + H)$^+$ |

TABLE 3-15

| 150 | 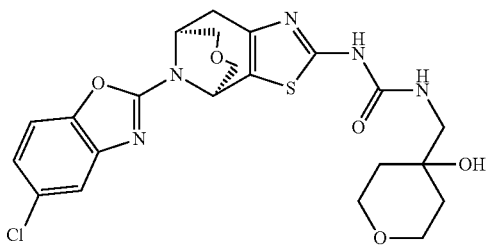 [SMILES: O=C(NCC1(O)CCOCC1)Nc1nc2c(s1)[C@@H]1COC[C@H](C2)N1c1nc2cc(Cl)ccc2o1] | ¹H NMR (400 MHz, CDCl₃): δ (ppm) = 7.34 (1H, d, J = 1.6 Hz), 7.18 (1H, d, J = 8.8 Hz), 7.04 (1H, dd, J = 8.4, 2.0 Hz), 5.27 (1H, s), 4.56 (1H, d, J = 7.2 Hz), 4.03 (2H, s), 3.96 (1H, d, J = 11.2 Hz), 3.79-3.73 (5H, m), 3.45-3.32 (3H, m), 2.83 (1H, d, J = 17.2 Hz), 1.72-1.61 (2H, m), 1.59-1.51 (2H, m). MS (ESI) m/z: 506 (M + H)⁺ |
|---|---|---|
| 151 | 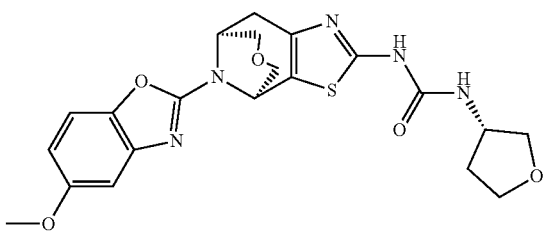 [SMILES: COc1ccc2oc(N3[C@@H]4COC[C@H]3c3sc(NC(=O)N[C@H]5CCOC5)nc3C4)nc2c1] | ¹H NMR (400 MHz, CDCl₃): δ (ppm) = 7.16 (1H, d, J = 8.8 Hz), 6.94 (1H, d, J = 2.8 Hz), 6.64 (1H, dd, J = 8.8, 2.4 Hz), 5.28 (1H, s), 4.65-4.36 (2H, m), 4.04 (2H, d, J = 1.6 Hz), 4.01-3.91 (2H m), 3.91-3.82 (2H m), 3.80 (3H, s), 3.76 (1H, dd, J = 11.2, 1.2 Hz), 3.71 (1H, dd, J = 9.2, 2.8 Hz), 3.42 (1H, dd, J = 17.2, 7.2 Hz), 2.85 (1H, d, J = 17.2 Hz), 2.36-2.22 (2H, m). MS (ESI) m/z: 458 (M + H)⁺ |
| 152 | 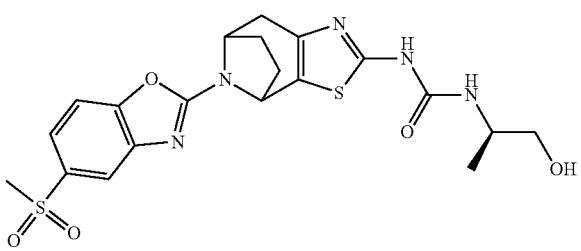 [SMILES: C[C@H](CO)NC(=O)Nc1nc2c(s1)C1CCC(C2)N1c1nc2cc(S(C)(=O)=O)ccc2o1] | ¹H NMR (400 MHz, CD₃OD): δ (ppm) = 7.82 (1H, s), 7.69 (1H, d, J = 8.4 Hz), 7.55 (1H, d, J = 8.4 Hz), 5.37 (1H, d, J = 5.2 Hz), 4.87-4.86 (1H, m), 3.89-3.82 (1H, m), 3.63-3.45 (2H, m), 3.42-3.38 (1H, m), 3.12 (3H, s), 2.61-2.38 (3H, m), 2.20 (1H, t, J = 10.8 Hz), 1.93-1.86 (1H, m), 1.18 (3H, t, J = 6.8 Hz). MS (ESI) m/z: 478 (M + H)⁺ |
| 153 | 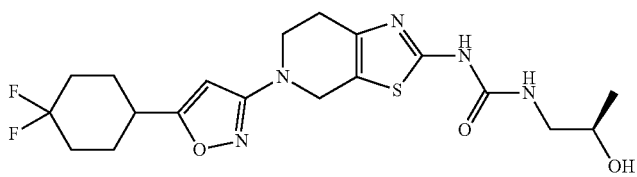 [SMILES: C[C@@H](O)CNC(=O)Nc1nc2c(s1)CN(c1cc(C3CCC(F)(F)CC3)on1)CC2] | ¹H NMR (400 MHz, CDCl₃): δ (ppm) = 5.73 (1H, s), 4.38 (2H, s), 4.00-3.91 (1H, m), 3.66-3.58 (2H, m), 3.54-3.41 (1H, m), 3.29-3.16 (1H, m), 2.85-2.71 (3H, m), 2.23-2.07 (4H, m), 1.95-1.74 (6H, m), 1.32-1.18 (4H, m). MS (APCI) m/z: 442 (M + H)⁺ |
| 154 | 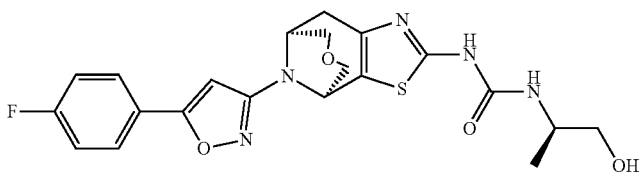 [SMILES: C[C@H](CO)NC(=O)Nc1nc2c(s1)[C@@H]1COC[C@H](C2)N1c1cc(-c2ccc(F)cc2)on1] | ¹H NMR (400 MHz, CDCl₃): δ (ppm) = 7.78-7.54 (2H, m), 7.13-7.09 (2H, m), 6.13 (1H, s), 4.69 (1H, s), 4.23-3.88 (5H, m), 3.78-3.64 (2H, m), 3.55 (1H, dd, J = 11.2, 5.9 Hz), 3.36 (1H, dd, J = 17.2, 6.8 Hz), 2.71 (1H, d, J = 17.2 Hz), 1.18 (3H, d, J = 6.8 Hz). MS (ESI) m/z: 460 (M + H)⁺ |
| 155 | 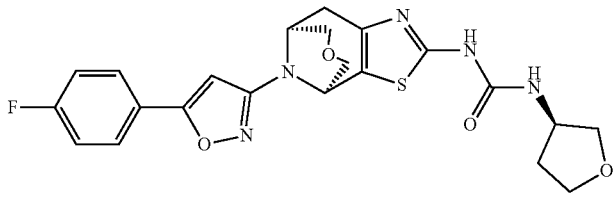 [SMILES: O=C(Nc1nc2c(s1)[C@@H]1COC[C@H](C2)N1c1cc(-c2ccc(F)cc2)on1)N[C@@H]1CCOC1] | ¹H NMR (400 MHz, CDCl₃): δ (ppm) = 7.71-7.64 (2H, m), 7.14-7.10 (2H, m), 6.14 (1H, s), 4.71 (1H, s), 4.54-4.40 (1H, m), 4.14-3.98 (4H, m), 3.95-3.70 (5H, m), 3.38 (1H, dd, J = 17.2, 6.8 Hz), 2.76 (1H, d, J = 17.2 Hz), 2.33-2.21 (1H, m), 1.88-1.84 (1H, m). MS (ESI) m/z: 472 (M + H)⁺ |

TABLE 3-16

| 156 | 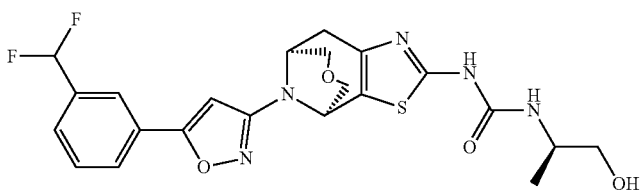 [SMILES: C[C@H](CO)NC(=O)Nc1nc2c(s1)[C@@H]1COC[C@H](C2)N1c1cc(-c2cccc(C(F)F)c2)on1] | ¹H NMR (400 MHz, DMSO-d₆): δ (ppm) = 10.09 (1H, br s), 7.96-7.84 (2H, m), 7.73-7.62 (2H, m), 7.30-6.92 (2H, m), 6.51 (1H, d, J = 7.6 Hz), 4.93-4.74 (2H, m), 4.09-4.02 (1H, m), 3.98-3.80 (3H, m), 3.75-3.56 (2H, m), 3.33-3.27 (2H, m), 3.15-3.03 (1H, m), 2.69-2.58 (1H, m), 1.05 (3H, d, J = 6.4 Hz). MS (ESI) m/z: 492 (M + H)⁺ |
|---|---|---|

TABLE 3-16-continued

| | | |
|---|---|---|
| 157 | 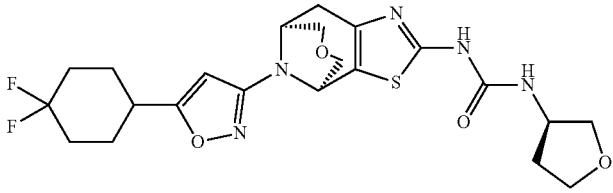 [SMILES: O=C(Nc1nc2c(s1)[C@@H]1COC[C@H](C2)N1c1cc(C2CCC(F)(F)CC2)on1)N[C@@H]1CCOC1] | $^1$H NMR (400 MHz, CDCl$_3$): δ (ppm) = 5.68 (1H, s), 4.65 (1H, s), 4.54-4.43 (1H, m), 4.08-3.65 (10H, m), 3.40-3.27 (1H, m), 2.80-2.66 (2H, m), 2.35-2.03 (5H, m), 1.96-1.63 (6H, m). MS (APCI) m/z: 496 (M + H)$^+$ |
| 158 | 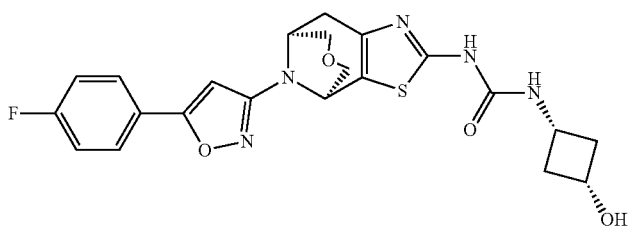 [SMILES: O=C(Nc1nc2c(s1)[C@@H]1COC[C@H](C2)N1c1cc(-c2ccc(F)cc2)on1)N[C@H]1C[C@@H](O)C1] | $^1$H NMR (400 MHz, DMSO-d$_6$): δ (ppm) = 10.04 (1H, br s), 7.83-7.73 (2H, m), 7.35 (2H, t, J = 8.8 Hz), 6.93 (1H, s), 6.76 (1H, d, J = 7.6 Hz), 5.05 (1H, br s), 4.87 (1H, s), 4.04 (1H, d, J = 6.4 Hz), 3.97-3.75 (4H, m), 3.66-3.56 (2H, m), 3.07 (1H, dd, J = 17.2, 7.2 Hz), 2.69-2.53 (3H, m), 1.72-1.61 (2H, m). MS (ESI) m/z: 472 (M + H)$^+$ |
| 159 | 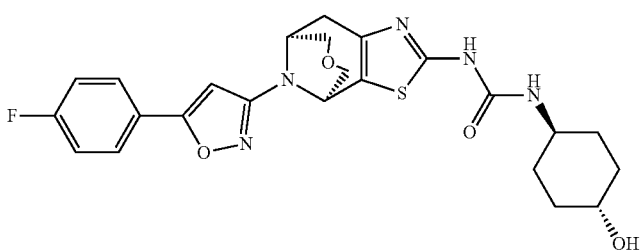 [SMILES: O=C(Nc1nc2c(s1)[C@@H]1COC[C@H](C2)N1c1cc(-c2ccc(F)cc2)on1)N[C@H]1CC[C@H](O)CC1] | $^1$H NMR (400 MHz, DMSO-d$_6$): δ (ppm) = 10.03 (1H, br s), 7.83-7.73 (2H, m), 7.35 (2H, t, J = 8.8 Hz), 6.93 (1H, s), 6.50 (1H, d, J = 7.6 Hz), 4.87 (1H, s), 4.44 (1H, br s), 4.04 (1H, d, J = 6.0 Hz), 3.98-3.76 (3H, m), 3.60 (1H, d, J = 10.4 Hz), 3.39-3.36 (2H, m), 3.07 (1H, dd, J = 16.8, 6.8 Hz), 2.68-2.58 (1H, m), 1.85-1.74 (4H, m), 1.27-1.14 (4H, m). MS (ESI) m/z: δ 00 (M + H)$^+$ |
| 160 | 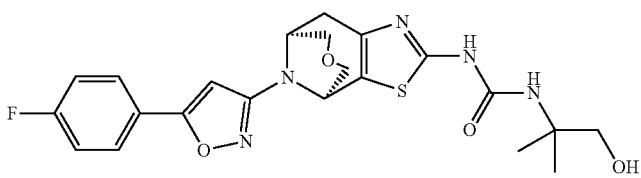 [SMILES: CC(C)(CO)NC(=O)Nc1nc2c(s1)[C@@H]1COC[C@H](C2)N1c1cc(-c2ccc(F)cc2)on1] | $^1$H NMR (400 MHz, DMSO-d$_6$): δ (ppm) = 10.11 (1H, br s), 7.83-7.73 (2H, m), 7.35 (2H, t, J = 8.8 Hz), 6.93 (1H, s), 6.49 (1H, s), 4.98 (1H, br s), 4.85 (1H, s), 4.04 (1H, d, J = 6.4 Hz), 3.98-3.79 (3H, m), 3.60 (1H, d, J = 10.4 Hz), 3.50-3.34 (2H, m), 3.07 (1H, dd, J = 17.2, 7.2 Hz), 2.72-2.56 (1H, m), 1.21 (6H, s). MS (ESI) m/z: 474 (M + H)$^+$ |
| 161 | 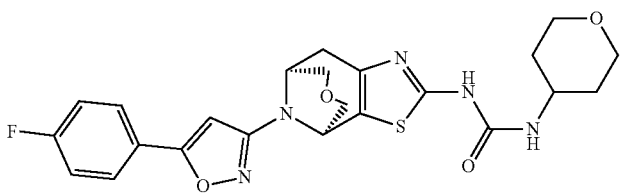 [SMILES: O=C(Nc1nc2c(s1)[C@@H]1COC[C@H](C2)N1c1cc(-c2ccc(F)cc2)on1)NC1CCOCC1] | $^1$H NMR (400 MHz, CDCl$_3$): δ (ppm) = 7.68 (2H, dd, J = 5.2, 8.8 Hz), 7.12 (2H, t, J = 8.8 Hz), 6.14 (1H, s), 4.71 (1H, s), 4.13-4.09 (1H, m), 4.07-4.00 (3H, m), 3.97-3.88 (4H, m), 3.75 (1H, d, J = 10.4 Hz), 3.54-3.46 (2H, m), 3.39 (1H, dd, J = 6.8, 17.2 Hz), 2.77 (1H, d J = 17.2 Hz), 1.98-1.91 (2H, m), 1.60-1.47 (2H, m) MS (APCI/ESI) m/z: 486 (M + H)$^+$ |

TABLE 3-17

| | | |
|---|---|---|
| 162 | 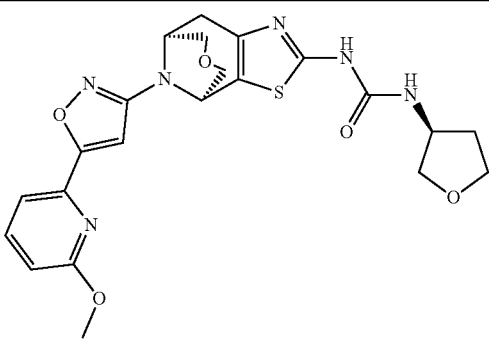 | $^1$H NMR (400 MHz, Acetone-d$_6$): δ (ppm) = 9.34 (1H, br s), 7.80 (1H, dd, J = 7.9, 7.0 Hz), 7.39 (1H, d, J = 7.0 Hz), 6.90 (1H, s), 6.83 (1H, d, J = 7.9 Hz), 6.78 (1H, br s), 4.98 (1H, s), 4.38-4.28 (1H, m), 4.18 (1H, d, J = 6.9 Hz), 4.01-3.93 (6H, m), 3.87-3.70 (4H, m), 3.60-3.55 (1H, m), 3.25 (1H, dd, J = 17.2, 7.1 Hz), 2.67 (1H, d, J = 17.4 Hz), 2.26-2.17 (1H, m), 1.85-1.78 (1H, m). MS (APCI/ESI) m/z: 485 (M + H)$^+$ |

TABLE 3-17-continued

| 163 | 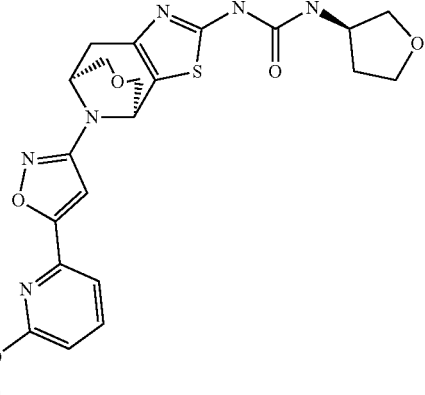 | ¹H NMR (400 MHz, Acetone-d₆): δ (ppm) = 9.33 (1H, br s), 7.80 (1H, dd, J = 8.4, 7.4 Hz), 7.40 (1H, d, J = 7.4 Hz), 6.90 (1H, s), 6.84 (1H, d, J = 8.4 Hz), 6.76 (1H, br s), 4.98 (1H, s), 4.38-4.32 (1H, m), 4.18 (1H, d, J = 7.3 Hz), 3.98-3.91 (6H, m), 3.85-3.79 (2H, m), 3.75-3.69 (2H, m), 3.58 (1H, dd, J = 9.1, 3.2 Hz), 3.25 (1H, dd, J = 17.2, 7.1 Hz), 2.73-2.65 (1H, m), 2.24-2.14 (1H, m), 1.83-1.76 (1H, m). MS (ESI) m/z: 485 (M + H)⁺ |
| --- | --- | --- |
| 164 | 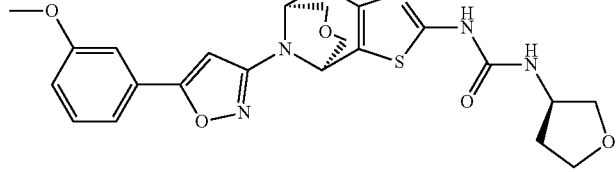 | ¹H NMR (400 MHz, DMSO-d₆): δ (ppm) = 10.31-10.02 (1H, br s), 7.41 (1H, dd, J = 8.0, 7.8 Hz), 7.29 (1H, d, J = 7.8 Hz), 7.24 (1H, s), 7.03 (1H, J = 8.0, 3.0 Hz), 6.98 (1H, br s), 6.97 (1H, s) 4.86 (1H, s), 4.19 (1H, s), 4.03 (1H, d, J = 7.5 Hz), 3.94-3.58 (10H, m), 3.48-3.45 (1H, m), 3.07 (1H, dd, J = 16.7, 7.1 Hz), 2.61 (1H, d, J = 17.4 Hz), 2.13-2.06 (1H, m), 1.71-1.68 (1H, m). MS (APCI/ESI) m/z: 484 (M + H)⁺ |
| 165 | 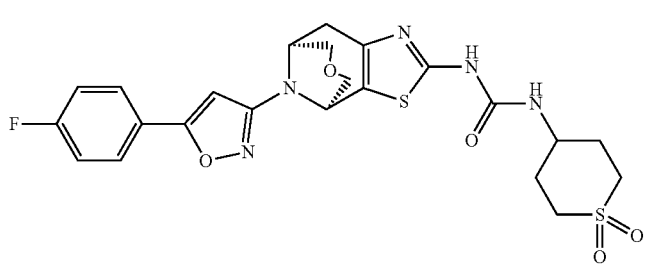 [SMILES: O=C(Nc1nc2c(s1)[C@@H]1COC[C@H](C2)N1c1cc(-c2ccc(F)cc2)on1)NC1CCS(=O)(=O)CC1] | ¹H NMR (400 MHz, Acetone-d₆): δ (ppm) = 9.54 (1H, br s), 7.84-7.79 (2H, m), 7.29-7.24 (2H, m), 6.88 (1H, br s), 6.77 (1H, s), 4.93 (1H, s), 4.14 (1H, d, J = 6.9 Hz), 4.06-3.90 (4H, m), 3.71 (1H, dd, J = 11.0, 1.8 Hz), 3.27-3.17 (3H, m), 3.09-3.01 (2H, m), 2.68 (1H, dd, J = 17.2, 5.7 Hz), 2.33-2.24 (2H, m), 2.15-2.09 (2H, m). MS (ESI) m/z: 534 (M + H)⁺ |
| 166 | 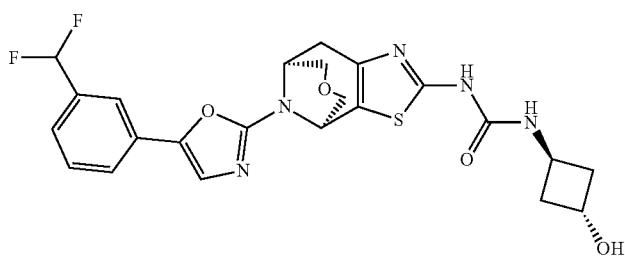 [SMILES: O=C(Nc1nc2c(s1)[C@@H]1COC[C@H](C2)N1c1ncc(-c2cccc(C(F)F)c2)o1)N[C@H]1C[C@H](O)C1] | ¹H NMR (400 MHz, CDCl₃): δ (ppm) = 7.61-7.51 (2H, m), 7.44 (1H, t, J = 7.6 Hz), 7.36 (1H, d, J = 7.6 Hz), 7.10 (1H, s), 6.66 (1H, t, J = 56.8 Hz), 5.16 (1H, s), 4.58-4.33 (3H, m), 4.09-3.94 (3H, m), 3.76 (1H, d, J = 10.8 Hz), 3.40 (1H, dd, J = 7.6, 17.6 Hz), 2.83 (1H, d, J = 17.6 Hz), 2.44-2.21 (5H, m). MS (ESI) m/z: 504 (M + H)⁺ |

TABLE 3-18

| 167 | 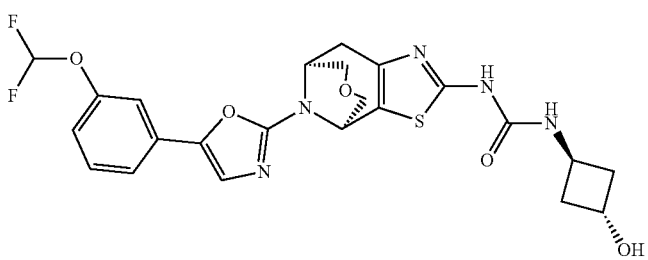 [SMILES: O=C(Nc1nc2c(s1)[C@@H]1COC[C@H](C2)N1c1ncc(-c2cccc(OC(F)F)c2)o1)N[C@H]1C[C@H](O)C1] | ¹H NMR (400 MHz, CD₃OD): δ (ppm) = 7.46-7.39 (2H, m), 7.35-7.30 (1H, m), 7.26 (1H, s), 7.09-6.64 (2H, m), 5.24 (1H, s), 4.45-4.37 (2H, m), 4.34-4.24 (1H, m), 4.09-3.91 (3H, m) 3.76 (1H, d, J =10.8 Hz), 3.31-3.25 (1H, m), 2.80 (1H, d, J =17.2 Hz), 2.37-2.21 (4H, m). MS (ESI) m/z: δ 20 (M + H)⁺ |
| --- | --- | --- |

TABLE 3-18-continued

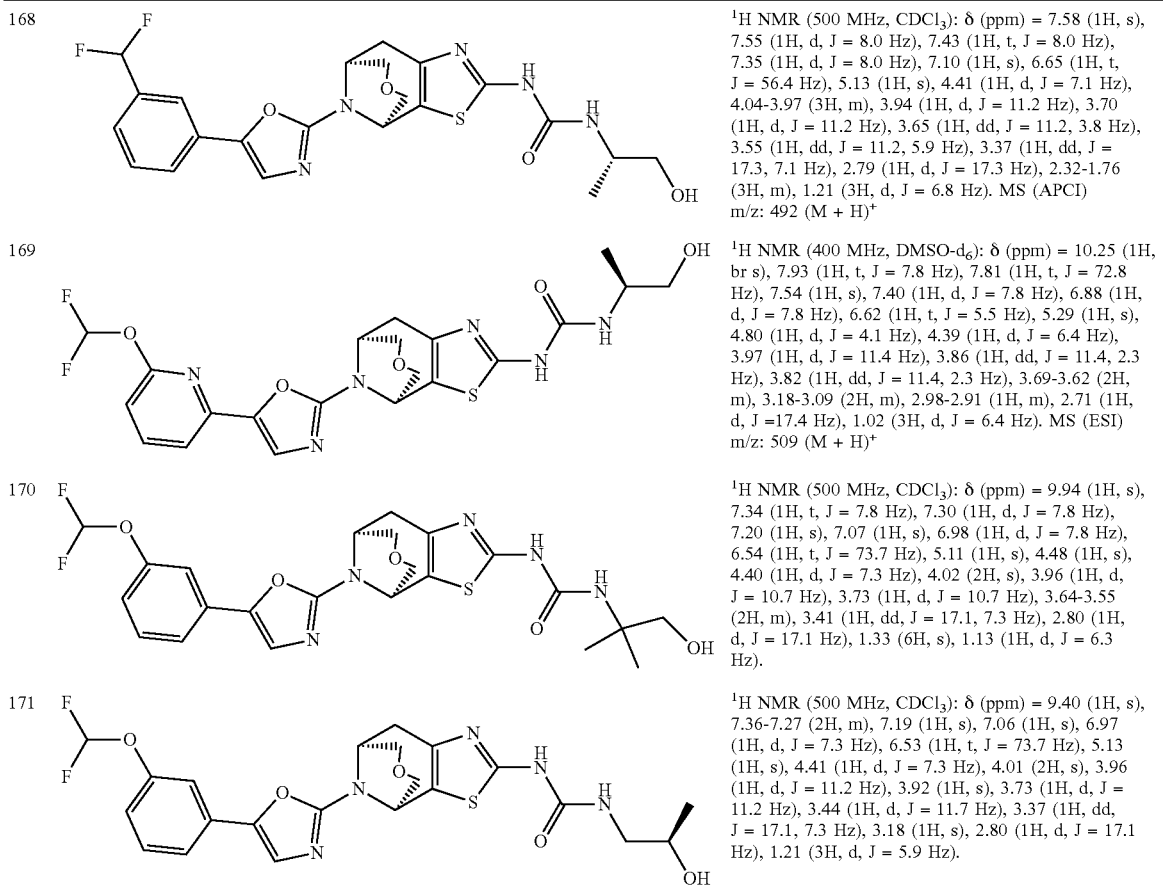

| 168 | (structure) | ¹H NMR (500 MHz, CDCl$_3$): δ (ppm) = 7.58 (1H, s), 7.55 (1H, d, J = 8.0 Hz), 7.43 (1H, t, J = 8.0 Hz), 7.35 (1H, d, J = 8.0 Hz), 7.10 (1H, s), 6.65 (1H, t, J = 56.4 Hz), 5.13 (1H, s), 4.41 (1H, d, J = 7.1 Hz), 4.04-3.97 (3H, m), 3.94 (1H, d, J = 11.2 Hz), 3.70 (1H, d, J = 11.2 Hz), 3.65 (1H, dd, J = 11.2, 3.8 Hz), 3.55 (1H, dd, J = 11.2, 5.9 Hz), 3.37 (1H, dd, J = 17.3, 7.1 Hz), 2.79 (1H, d, J = 17.3 Hz), 2.32-1.76 (3H, m), 1.21 (3H, d, J = 6.8 Hz). MS (APCI) m/z: 492 (M + H)⁺ |
| 169 | (structure) | ¹H NMR (400 MHz, DMSO-d$_6$): δ (ppm) = 10.25 (1H, br s), 7.93 (1H, t, J = 7.8 Hz), 7.81 (1H, t, J = 72.8 Hz), 7.54 (1H, s), 7.40 (1H, d, J = 7.8 Hz), 6.88 (1H, d, J = 7.8 Hz), 6.62 (1H, t, J = 5.5 Hz), 5.29 (1H, s), 4.80 (1H, d, J = 4.1 Hz), 4.39 (1H, d, J = 6.4 Hz), 3.97 (1H, d, J = 11.4 Hz), 3.86 (1H, dd, J = 11.4, 2.3 Hz), 3.82 (1H, dd, J = 11.4, 2.3 Hz), 3.69-3.62 (2H, m), 3.18-3.09 (2H, m), 2.98-2.91 (1H, m), 2.71 (1H, d, J =17.4 Hz), 1.02 (3H, d, J = 6.4 Hz). MS (ESI) m/z: 509 (M + H)⁺ |
| 170 | (structure) | ¹H NMR (500 MHz, CDCl$_3$): δ (ppm) = 9.94 (1H, s), 7.34 (1H, t, J = 7.8 Hz), 7.30 (1H, d, J = 7.8 Hz), 7.20 (1H, s), 7.07 (1H, s), 6.98 (1H, d, J = 7.8 Hz), 6.54 (1H, t, J = 73.7 Hz), 5.11 (1H, s), 4.48 (1H, s), 4.40 (1H, d, J = 7.3 Hz), 4.02 (2H, s), 3.96 (1H, d, J = 10.7 Hz), 3.73 (1H, d, J = 10.7 Hz), 3.64-3.55 (2H, m), 3.41 (1H, dd, J = 17.1, 7.3 Hz), 2.80 (1H, d, J = 17.1 Hz), 1.33 (6H, s), 1.13 (1H, d, J = 6.3 Hz). |
| 171 | (structure) | ¹H NMR (500 MHz, CDCl$_3$): δ (ppm) = 9.40 (1H, s), 7.36-7.27 (2H, m), 7.19 (1H, s), 7.06 (1H, s), 6.97 (1H, d, J = 7.3 Hz), 6.53 (1H, t, J = 73.7 Hz), 5.13 (1H, s), 4.41 (1H, d, J = 7.3 Hz), 4.01 (2H, s), 3.96 (1H, d, J = 11.2 Hz), 3.92 (1H, s), 3.73 (1H, d, J = 11.2 Hz), 3.44 (1H, d, J = 11.7 Hz), 3.37 (1H, dd, J = 17.1, 7.3 Hz), 3.18 (1H, s), 2.80 (1H, d, J = 17.1 Hz), 1.21 (3H, d, J = 5.9 Hz). |

TABLE 3-19

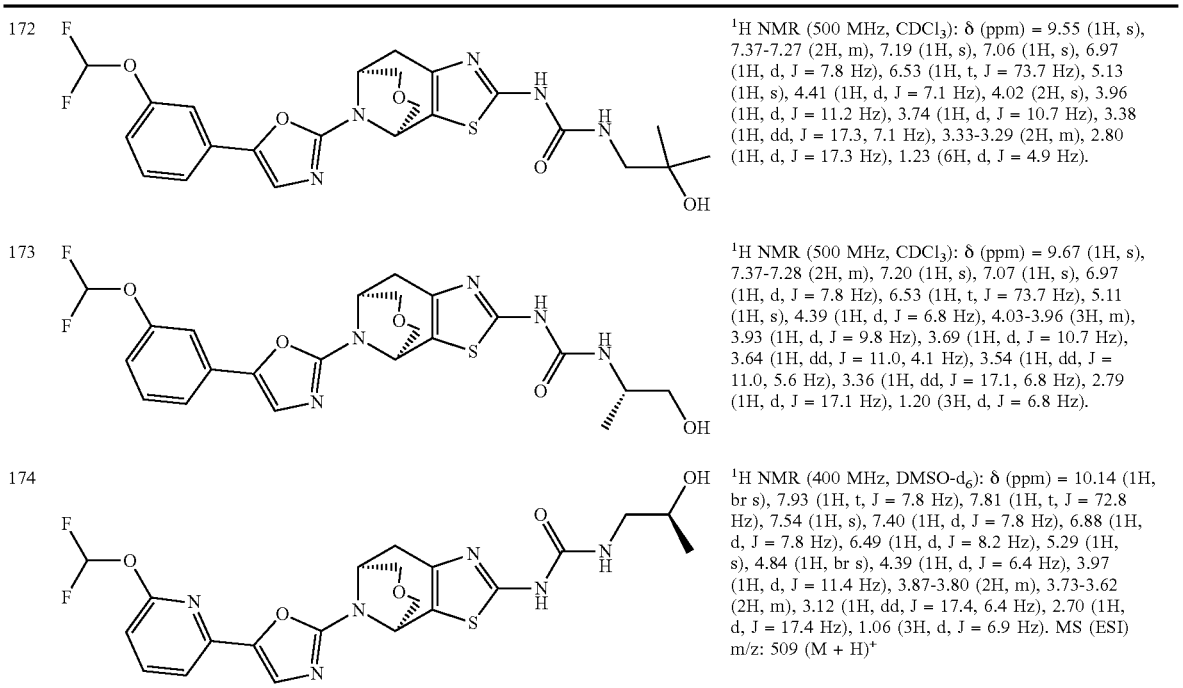

| 172 | (structure) | ¹H NMR (500 MHz, CDCl$_3$): δ (ppm) = 9.55 (1H, s), 7.37-7.27 (2H, m), 7.19 (1H, s), 7.06 (1H, s), 6.97 (1H, d, J = 7.8 Hz), 6.53 (1H, t, J = 73.7 Hz), 5.13 (1H, s), 4.41 (1H, d, J = 7.1 Hz), 4.02 (2H, s), 3.96 (1H, d, J = 11.2 Hz), 3.74 (1H, d, J = 10.7 Hz), 3.38 (1H, dd, J = 17.3, 7.1 Hz), 3.33-3.29 (2H, m), 2.80 (1H, d, J = 17.3 Hz), 1.23 (6H, d, J = 4.9 Hz). |
| 173 | (structure) | ¹H NMR (500 MHz, CDCl$_3$): δ (ppm) = 9.67 (1H, s), 7.37-7.28 (2H, m), 7.20 (1H, s), 7.07 (1H, s), 6.97 (1H, d, J = 7.8 Hz), 6.53 (1H, t, J = 73.7 Hz), 5.11 (1H, s), 4.39 (1H, d, J = 6.8 Hz), 4.03-3.96 (3H, m), 3.93 (1H, d, J = 9.8 Hz), 3.69 (1H, d, J = 10.7 Hz), 3.64 (1H, dd, J = 11.0, 4.1 Hz), 3.54 (1H, dd, J = 11.0, 5.6 Hz), 3.36 (1H, dd, J = 17.1, 6.8 Hz), 2.79 (1H, d, J = 17.1 Hz), 1.20 (3H, d, J = 6.8 Hz). |
| 174 | (structure) | ¹H NMR (400 MHz, DMSO-d$_6$): δ (ppm) = 10.14 (1H, br s), 7.93 (1H, t, J = 7.8 Hz), 7.81 (1H, t, J = 72.8 Hz), 7.54 (1H, s), 7.40 (1H, d, J = 7.8 Hz), 6.88 (1H, d, J = 7.8 Hz), 6.49 (1H, d, J = 8.2 Hz), 5.29 (1H, s), 4.84 (1H, br s), 4.39 (1H, d, J = 6.4 Hz), 3.97 (1H, d, J = 11.4 Hz), 3.87-3.80 (2H, m), 3.73-3.62 (2H, m), 3.12 (1H, dd, J = 17.4, 6.4 Hz), 2.70 (1H, d, J = 17.4 Hz), 1.06 (3H, d, J = 6.9 Hz). MS (ESI) m/z: 509 (M + H)⁺ |

TABLE 3-19-continued

| 175 | 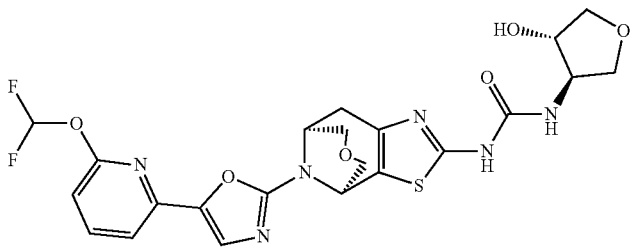 [SMILES: O=C(Nc1nc2c(s1)[C@@H]1COC[C@H](C2)N1c1ncc(-c2cccc(OC(F)F)n2)o1)N[C@@H]1COC[C@H]1O] | ¹H NMR (400 MHz, DMSO-d₆): δ (ppm) = 10.05 (1H, br s), 7.93 (1H, t, J = 7.3 Hz), 7.81 (1H, t, J = 72.8 Hz), 7.54 (1H , s), 7.40 (1H, d, J = 7.3 Hz), 6.89 (1H, d, J = 7.3 Hz), 6.83 (1H, d, J = 6.9 Hz), 5.35 (1H, d, J = 3.7 Hz), 5.30 (1H, s), 4.39 (1H, d, J = 5.9 Hz), 4.05 (1H, s), 3.98-3.92 (2H, m), 3.89-3.81 (4H, m), 3.63 (1H, d, J = 10.1 Hz), 3.54-3.48 (2H, m), 3.12 (1H, dd, J = 17.4, 5.9 Hz), 2.71 (1H, d, J = 17.4 Hz). MS (ESI) m/z: 537 (M + H)⁺ |

TABLE 3-20

| 176 | 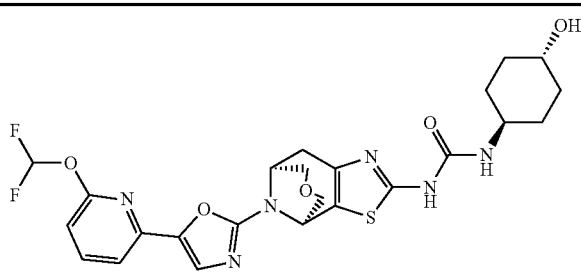 | ¹H NMR (400 MHz, DMSO-d₆): δ (ppm) = 10.04 (1H, s), 7.93 (1H, t, J = 7.8 Hz), 7.81 (1H, t, J = 72.8 Hz), 7.54 (1H, s), 7.40 (1H, d, J = 7.8 Hz), 6.89 (1H, d, J = 7.8 Hz), 6.44 (1H, d, J = 7.3 Hz), 5.29 (1H, s), 4.54 (1H, d, J = 3.7 Hz), 4.39 (1H, d, J = 6.4 Hz), 3.97 (1H, d, J = 11.4 Hz), 3.85 (1H, dd, J = 11.4, 2.5 Hz), 3.81 (1H, dd, J = 10.1, 2.5 Hz), 3.63 (1H, d, J = 10.1 Hz), 3.49-3.36 (2H, m), 3.11 (1H, dd, J = 16.9, 6.4 Hz), 2.70 (1H, d, J = 16.9 Hz), 1.85-1.73 (4H, m), 1.26-1.11 (4H, m). MS (ESI) m/z: 549 (M + H)⁺ |
| 177 | 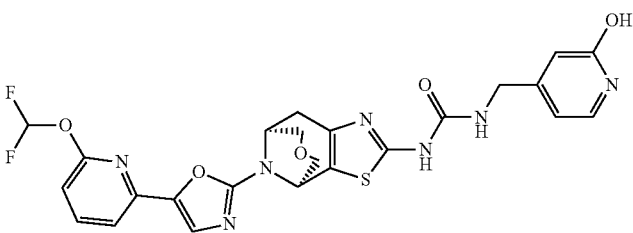 [SMILES: O=C(NCc1ccnc(O)c1)Nc1nc2c(s1)[C@@H]1COC[C@H](C2)N1c1ncc(-c2cccc(OC(F)F)n2)o1] | ¹H NMR (400 MHz, DMSO-d₆): δ (ppm) = 11.43 (1H, br s), 10.61 (1H, br s), 7.93 (1H, t, J = 7.8 Hz), 7.81 (1H, t, J = 72.8 Hz), 7.54 (1H, s), 7.40 (1H, d, J = 7.8 Hz), 7.28 (1H, d, J = 6.9 Hz), 7.03 (1H, t, J = 5.9 Hz), 6.88 (1H, d, J = 7.8 Hz), 6.11 (1H, s), 6.05 (1H, dd, J = 6.9, 1.6 Hz), 5.30 (1H, s), 4.40 (1H, d, J = 6.4 Hz), 4.14 (2H, d, J = 5.9 Hz), 3.98 (1H, d, J = 11.0 Hz), 3.86 (1H, dd, J = 11.0, 2.3 Hz), 3.82 (1H, dd, J = 10.1, 2.3 Hz), 3.63 (1H, d, J = 10.1 Hz), 3.13 (1H, dd, J = 17.4, 6.4 Hz), 2.72 (1H, d, J = 17.4 Hz). MS (ESI) m/z: 558 (M + H)⁺ |
| 178 | 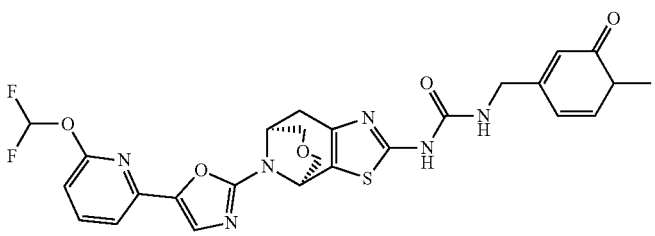 [SMILES: CC1C=CC(CNC(=O)Nc2nc3c(s2)[C@@H]2COC[C@H](C3)N2c2ncc(-c3cccc(OC(F)F)n3)o2)=CC1=O] | ¹H NMR (400 MHz, DMSO-d₆): δ (ppm) = 10.57 (1H, br s), 7.93 (1H, t, J = 7.8), 7.81 (1H, t, J = 72.8 Hz), 7.60 (1H, d, J = 6.9 Hz), 7.54 (1H, s), 7.40 (1H, d, J = 7.8 Hz), 7.04 (1H, t, J = 5.9 Hz), 6.88 (1H, d, J = 7.8 Hz), 6.18 (1H, s), 6.09 (1H, dd, J = 6.9, 1.8 Hz), 5.30 (1H, s), 4.40 (1H, d, J = 6.4 Hz), 4.14 (2H, d, J = 5.9 Hz), 3.98 (1H, d, J = 11.4 Hz), 3.86 (1H, dd, J = 11.4, 2.7 Hz), 3.83-3.81 (1H, dd, J = 10.5, 2.7), 3.63 (1H, d, J = 10.5 Hz), 3.36 (3H, s), 3.13 (1H, dd, J = 17.4, 6.4 Hz), 2.72 (1H, d, J = 17.4 Hz). MS (ESI) m/z: 572 (M + H)⁺ |

TABLE 3-21

| 179 | 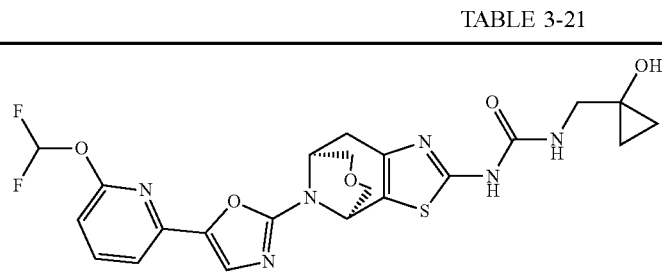 | ¹H NMR (400 MHz, DMSO-d₆): δ (ppm) = 10.21 (1H, br s), 7.93 (1H, t, J = 7.8 Hz), 7.81 (1H, t, J = 72.8 Hz), 7.54 (1H, s), 7.40 (1H, d, J = 7.8 Hz), 6.88 (1H, d, J = 7.8 Hz), 6.71 (1H, t, J = 5.5 Hz), 5.42 (1H, s), 5.29 (1H, s), 4.39 (1H, d, J = 6.4 Hz), 3.97 (1H, d, J = 11.4 Hz), 3.86 (1H, dd, J = 11.4, 2.5 Hz), 3.82 (1H, dd, J = 10.5, 2.5 Hz), 3.63 (1H, d, J = 10.5 Hz), 3.21 (2H, d, J = 5.5 Hz), 3.12 (1H, dd, J = 17.4, 6.4 Hz), 2.71 (1H, d, J = 17.4 Hz), 0.57-0.53 (2H, m), 0.50-0.46 (2H, m) MS (ESI) m/z: 521 (M + H)⁺ |

TABLE 3-21-continued

| 180 | 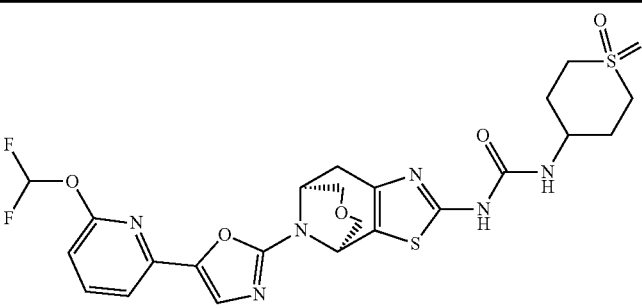 | ¹H NMR (400 MHz, DMSO-d₆): δ (ppm) = 10.14 (1H, s), 7.93 (1H, t, J = 7.8 Hz), 7.81 (1H, t, J = 73.2 Hz), 7.54 (1H, s), 7.40 (1H, d, J = 7.8 Hz), 6.88 (1H, d, J = 7.8 Hz), 6.82 (1H, d, J = 7.3 Hz), 5.30 (1H, s), 4.39 (1H, d, J = 6.4 Hz), 3.97 (1H, d, J = 11.4 Hz), 3.88-3.81 (3H, m), 3.63 (1H, d, J = 10.5 Hz), 3.30-3.24 (2H, m), 3.12 (1H, dd, J = 16.9, 6.4 Hz), 3.05-3.02 (2H, m), 2.71 (1H, d, J = 16.9 Hz), 2.16-2.08 (2H, m), 1.96-1.87 (2H, m). MS (ESI) m/z: 583 (M + H)⁺ |
| --- | --- | --- |
| 181 | 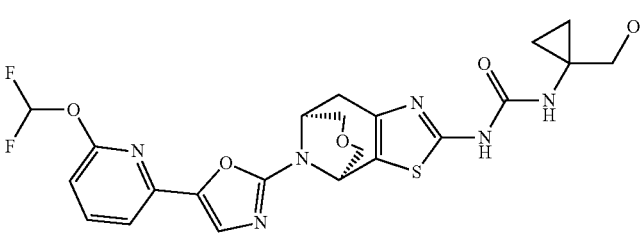 | ¹H NMR (400 MHz, DMSO-d₆): δ (ppm) = 10.13 (1H, s), 7.93 (1H, t, J = 7.8 Hz), 7.81 (1H, t, J = 72.8 Hz), 7.54 (1H, s), 7.40 (1H, d, J = 7.8 Hz), 6.88 (1H, d, J = 7.8 Hz), 6.88 (1H, br s), 5.29 (1H, s), 4.79 (1H, br s), 4.39 (1H, d, J = 6.9 Hz), 3.97 (1H, d, J = 11.4 Hz), 3.85 (1H, dd, J = 11.4, 2.7 Hz), 3.82 (1H, dd, J = 10.5, 2.7 Hz), 3.63 (1H, d, J = 10.5 Hz), 3.39 (2H, s), 3.12 (1H, dd, J = 16.9, 6.9 Hz), 2.71 (1H, d, J = 16.9 Hz), 0.80-0.52 (4H, m). MS (ESI) m/z: 521 (M + H)⁺ |
| 182 | 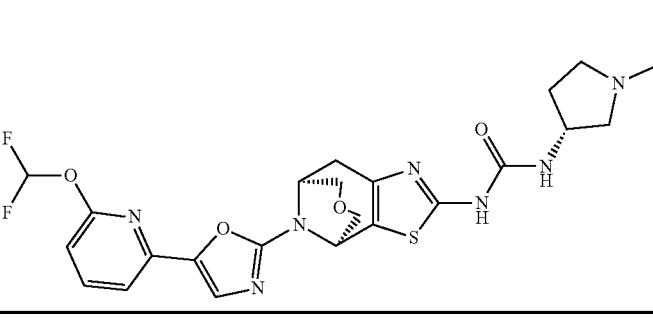 | ¹H NMR (400 MHz, DMSO-d₆): δ (ppm) = 10.12 (1H, s), 7.93 (1H, t, J = 7.8 Hz), 7.81 (1H, t, J = 72.8 Hz), 7.54 (1H, s), 7.40 (1H, d, J = 7.8 Hz), 6.93-6.88 (1H, m), 6.89 (1H, d, J = 7.8 Hz), 5.30 (1H, s), 4.39 (1H, d, J = 6.4 Hz), 4.26-4.12 (1H, m), 3.97 (1H, d, J = 11.4 Hz), 3.87-3.81 (2H, m), 3.69-3.46 (3H, m), 3.39-3.15 (2H, m), 3.12 (1H, dd, J = 17.2, 6.4 Hz), 2.71 (1H, d, J = 17.2 Hz), 2.16-1.99 (1H, m), 1.94-1.92 (3H, m), 1.90-1.71 (1H, m). MS (ESI) m/z: 562 (M + H)⁺ |

TABLE 3-22

| 183 | 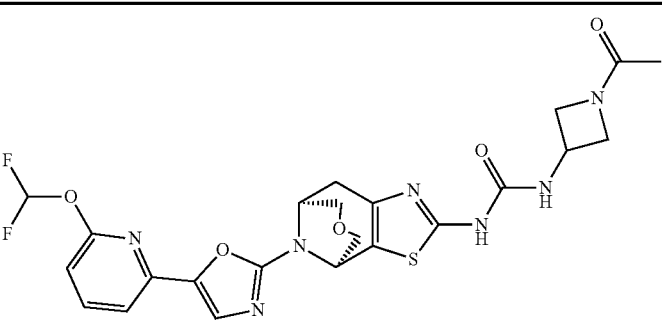 | ¹H NMR (400 MHz, DMSO-d₆): δ (ppm) = 10.55 (1H, s), 7.93 (1H, t, J = 7.8 Hz), 7.81 (1H, t, J = 72.8 Hz), 7.54 (1H, s), 7.40 (1H, d, J = 7.8 Hz), 7.23 (1H, d, J = 6.9 Hz), 6.89 (1H, d, J = 7.8 Hz), 5.30 (1H, s), 4.46-4.39 (2H, m), 4.35-4.30 (1H, m), 4.07-4.03 (1H, m), 3.99-3.93 (2H, m), 3.87-3.79 (2H, m), 3.70-3.62 (2H, m), 3.13 (1H, dd, J = 17.4, 7.1 Hz), 2.72 (1H, d, J = 17.4 Hz), 1.744-1.739 (3H, m) MS (ESI) m/z: 548 (M + H)⁺ |
| --- | --- | --- |
| 184 | 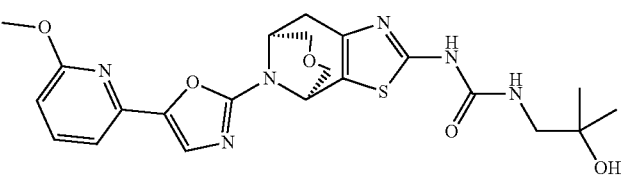 [SMILES: COc1cccc(-c2cnc(N3[C@@H]4COC[C@H]3c3sc(NC(=O)NCC(C)(C)O)nc3C4)o2)n1] | ¹H NMR (400 MHz, CDCl₃): δ (ppm) = 7.60-7.50 (1H, m), 7.34 (1H, s), 6.98 (1H, d, J = 7.2 Hz), 6.57 (1H, d, J = 8.4 Hz), 5.15 (1H, s), 4.44 (1H, d, J = 7.2 Hz), 4.07-3.90 (6H, m), 3.74 (1H, d, J = 9.6 Hz), 3.40 (1H, dd, J = 17.2, 7.2 Hz), 3.35-3.24 (2H, m), 2.80 (1H, d, J = 17.2 Hz), 1.22 (6H, d, J = 5.2 Hz). MS (ESI) m/z: 487 (M + H)⁺ |
| 185 | 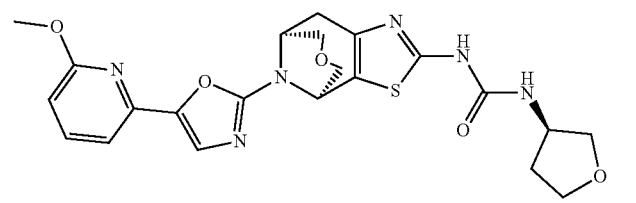 [SMILES: COc1cccc(-c2cnc(N3[C@@H]4COC[C@H]3c3sc(NC(=O)N[C@@H]5CCOC5)nc3C4)o2)n1] | ¹H NMR (400 MHz, CDCl₃): δ (ppm) = 7.55 (1H, dd, J = 8.4, 7.6 Hz), 7.35 (1H, s), 6.99 (1H, d, J = 7.2 Hz), 6.58 (1H, d, J = 8.4 Hz), 5.17 (1H, s), 4.56-4.39 (2H, m), 4.12-3.65 (11H, m), 3.40 (1H, dd, J = 17.2, 7.2 Hz), 2.82 (1H, d, J = 17.2 Hz), 2.34-2.19 (1H, m), 1.94-1.77 (1H, m). MS (ESI) m/z: 485 (M + H)⁺ |

TABLE 3-22-continued

| 186 | 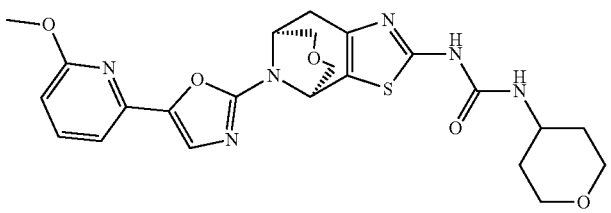 [SMILES: COc1cccc(-c2cnc(N3[C@@H]4COC[C@H]3c3sc(NC(=O)NC5CCOCC5)nc3C4)o2)n1] | $^1$H NMR (400 MHz, CDCl$_3$): δ (ppm) = 7.55 (1H, dd, J = 7.5, 8.2 Hz), 7.35 (1H, s), 6.99 (1H, d, J = 7.3 Hz), 6.58 (1H, d, J = 8.3 Hz), 5.17 (1H, s), 4.47 (1H, d, J = 7.0 Hz), 4.04 (2H, s), 4.00-3.89 (7H, m), 3.79-3.72 (1H, m), 3.56-3.36 (3H, m), 2.91-2.76 (1H, m), 2.03-1.89 (2H, m), 1.63-1.47 (2H, m). MS (ESI) m/z: 499 (M + H)$^+$ |
| --- | --- | --- |
| 187 | 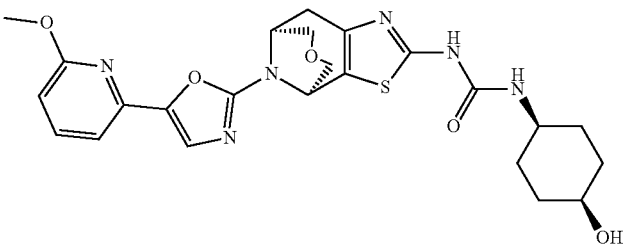 [SMILES: COc1cccc(-c2cnc(N3[C@@H]4COC[C@H]3c3sc(NC(=O)N[C@H]5CC[C@@H](O)CC5)nc3C4)o2)n1] | $^1$H NMR (400 MHz, CDCl$_3$): δ (ppm) = 7.55 (1H, dd, J = 7.6, 8.0 Hz), 7.34 (1H, s), 6.99 (1H, d, J = 7.2 Hz), 6.57 (1H, d, J = 8.4 Hz), 5.17 (1H, s), 4.45 (1H, d, J = 6.8 Hz), 4.03 (2H, s), 3.98 (1H, dd, J = 10.8, 1.6 Hz), 3.93 (3H, s), 3.85 (2H, s), 3.75 (1H, d, J = 10.0 Hz), 3.41 (1H, dd, J = 17.2, 7.2 Hz), 2.82 (1H, d, J = 17.2 Hz), 1.82-1.52 (8H, m). MS (ESI) m/z: 513 (M + H)$^+$ |

TABLE 3-23

| 188 | 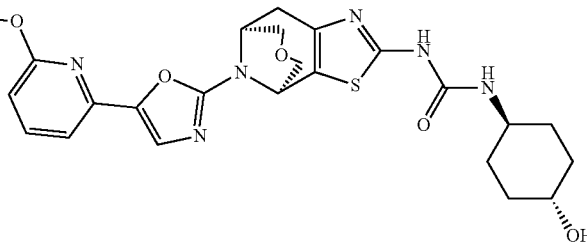 | $^1$H NMR (400 MHz, CDCl$_3$): δ (ppm) = 7.61-7.51 (1H, m), 7.35 (1H, s), 6.99 (1H, d, J = 7.2 Hz), 6.58 (1H, d, J = 8.2 Hz), 5.17 (1H, s), 4.46 (1H, d, J = 6.8 Hz), 4.03-3.97 (3H, m), 3.93 (3H, s), 3.75 (1H, d, J = 10.0 Hz), 3.72-3.55 (2H, m), 3.40 (1H, dd, J = 17.2, 7.2 Hz), 2.82 (1H, d, J = 17.2 Hz), 2.10-1.91 (4H, m), 1.47-1.14 (4H, m). MS (ESI) m/z: 513 (M + H)$^+$ |
| --- | --- | --- |
| 189 | 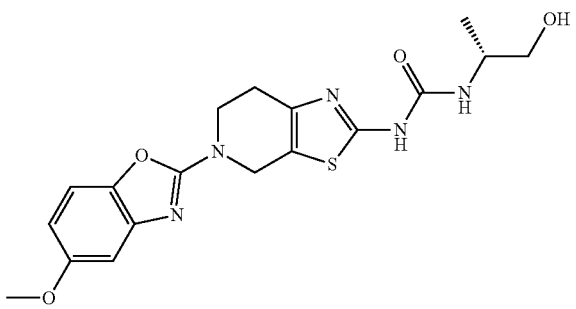 [SMILES: COc1ccc2oc(N3CCc4nc(NC(=O)N[C@H](C)CO)sc4C3)nc2c1] | $^1$H NMR (500 MHz, DMSO-d$_6$): δ (ppm) = 10.15 (1H, s), 7.31 (1H, d, J = 8.8 Hz), 6.91 (1H, d, J = 2.4 Hz), 6.59 (1H, dd, J = 8.8, 2.4 Hz), 6.49 (1H, d, J = 7.8 Hz), 4.88-4.85 (1H, m), 4.73 (2H, s), 3.93 (2H, t, J = 5.6 Hz), 3.74 (3H, s), 3.73-3.67 (1H, m), 3.37 (2H, t, J = 5.1 Hz), 2.76-2.71 (2H, m), 1.08 (3H, d, J = 6.8 Hz). MS (APCI) m/z: 404 (M + H)$^+$ |
| 190 | 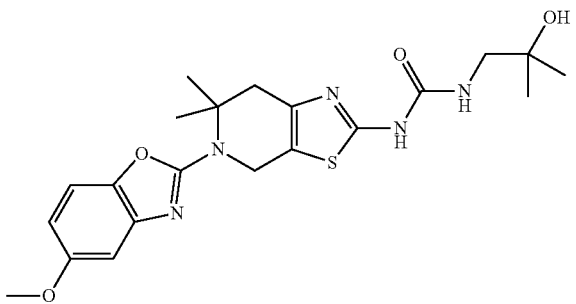 [SMILES: COc1ccc2oc(N3Cc4sc(NC(=O)NCC(C)(C)O)nc4CC3(C)C)nc2c1] | $^1$H NMR (500 MHz, DMSO-d$_6$): δ (ppm) = 10.26 (1H, s), 7.33 (1H, d, J = 8.3 Hz), 6.98 (1H, d, J = 2.4 Hz), 6.65 (1H, dd, J = 8.3, 2.4 Hz), 6.62 (1H, s), 4.72 (2H, s), 3.75 (3H, s), 3.50 (1H, s), 3.06 (2H, d, J = 5.4 Hz), 2.77 (2H, s), 1.58 (6H, s), 1.08 (6H, s). MS (APCI) m/z: 446 (M + H)$^+$ |

TABLE 3-23-continued

| 191 | 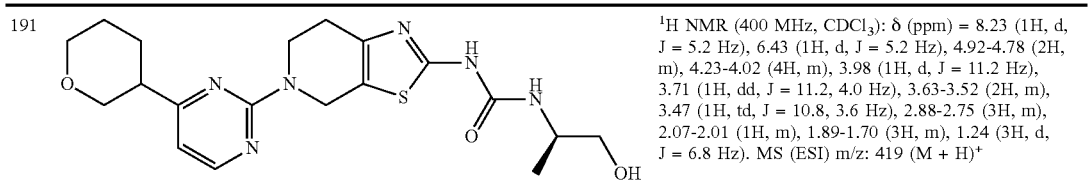 | ¹H NMR (400 MHz, CDCl$_3$): δ (ppm) = 8.23 (1H, d, J = 5.2 Hz), 6.43 (1H, d, J = 5.2 Hz), 4.92-4.78 (2H, m), 4.23-4.02 (4H, m), 3.98 (1H, d, J = 11.2 Hz), 3.71 (1H, dd, J = 11.2, 4.0 Hz), 3.63-3.52 (2H, m), 3.47 (1H, td, J = 10.8, 3.6 Hz), 2.88-2.75 (3H, m), 2.07-2.01 (1H, m), 1.89-1.70 (3H, m), 1.24 (3H, d, J = 6.8 Hz). MS (ESI) m/z: 419 (M + H)⁺ |

TABLE 3-24

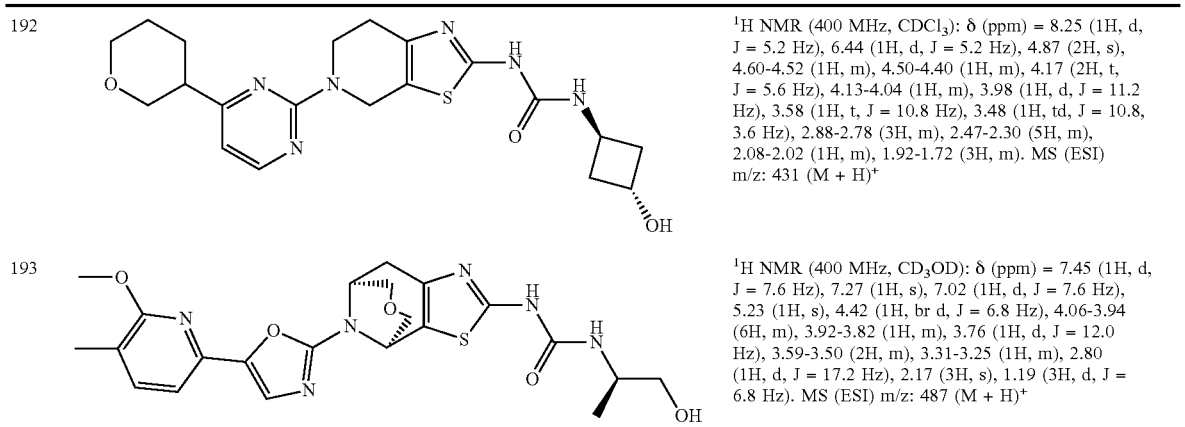

| 192 | | ¹H NMR (400 MHz, CDCl$_3$): δ (ppm) = 8.25 (1H, d, J = 5.2 Hz), 6.44 (1H, d, J = 5.2 Hz), 4.87 (2H, s), 4.60-4.52 (1H, m), 4.50-4.40 (1H, m), 4.17 (2H, t, J = 5.6 Hz), 4.13-4.04 (1H, m), 3.98 (1H, d, J = 11.2 Hz), 3.58 (1H, t, J = 10.8 Hz), 3.48 (1H, td, J = 10.8, 3.6 Hz), 2.88-2.78 (3H, m), 2.47-2.30 (5H, m), 2.08-2.02 (1H, m), 1.92-1.72 (3H, m). MS (ESI) m/z: 431 (M + H)⁺ |
| 193 | | ¹H NMR (400 MHz, CD$_3$OD): δ (ppm) = 7.45 (1H, d, J = 7.6 Hz), 7.27 (1H, s), 7.02 (1H, d, J = 7.6 Hz), 5.23 (1H, s), 4.42 (1H, br d, J = 6.8 Hz), 4.06-3.94 (6H, m), 3.92-3.82 (1H, m), 3.76 (1H, d, J = 12.0 Hz), 3.59-3.50 (2H, m), 3.31-3.25 (1H, m), 2.80 (1H, d, J = 17.2 Hz), 2.17 (3H, s), 1.19 (3H, d, J = 6.8 Hz). MS (ESI) m/z: 487 (M + H)⁺ |

Although the present invention has been described in detail with reference to specific embodiments, it will be apparent to those skilled in the art that various changes and modifications can be made without departing from the spirit and scope of the present invention. This application is based on a Japanese patent application (Japanese Patent Application No. 2019-010252) filed on Jan. 24, 2019, the content of which is incorporated herein by reference.

The invention claimed is:

1. A compound represented by Formula (1) or a pharmaceutically acceptable salt thereof,

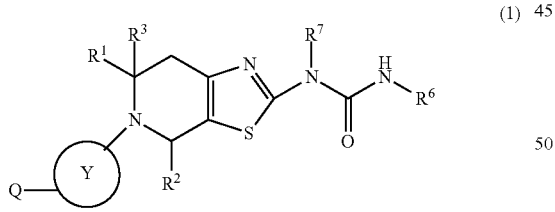

wherein the symbols in Formula (1) have the following definitions, $R^1$ and $R^2$ independently represent a hydrogen atom or a C1-C6 alkyl group and may be the same or different from each other, or $R^1$ and $R^2$ bond to each other to form a substituent and the substituent represents a group selected from the group consisting of

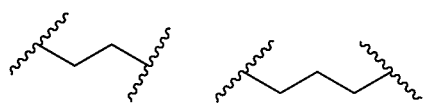

-continued $R^{12}$ represents a C1-C6 alkyl group, a hydroxy C1-C6 alkyl group, a C1-C6 alkylcarbonyl group, a C1-C6 alkoxycarbonyl group, or a C1-C6 alkylsulfonyl group, $R^3$ represents a hydrogen atom or a C1-C6 alkyl group, $R^6$ represents a C1-C6 alkyl group that may be substituted with one to three groups selected from a group G, a C3-C6 cycloalkyl group that may be substituted with one or two groups selected from the group G, and a 4- to 7-membered heterocyclic group that may be substituted with one or two groups selected from the group G, the group G consists of substituents selected from the group consisting of a hydroxyl group, a halogen atom, an amino group, a halo-C1-C6 alkyl group, a hydroxy C1-C6 alkyl group, an amino C1-C6 alkyl group, a C1-C6 alkoxy group, a C1-C6 alkylsulfonyl group, a hydroxy C1-C6 alkoxy group, a C1-C6 alkylcarbonyl group, a carbamoyl group that may be substituted with one or two groups selected from a group J, a C3-C6 cycloalkyl group that may be substituted with one or two groups selected from the group J, a 4- to 7-membered heterocyclic group that may be substituted with one or two groups selected from the group J, and a 5- to 6-membered heteroaryl group that may be substituted with one or two groups selected from the group J, the group J consists of substituents selected from the group consisting of a hydroxyl group, an oxo group, an amino C1-C6 alkyl group, an amino group, a C1-C6 alkyl group, and a C1-C6 alkylcarbonyl group, $R^7$ represents a hydrogen atom, or $R^6$ and $R^7$ bond to each other to form a substituent and the substituent represents a group shown below,

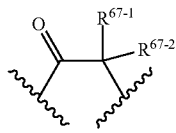

the group is oriented in either a rightward or leftward direction, $R^{67-1}$ and $R^{67-2}$ independently represent a hydrogen atom, a C1-C6 alkyl group, a hydroxy C1-C6 alkyl group, a C1-C4 alkylene group, or a C1-C6 alkoxy C1-C6 alkyl group and may be the same or different from each other,

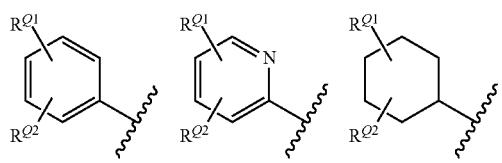

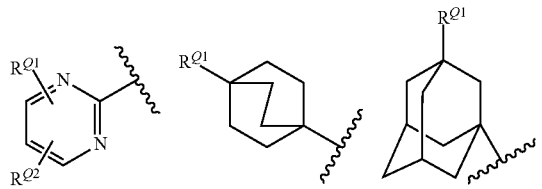

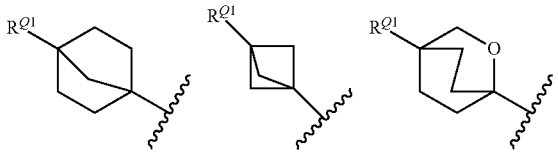

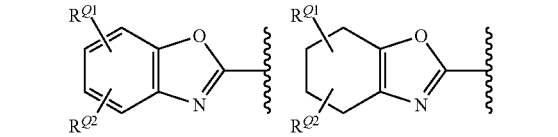

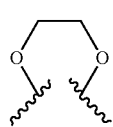

wherein Q is a substituent selected from the group consisting of a C3-C6 cycloalkyl group that is substituted with any of one to three groups selected from $R^{Q4}$, a phenyl group that is substituted with any of one to three groups selected from $R^{Q4}$, a pyridyl group that is substituted with any of one to three groups selected from $R^{Q4}$, and a 1,3-benzoxazol-2-yl group that is substituted any of one to three groups selected from $R^{Q4}$, and $R^{Q4}$ represents a halogen atom, a cyano group, a C1-C6 alkyl group, a C1-C6 alkoxy group, a halo-C1-C6 alkyl group, a halo-C1-C6 alkoxy group, a C1-C6 alkylsulfonyl group, a di-C1-C6 alkylamino group, or a C3-C6 cycloalkylcarbonyl group, and Y represents a group selected from the group consisting of or a single bond,

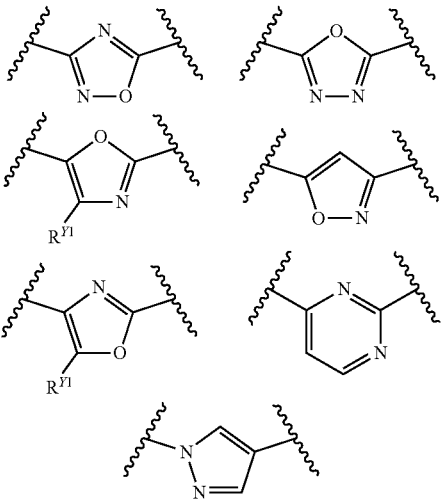

wherein the groups are oriented in either a rightward or leftward direction, $R^{Y1}$ represents a hydrogen atom or a C1-C6 alkyl group, and the following compounds or pharmaceutically acceptable salts thereof are excluded

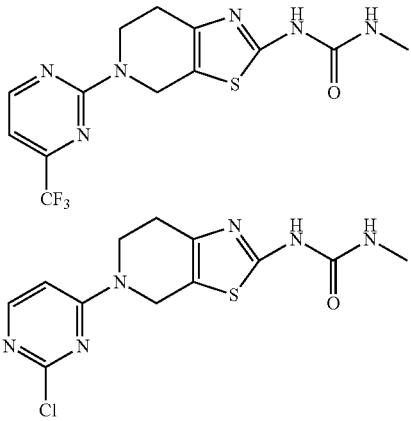

2. The compound or the pharmaceutically acceptable salt thereof according to claim 1, wherein both $R^1$ and $R^2$ represent a hydrogen atom, or $R^1$ and $R^2$ bond to each other to form a substituent and the substituent represents a group selected from the group consisting of

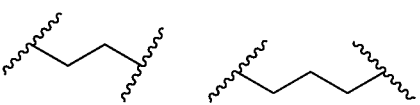

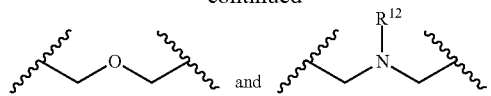

R[12] represents a methyl group, a hydroxyethyl group, an acetyl group, a methoxycarbonyl group, or a methanesulfonyl group, and R[3] represents a hydrogen atom or a methyl group.

3. The compound or the pharmaceutically acceptable salt thereof according to claim 1,
wherein both R[1] and R[2] represent a hydrogen atom, or R[1] and R[2] bond to each other to form a substituent and the substituent represents a group selected from the group consisting of

R[13] represents an acetyl group or a methoxycarbonyl group, and

R[3] represents a hydrogen atom.

4. The compound or the pharmaceutically acceptable salt thereof according to claim 1,
wherein both R[1] and R[3] represent a methyl group, and R[2] represents a hydrogen atom.

5. The compound or the pharmaceutically acceptable salt thereof according to claim 1,
wherein R[6] is selected from the group consisting of a C1-C6 alkyl group, a hydroxy C1-C6 alkyl group, a hydroxy C3-C6 cycloalkyl group, a C1-C6 alkoxy C1-C6 alkyl group, a tetrahydrofuranyl group, a tetrahydropyranyl group, and a dioxanylmethyl group, and R[7] represents a hydrogen atom.

6. The compound or the pharmaceutically acceptable salt thereof according to claim 1,
wherein R[6] is selected from the group consisting of a methyl group, an isobutyl group, a 2-hydroxy-1-methylethyl group, a 2-hydroxy-2-methylpropyl group, a 3-hydroxybutyl group, a 2-hydroxycyclopentyl group, a 4-hydroxycyclohexyl group, a 2-methoxypropyl group, a 3-tetrahydrofuranyl group, a 4-tetrahydropyranyl group, and a 1,4-dioxan-2-ylmethyl group, and R[7] represents a hydrogen atom.

7. The compound or the pharmaceutically acceptable salt thereof according to claim 1,
wherein Q is selected from the group consisting of a cyclohexyl group that is substituted with two fluorine atoms, a phenyl group that is substituted with a fluorine atom or a cyclopropylcarbonyl group, a pyridyl group that is substituted with one group selected from the group consisting of a methoxy group, an ethoxy group, and a difluoromethoxy group, and a 1,3-benzoxazol-2-yl group that is substituted with one or two groups independently selected from the group consisting of a fluorine atom, a methyl group, a methoxy group, an ethoxy group, a dimethylamino group, and a methanesulfonyl group.

8. The compound or the pharmaceutically acceptable salt thereof according to claim 1,
wherein Y represents a single bond or a group selected from the group consisting of

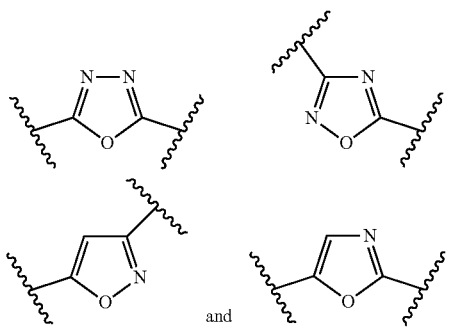

the groups are oriented in either a rightward or leftward direction.

9. The compound or the pharmaceutically acceptable salt thereof according to claim 1,
wherein Q represents a 1,3-benzoxazol-2-yl group that is substituted with one or two groups independently selected from the group consisting of a fluorine atom, a methyl group, a methoxy group, an ethoxy group, a dimethylamino group, and a methanesulfonyl group, and Y represents a single bond.

10. The compound or the pharmaceutically acceptable salt thereof according to claim 1,
wherein Q represents a cyclohexyl group that is substituted with two fluorine atoms, a phenyl group that is substituted with a fluorine atom or a cyclopropylcarbonyl group, or a pyridyl group that is substituted with one group selected from the group consisting of a methoxy group, an ethoxy group, and a difluoromethoxy group, and Y represents a group selected from the group consisting of

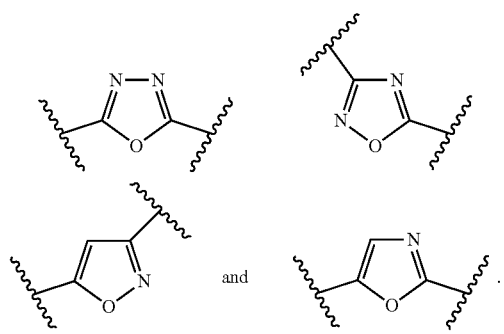

11. The compound or the pharmaceutically acceptable salt thereof according to claim 1,
wherein the compound is selected from the group consisting of
N-[(4S,8S)-10-{5-[3-(cyclopropanecarbonyl)phenyl]-1,3,4-oxadiazol-2-yl}-4,7,8,9-tetrahydro-5H-4,8-epiminooxocino[5,4-d][1,3]thiazol-2-yl]-N'-methylurea,
(−)-N-{(4R*,8R*)-6-acetyl-10-[3-(4-fluorophenyl)-1,2,4-oxadiazol-5-yl]-4,5,6,7,8,9-hexahydro-4,8-epimino[1,3]thiazolo[5,4-d]azocin-2-yl}-N'-methylurea,
(−)-methyl(4R*,8R*)-10-[3-(4-fluorophenyl)-1,2,4-oxadiazol-5-yl]-2-[(methylcarbamoyl)amino]-4,7,8,9-tetrahydro-4,8-epimino[1,3]thiazolo[5,4-d]azocin-6(5H)-carboxylate, N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1R,2R)-2-hydroxycyclopentyl]urea,
N-{5-[3-(4,4-difluorocyclohexyl)-1,2,4-oxadiazol-5-yl]-4,5,6,7-tetrahydro[1,3]thiazolo[5,4-c]pyridin-2-yl}-N'-[(1r,4r)-4-hydroxycyclohexyl]urea,
N-{5-[3-(4,4-difluorocyclohexyl)-1,2,4-oxadiazol-5-yl]-4,5,6,7-tetrahydro[1,3]thiazolo[5,4-c]pyridin-2-yl}-N'-(3-methoxypropyl)urea,
N-{[(2S)-1,4-dioxan-2-yl]methyl}-N'-{(4S,8S)-10-[3-(4-fluorophenyl)-1,2,4-oxadiazol-5-yl]-4,7,8,9-tetrahydro-5H-4,8-epiminooxocino[5,4-d][1,3]thiazol-2-yl}urea,
N-[(2R)-1-hydroxypropan-2-yl]-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea,
N-[(4S,8S)-10-(5-fluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea,
N-[(4S,8S)-10-(5-ethoxy-1,3-benzoxazol-2-yl)-4,7,8,9-tetrahydro-5H-4,8-epiminooxocino[5,4-d][1,3]thiazol-2-yl]-N'-(2-hydroxy-2-methylpropyl)urea,
N-{(4S,8S)-10-[5-(dimethylamino)-1,3-benzoxazol-2-yl]-4,7,8,9-tetrahydro-5H-4,8-epiminooxocino[5,4-d][1,3]thiazol-2-yl}-N'-(2-hydroxy-2-methylpropyl)urea,
N-[(4S,8S)-10-(5,6-difluoro-1,3-benzoxazol-2-yl)-4,7,8,9-tetrahydro-5H-4,8-epiminooxocino[5,4-d][1,3]thiazol-2-yl]-N'-[(2R)-1-hydroxypropan-2-yl]urea,
N-{(4S,8S)-10-[5-(methanesulfonyl)-1,3-benzoxazol-2-yl]-4,7,8,9-tetrahydro-5H-4,8-epiminooxocino[5,4-d][1,3]thiazol-2-yl}-N'-(2-methylpropyl)urea,
N-(2-hydroxy-2-methylpropyl)-N'-[(4S,8S)-10-(5-methoxy-6-methyl-1,3-benzoxazol-2-yl)-4,7,8,9-tetrahydro-5H-4,8-epiminooxocino[5,4-d][1,3]thiazol-2-yl]urea,
N-[(4S,8S)-10-(5-methoxy-6-methyl-1,3-benzoxazol-2-yl)-4,7,8,9-tetrahydro-5H-4,8-epiminooxocino[5,4-d][1,3]thiazol-2-yl]-N'-[(3R)-oxolan-3-yl]urea,
N-(2-hydroxy-2-methylpropyl)-N'-[(4S,8S)-10-(5-methoxy-1,3-benzoxazol-2-yl)-4,7,8,9-tetrahydro-5H-4,8-epiminooxocino[5,4-d][1,3]thiazol-2-yl]urea,
N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-[(3R)-oxolan-3-yl]urea,
N-[(4S,8S)-10-(5-methoxy-1,3-benzoxazol-2-yl)-4,7,8,9-tetrahydro-5H-4,8-epiminooxocino[5,4-d][1,3]thiazol-2-yl]-N'-methylurea,
N-methyl-N'-[(4S,8S)-10-(5-methyl-1,3-benzoxazol-2-yl)-4,7,8,9-tetrahydro-5H-4,8-epiminooxocino[5,4-d][1,3]thiazol-2-yl]urea,
N-(2-hydroxy-2-methylpropyl)-N'-[(4S,8S)-10-{5-[(2H3)methyloxy]-1,3-benzoxazol-2-yl}-4,7,8,9-tetrahydro-5H-4,8-epiminooxocino[5,4-d][1,3]thiazol-2-yl]urea,
N-{(4S,8S)-10-[5-(4-fluorophenyl)-1,2-oxazol-3-yl]-4,7,8,9-tetrahydro-5H-4,8-epiminooxocino[5,4-d][1,3]thiazol-2-yl}-N'-[(1s,4s)-4-hydroxycyclohexyl]urea,
N-{(4S,8S)-10-[5-(6-methoxypyridin-2-yl)-1,2-oxazol-3-yl]-4,7,8,9-tetrahydro-5H-4,8-epiminooxocino[5,4-d][1,3]thiazol-2-yl}-N'-oxan-4-ylurea,
N-[(4S,8S)-10-{5-[6-(difluoromethoxy)pyridin-2-yl]-1,3-oxazol-2-yl}-4,7,8,9-tetrahydro-5H-4,8-epiminooxocino[5,4-d][1,3]thiazol-2-yl]-N'-[(2R)-1-hydroxypropan-2-yl]urea,
N-[(2R)-1-hydroxypropan-2-yl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea,
N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-[(2R)-1-hydroxypropan-2-yl]urea,
N-[(2R)-1-hydroxypropan-2-yl]-N'-{5-[5-(methanesulfonyl)-1,3-benzoxazol-2-yl]-6,6-dimethyl-4,5,6,7-tetrahydro[1,3]thiazolo[5,4-c]pyridin-2-yl}urea,
N-(2-hydroxy-2-methylpropyl)-N'-{5-[5-(methanesulfonyl)-1,3-benzoxazol-2-yl]-6,6-dimethyl-4,5,6,7-tetrahydro[1,3]thiazolo[5,4-c]pyridin-2-yl}urea,
N-[(2R)-1-hydroxypropan-2-yl]-N'-[(4S,8S)-10-{5-[($^{2}$H$_3$)methyloxy]-1,3-benzoxazol-2-yl}-4,7,8,9-tetrahydro-5H-4,8-epiminooxocino[5,4-d][1,3]thiazol-2-yl]urea,
N-[(4S,8S)-10-{5-[(2H3)methyloxy]-1,3-benzoxazol-2-yl}-4,7,8,9-tetrahydro-5H-4,8-epiminooxocino[5,4-d][1,3]thiazol-2-yl]-N'-[(3R)-oxolan-3-yl]urea,
N-[(1r,3S)-3-hydroxycyclobutyl]-N'-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}urea,
N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-(2-hydroxy-2-methylpropyl)urea,
N-{(4S,8S)-10-[5-(6-ethoxypyridin-2-yl)-1,3-oxazol-2-yl]-4,7,8,9-tetrahydro-5H-4,8-epiminooxocino[5,4-d][1,3]thiazol-2-yl}-N'-[(1r,3S)-3-hydroxycyclobutyl]urea, and
N-{(4S,8S)-10-[5-(6-methoxypyridin-2-yl)-1,3-oxazol-2-yl]-4,7,8,9-tetrahydro-5H-4,8-epiminooxocino[5,4-d][1,3]thiazol-2-yl}-N'-oxan-4-ylurea.

12. A pharmaceutical composition containing:
the compound or the pharmaceutically acceptable salt thereof according to claim 1 as an active component and an excipient.

13. The pharmaceutical composition according to claim 12, wherein the pharmaceutical composition is an oral preparation.

14. The pharmaceutical composition according to claim 12, wherein the pharmaceutical composition is an external preparation.

* * * * *